United States Patent
Zieler et al.

(10) Patent No.: US 9,758,810 B2
(45) Date of Patent: Sep. 12, 2017

(54) IDENTIFICATION OF CENTROMERE SEQUENCES AND USES THEREFOR

(75) Inventors: Helge Zieler, Del Mar, CA (US); Robert Christopher Brown, San Diego, CA (US); Toby Howard Richardson, San Diego, CA (US); Douglas Gillette Smith, San Diego, CA (US)

(73) Assignee: Synthetic Genomics, Inc., La Jolla, CA (US)

( * ) Notice: Subject to any disclaimer, the term of this patent is extended or adjusted under 35 U.S.C. 154(b) by 0 days.

(21) Appl. No.: 12/431,701

(22) Filed: Apr. 28, 2009

(65) Prior Publication Data
US 2010/0041035 A1    Feb. 18, 2010

Related U.S. Application Data

(60) Provisional application No. 61/048,506, filed on Apr. 28, 2008.

(51) Int. Cl.
*C12Q 1/68*    (2006.01)
(52) U.S. Cl.
CPC .................................. *C12Q 1/6804* (2013.01)
(58) Field of Classification Search
None
See application file for complete search history.

(56) References Cited

U.S. PATENT DOCUMENTS

2005/0085628 A1 *    4/2005    Yoda et al. ............... 530/388.26
2008/0194414 A1 *    8/2008    Albert et al. ...................... 506/1

OTHER PUBLICATIONS

Infante et al. (1995) Genetics vol. 141 pp. 87-93.*
Robertson et al. (Jun. 11, 2007) Nature Methods vol. 4 No. 8 pp. 651-657.*
Masumoto et al. (1998) Chromosoma vol. 107: pp. 406-416.*
Goff et al. (2002) Science vol. 296 : pp. 92-100.*
MacLean et al. (Apr. 2009) nature reviews vol. 7: pp. 287-296.*
Xiong et al. (online publication Mar. 12, 2008) Traffic vol. 9: pp. 708-724.*
Wold et al. (on line publication Dec. 19, 2007) nature Methods (2008) vol. 5 No. 1 pp. 19-21.*
Maruyama et al. (2007) The Plant journal vol. 49: 1122-1129.*
Yan et al. (Intergenic Locations of Rice Centromeric Chromatin, PLoS Biol. Nov. 2008; 6(11): e286. Published online Nov. 25, 2008).*
Lee et al., "Chromatin immunoprecipitation cloning reveals rapid evolutionary patterns of centromeric DNA in *Oryza* species", *PNAS* 102:11793-11798, 2005.
Nagaki et al., "Chromatin Immunoprecipitation Reveals that the 180-bp Satellite Repeat is the Key Functional DNA Element of *Arabidopsis thaliana* Centromeres", *Genetics* 163:1221-1225, 2003.

* cited by examiner

*Primary Examiner* — Aaron Priest
(74) *Attorney, Agent, or Firm* — DLA Piper LLP (US)

(57) ABSTRACT

Provided herein are methods for identifying centromeres and centromeres identified by such methods. Centromeres of organisms such as algae, fungi, and protists can be used, for example, for constructing artificial chromosomes and cells containing such artificial chromosomes.

23 Claims, No Drawings

US 9,758,810 B2

IDENTIFICATION OF CENTROMERE SEQUENCES AND USES THEREFOR

CROSS REFERENCE TO RELATED APPLICATION

This application claims priority to U.S. provisional application No. 61/048,506, filed Apr. 28, 2008, which is herein incorporated by reference in its entirety.

REFERENCE TO SEQUENCE LISTING SUBMITTED VIA EFS-WEB

The entire content of the following electronic submission of the sequence listing via the USPTO EFS-WEB server, as authorized and set forth in MPEP §1730 II.B.2(a)(C), is incorporated herein by reference in its entirety for all purposes. The sequence listing is identified on the electronically filed text file as follows:

| File Name | Date of Creation | Size (bytes) |
| --- | --- | --- |
| 6168720023005eqlist.txt | 19 Oct. 2009 | 413,696 bytes |

BACKGROUND OF THE INVENTION

The present invention relates to the identification of centromeres that are useful, for example, in constructing artificial chromosomes and cells comprising such artificial chromosomes.

Genetic transformation of biological organisms is essential for genetic studies and for construction of novel strains used in biotechnology. There are two general ways of adding genes into the genome of a biological organism: the introduced gene(s) can be integrated into the organism's chromosome(s) or the introduced gene(s) can reside on a new, artificial chromosome that exists autonomously in the genome, independent of the existing chromosomes. If available, artificial chromosomes are generally the vehicles of choice for transformation of eukaryotic organisms, due to a number of reasons, among them: single copy number, stable and autonomous inheritance, lack of disruption of the existing chromosomes, the ability to transfer many genes on a single construct, and high transformation efficiency. As a result, extensive efforts have been directed into construction and testing of artificial chromosomes for transformation of eukaryotes.

The centromere is an important element in an artificial chromosome, mediating faithful chromosome segregation between the two daughter cells in a cell division. Accordingly, the isolation and identification of functional centromere sequences is an essential part of constructing artificial chromosomes for any specific organism. Eukaryotic centromeres vary greatly in size, ranging from 120-200 bp in budding yeasts to tens of megabases in plants and animals. They are also very diverse in structure and sequence, with centromeres in higher eukaryotes often composed of large tracts of tandem satellite repeats, interspersed with retrotransposons and other sequences, including in some cases functional genes. De novo centromere function (i.e., establishment of centromere function from naked DNA introduced into a cell) often requires the specific centromere sequences present in that organism, as sequences from a related organism may not work efficiently in establishing centromere function. The high amount of species specificity of centromere sequences correlates with the observation that centromere sequences evolve very rapidly and can lose all homology between related species within several million years of evolution (e.g., centromere repeat sequences within the genus *Arabidopsis*). As a result, it is generally not possible to use homology to centromere sequences from a related organism as a method for isolating centromeres from an organism where the centromere has not previously been characterized.

Identification of centromeres in organisms has been pursued in several organisms by searching for repetitive DNA or methylated DNA followed by labeling studies to determine whether the identified sequences hybridize to the centromere region of chromosomes, and/or functional studies to determine whether the identified sequence(s) function as centromeres (see, for example, U.S. Pat. No. 7,456,013, WO 08/112,972).

However, conserved centromere features other than sequence can be exploited to isolate centromere sequences from novel species. For example, CenH3 (known as CENP-A in humans) is a variant of the nucleosome protein histone H3 that is preferentially associated with centromeric chromatin. This protein differs from histone H3 in having longer and divergent N-terminal sequences. Antibodies raised against the unique N-terminal sequences of CenH3 have been used in some strategies for isolating centromere sequences from some species, for example, using chromatin immunoprecipitation ("ChIP"). Because immunoprecipitation of chromatin typically results in isolation of non-specific sequences as well as the sequence(s) of interest, when used for centromere identification, it has been performed in conjunction with hybridization or sequence comparisons with sequence motifs previously known to be associated or suspected of being associated with centromeres in the organism of interest (see, for example, Nagaki et al. Genetics 163: 1221-1225 (2003); Lee et al. Proceedings Natl. Acad. Sci. USA 102: 11793-11798 (2005)), thus relying on prior knowledge of centromere-associated sequences. Thus, there remains a need in the art for methods of identification of centromere sequences that can quickly process and specifically identify centromere sequences (as distinguished from non-specific sequences) among large pools of nucleic acids molecules, when there are no known centromeres for comparison, for example in several algal species where centromere identification has been particularly difficult.

BRIEF SUMMARY OF THE INVENTION

In one aspect, provided herein are methods of identifying a centromere sequence, in which the method includes: immunoprecipitating protein-DNA complexes from fragmented chromatin derived from a cell using an antibody to a centromere-associated protein; isolating nucleic acid molecules from the immunoprecipitated protein-DNA complexes; and sequencing the isolated nucleic acid molecules to identify a centromere sequence.

In another aspect, methods are provided for identifying a centromere sequence in which the methods include: immunoprecipitating protein-DNA complexes from fragmented chromatin isolated from a cell using an antibody to a centromere-associated protein; separately sequencing individual nucleic acid molecules of a population of nucleic acid molecules isolated from the protein-DNA complexes; calculating the frequency of occurrence of each nucleic acid sequence in the population of nucleic acid molecules isolated from the protein-DNA complexes; and identifying a nucleic acid molecule sequence which has an increased frequency of occurrence in the population as a centromere sequence.

The methods of the invention in some preferred embodiments use chromatin isolated from one or more cells of an algal, fungal, or protist species. An algal cell used in the methods is at least one green, yellow-green, brown, golden brown, or red algal cell, such as an alga of any of the Rhodophyta, Euglenophyta, Cryptophyta, Pyrrophyta, Raphidophyta, Haptophyta, Chrysophyta, Xanthophyta, Eustigmatophyta, Phaeophyta (Fucophyta), Prasinophyta, Bacillariophyta, Glaucophyta, or Chlorophyta phyla, and in some embodiments is a cell of an alga of the Chlorophyceae class.

In some preferred embodiments, individual nucleic acid molecules of a population of nucleic acid molecules isolated from immunoprecipitated protein-DNA complexes are sequenced separately using a machine that performs high-throughput parallel sequencing. In some embodiments of the methods provided herein, separate sequencing of individual nucleic molecules is performed using a machine that isolates single nucleic acid molecules of a population of nucleic acid molecules prior to sequencing, such as a high-throughput parallel sequencing machine, that performs, for example, at least 10,000 sequencing reactions simultaneously.

In some embodiments, the methods disclosed herein do not include addition of a cross-linking agent prior to immunoprecipitating protein-DNA complexes from the fragmented chromatin.

In some preferred embodiments, the methods provided herein do not include hybridizing a nucleic acid molecule isolated from the immunoprecipitated protein-DNA complexes to one or more known centromere-associated sequences, or comparing the sequence of a nucleic acid molecule isolated from the immunoprecipitated protein-DNA complexes to one or more known centromere sequences. In some preferred embodiments, the methods of identifying a centromere sequence do not include hybridizing a nucleic acid molecule isolated from the immunoprecipitated protein-DNA complexes to one or more repetitive sequences known in the organism from which the chromatin is isolated.

In any of the methods for centromere identification provided herein, immunoprecipitation can use an antibody that specifically binds any centromere-associated protein, including without limitation a centromere protein, a centromere protein-recruiting protein, or a kinetochore protein. In some embodiments, chromatin immunoprecipitation is performed with an antibody that specifically binds a centromere protein, such as for example, an antibody that specifically binds to CENP-A/CenH3 or a homolog of CENP-A/CenH3. In some embodiments, an antibody used for chromatin immunoprecipitation specifically binds to the N terminus of CENP-A/CenH3 or a homolog of CENP-A/CenH3.

In some embodiments, the method includes amplifying the nucleic acid molecules isolated from the immunoprecipitated protein-DNA complexes prior to sequencing the isolated nucleic acid molecules. In some preferred embodiments, individual nucleic acid molecules isolated from the immunoprecipitated protein-DNA complexes are amplified separately prior to sequencing the nucleic acid molecules. In some embodiments of the methods disclosed herein, the methods include, prior to sequencing the nucleic acid molecules, separately amplifying individual nucleic acid molecules of the population of immunoprecipitated nucleic acid molecules to generate single nucleic acid molecule amplification products corresponding to individual nucleic acid molecules of the immunoprecipitated nucleic acid molecule population using a machine that isolates single nucleic acid molecules from a population of nucleic acid molecules prior to amplification. In some preferred embodiments, a high throughput parallel sequencing system isolates single nucleic acid molecules from a population of nucleic acid molecules prior to amplification, performs amplification reactions on the isolated individual nucleic acid molecules to generate isolated amplification products of the individual nucleic acid molecules of the population, and performs parallel sequencing reactions on the isolated amplification products of the individual nucleic acid molecules of the population to provide sequences of the individual molecules of the population.

In some embodiments, the methods further include performing one or more assays to evaluate the centromere sequence. For example, an assay can be performed for stable heritability of an artificial chromosome comprising the centromere sequence in which the presence of the centromere sequence or a nucleic acid sequence linked thereto on an artificial chromosome is detected. An assay for centromere function in some embodiments detects the presence of a selectable or nonselectable marker on an artificial chromosome comprising the centromere sequence.

Also provided in a further aspect are recombinant nucleic acid molecules comprising centromere sequences identified by the methods of the invention, in which the centromere sequence is not adjacent to one or more sequences positioned adjacent to the centromere sequence in the genome from which the centromere sequence is derived. The recombinant nucleic acid molecule can include sequences adjacent to the identified centromere sequence that are derived from the same organism or species from which the centromere sequence is derived, can be adjacent to sequences derived from another organism or species, or can include synthetic sequences.

Included in the invention are recombinant nucleic acid molecules that comprise a sequence having at least 65%, at least 70%, at least 75%, at least 80%, at least 85%, at least 90%, or at least 95% identity to at least 30, between 30 and 40, between 40 and 50, between 50 and 60, between 60 and 70, between 70 and 80, between 80 and 90, between 90 and 100, or at least 100 bp, between 100 and 125 bp, between about 125 bp and about 150 bp, between about 150 bp and about 200 bp, between about 200 bp and about 300 bp, between about 300 bp and about 400 bp, between about 400 bp and about 500 bp, between about 500 bp and about 1 Kb, between about 1 Kb and about 2 Kb, between about 2 Kb and about 3 Kb, between about 3 Kb and about 4 Kb, between about 4 Kb and about 5 Kb, between about 5 Kb and about 6 Kb, between about 6 Kb and about 7 Kb, between about 7 Kb and about 8 Kb, between about 8 Kb and about 9 Kb, between about 9 Kb and about 10 Kb, or greater than 10 Kb of a centromere sequence identified by the methods disclosed herein, in which the nucleic acid sequence functions as a centromere.

Artificial chromosomes that comprise a centromere identified by the methods of the invention, or a sequence having at least 65%, at least 70%, at least 75%, at least 80%, at least 85%, at least 90%, or at least 95% identity to at least 30, between 30 and 40, between 40 and 50, between 50 and 60, between 60 and 70, between 70 and 80, between 80 and 90, between 90 and 100, or at least 100 bp, between 100 and 125 bp, between about 125 bp and about 150 bp, between about 150 bp and about 200 bp, between about 200 bp and about 300 bp, between about 300 bp and about 400 bp, between about 400 bp and about 500 bp, between about 500 bp and about 1 Kb, between about 1 Kb and about 2 Kb, between about 2 Kb and about 3 Kb, between about 3 Kb and about 4 Kb, between about 4 Kb and about 5 Kb, between about 5 Kb and about 6 Kb, between about 6 Kb and about 7 Kb, between about 7 Kb and about 8 Kb, between about 8 Kb and about 9 Kb, between about 9 Kb and about 10 Kb, or greater than 10 Kb to a sequence identified by the methods disclosed herein, in which the nucleic acid sequence functions as a centromere, are also provided herein. The artificial chromomosomes can have 1, 2, 3, 4, 5, between 5 and 10, between 10 and 20, or more than 20 copies of a sequence identified by the methods herein, or a variant thereof.

The invention further includes a recombinant nucleic acid molecule comprising an algal centromere sequence having at least 65%, at least 70%, at least 75%, at least 80%, at least 85%, at least 90%, or at least 95% identity, to at least 30, between 30 and 40, between 40 and 50, between 50 and 60, between 60 and 70, between 70 and 80, between 80 and 90, between 90 and 100, or at least 100 bp, between 100 and 125 bp, between about 125 bp and about 150 bp, between about 150 bp and about 200 bp, between about 200 bp and about 300 bp, between about 300 bp and about 400 bp, between about 400 bp and about 500 bp, between about 500 bp and about 1 Kb, between about 1 Kb and about 2 Kb, between about 2 Kb and about 3 Kb, between about 3 Kb and about 4 Kb, between about 4 Kb and about 5 Kb, between about 5 Kb and about 6 Kb, between about 6 Kb and about 7 Kb, between about 7 Kb and about 8 Kb, between about 8 Kb and about 9 Kb, between about 9 Kb and about 10 Kb, or greater than 10 Kb contiguous base pairs of any of SEQ ID NOs:21-167, or any of the sequences provided in Table 6, and artificial chromosomes that include an algal centromere sequence having at least 75% identity to at least 30 contiguous base pairs of any of SEQ ID NOs:21-167, or any of the sequences provided in Table 6. The artificial chromosome can include at least one selectable or nonselectable marker. In some embodiments, an artificial chromosome that includes a centromere sequence identified by the methods of the invention or a sequence derived therefrom includes at least one gene encoding a structural protein, a regulatory protein, an enzyme, a ribozyme, an antisense RNA, or an RNA that participates in gene silencing, such as but not limited to an shRNA, or an siRNA.

Also included in the invention are cells that comprise artificial chromosomes as disclosed herein. An artificial chromosome can be introduced into a cell by any feasible transformation method, or an artificial chromosome can be transmitted to a cell by means of sexual or asexual reproduction.

DETAILED DESCRIPTION OF THE INVENTION

Unless defined otherwise, all technical and scientific terms used herein have the same meaning as commonly understood by one of ordinary skill in the art to which this invention is related. The following terms are defined for purposes of the invention as described herein. The singular form "a", "an" and "the" include plural referents unless the context clearly dictates otherwise. Thus, for example, reference to "a cell" includes a plurality of cells and reference to "an antibody" includes a plurality of antibodies, etc.

As used herein, the terms "about" or "approximately" when referring to any numerical value are intended to mean a value of plus or minus 10% of the stated value. For example, "about 50 degree C." (or "approximately 50 degrees C.") encompasses a range of temperatures from 45 degree C. to 55 degree C., inclusive. Similarly, "about 100 mM" (or "approximately 100 mM") encompasses a range of concentrations from 90 mM to 110 mM, inclusive.

A "homolog" of a gene or protein refers to its functional equivalent in another species. A "variant" of a gene or protein sequence is a sequence having at least 65% identity with the referenced gene or protein sequence, and can include one or more base deletions, additions, or substitutions with respect to the referenced sequence.

The invention presented herein relates to methods of isolating and identifying centromeres. The term "centromere" is used herein to mean a nucleic acid sequence that confers the apportionment of a nucleic acid molecule that comprises the sequence to daughter cells during cell division. A centromere can be a naturally occurring sequence, a variant of a naturally-occurring sequence, or a fully synthetic sequence. A centromere may be derived from an organism other than the organism in which it promotes stable transmission of a nucleic acid molecule comprising the centromere sequence. A centromere as identified by the methods herein and used in compositions as disclosed herein, such as artificial chromosomes, can confer stable transmission of a nucleic acid molecule to between about 50 and about 100% of daughter cells, for example, to about 50%, about 55%, about 60%, about 65%, about 70%, about 75%, about 80%, about 90%, about 95% or greater than 95% of daughter cells. In particular embodiments of the invention, the centromere may confer stable segregation of a nucleic acid sequence, including a recombinant construct comprising the centromere, through mitotic or meiotic divisions, including through both meiotic and meitotic divisions.

The invention also relates to centromeres identified using the disclosed methods, and recombinant nucleic acid molecules that include centromere sequences and variants thereof. The invention includes artificial chromosomes that include centromeres. As used herein, an "artificial chromosome" is a recombinant linear or circular DNA molecule that is able to replicate in a cell and is stably inherited by the progeny of the cell. An artificial chromosomes typically includes: 1) an origin of replication, for initiation of DNA replication (which in some embodiments can be present within a centromere sequence (2) a centromere (which provides for the partitioning of the replicated chromosomes into daughter cells at mitosis or meiosis), and (3) if the chromosome is linear, telomeres (specialized DNA structures at the ends of linear chromosomes that function to stabilize the ends and facilitate the complete replication of the extreme termini of the DNA molecule). An artificial chromosome optionally includes one or more additional genes, regulatory elements, or chromatin organizing regions.

The invention includes methods of identifying a centromere sequence that include immunoprecipitating protein-DNA complexes from chromatin isolated from a cell using an antibody to a centromere-associated protein; isolating nucleic acid molecules from the immunoprecipitated protein-DNA complexes; and sequencing the isolated nucleic acid molecules to identify a centromere sequence. In some embodiments the nucleic acid molecules isolated from immunoprecipitated protein-DNA complexes are amplified prior to sequencing.

In preferred embodiments of these methods, the identification of a centromere sequence does not rely on the use of previously identified sequences. For example, in preferred embodiments, the methods of the invention do not include hybridization of nucleic acid molecules isolated from immunoprecipitated protein-DNA complexes (or nucleic acid molecules amplified therefrom) to confirmed or putative centromere sequences or clones, such as sequences having a repeated sequence motif, and do not include comparison of sequences obtained by sequencing of affinity-captured products to sequences previously identified as putative centromere sequences or centromere-proximal sequences.

In some aspects, one or more centromere sequences is identified by methods that include: immunoprecipitating protein-DNA complexes from chromatin isolated from a cell using an antibody to a centromere-associated protein; separately sequencing individual nucleic acid molecules of a population of nucleic acid molecules isolated from the protein-DNA complexes; calculating the frequency of occurrence of each nucleic acid sequence in the population of nucleic acid molecules isolated from the protein-DNA complexes; and identifying a nucleic acid molecule sequence which has an increased frequency of occurrence in the population as a centromere sequence.

In these aspects, a high frequency of occurrence of a sequence in a population of sequences isolated using chromatin precipitation with specific binding members that bind centromere-associated proteins is an indication of a high specificity of binding. In these methods, individual nucleic acid molecules (or amplified products thereof) are isolated from one another and sequenced separately, such that each independently obtained sequence correlates to a single molecule of a population of nucleic acid molecules isolated from immunoprecipitated protein-DNA complexes.

Separate sequencing of isolated individual nucleic molecules (or their amplification products) is preferably performed by a high-throughput parallel sequencing system that performs, for example, at least 10,000, at least 20,000, at least 50,000, at least 100,000, or at least 200,000 nucleic acid sequencing reactions simultaneously.

The methods of the invention in some preferred embodiments use chromatin isolated from one or more cells of an algal, fungal, or protist species, where a centromere sequence identified using the methods of the invention can be an algal, fungal, or protist centromere sequence. An algal species can be any algal species, including, without limitation, a species of green, yellow-green, brown, golden brown, or red algae, a diatom species or a dinoflagellate species. In some embodiments, a centromere sequence identified using the methods provided herein is a centromere sequence of an algae of the Chlorophyceae class, such as of the Dunaliellale, Volvocale, Chloroccale, Oedogoniale, Sphaerolpleale, Chaetophorale, Microsporale, or Tetrasporale order. For example, an algal cell can be a cell of an *Amphora, Ankistrodesmus, Asteromonas, Botryococcus, Chaetoceros, Chlamydomonas, Chlorococcum, Chlorella, Cricosphaera, Crypthecodinium, Cyclotella, Dunaliella, Emiliania, Euglena, Haematocoecus, Halocafeteria, Isochrysis, Monoraphidium, Nannochloris, Nannochloropsis, Navicula, Neochloris, Nitzschia, Ochromonas, Oedogonium, Oocystis, Ostreococcus, Pavlova, Phaeodactylum, Pleurochrysis, Pleurococcus, Pyramimonas, Scenedesmus, Skeletonema, Stichococcus, Tetraselmis, Thalassiosira* or *Volvox* species.

In some other embodiments, the cell used for isolation of chromatin is a fungal cell, for example, a cell of a chytrid, blastocladiomycete, neocallimastigomycete, zgomycete, trichomycete, glomeromycete, ascomycete, or basidiomycete.

In yet other embodiments, the methods of the invention are used to identify centromeres of protists, including members or the Labyrinthulomycota group (such as but not limited to thraustochytrids, water molds, slime molds (mxomycota), and protozoans (e.g., members of the rhizopoda, apicomplexa, and cilophora). In some embodiments, a *Schizochytrium* or *Thraustochytrium* species is used in the methods of the invention. Organisms from the orders Chlorophyta, Bacillariophyta, Prymnesiophyceae, Crysophyta, Prasinophyceae are contemplated for use in the invention.

In some embodiments, the methods are used to identify a centromere of a microorganism, such as a eukaryotic microalga, protist, or fungus. In these embodiments, a microorganism is collected or cultured prior to isolation of chromatin. The microorganism can be cultured on liquid, solid, or semi-solid media, such as, for example, agar plates. In some embodiments nucleii are isolated to provide a source of chromatin. For example, nucleii and/or chromatin can be isolated using osmotic shock or homogenization to isolate and/or can use enzymes that degrade the cell wall, coat, or membrane of an organism, and/or one or more detergents.

Chromatin isolation and chromatin immunoprecipitation can be performed under a variety of conditions (see, for example, U.S. Pat. No. 6,410,233; U.S. Pat. No. 6,410,243; Wang et al. The Plant J. 32: 831-843 (2002)), some of which are disclosed herein. Buffers, detergents, and fragmentation conditions, where used, can be altered to increase specificity and allow for high quality sequencing of nucleic acid molecules isolated from immunoprecipitated complexes.

In some embodiments, the methods disclosed herein do not include addition of a cross-linking agent prior to immunoprecipitating protein-DNA complexes from the fragmented chromatin.

In addition to immunoprecipitation, it is contemplated that affinity capture, in which one or more specific binding partners for one or more proteins that associates with the centromere, can be used for affinity capture of protein-DNA complexes that include centromere sequences. For example, one protein that participates in a centromere protein complex can be used as a specific binding member for capture of another member of the complex that directly binds the centromere. Immunoprecipitation or affinity capture can be performed in any format, and can include, for example, capture to a solid support, such as a matrix, bead, particle, fiber, membrane, filter, or chip.

Proteins useful for targets for immunoprecipitation or affinity capture of chromatin to isolate or identify centromere sequences include centromere-associated proteins, or proteins that directly or indirectly bind the centromere of a chromosome, and include, without limitation, centromere proteins (proteins that directly bind the centromere), centromere protein-recruiting proteins, and kinetochore proteins (Vos et al. Biochem. Cell Biol. 84: 619-639 (2006)). Centromere proteins include, without limitation, CENP-A/CenH3, CENP-B, CenH3, CENP-C, CENP-G, CENP-H, CENP-I, CENP-U (50), M is 12, PARP-1, and PARP-2, and homologs thereof. Centromere protein-recruiting proteins include, without limitation, RbAp46 and RbAp48 and homologs thereof. Kinetochore proteins include, without limitation, PMF1, DC8, c20orf172, Zwint-1, Zw10, Rod, Zwilch, Dynein, p150 (Glued), Ndc80/Hec1, Nuf2, Spc24, Spc25, KNL-3, KNL-1, Bub1, Bub3, BubR1, Mad1, Mad2, or homologs thereof. Immunoprecipitation or affinity capture can use antibodies or specific binding members that bind to more than one centromere-associated protein. In some embodiments, chromatin immunoprecipitation is performed with an antibody that specifically binds a centromere protein, such as for example, an antibody that specifically binds to CENP-A/CenH3 or a homolog of CENP-A/CenH3. In some embodiments, an antibody used for chromatin immunoprecipitation specifically binds to the N terminus of CENP-A/CenH3 or a homolog of CENP-A/CenH3.

In some embodiments, the chromatin is fragmented prior to sequencing of the nucleic acid molecules of the captured protein-DNA complexes. In some embodiments, the chromatin may be fragmented to some extent during the course of the chromatin isolation procedure, and no separate fragmentation step is performed. In embodiments that include a separate chromatin fragmentation step, the fragmentation can be performed prior to immunoprecipitation (or affinity capture), after immunoprecipitation (or affinity capture), or both. Chromatin can be fragmented by physical (mechanical) or chemical means, for example, by sonicating, shearing, or enzymatically digestion or chemical cleavage of DNA.

Following isolation of a population of nucleic acid molecules isolated by immunoprecipitation with an anti-centromere-associated protein antibody, the nucleic acid molecules are individually sequenced using any nucleic acid sequencing techniques that provide accurate sequences of a large number of individual nucleic acid molecules. For example, solid phase sequencing performed by a high throughput parallel sequencing system can be used to sequence at least 10,000, at least 20,000, at least 50,000, at least 100,000, or at least 200,000 or more, nucleic acid molecules in parallel.

In preferred embodiments of the methods provided herein, separate sequencing of individual nucleic molecules (or their amplification products) is performed using a high throughput parallel sequencing machine that isolates single nucleic acid molecules of a population of nucleic acid molecules prior to sequencing. Such machines or "Next Generation sequencing systems" include, without limitation, sequencing machines developed by Illumina and Solexa (the Genome Analyzer), sequencing machines developed by Applied Biosystems, Inc. (the SOLiD Sequencer), sequencing systems developed by Roche (e.g., the 454 GS FLX sequencer), and others.

To identify centromere sequences of the population of nucleic acid molecules isolated from protein-DNA complexes immunoprecipitated using antibodies to one or more centromere-associated proteins, sequences of a large number of the individual nucleic acid molecules of the population are determined (or as many as can be determined with high accuracy), for example, 10,000 or more, 20,000 or more, 50,000 or more, 100,000 or more, or 200,000 or more 500,000 or more, 1,000,000 or more, 2,000,000 or more, 5,000,000 or more or 10,000,000 or more. A baseline frequency of the occurrence of a non-centromere sequence in the immunoprecipitated population is determined by mapping the sequences onto the genome of the organism, if available, and computing the average sequence coverage in regions of the genome, excluding peaks of high coverage that may represent centromere sequences. Averaging of sequence coverage may be done across entire chromosomes excluding peaks of high coverage, or across specific chromosomal regions. Sequences occurring at greater than a selected frequency above background, such as above a frequency that is 2-fold, between 2 and 5-fold, 5-fold, between 5 and 10 fold, 10 fold, or more than 10 fold background frequency in the population of nucleic acid molecules isolated from immunoprecipitated protein-DNA complexes are identified as centromere sequences. For identification of sequences occurring at greater than a selected frequency above background, a further normalization step can be performed in which the frequency of sequences across the genomic locus corresponding to the obtained sequence frequency peak is normalized to reflect equal representation of repetitive and nonrepetitive sequence across the locus.

In some methods, identifying a high frequency occurrence sequence as a centromere sequence also includes identifying one or more regions of higher than average A+T content of the genome. In some methods, identifying a high frequency occurrence sequence as a centromere sequence also includes identifying one or more repeated sequences within the high frequency occurrence sequence. In some embodiments, a repeated sequence ("motif") found in one or more high frequency occurrence sequences is used in identifying further putative centromere sequences. In some cases, a repeated sequence is at least 10 base pairs in length, such as between about 10 base pairs and about 1 Kb, or between about 10 base pairs and about 500 base pairs, or between about 25 base pairs and about 350 base pairs, or between about 50 base pairs and about 250 base pairs. In some cases a repeated sequence motif identified within a high frequency occurrence sequence is less than 10 bp, such as a dinucleotide repeat, a trinucleotide repeat, a tetranucleotide repeat, a pentanucleotide repeat, a sextanucleotide repeat, a heptanucleotide repeat, an octonucleotide repeat, or a nonanucleotide repeat. In some instances a repeated sequence motif identified within a high frequency occurrence sequence is a dinucleotide repeat or a trinucleotide repeat.

A repeated sequence of greater than 10 base pairs, such as, for example a repeated motif of between about 10 and about 500 base pairs, can be present in 2, 3, 4, 5, 6, 7, 8, 9, 10, 11, 12, 13, 14, 15, 16, 17, 18, 19, 20, between 20 and 30, between 30 and 40, between 40 and 50, between 50 and 60, between 60 and 70, between 70 and 80, between 80 and 90, between 90 and 100, between 100 and 125, between 125 and 150, between 150 and 200, between 250 and 300, between 300 and 350, between 350 and 400, between 400 and 450, between 450 and 500, between 500 and 1000 copies at a locus identified using the present methods.

A repeated sequence of less than 10 base pairs, such as, for example, a repeat of dinucleotide or trinucleotide repeat, is in some cases found in repeats of 2, 3, 4, 5, 6, 7, 8, 9, 10, 11, 12, 13, 14, 15, 16, 17, 18, 19, 20, between 20 and 30, between 30 and 40, between 40 and 50, between 50 and 60, between 60 and 70, between 70 and 80, between 80 and 90, between 90 and 100, between 100 and 125, between 125 and 150, between 150 and 200, between 250 and 300, between 300 and 350, between 350 and 400, between 400 and 450, between 450 and 500, between 500 and 1000 copies at a locus identified using the present methods.

The cutoff frequency level above which a sequence is identified as a centromere can take into account the expected number of centromeres in the organism used for chromatin isolation. Selection of a cutoff frequency level above which a sequence is identified as a centromere in some embodiments takes into account the percentage of A+T in sequences that are above or below a proposed cutoff level. Selection of a cutoff value can in some embodiments take into account the presence or absence of repeated sequence motifs within individual nucleic acid molecule sequences above a frequency value, such as the presence or absence of repeated dinucleotide or trinucleotide sequence motifs, or the presence or absence of satellite sequences within individual nucleic acid molecule sequences above a frequency value.

In some preferred embodiments, the methods provided herein do not include hybridizing a nucleic acid molecule isolated from the immunoprecipitated protein-DNA complexes to one or more known centromere sequences or centromere-linked sequences. In some preferred embodiments, the methods do not include hybridizing a nucleic acid molecule isolated from the immunoprecipitated protein-DNA complexes to one or more repetitive sequences previously known in the organism from which the chromatin is isolated.

In some embodiments, the method includes amplifying the nucleic acid molecules isolated from the immunoprecipitated protein-DNA complexes prior to sequencing the isolated nucleic acid molecules. In some preferred embodiments, individual nucleic acid molecules isolated from the immunoprecipitated protein-DNA complexes are amplified separately prior to sequencing the nucleic acid molecules. In some preferred embodiments, individual nucleic acid molecules of a population of nucleic acid molecules isolated from immunoprecipitated protein-DNA complexes are sequenced separately using a machine that performs high-throughput parallel sequencing.

In some preferred embodiments, a high-throughput parallel sequencing system isolates single nucleic acid molecules from a population of nucleic acid molecules prior to amplification, performs amplification reactions on the isolated individual nucleic acid molecules to generate isolated amplification products of the individual nucleic acid molecules of the population, and performs parallel sequencing reactions on the isolated amplification products of the individual nucleic acid molecules of the population to provide sequences of the individual molecules of the population.

In some embodiments, the methods further include performing one or more assays to evaluate the centromere sequence. For example, an assay can be performed for nonintegration into chromosomes and for stable heritability of a nucleic acid construct introduced into a cell, that is, for a nucleic acid construct that includes the sequence to behave as an artificial chromosome.

An artificial chromosome vector of the present invention minimally includes a centromere for conferring stable heritability of the artificial chromosome and an origin of replication or "autonomous replication sequence" (ARS) allowing for continuing synthesis of the artificial chromosome, which in some cases may be included in the centromere sequences. An artificial chromosome may optionally also contain any of a variety of elements, including one or more exogenous nucleic acids, including, for example, genes that can be expressed in the host organism (including but not limited to marker genes); a bacterial or yeast plasmid backbone for propagation of the plasmid in bacteria; sequences that function as telomeres in the host organism, where the artificial chromosome is not configured as a circular molecule, cloning sites; such as restriction enzyme recognition sites or sequences that serve as recombination sites; and "chromatin packaging sequences" such as cohesion and condensing binding sites or matrix attachment regions (MARs). Other sequences may be used to intervene between genes or other genetic elements on the artificial chromosome.

An assay for centromere function in some embodiments detects the presence of a selectable or nonselectable marker on an artificial chromosome comprising the centromere sequence, or detects the presence of the centromere sequence or a nucleic acid sequence linked thereto on an artificial chromosome.

For example, a nucleic acid molecule construct that includes a sequence as identified by the invention or a variant thereof can be introduced into cells using any feasible method, including, without limitation, microparticle bombardment, electroporation, calcium phosphate precipitation of DNA, liposome-mediated transfection, the use of lipid-based transfection agents (such as but not limited to, cationic lipid transfection agents) (e.g., U.S. Pat. No. 7,479, 573; U.S. Pat. No. 7,145,039), the use of glass beads or metal "whiskers" with or without agitation, etc., and the cells or nucleic acids isolated from the cells can be examined to determine whether the nucleic acid molecule construct is an autonomous DNA molecule, or whether it is integrated into the chromosomes of the cells. The host cells can be of any species, for example, algal cells, fungal cells, cells or protists, or cells of plants, such as but not limited to higher plants. Typically the host cells will be of the same species or class of organism from which the centromere species is derived, although this is not a requirement of the invention. For example, in some embodiments identified sequences can be tested for their ability to function as centromeres in species other than the species from which the sequence was derived.

Methods used for functional analysis of centromeres include, but are not limited to the following techniques: 1) Detection of marker protein expression by microscopy, flow cytometry, fluorimetry, enzymatic assays, cell staining or any other technique that allows the detection of a marker protein having a specific enzymatic activity, or conferring a specific color or fluorescence or emission property, or other observable property, onto the cells. For example, if a cell line has been selected for containing an artificial chromosome by selecting for the function of a resistance gene encoded by the artificial chromosome, and if a marker protein is also encoded by the artificial chromosome, then expression of this marker protein in the selected cells is an indication of the presence of the entire artificial chromosome, and could indicate autonomy of this artificial chromosome from the cell's other chromosomes. 2) Use of gel electrophoresis to detect an artificial chromosome in genomic DNA isolated from the plant cells, tissue or entire plants. For example, genomic DNA isolated from the cells, tissues or organisms can be fractionated by gel electrophoresis, either intact or following digestion with restriction endonucleases or homing endonucleases, allowing the detection of an artificial chromosome or a fragment of an artificial chromosome. 3) Use of southern blots or dot blots of DNA extracted from the cells, tissue or organisms to detect the presence of specific sequences contained on the artificial chromosome. For example, digestion of genomic DNA extracted from the cells, tissues or organisms can be fractionated by agarose gel electrophoresis, blotted onto a DNA-binding membrane, and probed with labeled DNA sequences corresponding to sequences present on the artificial chromosome to detect specific fragments of artificial chromosome DNA, and thus allowing the determination of the autonomous, or integrated structure of the artificial chromosome. 4) Cytological techniques for directly visualizing the artificial chromosome in the transformed cells, such as staining of cells with DNA-binding dyes or in situ hybridization with labeled DNA probes corresponding to sequences present on the artificial chromosome. 5) Genetic analysis of marker segregation by scoring marker inheritance in progeny of a sexually-reproducing organism containing an artificial chromosome. For example, markers present on an autonomous artificial chromosome will segregate independently from markers on the arms of the host chromosomes in a population of F2 progeny generated from a cross between a line carrying an artificial chromosome and a second marked line that doesn't carry the artificial chromosome. 6) Introduction of DNA extracted from the cells and its introduction into *E. coli*, yeast (*Saccharomyces cerevisiae*) or any other suitable cloning organism, and observation of colony formation of that organism under antibiotic selection or auxotrophic selection corresponding to a selectable marker gene present on the artificial chromosome, as an indication of transformation with a DNA molecule that is present in an autonomous state in the cell from which the DNA was extracted. For example, if the artificial chromosome contains an antibiotic resistance marker for *E. coli* and an *E. coli* origin of replication, then DNA extracts from a cell in which the artificial chromosome is present in an autonomous state will be expected to form antibiotic-resistant colonies when transformed into *E. coli*, and the structure and sequence of the resulting plasmid in *E. coli* will partially or completely resemble the structure and sequence of the artificial chromosome, whereas DNA extracted from a cell with an integrated copy of the same DNA will not give rise to such colonies, and/or the structure and sequence of any colonies that should arise would provide clear indication of the DNA having been in an integrated state in that cell. 7) Analysis of the genome of a transformed organism by sequencing and bioinformatic assembly of the sequences, or by molecular or physical mapping methods such as optical mapping that give information about the physical structure and/or number of the different DNA molecules (i.e. chromosomes) present in the genome of that organism. For example, an optical map of an organism transformed with an autonomous artificial chromosome would be expected to result in a physical map of that organism's genome showing an extra chromosome, unlinked to the other chromosomes, compared to the untransformed organism or compared to an organism with an integrated copy of the same DNA.

Markers that can be used in the nucleic acid constructs include but are not limited to: visible markers conferring a visible characteristic to the plant; selectable markers, conferring resistance to an antibiotic, herbicide, or other toxic compound; enzymatic markers, conferring an enzymatic activity that can be assays in the plant or in extracts made from the plant; protein markers, allowing the specific detection of a protein expressed in the plant; molecular markers, such as restriction fragment length polymorphisms, amplified fragment length polymorphisms, short sequence repeat (microsatellite) markers, presence of certain sequences in the DNA of the plant as detected by the polymerase chain reaction, single nucleotide polymorphisms or cleavable amplified polymorphic sites.

The inheritance of artificial chromosomes can also be measured through one or more cell divisions. After isolating cells that contain the artificial chromosome (for example, by selection for the presence of a marker present on the nucleic acid construct that includes the centromere sequence), the population of cells is allowed to grow (either with or without selection), and the presence of the artificial chromosome is monitored as the cells divide. Artificial chromosomes can be detected in cells by a variety of methods, including but not limited to: detection of fluorescence or any other visual characteristic arising from a marker protein gene present on the artificial chromosome; resistance to an antibiotic, herbicide, toxic metal, salt, mineral or other substance, or abiotic stress as outlined above (isolating cells containing artificial chromosomes); staining of cells with DNA-binding molecules to allow detection of an additional chromosome; in situ hybridization with labeled DNA probes corresponding to sequences present on the artificial chromosome; southern blots or dot blots of DNA extracted from the cell population and probed with labeled DNA sequences corresponding to sequences present on the artificial chromosome; expression of a marker enzyme encoded by a gene present on the artificial chromosome (e.g., luciferase, alkaline phosphatase, beta-galactosidase, etc.) that can be assayed in the cells or in an extract made from the cells, and observation or measurement of the cells to find indications of the expression of any gene that confers an observable or measurable phenotype onto the cell.

The percentage of cells containing the chromosome is determined at regular intervals during this growth phase. The change in the fraction of cells harboring the artificial chromosome, divided by the number of cell divisions, represents the average artificial chromosome loss rate. Artificial chromosomes with the lowest loss rates have the highest level of inheritance.

The presence of a functional centromere on an artificial chromosome can be detected by a variety of methods relating to the presence of proteins normally found associated with centromeres. Examples of such proteins include but are not limited to CenH3, CenpA, CenpB and other proteins normally found associated with the centromere or kinetochore. Methods for detecting such proteins to demonstrate centromere function include but are not limited to immunocytochemistry, chromatin immonoprecipitation (ChIP) followed by selective hybridization, PCR or sequencing to demonstrate enriched presence of particular sequences, fluorescence activated chromosome sorting or other methods of fractionating a cell's genome followed by immunocytochemistry or chromatin immonoprecipitation (ChIP).

Recovery of artificial chromosomes from cells can be achieved by any of a variety of techniques, including, but not limited to, the following: 1) Extracting the genomic DNA of transformed cells and introducing that DNA into *E. coli*, other bacteria or yeast and selecting for the antibiotic resistance genes present on the artificial chromosome. 2) Isolation of chromosomes from cells, tissues or organisms containing artificial chromosomes, and sorting these by flow cytometry to allow the separation of chromosomes of different size; 3) Isolation of individual chromosomes from a cell harboring artificial chromosomes by micro-manipulation involving mechanical devices such as needles made of glass, metal or other suitable substances, or other techniques such as optical tweezers, or micro-suction devices. 4) Combinations of the above, for example chromosome isolation by flow cytometry or micromanipulation followed by introduction into *E. coli*, other bacteria, yeast, algal, or plant cells.

The resulting artificial chromosomes recovered after being passaged through host cells in this way may differ from their parental molecules in total size, size of the centromere, presence or absence of additional sequences, and overall arrangement of the sequences. These procedures allow the isolation of DNA molecules capable of replicating and segregating in cells of an organism of interest, such as an alga, fungus, or protist, without having to test artificial chromosomes individually. For example, after delivery of pools of artificial chromosomes, or pools of centromere clones into algal cells and recovering them by the methods listed above, facilitates the selection of specific artificial chromosomes or centromere clones that remain autonomous in algal cells. In some embodiments, pools of centromere clones can be delivered into cells of an organism followed by recovery of the ones that successfully replicate and persist, such that the recovered clones can guide the design of optimal artificial chromosome constructs.

The invention includes recombinant nucleic acid molecules comprising centromere sequences identified by the methods of the invention, in which the centromere sequence is no longer adjacent to one or more sequences positioned adjacent to the centromere sequence in the genome from which the centromere sequence is derived. In some embodiments, a centromere sequence identified using the methods provided herein is a centromere sequence derived from an alga, such as of an alga of the Chlorophyceae class, such as a centromere sequence of an algal of the Dunaliellale, Volvocale, Chloroccale, Oedogoniale, Sphaerolpleale, Chaetophorale, Microsporale, or Tetrasporale order. For example, an algal cell can be a cell of an *Amphora, Ankistrodesmus, Asteromonas, Botryococcus, Chaetoceros, Chlamydomonas, Chlorococcum, Chlorella, Cricosphaera, Crypthecodinium, Cyclotella, Dunaliella, Emiliania, Euglena, Haematococcus, Halocafeteria, Isochrysis, Monoraphidium, Nannochloris, Nannochloropsis, Navicula, Neochloris, Nitzschia, Ochromonas, Oedogonium, Oocystis, Ostreococcus, Pavlova, Phaeodactylum, Pleurochrysis, Pleurococcus, Pyramimonas, Scenedesmus, Skeletonema, Stichococcus, Tetraselmis, Thalassiosira* or *Volvox* species.

In some embodiments, a recombinant nucleic acid molecule comprises a centromere sequence derived from a fungal or protist cell.

The nucleic acid molecules that comprise centromere sequences in some embodiments comprise one or more copies of a repeated sequence of greater than 10 base pairs, such as, for example a repeated motif of between about 10 and about 500 base pairs, can be present in 2, 3, 4, 5, 6, 7, 8, 9, 10, 11, 12, 13, 14, 15, 16, 17, 18, 19, 20, between 20 and 30, between 30 and 40, between 40 and 50, between 50 and 60, between 60 and 70, between 70 and 80, between 80 and 90, between 90 and 100, between 100 and 125, between 125 and 150, between 150 and 200, between 250 and 300, between 300 and 350, between 350 and 400, between 400 and 450, between 450 and 500, between 500 and 1000 copies at a locus identified using the present methods.

In some embodiments, a repeated motif is the 184 base pair sequence of Table 7, for example, SEQ ID NO:168, SEQ ID NO:169, or SEQ ID NO:170, as disclosed in Example 10. The invention includes an algal centromere sequence that comprises two or more copies of the sequence of SEQ ID NO:168, SEQ ID NO:169, or SEQ ID NO:170, as well as algal centromeres having two or more copies of sequences having at least 65%, at least 70%, at least 75%, at least 80%, at least 85%, at least 90%, or at least 95% identity to SEQ ID NO:168. The invention includes an artificial chromosome that comprises an algal centromere sequence that comprises two or more copies of the sequence of SEQ ID NO:168, as well as algal artificial chromosomes having two or more copies of sequences having at least 65%, at least 70%, at least 75%, at least 80%, at least 85%, at least 90%, or at least 95% identity to SEQ ID NO:168. In certain preferred embodiments the artificial chromosome is a *Chlamydomonas* artificial chromosome. The invention further includes an algal cell, such as a *Chlamydomonas* cell, that includes an artificial chromosome having a centromere that comprises two or more copies of sequences having at least 65%, at least 70%, at least 75%, at least 80%, at least 85%, at least 90%, or at least 95% identity to SEQ ID NO:168.

In some embodiments, a repeated motif is the 111 or 112 base pair sequence of Table 8, for example SEQ ID NO:171, SEQ ID NO:172, SEQ ID NO:173, SEQ ID NO:174, SEQ ID NO:175, or SEQ ID NO:176, as disclosed in Example 10. The invention includes an algal centromere sequence that comprises two or more copies of the sequence of SEQ ID NO:171, SEQ ID NO:172, SEQ ID NO:173, SEQ ID NO:174, SEQ ID NO:175, or SEQ ID NO:176, as well as algal centromeres having two or more copies of sequences having at least 65%, at least 70%, at least 75%, at least 80%, at least 85%, at least 90%, or at least 95% identity to SEQ ID NO:171, SEQ ID NO:172, SEQ ID NO:173, SEQ ID NO:174, SEQ ID NO:175, or SEQ ID NO:176. The invention includes an artificial chromosome that comprises an algal centromere sequence that comprises two or more copies of the sequence of SEQ ID NO:171, SEQ ID NO:172, SEQ ID NO:173, SEQ ID NO:174, SEQ ID NO:175, or SEQ ID NO:176, as well as algal artificial chromosomes having two or more copies of sequences having at least 65%, at least 70%, at least 75%, at least 80%, at least 85%, at least 90%, or at least 95% identity to SEQ ID NO:171, SEQ ID NO:172, SEQ ID NO:173, SEQ ID NO:174, SEQ ID NO:175, or SEQ ID NO:176. In some embodiments the artificial chromosome is a *Chlamydomonas* artificial chromosome. The invention further includes an algal cell, such as a *Chlamydomonas* cell that includes an artificial chromosome having a centromere that comprises two or more copies of sequences having at least 65%, at least 70%, at least 75%, at least 80%, at least 85%, at least 90%, or at least 95% identity to SEQ ID NO:171, SEQ ID NO:172, SEQ ID NO:173, SEQ ID NO:174, SEQ ID NO:175, or SEQ ID NO:176.

Short repeated sequences of less than ten base pairs are also identified at genomic loci using the present methods for identifying centromeres. A short repeated sequence can be, for example, a repeat of dinucleotide or trinucleotide repeat, and is in some cases found in repeats of 2, 3, 4, 5, 6, 7, 8, 9, 10, 11, 12, 13, 14, 15, 16, 17, 18, 19, 20, between 20 and 30, between 30 and 40, between 40 and 50, between 50 and 60, between 60 and 70, between 70 and 80, between 80 and 90, between 90 and 100, between 100 and 125, between 125 and 150, between 150 and 200, between 250 and 300, between 300 and 350, between 350 and 400, between 400 and 450, between 450 and 500, between 500 and 1000 copies at a locus identified using the present methods.

In some embodiments, a repeated motif is the dinucleotide sequence GA, AT, CT, CA, GT (or, reading from the opposite strand, TC, TA, AG, TG. AC), as disclosed in Example 10. The invention includes an algal centromere sequence that comprises two or more copies of any of the dinucleotide sequences of Table 9, between two and ten copies of a dinucleotide sequence of Table 9, or ten or more copies of any of the dinucleotide sequences of Table 9. The invention includes an artificial chromosome having an algal centromere that comprises two or more copies of any of the dinucleotide sequences of Table 9, between two and ten copies of a dinucleotide sequence of Table 9, or ten or more copies of any of the dinucleotide sequences of Table 9. In some embodiments the artificial chromosome is a *Chlamydomonas* artificial chromosome. The invention further includes an algal cell, such as a *Chlamydomonas* cell, that includes an artificial chromosome having a centromere that comprises two or more copies, for example between two and ten copies, or ten or more tandemly repeated copies, of any of the dinucleotide sequences of Table 9.

In some embodiments, a repeated motif is the tandemly repeated trinucleotide sequence AAT, TAT, TAA, CAA, CCA, GCT, AGG, or CGT (or, reading from the opposite strand, ATT. ATA, TTA, TTG, TGG, AGC, CCT, or CAG), as disclosed in Example 10. The invention includes an algal centromere sequence that comprises two or more copies of any of the trinucleotide sequences of Table 9, between two and ten copies of a trinucleotide sequence of Table 9, or ten or more copies of any of the trinucleotide sequences of Table 9. The invention includes an artificial chromosome having an algal centromere that comprises two or more repeats of any of the trinucleotide sequences of Table 9, between two and ten repeats or a trinucleotide sequence of Table 9, or ten or more repeats of any of the trinucleotide sequences of Table 9. In some embodiments the artificial chromosome is a *Chlamydomonas* artificial chromosome. The invention further includes a *Chlamydomonas* cell that includes an artificial chromosome having a centromere that comprises two or more copies, between two and ten copies, or ten or more tandemly repeated copies of any of the trinucleotide sequences of Table 9.

In some embodiments, the invention includes recombinant nucleic acid molecules comprising a centromere sequence identified by the methods of the invention, in which the centromere sequence not adjacent to one or more sequences that is positioned next to the centromere sequence in the genome from which the centromere sequence is derived. The invention includes recombinant nucleic acid molecules comprising a centromere sequence identified using the methods of the invention, in which the centromere sequence is adjacent to one or more sequences not positioned adjacent to the centromere sequence in the genome from which the centromere sequence is derived. A recombinant nucleic acid molecule that includes a centromere sequence can include sequences adjacent to the identified centromere sequence that are derived from the same organism or species from which the centromere sequence is derived (but are not adjacent to the centromere sequences in the naturally-occurring genome), can be adjacent to sequences derived from another organism or species, or can include synthetic sequences that are adjacent to the centromere sequence.

Also included in the invention are recombinant nucleic acid molecules that comprise a sequence having at least 65%, at least 70%, at least 75%, at least 80%, at least 85%, at least 90%, or at least 95% identity to at least 30, between 30 and 40, between 40 and 50, between 50 and 60, between 60 and 70, between 70 and 80, between 80 and 90, between 90 and 100, or at least 100 bp, between 100 and 125 bp, between about 125 bp and about 150 bp, between about 150 bp and about 200 bp, between about 200 bp and about 300 bp, between about 300 bp and about 400 bp, between about 400 bp and about 500 bp, between about 500 bp and about 1 Kb, between about 1 Kb and about 2 Kb, between about 2 Kb and about 3 Kb, between about 3 Kb and about 4 Kb, between about 4 Kb and about 5 Kb, between about 5 Kb and about 6 Kb, between about 6 Kb and about 7 Kb, between about 7 Kb and about 8 Kb, between about 8 Kb and about 9 Kb, between about 9 Kb and about 10 Kb, or greater than 10 Kb of a centromere sequence identified by the methods disclosed herein, in which the nucleic acid sequence functions as a centromere.

Exemplary embodiments of centromere nucleic acid sequences according to the present invention include any of SEQ ID NOs 21-167 (sequences of Table 6), variants, fragments, or variants of fragments of any of SEQ ID Nos 21-167 (sequences of Table 6), such as fragments or variants of SEQ ID NOs 21-167 that retain the ability to segregate during mitotic or meiotic division as described herein. Variants of such sequences include artificially produced modifications as described herein and modifications produced via passaging through one or more bacterial, plant or other host cells as described herein. In certain embodiments, a variant sequence has at least at least 65%, at least 70%, at least 75%, at least 80%, at least 85%, at least 90%, or at least 95% identity to at least 30, between 30 and 40, between 40 and 50, between 50 and 60, between 60 and 70, between 70 and 80, between 80 and 90, between 90 and 100, or at least 100 bp, between 100 and 125 bp, between about 125 bp and about 150 bp, between about 150 bp and about 200 bp, between about 200 bp and about 300 bp, between about 300 bp and about 400 bp, between about 400 bp and about 500 bp, between about 500 bp and about 1 Kb, between about 1 Kb and about 2 Kb, between about 2 Kb and about 3 Kb, between about 3 Kb and about 4 Kb, between about 4 Kb and about 5 Kb, between about 5 Kb and about 6 Kb, between about 6 Kb and about 7 Kb, between about 7 Kb and about 8 Kb, between about 8 Kb and about 9 Kb, between about 9 Kb and about 10 Kb, or greater than 10 Kb of any of SEQ ID NO:21-SEQ ID NO:167 (the sequences listed in Table 6)

A centromere in a recombinant nucleic acid molecule or artificial chromosome of the present invention may comprise novel repeating centromeric sequences.

Nucleic acid constructs, including artificial chromosome constructs, can comprise one, two, three, four, five, six, seven, eight, nine, ten, 15 or 20 or more of the elements contained in any of the exemplary vectors described in the examples below are also contemplated.

The invention specifically contemplates the alternative use of fragments or variants (mutants) of any of the nucleic acids described herein that retain the desired activity, including nucleic acids that function as centromeres, nucleic acids that function as promoters or other regulatory control sequences, or exogenous nucleic acids. Variants may have one or more additions, substitutions or deletions of nucleotides within the original nucleotide sequence or consensus sequence. Variants include nucleic acid sequences that are at least 50%, 55%, 60, 65, 70, 75, 80, 81, 82, 83, 84, 85, 86, 87, 88, 89, 90, 91, 92, 93, 94, 95, 96, 97, 98, 99, or 100% identical to the original nucleic acid sequence.

Genes used in constructs of the invention, such as artificial chromosome constructs, may be modified to accommodate the codon usage of the intended host organism, to insert preferred motifs near the translation initiation ATG codon, to remove sequences recognized by the host organism as 5' or 3' splice sites, or to better reflect the GC/AT content of the host organism. The nucleotide sequence of genes can be altered to reflect the codon bias or GC content of the intended host organism.

Genes used in constructs of the invention, such as artificial chromosome constructs, may include a promoter, a coding region and a terminator sequence, which may be separated from each other by restriction endonuclease sites or recombination sites or both. Genes may also include introns, which may be present in any number and at any position within the transcribed portion of the gene, including the 5' untranslated sequence, the coding region and the 3' untranslated sequence. Introns may be natural introns derived from any species, or artificial introns based on the splice site consensus that has been defined for the host species or a related species. Optionally the exogenous nucleic acid may include at transcriptional terminator, non-translated leader sequences that enhance expression, a minimal promoter, or a signal sequence controlling the targeting of gene products to plant compartments or organelles such as but not limited to the chloroplast of an algal host cell.

The coding regions of the genes can encode any protein, including but not limited to visible marker genes (for example, fluorescent protein genes, other genes conferring a visible phenotype to the plant) or other screenable or selectable marker genes (for example, conferring resistance to antibiotics, herbicides or other toxic compounds or encoding a protein that confers a growth advantage to the cell expressing the protein) or genes which confer some commercial or environmental remediation value to the organism. Multiple genes can be placed on the same mini-chromosome vector, limited only by the number of restriction endonuclease sites or site-specific recombination sites present in the vector. The genes may be separated from each other by restriction endonuclease sites, homing endonuclease sites, recombination sites or any combinations thereof. Any number of genes can be present, for example, 1, 2, 3, 4, 5, 6, 7, 8, 9, 10, or more than 10 genes may be present on an artificial chromosome.

The artificial chromosome vector may also contain a bacterial plasmid backbone for propagation of the plasmid in bacteria such as *E. coli*. The plasmid backbone may be that of a low-copy vector or in other embodiments it may be desirable to use a mid to high level copy backbone. In one embodiment of the invention, this backbone contains the replicon of the F' plasmid of *E. coli*. However, other plasmid replicons, such as the bacteriophage P1 replicon, or other low-copy plasmid systems such as the RK2 replication origin, may also be used. The backbone may include one or several antibiotic-resistance genes conferring resistance to a specific antibiotic to the bacterial cell in which the plasmid is present. Bacterial antibiotic-resistance genes include but are not limited to kanamycin-, ampicillin-, chloramphenicol-, streptomycin-, spectinomycin-, tetracycline- and gentamycin-resistance genes.

The artificial chromosome vector may optionally also contain telomeres. Telomeres are specialized DNA structures at the ends of linear chromosomes that function to stabilize the ends and facilitate the complete replication of the extreme termini of the DNA molecule. An exemplary telomere sequence identified in the green unicellular alga *Chlamydomonas reinhardtii* is TTTTAGGG or its complement (Petracek et al. Proceedings of the National Academy of Sciences 87: 8222-8226 (1990)).

Additionally the artificial chromosome vector may contain "stuffer DNA" sequences that serve to separate the various components on the artificial chromosome (centromere, genes, telomeres) from each other. The stuffer DNA may be of any origin, prokaryotic or eukaryotic, and from any genome or species, plant, animal microbe or organelle or may be of synthetic origin. The stuffer DNA can range from 100 bp to 10 Mb in length and can be repetitive in sequence, with unit repeats from 10 to 1,000,000 bp. Examples of repetitive sequences that can be used as stuffer DNAs include but are not limited to: rDNA, satellite repeats, retroelements, transposons, pseudogenes, transcribed genes, microsatellites, tDNA genes, short sequence repeats and combinations thereof. Alternatively, the stuffer DNA can consist of unique, non-repetitive DNA of any origin or sequence. The stuffer sequences may also include DNA with the ability to form boundary domains, such as but not limited to scaffold attachment regions (SARs) or matrix attachment regions (MARs). The stuffer DNA may be entirely synthetic, composed of random sequence. In this case, the stuffer DNA may have any base composition, or any A/T or G/C content. For example, the G/C content of the stuffer DNA could resemble that of the organism or could be much lower or much higher.

Alternatively, the stuffer sequences could be synthesized to contain an excess of any given nucleotide such as A, C, G or T. Different synthetic stuffers of different compositions may also be combined with each other. For example a fragment with low G/C content may be flanked or abutted by a fragment of medium or high G/C content, or vice versa. In one embodiment of the invention, the artificial chromosome has a circular structure without telomeres. In another embodiment, the artificial chromosome has a circular structure with telomeres. In a third embodiment, the artificial chromosome has a linear structure with telomeres, as would result if a "linear" structure were to be cut with a unique endonuclease, exposing the telomeres at the ends of a DNA molecule that contains all of the sequence contained in the original, closed construct with the exception of the an antibiotic-resistance gene. In a fourth embodiment of the invention, the telomeres could be placed in such a manner that the bacterial replicon, backbone sequences, antibiotic-resistance genes and any other sequences of bacterial origin and present for the purposes of propagation of the artificial chromosome in bacteria, can be removed from the plant-expressed genes, the centromere, telomeres, and other sequences by cutting the structure with an unique endonuclease. This results in an artificial chromosome from which much of, or preferably all, bacterial sequences have been removed. In this embodiment, bacterial sequence present between or among the plant-expressed genes or other artificial chromosome sequences would be excised prior to removal of the remaining bacterial sequences by cutting the artificial chromosome with a homing endonuclease and re-ligating the structure such that the antibiotic-resistance gene has been lost. The unique endonuclease site may be the recognition sequence of a homing endonuclease. Alternatively, the endonucleases and their sites can be replaced with any specific DNA cutting mechanism and its specific recognition site such as rare-cutting endonuclease or recombinase and its specific recognition site, as long as that site is present in the artificial chromosomes only at the indicated positions.

Various structural configurations are possible by which mini-chromosome elements can be oriented with respect to each other. A centromere can be placed on an artificial chromosome either between genes or outside a cluster of genes next to one telomere or next to the other telomere. Stuffer DNAs can be combined with these configurations to place the stuffer sequences inside the telomeres, around the centromere between genes or any combination thereof. Thus, a large number of alternative artificial chromosome structures are possible, depending on the relative placement of centromere DNA, genes, stuffer DNAs, bacterial (or yeast) sequences, telomeres, and other sequences. The sequence content of each of these variants is the same, but their structure may be different depending on how the sequences are placed. These variations in architecture are possible both for linear and for circular mini-chromosomes.

Artificial chromosomes that comprise a centromere identified by the methods of the invention, or a sequence having at least at least 65%, at least 70%, at least 75%, at least 80%, at least 85%, at least 90%, or at least 95% identity to at least 30, between 30 and 40, between 40 and 50, between 50 and 60, between 60 and 70, between 70 and 80, between 80 and 90, between 90 and 100, or at least 100 bp, between 100 and 125 bp, between about 125 bp and about 150 bp, between about 150 bp and about 200 bp, between about 200 bp and about 300 bp, between about 300 bp and about 400 bp, between about 400 bp and about 500 bp, between about 500 bp and about 1 Kb, between about 1 Kb and about 2 Kb, between about 2 Kb and about 3 Kb, between about 3 Kb and about 4 Kb, between about 4 Kb and about 5 Kb, between about 5 Kb and about 6 Kb, between about 6 Kb and about 7 Kb, between about 7 Kb and about 8 Kb, between about 8 Kb and about 9 Kb, between about 9 Kb and about 10 Kb, or greater than 10 Kb of a centromere sequence identified by the methods disclosed herein, in which the nucleic acid sequence functions as a centromere, are also provided herein.

The invention further includes a recombinant nucleic acid molecule comprising an algal centromere sequence having at least at least 65%, at least 70%, at least 75%, at least 80%, at least 85%, at least 90%, or at least 95% identity to at least 30, between 30 and 40, between 40 and 50, between 50 and 60, between 60 and 70, between 70 and 80, between 80 and 90, between 90 and 100, or at least 100 bp, between 100 and 125 bp, between about 125 bp and about 150 bp, between about 150 bp and about 200 bp, between about 200 bp and about 300 bp, between about 300 bp and about 400 bp, between about 400 bp and about 500 bp, between about 500 bp and about 1 Kb, between about 1 Kb and about 2 Kb, between about 2 Kb and about 3 Kb, between about 3 Kb and about 4 Kb, between about 4 Kb and about 5 Kb, between about 5 Kb and about 6 Kb, between about 6 Kb and about 7 Kb, between about 7 Kb and about 8 Kb, between about 8 Kb and about 9 Kb, between about 9 Kb and about 10 Kb, or greater than 10 Kb of any of SEQ ID NO:21-167 (the sequences listed in Table 6), and artificial chromosomes that include an algal centromere sequence having at least at least 65%, at least 70%, at least 75%, at least 80%, at least 85%, at least 90%, or at least 95% identity to at least 30, between 30 and 40, between 40 and 50, between 50 and 60, between 60 and 70, between 70 and 80, between 80 and 90, between 90 and 100, or at least 100 bp, between 100 and 125 bp, between about 125 bp and about 150 bp, between about 150 bp and about 200 bp, between about 200 bp and about 300 bp, between about 300 bp and about 400 bp, between about 400 bp and about 500 bp, between about 500 bp and about 1 Kb, between about 1 Kb and about 2 Kb, between about 2 Kb and about 3 Kb, between about 3 Kb and about 4 Kb, between about 4 Kb and about 5 Kb, between about 5 Kb and about 6 Kb, between about 6 Kb and about 7 Kb, between about 7 Kb and about 8 Kb, between about 8 Kb and about 9 Kb, between about 9 Kb and about 10 Kb, or greater than 10 Kb of any of SEQ ID NO:21-SEQ ID NO:167 (the sequences listed in Table 6).

Artificial chromosomes as disclosed herein can include at least one selectable or nonselectable marker. In some embodiments, an artificial chromosome that includes a centromere sequence identified by the methods of the invention or a sequence derived therefrom includes at least one gene encoding a structural protein, a regulatory protein, an enzyme, a ribozyme, an antisense RNA, or an RNA that functions in gene silencing, such as but not limited to an shRNA, or an siRNA.

Also included in the invention are cells that comprise an artificial chromosome as disclosed herein. An artificial chromosome can be introduced into a cell by any feasible transformation method, or an artificial chromosome can be transmitted to a cell by means of sexual or asexual reproduction.

The following examples are offered to illustrate but not to limit the invention.

EXAMPLES

The following examples illustrate the isolation and identification of centromere sequences in *Chlamydomonas reinhardtii*. *Chlamydomonas reinhardtii* centromere sequences were isolated and identified by immunoprecipitation of sheared, native chromatin with antisera raised against epitopes present in the N-terminal part of *Chlamydomonas reinhardtii* CenH3, and characterized by sequencing.

Example 1. Identification of *Chlamydomonas Reinhardtii* CenH3 and Design of Peptides for Antiserum Production The sequence of a centromere specific histone H3 from the recently sequenced genome of *Chlamydomonas reinhardtii* was compared with centromere specific genes from other species. Antibodies to this protein were used to immunoprecipitate the centromere region in *Chlamydomonas reinhardtii*.

Based on amino acid sequence alignment of the *Chlamydomonas reinhardtii* CenH3 protein with the CenH3 gene of *Arabidopsis suecica*, *Olimarabidopsis pumila*, rice, maize, and *Luzula nivea*, the N-terminal sequence QSKPARPGRKAQAEAATPTKSKRPSGAAATPTR GGRSPGGGTPTG (SEQ ID NO:1) from the *C. reinhardtii* CenH3 protein was selected for peptide design for antiserum production.

The peptide RTKQSPARPGRKAQAEAC (SEQ ID NO:2) was synthesized conjugated to keyhole limpet hemocyanin carrier protein. A cysteine was added to the C-terminus for coupling purposes and the peptide was acetylated at its N-terminus. The peptide was injected into rabbits at ProSci Incorporated (Poway, Calif.). Each rabbit was immunized over an 8 week period.

An ELISA was performed on each animal's serum, run against a negative and positive control.

TABLE 1

ELISA titers below are estimates from pre and 1$^{st}$ bleed at week 5.

| Dilutions | PAS 11149 Pre-bleed | PAS 11149 1$^{st}$ bleed | PAS 11150 Pre-bleed | PAS 11150 1$^{st}$ bleed |
|---|---|---|---|---|
| 1:1,000 | 0.079 | 2.103 | 0.073 | 1.945 |
| 1:5,000 | 0.056 | 1.390 | 0.073 | 1.337 |
| 1:25,000 | 0.054 | 0.494 | 0.057 | 0.537 |
| 1:125,000 | N/A | 0.154 | N/A | 0.212 |
| 1:625,000 | N/A | 0.079 | N/A | 0.087 |
| ELISA TITER | N/A | >1:125,000 | N/A | >1:345,000 |

Example 2. Affinity Purification

Serum was collected at week 8 and purified by IgG affinity chromatography; 25 ml of serum yielded 2.9 mg at a concentration of 1 mg ml$^{-1}$. The data indicated that the sera and the polyclonal IgG had very good affinity for the immunized peptide.

TABLE 2

ELISA DATA for Affinity Purified Material

| Dilutions | Serum | Flow-thru | Purified Antibody at 1.0 mg ml$^{-1}$ |
|---|---|---|---|
| 1:1,000 | 2.589 | 1.303 | 2.858 |
| 1:5,000 | 2.415 | 1.155 | 2.450 |
| 1:25,000 | 1.786 | Not tested | 2.280 |
| 1:125,000 | 1.224 | Not tested | 1.673 |
| 1:625,000 | 0.973 | Not tested | 1.246 |

Example 3. Isolation of Chromatin from *Chlamydomonas*

| Buffers: | |
|---|---|
| M1 buffer: | 10 mM potassium phosphate, pH 7.0 |
| | 1 M 2-methyl 2,4-pentanediol |
| | 0.1 M NaCl, |
| | 10 mM β-mercaptoethanol added just prior to use |
| M2 buffer: | M1 buffer with 10 mM MgCl2, 0.5% Triton X-100 |
| M3 buffer: | M1 buffer without 2-methyl 2,4-pentanediol |
| Sonication buffer: | 10 mM potassium phosphate, pH 7.0 |
| | 0.1 mM NaCl |
| | 0.5% N-lauryl sarcosine |
| | 10 mM EDTA |
| | 1 mM PMSF added just prior to use |
| 1x IP buffer: | 50 mM Hepes, pH 7.5 |
| | 150 mM KCl |
| | 5 mM MgCl2 |
| | 10 μM ZnSO4 |
| | 1% Triton X-100 |
| | 0.05% SDS |

A 1:20 dilution culture of *Chlamydomonas reinhardtii* strain CC-1690 (21 gr mt+) was grown for 5 days in 200 ml TAP medium in a 2 L flask, under lights with shaking (100-150 rpm). The cells were collected from 180 ml total culture volume by centrifugation in 50 ml tubes at 3000 rpm, 5 minutes. The supernatant was discarded and cells were combined into a single 50 ml tube and washed twice with M1 buffer.

The cell pellet was resuspended in 5 ml M1 and poured into liquid nitrogen in a mortar; another 5 ml M1 were added to the tube, sloshed around to remove the remaining cells and added to the mortar also. The cells were ground for 5 minutes to a very fine powder, and then the ground cells were added to 150 ml M1 buffer in a beaker, stirred briefly to melt and suspend all cells, and filtered through a 40 μm plastic netting (all material passed through the netting).

The filtrate was poured into 50 ml centrifuged tubes and spun at 3000 rpm for 10 min at 4° C. The pellet was washed four times with 50 ml each of M2 buffer then washed once with M3 buffer; about half of the pigment was removed from the pellet in the process but significant pigment remained, possibly indicating semi-intact cells with intact chloroplasts. The pellet was resuspended in 10 ml of sonication buffer and was sonicated with a probe sonicator (Fisher Model 60) at full power (power setting 20) for 4×20 seconds with extensive chilling in between sonications. Sonication caused the liquid to froth extensively, effectively absorbing all of the sonication energy so that no sound was audible in during sonication; chilling in between sonications allowed the froth to settle somewhat. The mixture was kept on ice after sonication to allow the froth to settle; the suspension was distributed among 6 2 ml Eppendorf tubes and spun at 12,000×g, 4° C. for 10 minutes. The clear but green supernatant was removed and distributed into a 15 ml tube for immunoprecipitation.

Example 4. Immunoprecipitation of Chromatin with the Anti-CenH3 Antisera

500 μl of the chromatin preparation was mixed with 500 μl pre-immunized sera, gently agitated at 4° C. overnight. Non-specific immunoprecipitate was collected by centrifugation at 15,000 g 4° C., 5 min. The supernatant was then mixed with 75 μl of anti-peptide IgG (peptide $NH_2$—RTKQSPARPGRKAQAEAC, SEQ ID NO:2), and incubated at 4° C. overnight. The immunoprecipitate was collected again by centrifugation at 15,000 g 4° C., 5 min. The pellet was washed three times in phosphate buffered saline (PBS) 15,000 g at 4° C., for 5 min. The final pellet was resuspended in 50 μl PBS.

Example 5. Cloning and Sequencing of the Immunoprecipitated DNA

The immunoprecipitated DNA was purified by addition of SDS to 1% and extracted once with phenol-chloroform and once with chloroform. The DNA was precipitated in ethanol and dissolved in TE buffer. The ends of the DNA were repaired by treatment with T4 DNA polymerase, and the DNA molecules were then treated with Taq polymerase in the presence of deoxynucleotide triphosphates to allow nucleotide addition to the ends of the DNA. The DNA fragments were cloned using T/A topoisomerase cloning into pCR4-TOPO (Invitrogen). The topoisomerase ligation products were transformed into *E. coli*, and transformants were selected on LB-kanamycin plates. Individual colonies were picked from the plates and used to inoculate cultures. After the cultures grew to saturation, plasmid DNA was prepped from them for use as sequencing templates. For each template, both forward and reverse Sanger sequencing reactions were done. The products of the sequencing reactions were analyzed on ABI 3730 capillary sequencers.

Example 6. Analysis of Cloned Sequences

The sequences were trimmed of vector sequence and low-quality sequences and were assembled into contigs. The majority of the recovered contigs were derived from the *Chlamydomonas* chloroplast. Of the remaining 18 non-chloroplast contigs, 17 matched *Chlamydomonas reinhardtii* nuclear genome sequences including known genes, and one did not match any known genome but had a high G/C content characteristic of *Chlamydomonas* (contig 39). These contigs, of putative centromere origin, are summarized in the table below and their sequences listed. All of the contigs show aG/C content similar to the 64% average for the *Chlamydomonas reinhardtii* genome. Stretches of low complexity, primarily highly G/C-rich sequences can be found in all of these contigs.

TABLE 3

Contigs isolated after chromatin precipitation

| Contig number | GC content (%) | Length (bp) | Top BLASTn Hit (organism) | BLASTX hit |
|---|---|---|---|---|
| 19 SEQ ID NO: 3 | 57.5 | 1096 | *C. reinhardtii* | Hypothetical protein |
| 30 SEQ ID NO: 4 | 62.9 | 1007 | *C. reinhardtii* | Hypothetical |

TABLE 3-continued

Contigs isolated after chromatin precipitation

| Contig number | GC content (%) | Length (bp) | Top BLASTn Hit (organism) | BLASTX hit |
|---|---|---|---|---|
| 31 SEQ ID NO: 5 | 54.7 | 643 | C. reinhardtii | Phosphoglycerate mutase-like protein |
| 37 SEQ ID NO: 6 | 61.6 | 993 | C. reinhardtii | Hypothetical protein |
| 39 SEQ ID NO: 7 | 58.6 | 1006 | No hit | No Hit |
| 64 SEQ ID NO: 8 | 57.4 | 1034 | C. reinhardtii | nucleoredoxin |
| 86 SEQ ID NO: 9 | 63.4 | 812 | C. reinhardtii | Hypothetical protein |
| 122 SEQ ID NO: 10 | 56.4 | 1127 | C. reinhardtii | S-adenosyl -L methionine dependent uroporphrinogen III |
| 131 SEQ ID NO: 11 | 59.5 | 1281 | C. reinhardtii | Hypothetical protein |
| 138 SEQ ID NO: 12 | 63.7 | 1361 | C. reinhardtii | Hypothetical protein |
| 141 SEQ ID NO: 13 | 58.7 | 1103 | C. reinhardtii | Hypothetical protein |
| 183 SEQ ID NO: 14 | 58.8 | 1153 | C. reinhardtii | Hypothetical protein |
| 192 SEQ ID NO: 15 | 60.2 | 965 | C. reinhardtii | Hypothetical protein |
| 207 SEQ ID NO: 16 | 50.0 | 1035 | C. reinhardtii | 5.8 rRNA ITS |
| 215 SEQ ID NO: 17 | 65.3 | 818 | C. reinhardtii | Hypothetical protein |
| 300 SEQ ID NO: 18 | 69.2 | 746 | C. reinhardtii | Hypothetical protein |
| 301 SEQ ID NO: 19 | 73.4 | 906 | C. reinhardtii | Hypothetical protein |
| 302 SEQ ID NO: 20 | 60.2 | 996 | C. reinhardtii | Hypothetical protein |

TABLE 4

Sequences of Contigs Isolated after Chromatin Precipitation

>Contig [0019], SEQ ID NO: 3

GAGGCAGGTGATTTAATCAGTCTCCTTATAGGCGATGATTTAGCGGCCGC

GAATTCGCCCTTTTGGCATGGCGACGGGAAAGCTACGACAGTGTGTACTG

GAGTCACATGTTTTATTGCCCGGGCATGCGACAGCTTCATACCTCAAATT

CTGCCACTGCATAGTGCACAGCGTCTGACTGTGGTAAAACCGGTCTCACC

TGCCCGCACAGATGATGAAGCTGCAGCGGAAGCTGCAGGGCGGCGCGGCC

GCTGGCCCGTAAACCCCTGCTGTACGGTGCTGAAGGCTTCAGTGTGCGGT

TGGATATGGTGGACTGCAGCACTTGATTTCATCATGCGCCCATTCCTGT

ACAAAGCGACGGCCCGTGGCCGCATGGTGGGCAGGGCCGCAGCACTGGCT

GAGCCTATTTGAGTTGAGGGCGGACAGCGTGGCGTGCTTGGGAGCGGAGG

TGCTGCACTCACAGGCGTGCACGGGCCCAAAATGACACTGGGGCGAGGCG

CACACAGACAGGTCCACAGGTTAAGTGCGTGCGTGGTCGACGAGCGGACG

AGCGGTCAGGCCAAAGGCTGGGGAGGATAGGGCGATGCGTGCCCGATGT

GAACCCAGCTAGGCCAATTCTGGTTGTTCTGGGCGATGAAGACGGCTGGT

TTGATCTTGCAAGGCGTGAAGTTGCAGGGACTTGTGGCCGTCATGCGCTC

ATGGGATGTTGAGGGCTTGGAGCGTGAAGGCGGTTGATACGTTCGGTACG

GCCATGTAGGTGGAGCACAGTTTGACGGTGTTGGGGTTCAGCCATACGGT

AAGCAATGAAATGTGATGCGCCAATTGTGCCTCTGCCTCACCGCGACTTG

TAAATGAACTGGTGTGCAGCCCAAGGTGCAGCCCTTGTCCCTGCCTACGT

ACCGCGCCAACTCGGGCGGCCCCCCAATTCAATCTGTGCTATCAGCCGCA

GTCACACAGCAGTGGTGCACACTCTCGACAAAGGGCGAATTCGTTTAAYC

TGCAGGCTNGTCCCTTTAGTGAGGGTTATTCTGAGCTGGCGTATCATGGT

CAAACTGTTTCTCGGTGGAATTGTTTCCCCTCCAATCCCCCACTAC

>Contig [0030], SEQ ID NO: 4

CTCAGTATTCACCCTCACTAAAGGAGACTAGTCCTGCAGGTTTAAACGA

ATTCGCCTTTGCACTGGTGGAGGACTGCGTGGTAAAGCAGGGCGCGGTGG

GTCGACTCATACGGCAACTGGACGCGGCGGCATCGGCGTCAGAGGTGGCA

AGCTGGCGGGTGGCGGATGCTGAGGGCCGCTACAGGTGCGGCGGAGGCAC

GGGCGTGCAGCAGCACACTGTGTGGGTCTTGTGTGCGTGTATTTGAGCGG

TGTAGTGGGTGGTGCCTGATGGACCGCCAGCTGCCCTGTGCTCTACACGC

AGGGCTGCAAACGACGACAACGCAAAGCTGCGGCAGCTGCTGCACGAGGA

AAAGGAGGTGCGCGCGTGCTGTCCCCGTGCCTGGCTCCGCCTCCTTGCCC

AAGGGGCCGGAGCCCGTGCCGGCTACTTGTCAACTTAGTTGACGGTACAG

TABLE 4-continued

Sequences of Contigs Isolated after
Chromatin Precipitation

ACTGCTTAAGCTCACCCTCCTTCCCCTCGCTCCTTCGTTCCCCGTACCGG

TCCATCTATGCTTCAGGCCTGGCGGATACCCCAGCTGCTGCCGGACGCCG

CCGGCCTCAGCCGGGACGAGCTGGTGGAGAGGTGGGTGGTGGTGGGTTGG

TTGGCGGGGGGTGTTTGTAATGACCGAGGGCAGTCCAAGGGGTTGGCATGT

AGGGGACGGGGTGGTTGAGCGCAGGCACGAATGCATGGGGCGGGCATAC

ACAAGCAGCCNCACCCTTTCGTCGTTCAACCTTGCCCCCATCCGCCTTCN

CGGTCCCGCCCCTGCCGTGCTCGACCCATCACCCGCCATACGCCACCCAC

GCNAGGTGTGAGAGCGCCATGGCGGCGTACGGCCGAGAGCGCCGCCGCAA

CGCCGAGCTGGTGCACCGCCTGCAGCAAAGGGCGAATTCGCGGCCGGCTA

AATCGATTCACCTATAGTGAGTCGTATACAGTTCTCTGGACGTCGTTTTA

CAACGTCATGACTGGGAAACCATGGCGTACGCAGGTAATCTGCGTAGAGC

AGGTCATC

>Contig [0031], SEQ ID NO: 5

CAGAATTAACCCTCACTAAAGGGACTAGTCCTGCAGGTTTAAACGAATTC

GCCCTTTACACTGGACGTGCGGGCAACAGATGCAGACAGC

GCATTGCTCACACGGGCCTACGGGCATTGCGGCATAGGCCGTGGGCATTG

TGCATGGCCAGAACGAAAGGGCAGAAGTTGCCCTCTCATGAGGGCACCGG

CGGGGCATGCGTTTGTGTGGGCTCGCTGCCGTGCAGAGAAGGTTGCATGA

GCTTAAGGGCGTGCCGTGAGGCGGCTTGTCGCTTGTGTTCAGGTCCTGCG

ACTTCATGGCTGGTTGGTGTGCTGCTTCAGTTGTCCTGCGTTGTGCAATG

ATCAGGAGCGCTGCGCATGATCGCCTATGGCTAGCAATGCCAGCTTTGGT

ACAGCAATGCGCCCCAGACGCAGGTGCGCCTGGCATGGTGCAAATGCGTT

GACTGCTGAGAGTAAATGAGTGACATGACTAGGTATTCTTGGCTGTGTAC

CTGTGCTGATGACGCTGCTCGTGATCCGTCCTATTAAGACCCGGAAAACT

TGGCACTTTCTATTGATTCTTCCCTATAGATTCTCCTCTTCCTCCCTTGT

CCATTGATTTCTCCGCATCTTCCTCACCAAGGGCGAATTCGCGGCCGCTA

AAT

>Contig [0037], SEQ ID NO: 6

ATACGACTCACTATAGGGCGAATTGAATTTAGCGGCCGCGAATTCGCCCT

TCCCACCGATTTGGCGCACTGCTCTGAGACCACATAAGCACACGCCA

GGTTAGAGGGGTCCGAGGTGGTGGGATAGCCGCCCGCCTGCAGCACCAAA

TCGGTGCGACCGCGGAAAGCCCCCCACACAGGGCCCCCTACCATCTTGAC

CGTGACGGTGTAGGTGCCCGGAATGATGGGCCGGGTGTCCACCGGCACGT

GAACCGTGAGGACAGCCTGACCGCGCTGGAGCGGTACCGCCAGCGGTGAC

CTGCGCATGAGCTCCGCTGTGAAGGCTGCTTTGCTGGCGCTGGTCGCGCG

CCGGCTGAAGGCCAGCCCCGCAAACGTGCGGGAGGGGCGGCCTGTGCTGT

GCAGAGAGTGGCCCTGCAAGAGCTGCGGCTGGTTGCCCTGCCTGCACAGG

GTGTCCAGCACTGACAAGGCAGCGCTGGTCACTTCCCGGACGCCGGCTGA

GGACAGCTGCTCGCCCTCTGGGAGCCCCGTGGTGGCACCCACCAGAAGGA

CTGGGTAGGTAGGCAGGCTGGGGCCCTGAGGCTGCGTCGTCAGGTCCTGC

ACGCCGTGCGCCACGCTATGCGTGGACAGGGCAAGGTGGAGCTGCAGCCC

GGGGCTGAAGAACGGGCTGGCAAAGGGCGAATTCGTTTAAWCTCTRCAGR

ACTAGTCCCTTTAGTGAGGGTTAATTCTGAGCTTGGCGTAATCATGGTCA

TAGCTGTTTCCTGTGTGAAATTGTTATCCGCTCACAATTCCACACAACAT

ACGAGCCGGAAGCATAAAGTGTAAAGCCTGGGGTGCCTAATGAGTGAGCT

AACTCACATTAATTGCGTTGCGCTCACTGCCCGCTTTCCAGTCGGGAAAC

CTGTCGTGCCAGCTGCATTAATGAATCGGCAACGCGCGGGGAGAGGCGGT

TTGCGTATTGGGCGCTCTTCCGCTTCTCGCTCACTGACTCGCTGCG

>Contig [0039], SEQ ID NO: 7

CTAGTCTGCAGGTTTAAACGAATTCGCCTTCGCTGGGTACGGCCGGCTAA

TGCAGGAATAAGGGATGTCAGTTAGAAGCGGGTGCTTCACGAGTGTAAAA

CTACGG

TACTCGAAAGGTCTCCAGCATCAAGGCACGCCATTCCATGCTCTGGCGCG

GGTTGGCAGGGTGCATGCCTGCCACAACGTCGATAATAGTACTAGATCGG

GGCTGGGGGGTGGGTGTGGGCCAGGATGTAGGTTGCTTATCTCCAAGTGC

ACACGGCCACGCCATGCTTCTGCGGCATCGCACAGGGTGTGCTGGCTTGC

AACAGCATAGCATGCGCTGATTTGCTTCGGCAACCGCACCTCAACATACG

GTAGCAAGACTCCGAGCGACATATGCACCCGGGGAGGTGCCTGCACTGCT

CGTGTACGGCACCCACACGCGCTGCAAGTCTGCACCGACAGTCTCCGGCG

CGGGGCGTCGTCGTTCAATTATCGTCCATGCCTGGGCTGGGTGCAGTCTG

TTTCTCGGGACTCAACTATGTCAGCCACTTGCTTCCCTTGCGATGTCCCA

CCGCACCCACGGCTTGCACCGTATCACGCCATATCAGGCAGGTGTCAGGG

AAGCCCGGGGGCCATGTCGAGCTCTTCCTCGGGAAACAACGCCCGCCGC

AATAATAATAATAATGCAAACGCCGGCCCATGGGGCCTGGCGTGGATTAT

CGGGGGTAAGGTGGGCTAGGGGCGAGGAGGCCCACCCCCCTCGCGCTGCC

ACCTCGCCACGCACTCCGAGGAGGGTGTGGGGGGAGCCGTGGCTCACCCG

CCTCTCGGTTTGAGTAARGGCGAATTCGCGGCCGCTAATACKTCAATTCG

CCCTATAGTGAGTCGTATACATTCACTGGCCGTCGTTTACACGTCGTGAC

TGGGAAACCCTGGCGTACCCACTTATCGCTTGCAGCACATCCCCTTCGCA

GCTGGGTAATACGAAAAGCCGCCCGATCGCCTTCCCACAGTGGCAGCTAT

ACGTCGGGAGTTAAGTTATCTTAAAAAA

>Contig [0064], SEQ ID NO: 8

GATTCCCCCTCAATAGAGGGACTAGTCCTGCAGGTTTAAACGAATTCGCC

TTATTCTCTTTCAACTTATTATATGTTATAAGAAAACAC

AGCTGCAGTGCGGAGAGCAGCCATGGTTCGCGAACTTCGACGGACATCCT

TTCCAGCACCCCTCGCGCCCCTCGCCCCGCCACGGCGCTGCCACGGCCCA

CCCTGCTGGTTTCCCCAGCACAACGTATTTTCAAACGTACTAGCCGACGA

TABLE 4-continued

Sequences of Contigs Isolated after Chromatin Precipitation

```
GGGCAGCGTACAGTACGTAGTACAGTACGTAGTACATAGTACGCGTACTA
CGAACTACGCAACCCTGCCGCGCGCAGGACACACGCACAGCGCACGCACT
AACCAGGGCGCAAGCGTCCAGGTACTAGAACGGTCGCCCACACGTGCATC
CTGCCCACACACAAAGCCACCAACCACGCACAACCTCTCGCGGCGAGGGA
GGCGGGGAATCAGCGTCATACGGCAAGCGCAAAACCATGCCGTCACCAAC
AGCCCGAGATAGGAAAGGATGCGCAAACGGCACAACGTCCCAACCCTTTG
GCCTGATACCCAAAGTCACAAACGTCTGGAGACGACCCCAGAAGTCAGCT
ACGACGGCAAGTCCAATCCGCGGTTTTATGGACAAACCACTGGGCCCTGC
TACTGTACGTAATCCAGCTTCCGCAATGTGTGGCCGGCCCCTGGTCGCTC
TGCCCCCCCTTGCTTTGTGGTCTCGCCGCTTGATCGTGTGGGGGTGTGTC
TGGGGGTGGTTGTGTTCCCTCGGCCTTGTCTTTCGCGCGTGCGGTGTGGG
GACTGTGGGGCTCTGCCCAATGTTTAGGCTAGTACTGTGCCTGTGGCACG
TGAAGTGGAGGCTTTGCCTTGTGTTGGGCCTTCGGGGCTTGGAAGGGCGA
ATTCGCGGCCGCTAATAGTTCAATCGCCCTATAGTGAGTCGTATTACATT
CACTGGCCGTCGTTTTACAACGTCGTGACTGGGAAACCCTGGCGTACCCA
CTAATCGCCTTGCAGCACATCCCCTTCCTCAGCTGGCGTTATAGC
```

>Contig [0086], SEQ ID NO: 9

```
ACCCTCACTAAAGGGACTAGTCCTGCAGGTTTAAACGAATTCGCCCTTGA
GCAGGTGTTCATCGTCGGCGGCACAGGCAATTACGTGAAGGACCTGGGCG
AGAAGGGTGAGCTTGGCGGGGACCTGAAATCTTTGACTGGGAACAGGGC
CGTTTGTTTGCGCCTTGGCGCTCCCCGGCATTCATGCAGCTGCAGATCTC
GACGCGAGTCTGACAGCACGCTATGATAGGTAGAGTTGCCTGCTTGTCGC
CTGGCGGCCTTCAGCGCGTTGACATTGCCGCCTGCCTTGACTTTGCCCTC
TGACGCCTCACTGACTTCGCTACTGCTGCCACTGCCGTCTGTGTGATGCA
GGGTTCATAGACGCCTGCAAGACCACCAGCGCTACCCGGATCTTCCCCGA
CACGCAGCATCACAATGTGCTCGGCTTGCCCTTCACCGGGATGAGCAACG
TCGCTGGCGTCAATGGCCCAGACGCGCTGTCACCCTTCGCTATCGTCACG
GACAAGGACATCGACCGCGCTGACAACGACCCCAACCACATTTTCGTGCG
GCCCGACCATCCCGGCGTCACCCTTCCACATCCTCGCACTACCCATGGCG
GTGGCGGCCGACGACACTTYCCGCGGCGCGGSGCCTGGCGGTCGGCACGA
CGCCGGCGCCCAACGGCGCGCTGCACCGGTCCCACACCCCCGCCAGCCCC
CTGGCGACCCTGACGACCCCCGGCATGCTCAGGGTCGGCGCTCGTGRGGC
CACGGTGGCCAGGCCGTCGAGACGGAGGTCTGAAGGGCGAATTCGCGGCC
GCTAAATTCAATT
```

>Contig [0122], SEQ ID NO: 10

```
CGTACTCGAAGGTTTACGATTCGCCCTTGGGTGCACCGTGGCCGCCCCGC
ACGCCCGCACCTTGGTTCCGCTCCCGGATGGCCTKGARGAATGYTCGAG
TTGCAGCACGTCGCAATCCTTCAGTCGCTCCGCGTCATGGCCATCCGCAA
TGCTTCGCGTAACAACAGACGCAACGCGGCGAGCGGCAGGCCTCCCGCTG
CAGGCAACGTTGCAGGCCAACAGAGCCGCCGGTCCYGAAACCCCAAGTCC
ACGAGGTGTAGCACGCGCCCTTGTGATTACAGCAGGATATCTTCCACTTG
TGCTAGGGCTACTCGCCGAGCTAGCCAACGAGCCGCTGGGCCCCGAAGA
AGAGAATTCGTCATTTGATTGAAACGCGTGCAGGCCCGATTCGACCTTAC
AAACTACAGACTGATAAATAAAAGCTTAAAAGATGGTGCAATTTAGATCA
CAGCCCAAAATAGCAGGGCGTTTGCGTGGTCGCTTATGCGTGCGACGTGT
TTTGCTGCGTGCGTATCAAGTTGGCTGAATATGACAAGCAAACTTTGGAG
GAGAACAAGTTTAAGGTTGGAAAGCAGCCGGAGGGTTAAGAAGAGCTCGC
AGAAGGCCTYTGKGGGGTTGGGGGCCAAAAGGCCCTGCCCATGCAGCGGT
CCATGAAGCGGTCTTCAGCGCAGCCAAAGCTCTTACAGTACACTTTATAC
CCTTGTTTATATCAGCATTCAGCTGGAGGCTAACACGCAAAGAAAAGTCC
CTTCACGATGGCTTCCAGAGAGGGCACTTCAGGCACCCTCAAGCCATTTA
CCTCACCAAGCAAGAGCTAGGGAGGAGTCAACCATATGGACGTTTGCAGT
CCCCATGCCCACACACATCAGACAAGTACCGGCCCAACCATCCGAGCCAT
CCTCCAGGCCATCTCGCCTGCGCGGCGCAGCATCATACATCCGCCGGCCG
TGTGTTGCGCAGCGATGTATCACATGGGGCTTGGAACCTCTTGCACACCC
CGCAACCTCAAGTCAAAAGACACATATTCGTAGCACCAACCATACTCTGG
CCCCATACCGCGTATGCGCTCTGAACACCCGGCCCGCTTTGCGGGTCAAA
GGGCGAATCGCGGCCGGCTCTACCTAG
```

>Contig [0131], SEQ ID NO: 11

```
CCTATAGCGGCGCGATTCGCCCTTTGGTATGCTTGCACCTGACGGCGCTT
GCCTCGTTTAACTCCCTGCGCAGAATCACGTGTACTTCACGGATGTCAGT
AAGTAGGGGCGTTGGGTCAGCTGTGCCCTGTCAGGATCAGCTGCGGAATA
CCCTGGCAGCACTGCTGCACCGCACGCATACGGCACCCAATGTGCCAATC
TCTGCCCCCCCTTCCTCAACTAATCATGATTGCAACCCCACCCGCCATGC
CTGTAACTCCGTCCCGCGCCTTAAACCCAGTGTGCTTGGCGATGCCGCAC
ATCCTGCACTTGAGCGTGGCGGGGTCACCGCGTTCCTGTTCTTCGCCAT
CACAGCCTTCATGTGAGTTGGCAAACGGGGGGCATGGGTGCCCTTTAAGT
ACCGTATCCATACTTGGGCTGTGTGCTCCGTGCTTGTGATACGGTATGGC
AGAGATCGCGCCCACCCGGGGCCCCTTYCCTCAGGTGCTCCCCGCTCTTG
CTGTGGAGACCTGTCTCTCATCTAAACCCCTTCCTGCTCCATCCATCAGG
GTCATCGCCTCGTCAGACCTCAACCCTGTATCGCGTGGGTACTTAGCCTC
GCCCGCTGCTGTCACGCGACTGAAGATCCTGTGCGCAAAAGCCATCTACG
TCGTAAGTCTGCACACCGCTGTTGCCGTAGTTTATGCAACCCCGCCCAT
TCGACAGGCGGGCCTGAACGCAAGCAAGGGCACTGACACGTGTGCGTGTC
GCTGCCCTGCCGCCCGCAGATTGTGGCTGACGATATGCAGAGCTGGCCCA
AACCCCAGGCCATTATCATCCTCCTCAGCGTCCTCCTCATCTGGTGGTGG
AACTTCCGAAGGGTGGGTGCGGTGGCGGGTTCGTTTGCGGCGTTGCGCTC
```

TABLE 4-continued

Sequences of Contigs Isolated after Chromatin Precipitation

TCAGGTGGTAAAGGGCCGCGGGCTTTTGGGTTGCGGAACTTGTATCCGCC

GCTCAGAGTTGGACCGTGAGCACCCSCCGAGGTAGGCTTGAGAGGAGGCA

CGCGCTTACTTCGTTTAGTCGCGTCGCTGCACTCCCGCGGAGCTGCTCGT

GTTCGTACATGGCACGTGACACTCTCAGAGGGCGCATCAGGGAGTATCTG

GGTTAGTCATGTTCACCTGCGGCTTCTCCCATGCAAGACTTGTTCCCAGC

ACTTGCTGGAACACGCTCTCATCCCATGACGACCAACTGCCTGCAGTTGC

CCTTCTACCGACCGGTCGTCAACGTGGTGTGGTGTTCCATGTGGTCGGGC

ATCCAAGGGCGAATCGTAACTGCAGATTTCG

>Contig [0138], SEQ ID NO: 12

GCAGGTACAGGGCGTGCGGCAGAACTTATCTTTGCATTTCTAGCGCGACG

GACCTTTGCGAAAGTCGCTCACCGAGTGGCCCAAAGTCGCCACTTTCCTG

GCGTCGGTTCCTCCATTACCCTATCAACACATAGGTTGGCCCCAATGATC

GTAAATAAGCGGCCTTCAAGTGGGGGTAGCCCGAATCCTAGCGAAATGCG

CACTCGCCGAACATGCCGGCATGCCCGCACGCGCGCCTGGGGTGCGCTCC

AAGGCCAGCTAGCTTACTCCTGGCGTGCCTATGCAGTCATATGTGTGAAA

GAGCCAGGCCTGCTCATTTGTAGGGCCGCCGCTTGGGCGCTGGGCCCGGC

CATCGGCACGCCCACGTGCCTACCTCCCTGACGCCTGACCCCCATGTGC

CCAGACCACGACTCGCTTGGGCGGCCCGAGTGCTGGCATTGCATGCCGAC

TAGTATGGCTTGGTATAGCGGGCCGGGCGGGCGCGTCACACAGACTCCAG

GGCACTGGAGCGGACCCCACATCGCCGCAACAGGCGCGCGCCGTGCGTCA

CCYYATCACGCAGCCTGTACCCGCGGCCGCACCCGCTTGCCACACACTCC

CCGCCGAGCTCGTCACCACGTAGCTGGACACGTCAGAAGCACCTGGTCAC

GACATCAGGCCTCGGACCTGCACCCAGGCTCACACCTGGCCCGAACAGTG

CGTGTGCGGTRTGCCGTGTGCAGCGGGTGGCTGTGGGTAGGGGTGAGGAC

TGAGGGGCGCAGGTGCTGGACTGTCACGCATCCGCTGCGCCGAGTATTTC

TGGCGCCCTCGATGCACCTATGACACGCACCACGGCCATGGCGGCGTGTG

CTGCCCGCCCCGGTGGCCGCTGTTGGCTCCGGTCAGTGTCTCAGGGTGTG

CAGACACACCGGGGCTGAGCGCCGCCTCAGGGGCGCCCATGTGCGGCCCG

CTGTCCTTGTGAGCGGCCCTAATGGCCGCTGTCCGTGTGGATGAAAGCAA

ACGGGTGTTGGGGGCCCACGTCGGAGGCATCAGGGTAGGCCTGGCGGGC

CCGGGATAGCCCGCGTGGGCGGCCAGGAGCACCGTGCCATACCGCGGCGA

GGTGCACCTCCGTGCTTGTGCTGGCGACCTTTGCGTATAATTATAAATAC

AAGTATATTAGCGAGCCACGGAAGTCGCGGATCACGCAGTACAGGCGTGC

GGCAGACTTATCTTTGCATTTCTAGCGCGACGGACTTTGCGAAGTCGCTC

ACGAGTGGCCCAAGTCGCACTTTCCTGGCGTCGGTCCTCATACCCTATCA

ACACATAGTGGCCCCATGATCGTAATAAGCGGCCTTCAGGGGGGTAGCCG

ATCTACGAATG

>Contig [0141], SEQ ID NO: 13

TTATACGGCAGGTTTTCCAGTCAGACGTGTAAACGACGGCCAGTGAATTG

TATGCGACTCAGATAGGGCGACTGMTWTAGCGGCSSGAWTCGCCCTTCCT

GCCTCCCAGCTAGCCCGCTGCCCACCTGAAKGTTCCGGGCCGCTCCCACT

CAAGCAAGGCCGCCAATGTGCYGCYCAGGCTGTGACCCATGCAGAAGGCG

CCTGCGTGTGTGTGTAGGGAAGTGCAGGGGGGCAGGTGAGGTGCAGGT

GGAAACCCCACACACGCGGCGGCYGCATGCGGCGTCCTCCCCTGCTGGTC

CAGGAGAGAATCTCCTCCTCCTCCCCTGATGGTACGACACCCACACTCCA

GACCACGACCCCAGACCATGTGCTACTCAAGTANCCCCCTCCCCCAGTCC

CCTTKCAACGCTCCCTGCTTCGTTGGGCTCGGGCACATAATCCCCCACTG

ACTCCCCGCCTCACCCCGCACGCCCTCCCGCTCCACGTAATCCTGAACTG

CTGCGACCAGGTCTGCCTCGCTGATGGGCCCTGTTGGCGCGGGGCCTGG

CCGTGGCCAGGCAGGTCGAGAGCTACGCAACGAAAGTGCTTGGAGAGCAG

GGGCACCTGCAGCGAGCGACGCCCAGCCATGTCATGGATGAAATGTCAAT

TACGCGGAACTCGGGGGCTGGGTTGACTGCCGCTGTTTGTTATTTGATGT

ATTAATTTGATACAAGTTGCTCACCATTGGCAAGAAGATGCGACCGTGAA

AGCCATTCGCGTGCAGCAGCAGAAGCAAAGGGCCGCTGCCGCCCAACTCG

TGCGCCACGACGCTAAGTTTTGGCATCCTGCTGAGTTAAAGATACTTAAG

TACAACGGGCAGCAACATATTGCATTCTCTTTCGCTAACGCAGGCGGACC

TGCATGGGTAGGGCGCGTGCAGGCCAGCGCACACCGGCTCCCCCACTCT

CCCAGGCGATCGTTTAACTGCAGACTAGTCCCTTTAGTGAGGTATCTGAG

CTGCGTATCATGTCATAGCTGTTCTGTGTGAATGTATCGCTCCATCCACC

AACTACAGCGAGCATAATGTAAGCTGGGTGCTATGATGGCTACTCAATAT

GCT

>Contig [0183], SEQ ID NO: 14

GGCTGTAGTTGGTGGATTGGAGGGATAACATCACACAGAAACAGCTATGA

CATGATACGCCAGCTCAGAATACCTCATAAGGGACTAKCTCKRCRGTTWA

CGAATTCSYCYTTCAAGGCCATGCCCACCCGGTCACCTACCGGCGAACWT

CGTCATGACCTCGATATGTTGGCTGYCTCTCCCGCCTGCAGGTGCACCAG

GTGCTGCAGCGAGTGGCGCYCGACCTGCYCGCCGCCTGGTGGGACCGCTG

GAGCYYCGACGCGCYYYAGTCCTRCCGGCTGCCGCAGCAGCCGCTGCCGC

AGGTGCAGGCGCAGGCGCAGGCGCCGCAGCCAGACCTAGCAGCTGATACA

GGTGCGAGCATGTCGGCAGCGGCAGCAGTAACTCCAGCYCCAGGTGTAGG

CCAGGCATTAGGGGGCGGCGGAGCYCGGGGTTTCGCTATAGGTGGTGGG

AAGGGGTCTGGCGGCGCGACCTGCAGCATGGCCACCTTGTTCCTGCAGCA

CTACCTCGACAGCCTGGGCTCCCTCAACACGTTCGGGTAGGGCGCTCTCC

GGCAGCCGCATGTGACGCCTGCGTCATCACCGGAGCGTGTAATGAATGTG

ATGGGACTGATTCTGTTCACTGCGTACATGCGGTGGCAGACGTGAGCGTG

TABLE 4-continued

Sequences of Contigs Isolated after
Chromatin Precipitation

TTGCTGTGTCAATTGTGATTGGACTGGACTGGAGAGGGGTGATGTGACAA

GCAAATATGAGAGAGTCAGWGGGCACGTACATGAAGGGCAGCAAGAAAGA

AATGTGGCCGAGGTGCCTGTGCCCCGGCTGGCAGGGCGTCACCGTACATA

CAGATGAAGAGGTATGAGAGCGTGGCGAGATGTAACCGCAGTTGCGCCTG

CAGAAGGCGTACGCATTTATCGAACACTGTTCTTTTCTTCTCCCGGCCGA

TATGAAGGTTTGTGAAGCTTTCCSGGCAGATACCGTAGGATCTTCAAGCT

TGTCAGATAGACGTAGCCGCTGGTAAGGCGCGGCAACAATGAGCGGCCCC

TGASGTGGGGCGAGTTGGSCGAACTTCCTGGGKRAAGGGCGAAATCSCGG

CCGGCTSATMRTCCCCTATAATAGGCGATAAATTACGGCGGCGTTTAAAC

TCTGCCGGGAAGACAGGCGTACCACATTATGCTTGGAATACTTTCACTGC

TTT

>Contig [0192], SEQ ID NO: 15

GTCGCATRGYARWASRATTCGCCCTTCMCCGAATYGTTGKGATTGGGCGT

AATGACGTCTGCGCACGAGCAMCAGAAGGTGAAGGTTCAACACGGCGTAC

CGTGCATGCTTACTGCGGTGGGGGCTGCATGGCTGCTGCCTGCGTGCGGC

AGACTGCTCCTTGTNNNNNNNNNNNNNNNNNNNNNNNNNAGCCAGGTCATT

TGTTCCGGGCCGCCAGCGCCGGCTGCCCAAACATATGAGATTTGGCCATG

CATGCTTGAAAAAAGCAGCAGCAGCAATCATGTAGACCCACCCAGGAAGT

GGTCTGCCGGGTTCTCGTGCAGGGGGCAGGGAAATCCGGAGCGGTCGAAA

AAGTCCAGGGCGTCATGCGCCGGGCCCTGGTACACGATCGAGCCGCGGTT

GAGCAGCAGCAGCTGGTCAAACAGCGCGAAGATCTTGGCCTGGGGCCTGC

AGCGGCGGAAGCAGAAACAGGAGCATGGGTCAGGCGGGCGCGGATGCGGA

CGTGCGTGCACATGTATGTGTGCTTGCGCTTGCTGCTTGGGAATATGAGC

ATGCAAGGCGCTGCGACATAGCTGCGGGCGTATGAGCACCCGCCCATCTG

CTGCTGGGAGTTCGTGCTAGCTAAATGCGAGCTGTAGCGCTGCAACAGCA

GGCTGGCCACCAACAGCAGGCCTACGCGGCTGCCTCACTCACTGGTGGAT

GGTGGTGACGACGGTGCAAAGGCGGCTCATGGCGAGGCGGCGCAGCAGGC

GGCACAGCGACAGCGCTGCACGCACGAACACGCACACGTCGGGTAGGCAG

GTTAGGGAGCAGGTTGGGGTGACGTGCGTGGTGAAGCAGCGGCAAGAGGG

ATGGACRGACCGCAGCGACTGACGCTGCACATCGAGCGCTACGCACGGTA

CGAAGTACGAAGAGCGCGAAACCCTCAAGCAAGCAASGACGTGGCCMACT

TGGGATGGCATGACT

>Contig [0207], SEQ ID NO: 16

TTAAAA

CCGAAGTATCTAGCTTAGAGCTAGTGCTCACTAACCAAGACAACTCTCAA

CAACGGATATCTTGGCTCTCGGATCGATGAAGAACGCAGCGAAATGCGAT

ACGTAGTGTGAATTGCAGAAATACGTGAATCATCGAATCTTTGAACGCAT

ATTGCGCTCGAGGCTTCGGCCAAGAGCATGTCTGCCTCAGCGTCGGGTTA

ATACTCGCYCTACTCCAACATGTTTGGAGCAAGAGCGGACCTGGCTGTCT

CGGTGTTTGATTTTCGGATCAGACGCCGGGTCAGCTGAAGTACAGAGGTT

GATGCATGGACCCGCTTATGGGCCTCTACTGGGTAGGCAACTCGTTGCTA

ATGCTTTAGTAGATGGCTTGGAGCTGTGCTTGTCGACCCAAACCAGGAAC

TTTGGCCCTGTGCCGAAGCAAACCCCTATTTTCTCGACCTGAGCTCAGGC

AAGATTACCCGCTGAACTTAAGCATATCAATAAGCGGAGGAAAAGAAACT

AACAAGGATTTCCCCTAGTAACGGCGAGCGAACCGGGAATAGCCCAACTT

GAAAATCTCCCTTTGGAGAATTTGTAGTCTAGAGAAAGCGCTTTCTAGGG

CTGGGCGGAACTCAAGTCGGATCGAATGCCCGCGTCAGWARRGGGTGAWA

ACCCCCGTCGGTTCCTGCCYTAGTCCTTCCACGAAGTGCTTTCCACGAGT

CGGGTTGTTTTGGGAATGCAGCCCTAATTTGGAGGTAAATCCCTTCTAAG

GCTAAATACTGCCGAGAGACCGATAGCGAACAAGTACCGTGAGGGAAAGA

TGAAAAGAACTTTGAAAGAGAGTTAAAGTGCTTGAAATTGTTGAGAGGGA

GCGATGGCGCTAAGGCGATTCTTTAAACTGCAGGCTAGTCCTTTAATGAG

GGTAATCTGAGCTGGCGTATCACGTCATACTGTTCTCGTGGGATTGTATC

CCTCCATCCCCCACAACACGAACAAAAGTAAGCTGTCCATGATACACCAT

AATGGTGGTCTCCCCTCCTCGGACGCGCA

>Contig [0215], SEQ ID NO: 17

AATTTAGCGGCCGCGAATTCGCCCTTGTGGGGACGGAGAGTGCGCTGA

GCTGCTCGGGGGTGCAGTCATTAAGTCCAGGGCCGCAAGGCGTAAGAACG

CGTGCCCTATGCATGTGTATGAAGCCCTGAGCAGTTTATTCTGCTGGCCC

AATCTGCGCAAACAGATTCTGCCGGGCATCGGCGGCACGGTGCGCAAGCA

TACGGGCCTGCTGTCCGGCATCTCCACCCTCCTGCGAGGGCTGGGCGTCG

GCGGGGGCAAAAACCCGCGTGCGCGCGGCGGCCGGGCACGCGCACAGAGC

GGCGCTGGCGACAAGGCGCAGCGGAGGCTGCTGGGACTCGACGGGTGGTG

GAGCAGGTGGCAGTCGCAGGAGGGCGCACGCAGCTCAGCGCAGCAGGCGT

GGGTGTGRGAGGAGCCGGAGAGCGAGGAGGCGCAGCTGCGCGRGCGGCGG

ACGCTGGCCGGCGCCATGYAGGACGATGAGCGCATTGCGGCGCGRGAGGA

CTRRGCCGGRAAGGTGGAGCRGCTGCTGTCGCGRGCGATGCGGTCCGTGC

GGCRGGCGCTGCCGRGCTGGCRGTGAGGTAACGGCGAACGTGAGTATTGT

AGGCGTGTGCGCRCGTGRRRRCRAGTGCRTGTGCRTGCAGTGRRCRAGRR

RCTGMGATCGGCGCAGRACTGACGGCYGCTGACTGAACCGGCAAGAGACC

CRGATTGGTAGTGCCTAGRCAGACGAAGAACGGACCAGACCTGTGAGGGA

TAGTTGTATTGATGTCAAAGGGCGAATTCGTTTAAACCTGCAGGACTAGT

CCCTTTAGTGAGGGTAATTC

>Contig300, SEQ ID NO: 18

AAACACGCAGTTACGATTCGCCCTTCACCTGACCCCAAAGTGCTGCGCCA

GCTCGTCCAGCTGCTGCTGCGGGTCGTCGCTGCCCAGCACGTGCGGCGCC

GCCACGTCACGCCGCTCTGCCAGGCGCTGGTCGCGGGTCAGGAACACGCG

TABLE 4-continued

Sequences of Contigs Isolated after
Chromatin Precipitation

GCCCTCGGAGGCGGCGCGCGGTCAGCTGGAGGCGGGGAGGCGCAGGGT

GTGGAGGGGTGAAGGGGATTGAGGGAGGCGAACGGAGATGAGGGGCAGGT

GGGGGCAAGGAACGACTGCGATGTCGCCATGGAATTCCCCGCTGCCGCTG

CCCCTGGCGCTGTTTCACGCACCCGCGCCAGCTCCTGTTTGCCGGGCGAG

GTGCGGCCCACGTACTCGGCGTCCAGCCCCAGGCAGCGCAGCCACCTGCA

CCCACCCACGTGCGCGTCACGTGTTGCACCGCGATGCGAATGATACTGCA

ATGCCGTGAGTGTTACCCCCATCAAGGAGATAGGGGTGGCAGTGAGGTCC

ACGACACAGTGCAAACTGCGCGGTGCCGGCTAGCCAGCCGTGTGCCTAGT

ATCTCAGGAGGCGAATGCTGGGGCTGTGCCGAGCGCCGTGACTTGACGGG

GTGTGACGCCGCCCGCACCTGCACAGCCGCCCTAGCATGGAGTCCAGCAG

GAAGCGGCTGGGCGGCCCGGCAGTAGCCACTGCCGCAGCCGCGGCGGCTG

TAGCAGCCGCGTCGCCGGCACCGGCAGTAGCAGGAGCGCCAGCGGT

>Contig301, SEQ ID NO: 19

CCTATAGCGGCGCGATTCGCCCTTGCTAGGGCCGCTGGGGCCAGGGCCGC

CGTGCGCTGACGTCCGCAGCGCACTCGGCGCCACGCCTGGTGACGCCGCC

GCGCTGACGTGCCGGTTAGACACGGAGCGGGAGGGGTAGGTGGCGAGGTC

GACCGGCTCATCATCAATGACCACCCTGCCGGCGGCGCTGACACGCCGGC

CCGCGCTGCCCGGCGCGTGTAAGCACCCCGCCACCGCCGCTGCTGGCGAC

GCCGCTGCGGCCGCTAACGGACTGGCGCTGTGGCCGCGCCGGTGTCGTGG

CTGAGCTGCTGTTCAGCATGGCGTCACGGGCGGTGCGGACACGGCCAGGC

GGCGCGCTGGCGGCGGCAACGGCGCCCACGCCCGCGGCACCCGCCGCAGG

CGAAATGCCTGCGGGCGTGTCGCGTGGCGGCACGGCCATGGCTGACGTGT

TGATTGTGGCGCGGTTGGCGGCGCCCTTGAAGAAGTCCGCGGCGGTTCGC

ACTGCGGGCATGTCGGACGGCAGCGCCCGCTCATCCTCTGCTGCGGCGTT

CCGCGGCCGTCCTTTGGTGCCGCCAGACACCGGCACCACGGTTGAGGCAA

AGTAGTCCAGCGCGGTGCCGAGGGCGGGAGGCAGGCCGTCGGCCACGGGC

GGCGGCACCGTCTGAGTGGCAGTCTCCACCTTGCTGGTGGAGGCGGGGGA

GGAGGGCGTGCCCACGGCGGCGGGGCGCGGCGAGAGGGAGGAAGAGGTGT

AGGGCTCAAGCGGCGGAGAGCTGGTTAGCGTGCCTGCGCTCTGCGCGTGC

GCGAGCGAGGCTGCGGCGCCGCCAGCGGGCGGAGCGCGGATGGCGCGGAC

AGGTGCTGACGTGGCAGCAGTGGCTGCGTGAAGGGCGAATTCGTTAACCG

CATATG

>contig302, SEQ ID NO: 20

TATCATGCGGTTACGATTCGCCCTTGGCCGCCGCCCGCCCGTGGGCTTTG

TATGCGGGTGGTCTTGCGCCACGATGCCGGAGTTGGGTGCCGTAGTCACA

TCAAGGTCGCAAGATCGAAACCCATCAGGAACGGTTCGGCTCCGTTACCT

GTGTTGGCACTGAACATACTTGTGCCGAACTTCCCCGAACGAGCGCCATC

TCGGCCTTCCTAGGTCGCTGCTCTACGGGTGAGGACGCTGGTGCGGCGGG

TTCTGATGGTTTCCCCGCGAGAGCTATCCTGCTTTCTAGAAGCCGGTCTG

CGAGCCAGTTGGCGCTGATGCGCCGGGGCAGGAGGAGGCCCCTGATTAGG

GAATGCGCGTCACCCAGCGCCGATCTGCGAGCCCGTGTTTCGAGGCGTTA

CCGTGGCCCAGTATGGCCGATGGTTGCAGACAACCCCCCTCCCCCAAATT

CGCTAACCGGGCTTCGGGCTGCACCCAACAGTGTGAGGGCCCTGCCCTGT

TGGTGCTGGTGTTTTGGGGTAGGAGTTGCACTTTGCAAAGTGGCAGTCAG

TCTGACGCCGACCCGCGGCTTAGGTGAGCAGCGCTAGCGTTTGCGGTGAG

CCTTGCTCGGGGTTCCTCCCCTCCTTTAGTGAGGCGAGGAGCATGGGGGT

CATTCGAGGTTCTCTCCTCGAGTGTGCGTACGTGTCTCGTGCGTTTATGA

AGCCCTGGCTTGCCCGCGGCTGTCATCCCACATGTAACCTCTATTCGCTA

ACCGCATGGGGGTCATTCGGGGATCTCTCCTCGGGTGAGCGTGCGTGTCT

CGTACGTTTTTGGGGCCCTGGCTAGTCCACGGCTGTCGTCCCACATGTAA

CCTCTATCAGCTAACCGCCATATCAGCTATACTCGTCTACTCCGCTGGGT

GTGCGTTAAGGCGCCTCGGCGCCCTGACCTTCAAGGCGAATCGCGGCCGC

TAATTCAATCGCCCTATAAGGAGTCGTATTACCATTCACTGCGTCT

Example 7. Chromatin Isolation from *Chlamydomonas reinhardtii*

*Chlamydomonas reinhardtii* cells of strains CC503 (cw92 mt+) and CC3491 (cw15 mt−) were inoculated from plate cultures into 100 ml TAP medium in a 500 ml flask and grown for 4 days, then spun down and resuspended in fresh medium and grown for another 1.5 days under lights with shaking (100 rpm). Cells (400 ml total for each strain) were collected by centrifugation in 500 ml centrifuge bottles at 9000 rpm for 15 minutes. The supernatant was discarded and the cells were resuspended gently in approximately 5 ml TAP medium, then the resuspended cells were added dropwise to liquid nitrogen with a 5 ml pipet to flash freeze the cells in small pellets. The centrifuge bottles were then rinsed with another 2 ml TAP medium which was then frozen in the same manner.

The frozen cell pellets were transferred into 50 ml polycarbonate tubes which had been prechilled in liquid nitrogen, each tube containing one ½ in stainless steel ball, then two ⅜ inch diameter stainless steel balls were added to each tube and on top of the cell pellets and the frozen drops were fragmented by shaking in a Spex GenoGrinder 6× for 1 min each at 1,500 rpm with re-cooling in liquid nitrogen in between shaking cycles. The ground cells of each strain were then added to 250 ml MEB buffer (1 M 2-methyl-2, 4-pentanediol, 10 mM PIPES KOH, 10 mM MgCl2, 4% (w/v) polyvinylpyrrolidone (PVP)-10, 10 mM sodium metabisulfite, 0.5% (w/v) sodium diethyldithiocarbamate, 0.2% (v/v) β-mercaptoethanol, 2% (v/v) Triton X-100, pH 6.0 with HCl) in a beaker, stirred vigorously to melt and suspend all cells, and then allowed to stir at moderate speed for 20 minutes at room temperature. At end of stirring both samples were very homogenous with few cell aggregates visible.

The cell homogenates were poured into 5×50 ml centrifuged tubes for each sample and spun at 4000 rpm for 10 min at 4° Centigrade in a Beckman clinical centrifuge (GH-3.8 swinging bucket rotor). The pellets were resuspended in 40 ml MPDB buffer (1 M 2-methyl-2,4-pentanediol, 10 mM PIPES KOH, 10 mM MgCl2, 10 mM sodium metabisulfite, 0.5% (w/v) sodium diethyldithiocarbamate, 0.2% (v/v) β-mercaptoethanol, 1% (v/v) Triton X-100, pH 7.0 with NaOH) in a 50 ml tube, then passed through a 40 ml dounce homogenizer for 15 strokes to break up remaining cell clumps. The cells were respun and washed with 50 ml each of MPDB buffer and then spun again; the last spin was done at 3,000 rpm for 10 minutes. Each pellet was resuspended in 40 ml of sonication buffer without detergent (the pellets did not resuspend completely; but there was no visible lysis of the nuclei) and the cells were respun at 3,000 rpm for 10 minutes. Each pellet then was resuspended in 2 ml sonication buffer without detergent by pipetting up and down with a 1 ml pipet tip, 1 ml of each resuspension was transferred to a 15 ml tube containing 5 ml sonication buffer (10 mM potassium phosphate, pH 7.0, 0.1 mM NaCl, 10 mM EDTA, protease inhibitor cocktail without EDTA was added to the buffer just before use at manufacturer's recommended concentration (Roche Cat #04693159001), either N-lauryl sarcosine (NLS) or sodium deoxycholate (DOC) was added to the buffer just before use at 0.1%); 6 ml total volume for each of 4 samples were sonicated with a Fisher Scientific Model 60 sonicator fitted with a ⅛ in tip point probe at full power (power setting 20) for 3×30 seconds with chilling on ice in between sonications. Each sample, well-homogenized with sonication, was distributed among 4×2 ml Eppendorf tubes and spun at 12,000×g, 4° C. for 10 minutes at 4° C. The clear supernatants were removed and distributed into 15 ml tubes (~6 ml total for each sample) and used for chromatin immunoprecipitation.

Example 8. Immunoprecipitation of Chromatin with the Anti-CenH3 Antisera

Three ml of the chromatin preparation was mixed with 300 µl pre-immune sera, gently agitated at 4° C. overnight. Non-specific immunoprecipitate was collected by centrifugation at 15,000 g at 4° C. for 5 mins. The supernatant was then mixed with 50 µl of anti-peptide IgG (peptide $NH_2$— RTKQSPARPGRKAQAEAC, SEQ ID NO:2), and incubated at 4° C. overnight. The immumoprecipiate was mixed with 100 µl BcMag Protein G Beads (BioClone Inc.) in 1× binding buffer (58 mM $Na_2HPO_4$, 42 mM $NaH_2PO_4$, pH 7.0) and left to bind for one hour at room temperature and then for an additional 12 hrs at 4° C. with moderate agitation. The bound complex was placed on the magnetic separator and the supernatant removed (a sample of the supernatant was retained for analysis). The beads were then washed with 10 volumes (1 ml) of wash buffer (57.7 mM $Na_2HPO_4$, 42.3 mM $NaH_2PO_4$, pH 7.0) by placing on a roller mixer for 10 mins, and then on the magnetic separator and the supernatant removed. This was repeated four times. The washed bead slurry (100 µl) with IgG:centromeric:DNA complex was then subjected to DNA purification.

Example 9. Isolating DNA from Protein/DNA Complexes

Method 1:
To wash the samples bound to magnetic beads, each immunoprecipitated sample was resuspended in 0.5 ml 1× phosphate buffered saline, the samples were placed on magnetic particle collector, the beads were collected, and the supernatant was removed and discarded. This was repeated three times for a total of four washes. Like samples were combined at the final resuspension step.

To deproteinate the samples, each sample was suspended in 150 µl of 10 mM Tris pH 8.0, 0.1 mM EDTA (TE) with 0.75% SDS and 100 µg/ml proteinase K. The samples were incubated at 50° C. with mild agitation for four hours. The samples were then briefly vortexed, then placed on a magnetic particle separator. Supernatants were removed and transferred to fresh tubes. ⅒ volume (15 ul) of 3.5M sodium acetate was added to each sample.

Each sample was extracted 1× with phenol/chloroform 1:1 pH8.0, and after centrifuging samples at 10,000 rpm for 10 minutes to separate the phases, the aqueous phases were transferred to fresh tubes. The samples were then extracted 1× with chloroform and centrifuged again for 10 minutes at 10,000 rpm to separate the phases. The aqueous phases were transferred to fresh tubes.

To precipitate nucleic acids, 1 µl glycoblue (Ambion) was added to each sample, samples were vortexed to mix. 0.6 volumes of 100% Isopropyl Alcohol (IPA) was added to each sample, samples were vortexed to mix. The samples were incubated at −20° C. overnight. The samples were centrifuged at the maximum speed for 25 minutes in an Eppendorf 5417R centrifuge that had been pre-cooled to 4° C., the supernatants were carefully removed and discarded, and the pellets were washed 2× with 80% ethanol chilled to −20° C. After two 80% ethanol washes, the pellets were washed with 100% ethanol and spun again. The supernatants were again carefully removed, then discarded. The pellets were dried in a rotovap with no heat. Once the pellets were dry, they were suspended in 50 µl of TE. The resuspended samples were quantified by qubit (Invitrogen) and characterized for size on the Agilent bioanalyzer 2100 microcapillary electrophoresis apparatus.

The DNA was fragmented to the optimal size range for 454 sequencing using a Covaris sonicator. The sheared DNA was subjected to titanium 454 sequencing (Roche) essentially according to the manufacturer's protocols.

Method 2: After washing the bead-bound samples as in Method 1, above, like samples were combined. and each sample was suspended in 500 µl of CNET buffer (2% CTAB (cetyl trimethylammonium bromide), 1.4M NaCl, 40 mM EDTA, 100 mM Tris 8.5, 140 mM beta-mercaptoethanol (added just before use)). The samples were suspended by mixing on a rotating wheel for 10 min at RT. Proteinase K was then added to 200 ug/ml and the samples were incubated for two hours at 50° C. with mild agitation.

For organic extraction of the samples, 250 µl of 7.5M guanidine was then added to each sample and the samples were briefly vortexed, then placed on the magnetic particle collector. After the beads the separated, the supernatants were removed and transferred to fresh tubes. ⅒ volume (75 µl) of 3.5M sodium acetate was added to each supernatant. and an equal volume of chloroform (750 µl) was added to each sample. The phases were mixed by inverting several times. The phases were separated by centrifugation at 10,000 rpm for 10 minutes, and the aqueous phases were transferred to fresh tubes. The tube with the organic phase was set aside for back extraction. The aqueous phases were then extracted with phenol/chloroform 1:1 pH 8.0. The phases were mixed and separated as before. The aqueous phases were transferred to fresh tubes. The tube with the organic phase was set aside for back extraction. The aqueous phases were then extracted a second time with chloroform. The phases were mixed and separated as before. The aqueous phases were transferred to fresh tubes. The tube with the organic phase was set aside for back extraction.

For back extractions, 250 µl of fresh TE with 25 µl 3.5M NaOAc was added to the original tube still containing the remaining organic phase from Extraction 1. The phases were mixed by inverting several times then separated by centrifugation at 10,000 rpm for 10 minutes. The aqueous phase was then transferred to the tube with the remaining organic phase from Extraction 2. The phases were mixed by inverting several times then separated by centrifugation at 10,000 rpm for 10 minutes. The aqueous phase was then transferred to the tube containing the remaining organic phase from Extraction 3. The phases were mixed by inverting several times then separated by centrifugation at 10,000 rpm for 10 minutes. The aqueous phases were removed.

To precipitate nucleic acids, 1 µl glycoblue (Ambion) was added to each sample, samples were vortexed to mix, and 0.6 volumes of 100% Isopropyl Alcohol (IPA) was added to each sample, and the samples were again vortexed to mix. The samples were incubated at −20° C. overnight and then centrifuged at the maximum speed for 25 minutes in an Eppendorf 5417R centrifuge that had been pre-cooled to 4° C. The supernatants were carefully removed and discarded, and the pellets were washed 2× with 80% ethanol chilled to −20° C. The Samples were spun each time to collect pellet and supernatants were carefully removed and discarded. After two 80% ethanol washes, the pellets were washed with 100% ethanol and spun again to collect the pellets. After removal of the supernatants, the pellets were dried in a vacuum concentrator with no heat. Once the pellets were dry, they were suspended in 50 µl of 10 mM Tris, 0.1 mM EDTA pH 8.0. The samples were quantified by qubit (Invitrogen) and characterized for size on the Agilent bioanalyzer 2100 microcapillary electrophoresis apparatus. The DNA was further fragmented to the optimal size range for 454 sequencing using a Covaris sonicator and the samples were sequenced using the Roche GD FLX Titanium series pyrosequencer.

From the two extractions a total of 828,388 and 751,683 high quality reads were generated with an average read length of 307 bp and 219 bp respectively. The reads were mapped to the most current version of the *Chlamydomonas reinhardtii* genome sequence (version 4.0) which was downloaded from the website at internet address: genome.jgi-psf.org/Chlre4/Chlre4.info.html. The reference sequence includes 88 scaffolds with total length of 112,305,447 bp. The reads from both extractions were mapped separately and together to the *Chlamydomonas* genome using the default parameters of the GS Reference Mapper within the Newbler software. The percentage of reads from extraction 1 and 2 that mapped to reference genome was 84% and 76% respectively. For every position in the reference sequence a normalized coverage score was computed by counting the number of sequenced reads mapped to that position. For example, reads that mapped to a unique locus in the reference genome contributed a score of 1 to each position they covered, and reads that mapped to multiple loci in the genome contributed a score of 1/no. of loci (1 divided by the number of loci) to each position they covered. Coverage peaks were defined as loci with a normalized coverage score of 25 or greater. The peaks were then extended in both directions as long as the normalized coverage score was 5 or greater to define the start and end loci of each peak. The peak coverage was defined as the maximal normalized coverage score of any loci between the start and end loci of each peak. The average coverage was defined as the average normalized coverage score of all loci between the start and end positions of each peak. The length was defined as the distance in bp between the start and end loci of each peak. The coverage area was defined as the sum of normalized coverage scores of all loci between the start and end positions of each peak.

Overall, 1,052 peaks were identified covering a total of 1.3 Mb of the reference sequence. The 100 peaks with the largest coverage as well as any peak with peak coverage of 100 or greater were used to define the set of 147 frequency peaks as provided in Tables 5 and 6.

TABLE 5

Selected Frequency Peaks

| Chromosome | Start | End | Peak | Peak coverage | Ave. coverage | Length | Coverage Area | Description |
|---|---|---|---|---|---|---|---|---|
| Chrom 1 SEQ ID NO: 21 | 14 | 3060 | 1216 | 1,334 | 545 | 3,047 | 1,659,213 | 26S ribosomal RNA gene |
| Chrom 1 SEQ ID NO: 22 | 1335855 | 1336219 | 1335984 | 111 | 77 | 365 | 28,167 | |
| Chrom 1 SEQ ID NO: 23 | 3052742 | 3057145 | 3053261 | 93 | 35 | 4,404 | 153,876 | X56231 *C. reinhardtii* transposon |
| 1 SEQ ID NO: 24 | 3366603 | 3366816 | 3366622 | 132 | 31 | 214 | 6,696 | |
| 1 SEQ ID NO: 25 | 3848803 | 3849305 | 3848828 | 449 | 61 | 503 | 30,467 | |
| 1 SEQ ID NO: 26 | 7694634 | 7697323 | 7695270 | 86 | 47 | 2,690 | 125,892 | |
| 1 SEQ ID NO: 27 | 9978798 | 9981684 | 9979880 | 93 | 46 | 2,887 | 132,802 | |
| 10 SEQ ID NO: 28 | 249 | 2789 | 2098 | 45 | 25 | 2,541 | 63,118 | |
| 10 SEQ ID NO: 29 | 4634 | 6903 | 6423 | 46 | 24 | 2,270 | 53,663 | |
| 10 SEQ ID NO: 30 | 1035928 | 1035967 | 1035928 | 154 | 154 | 40 | 6,160 | |
| 10 SEQ ID NO: 31 | 4607716 | 4607939 | 4607836 | 119 | 104 | 224 | 23,197 | |
| 10 SEQ ID NO: 32 | 5242640 | 5248262 | 5245942 | 40 | 15 | 5,623 | 86,426 | |

TABLE 5-continued

Selected Frequency Peaks

| Chromosome | Start | End | Peak | Peak coverage | Ave. coverage | Length | Coverage Area | Description |
|---|---|---|---|---|---|---|---|---|
| 10<br>SEQ ID NO: 33 | 6576722 | 6579068 | 6577982 | 88 | 39 | 2,347 | 92,237 | M60659<br>*C. reinhardtii*<br>telomere repeat<br>sequence |
| 11<br>SEQ ID NO: 34 | 117679 | 118353 | 117836 | 166 | 33 | 675 | 21,971 | |
| 11<br>SEQ ID NO: 35 | 536448 | 539162 | 538452 | 38 | 17 | 2,715 | 45,042 | |
| 11<br>SEQ ID NO: 36 | 1166430 | 1167933 | 1167165 | 86 | 37 | 1,504 | 55,874 | X56231<br>*C. reinhardtii*<br>transposon |
| 11<br>SEQ ID NO: 37 | 1168175 | 1170910 | 1168811 | 105 | 32 | 2,736 | 87,908 | X56231<br>*C. reinhardtii*<br>transposon |
| 11<br>SEQ ID NO: 38 | 1264340 | 1267936 | 1265205 | 32 | 20 | 3,597 | 71,616 | 184 bp<br>tandem repeat |
| 11<br>SEQ ID NO: 39 | 1278140 | 1283501 | 1282674 | 32 | 18 | 5,362 | 95,926 | 184 bp<br>tandem repeat |
| 11<br>SEQ ID NO: 40 | 1290543 | 1293223 | 1292603 | 26 | 17 | 2,681 | 46,006 | 184 bp<br>tandem repeat |
| 11<br>SEQ ID NO: 41 | 1307963 | 1313225 | 1308634 | 29 | 19 | 5,263 | 100,418 | 184 bp<br>tandem repeat |
| 11<br>SEQ ID NO: 42 | 2692217 | 2692829 | 2692533 | 230 | 25 | 613 | 15,202 | |
| 12<br>SEQ ID NO: 43 | 1059907 | 1060802 | 1060237 | 244 | 50 | 896 | 44,603 | |
| 12<br>SEQ ID NO: 44 | 2711973 | 2714333 | 2713674 | 61 | 22 | 2,361 | 52,202 | X56231<br>*C. reinhardtii*<br>transposon |
| 12<br>SEQ ID NO: 45 | 2716571 | 2718486 | 2717106 | 91 | 27 | 1,916 | 51,406 | X56231<br>*C. reinhardtii*<br>transposon |
| 12<br>SEQ ID NO: 46 | 4164533 | 4165084 | 4164612 | 1,397 | 120 | 552 | 66,063 | |
| 12<br>SEQ ID NO: 47 | 4559302 | 4563635 | 4560195 | 66 | 34 | 4,334 | 146,749 | |
| 12<br>SEQ ID NO: 48 | 6975776 | 6977273 | 6976511 | 151 | 58 | 1,498 | 87,603 | X56231<br>*C. reinhardtii*<br>transposon |
| 12<br>SEQ ID NO: 49 | 6977511 | 6979714 | 6978141 | 71 | 31 | 2,204 | 68,588 | X56231<br>*C. reinhardtii*<br>transposon |
| 12<br>SEQ ID NO: 50 | 6979759 | 6981850 | 6980136 | 90 | 33 | 2,092 | 69,203 | X56231<br>*C. reinhardtii*<br>transposon |
| 12<br>SEQ ID NO: 51 | 7449443 | 7450629 | 7449971 | 209 | 19 | 1,187 | 22,458 | |
| 12<br>SEQ ID NO: 52 | 8393285 | 8393475 | 8393365 | 123 | 64 | 191 | 12,222 | |
| 12<br>SEQ ID NO: 53 | 8447669 | 8447777 | 8447702 | 109 | 93 | 109 | 10,172 | |
| 12<br>SEQ ID NO: 54 | 8682813 | 8685765 | 8684173 | 42 | 23 | 2,953 | 68,805 | |
| 12<br>SEQ ID NO: 55 | 8686374 | 8689083 | 8687677 | 41 | 23 | 2,710 | 63,604 | |
| 12<br>SEQ ID NO: 56 | 8689316 | 8691546 | 8690210 | 41 | 22 | 2,231 | 50,019 | |
| 12<br>SEQ ID NO: 57 | 9347799 | 9349515 | 9349065 | 478 | 75 | 1,717 | 129,118 | |
| 13<br>SEQ ID NO: 58 | 536 | 3266 | 1774 | 121 | 45 | 2,731 | 122,321 | |
| 13<br>SEQ ID NO: 59 | 214114 | 214994 | 214727 | 116 | 53 | 881 | 46,834 | |
| 13<br>SEQ ID NO: 60 | 1025954 | 1026009 | 1025955 | 170 | 167 | 56 | 9,331 | |
| 13<br>SEQ ID NO: 61 | 1717738 | 1717790 | 1717747 | 137 | 127 | 53 | 6,705 | |
| 13<br>SEQ ID NO: 62 | 6583785 | 6588390 | 6587475 | 62 | 39 | 4,606 | 178,943 | M60661<br>*C. reinhardtii*<br>telomere repeat<br>sequence |
| 14<br>SEQ ID NO: 63 | 2329091 | 2331019 | 2329917 | 45 | 23 | 1,929 | 44,078 | |
| 14<br>SEQ ID NO: 64 | 3039879 | 3040915 | 3040284 | 251 | 49 | 1,037 | 50,440 | |

TABLE 5-continued

Selected Frequency Peaks

| Chromosome | Start | End | Peak | Peak coverage | Ave. coverage | Length | Coverage Area | Description |
|---|---|---|---|---|---|---|---|---|
| 14 SEQ ID NO: 65 | 4026081 | 4033708 | 4028549 | 1,841 | 486 | 7,628 | 3,707,055 | 26S ribosomal RNA gene |
| 14 SEQ ID NO: 66 | 4034008 | 4036741 | 4035266 | 1,182 | 538 | 2,734 | 1,471,603 | 26S ribosomal RNA gene |
| 14 SEQ ID NO: 67 | 4036883 | 4041504 | 4041092 | 630 | 426 | 4,622 | 1,970,913 | 26S ribosomal RNA gene |
| 14 SEQ ID NO: 68 | 4094729 | 4096739 | 4095910 | 1,502 | 528 | 2,011 | 1,062,391 | small subunit ribosomal RNA gene |
| 14 SEQ ID NO: 69 | 4102457 | 4109663 | 4103692 | 1,789 | 587 | 7,207 | 4,229,212 | 26S ribosomal RNA gene |
| 14 SEQ ID NO: 70 | 4111677 | 4114339 | 4112492 | 580 | 355 | 2,663 | 944,300 | 26S ribosomal RNA gene |
| 15 SEQ ID NO: 71 | 2747 | 4686 | 3539 | 94 | 48 | 1,940 | 93,120 | |
| 15 SEQ ID NO: 72 | 10595 | 13470 | 12863 | 177 | 68 | 2,876 | 194,676 | |
| 15 SEQ ID NO: 73 | 13820 | 16127 | 14601 | 49 | 20 | 2,308 | 45,698 | |
| 15 SEQ ID NO: 74 | 16642 | 18636 | 17485 | 93 | 47 | 1,995 | 93,107 | |
| 15 SEQ ID NO: 75 | 23875 | 25873 | 25372 | 115 | 50 | 1,999 | 99,210 | |
| 15 SEQ ID NO: 76 | 26255 | 28556 | 26549 | 75 | 28 | 2,302 | 65,101 | |
| 15 SEQ ID NO: 77 | 29071 | 33390 | 29914 | 93 | 35 | 4,320 | 150,638 | |
| 15 SEQ ID NO: 78 | 1165758 | 1168356 | 1167045 | 30 | 18 | 2,599 | 46,366 | |
| 15 SEQ ID NO: 79 | 1610293 | 1615949 | 1610749 | 36 | 16 | 5,657 | 92,662 | |
| 15 SEQ ID NO: 80 | 1844009 | 1846477 | 1846384 | 439 | 43 | 2,469 | 106,636 | X84663 C. reinhardtii TOC2 transposon-like sequence |
| 15 SEQ ID NO: 81 | 1866711 | 1870177 | 1869520 | 38 | 15 | 3,467 | 52,490 | |
| 15 SEQ ID NO: 82 | 2000410 | 2004921 | 2003313 | 41 | 16 | 4,512 | 73,185 | |
| 15 SEQ ID NO: 83 | 2008185 | 2009414 | 2009199 | 104 | 12 | 1,230 | 14,945 | |
| 15 SEQ ID NO: 84 | 2220856 | 2224476 | 2223249 | 41 | 17 | 3,621 | 62,317 | |
| 16 SEQ ID NO: 85 | 5451424 | 5451481 | 5451442 | 267 | 231 | 58 | 13,387 | |
| 16 SEQ ID NO: 86 | 5738770 | 5739932 | 5739403 | 185 | 31 | 1,163 | 36,600 | |
| 16 SEQ ID NO: 87 | 6358983 | 6359026 | 6358986 | 266 | 247 | 44 | 10,888 | |
| 17 SEQ ID NO: 88 | 421 | 801 | 594 | 105 | 72 | 381 | 27,478 | M60661 C. reinhardtii telomere repeat sequence |
| 17 SEQ ID NO: 89 | 4888725 | 4888785 | 4888741 | 290 | 247 | 61 | 15,080 | |
| 17 SEQ ID NO: 90 | 5008817 | 5012461 | 5011184 | 38 | 13 | 3,645 | 48,624 | |
| 17 SEQ ID NO: 91 | 5037832 | 5041096 | 5040320 | 60 | 18 | 3,265 | 59,913 | |
| 17 SEQ ID NO: 92 | 6385534 | 6387306 | 6386763 | 285 | 36 | 1,773 | 63,527 | |
| 2 SEQ ID NO: 93 | 460 | 3534 | 1265 | 216 | 68 | 3,075 | 210,023 | |
| 2 SEQ ID NO: 94 | 5116 | 8661 | 6006 | 57 | 36 | 3,546 | 125,883 | |
| 2 SEQ ID NO: 95 | 3187813 | 3187912 | 3187864 | 173 | 160 | 100 | 15,993 | |
| 2 SEQ ID NO: 96 | 6189188 | 6192525 | 6189821 | 38 | 14 | 3,338 | 48,334 | |
| 2 SEQ ID NO: 97 | 6200792 | 6203665 | 6201882 | 38 | 18 | 2,874 | 51,157 | |
| 2 SEQ ID NO: 98 | 6779340 | 6779813 | 6779502 | 427 | 58 | 474 | 27,369 | |
| 2 SEQ ID NO: 99 | 9238305 | 9241333 | 9239006 | 35 | 19 | 3,029 | 59,035 | |

TABLE 5-continued

Selected Frequency Peaks

| Chromosome | Start | End | Peak | Peak coverage | Ave. coverage | Length | Coverage Area | Description |
|---|---|---|---|---|---|---|---|---|
| 3<br>SEQ ID NO: 100 | 1245497 | 1246199 | 1245965 | 130 | 25 | 703 | 17,828 | |
| 3<br>SEQ ID NO: 101 | 1249804 | 1252509 | 1251206 | 42 | 21 | 2,706 | 56,068 | |
| 3<br>SEQ ID NO: 102 | 3092783 | 3092932 | 3092856 | 100 | 87 | 150 | 13,014 | |
| 3<br>SEQ ID NO: 103 | 7009377 | 7009422 | 7009383 | 106 | 106 | 46 | 4,853 | |
| 4<br>SEQ ID NO: 104 | 870773 | 871081 | 870926 | 324 | 91 | 309 | 28,002 | |
| 6<br>SEQ ID NO: 105 | 889319 | 889432 | 889366 | 488 | 217 | 114 | 24,741 | |
| 6<br>SEQ ID NO: 106 | 2260305 | 2261656 | 2260676 | 763 | 41 | 1,352 | 55,473 | |
| 6<br>SEQ ID NO: 107 | 2336039 | 2336085 | 2336041 | 191 | 186 | 47 | 8,720 | |
| 6<br>SEQ ID NO: 108 | 3654094 | 3656692 | 3655658 | 105 | 37 | 2,599 | 96,371 | X56231<br>*C. reinhardtii*<br>transposon |
| 6<br>SEQ ID NO: 109 | 3656757 | 3658217 | 3657588 | 162 | 59 | 1,461 | 85,761 | X56231<br>*C. reinhardtii*<br>transposon |
| 6<br>SEQ ID NO: 110 | 3658461 | 3660208 | 3659218 | 146 | 47 | 1,748 | 82,296 | X56231<br>*C. reinhardtii*<br>transposon |
| 6<br>SEQ ID NO: 111 | 4221133 | 4221184 | 4221149 | 183 | 176 | 52 | 9,143 | |
| 6<br>SEQ ID NO: 112 | 6411072 | 6414565 | 6412816 | 49 | 16 | 3,494 | 57,406 | |
| 7<br>SEQ ID NO: 113 | 843560 | 843614 | 843572 | 772 | 757 | 55 | 41,651 | |
| 7<br>SEQ ID NO: 114 | 2563912 | 2564270 | 2564118 | 166 | 33 | 359 | 11,746 | |
| 7<br>SEQ ID NO: 115 | 2839539 | 2840115 | 2840010 | 139 | 28 | 577 | 16,173 | |
| 7<br>SEQ ID NO: 116 | 3894553 | 3895894 | 3895137 | 144 | 60 | 1,342 | 80,601 | X56231<br>*C. reinhardtii*<br>transposon |
| 7<br>SEQ ID NO: 117 | 3896137 | 3900499 | 3896767 | 167 | 46 | 4,363 | 202,487 | X56231<br>*C. reinhardtii*<br>transposon |
| 7<br>SEQ ID NO: 118 | 5095711 | 5096152 | 5095876 | 111 | 67 | 442 | 29,618 | |
| 7<br>SEQ ID NO: 119 | 5551228 | 5555200 | 5553406 | 56 | 31 | 3,973 | 124,395 | |
| 7<br>SEQ ID NO: 120 | 5557131 | 5561101 | 5558225 | 56 | 32 | 3,971 | 128,660 | |
| 8<br>SEQ ID NO: 121 | 2495125 | 2497472 | 2495588 | 362 | 143 | 2,348 | 336,656 | 28S ribosomal<br>RNA gene |
| 8<br>SEQ ID NO: 122 | 4139587 | 4143715 | 4141199 | 1,844 | 614 | 4,129 | 2,534,009 | 18S ribosomal<br>RNA gene |
| 8<br>SEQ ID NO: 123 | 4143820 | 4147990 | 4147009 | 1,331 | 508 | 4,171 | 2,118,701 | 26S ribosomal<br>RNA gene |
| 8<br>SEQ ID NO: 124 | 4182479 | 4183397 | 4182772 | 253 | 126 | 919 | 115,950 | |
| 8<br>SEQ ID NO: 125 | 4188343 | 4189011 | 4188486 | 227 | 140 | 669 | 93,533 | |
| 9<br>SEQ ID NO: 126 | 800354 | 803135 | 802629 | 33 | 18 | 2,782 | 50,549 | |
| 9<br>SEQ ID NO: 127 | 830320 | 835132 | 834509 | 28 | 13 | 4,813 | 61,269 | |
| 9<br>SEQ ID NO: 128 | 3730713 | 3731517 | 3731142 | 162 | 19 | 805 | 15,287 | |
| 9<br>SEQ ID NO: 129 | 4659396 | 4662211 | 4661722 | 293 | 30 | 2,816 | 84,142 | |
| 9<br>SEQ ID NO: 130 | 4731519 | 4732730 | 4732442 | 348 | 202 | 1,212 | 244,279 | |
| scaffold_18<br>SEQ ID NO: 131 | 1271075 | 1272518 | 1272114 | 71 | 38 | 1,444 | 55,305 | |
| scaffold_19<br>SEQ ID NO: 132 | 3207 | 4875 | 4172 | 71 | 37 | 1,669 | 62,537 | |
| scaffold_19<br>SEQ ID NO: 133 | 711803 | 711977 | 711895 | 142 | 119 | 175 | 20,794 | |
| scaffold_20<br>SEQ ID NO: 134 | 9817 | 11975 | 10543 | 81 | 50 | 2,159 | 106,892 | |

TABLE 5-continued

Selected Frequency Peaks

| Chromosome | Start | End | Peak | Peak coverage | Ave. coverage | Length | Coverage Area | Description |
|---|---|---|---|---|---|---|---|---|
| scaffold_20 SEQ ID NO: 135 | 95743 | 95784 | 95746 | 1,388 | 1,322 | 42 | 55,544 | |
| scaffold_21 SEQ ID NO: 136 | 194224 | 195160 | 194933 | 263 | 51 | 937 | 47,853 | |
| scaffold_21 SEQ ID NO: 137 | 314592 | 315574 | 314918 | 218 | 39 | 983 | 38,730 | |
| scaffold_21 SEQ ID NO: 138 | 317723 | 318564 | 318234 | 205 | 36 | 842 | 30,430 | |
| scaffold_22 SEQ ID NO: 139 | 404562 | 408933 | 408296 | 105 | 29 | 4,372 | 128,362 | X56231 *C. reinhardtii* transposon |
| scaffold_22 SEQ ID NO: 140 | 409185 | 410249 | 409947 | 86 | 47 | 1,065 | 50,076 | X56231 *C. reinhardtii* transposon |
| scaffold_22 SEQ ID NO: 141 | 428557 | 430347 | 429092 | 92 | 27 | 1,791 | 48,393 | X56231 *C. reinhardtii* transposon |
| scaffold_25 SEQ ID NO: 142 | 63632 | 64707 | 64202 | 128 | 19 | 1,076 | 20,315 | |
| scaffold_25 SEQ ID NO: 143 | 150681 | 152929 | 151339 | 47 | 22 | 2,249 | 49,366 | |
| scaffold_29 SEQ ID NO: 144 | 381 | 4508 | 2894 | 60 | 30 | 4,128 | 122,395 | |
| scaffold_32 SEQ ID NO: 145 | 12470 | 14453 | 13554 | 70 | 42 | 1,984 | 84,062 | |
| scaffold_33 SEQ ID NO: 146 | 29770 | 30775 | 30526 | 100 | 38 | 1,006 | 38,661 | |
| scaffold_34 SEQ ID NO: 147 | 87184 | 88224 | 87635 | 176 | 29 | 1,041 | 30,095 | |
| scaffold_35 SEQ ID NO: 148 | 5230 | 10027 | 6130 | 40 | 16 | 4,798 | 74,513 | |
| scaffold_35 SEQ ID NO: 149 | 19703 | 23600 | 21109 | 59 | 18 | 3,898 | 70,983 | |
| scaffold_35 SEQ ID NO: 150 | 29953 | 30555 | 30337 | 134 | 24 | 603 | 14,514 | |
| scaffold_35 SEQ ID NO: 151 | 161264 | 161682 | 161504 | 146 | 76 | 419 | 31,940 | 112 bp tandem repeat |
| scaffold_35 SEQ ID NO: 152 | 161691 | 161963 | 161846 | 138 | 76 | 273 | 20,800 | |
| scaffold_36 SEQ ID NO: 153 | 63431 | 65320 | 64382 | 223 | 30 | 1,890 | 57,437 | |
| scaffold_37 SEQ ID NO: 154 | 76260 | 76485 | 76448 | 115 | 27 | 226 | 6,091 | |
| scaffold_38 SEQ ID NO: 155 | 118982 | 120197 | 119951 | 343 | 179 | 1,216 | 218,138 | M60661 *C. reinhardtii* telomere repeat sequence |
| scaffold_39 SEQ ID NO: 156 | 34472 | 34740 | 34659 | 145 | 47 | 269 | 12,686 | |
| scaffold_39 SEQ ID NO: 157 | 38426 | 39339 | 38626 | 225 | 35 | 914 | 31,963 | |
| scaffold_39 SEQ ID NO: 158 | 94144 | 95380 | 94287 | 182 | 22 | 1,237 | 26,620 | |
| scaffold_39 SEQ ID NO: 159 | 110999 | 112873 | 111678 | 58 | 25 | 1,875 | 47,419 | |
| scaffold_39 SEQ ID NO: 160 | 113195 | 116132 | 114175 | 43 | 19 | 2,938 | 55,499 | |
| scaffold_49 SEQ ID NO: 161 | 11 | 2233 | 805 | 243 | 76 | 2,223 | 169,393 | |
| scaffold_50 SEQ ID NO: 162 | 32364 | 34312 | 33557 | 137 | 43 | 1,949 | 83,242 | X56231 *C. reinhardtii* transposon |
| scaffold_50 SEQ ID NO: 163 | 34557 | 38912 | 35187 | 171 | 47 | 4,356 | 203,904 | X56231 *C. reinhardtii* transposon |
| scaffold_58 SEQ ID NO: 164 | 4193 | 9724 | 6991 | 40 | 23 | 5,532 | 124,470 | |
| scaffold_71 SEQ ID NO: 165 | 9120 | 12607 | 11863 | 30 | 15 | 3,488 | 52,146 | |
| scaffold_77 SEQ ID NO: 166 | 3811 | 4295 | 3898 | 109 | 45 | 485 | 21,820 | 112 bp tandem repeat |
| scaffold_80 SEQ ID NO: 167 | 13170 | 15305 | 14735 | 185 | 17 | 2,136 | 36,889 | |

TABLE 6

Sequences Corresponding to Frequency Peaks (SEQ ID NOs 21-167)

>SEQ ID NO: 21

ATACCCAATCCTGAAAAGCGATTTCCACATACATAAACGCCACCCACTGGACTATCTAAAATCAAACAGCACCACGG

AACCTTTACCTACCGACCTACCCACCTTGCCCTACCCTACCTAACCTCTACCCACCCACCCACCCACCCAGGACACA

TGCGCCACTGCCTTACAAGATAGCTTCCAGCGCCAGAGTCGAACTGGCCACTAAGCCACACGCATACACACATACCA

CACTAGGCCGCCTAAGTAAGGGCACATGCATGCTGTTGCTCTCACTCGCACACACAGGGAAGGTACCCTTGAGCA

CTTTGGCTGTGTGGGGAGGAGGGGCAGTGCATGCACACGCATGTGGGCACTTAGACGGATTCGGCGGCGTTGGCAC

GCGCTCAGCTCAGCTACACCACTTGGAAGAGAGAGAGAGGGCCCTCCCTGGAGCTGTCGCTCCGAGAGGAGGAGGGG

TTGCCCCGAAGGGCAGTGACAAATCTTAGCAACACGGGATGAATCTCAGTGGATCGTAGCAGCAAGGCCACTCTACC

ACTTACAATACCCAGTTGCAACAAAGTCGTCTACAGAGGATTTACCCCAATGACGAGTGGAATTGTCATGCTTGGCG

CCTGCTTCGGCCATGTGGACCTAACAGGGGAACCAACGGGTATGCTCCAGCATCCGCACAGGCGGATGTATCCTTAG

TCGGGTGACATCATTGGGTAAGTGACTCCGCACCTAGCACGTCTTCTGACTTAGAGGCGTTCAGTCATTAGACTACA

GATGTTAGCTTCGCCCCATTGTCTTTTCAGACAAGGGCATTACCAATTATCTGACTCGGCGGTTCCTCTCGTACTGA

GCCGAATTACTATGGCGGAATCGGTCCAACAGTAGGGTAAAACTAACCTGTCTCACGACGGTCTAAACCCAGCTCAC

GTTCCCTATTAGTGGGTGAACAATCCAACGCTTGGTGAATGCTGCTTCACAATGATAGGAAGAGCCGACATCGAAGG

ATCAAAAAGCAACGTCGCTATGAACGCTTGGCTGCCACAAGCCAGTTATCCCTGTGGTAACTTTTCTGACACCTCTA

GCTTCAAATCCCGAAAGGCTAAAGGATCGATAGGCCATGCTTTCACAGTTTGTATTCGTACTGAAAATCAAATCAA

ATGAGCTTTTACCCTTTTGTTCTACACGAGATTTCTGTTCTCGTTGAGCTCATCTTAGGACACCTGCGTTATCTTTT

AACAGATGTGCCGCCCCAGCCAAACTCCCCACCTGACAATGTCTTCCACCTGGATCGACGTGCAAAAGCCGTCTTAG

AGCTAGAAGCAGGGACAGAGTCCCGCCTCCAAGTAATGGAATAAGTAAAACAACGTTAAAAGTAGTGGTATTTCACC

GTCGCCGAAGCTCCCACTTATTCTACACCTCTTAAGTTATTTCACAAAGTCGGACTAGAGTCAAGCTCAACAGGGTC

TTCTTTCCCCGCTGTTTATTCCAAGCCCGTTCCCTTGGCTGTGGTTTCGCTAGATAGTAGATAGGGACAGTGGGAAT

CTCGTTAATCCATTCATGCGCGTCACTAATTAGATGACGAGGCATTTGGCTACCTTAAGAGAGTCATAGTTACTCCC

GCCGTTTACCCGCGCTTGGTTGAATTTCTTCACTTTGACATTCAGAGCACTGGGCAGAAATCACATTGTGTCAACAT

CCTTTAGGACCATCACAATGCTTTGTTTTAATTAAACAGTCGGATTCCCCTTGTCCGTACCAGTTCTGAGTTGGCTG

TTCGTCGCCTAGGGAACGCCGAAGCTTCTACAGCCGTCCACCCAGGACACGCAGCAGTCCGCCCAGCCGTTTCCAGC

TGGGTAGACCACCGCAGTCCCGAGCTTCGCAGCTGCAGACCCCTAGGCCCAGCCCTCAGAGCCAATCCTTTTCCCGA

AGTTACGGATCCATTTTGCCGACTTCCCTTATCTACATTGTTCTATCGACTAGAGGCTGTTCACCTTGGAGACCTGA

TGCGGTTATGAGTACGACTTGGCAAGATCGGGAATGCTCCCCCGGATTTTCAAGGACCGTCAACGGCGCGCCGGACA

CCGCGAGAAGTGCGGTGCTTTACCAACGTCTGAGCCCTATCTCCGAATGATTCGATTCCAGGGCCTTCGCGTTGTTA

AAAAGAAAAGAGAACTCTTCCCAGGGCCGATGCCGATGTCTCCGGGCTCGCTTGCGTTACCGCCAGCCGCCTTGTCC

AAGTAAGGGAATCTTAACCCTTTTCCCTTTCGATGGGCAGCGCGAATCGCGCTCTTCACACAGGATTACCCCATCTC

TTAGGATCGACTAACCCATGTCCAATTGCTGTTCACATGGAACCTTTCTCCACTTCAGTCTTCAAAGTTCTCATTTG

AATATTTGCTACTACCACCAAGATCTGCACTAGATGCCGATTCACCCAGGCTCACGCCAGAGGCTTAGTCTCGACAC

CCACGCCCTCCTACTCATGGAAGCGTCGCACTTGCTTCCATGGCCGAGTATAGGTCACGCGCTTAAGCGCCATCCAT

TTTCGGGGCTAATTGATTCGGCAGGTGAGTTGTTACACACTCCTTAGCGGATTTCGACTTCCATGACCACCGTCCTG

CTGTTTATATCAATCAACACCCTTTGTGGGATCTAGGTTAGCGCGTAGTTTGGCACCTTAACTCGACTATCGGTTCA

TCCCGCATCGCCAGTTCTGCTTACCAAAAATGGCCCACTTGGAGCTCACATTGAATGTGCCGGTTCAATTAAGCAAC

CGACACGTCTTACCTATTTAAAGTTTGAGAATAGGTGAAGGATGTTTCATCCCCGAACCTCTAATCATTCGCTTTA

CCCGATAAAACTGATCAAGCTCCAGCTATCCTGGGGGAAACTTCGGAGGGAACCAGCTACTAGATGGTTCGATTAGT

TABLE 6-continued

Sequences Corresponding to Frequency Peaks (SEQ ID NOs 21-167)

CTTTCGCCCCTATACCCAAGTCTGAAAAGCGATTTGCACGTCAGCACATCTACGAGCCTACGAGGCATTCTTGTGAC
AATCTCGTGCGGCTGCTGGCCCTCTGGAATGCCTTTGGAAATTC

>SEQ ID NO: 22

CACGCGGCCGGCCGGTGGCCGTAGGTCACGTAGACTACGCTTTTGCTAGCGTACAACACCTAATGACTGATGTACCT
TCTGGTATGATCTTGCGTTACGCTCACGCTAACGGCGCCAGCTTGTTCTTTATTGTAGTCTATTTGCACGTATTGCG
TGGTATGTACTACGGTAGCGGCGCTCAGCCACGTGAGATCGTCTGGATCAGTGGTGTCGTTATCTTGTTGGTAATGA
TTATCACCGCCTTCATTGGTTATGTACTACCATGGGGCCAAATGTCTTTCTGGGGTGCTACCGTAATTACTAGTTTG
GCTACTGCCATTCCAGTAGTAGGTAAACACATCATGTACTGGTTGGCCGGCCGACCG

>SEQ ID NO: 23

GGACAATTTACGGCGTACGTGCCCTCATGATACAGCCTGTGCGCCGCAGGCAACGGGCTCCGCGCCCTTGCTCCATG
GACACTTCACGGCGTACGTGCCCTCATGATACGGCCTGTGTGCCGCAGGCAACGGGCTCCGCGCCCTTGCTTCATGG
ACAATGCGCCGCGTACGTGTTCTTATGATACGGCCTGTGCGCCGCAAGCAACGGGCTCCGCACCCTTGTTTTATGGA
CAATTCACGGCATACGTGCCCGTATGATGTGACCTGTGTGCCGCAAGTAACGGCTTCGCACCCTTGCTTTTGGGTAA
TAGATGGCATACGTGCCCTTATGATACGACCTGTGTGCCGCAAGCAACGGGCTCCACACTCTTGCGTTGTGGATTAT
AGACGGCATTGAAATGCTTACGTGCCTTCGTTGTACATGCCTTTGCGTTGTGGACAATGTGTGGTCTGAGCGCCACG
TTCGGATACGGCGTGTGTGCCGCCAGCAACAGGCTTTGCGCCTCGCATCATGTGTCTTGCGATATGGCCCGTGTGCC
GCATGCAATTATGCTGCCTGCCCTGTCGTTATGGACGCTTCGACTTGTTGCGTGCCCTGCTGCGTGCCCTGTCGCAA
TACGCCTTGAGTGTACCGTGCACGGCAAGCCTGCGCCTCGCTATTGCTTCGTGTTGACAACGGAGCGGGCTTACGTG
ATCATGCGTCACCCTGTACGTCTTGAGGTCCGCACGCACATCATACTATCACGCGGCATCACCCTTGTAGTTTGGCT
GACGCACCCCAAGCCAACCTATATGCATTCGATGTGTGCGCTAGGCCCAAGTGCCGAATTTGTTTTTCCGGATATTT
CGCCCTCAGTGAGCGATGTGGAGTTTTGTGCAGTTCGGCCAGCATGCTATTGCCCAGCCAATAACAATACCGCATGA
CGCATAAGCATGCCTTCGTGCCCTGCACCAGGCATCGGACGCTGTGTCACGCAGTGAGCCCGACCCTGCGCAACCAA
CATTTTGTTGCGAGATACGGTCGGAGCTGGGATTACAGCCTGCCTGGTGGGTTTGGATGGCGCCCGTGTGTTCGGCT
GGGCTGTTGCTGCTCGCGGTGGGGCCCACCACCAAGTCACGGCACCCATCCGCCCTCCCCTCTTGTTGGCCCACCCG
CCTGTACACATGCCAGTCACCCGCTCGCCATCCTGTGAAAGCGGGTAGCCGACTTGGCAAGCGCTTTTCCTGACACT
TGGCGCAGGTTTGAGTGGGATACCAGAATGGTCTGAATGTAGTTGTTGGATAACCAGTACACTGCGGTGTGTAGCTG
GTTAGCGGGAGTGCCGTGCATGAAACACGCTACTCGACCCGCCATGCCCGCGCGATGGTACCACCAACCGTTCAACC
CAGATCCATGCCGGGGTAGCATCGACCCCACAGTCAGACTGATAGCTCCTATCCAGGTGTCAGGCGCCATGTATGTA
TCTGTGGACGCGTCAAGCTGGCTTGTGCCGTAGCGTTGGCCGCCTGTATGGCACGCCCGGCATCTGTGTCACGTTAT
GGCCTCATGCTTACCGTAGTCACGCGGCTTGCGTGCTGTGCGGCACGCTCCCTGCCAATCCTTCAGGACATGTATGC
ATACATGTTACTTCGTCAGAGCCATAGCAGGGGCAGCGTGTTCTGTCAATGCCTCATGAACCCAGAGACCCAAGCCA
ACGTACGCATTAGTTCCGCAACGCACGTCAATGCCAACTGTATGTCGCCTGCCCACTCGCGAGTGGACGCCTAGG
GTACCAACCTTGGTTCCCTTCAGCCCCGGCCTTACTTCACCCGGCGGGCAATTACTTATCACCGAAGTGCTAGGAG
CAGTGTGCTATATGTCATTACTATTAAGTAAGAGCGTATGGCGACACAGGCTCACATGTGGGTAGCCAGGCTGACAG
TGCCCTGCGGGCTTGGCAGTCGGCAGGCATCCCAACTCAGCCCGGCCTCCTCACAGCAGTACCACGACGTGCCCGTA
CGTGGTCGAGTGCGGAGTTTGGCTGCCGGCGTGGCTGTATCATCTCTCACATTGGATGACCCATCCGCCACTGCTGT
TCAGTACTGGCACGTCCCTCGAGTCGCTCACCCACCGGCTCCGCCCAGCGTTCGCTCCCTTTCGCTGGGCCGGGCC
CGTGGCGCATCCAACCCGCCATCGCGCCCCGAGTGCTCCTTATTTCCTCCCATCACTACGCCTTCTATCACTATAG
ATACATTGCGCGTTCCACGCGTGCCGGGTATCCTTCACCCCTCCGCGCCGCTCGACCAGGCCAGCCTTGCTGGGGTT

TABLE 6-continued

Sequences Corresponding to Frequency Peaks (SEQ ID NOs 21-167)

GCTGAGGTGTTACCCTTCATGTTGCCCTCCCTGCTATTACGGTACACCCCACAGCCGCCGTGGCGTACGGTATCGGC
ACGTACGGGACATTGTGTGCATGCATCCCCGCGGCGTTTGGAGGCAAACATTCACGTGCGCGCCTGTCCTGCGTCCG
CCGGGGTGATGCTATCTATGGGCGTACCTACTGCTTGATGGGTAGTGACTCTTATGCAAGACACTGCAAATCTCAAG
CATGGCACCTAGCTAGCAAGAAAGAAATTAGTGTTCGTGGCCATGCTGCACGGCTGGGCATGGCTGCCCGCATCCTA
CACCACGACGGCGCGGGTGAAGGGCAGGTTGCCGCGCGTGACTCGCGTACGTAAAACCGCTCTAGTGTTGCAACTCG
CGCCTTCTCCTGCGTGGCGCATGTTGGCTAGCCTGTCCCAGCTTCGAGTCACGACGTTGTTATTATTCCCAAGGTTG
TTCCGAGCAGCCTAAACGTCAACACGTGTTATGGCATGGCCCTGGGGGCCGGTAGAGAGTACCGAGGTCTCCAGTGG
TTCGTGCCAACACGTGCCAACACGCACTGTTACCTTTCCTGGGCACACGGACGGCCACAGCTGCCCAGAAGCCACAC
ACCTGAACAAGGATGCATGTGTTTCCCTGTAACGCCCCGGCGTCGTCTGCATGGCTGGCGCACGCGGGACAACGCAT
GTGTGTTTCTGTCGTGGCCATTGGTGCACCTGATACGTTTGTGAGTCTGGTATCATGGCCCTTGCAAAGCCAGTCGT
GTTCCTATTGCTGCTTGTCTTCTGGTAGTGACCATTGGCCGCCCATGACCGACGGAGTGTGGCGCTGTCAGGCCCCG
CGTTGGCGTCGCCCTGCGCCTGCAGCAGGTGCCGGCGGCGCCTCCGGCGGCGCTCATCCCCGCGTGATGGTGCTGCT
CGTGCAGCCAATATCCCCAAGCACGAAGCTCGTTCTATTGACCGCTGTCGAGTGTGCAACTAGGACCGTACGTTCGT
GCGCAAGCTAGGCGATGGGCGGAGCGCTCCGCGGTGTTCGAGACACATGATTTCGGTAGCGCAAGGGCACGAACGCC
ACCGCCATCACCGCCGACCGCACCTTGGTTTGCATGACCGGCCGTTGGGCCGAGCGCTTTGCGAGAAGAGCTGCATA
CGCGAAGCCAATCAAGCCCAGCCACCAGGGCTGCCGTCGCCCGCACCATGACCTCCCGGCGTTGAGGACTACTACCA
AACTCTGGCAGCACTTTCGGCCACTAGTGCAACCTCAACACGGGCGGGCTGGGGCGGGCACGGCGGACTTGGTGGGG
TTATCGGGAGCTGCGAGGCCGGAGGTAGGAGGCCGCTGAGGGCCACGAATGAGTTGCTAGGCCGCTTGAGGCATGAG
TGGAGGCTATTGTCGGTTTGAGAGATTGGGATTGTCGTTTGGGGCCGTGGCGGTTTGTAACGCTACACGGCAGTAAG
GAGTCAATAAGCGCTGACTTATCGCAGCGCAGTGGAGATAAGTCTAGTTATTGCGACGTAACTGCCGTGTTGCGTTA
GAGTCACGCACGGCGCAGGACGCTCGGGTACGTGCCTGTGCATGGGCCGAACCGAGCTGGGTCTTGTACGCGTCAG
GAGCACACGGCGCCTTATCTGCCGTTGTGCTTCTGTACTGTATTTCGGATCGTCCCTCTGCCGGGACGGTGACAACC
CACCCGCCCCCCCTGGTGCCGCCGCGGATTAATGTGGTGGCACCCGTGGGCGCTGCGGCGTGCGTGGTTGTCTGGAC
TCTGCTGCTATCAGGCACTTCATACATGCGACACACCCAGTACTGGCAGCACTTTCGGCCACTAGTGCAACCTCAAC
ACGGGCGGGCTGGGGCGGGCACGGCGGACTTGGTGGGGTTATCGGGAGCTGCGAGGCCGGAGGTAGGAGGCCGCTGA
GGGCCACGAATGAGTTGCTAGGCCGCTTGAGGCATGAGTGGAGGCTATTGTCGGTTTGAGAGATTGGGATTGTCGTT
TGGGGCCGTGGCGGTTTGTAACGCTACACGGCAGTAAGGAGTCAATAAGATACTAATAGCGGATGTCCGTGGCTCGA
CAGGTCGACTCACCC

>SEQ ID NO: 24

GGGACGGGCAGAGGAGGCAGTTGCCTGCCAACTGCCTAGGCAAGTAAGGTGGCTGTATGGCGTGGCGTCACGATGAA
CATGACGTACGAGTGTGTGGCTGGAGCGGAGCAAGATCATTTGTACGCATGCGTGGTGAAGGATCTCTTGTCTGCAG
CCGACCATCTCAAACCGCGATCAAGATGAGCCGCACGCCGCGTGCCTTACTCGTGTCGCT

>SEQ ID NO: 25

ATCCCGAAGGGGACAAATTTATTTATTGTCCCGTAAGGGAAAGTCGTGGAGTATTTAATACAGCTTTAGTTGAAATC
TTCGGTGATGACGCATGTCGTCAAGGTCAAAGGACGGCATGGCCCGCCCGGCGTTGTGCACCCTCCCCTGCTGTGCA
CAGACGCTGTTGCAGTGAGGAGTGCCACTGTGCCGGGTGCGCCGCCGCAGTAATGGGGTCCCGCAGCTCCAGGTACG
AGCGTCAGCTTCAGCGGCCAGCTGACGTGCGAGCCCAGTAGCCATTCCCCTGGACTATAATCTGTGCGTCTGGCACG
ATTTCCTCGTAAAGCGCAAAATTCTGCCAGCCCATCCTCCTCAATCAGGATCGTCCTGGCCACGTGGGTTCATTCCT

TABLE 6-continued

Sequences Corresponding to Frequency Peaks (SEQ ID NOs 21-167)

GCCTTTCTACCTCGTGCACCCGCAGCCCTGCGACAAAGCTCACAGCTCCAGGGCGCTGATGCCTGCGTGCAGTTGCT

CCGCGGCCTGCTGCTGCGGGCCCGAGCACGCAAAAGGGGGG

>SEQ ID NO: 26

AAGAACATGCCACTCAGGCGCCTTGTCACATGGGGGGTGCCACCCAGCCAACCGCACACCACGCCTGTCACTCTCAG

CCCTGTGTGGACCTCTTTCACATCTTCACATGTCCCTTTTGTCAAACATGTTTGTGATGCAACCGCAAGCTGGCAGC

TGCAGTGCCACCACAGCCCTTGCAGTCCAACAAGTGGCTTTGCATGTCAGGACAAGTGCGCATTCCCCCCCGCCCTC

CCCTCTAGTGGGGCAGGGCCTGCTAGTATCATGCAAACTGTCAAGTAATGTGCAGCCATGCTGAGCACATTCAATTT

GCACCATATGTGAAACGATGGGCTTTGGGAGTGCAAGCAGCAGCAGCCACAGCATGTTGGCGAGTCAAGTCCTCTTG

CAGGCCTGCAGACCACACCAGTCATGACAAGTCCGCAACATCTGCACCTCAGCGAGGTCCAGCTCATGCCAGCAATA

CAACAGCAGTCGCTATATGTATTGAACCGATTGCCGGGCCTAACGGCTGCGTGGCTGGACTGCTGCACTCACTCACG

TGGCCCCTGGTGCAGGGTGGCCTAAATCAGGGTTTCAAGGGGTTTTGCAGGGTTTGGAAAGAGTGACATGTCAGAAA

TGATTTGTACAGTGTATTTAGGTGTTTTATATCTTAGATGATCATTGGAAGCATTGGTGGGTGACTGGGAGGAGGTT

TGGGCACATAAGTCTGACTTTGTGCACCCCATGACTTACTTGGCACAGTGCACATAAGTATGCAGACAGCCTAGCAC

TTCCATGGTCCCGCACCCCACTGGGGCTTCTCTTTCACCAGGCCTAACTGAGCCTTGTACTGTGCTGTGGTGTAGAT

TTACTTGTTAGGCATGCATGGTATGCAAGAACATGCCACTCAGGCGCCTTGTCACATGGGGGGTGCCACCCAGCCAA

CCGCACACCACGCCTGTCACTCTCAGCCCTGTGTGGACCTCTTTCACATCTTCACATGTCCCTTTTGTCAAACATGT

TTGTGATGCAACCGCAAGCTGGCAGCTGCAGTGCCACCACAGCCCTTGCAGTCCAACAAGTGGCTTTGCATGTCAGG

ACAAGTGCGCATTCCCCCCCGCCCTCCCCTCTAGTGGGGCAGGGCCTGCTAGTATCATGCAAACTGTCAAGTAATGT

GCAGCCATGCTGAGCACATTCAATTTGCACCATATGTGAAACGATGGGCTTTGGGAGTGCAAGCAGCAGCAGCCACA

GCATGTTGGCGAGTCAAGTCCTCTTGCAGGCCTGCAGACCACACCAGTCATGACAAGTCCGCAACATCTGCACCTCA

GCGAGGTCCAGCTCATGCCAGCAATACAACAGCAGTCGCTATATGTATTGAACCGATTGCCGGGCCTAACGGCTGCG

TGGCTGGACTGCTGCACTCACTCACGTGGCCCCTGGTGCAGGGTGGCCTAAATCAGGGTTTCAAGGGGTTTTGCAGG

GTTTGGAAAGAGTGACATGTCAGAAATGATTTGTACAGTGTATTTAGGTGTTTTATATCTTAGATGATCATTGGAAG

CATTGGTGGGTGACTGGGAGGAGGTTTGGGCACATAAGTCTGACTTTGTGCACCCCATGACTTACTTGGCACAGTGC

ACATAAGTATGCAGACAGCCTAGCACTTCCATGGTCCCGCACCCCACTGGGCTTCTCTTTCACCAGGCCTAACTGA

GCCTTGTACTGTGCTGTGGTGTAGATTACTTGTTAGGCATGCATGGTATGCAAGAACATGCCACTCAGGCGCCTTG

TCACATGGGGGGTGCCACCCAGCCAACCGCACACCACGCCTGTCACTCTCAGCCCTGTGTGGACCTCTTTCACATCT

TCACATGTCCCTTTTGTCAAACATGTTTGTGATGCAACCGCAAGCTGGCAGCTGCAGTGCCACCACAGCCCTTGCAG

TCCAACAAGTGGCTTTGCATGTCAGGACAAGTGCGCATTCCCCCCCGCCCTCCCCTCTAGTGGGGCAGGGCCTGCTA

GTATCATGCAAACTGTCAAGTAATGTGCAGCCATGCTGAGCACATTCAATTTGCACCATATGTGAAACGATGGGCTT

TGGGAGTGCAAGCAGCAGCAGCCACAGCATGTTGGCGAGTCAAGTCCTCTTGCAGGCCTGCAGACCACACCAGTCAT

GACAAGTCCGCAACATCTGCACCTCAGCGAGGTCCAGCTCATGCCAGCAATACAACAGCAGTCGCTATATGTATTGA

ACCGATTGCCGGGCCTAACGGCTGCGTGGCTGGACTGCTGCACTCACTCACGTGGCCCCTGGTGGTGCGGGCAAACA

TTTTATTTTTCACACAGACCGTGTTCGAGGATTCAGTGTAAGTCTTAGGAAAAGTTAGAAGATAATACATAAGATTA

GCTTCACTTATCGGGAAAATCTGAGAAGGTGACGTCCATGCTCGGCGAGTTGACCAGCGAGCAGTCGCAACCATTCT

GGCTCGGTGTCTGGTAAACGTATCGGCATTTAAAATCATTCAATGCATTAAATATGTGCCCGCAATCATGCATATAT

GCTCTGTGCAGCTGTCAAAAACGATTTCAATGGAGTTTCTTTCACTTAGGTCAATCCTTTCTCGCGGCTCCTTTATC

AACTGTTAATAGCATGAGATTTCAATGCCAAACCGCGTTTTGGCGGCTGGACTGGAAGCTGAAGGGCAGACC

TABLE 6-continued

Sequences Corresponding to Frequency Peaks (SEQ ID NOs 21-167)

>SEQ ID NO: 27

TTGACTCGTTTGACAGCTGCAACTTGTAAGGCTTACCTCAGCCAAGATAATTACACTGCATGTATCGACTGTGAATG
TGGCATATTTCAACTTGGCGTGACCTTGACCATGACCGCCGAAGCTCCTCGGCCAACTTCGCCGAGCGAGGCGATGT
CACACCCACCAACACCAGCTAGCGGGAGCACGTAAGCACTGCATACCATTCATTGGTCTCTTTTTTATCTGTTGCGT
TTATTACCGCCATGTAAGATGGCCTGTATCAAAATATAATTGTTTGCTCTCACCACCAGGGGCCACGTGAGTGAGTG
CAGCAGTCCAGCCACGCAGCTGTTTGGCCTAGCTATTGATTATATACATATAGCGACTGCCGTTGTATTGCTGGCAT
GAGCTGGACCTCGCTGAGGTGCAGCGGTTGCCGACTTGTCGCCACTGGTGTAGTCTGCAGGCCTGCAAGAGGACTTG
ATGCACCAGTGCCGTGGCTGCTTTCACTTGTGCTCCCAAAGCCCATCGTTCACATGTGGTGCAAATGAAATGTCTTC
AGCATGGCTGCACATTACTTGACAGCCTGCATGATACCAGCAGGCCCTGACCCACTAGAGGGGAGGGGAGGAATGCA
CACTTGTCCTGATATGCAGAGCCACTTGATGGGCTGCAAGGGCTGGCACCCTGGCTGCCAGCTTGTGGTTGCATCAC
AAACATGTCCGGCAACATGGACACTTGAAGATGTGAAAGAGCTCCCACAGGGCTGAGACTGACAGGCGGTGTGTGTG
ATTGGCTGGGCTGCACCCGTCCCCTGTGGGGACAAGGGGACTGAGTGGTATGTGCGTGCATACCATGCATGCCTCAC
ATGTCAAAGTGCACCACAGCACAGTACAAGGCTCAGTTATACCTGGCAAGTGAGAAGCCCCAGTGTGTGTATGTGGA
ACCCTGGGAGTGTGATTCCTTCTGCATACTTGTGTGTGCTGTGCGTGGCAAGTAAGCAGTGGGAGCACAAAGTCATT
GCTATGTGCCCAAATCTCATCACGGTCACCCACAAGGAGTTCAAACAATTATTCTAGTTATAGTTAGCTGAATTATA
CTGTGCAAATCATTTCGGACATGTCACACTTTCCAAATCCTGCAAAACCCCATAAAACCCTGATTTAGGCCACCCTG
CTACCAGGGGCCACGTGAGTGAGTGCAGCAGTCCAGCCACGCAGCTGTTTGGCCTAGCTATTGATTATATACATATA
GCGACTGCCGTTGTATTGCTGGCATGAGCTGGACCTCGCTGAGGTGCAGCGGTTGCCGACTTGTCGCCACTGGTGTA
GTCTGCAGGCCTGCAAGAGGACTTGATGCACCAGTGCCGTGGCTGCTTTCACTTGTGCTCCCAAAGCCCATCGTTCA
CATGTGGTGCAAATGAAATGTCTTCAGCATGGCTGCACATTACTTGACAGCCTGCATGATACCAGCAGGCCCTGACC
CACTAGAGGGGAGGGGAGGAATGCACACTTGTCCTGATATGCAGAGCCACTTGATGGGCTGCAAGGGCTGGCACCCT
GGCTGCCAGCTTGTGGTTGCATCACAAACATGTCCGGCAACATGGACACTTGAAGATGTGAAAGAGCTCCCACAGGG
CTGAGACTGACAGGCGGTGTGTGTGATTGGCTGGGCTGCACCCGTCCCCTGTGGGGACAAGGGGACTGAGTGGTATG
TGCGTGCATACCATGCATGCCTCACATGTCAAAGTGCACCACAGCACAGTACAAGGCTCAGTTATACCTGGCAAGTG
AGAAGCCCCAGTGTGTGTATGTGGAACCCTGGGAGTGTGATTCCTTCTGCATACTTGTGTGTGCTGTGCGTGGCAAG
TAAGCAGTGGGAGCACAAAGTCATTGCTATGTGCCCAAATCTCATCACGGTCACCCACAAGGAGTTCAAACAATTAT
TCTAGTTATAGTTAGCTGAATTATACTGTGCAAATCATTTCGGACATGTCACACTTTCCAAATCCTGCAAAACCCCA
TAAAACCCTGATTTAGGCCACCCTGCTACCAGGGGCCACGTGAGTGAGTGCAGCAGTCCAGCCACGCAGCTGTTTGG
CCTAGCTATTGATTATATACATATAGCGACTGCCGTTGTATTGCTGGCATGAGCTGGACCTCGCTGAGGTGCAGCGG
TTGCCGACTTGTCGCCACTGGTGTAGTCTGCAGGCCTGCAAGAGGACTTGATGCACCAGTGCCGTGGCTGCTTTCAC
TTGTGCTCCCAAAGCCCATCGTTCACATGTGGTGCAAATGAAATGTCTTCAGCATGGCTGCACATTACTTGACAGCC
TGCATGATACCAGCAGGCCCTGACCCACTAGAGGGGAGGGGAGGAATGCACACTTGTCCTGATATGCAGAGCCACTT
GATGGGCTGCAAGGGCTGGCACCCTGGCTGCCAGCTTGTGGTTGCATCACAAACATGTCCGGCAACATGGACACTTG
AAGATGTGAAAGAGCTCCCACAGGGCTGAGACTGACAGGCGGTGTGTGTGATTGGCTGGGCTGCACCCGTCCCCTGT
GGGGACAAGGGGACTGAGTGGTATGTGCGTGCATACCATGCATGCCTCACATGTCAAAGTGCACCACAGCACAGTAC
AAGGCTCAGTTATACCTGGCAAGTGAGAAGCCCCAGTGTGTGTATGTGGAACCCTGGGAGTGTGATTCCTTCTGCAT
ACTTGTGTGTGCTGTGCGTGGCAAGTAAGCAGTGGGAGCACAAAGTCATTGCTATGTGCCCAAATCTCATCACGGTC
ACCCACAAGGAGTTCAAACAATTATTCTAGTTATAGTTAGCTGAATTATACTGTGCAAATCATTTCGGACATGTCAC
ACTTTCCAAATCCTGCAAAACCCCATAAAACCCTGATT

TABLE 6-continued

Sequences Corresponding to Frequency Peaks (SEQ ID NOs 21-167)

>SEQ ID NO: 28

ACTCCGGCGACCTCCAGCTTATGCCAAGCATACAACGGCAGTCACTGTATGTATATAATCGATAGCCGGGCCAAACG
GCTGCGTGGCTGGACTGCTGCACTCACTCACGTGGCCCCTGGCCCCGGGGTCGCCTAAATGGGGGTTTTAAGGGGTT
TTGAGGGTTTTGACAAGTGACACATGTCGGAAATGATCGGCACAGTGTATTTAAGTGTATTATATCTAAGATGATCA
TTGGAAGCATTGGTGAGTGACTGGGATGAGGTTGGGGCACATAAGTCTGGCTTTGTGCACCCCACGGCTTACTTGGC
ACAGTGCACATAAGTATGTAGACAGCCCAGCACTTCCATGGTCCCACATGCACACCCCACTGGGGCTTCTCTCTTGC
CAGGCCTAATCTAGCCTTGTACTGTGCTGTGGTGTAAATTGACATGTTAGGCATGCATGGTATGCAAGCACATGCCA
CTTAGGCCCCTTGTCCCCACATGGGCGGTGCCACCCAGCCAACCGCACACCCTGCCTGTCACTGTCAGCCCTGTGTG
GAACTCTTTCACATCTTCACATGTCCATTATGTCTAACATGTTTGTGATGCAACCGCAAGCCGGCAGCTGGGGTGCC
ACCGCAGCCCTTGCAGTTCATCAAGTGGCTTTGCATGTCAGGACAAGTGCGCATTCCTCCCCTCCCCTCTAGTGGGG
CAGGGCCTGCTAGGATCATGCAAGCTGTCAAGTAATGTGCAGCCATGCTGAGCACATTCAGTTTGCACCCTATGTGA
ATGATGGGCTTTGGGAGTGCAAGTGGAATCAGCCACAGACCAATGCCAAGAGGGGCATGCCTCCTGCCCCTTGCAGG
CCTGCGGAGGCGCCAAGTGTGCGACCGCTTCACTCCGGCGACCTCCAGCTTATGCCAAGCATACAACGGCAGTCGCT
GTATGTATATAATCGATAGCCGGGCCAAACGGCTGCGTGGCTGGACTGCTGCACTCACTCACGTGGCCCCTGGCCCC
GGGGTCGCCTAAATGGGGGTTTTAAGGGGTTTTGAGGGTTTTGACAAGTGACACATGTCGGAAATGATCGGCACAGT
GTATTTAAGTGTATTATATCTAAGATGATCATTGGAAGCATTGGTGAGTGACTGGGATGAGGTTGGGGCACATAAGT
CTGGCTTTGTGCACCCCACGGCTTACTTGGCACAGTGCACATAAGTATGTAGACAGCCCAGCACTTCCATGGTCCCA
CATGCACACCCCACTGGGGCTTCTCTCTTGCCAGGCCTAATCTAGCCTTGTACTGTGCTGTGGTGTAAATTGACATG
TTAGGCATGCATGGTATGCAAGCACATGCCACTTAGGCCCCTTGTCCCCACATGGGCGGTGCCACCCAGCCAACCGC
ACACCCTGCCTGTCACTGTCAGCCCTGTGTGGAACTCTTTCACATCTTCACATGTCCATTATGTCTAACATGTTTGT
GATGCAACCGCAAGCCGGCAGCTGGGGTGCCACCGCAGCCCTTGCAGTTCATCAAGTGGCTTTGCATGTCAGGACAA
GTGCGCATTCCTCCCCTCCCCTCTAGTGGGGCAGGGCCTGCTAGGATCATGCAAGCTGTCAAGTAATGTGCAGCCAT
GCTGAGCACATTCAGTTTGCACCCTATGTGAATGATGGGCTTTGGGAGTGCAAGTGGAATCAGCCACAGACCAATGC
CAAGAGGGGCATGCCTCCTGCCCCTTGCAGGCCTGCGGAGGCGCCAAGTGTGCAACCGCTTCACTCCGGCGACCTCC
AGCTTATGCCAAGCATACAACGGCAGTCGCTGTATGTATATAATCGATAGCCGGGCCAAACGGCTGCGTGGCTGGAC
TGCTGCACTCACTCACGTGGCCCCTGGCCCCGGGGTCGCCTAAATGGGGTTTTAAGGGGTTTTGAGGGTTTTGACA
AGTGACACATGTCGGAAATGATCGGCACAGTGTATTTAAGTGTATTATATCTAAGATGATCATTGGAAGCATTGGTG
AGTGACTGGGATGAGGTTGGGGCACATAAGTCTGGCTTTGTGCACCCCACGGCTTACTTGGCACAGTGCACATAAGT
ATGTAGACAGCCCAGCACTTCCATGGTCCCACATGCACACCCCACTGGGGCTTCTCTCTTGCCAGGCCTAATCTAGC
CTTGTACTGTGCTGTGGTGTAAATTGACATGTTAGGCATGCATGGTATGCAAGCACATGCCACTTAGGCCCCTTGTC
CCCACATGGGCGGTGCCACCCAGCCAACCGCACACCCTGCCTGTCACTGTCAGCCCTGTGTGGAACTCTTTCACATC
TTCACATGTCCATTATGTCTAACATGTTTGTGATGCAACCGCAAGCCGGCAGCTGGGGTGCCACCGCAGCCCTTGCA
GTTCATCAAGTGGCTTTGCATGTCAGGACAAGTGCGCATTCCTCCCCTCCCCTCTAGTGGGGCAGGGCCTGCTAGGA
TCATGCAAGCTGTCAAGTAATGTGCAGCCATGCTGAGCACATTCAGTTTGCACCCTATGTGAATGATGGGCTTTGGG

>SEQ ID NO: 29

CGACCTCCAGCTTATGCCAAGCATACAACGGCAGTCGCTGTATGTATATAATCGATAGCCGGGCCAAACGGCTGCGT
GGCTGGACTGCTGCACTCACTCACGTGGCCCCTGGCCCCGGGGTCGCCTAAATGGGGGTTTTAAGGGGTTTTGAGGG
TTTTGACAAGTGACACATGTCGGAAATGATCGGCACAGTGTATTTAAGTGTATTATATCTAAGATGATCATTGGAAG
CATTGGTGAGTGACTGGGATGAGGTTGGGGCACATAAGTCTGGCTTTGTGCACCCCACGGCTTACTTGGCACAGTGC

TABLE 6-continued

Sequences Corresponding to Frequency Peaks (SEQ ID NOs 21-167)

ACATAAGTATGTAGACAGCCCAGCACTTCCATGGTCCCACATGCACACCCCACTGGGGCTTCTCTCTTGCCAGGCCT
AATCTAGCCTTGTACTGTGCTGTGGTGTAAATTGACATGTTAGGCATGCATGGTATGCAAGCACATGCCACTTAGGC
CCCTTGTCCCCACATGGGCGGTGCCACCCAGCCAACCGCACACCCTGCCTGTCACTGTCAGCCCTGTGTGGAACTCT
TTCACATCTTCACATGTCCATTATGTCTAACATGTTTGTGATGCAACCGCAAGCCGGCAGCTGGGGTGCCACCGCAG
CCCTTGCAGTTCATCAAGTGGCTTTGCATGTCAGGACAAGTGCGCATTCCTCCCCTCCCCTCTAGTGGGGCAGGGCC
TGCTAGGATCATGCAAGCTGTCAAGTAATGTGCAGCCATGCTGAGCACATTCAGTTTGCACCCTATGTGAATGATGG
GCTTTGGGAGTGCAAGTGGAATCAGCCACAGACCAATGCCAAGAGGGGCATGCCTCCTGCCCCTTGCAGGCCTGCGG
AGGCGCCAAGTGTGCAACCGCTTCACTCCGGCGACCTCCAGCTTATGCCAAGCATACAACGGCAGTCGCTGTATGTA
TATAATCGATAGCCGGGCCAAACGGCTGCGTGGCTGGACTGCTGCACTCACTCACGTGGCCCCTGGCCCCGGGGTCG
CCTAAATGGGGGTTTTAAGGGGTTTTGAGGGTTTTGACAAGTGACACATGTCGGAAATGATCGGCACAGTGTATTTA
AGTGTATTATATCTAAGATGATCATTGGAAGCATTGGTGAGTGACTGGGATGAGGTTGGGGCACATAAGTCTGGCTT
TGTGCACCCCACGGCTTACTTGGCACAGTGCACATAAGTATGTAGACAGCCCAGCACTTCCATGGTCCCACATGCAC
ACCCCACTGGGGCTTCTCTCTTGCCAGGCCTAATCTAGCCTTGTACTGTGCTGTGGTGTAAATTGACATGTTAGGCA
TGCATGGTATGCAAGCACATGCCACTTAGGCCCCTTGTCCCCACATGGGCGGTGCCACCCAGCCAACCGCACACCCT
GCCTGTCACTGTCAGCCCTGTGTGGAACTCTTTCACATCTTCACATGTCCATTATGTCTAACATGTTTGTGATGCAA
CCGCAAGCCGGCAGCTGGGGTGCCACCGCAGCCCTTGCAGTTCATCAAGTGGCTTTGCATGTCAGGACAAGTGCGCA
TTCCTCCCCTCCCCTCTAGTGGGGCAGGGCCTGCTAGGATCATGCAAGCTGTCAAGTAATGTGCAGCCATGCTGAGC
ACATTCAGTTTGCACCCTATGTGAATGATGGGCTTTGGGAGTGCAAGTGGAATCAGCCACAGACCAATGCCAAGAGG
GGCATGCCTCCTGCCCCTTGCAGGCCTGCGGAGGCGCCAAGTGTGCAACCGCTTCACTCCGGCGACCTCCAGCTTAT
GCCAAGCATACAACGGCAGTCGCTGTATGTATATAATCGATAGCCGGGCCAAACGGCTGCGTGGCTGGACTGCTGCA
CTCACTCACGTGGCCCTGGTGGTGAGAGCAAACATTTATATTTTGATACAGGCCGTGTTTGAGGCCGCTGTTAATT
GCAGTAAATAATCAAGAATTCAAAGCATACGATCAGCCTCTCAAGTCTTGCATATCGATCATGGTAAGGCATGCTTA
GCAGCGAGCTCACGGCCATGTTGACTCGGTCGCGCGGGTCAACTGATCAGCATTCTAAGTTCTTTTCTATCGCTCT
TATCGTCAATCATTCGTTCTTTATATGCGGCTGTTGTGACTATGCAGCTGTCAAATTGACAAAACGAGCATAAAATT
GTCTCAGCCGAGCTTGGCCTTTCTCAGTCGCCGCTTTTCATTTCCTGCCAATCGTCAGCATTTATCCAAGTAACAGA
TCTTCGTTATACTCGACAGGATTGTGGGCAACAAGGG

>SEQ ID NO: 30

CAGTCATGAGACCTTCAGGCGTTGAAACCATAACAACACA

>SEQ ID NO: 31

CAGGAAGGCACCCAACACGAGTAACGTCAGCAGGACCACGTGGCAAACCATGTACAACACGGTTGAAAGCCCGGAAG
CCGTAAGCAGCACCTAGTACTTGGCATACGCAGAACACGTAAGCAAGCAACTCGTGTACAGCGAAGATGCTTACCAT
GCACAATACCTCGGCAATGAAGTTAGGGAATAGTGGGAAGGCCAAGTTACCCAAAGTAAACAGGAAGACG

>SEQ ID NO: 32

GCGCGGCAGGGTGGTGTCGCGCCCATGCTGCCCCGCTTGCGGGGCTTGTTCCCGGCCGGTCTCTGATGGCTATGGTG
TAGTCCTATGAATTATCTGTGCGCGGGTTGGTGCCCGGCGAATTTCTGTTGCATGGGGCCTGCGCGCATGGCGTGCC
CCTCGGGGGTAATCGCGCTCGGATCACATAAGGGCCGCTCGAACTAAAATTTGCCACTCATACAATAATTACAGCT
ACTGTATGTCTACTCGCCCATGTGTAGCACGCTTGGGCGCTAGCTCGCATTTGAGAGAACCAACACCCTTGCTCCCC
CCATTTTCGTCAAAACCAACATTCTGCAAATTGATACTGTAGTTCTCACTCTGAGTAGCAGCTACGGCTGTCGTTCC
CGTGGTTGAGAGCCCTTACCGTTGTGGTTCTACTGTGGAGGCAGCGGGCGTAGCGACCGGGCGCAAGCAGCCGAGCG

TABLE 6-continued

Sequences Corresponding to Frequency Peaks (SEQ ID NOs 21-167)

```
GGCGGTGGAGAACCAGTCGCAAAAGTCTGCGGAATTGTGGGATCCAGTGAAGGCGGGTTCGTGTGTCGGTTGTGACA

GAGCGAGGTGAGCCCGAGCGCGAAGCCCAGCTGGCGCTACAACCTTTGGGTCAAAAGTCAACGATAGCCGCTGCGGG

CCAGGCGCGTGGCCTCGCTGGGTCGCTGGTTGCACCCAGCATGGCGTTTCGCAAGCTTAACTGGTTTTGGTTGCAAG

TTCCTTCGCGGCGATGCTCCAATTGCGCCCTATGCACTGGTTGCAGGTCGTCGGCGGTGTTCCGGCGTCATGCTTCC

GTGGCAAAATGTATGATGCGCTCCGGTCATCGAGTCGCATGTGCCGGAGGGACCAATAGCAGGCAGCGCAGCTTAGA

ATTGCAATCGGTGAGTATATGTAGACAGCCACTACTAACGTGTATCATTAGCGACCAGTCATACTTGTGGCGCGTCG

GCACGCCGCACGCGTGCCCGCCGTCACTCACCCCAAAGGGGTCTGTTCCCGACACTCGCGCCAGCCGTACCGATGCG

CCAGCATTTCGCGCAACCATACCATCTGACGGAGCGCTATGCGCAATCATCGCTTACCGAATGCCGGCTCAGGTTCC

TATCCGCAACTGCTCCATCCCCACTAAGTTACGGTACTCACTTCCCCTCCTTCACACCCTTTCCTGCCTGCCTCCAC

CCTCAGCGAAACTTCTTGGCCGGCCAGTGCCCGCCCGCCTTCAGCACCGCCGGCAACGTGTGTGCCAGCATCCGCTT

CATACAGTCACGCACAAACTGTGGCGTGATGACCTTCTGAACCACCTTCTCCATCTCGTCCAGGTAGGGCTGCAGGG

GGTCCTCGCCAGCCTCGGTGGGCCGCCGTGCGTTGCAGAACTGCCGCATGACGAGGGCAACGGCCGCGTGCGACTGC

TCCACTGGGCAGTGCATGTCGCCGCTGTACGTGGGAAGCTTCATGAAATTGGCCTTAGTGACGCCCACACCACGGAA

GTCAGCAATCTCGCCGTTGCCGTGGCATGCCGGGTTGTCCCATGACACGTAGGGCTTGATAGGGGCCACGGGCGGGG

GTGGCGGCGGCTTCCTCTTACCCCGCCGGCCCTGCTTCTGCGCGGCCTTCACCGCCGCGGTTTGCTTTGCAGCCAGC

CTTGCAGCCTTCTCCCGGAACGCGCCCAGCATGCGCCCTATGTACTTAACAAACTCCGCCTTCGTGATGAACCTTGC

ATCCTTCCCCGCCAGGGTCTGCGGTGGTGACAGGCAGTGGCGGGCGGCAGCTTGAGCATGGCGCGTGGAGGACACAA

CCGGCGGCGCTTCCCACCCTCTGTGGCAGCGCGATACAGCCCCCTGAACCGGGAGCCGCTAAACGCACGGGGACAG

ATGACCGGCGGCCCGTGCTGTGGAGGCTGCAGTGTGGGTGCTTTGTCTACAAGGCACGGCACACAGTGGCTAACAGT

ATTCGGCGATGTGCCCCGCACGCACCCAGCTGCTTCAACTGCACCTATCACACCTCCGGCCGAGGTGCAAGTGAGGC

CGCACAGCGCGCGTTTCGCATGCTGATTGACCTTGCGCGGCGGCTGGGGGAGGCGTGTACGGTGGTGTGGGAGGCGC

GGGTGGTTGAGGGGTGTGGCCCCTTCGACTTTTGGCTGTGGGAGTGGGGTGTGGTGGTTGAAGTGGATGGCATGCAG

CACACGGATACCCCGCATCACGGCACGGAAGCGCAAGCACAGTGGCTGGTGGATCGGTGGAAGGAAGCAGCTGCTGT

TCGCAAGCGGCTGCATGTGGCGCGGTTGCATGTGATGGACATGGTGTGCTGGGAGGCCGTGGTTGCGCGTGCACTGT

GTGCTGCTCGTAACGGCATTCCGCCGTGCGTGCACTACAGCGACTACTACCTGCGGCCTGTGATTACACAGTCATGA

GCTCCCAACGCACCTGGTACTGTAGCTCGGGTGGCGGCGTGTAGGCCCTGCCTGTGGTGCCGGCAACAGGCTCCCAT

CGCACGACGCCGAAGGCAGGGCACACGGTGATGATGTACTTGATGGTGTTGGGTCGTGATGATCCGCAGCGGTAGTC

CTCAATGGTGATGCTCTGCCCGCGCGGGCCTGCAGTCCAGGCGGTGTAGTCGGTTGGGTTGCAGATGAAGGTCTTTT

CGTCGGTCATGGCGAAACCGTTGAAGATGGTTAAGTTGAGCCATGCGTCGCTTTCAAACTCCGCTGTGCCAATGTCT

GGTGGCAAGGGAAAGGCGCCATCGCTGACACCGTACTCCCTTTCAGCCTCCACGGCTGAGACCATCTTCACGCCTGG

AGCATTGGGGTTGACAAGCTTGCGCAACCACGCTGCTGAGCGGTCCAGCCGGTCACCCCACTGCTCGGGGCTGAGGA

AGGGGCGGTGCTCCACCTTTAAGTTCTTTTGGAGGGTTGGATCGTAGTGTTGCATGGAGCGCCACAGGGATTTGAAA

GTGATCTTGTGGGATTTGAGAACGTCTTGAAAGGGCGCGTCGTGCTCGTACTTGGCGGCAGAGTCATAGTGGACGCT

CTTGACGTGGTCGACCAGGGTTTTCAGGATGGGGTCCGACACCGTGCGCGGCCGGCCTGGGCGTGGCTTGGGCTCTG

TCCCGCCAGTGTGCACGTAGCGCACGTACCACTTCTTAATCTGCTCTGCCATATGCTTGGGTGATGCCTCCCATGGT

GTGTAATCAACTGGCTGCGGGAAGATCTCTGGGCATGCCTCGCGTGCCTTGAACTCCGCCACGGCAATGGGCCCCA

GCGCTGAGGTGTGGTGCCACGTGTGGTAAGCCCAGAACGGTAACAGGCCTGAATGGCAATGGCGGCTACTAGCGCAG

CTACCATTCGCCGCCATGCGTCCGTTGACAGGTTGGAATAGATGGTGCCAGTGGTAGCATCCATCCTTTCACCTGTG

TGCGTCGGTGATGGGGTTTGCGGGTGCGTGGTGAGAGAGGGGGACAGGTGCACGCTATCATGAACCAGGCTAAATTC
```

TABLE 6-continued

Sequences Corresponding to Frequency Peaks (SEQ ID NOs 21-167)

GTAATAATTCGCCCCCCATGCGCCACAAACCCCACCCAACCTGAAACCCCTTAGTTCCCCAGATCCATTTCCACGTC
ACTGTGTCGCACAATTCCGCCGACCTTTGCGCACCCCAGCATATGTGTGCCCGCGGTTTCCAATGCTCTATTGAATG
CACCAAAAGCCAGCCCAGGCCCTGCGTCCTAGGGCCCAAACGAGCTCCTCCGTACAATGTTTGCTCGCACACTCCGG
CGCACGCGATTAGGTGTCGCGCGCTACTGTATGGTAGCCCTTGTGTCGCACAAGTGGTTGGAGCGTGTTTGGGGTGA
GTTGGCGCGGCAGGGTGGTGTCGCGCCCATGCTGCCCCGCTTGCGGGGCTTGTTCCCGGCCGGTCTCTGATGGCTAT
GGTGTAGTCCTATGAATTATCTGTGCGCGGGTTGGTGCCCGGCGAATTTCTGTTGCATGGGGCCTGCGCGCATGGCG
TGCCCCTCGGGGGGTAATCGCGCTCGGATCACATAAGGGCCGCTCGAACTAAAATTTGCCACTCATACAATAATTAC
AGCTACTGTATGTCTACTCGCCCATGTGTAGCACGCTTGGGCGCTAGCTCGCATTTGAGAGAACCAACACCCTTGCT
CCCCCCATTTTCGTCAAAACCAACATTCTGCAAATTGATACTGTAGTTCTCACTCTGAGTAGCAGCTACGGCTGTCG
TTCCCGTGGTTGAGAGCCCTTACCGTTGTGGTTCTACTGTGGAGGCAGCGGGCGTAGCGACCGGGCGCAAGCAGCCG
AGCGGGCGGTGGAGAACCAGTCGCAAAAGTCTGCGGAATTGTGGGATCCAGTGAAGGCGGGTTCGTGTGTCGGTTGT
GACAGAGCGAGGTGAGCCCGAGCGCGAAGCCCAGCTGGCGCTACAACCTTTGGGTCAAAAGTCAACGATAGCCGCTG
CGGGCCAGGCGCGTGGCCTCGCTGGGTCGCTGGTTGCACCCAGCATGGCGTTTCGCAAGCTTAACTGGTTTTGGTTG
CAAGTTCCTTCGCGGCGATGCTCCAATTGCGCCCTATGCACTGGTTGCAGGTCGTCGGCGGTGTTCCGGCGTCATGC
TTCCGTGGCAAAATGTATGATGCGCTCCGGTCATCGAGTCGCATGTGCCGGAGGGACCAATAGCAGGCAGCGCAGCT
TAGAATTGCAATCGGTGAGTATATGTAGACAGCCACTACTAACGTGTATCATTAGCGACCAGTCATACTTGTGGCGC
GTCGGCACGCCGCACGCGTGCCCGCCGTCACTCACCCCAAAGGGGTCTGTTCCCGACACTCGCGCCAGCCGTACCGA
TGCGCCAGCATTTCGCGCAACCATACCATCTGACGGAGCGCTATGCGCAATCATCGCTTACCGAATGCCGGCTCAGG
TTCCTATCCGCAACTGCTCCATCCCCACTAAGTTACGGTACTCACTTCCCCTCCTTCACACCCTTTCCTGCCTGCCT
CCACCCTCAGCGAAACTTCTTGGCCGGCCAGTGCCCGCCCGCCTTCAGCACCGCCGGCAACGTGTGTGCCAGCATCC
GCTTCATACAGTCACGCACAAACTGTGGCGTGATGACCTTCTGAACCACCTTCTCCATCTCGTCCAGGTAGGGCTGC
AGGGGGTCCTCGCCAGCCTCGGTGGGCCGCCGTGCGTTGCAGAACTGCCGCATGACGAGGGCAACGGCCGCGTGCGA
CTGCTCCACTGGGCAGTGCATGTCGCCGCTGTACGTGGGAAGCTTCATGAAATTGGCCTTAGTGACGCCCACACCAC
GGAAGTCAGCAATCTCGCCGTTGCCGTGGCATGCCGGGTTGTCCCATGACACGTAGGGCTTGATAGGGGCCACGGGC
GGGGGTGGCGGCGGCTTCCTCTTACCCCGCCGGCCCTGCTTCTGCGCGGCCTTCACCGCCGCGGTTTGCTTTGCAGC
CAGCCTTGCAGCCTTCTCCCGGAACGCGCCCAGCATGCGCCCTATGTACTTAACAAACTCCGCCTTCGTGATGAACC
TTGCATCCTTCCCCGCCAGGGTCTGCGGTGGTGACAGGCAGTGGCGGGCGGCAGCTTGAGCATGGCGCGTGGAGGAC
ACAACCGGCGGCGCTTCCCACCCTCTGTGGCAGCGCGATACAGCCCCCTGAACCGGGAGCCGCTAAACGCACGGGGG
AC

>SEQ ID NO: 33

CATCTGATGTATTATCTCCTAGCGTACTGAGATATTGACAAAGCATCCTCAAACACGGCTTGTACAGAAATATAAAT
GTTTGCCCGCACCACCAGGGGCCACGTGAGTGAGTGCAGCAGTCCAGCCACGCAACCGTTTGACCAATCTATTGCTT
ATACGCATATAGCAACTGCCGTTGTATGGTTGGCATGAGCTGGAGCTTGCTGGGGTGGAGCGGTTGCCAACTTGGCA
CCACAGCAGGCGACACGCCAACATGCTGTGGCTGCTTCCAGTTGCATCCCCAAGGCCAATCAACATCTGGTGCATGA
GAGGGGAGGCAAGCTGGGCACACTTGTCCTGTTGTGCAGAGCTGCATGGGGCACTGCAAGGGCTGGCACCACCACGC
TTAGCTTGTGGTTGCATCACAAACAGTCAGGCAACATGTACATACACGAATATGCAAGGGTCTTGCACACGGGTGAG
TGAGGCAGGCAGGTTGGATGGTTAGTTGTGCAGCATGGCCCCAACATGAGAACAAGGGGAATGGGCAGCACATGCAT
GCACACCATGGTTGCGTGATCTGTCAACATGCACCATAGCACAATGCAGTATTCAGTATAATCTGGGTGAATGAGAA
GCCACAGTGGTGCAAGGTCACAGGACCATATAAGCCGCATTCCTTCCCCTACTTGCGCCCTGCAACTGTAACAAGAG

TABLE 6-continued

Sequences Corresponding to Frequency Peaks (SEQ ID NOs 21-167)

GATTGTCGCCTAGGTTGACAAGGGAGCGAGTCTCCCGTTACAGTCCTCCCCCCCTGGAAGCGAACGTCCTCGTGAGA
CCACCAGCGCATCCGTAGATGTTATAGGCTCACTGCAGGCGCGGGGTGGGTTTACTGCCTTTGGCCCAGTTGCGCTG
TTGCCTCGCTCTCACGGGTCATCCACCTCAGGGCAAGGAGGGTTTAACCCTCTTGTGCACTAGTTCGGACCCATGCA
CCCATCCGGGATCGAACCCGGGACCTCAACAGTCAGGGTGACTCCTGGCATTTTGCACCAATGTAACAAGAAAATTG
TCGCCTAGGTTGACAAGGGAGCGAGTCTCCCGTTACAGCAACAAGGAAGCAGTGGGGCACACAAAGTCATTGCTATC
TGCCCAAATCACACCATGCCACCCCCACAAGTGCTTCCACCAATCATTCTAGCTATAATTATGCTAATTATACGGTC
TATACAATTTCTGACATGTCACACATTTCAAACCTTTCAAAACCCCTCAAAACCCCCCTTTAGGCCACCCCGCTACC
AGGGGCCACGTGAGTGAGTGCAGCAGTCCAGCCACGCAACCGTTTGACCAATCTATTGCTTATACGCATATAGCGAC
TGCCGTTGTATGGTTGGCATGAGCTGGAGCTTGCTGGGGTGGAGCGGTTGCCAACTTGGCACCACAGCAGGCGACAC
GCCAACATGCTGTGGCTGCTTCCAGTTGCATCCCCAAGGCCAATCAACATCTGGTGCATGAGAGGGGAGGCAAGCTG
GGCACACTTGTCCTGTTGTGCAGAGCTGCATGGGGCACTGCAAGGGCTGGCACCACCACGCTTAGCTTGTGGTTGCA
TCACAAACAGTCAGGCAACATGTACATACACGAATATGCAAGGGTCTTGCACACGGGTGAGTGAGGCAGGCAGGTTG
GATGGTTAGTTGTGCAGCATGGCCCCAACATGAGAACAAGGGGAATGGGCAGCACATGCATGCACACCATGGTTGCG
TGATCTGTCAACATGCACCATAGCACAATGCAGTATTCAGTATAATCTGGGTGAATGAGAAGCCACAGTGGTGCAAG
GTCACAGGACCATATAAGCCGCATTCCTTCCCCTACTTGCGCCCTGCAACTGTAACAAGAGGATTGTCGCCTAGGTT
GACAAGGGAGCGAGTCTCCCGTTACAGTCCTCCCCCCCTGGAAGCGAACGTCCTCGTGAGACCACCAGCGCATCCGT
AGATGTTATAGGCTCACTGCAGGCGCGGGTGGGTTTACTGCCTTTGGCCCAGTTGCGCTGTTGCCTCGCTCTCACG
GGTCATCCACCTCAGGGCAAGGAGGGTTTAACCCTCTTGTGCACTAGTTCGGACCCATGCACCCATCCGGGATCGAA
CCCGGGACCTCAACAGTCAGGGTGACTCCTGGCATTTTGCACCAATGTAACAAGAAAATTGTCGCCTAGGTTGACAA
GGGAGCGAGTCTCCCGTTACAGCAACAAGGAAGCAGTGGGGCACACAAAGTCATTGCTATCTGCCCAAATCACACCA
TGCCACCCCCACAAGTGCTTCCACCAATCATTCTAGCTATAATTATGCTAATTATACGGTCTATACAATTTCTGACA
TGTCACACATTTCAAACCTTTCAAAACCCCTCAAAAC

>SEQ ID NO: 34

CGAACGAGGGCGCGGCGCGGCGTCTATGGCGCCGTAACCCAAAATGTGTAGCGAGACCCTTAAGAGCGGGGCAATA
ATAATAATAATAATAATAATAATAATAATAATAATAATAATAATAATAATAATAATAATAATAATAATAATAATAAT
AATAATAATAATAATAATAATAATAATAATAATAATAATAATAATAATAGGAATAATAATAATAATAATAATTA
CAATGCCGGCCCATAGGGCCTGGCATGGATTAACGGGGCAAGGTGACTAGGGCGAGAGGGCCCGCCCCAGTGTTTCC
AAAACCGGGTACTAGTACCCATTCGGGTACTGAGAAAATAATTCGCCGAAATTGACGCGGGTACTGGAAACTAATTA
TTGGGGCCTCGAGTACCCACACGGGTACCAAAAATTTAATCCGCCGGACCCTATACTACCCGGGCCCTGTTCAGCAC
GGAGGCAATCGACCACGCGAGCTCTGTCTTAGAGGCTGCTGCATCTGGCACCGTGACGCTGCCGCAGGGCAGCTTCG
TGGCGTTCTGGCAATCGCTGACTCGCGCGCAGTACATTGCCGACAGCTGCAGTGAGTTCGTGCGCCTGGCCAAGCTG
GCGGCTACCATTGTACCCGGATCAGTGGAGGCGGAGCGTGTGTTCAGCACCATGAGCTA

>SEQ ID NO: 35

CAGCCCGGTGGTGGCACGTGCGTGTCAAGCCGCCGAGGTCGCACCACGTCCTTCTTTGCGACTGCTGGCACCTTTGG
TCCGCCTCACCGCGATCGAGTCGAGCGCAACCTCAATGGTGTGCGCTTCATTTTCCTAGATGAGTTTAGCACGTGTG
GGCTGTCCCACTGGGCGCGCATTTGCATGCATGTGCACGCGGCACGGAGGCACGTGGGTATAGACAGCACGCACCTA
TATCACGGGCCGCTGTCAGATCTGCATGGCCTGCTTGTTGGCGACTTGCGTCAGTTGCCACAGCCACGGCACGTGCC
GCTATATAGCGGTGCTGCGGAAGAGAGCTTGCGGCAGCTGCTGGCGCGGGCGCGGGGACGGCGGGGCCATGGAGC
GCCAGATCCGGCAGCTGGAGCATCCGGAGGGCAGCATGAACCTCATGGGGCGGGAGCTGTGGAATATGGTGCCGTTC

TABLE 6-continued

Sequences Corresponding to Frequency Peaks (SEQ ID NOs 21-167)

GCGTTCGTTCTCACTCACCAGCATCGGCAGCAAGCAGGCGTAGGTGACAACAACGAACCTCTCTTCATGCTAGCGGA

GAAGTTTGGTGGCGTGCAGGAAATCTCTCAGGCAGATCTGGATACAGCGTGCCAGCAGCTCAACGCGCGTGTTTGGC

AGCCCCGAAGCCAGGGATTGACCCCGTGCCCCAGCCCTTTGCAGTTGTCCAGCGCCATGTTGTGCGGGTTCCACTG

GCATTGCAGCTCGTGCAGCTGCATGCGCTCGCGCAGCGTCAGCAGCTGCTGCTATGGCGTAGCGCGGACTTGTCGCC

GGACGGGAGCAGCTTACCTATTTCGCATGTGCATCAATTAGAGGCGCTTGGCGGGGCCGAGGATGATAGCGGTGTGC

CCGCTGTGTGCGCATTCTTTGCTGGCATTCGTTACGTGTTTACATCAAATGAGCATGTGCGTCTGTATCACATCAAC

AACAACAGTGCCACAGGCACCGGCATTGTTCTGCATCCCAACGAGTCACCATTGCCAGATGCAAGCATTGCCCCCGT

GCATGTCCTCAAGTTCGTGCCCTCGGCTGTAATGGTGCGCCCCGACGGGCCTGATGCGGGTCGGGTGTCTGTCGATC

AGGCCCTGGATGTCGGGGAGATTCCTGTTTTACCGTGCAGTGCTATGTTCACATCGCAGCATGCAACCCTGCGGTTG

CCTGTGATGCGCTGGGGCTTTCGTGTGGAGCTTGCGTATGCAGTCACCGATTACTTTGCGCAGGGGCAAACTCTGCC

AGCGCACGAACTGTGGCTGGTGGATATGTGCAAACCGCAGCACGGCAGTTGGCGGCGGGCTTCAATTTACGTAATGC

TCACCAGGTTTCGTGGGTTGCATGCCTTACATTTAGTGCGTCCGCTGTGGGCCTCGCGGGCCGAAGAGCGCCGGCTT

AAAAAGGCGCTGCGTACCATGCTAACGCCCGAGGCAGATCTAGCCGCGGAATGGCAGCGGCTATTGAGGCTCTCGCA

GAGCACAGCAGTAGCAGTGCCAGGTATGATTGTGCGCATTCAGGCCAGCATGGCTGCCTCATAACCAAGGCTTTCAA

TGCATGCAGTAGTGTTTTTAACATGCGCGAGGTGTACTGACAGATGACCTGGAAGCGTGGAGTACCTTGTGGGTGGT

GAGTGCTGACTGCAATTTACAGCAGTGACTTTCTTGTTGGTGTTTGGTGTGGTGACCATCATGCTTGGCTTCGCTGG

CTGGACGTATGTCACTGAGCTACGTTCGGGTTTAGTTTCTACCTGTCCTGTCTCTGCGTGAAGCCGGGGTATTGTTT

ATCTGCTTGCTTGTCGTGCGTTGGATTGTTGTGTGTTTACAACAGGTTGATGTGTGGCGTGGTTAATCCCTTGCACT

TTGAGGAGGTTATTGTTAGCCAGCTGGTGTTCGCACAGGAGGTTGGTGGTCGATGAACAGTCGACCGACAGATGGAT

CGCGGGATTTGTTTTTGGCATTTACCGCTTGGATTCTATTCGCAACGTAGCTCGGAATACACGCTTAATATGCATAG

TTAGAAGACTTCGGGGACGCAAATCGCTCGGAAATGGAGGAGGGTCTCAATATGCTCGGCTCGCGATGTCGCGCTCT

TGAGCTTGTATTATGCACTGTGCGCAATGCGCGTTCAGCATGCATATTCTTACGAACAACTAGGGACTTGAGTGACG

CGGTGTGAAAATCAGTCGGGTCTCGACATGCTTGGCTCGCCATTTCGCGCTCCCGAGCTCGTTGTGTGTGTTCCGA

ACAATGCACGCTCAGAATTACATGTTCAATATGTCCGTCGCGATGTTCGAGCTTGAAAACCGACAAGCATGGTGTAT

AGATACACCTGGTAGCCTGAATTCCTGTGTTTTTGGTGTATTTTGTTGATGTTGCATCACGCCGTGCCTTGTCACAT

TCATGTTTTTTGTACCGGCGTGGCCTTGTTTGTAAATTTCGCGGCGCCCTGATCTTATCTACTTCTTCGCTGTGATC

TGGCAAAAAAAACTGTTCTTGACGGGATTCGAACCTGTGACAGCATCTCACTAAGCGCCATAATCAGACCCTCCAGA

GGAGGGTGTGCACTGAGTTAGCGATCCGGTGATGAAGCATCTGCCAACATGTGCCCCACCCTCAGCAACCGCACCCT

CGCCAGCTCCACCAGGCACCCTGGCTGGTCAAGCAAATACTCTACGCCCGCTATGGCTACCTCTTCAACGCACAGC

TTAAACGGCGCTACCGCCTG

> SEQ ID NO: 36

ATGGGGCAGGTAGGACAAGCGTAAGCGTTTGGAAAATGGAGGGCTTGAATGTCTGAGCTCATCCATGTGTACAAGAA

CAGAAATACTGTCAAGTTTTGTGTCATTGATTGCTGATTCGTTTGTGGTATTGTTCAATTATTGTTGTTCGGGCATT

GCATCGCACTCGAGGGGCTGGGTGGTTCATTGGGGTTGGGACCGGGTATCCCAGCTTGTATCCCAGGGGTTGTGCGC

GGGGAGCAAGCGGCGGGGGCTGCAGATGCTGAAGCGCGTGCTAGGCTGCCTATCTGTCTCGAAGATGCTTCAAGACT

GTGTGAACGTTGCTTCACGATATTATGGGGTGGTTTATGCTGGCTGCACGCACCATACACCATACAGCTACTAACAT

TCGTCACACTTGCACCCAAGTGTGCGCGAGGGAATCCATGTAACAATATCTTGGCTTGATATGCGCTGACTTATCGC

AGCGCAGTGGAGATAAGTCTAGTTATTGCGACGTAACTGCCGTGTTGCGTTAGAGTCACGCACGGCGCAGGACGCTC

GGGTACGTGCCTGTGCATGGGGCCGAACCGAGCTGGGTCTTGTACGCGTCAGGAGCACACGGCGCCTTATCTGCCGT

TABLE 6-continued

Sequences Corresponding to Frequency Peaks (SEQ ID NOs 21-167)

TGTGCTTCTGTACTGTATTTCGGATCGTCCCTCTGCCGGGACGGTGACCTCAGTGTGTCGCACTTAAACGTTCCCTA

CATTTCTGGACTTTCTTTGCAATCCTATACCTGGTTCTAACTATACTTTACCATGTCTGGACCGAATAAGCGTTTAA

TATACACTCAGACGGAGTTGCAGCGCTTTGTTGCGCGATCCTGCTCAATGGAACCCCTTAGCTTGATCACGCTCGCT

CTCTGATCGTAAGGGAATGCCCTTCGACGCTTCTCTGGCGCTTTGGACCACGCTTTGGTTCGGGGGCCGCATTCGGG

AGCAAATCGGAGCAGAGCGGAGCTTTCAAGCGGAGCAAAGGCGCGCGAAGCGTTGCGGACAAGGCGTTCGGCAAGTC

ACTGAAAGCAAAAGGGCATGCACAGCTGTGCGGGCGGGCTACTTGCTTGCCATGCGCGGTCCTGCTTGCCGTGCCTT

CGTGTCTACCCGTCGCTTTACAGTTCACAGCTTTGTGCAATACCTTTCATCTTCCATCGTGCCACCCCCACCTCCCC

AAGACCTCAGGGCTTTTGGCGCGGTACTTCTCCTGTCTGCCTATCCAGGCCGCAGGGCCCGCGTGCCCTTGGGGAAA

GGGCGTGTGTGCCGTTGGGATCCGCCTGTGCGCCGCAAGCAACGGGCTTTGCGCCCTTGCCTTATGGACAATGGAT

GGCATACGTGCCCTTATGATACGGCCTGTGTGCCGCAAGCAATGGGCTCCGCGCCCTTGCTTTATGGACAATGGACG

GCATACGTGCCCTTATGATACGGCCTGTGCGCCGCAAGCAACGGGCTCCGCGCCCTTGCTTTATGGACAATGGACGG

CATACGTGCCCTTATGATACGGCCTGTGTGCCGCAAGCAAT

>SEQ ID NO: 37

TTGCTACATGGACAATTTACGGCGTACGTGCCCTCATAATACGGCCTGTGCGCCGCAGGCAACGGGCTCCGCGCCCT

TGCTTCATGGACACTTCACGGCGTACGTGCCCTCATGATACGGCCTGTGTGCCGCAGGCAACGGGCTCCGCGCCCTT

GCTTCATGGACAATGCGCCGCGTACGTGTTCTTATGATACGGCCTGTGCGCCGCAAGCAACGGGCTCTGCACCCTTG

TTTTATGGACAATTCACGGCATACGTGCCCGTATGATGTGACCTGTGTGCCGCAAGCAACAGCTCACCCTTGCTTTT

GGGTAATAGATGGCATACGTGCCCTTATGATACGACCTGTGTGCCGCAAGCAACGGGCTCCACACTCTTGCGTTGTG

GATTATAGACGGCATTGAAATGCTTACGTGCCTTCGTTGTACATGCCTTTGCGTTGTGGACAATGTGTGGTCTGAGC

GCCACGTTCGGATACGGCGTGTGTGCCGCCAGCAACAGGCTTTGCGCCTCGCATCATGTGTCTTGCGATATTGCCCG

TGTGCCGCATGCAATTATGCTGCCTGCCCTGTCGTTATGGACGCTTCGACTTGTTGCGTGCCCTGCTGCGTGCCCTG

TCGCAATACGCCTTGAGTGTGCCGTGCACGGCAAGCCTGCGCCTCGCTATTGCTTCGTGTTGACAACGGAGCGGGCT

TACGTGATCATGCGTCACCCTGTACGTCTTGAGGTCCGCACGCACATCATACTATCACGCGGCATCACCATTGTAGT

TTGGCTGACGCACCCCAAGCCAACCTATATGCATTCGATGTGTGCGCTAGGCCCAAGTGCCGAATTGTGGAGTTTTG

TGCAGTTCGGCCAGCATGCTATTGCCAATAACAATACCGCATGACGCATAACAATACCGCATGACGCATAAACATGC

CTTCGTGCAGCCCTGCACCAGGCATCGGACGCTGTGTCACGCAGTGAGCCCGACCCTGCCCAACCAACATTTTGTTG

CGAGATACGGTCGGAGCTGGGATCACAGCCTGCTTGGTGGGTTTAGATGGCGCCCGTGTGTTGGGCTGGGCTGTTGC

TGCTCGCGGTGGGGCCCACCACCGAGTCACGGCACCCATCCGCCCTCCCCTCTTGTTGGCCCACCCGCCTGTACACA

TGCCAGCCACCCGCTCGCCATCCTGTGAAAGCGGGTAGCCGACTTGGCAAGCGCTTTTCCTGACACTTGGCGCAGGT

TTGAGTGGGATACCAGAATGGTCTGAATGTAGTTGTTGGATAACCAGTACACTGCGGTGTGTAGCTGGTTAGCGGGA

GTGCCGTGCATGAAACACGCTACTCGACCCGCCACGCCCGCGCGATGGTACCACCAACCGTTCAACCCAGATCCATG

CCGGGGTAGCATCGACCCACAGTCAGACTGATAGCTCCTATCCAGGTGTCAGGCGCCATGTATGTATCTGTGGACGC

GTCAAGCTGGCTTGTGCCGTAGCGTTGGCCGCCTGTATGGCATGCCCGGCATCTGTGTCACGTTATGGCGTCATGCT

TACCGTAGTCACGCGGCTTGCGTGCTGTGCGGCACGCTCCCTGCCAATCCTTCAGGACATGTATGCATACATGTTCC

TTGGTCAGAACCATAGCAGGGCAGCGTGTTCTGTCAATGCCTCATGAACCCAGAGACCCAAGCCAACGTACGCATT

AGTTCCGCAACGCACGTCAACAGGAACCCCTGCACGTCAATGCCAACTGAATGTGTCGCCTGCCCACTCGCCAGTGG

ACGCCTAGGGAACCAGCCTTGGTTCCTTTCAGCCCCGGCCTTACTTCACCCGGCGGGCAATTACTTATCACCGAAG

TGCTAGGAGCAGTGTGCTATATGTCATTACTATTAAGAGCGTATGGCGACACAGGCTCACATGTGGGTAGCCAGGCC

GACAGTGCCCTGCGGGCTTGGCAGTCGGCAGGCATCCCAACTCAGCCCGGCCTCCTCACAGCAGTACCACAACGTGC

TABLE 6-continued

Sequences Corresponding to Frequency Peaks (SEQ ID NOs 21-167)

CCGTACGTGGGCGAGTGCGGAGTTTGGCTGCCGGCGTGGCTGTATCATCTCTCACATTGGATGACCCATCCGCCACT
GCGATGGGTTCACTACTGGCACGTCCCTCGAGTCGCTCACCCACCGGCTCCGCCCGGCGTTCGCTCCCTTTGGCTGG
GCCGGGGCCCGTGGCGCATCCAACCCGCCATCGCGGCCCCGAGTGCTCCTTATTTCCTCCCATCACTACGCCTTCTA
TCACTATAGATACATTGCGTGTTCCACGCGTGCCGGGTATCCTTCACCCCTCCGCGCCGCTCGACCAGGCCAGCCTT
GCTGGGGTTGCTGAGGTGTTACCCTTCATGTTGCCCTCCCTGCTATTACGGTACACCCCACAGCCGCCGTGGCGTAC
GGTATCGGCACGTACGGGACATTGTGTGCATGCATCCCCGCGGCGTTTGGAGGCATTCACGTGCGCGCCTGTCCTGC
GTCCGCCGGGGTGATGCTATCTATGGGTGTACCTACTGCTTGATTGGTAGTGACTCTTATGCAAGACACTGCAAATC
TCAAGCATGGCACCTAGCTAGCAAGAAAGAAATTAGTGTTCGTGGCCATGCTGCACGGCTGGGCATGGCTGCCCGCA
TCCTACACCACGACGGCGCGGGTGAAGGGCAGGTTGCCGCGCGTGACTCGCGTACGTAAAACCGCTCTAGTGTTGCA
CCTCGCGCCTTCTCCTGCGTGGCTCATGTTGGCTAGTCTGT

>SEQ ID NO: 38

TGCCTGACCTACTTGCAATGCAGACACGAGCAGGGAGCCATGTTGCCAGCCCTCACAGTGCCTTCAGTGCCCCTGCA
CGCCTGGACAAGGCGGGTGGGGTCCACACCGCCCAGCCATCACCAGACACCCCACCTGCCACACCCACCCTTGTGCA
CTGTTGTTTCACATTTTCATATGTGCATGTTGCCTGACCTATTTGCAATGCAGAGACGAGCAGGGAGCCATGTTGCC
AGCCCTCACAGTGCCTTCCGTGCCCCTGCACGCCTGGACAAGGCGGGTGGGGCCCCTGCCACCCAGCCATCACCAGA
CACCCCACCTGCCACACCCACCCTTGTGCACTGTTGTTTCACATTTTCATATGTGCATGTTGCCTGACCTATTTGCA
ATGCAGACACGAGCAGGGAGCCATGTTGCCAGCCCTCACAGTGCCTTCCGTGCCCCTGCACGCCTGGACAAGGCGGG
TGGGGTCCACACCGCCCAGCCATCACCACACACCCCACCTGCCACACCCACCCTTGTGCACTGTTGTTTCACATTTT
CATATGTGCATGTTGCCTGACCTATTTGCAATGCAGACACGAGCAGGGAGCCATGTTGCCAGCCCTCACAGTGCCTT
CAGTGCCCCTGCACGCCTGGACAAGGCGGGTGGGGTCCACACCGCCCAGCCATCACCACACACCCCACCTGCCACAC
CCACCCTTGTGCACTGTTGTTTCACATTTTCATATGTGCATGTTGCCTGACCTATTTGCAATGCAGACACGAGCAGG
GAGCCATGTTGCCAGCCCTCACAGTGCCTTCAGTGCCCCTGCACGCCTGGACAAGGCGGGTGGGGCCCCTGCCACCC
AGCCATCACCACACACCCCACCTGCCACACCCACCCTTGTGCACTGTTGTTTCACATTTTCATATGTGCATGTTGCC
TGACCTATTTGCAATGCAGACACGAGCAGGGAGCCATGTTGCCAGCCCTCACAGTGCCTTCAGTGCCCCTGCACGCC
TGGACAAGGCGGGTGGGGTCCACACCGCCCAGCCATCACCACACACCCCACCTGCCACACCCACCCTTGTGCACTGT
TGTTTCACATTTTCATATGTGCATGTTGCCTGACCTATTTGCAATGCAGACACGAGCAGGGAGCCATGTTGCCAGCC
CTCACAGTGCCTTCAGTGCCCCTGCACGCCTGGACAAGGCGGGTGGGGTCCTGCCACCCAGACATCACCACACACC
CCACCTGCCACACCCACCCTTGTGCACTGTTGTTTCACATTTTCATATGTGCATGTTGCCTGACCTATTTGCAATGC
AGACACGAGCAGGGAGCCATGTTGCCAGCCCTCACAGTGCCTTCAGTGCCCCTGCACGCCTGGACAAGGCGGGTGGG
GTCCACACCGCCCAGCCATCACCACACACCCCACCTGCCACACCCACCCTTGTGCACTGTTGTTTCACATTTTCATA
TGTGCATGTTGCCTGACCTATTTGCAATGCAGACACGAGCAGGGAGCCATGTTGCCAGCCCTCACAGTGCCTTCAGT
GCCCCTGCACGCCTGGACAAGGCGGGTGGGGTCCACACCGCCCAGCCATCACCACACACCCCACCTGCCACACCCAC
CCTTGTGCACTGTTGTTTCACATTTTCATATGTGCATGTTGCCTGACCTATTTGCAATGCAGACACGAGCAGGGAGC
CATGTTGCCAGCCCTCACAGTGCCTTCAGTGCCCCTGCACGCCTGGACAAGGCGGGTGGGGTCCACACCGCCCAGCC
ATCACCACACACCCCACCTGCCACACCCACCCTTGTGCACTGTTGTTTCACATTTTCATATGTGCATGTTGCCTGAC
CTATTTGCAATGCAGACACGAGCAGGGAGCCATGTTGCCAGCCCTCACAGTGCCTTCAGTGCCCCTGCACGCCTGGA
CAAGGCGGGTGGGGTCCACACCGCCCAGCCATCACCACACACCCCACCTGCCACACCCACCCTTGTGCACTGTTGTT
TCACATTTTCATATGTGCATGTTGCCTGACCTATTTGCAATGCAGACACGAGCAGGGAGCCATGTTGCCAGCCCTCA
CAGTGCCTTCAGTGCCCCTGCACGCCTGGACAAGGCGGGTGGGGTCCACACCGCCCAGCCATCACCACACACCCCAC

TABLE 6-continued

Sequences Corresponding to Frequency Peaks (SEQ ID NOs 21-167)

CTGCCACACCCACCCTTGTGCACTGTTGTTTCACATTTTCATATGTGCATGTTGCCTGACCTATTTGCAATGCAGAC
ACGAGCAGGGAGCCATGTTGCCAGCCCTCACAGTGCCTTCAGTGCCCCTGCACGCCTGGACAAGGCGGGTGGGGCCC
CTGCCACCCAGCCATCACCCCACACCCCACCTGCCACACCCACCCTTGTGCACTGTTGTTTCACATTTTCATATGTG
CATGTTGCCTGACCTATTTGCAATGCAGACACGAGCAGGGAGCCATGTTGCCAGCCCTCACAGTGCCTTCAGTGCCC
CTGCACGCCTGGACAAGGCGGGTGGGCCCACACCGCCCAGCCATCACCACACACCCCACCTGCCACACCCACCCTT
GTGCACTGTTGTTTCACATTTTCATATGTGCATGTTGCCTGACCTATTTGCAATGCAGACACGAGCAGGGAGCCATG
TTGCCAGCCCTCACAGTGCCTTCAGTGCCCCTGCACGCCTGGACAAGGCGGGTGGGGTCCACACCGCCCAGCCATCA
CCACACACCCCACCTGCCACACCCACCCTTGTGCACTGTTGTTTCACATTTTCATATGTGCATGTTGCCTGACCTAT
TTGCAATGCAGACACGAGCAGGGAGCCATGTTGCCAGCCCTCACAGTGCCTTCAGTGCCCCTGCACGCACGCCTGGA
CAAGGCGGGTGGGGTCCACACCGCCCAGCCATCACCACACACCCCACCTGCCACACCCACCCTTGTGCACTGTTGTT
TCACATTTTCATATGTGCATGTTGCCTGACCTATTTGCAATGCAGACACGAGCAGGGAGCCATGTTGCCAGCCCTCA
CAGTGCCTTCAGTGCCCCTGCACGCACGCCTGGACAAGGCGGGTGGGGTCCACACCGCCCAGCCATCACCACACACC
CCACCTGCCACACCCACCCTTGTGCACTGTTGTTTCACATTTTCATATGTGCATGTTGCCTGACCTATTTGCAATGC
AGACACGAGCAGGGAGCCATGTTGCCAGCCCTCACAGTGCCTTCAGTGCCCCTGCACGTACGCCTGGACAAGGCGGG
TGGGGTCCACACCGCCCAGCCATCACCACACACCCCACCTGCCACACCCACCCTTGTGCACTGTTGTTTCACATTTT
CATATGTGCATGTTGCCTGACCTATTTGCAATGCAGACACGAGCAGGGAGCCATGTTGCCAGCCCTCACAGTGCCTT
CAGTGCCCCTGCACGCACGCCTGGACAAGGCGGGTGGGTCCACACCGCCCAGCCATCACCACACACCCCACCTGCC
ACACCCACCCTTGTGCACTGTTGTTTCACATTTTCATATGTGCATGTTGCCTGACCTATTTGCAATGCAGACACGAG
CAGGGAGCCATGTTGCCAGCCCTCACAGTGCCTTCAGTGCCCCTGCACGCCTGGA

>SEQ ID NO: 39

ACACGAGCAGGGAGCCATGTTGCCAGCCCTCACAGTGCCTTCAGTGCCCCTGCACGCACGCCTGGACAAGGCGGGTG
GGGTCCACACCGCCCAGCCATCACCACACACCCCACCTGCCACACCCACCCTTGTGCACTGTTGTTTCACATTTTCA
TATGTGCATGTTGCCTGACCTATTTGCAATGCAGACACGAGCAGGGAGCCATGTTGCCAGCCCTCACAGTGCCTTCA
GTGCCCCTGCACGCCTGGACAAGGCGGGTGGGGTCCACACCGCCCAGCCATCACCACACACCCCACCTGCCACACCC
ACCCTTGTGCACTGTTGTTTCACATTTTCATATGTGCATGTTGCCTGACCTATTTGCAATGCAGACACGAGCAGGGA
GCCATGTTGCCAGCCCTCACAGTGCCTTCAGTGCCCCTGCACGCCTGGACAAGGCGGGTGGGGTCCACACCGCCCAG
CCATCACCACACACCCCACCTGCCACACCCACCCTTGTGCACTGTTGTTTCACATTTTCATATGTGCATGTCGCCTG
ACCTATTCGCAATGCAGACACGAGCAGGGAGCCATGTTGCCAGCCCTCACAGTGCCTTCAGTGCCCCTGCACGCCTG
GACAAGGCGGGTGGGGTCCACACCGCCCAGCCATCACCACACACCCCACCTGCCACACCCACCCTTGTGCACTGTTG
TTTCACATTTTCATATGTGCATGTTGCCTGACCTATTTGCAATGCAGACATGAGCAGGGAGCCATGTTGCCAGCCCT
CACAGTGCCTTCAGTGCCCCTGCACGCCTGGACAAGGCGGGTGGGGTCCACACCGCCCAGCCATCACCACACACCCC
ACCTGCCACACCCACCCTTGTGCACTGTTGTTTCACATTTTCATATGTGCATGTTGCCTGACCTATTCGCAATGCAG
ACACGAGCAGGGAGCCATGTTGCCAGCCCTCACAGTGCCTTCAGTGCCCCTGCACGCCTGGACAAGGCGGGTGGGGT
CCACACCGCCCAGCCATCACCACACACCCCACCTGCCACACCCACCCTTGTGCACTGTTGTTTCACATTTTCATATG
TGCATGTTGCCTGACCTATTTGCAATGCAGACACGAGCAGGGAGCCATGTTGCCAGCCCTCACAGTGCCTTCAGTGC
CCTGCACGCCTGGACAAGGCGGGTGGGGTCCACACCGCCCAGCCATCACCACACACCCCACCTGCCACACCCACCC
TTGTGCACTGTTGTTTCACATTTTCATATGTGCATGTCGCCTGACCTATTTGCAATGCAGACACGAGCAGGGAGCCA
TGTTGCCAGCCCTCACAGTGCCTTCAGTGCCCCTGCACGCCTGGACAAGGCGGGTGGGGTCCACACCGCCCAGCCAT
CACCATACACCCCACCTGCCACACCCACCCTTGTGCACTGTTGTTTCACATTTTCATATGTGCATGTTGCCTGACCT

TABLE 6-continued

Sequences Corresponding to Frequency Peaks (SEQ ID NOs 21-167)

ATTCGCAATGCAGACACGAGCAGGGAGCCATGTTGCCAGCCCTCACAGTGCCTTCAGTGCCCCTGCACGCCTGGACA

AGGCGGGTGGGGTCCACACCGCCCAGCCATCACCACACACCCCACCTGCCACACCCACCCTTGTGCACTGTTGTTTC

ACATTTTCATATGTGCATGTTGCCTGACCTATTTGCAATGCAGACACGAGCAGGGAGCCATGTTGCCAGCCCTCACA

GTGCCTTCAGTGCCCCTGCACGCCTGGACAAGGCGGGTGGGGTCCACACCGCCCAGCCATCACCACACACCCCACCT

GCCACACCCACCCTTGTGCACTGTTGTTTCACATTTTCATATGTGCATGTCGCCTGACCTATTTGCAATGCAGACAC

GAGCAGGGAGCCATGTTGCCAGCCCTCACAGTGCCTTCAGTGCCCCTGCACGCCTGGACAAGGCGGGTGGGGTCCAC

ACCGCCCAGCCATCACCACACACCCCACCTGCCACACCCACCCTTGTGCACTGTTGTTTCACATTTTCATATGTGCA

TGTCGCCTGACCTATTTGCAATGCAGACACGAGCAGGGAGCCATGTTGCCAGCCCTCACAGTGCCTTCAGTGCCCCT

GCACGCCTGGACAAGGCGGGTGGGGTCCACACCGCCCAGCCATCACCATACACCCCACCTGCCACACCCACCCTTGT

GCACTGTTGTTTCACATTTTCATATGTGCATGTTGCCTGACCTATTTGCAATGCAGACACGAGCAGGGAGCCATGTT

GCCAGCCCTCACAGTGCCTTCAGTGCCCCTGCACGCCTGGACAAGGCGGGTGGGGCCACACCGCCCAGCCATCACC

ACACACCCCACCTGCCACACCCACCCTTGTGCACTGTTGTTTCACATTTTCATATGTGCATGTTGCCTGACCTATTT

GCAATGCAGACACGAGCAGGGAGCCATGTTGCCAGCCCTCACAGTGCCTTCAGTGCCCCTGCACGCCTGGACAAGGC

GGGTGGGGTCCACACCGCCCAGCCATCACCACACACCCCACCTGCCACACCCACCCTTGTGCACTGTTGTTTCACAT

TTTCATATGTGCATGTCGCCTGACCTATTTGCAATGCAGACACGAGCAGGGAGCCATGTTGCCAGCCCTCACAGTGC

CTTCAGTGCCCCTGCACGCCTGGACAAGGCGGGTGGGTCCACACCGCCCAGCCATCACCACACACCCCACCTGCCA

CACCCACCCTTGTGCACTGTTGTTTCACATTTTCATATGTGCATGTCGCCTGACCTATTTGCAATGCAGACACGAGC

AGGGAGCCATGTTGCCAGCCCTCACAGTGCCTTCAGTGCCCCTGCACGCCTGGACAAGGCGGGTGGGGTCCACACCG

CCCAGCCATCACCATACACCCCACCTGCCACACCCACCCTTGTGCACTGTTGTTTCACATTTTCATATGTGCATGTT

GCCTGACCTATTCGCAATGCAGACACGAGCAGGGAGCCATGTTGCCAGCCCTCACAGTGCGTTCAGTGCCCCTGCAC

GCACGCCTGGACAAGGCGGGTGGGTCCACACCGCCCAGCCATCACCACACACCCCACCTGCCACACCCACCCTTGT

GCACTGTTGTTTCACATTTTCATATGTGCATGTTGCCTGACCTATTTGCAATGCAGACACGAGCAGGGAGCCATGTT

GCCAGCCCTCACAGTGCCTTCAGTGCCCCTGCACGCCTGGACAAGGCGGGTGGGTCCACACCGCCCAGCCATCACC

ACACACCCCACCTGCCACACCCACCCTTGTGCACTGTTGTTTCACATTTTCATATGTGCATGTTGCCTGACCTATTT

GCAATGCAGACACGAGCAGGGAGCCATGTTGCCAGCCCTCACAGTGCCTTCAGTGCCCCTGCACGCACGCCTGGACA

AGGCGGGTGGGGTCCACACCGCCCAGCCATCACCACACACCCCACCTGCCACACCCACCCTTGTGCACTGTTGTTTC

ACATTTTCATATGTGCATGTTGCCTGACCTATTTGCAATGCAGACACGAGCAGGGAGCCATGTTGCCAGCCCTCACA

GTGCCTTCAGTGCCCCTGCACGCCTGGACAAGGCGGGTGGGTCCACACCGCCCAGCCATCACCACACACCCCACCT

GCCACACCCACCCTTGTGCACTGTTGTTTCACATTTTCATATGTGCATGTCGCCTGACCTATTTGCAATGCAGACAC

GAGCAGGGAGCCATGTTGCCAGCCCTCACAGTGCCTTCAGTGCCCCTGCACGCCTGGACAAGGCGGGTGGGGTCCAC

ACCGCCCAGCCATCACCACACACCCCACCTGCCACACCCACCCTTGTGCACTGTTGTTTCACATTTTCATATGTGCA

TGTCGCCTGACCTATTTGCAATGCAGACACGAGCAGGGAGCCATGTTGCCAGCCCTCACAGTGCCTTCAGTGCCCCT

GCACGCCTGGACAAGGCGGGTGGGTCCACACCGCCCAGCCATCACCACACACCCCACCTGCCACACCCACCCTTGT

GCACTGTTGTTTCACATTTTCATATGTGCATGTTGCCTGACCTATTTGCAATGCAGACACGAGCAGGGAGCCATGTT

GCCAGCCCTCACAGTGCCTTCAGTGCCCCTGCACGCCTGGACAAGGCGGGTGGGTCCACACCGCCCAGCCATCACC

ACACACCCCACCTGCCACACCCACCCTTGTGCACTGTTGTTTCACATTTTCATATGTGCATGTTGCCTGACCTATTT

GCAATGCAGACACGAGCAGGGAGCCATGTTGCCAGCCCTCACAGTGCCTTCAGTGCCCCTGCACGCCTGGACAAGGC

GGGTGGGGTCCACACCGCCCAGCCATCACCACACACCCCACCTGCCACACCCACCCTTGTGCACTGTTGTTTCACAT

TTTCATATGTGCATGTTGCCTGACCTATTTGCAATGCAGACACGAGCAGGGAGCCATGTTGCCAGCCCTCACAGTGC

TABLE 6-continued

Sequences Corresponding to Frequency Peaks (SEQ ID NOs 21-167)

CTTCAGTGCCCCTGCACGCCTGGACAAGGCGGGTGGGGCCCCTGCCACCCAGCCATCACCACACACCCCACCTGCCA

CACCCACCCTTGTGCACTGTTGTTTCACATTTTCATATGTGCATGTTGCCTGACCTATTTGCAATGCAGACACGAGC

AGGGAGCCATGTTGCCAGCCCTCACAGTGCCTTCAGTGCCCCTGCACGCCTGGACAAGGCGGGTGGGGTCCACACCG

CCCAGCCATCACCACACACCCCACCTGCCACACCCACCCTTGTGCACTGTTGTTTCACATTTTCATATGTGCATGTT

GCCTGACCTATTTGCAATGCAGACACGAGCAGGGAGCCATGTTGCCAGCCCTCACAGTGCCTTCAGTGCCCCTGCAC

GCCTGGACAAGGCGGGTGGGGTCCACACCGCCCAGCCATCACCACACACCCCACCTGCCACACCCACCCTTGTGCAC

TGTTGTTTCACATTTTCATATGTGCATGTCGCCTGACCTATTTGCAATGCAGACACGAGCAGGGAGCCATGTTGCCA

GCCCTCACAGTGCCTTCAGTGCCCTGTACGCCTGGACAAGGCGGGTGGGGTCCACACCGCCCAGCCATCACCACAC

ACCCCACCTGCCACACCCACCCTTGTGCACTGTTGTTTCACATTTTCATATGTGCATGTCGCCTGACCTATTTGCAA

TGCAGACACGAGCAGGGAGCCATGTTGCCAGCCCTCACAGTGCCTTCAGTGCCCCTGCACGCCTGGACAAGGCGGGT

GGGGCCCTGCCACCCAGCCATCACCACACACCCCACCTGCCACACCCACCCTTGTGCACTGTTGTTTCACATTTTCA

TATGTGCATGTTGCCTGACCTATTTGCAATGCAGACACGAGCAGGGAGC

>SEQ ID NO: 40

ACTTTCATATGTGCATGTTGCCTGACCTATTTGCAATGCAGACACGAGCAGGGAGCCATGTTGCCAGCCCTCACAGT

GCCTTCAGTGCCCCTGCACGCCTGGACAAGGCGGGTGGGGTCCACACCGCCCAGCCATCACCACACACCCCACCTGC

CACACTCACCCTTGTGCACTGTTGTTTCACATTTTCATATGTGCAAGTTGCCTGACCTATTTGCAATGCAGACACGA

GCAGGGAGCCATGTTGCCAGCCCTCACAGTGCCTTCAGTGCCCCTGCACGCCTGGACAAGGCGGGTGGGGTCCACAC

CGCCCAGCCATCACCACACACCCCACCTGCCACACCCACCCTTGTGCACTGTTGTATCACATTTTCATATGTGCATG

TTGCCTGACCTATTTGCAATGCAGACACGAGCAGGGAGCCATGTTGCCAGCCCTCACAGTGCCTTCAGTGCCCCTGC

ACGCCTGGACAAGGCGGGTGGGGTCCACACCGCCCAGCCATCACCACACACCCCACCTGCCACACCCACCCTTGTGC

ACTGTTGTTTCACATTTTCATATGTGCATGTTGCCTGACCTATTTGCAATGCAGACACGAGCAGGGAGCCATGTTGC

CAGCCCTCACAGTGCCTTCAGTGCCCCTGCACGCCTGGACAAGGCGGGTGGGGTCCACACCGCCCAGCCATCACCAC

ACACCCCACCTGCCACACCCACCCTTGTGCACTGTTGTTTCACATTTTCATATGTGCATGTTGCCTGACCTATTTGC

AATGCAGACACGAGCAGGGAGCCATGTTGCCAGCCCTCACAGTGCCTTCAGTGCCCCTGCACGCCTGGACAAGGCGG

GTGGGGTCCCTGCCACCCAGACATCACCACACACCCCACCTGCCACACCCACCCTTGTGCACTGTTGTTTCACATTT

TCATATGTGCATGTTGCCTGACCTATTTGCAATGCAGACACGAGCAGGGAGCCATGTTGCCAGCCCTCACAGTGCCT

TCAGTGCCCCTGCACGCCTGGACAAGGCGGGTGGGGTCCACACCGCCCAGCCATCACCACACACCCCACCTGCCACA

CCCACCCTTGTGCACTGTTGTTTCACATTTTCATATGTGCATGTTGCCTGACCTATTTGCAATGCAGACACGAGCAG

GGAGCCATGTTGCCAGCCCTCACAGTGCCTTCAGTGCCCCTGCACGCCTGGACAAGGCGGGTGGGGTCCACACCGCC

CAGCCATCACCACACACCCCACCTGCCACACTCACCCTTGTGCACTGTTGTTTCACATTTTCATATGTGCATGTTGC

CTGACCTATTTGCAATGCAGACACGAGCAGGGAGCCATGTTGCCAGCCCTCACAGTGCCTTCAGTGCCCCTGCACGC

CTGGACAAGGCGGGTGGGGTCCATGCCACCCAGCCATCACCACACACCCCACCTGCCACACCCACCCTTGTGCACTG

TTGTTTCACATTTTCATATGTGCATGTTGCCTGACCTATTTGCAATGCAGACACGAGCAGGGAGCCATGTTGCCAGC

CCTCACAGTGCCTTCAGTGCCCCTGCACGCCTGGACAAGGCGGGTGGGGTCCACACCGCCCAGCCATCACCACACAC

CCCACCTGCCACACCCACCCTTGTGCACTGTTGTTTCACATTTTCATATGTGCATGTCGCCTGACCTATTTGCAATG

CAGACACGAGCAGGGAGCCATGTTGCCAGCCCTCACAGTGCCTTCAGTGCCCCTGCACGCCTGGACAAGGCGGGTGG

GGTCCACACCGCCCAGCCATCACCACACACCCCACCTGCCACACCCACCCTTGTGCACTGTTGTTTCACATTTTCAT

ATGTGCATGTTGCCTGACCTATTCGCAATGCAGACACGAGCAGGGAGCCATGTTGCCAGCCCTCACAGTGCCTTCAG

TGCCCCTGCACGCCTGGACAAGGCGGGTGGGGTCCACACCGCCCAGCCATCACCACACACCCCACCTGCCACACCCA

TABLE 6-continued

Sequences Corresponding to Frequency Peaks (SEQ ID NOs 21-167)

CCCTTGTGCACTGTTGTTTCACATTTTCATATGTGCATGTTGCCTGACCTATTTGCAATGCAGACACGAGCAGGGAG
CCATGTTGCCAGCCCTCACAGTGCCTTCAGTGCCCCTGCACGCCTGGACAAGGCGGGTGGGGTCCACACCGCCCAGC
CATCACCACACACCCCACCTGCCACACCCACCCTTGTGCACTGTTGTTTCACATTTTCATATGTGCATGCTGCCTGA
CCTATTTGCAATGCAGACACGAGCAGGGAGCCATGTTGCCAGCCCTCACAGTGCCTTCAGTGCCCCTGCACGCCTGG
ACAAGGCGGGTGGGGTCCACACCGCCCAGCCATCACCACACACCCCACCTGCCACACCCACCCTTGTGCACTGTTGT
TTCACATTTTCATATGTGCATGCTGCCTGACCTATTTGCAATGCAGACACGAGCAGGGAGCCATGTTGCCAGCCCTC
ACAGTGCCTTCAGTGCCCCTGCACGCCTGGACAAGGCGGGTGGGGTCCACAGCGCCCAGCCATCACCACACACCCCA
CCTGCCACACCCACCCTTGTGCACTGTTGTTTCACATTTTCATATGTGCATGCTGCCTGACCTATTTGCAATGCAGA
CACGAGCAGGGAGCCATGTTGCCAGCCCTCACAGTGCCTTCAGTGCCCCTGCACGCCTGGACA

>SEQ ID NO: 41

ACCCGACCTGCCACACCCACCCTTGTGCACTGTTGTTTCACATTTTCATATGTGCATGTTGCCTGACCTATTTGCAA
TGCAGACACGAGCAGGGAGCCATGTTGCCAGCCCTCACAGTGCCTTCAGTGCCCTTGCACGCCTGGACAAGGCGGGT
GGGGGCCCTGCCACCCAGCCATCACCACACACCCCACCTGCCACACCCACCCTTGTGCACTGTTGTTTCACATTTTC
ATATGTGCATGTTGCCTGACCTATTTGCAATGCAGACACGAGCAGGGAGCCATGTTGCCAGCCCTCACAGTGCCTTC
AGTGCCCTTGCACGCCTGGACAAGGCGGGTGGGGCCCCTGCCACCCAGCCATCACCACACACCCCACCTGCCACACC
CACCCTTGTGCACTGTTGTTTCACATTTTCATATGTGCATGTCGCCTGACCTATTTGCAATGCAGACACGAGCAGGG
AGCCATGTTGCCAGCCCTCACAGTGCCTTCAGTGCCCCTGCACGCCTGGACAAGGCGGGTGGGGCCCCTGCCTCCCA
GCCATCACCACACACCCCACCTGCCACACCCACCCTTGTGCACTGTTGTTTCACATTTTCATATGTGCATGTTGCCT
GACCTATTTGCAATGCAGACACGAGCAGGGAGCCATGTTGCCAGCCCTCACAGTGCCTTCAGTGCCCCTGCACGCCT
GGACAAGGCGGGTGGGGTCCCTGCCACCCAGCCATCACCACACACCCCACCTGCCACACCCACCCTTGTGCACTGTT
GTTTCACATTTTCATATGTGCATGTTGCCTGACCTATTTGCAATGCAGACACGAGCAGGGAGCCATGTTGCCAGCCC
TCACAGTGCCTTCAGTGCCCCTGCACGCCTGGACAAGGCGGGTGGGGTCCACACCGCCCAGCCATCACCACACACCC
CACCTGCCACACCCACCCTTGTGCACTGTTGTTTCACATTTTCATATGTGCATGTTGCCTGACCTATTTGCAATGCA
GACACGAGCAGGGAGCCATGTTGCCAGCCCTCACAGTGCCTTCAGTGCCCCTGCACGCCTGGACAAGGCGGGTGGGG
TCCACACCGCCCAGCCATCACCACACACCCCACCTGCCACACCCACCCTTGTGCACTGTTGTTTCACATTTTCATAT
GTGCATGTTGCCTGACCTATTTGCAATGCAGACACGAGCAGGGAGCCATGTTGCCAGCCCTCACAGTGCCTTCAGTG
CCCCTGCACGCCTGGACAAGGCGGGTGGGGTCCACACCGCCCAGCCATCACCACACACCCCACCTGCCACACCCACC
CTTGTGCACTGTTGTTTCACATTTTCATATGTGCATGTTGCCTGACCTATTTGCAATGCAGACACGAGCAGGGAGCC
ATGTTGCCAGCCCTCACAGTGCCTTCAGTGCCCCTGCACGCCTGGACAAGGCGGGTGGGGTCCTGCCACCCAGACA
TCACCACACACCCCACCTGCCACACCCACCCTTGTGCACTGTTGTTTCACATTTTCATATGTGCATGTTGCCTGACC
TATTTGCAATGCAGACACGAGCAGGGAGCCATGTTGCCAGCCCTCACAGTGCCTTCAGTGCCCCTGCACGCCTGGAC
AAGGCGGGTGGGGTCCACACCGCCCAGCCATCACCACACACCCCACCTGCCACACCCACCCTTGTGCACTGTTGTTT
CACATTTTCATATGTGCATGTTGCCTGACCTATTTGCAATGCAGACACGAGCAGGGAGCCATGTTGCCAGCCCTCAC
AGTGCCTTCAGTGCCCCTGCACGCCTGGACAAGGCGGGTGGGGTCCACACCGCCCAGCCATCACCACACACCCCACC
TGCCACACCCACCCTTGTGCACTGTTGTTTCACATTTTCATATGTGCATGTTGCCTGACCTATTTGCAATGCAGACA
CGAGCAGGGAGCCATGTTGCCAGCCCTCACAGTGCCTTCAGTGCCCCTGCACGCCTGGACAAGGCGGGTGGGGTCCA
CACCGCCTAGCCATCACCACACACCCCACCTGCCACACCCACCCTTGTGCACTGTTGTTTCACATTTTCATATGTGC
ATGTTGCCTGACCTATTTGCAATGCAGACACGAGCAGGGAGCCATGTTGCCAGCCCTCACAGTGCCTTCAGTGCCCC
TGCACGCCTGGACAAGGCGGGTGGGGTCCACACCGCCCAGCCATCACCACACACCCCACCTGCCACACCCACCCTTG

TABLE 6-continued

Sequences Corresponding to Frequency Peaks (SEQ ID NOs 21-167)

```
TGCACTGTTGTTTCACATTTTCATATGTGCATGTTGCCTGACCTATTTGCAATGCAGACACGAGCAGGGAGCCATGT

TGCCAGCCCTCACAGTGCCTTCAGTGCCCCTGCACGCCTGGACAAGGCGGGTGGGGTCCACACCGCCCAGCCATCAC

CACACACCCCACCTGCCACACCCACCCTTGTGCGCTGTTGTTTCACATTTTCATATGTGCATGTTGCCTGACCTATT

TGCAATGCAGACACGAGCAGGGAGCCATGTTGCCAGCCCTCACAGTGCCTTCAGTGCCCCTGCACGCCTGGACAAGG

CGGGTGGGGTCCACACCGCCCAGCCATCACCAGACACCCCACCTGCCACACTCACCCTTGTGCACTGTTGTTTCACA

TTTTCATATGTGCATGTCGCCTGACCTATTTGCAATGCAGACACGAGCAGGGAGCCATGTTGCCAGCCCTCACAGTG

CCTTCAGTGCCCCTGCACGCCTGGACAAGGCGGGTGGGGTCCACACCGCCCAGCCATCACCAGACACCCCACCTGCC

ACACTCACCCTTGTGCACTGTTGTTTCACATTTTCATATGTGCATGTTGCCTGACCTATTTGCAATGCAGACACGAG

CAGGGAGCCATGTTGCCAGCCCTCACAGTGCCTTCAGTGCCCCTGCACGCCTGGACAAGGCGGGTGGGGTCCACACC

GCCCAGCCATCACCACACACCCCACCTGCCACACCCACCCTTGTGCACTGTTGTTTCACATTTTCATATGTGCATGT

TGCCTGACCTATTTGCAATGCAGACACGAGCAGGGAGCCATGTTGCCAGCCCTCACAGTGCCTTCAGTGCCCCTGCA

CGCCTGGACAAGGCGGGTGGGGTCCACACCGCCCAGCCATCACCACACACCCCACCTGCCACACCCACCCTTGTGCA

CTGTTGTTTCACATTTTCATATGTGCATGCTGCCTGACCTATTTGCAATGCAGACACGAGCAGGGAGCCATGTTGCC

AGCCCTCACAGTGCCTTCAGTGCCCCTGCACGCCTGGACAAGGCGGGTGGGGTCCACACCGCCCAGCCATCACCACA

CACCCCACCTGCCACACCCACCCTTGTGCACTGTTGTTTCACATTTTCATATGTGCATGTTGCCTGACCTATTTGCA

ATGCAGACACGAGCAGGGAGCCATGTTGCCAGCCCTCACAGTGCCTTCAGTGCCCCTGCACGCCTGGACAAGGCGGG

TGGGGTCCACACCGCCCAGCCATCACCACACACCCCACCTGCCACACCCACCCTTGTGCACTGTTGTTTCACATTTT

CATATGTGCATGTTGCCTGACCTATTTGCAATGCAGACACGAGCAGGGAGCCATGTTGCCAGCCCTCACAGTGCCTT

CAGTGCCCCTGCACGCCTGGACAAGGCGGGTGGGGTCCACACCGCCCAGCCATCACCACACACCCCACCTGCCACAC

CCACCCTTGTGCACTGTTGTTTCACATTTTCATATGTGCACGTTGCCTGACCTATTTGCAATGCAGACACGAGCAGG

GAGCCATGTTGCCAGCCCTCACAGTGCCTTCAGTGCCCCTGCACGCCTGGACAAGGCGGGTGGGGCCTTGCCACCC

AGCCATCACCACACACCCCACCTGCCACACCCACCCTTGTGCACTGTTGTTTCACATTTTCATATGTGCATGTCGCC

TGACCTATTTGCAATGCAGACACGAGCAGGGAGCCATGTTGCCAGCCCTCACAGTGCCTTCAGTGCCCCTGCACGCC

TGGACAAGGCGGGTGGGGTCCACACCGCCCAGCCATCACCACACACCCCACCTGCCACACCCACCCTTGTGCACTGT

TGTTTCACATTTTCATATGTGCATGTCGCCTGACCTATTTGCAATGCAGACACGAGCAGGGAGCCATGTTGCCAGCC

CTCACAGTGCCTTCAGTGCCCTTGCACGCCTGGACAAGGCGGGTGGGGCCCTGCCACCCAGGCATCACCACACACCC

CACCTGCCACACCCACCCTTGTGCACTGTTGTTTCACATTTTCATATGTGCATGTTGCCTGACCTATTTGCAATGCA

GACACGAGCAGGGAGCCATGTTGCCAGCCCTCACAGTGCCTTCAGTGCCCCTGCACGCCTGGACAAGGCGGGTGGGG

TCCACACCGCCCAGCCATCACCACACACCCCACCTGCCACACCCACCCTTGTGCACTGTTGTTTCACATTTTCATAT

GTGCATGTTGCCTGACCTATTTGCAATGCAGACACGAGCAGGGAGCCATGTTGCCAGCCCTCACAGTGCCTTCAGTG

CCCTTGCACGCCTGGACAAGGCGGGTGGGGTCCACACCGCCCAGCCATCACCACACACCCCACCTGCCACACCCACC

CTTGTGCACTGTTGTTTCACATTTTCATATGTGCATGTTGCCTGACCTATTTGCAATGCAGACACGAGCAGGGAGCC

ATGTTGCCAGCCCTCACAGTGCCTTCAGTGCCCCTGCACGCCTGGACAAGGCGGGTGGGTCCACACCGCCCAGCCA

TCACCACACACCCCACCTGCCACACCCACCCTTGTGCACTGTTGTTTCACATTTTCATATGTGCATGTTGCCTGACC

TATTTGCAATGCAGACACGAGCAGGGAGCCATGTTGCCAGCCCTCACAGTGCCTTCAGTGCCCCTGCACGTACGCCT

GGACAAGGCGGGTGGGGTCCACACCGCCCAGCCATCACCACACACCCCACCTGCCACACCCACCCTTGTGCACTGTT

GTTTCACATTTTCATATGTGCATGTTGCCTGACCTATTCGCAATGCAGACACGAGCAGGGAGCCATGTTGCCAGCCC

TCACAGTGCCTTCAGTGCCCCTGCACGCCTGGACAAGGCGGGTGGGTCCACACCGCCCAGCCATCACCACACACCC
```

TABLE 6-continued

Sequences Corresponding to Frequency Peaks (SEQ ID NOs 21-167)

CACCTGCCACACCCACCCTTGTGCACTGTTGTTTCACATTTTCATATGTGCATGTTGCCTGACCTATTTGCAATGCA
GACACGAGCAGGGAGCCATGTTGCCAG

>SEQ ID NO: 42

CGGGAAACGTTTCCGGGCGTAGACGCCGCGGGCCTGAGGGCATCTACAAGATACGGGCACTGGCGCCCAGGCAGGCG
AGCAGCACCCACGCATGACGTGATCTCGCTCGATCTGCAATATTGTACTGTATTACGTATTGTACGCTGTTTTACAG
GGACTGTCCAGGACCAAAATGTCGCAGATTACGTTGGGCACGGGAGGGGGGGGGACCATAACTCATAAGGGGTCCTG
GGTCTGCGCCCAGCGTCTTGATGTCTTTGACACAGTGCGCCGCACAGCATGCCCAGCACCAGTTCTTAAAACTCTTT
TGGGTTGCAAAGCAACCATATAAATAACCGGCGTCCTTCAGGATTTGCTTACTTCCAGCCCATAAGTATTCATTAAT
CCGCCATGGACTATGTTGCCAAGCCGAAACACACAGTTGAACCCCATGTGCGTTTCTAACACATCACATGCGCCGTG
TGGTCACCCCTGTTGTCCCCCTGTCCCGAGTCCCTGGTCGCGAGAGTGGGCTGTACTGTGTTGGAAATCCCAGGACG
TCGTAGTACTAGGCGTATCAGGAGGACAGGGTCACGTACCGTATTGTGCAAACCTGCCCCTAAGCACGGGAAAT

>SEQ ID NO: 43

TTGCCGAAACTTGGGTCATCTGAGGGCCGAAGCCCTGCCTCCCCGCCGCTTCGGCACCCCAGCCAGCATGCCGGGTC
AGCGCCCCGAACCCGCACCCTGATCCGCCACCGCACGCCCGGCCCGGATTAACCATAGTTCATTTTGGGATCGGAAC
CAACGCTCCTCCCCACCCCACTACCCCGGATGTATGCTCCGTGCCTGGCGGCGTCGGGGATAATAATAATAATAAT
AATAATAATAATAATAATAATAATAATAATAATAATAATAATAATAATAATAATAATAATAATAATAATAATAATAA
TAATAATAATAATAATAATAATAATAATAATAATAATAATAATAATAATAATAATAATAATAATAATAATAATAATA
ATAATAATAATAATAATAATAATTACAACGCCGGCCCATAGGGCCTGGCATGGATTAACGGGGCAAGGTGACTA
GGGCGAGAGGGCCCGCCCCCCTCACGCTGACGCCTCACCACGAAAGAGTCACAACCTCCGAAACTACAACCTCCAAG
TCCTAGGCCGCTCTTCAAAGTCCACTACATCCGAGCCTGCACACCTAGCATATCGAGCTAGGGAAACGCCGCGTTAT
AGTAGTGGAGCACTGCCAGTTCGTGCAAACCGAGGAGCCATGGCGCTCCTCCTCGAGCCTTGGATCTTGAGCCTTGT
CTTGAACCTTGGACCTCGCCACTAAATCGGACTTCTGCACCACGACCTTTCTAGGTTGCAGCGGGCATAAGCCCGCA
ATTGCCACTAAGGGCAATTACCTATCATTCGTGGGATCACCAATCGGTTGCGCACCAATCTTTCGCCTTTTGCATAA
TTGGGCTTTTATCCGGATTCGTACCCGGGTCCCTTCTGCCGTAAGGACG

>SEQ ID NO: 44

CCACTTATTGACTCCTTACTGCCGTGTAGCGTTACAAACCGCCACGGCCCCAAACGATAATCCCAATCTCTCAAACC
GACAATAGCCTCCACTCATGCCTCAAGCGGCCTAGCAACTCATTCGTGGCCCTCAGCGGCCTCCTACCTCCGGCCTC
GCAGCTCCCGATACCCCACCAAGTCCGCCGTGCCCGCCCCAGCCCGCCCGTGTTGAGGTTGCACTAGTGGCCGAAAG
TGCTGCCAGTACTGGGTGTGTCGCATGTATGAAGTGCCTGATAGCAGCAGAGTCCAGACAACCACGCACGCCGCAGC
GCCCACGGGTGCCACCACATTAATCCGCGGCGGCACCAGGGGGGCGGGTGGGTTGTCACCGTCCCGGCAGAGGGAC
GATCCGAAATACAGTACAGAAGCACAACGGCAGATAAGGCGCCGTGTGCTCCTGACGCGTACAAGACCCAGCTCGGT
TCGGCCCCATGCACAGGCACGTACCCGAGCGTCCTGCGCCGTGCGTGACTCTAACGCAACACGGCAGTTACGTCGCA
ATAACTAGACTTATCTCCACTGCGCTGCGATAAGTCAGCGCTTATTGACTCCTTACTGCCGTGTAGCGTTACAAACC
GCCACGGCCCCAAACGATAATCCCAATCTCTCAAACCGACAATAGCCTCCACTCATGCCTCAAGCGGCCTAGCAACT
CATTCGTGGCCCTCAGCGGCCTCCTACCTCCGGCCTCGCAGCTCCCGATACCCCACCAAGTCCGCCGTGCCCGCCCC
AGCCCGCCCGTGTTGAGGTTGCACTAGTGGCCGAAAGTGCTGCCAGAGTTTGGTAGTAGTCCTCAACGCGGGGAGGT
CATGGTGCGGGCGACGGCAGCCCTGGTGGCTGGGCTTGATTGGCTTCGCGTATGCAGCTCTTCTCGCAAAGCGCTCG
GCCCAACGGCCGGTCACGCAAACCAAGGTGCGGTCGGCGGTGATGGCGGCGGCGTTCGTGCCCTTGCGCTACCGAAA
TCATGTGTCTCGAACACCGCGGAGCGCTCCGCCCATCGCCTTGCTTGCGCACGAACGTACGGTCCTAGTTGCACACT

TABLE 6-continued

Sequences Corresponding to Frequency Peaks (SEQ ID NOs 21-167)

CGACAGCGGTCGATAGAACGAGCTTCGTGCTTGGGGATATTGGCTGCACGAGCAGCACCATCACATGGGGATGAGCG
CCGCCGGAGGCGCCGCCGGCACCTGCTGCAGGCGGCGCAGGGCGACGCCAACGCGGGGCCTGACAGCGCCACACTCC
GTCGGTCATGGGCGGTCAATGGTCACTACCAGAAGACAAGCAGCAATAGGAACACGACTGGCGTTGCAAGGGCCATG
ATACCAGACTCACAAACGTATCAGGTGCACCAATGGCCACGACAGAAACACACATGCATTGTCCCGCGTGCGCCAGC
CACGCAGACGACGCCGGGGCGTTACAGGGAAACACATGCATCCTTGTTCAGGTGTGTGGCTTCTGGGCAGCTGTGGC
CGTCCGTGTGCCTAGGAAAGGTAACAGTGCGTGTTGGCACGTGTTGGCACGAAGCACTGGAGACCTCGCTCGGTACT
CTCTACCGGCCCCCAGGGCCATGCCATAACACGTGTTGACGTTGTAGGCTGCTCGGAACAACCTTGGGAATAATAAC
AACTTCGTGACTCGAAGCTGGGACAGACTAGCCAACATGAGCCACGCAGGAGAAGGCGCGAGGTGCAACACTAGAGC
GGTTTTACGTACGCGAGTCACGCGCGGCAACCTGCCCTTCACCCGCGCCGTCGTGGTGTAGGATGCGGGCAGCCATG
CCCAGCCGTGCAGCATGGCCACGAACACTAATTTCTTTCTTGCTAGCTAGGTGCCATGCTTGAGATTTGCAGTGTCT
TGCATAAGAGTCACTACCAATCAAGCAGTAGGTACACCCATAGATAGCATCACCCCGGCGGACGCAGGACAGGCGCG
CACGTGAATGCCTCCAAACGCCGCGGGGATGCATGCACACAATGTCCCGTACGTGCCGATACCGTACGCCACGGCGG
CTGTGGGGTGTACCGTAATAGCAGGGAGGGCAACATGAAGGGTAACACCTCAGCAACCCCAGCAAGGCTGGCCTGGT
CGAGCGGCGCGGAGGGGTGAAGGATACCCGGCACGCGTGGAACACGCAATGTATCTATAGTGATAGAAGGCGTAGTG
ATGGGAGGAAATAAGGAGCACTCGGGGCCGCGATGGCGGGTTGGATGCGCCACGGGCCCCGGCCCAGCCAAAGGGAG
CGAACGCCGGGCGGAGCCGGTGGGTGAGCGACTCGAGGGACGTGCCAGTAGTGAACCCATCGCAGTGGCGGATGGGT
CATCCAATGTGAGAGATGATACAGCCACGCCGGCAGCCAAACTCCGCACTC

>SEQ ID NO: 45

ATGGACAATTTACGGCGTACGTGCCCTCATGATACAGCCTGTGCGCCGCAGGCAACGGGCTCCGCGCCCTTGCTCCA
TGGACACTTCACGGCGTACGTGCCCTCATGACACGGCCTGTGTGCCGCAGGCAACGGGCTCCGCGCCCTTGCTTCAT
GGACAATGCGCCGCGTACGTGTTCTTATGATACGGTCTGTGCGCCGCAAGCAACGGGCTCCGCACCCTTGTTTTATG
GACAATTCACGGCATACGTGCCCGTATGATGTGACCTGTGTGCCGCAAGCAACGGCTTCGCACCCTTGCTTTTGGGT
AATAGATGGCATACGTGCCCTTATGATACGACCTGTGTGCCGCAAGCAACGGGCTCCACACTCTTGCGTTGTGGATT
ATAGACGGCATTGAAATGCTTACGTGCCTTCGTTGTACATGCCTTTGCGTTGTGGACAATGTGTGGTCTGAGCGCCA
CGTTCGGATACGGCGTGTGTGCCGCCAGCAACAGGCTTTGCGCCTCGCATCATGTGTCTTGCGATATGGCCTGTGTG
CCGCATGCAATTATGCTGCCTGCCCTGTCGTTATGGACGCTTCGACTTGTTGCGTGCCCTGCTGCGTGCCCTGTCGC
AATACGCCTTGAGTGTACCGTGCACGGCAAGCCTGCGCCTCGCTATTGCTTCGTGTTGACAACGGAGCGGGCTTACG
TGATCATGCGTCACCCTGTACGTCTTGAGGTCCGCACGCACATCATACTATCACGCGGCATCACCCTTGTAGTTTGG
CTGACGCACCCCAAGCCAACCTATATGCATTCGATGTGTGCGCTAGGCCCAAGTGCCGAATTTGTTTTTCCGGATAT
TTCGCCCTCAGTGAGCGATGTGGAGTTTTGTGCAGTTCGGCCAGCATGCTATGCCCAGCCAATAACAATACCGCATG
ATGCATAACTATACCGCATGACGCATAACTATACCGCATGACGCATAAACATGCCTTCGTGCCCTGCACCAGGCATC
GGACGCTGTGTCACGCAGTGAGCCCGACCCTGCGCAACCAACATTTTGTTGCGAGATACGGTCGGAGCTGGGATTAC
AGCCTGCCTGGTGGGTTTGGATGGCGCCCGTGTGTTGGGCTGGGCTGTTGCTGCTCGCGGTGGGGCCCACCACCAAG
TCACGGCACCCATCCGCCCTCCCCTCTTGTTGGCCCACCCGCCTGTACACATGCCAGTCACCCGCTCGCCATCCTGT
GAAAGCGGGTAGCCGACTTGGCAAGCGCTTTTCCTGACACTTGGCGCAGGTTTGAGTGGGATACCAGAATGGTCTGA
ATGTAGTTGTTGGATAACCAGTACACTGCGGTGTGTAGCTGGTTAGCGGGAGTACCGTGCATGAAACACGCTACTCG
ACCCGCCATGCCCGCGCGATGGTACCACCAACCGTTCAACCCAGATCCATGCCGGGGTAGCATCGACCCCACAGTCA
GACTGATAGCTCCTATCCAGGTGTTAGGCGCCATGTATGTATCTGTGGACGCGTCAAGCTGGCTTGTGCCGTAGCGT
TGGCCGCCTGTATGGCACGGCATCTGTGTCACGTTATGGCCTCATGCTTACCGTAGTCACGCGGCTTGCGTGCTGTG

TABLE 6-continued

Sequences Corresponding to Frequency Peaks (SEQ ID NOs 21-167)

CGGCACGCTCCCTGCCAATCCTTCAGGACATGTATGCATACATGTTACTTCGTCAGAGCCATAGCAGGGGCAGCGTG

TTCTGTCAATGCCTCATGAACCCAGAGACCCAAGCCAACGTACGCATTAGTTCCGCAACGCACGTCAATGCCAACTG

TATGTGTCGCCTGCCCACTCGCGAGTGGACGCCTAGGGAACCAACCTTGGTTCCTTTCAGCCCCGGCCTTACTTCAC

CCGGCGGGGCAATTACTTATCACCGAAGTGCTAGGAGCAGTGTGCTATATGTCATTACTATTAAGAGC

>SEQ ID NO: 46

GGGGGCCTGAACGCTGTGGTACGGTGGGGCAAGCACACCCTTGCCGCAGAGCCCGAAGGGGAAGGAGGCAGTGGCGG

TACCACTGCCACTGGCGTCCTCCTTCGGGCTGGCTGGGATACAGACCGACACGCGAACCGGTGCATTATTCAGGGCT

TCAGCTATCGACGCAGCATAGCCTACTTACCATGTCATGCTCTATCTTTTTGTTTTGCGTCCAAAGCTGGAAGGCAT

CTCTTAGCTCGTTAAGCTCAGGCGAGTGCGGTGGCAGCTTTTTTAATCGCTCTTCGCAGTATGGAAGACGTGATAGC

TTAGGTAGCTGGTCGCCTGATAGATGGCCCGCCAGCACAAGCAACAGGGCAAGGCCTAACTGCAGCCGAGCCTGTCG

CCCGCGGTCACGTGTAATTACCATAGTTGGCTCAGTTCATTTTACTATATACTGTATGTCATCCGTGTGTGCTGAAG

CAAAACAAACTGCGCTCTTACTGATGATCAACACAGCTGAGTCTGAGTCCCCCACGATTGGATACAAGAGAGGAGTG

CCGAGGGAGATGC

>SEQ ID NO: 47

AGGATGTGCGGCGATCGCTGAAATGCAGTTGTGGGGTCCACACTCATATGGCACCCACGCCCCACACAGCACTGATG

CAGGGCTCCTGCAGCCGTCACGCCATGGGAATCAGCATATGGGCAGTGGCCTGTGCATACTTCTCTGTGGCCTGGCG

GGGCATCTGGCCAGGGCGTTTGACTAGCGGCATGGGGCCTGCACGCCGGTAGGGGGGCGCAGGCCCAAAATGATGCA

AGGAAGCTGATGTGTTGCGTGAGGTGCGCAGCGGTTCCTGATGGACGTGGGTGCTTTCATGCGTATGTATATTGGCT

ATGTGTGTTGATCTTTGCACCAGGGTGGTGTCGCCGCGCAGCGGAGCATTGGTGTTGGTGCACGGGGCGTGAACATT

GGGGCCCGCAGTTGGGATCGCGCCGGCACGGTCGCGGGCACCGCTGAAGATATGTTGGCGCGACCGGTCGCTTATGG

TGCACGCTAATACCCGCATACTGTGTGTAAGCACCGATTGCAATTATAAGTTGCGCATGTAGATATCGGTCTTCTCC

CGACATGCGCTCTGATGACGGTTCCATTTCCGCCAACTTAGGGTGAGAGTTAAGAGCCGGAGCCCTGTTGCCACCTG

CAAAATGCCTTAGCAACATGTGGCAACTATCTGCCCGAAGCAAGTTGCAAGCCAGCCCAGTTCAGGTTGCCACATGC

CATGCTGGGTATTCCCAGCGCGCTAGCGCACCTGCTTGGGCAGCTCGCTATGGCTGCCGTCGACAGTTGACCCTGGT

ATGCCATCGCTAGAGTCGCAGCCCGCTCCGGCCAACCTCGCTCCTCCGCAACCGACACACGAACCCGACGTCACTTG

ATCCCACAATTCCAGCGACTTTTGCGACCGGCTCTCCACCGACCGCTTGGATGCTTGCGCCCGGTCGCTGCCCCAGC

TACTTCCGCGGTGAAATAACAACGGTGAGCACTCTCAACCACTGCGAGGACAGCCCTAGCAACCGCACTGCGTAAGA

AGTACAGCATCGATTTGCTGCATGTTGATTTTGGCGCAAATGGGGGGTGCAAGCAGTTTGTTTCTCTCAGACGCGAG

CTAGCGCCCAAGCGCGCGATATGGGGGCGAGGAGCCACTATGTAGCTGTAACGATTGCATGAGTGGCGAATTTTACT

TCGAGGGTCTAGGGTGCGAGCGGAGTGGGATTACCCCCCGAGGGGCACGCCATGCGCTCAGGCCCCATGCAACAGAA

ATTCGCCGGGCACCAACCCACGCACAGATAATTCATAGGACTACACCATAGCCATCAGAGACCGGCCGGGAACAAGC

CCCGCAAGCGGGGCAGCATGGGCGCGACACCACCCTGCCGCGCCAACTCACCCCAAACACGCCCCAACCACTTGTGC

GACACAAGGGCTACCATACAGTAGCGCGCGACACCTAATCGCGTGCGCCGGAGTGTGCGAGCAAACATTGTACGGAG

GAGCTCGTTTGGGCCCTAGGACGCAGGGCCTGGGCTGGCATTTGGTGCATTCAATAGAGCATAGAAAACCGAGGCCA

CATATGTGCTCGGGTGCGCAAAGGTCGGCGGAATTGTGGGATCAAGTGACGTGGAAATGGATCTGGGGGACTGCGGG

GTTTTGGGGTGTGTTGGGTTGGTGGCGTGAAGGGTGTGATTTGTGAGGAATTTATCGATGCATGCCAAGTTGCACGC

CTTTCCCCTGTGTTTCCTACATGCCCCTGAACCCTCCCTTTGCTGGCTGCAGGCGAAGCGACAAGTGGTACCGCTGG

TACCACCCACGGGGGCCTTGTGCCCAAGCCGTGGTGGCGCATGGTAACTATACACGTGGCGGTCATCGACATTGCTT

TGTGCCGGCGCGCAGCACCCAGGATGTGCGGCGATCGCTGAAATGCAGTTGTGGGGTCCACACTCATATGGCACCCA

TABLE 6-continued

Sequences Corresponding to Frequency Peaks (SEQ ID NOs 21-167)

```
CGCCCCACACAGCACTGATGCAGGGCTCCTGCAGCCGTCACGCCATGGGAATCAGCATATGGGCAGTGGCCTGTGCA
TACTTCTCTGTGGCCTGGCGGGGCATCTGGCCAGGGCGTTTGACTAGCGGCATGGGGCCTGCACGCCGGTAGGGGGG
CGCAGGCCCAAAATGATGCAAGGAAGCTGATGTGTTGCGTGAGGTGCGCAGCGGTTCCTGATGGACGTGGGTGCTTT
CATGCGTATGTATATTGGCTATGTGTGTTGATCTTTGCACCAGGGTGGTGTCGCCGCGCAGCGGAGCATTGGTGTTG
GTGCACGGGCGTGAACATTGGGGCCCGCAGTTGGGATCGCGCCGGCACGGTCGCGGGCACCGCTGAAGATATGTTG
GCGCGACCGGTCGCTTATGGTGCACGCTAATACCCGCATACTGTGTGTAAGCACCGATTGCAATTATAAGTTGCGCA
TGTAGATATCGGTCTTCTCCCGACATGCGCTCTGATGACGGTTCCATTTCCGCCAACTTAGGGTGAGAGTTAAGAGC
CGGAGCCCTGTTGCCACCTGCAAAATGCCTTAGCAACATGTGGCAACTATCTGCCCGAAGCAAGTTGCAAGCCAGCC
CAGTTCAGGTTGCCACATGCCATGCTGGGTATTCCCAGCGCGCTAGCGCACCTGCTTGGGCAGCTCGCTATGGCTGC
CGTCGACAGTTGACCCTGGTATGCCATCGCTAGAGTCGCAGCCCGCTCCGGCCAACCTCGCTCCTCCGCAACCGACA
CACGAACCCGACGTCTGACGTGGAAATGGATCTGGGGGACTGCGGGGTTTTGGGGTGTGTTGGGTTGGTGGCGTGAA
GGGTGTGATTTGTGAGGAATTTATCGATGCATGCCAAGTTGCACGCCTTTCCCCTGTGTTTCCTACATGCCCCTGAA
CCCTCCCTTTGCTGGCTGCAGGCGAAGCGACAAGTGGTACCGCTGGTACCACCCACGGGGGCCTTGTGCCCAAGCCG
TGGTGGCGCATGGTAACTATACACGTGGCGGTCATCGACATTGCTTTGTGCCGGCGCGCAGCACCCAGGATGTGCGG
CGATCGCTGAAATGCAGTTGTGGGGTCCACACTCATATGGCACCCACGCCCCACACAGCACTGATGCAGGGCTCCTG
CAGCCGTCACGCCATGGGAATCAGCATATGGGCAGTGGCCTGTGCATACTTCTCTGTGGCCTGGCGGGGCATCTGGC
CAGGGCGTTTGACTAGCGGCATGGGGCCTGCACGCCGGTAGGGGGGCGCAGGCCCAAAATGATGCAAGGAAGCTGAT
GTGTTGCGTGAGGTGCGCAGCGGTTCCTGATGGACGTGGGTGCTTTCATGCGTATGTATATTGGCTATGTGTGTTGA
TCTTTGCACCAGGGTGGTGTCGCCGCGCAGCGGAGCATTGGTGTTGGTGCACGGGCGTGAACATTGGGGCCCGCAG
TTGGGATCGCGCCGGCACGGTCGCGGGCACCGCTGAAGATATGTTGGCGCGACCGGTCGCTTATGGTGCACGCTAAT
ACCCGCATACTGTGTGTAAGCACCGATTGCAATTATAAGTTGCGCATGTAGATATCGGTCTTCTCCCGACATGCGCT
CTGATGACGGTTCCATTTCCGCCAACTTAGGGTGAGAGTTAAGAGCCGGAGCCCTGTTGCCACCTGCAAAATGCCTT
AGCAACATGTGGCAACTATCTGCCCGAAGCAAGTTGCAAGCCAGCCCAGTTCAGGTTGCCACATGCCATGCTGGGTA
TTCCCAGCGCGCTAGCGCACCTGCTTGGGCAGCTCGCTATGGCTGCCGTCGACAGTTGACCCTGGTATGCCATCGCT
AGAGTCGCAGCCCGCTCCGGCCAACCTCGCTCCTCCGCAACCGACACACGAACCCGACGTCAGACGTGGAAATGGAT
CTGGGGGACTGCGGGGTTTTGGGGTGTGTTGGGTTGGTGGCGTGAAGGGTGTGATTTGTGAGGAATTTATCGATGCA
TGCCAAGTTGCACGCCTTTCCCCTGTGTTTCCTACATGCCCCTGAACCCTCCCTTTGCTGGCTGCAGGCGAAGCGAC
AAGTGGTACCGCTGGTACCACCCACGGGGGCCTTGTGCCCAAGCCGTGGTGGCGCATGGTAACTATACACGTGGCGG
TCATCGACATTGCTTTGTGCCGGCGCGCAGCACCCAGGATGTGCGGCGATCGCTGAAATGCAGTTGTGGGGTCCACA
CTCATATGGCACCCACGCCCCACACAGCACTGATGCAGGGCTCCTGCAGCCGTCACGCCATGGGAATCAGCATATGG
GCAGTGGCCTGTGCATACTTCTCTGTGGCCTGGCGGGGCATCTGGCCAGGGCGTTTGACTAGCGGCATGGGGCCTGC
ACGCCGGTAGGGGGGCACAGGC
```

>SEQ ID NO: 48

```
GATGTGTGGGTTGCGGAGATGGAGGCCGTGGCCGCGGAAGGGATGAGCGATGGAAGTTAGGACCATGCACGGACCTT
CCGCCGCGTCCCTCACTCACTCCCAGGTCAACGTGAAGTGCGAATCAGCTTGTAACGAGGCGCAGAAGTGTGCACAA
GCCGCAGAACCTGCGAGTGAAGCCATACCCACCACCCTCACCTGGCGGGCGGGCGCCTTGGCTAGGCCTGCTGCCCA
CCACCAGTGCCAAGGCAGGCCATCGCATCTTCTGTGTGGCGCCGCGGCCTTGACAGATATATTGAACTCAGCACGCA
AAATGCTAATTACCGTCTGAGCAAGATAAAGCCGCTTATGCAAAGAAACACGAGTCAACGCGGGCTACAAAAGAAAA
TGCTCCGAGTTGCTTCTAACCGTCATCGAACGAATTATTTATGCGCTGACTTATCGCAGCGCAGTGGAGATAAGTCT
```

TABLE 6-continued

Sequences Corresponding to Frequency Peaks (SEQ ID NOs 21-167)

AGTTATTGCGACGTAACTGCCGTGTTGCGTTAGAGTCACGCACGGCGCAGGACGCTCGGGTACGTGCCTGTGCATGG

GGCCGAACCGAGCTGGGTCTTGTACGCGTCAGGAGCACACGGCGCCTTATCTGCCGTTGTGCTTCTGTACTGTATTT

CGGATCGTCCCTCTGCCGGGACGGTGACCTCAGTGTGTCGCACTTAAACGTTCCCTACATTTCTGGACTTTCTTTGC

AATCCTATACCTGGTTCTAACTATACTTGACCATGTATGGACCGAATAAGCGTTTAATATATACTCAGACGGAGTTG

CAGCGTTTTGTTGCGCGATCCTGCTCAATGGAACCCCTTAGCTTGATCACGCTCGCTCTCTGATCGTAAGGGAATGC

CCTTCGAAGCTTCTCTGGCGCTTTGAACCACGCTTTGGTTCGGGGGCCGCATTCGGGAGCAAATCGGAGCAGAGCGG

AGCTTTCAAGCGGAGCAAAGGCGCGCGAAGCGTTGCGGACAAGGCGTTCGGCAAGTCACTGAAAGCAAAAGGGCATG

CACAGCTGTGCGGGCGGGCTACTTGCTTGCCATGCGCGGTCCTGCTTGCCGTGCCTTCGTGTCTACCCGTCGCTTTA

CAGTTCACAGCTTTGTGCAATACCTTTCCACATCTTCCATTGTGCCACCCCCACCTCCCCAAGACCCTCAGGACTTT

TGGCGCGGTACTTCTCCTGTCTGCCTATCCAGGCCGCAGGGCCCGCGTGCCCTTGGGGAAAGGGCGTGTGTGCCGTT

GGGATCCGGCCTGTGCGCCGCAAGCAACGGGCTTTGCGCCCTTGCCTTATGGACAATGGACGGCATACGTGCCCTTA

TGATACGGCCTGTGTGCCGCAAGCAATGGGCTCCGCGCCCTTGCTTTATGGACAATGGACGGCATACGTGCCCTTAT

GATACGGCCTGTGCGCCGCAAGCAACGGGCTCCGCGCCCTTGCTTTATGGACAATGGACGGCATACGTGCCCTTATG

ATACGGCCTGTGTGCCGCAAGCAACGGGCTCCGCG

>SEQ ID NO: 49

CATGGACAATTTACGGCGTACGTGCCCTCATGATACAGCCTGTGCGCCGCAGGCAACGGGCTCCGCGCCCTTGCTCC

ATGGACACTTCACGGCGTACGTGCCCTCATGATACGGCCTGTGTGCCGCAGGCAACGGGCTCCGCGCCCTTGCTTCA

TGGACAATGCGCCGCGTACGTGTTCTTATGATACGGCCTGTGCGCCGCAAGCAACGGGCTCCGCACCCTTGTTTTAT

GGACAATTCACGGCATACGTGCCCGTATGATGTGACCTGTGTGCCGCAAGCAACGGCTTCCCACCCTTGCTTTTGGG

TAATAGATGGCATACGTGCCCTTATGATACGACCTGTGTGCCGCAAGCAACGGGCTCCACACTCTTGCGTTGTGGAT

TATAGACGGCATTGAAATGCTTACGTGCCTTCGTTGTACATGCCTTTGCGTTGTGGACAATGTGTGGTCTGAGCGCC

ACGTTCGGATACGGCGTGTGTGCCGCCAGCAACAGGCTTTGCGCCTCGCATCATGTGTCTTGCGATATGGCCTGTGT

GCCGCATGCAATTATGCTGCCTGCCCTGTCGTTATGGACGCTTCGACTTGTTGCGTGCCCTGCTGTGTGCCCTGTCG

CAATACGCCTTGAGTGTACCGTGCACGGCAAGCCTGCGCCTCGCTATTGCTTCGTGTTGACAACGGAGCGGGCTTAC

GTGATCATGCGTCACCCTGTACGTCTTGAGGTCCGCACGCACATCATACTATCACGCGGCACCACCCTTGTAGTTTG

GCTGACGCACCCCAAGCCAACCTATATGCATTCGATGTGTGCGCTAGGCCCAAGTGCCGAATTTGTTTTTCCGGATA

TTTCGCCCTCAGTGAGCGATGTGGAGTTTTGTGCAGTTCGGCCAGCATGCTATGCCCAGCCAATAACAATACCGCAT

GACGCATAACTATACCGCATGACGCATAAACATGCCTTCGTGCCCTGCACCAGGCATCGGACGCTGTGTCACGCAGT

GAGCCCGACCCTGCGCAACCAACATTTTGTTGCGAGATACGGTCGGAGCTGGGATTACAGCCTGCCTGGTGGGTTTG

GATGGCGCCCGTGTGTTGGGCTGGGCTGTTGCTGCTCGCGGTGGGCCCACCACCAAGTCACGGCACCCATCCGCCC

TCCCCTCTTGTTGGCCCACCCGCCTGTACACATGCCAGTCACCCGCTCGCCATCCTGTGAAAGCGGGTAGCCGACTT

GGCAAGCGCTTTTCCTGACACTTGGCGCAGGTTTGAGTGGGATACCAGAATGGTCTGAATGTAGTTGTTGGATAACC

AGTACACTGCGGTGTGTAGCTGGTTAGCGGGAGTGCCGTGCATGAAACACGCTACTCGACCCGCCATGCCCGCGCGA

TGGTACCACCAACCGTTCAACCCAGATCCATGCCGGGGTAGCATCGACCCCACAGTCAGACTGATAGCTCCTATCCA

GGTGTCAGGCGCCATGTATGTATCTGTGGACGCGTCAAGCTGGCTTGTGCCGTAGCGTTGGCCGCCTGTATGGCACG

GCATCTGTGTCACGTTATGGCCTCATGCTTACCGTAGTCACGCGGCTTGCGTGCTGTGCGGCACGCTCCCTGCCAAT

CCTTCAGGACATGTATGCATACATGTTACTTCGTCAGAGCCATAGCAGGGGCAGCGTGTTCTGTCAATGCCTCATGA

ACCCAGAGACCCAAGCCAACGTACGCATTAGTTCCGCAACGCACGTCAATGCCAACTGTATGTGTCGCCTGCCCACT

CGCGAGTGGACGCCTAGGGAACCAACCTTGGTTCCTTTCAGCCCCGGCCTTACTTCACCCGGCGGGGCAATTACTTA

TABLE 6-continued

Sequences Corresponding to Frequency Peaks (SEQ ID NOs 21-167)

TCACCGAAGTGCTAGGAGCAGTGTGCTATATGTCATTACTATTAAGAGCGTATGGCGACACAGGCTCACATGTGGGT

AGCCAGGCTTGGCAGGCATCCCAACTCAGCCCGGCCTCCTCACAGCAGTACCACGACGTGCCCGTACGTGGTCGAGT

GCGGAGTTTGGCTGCCGGCGTGGCTGTATCATCTCTCACATTGGATGACCCATCCGCCACTGCTGTTCACTACTGGC

ACGTCCCTCGAGTCGCTCACCCACCGGCTCCGCCCAGCGTTCGCTCCCTTTGGCTGGGCCGGGGCCCGTGGCGCATC

CAACCCGCCATCGCGGCCCCGAGTGCTCCTTATTTCCTCCCATCACTA

>SEQ ID NO: 50

CCGCGCCGCTCGACCAGGCCAGCCTTGCTGGGGTTGCTGAGGTGTTACCCTTCATGTTGCCCTCCCTGCTATTACGG

TACACCCCACAGCTGCCGTGGCGTACGGTATCGGCACGTACGGGACATTGTGTGCATGCATCCCCGCGGCGTTTGGA

GGCAAACATTCACGTGCGCGCCTGTCCTGCGTCCGCCGGGGTGATGCTATCTATGGGTGTACCTACTGCTTGATTGG

TAGTGACTCTTATGCAAGACACTGCAAATCTCAAGCATGGCACCTAGCTAGCAAGAAAGAAATTAGTGTTCGTGGCC

ATGCTGCACGGCTGGGCATGGCTGCCCGCATCCTACACCACGACGGCGCGGGTGAACGAAGGGCAGGTTGCCGCGCG

TGACTCGCGTACGTAAAACCGCTCTAGTGTTGCAACTCGCGCCTTCTCCTGCGTGGCGCATGTTGGCTAGCCTGTCC

CAGCTTCGAGTCACGACGTTGTTATTATTCCCAAGGTTGTTCCGAGCAGCCTACAACGTCAACACGTGTTATGGCAT

GGCCCTGGGGGCCGGTAGAGAGTACCGAGGTCTCCAGTGGTTCGTGCCAACACGTGCCAACACGCACTGTTACCTTT

CCTGGGCACACGGACGGCCACAGCTGCCCACAAGCCACACACCTGAACAAGGATGCATGTGTTTCCCTGTAACGCCC

CGGCGTCGTCTGCATGGCTGGCGCACGCGGGATAACGCATGTGTGTTTCTGTCGTGGCCATTGGTGCACCTGATACG

TTTGTGAGTCTGGTATCATGGCCCTTGCAAAGCCAGTCGTGTTCCTATTGCTGCTTGTCTTCTGGTAGTGACCATTG

GCCGCCCATGACCGACGGAGTGTGGCGCTGTCAGGCCCCGCGTTGGCGTCGCCCTGCGCCTGCAGCAGGTGCCGGCG

GCGCCTCCGGCGGCGCTCATCCCCGCGTGATGGTGCTGCTCGTGCAGCCAATATCCCCAAGCACGAAGCTCGTTCTA

TTGACCGCTGTTGAGTGTGCAACTAGGACCGTACGTTCGTGCGCAAGCTAGGCGATGGGCGGAGCGCTCCGCGGTGT

TCGAGACACATGATTTCGGTAGCGCAAGGGCACGAACGCCACCGCCATCACCGCCGACCGCACCTTGGTTTGCATGA

CCGGCCGTTGGGCCAAGCGCTTTGCGAGAAGAGCTGCATACGCGAAGCCAATCAAGCCCAGCCACCAGGGCTGCCGT

CGCCCCGCACCATGACCTCCCGGCGTTGAGGACTACTACCAAACTCTGGCAGCACTTTCGGCCACTAGTGCAACCTCA

ACACGGGCGGGCTGGGCGGGCACGGCGGACTTGGTGGGGTTATCGGGAGCTGCGAGGCCGGAGGTAGGAGGCCGCT

GAGGGCCACGAATGAGTTGCTAGGCCGCTTGAGGCATGAGTGGAGGCTATTGTCGGTTTGAGAGATTGGGATTGTCG

TTTGGGGCCGTGGCGGTTTGTAACGCTACACGGCAGTAAGGAGTCAATAAGCGCTGACTTATCGCAGCGCAGTGGAG

ATAAGTCTAGTTATTGCGACGTAACTGCCGTGTTGCGTTAGAGTCACGCACGGCGCAGGACGCTCGGGTACGTGCCT

GTGCATGGGCCGAACCGAGCTGGGTCTTGTACGCGTCAGGAGCACACGGCGCCTTATCTGCCGTTGTGCTTCTGTA

CTGTATTTCGGATCGTCCCTCTGCCGGGACGGTGACAACCCACCCGCCCCCCCTGGTGCCGCCGCGGATTAATGTGG

TGGCACCCGTGGGCGCTGCGGCGTGCGTGGTTGTCTGGACTCTGCTGCTATCAGGCACTTCATACATGCGACACACC

CAGTACTGGCAGCACTTTCGGCCACTAGTGCAACCTCAACACGGGCGGGCTGGGCGGGCACGGCGGACTTGGTGGG

GTTATCGGGAGCTGCGAGGCCGGAGGTAGGAGGCCGCTGAGGGCCACGAATGAGTTGCTAGGCCGCTTGAGGCATGA

GTGGAGGCTATTGTCGGTTTGAGAGATTGGGATTGTCGTTTGGGGCCGTGGCGGTTTGTAACGCTACACGGCAGTAA

GGAGTCAATAAGT

>SEQ ID NO: 51

GCGGACGTGGAAGCTTGGGCGGACGTCCCAGCATTGACTGCTACCCTGGGTAGGTCTCTGATAACCATGTGCTCCGG

GCTGTATCAGTGAATGTGACGCCTCTCAATCAGCAAGTTCTGTGACACCAGTCACACCACAATCGGTGCAAGTAACC

CGTCACAGCGCGCATCAATCCCCGACCCCGCCACACAATCCCCGACACGGGAGCTACCCACCAGCGTTAAGGACGGC

CGCCCAGCAGGCCCTTCCAACATTGTTTCCGCGCGCGTCAGCACACCATAGTAGTGCGCTTGTTAACGCTGGATGGA

TABLE 6-continued

Sequences Corresponding to Frequency Peaks (SEQ ID NOs 21-167)

GCATGCCTCAGCCCATCCAAACACGCAGCGGCATTCCCGCCATGCATGCAGGTGCACTTCGAAAGCATTGCCCCGCC
TGGGTGCACCGACACCAGTTGTTTGTGTTGGCTACTGCCCAACCTCCTCGCAGTCCAACTACTGCCCAGTCCCACTG
CACCGGAATCACCACCAGCAGTCCTGCGGCTATCATAGCTTTCAATGAAGCACGTGTAATACCTAATACAATAGGTT
CATGCAAGTTGGTGATAAAATGCACATCATCACTCTCGTGTCTCGATTGTCTTCTCTGATGCGTGCTGTCATCGTGT
GCACGCCACATCTGTAGCGACTCACATCTCTCACATCTTCACGCCGCACCAATTTCACAGAATCCACAATCATTCTC
AAACCCGCCCTGCGTGCGCCGCCTGTGGTACACGTGTGCGTGCCGCCCACAGCCCGATTACTCCTGCGTCCGACATC
CTGCTCAACCCACCCTATTCGTTGGCTACACGACTTGCGCTTGACAATATGCAATGACTGTCCCTCGCTTCTGCGTC
TTGCCTCTTTAGGACGTACGTCACAAACACAGTGCGTGCATGGCCATGTGCCCTCACACTCTTCTACACTCGTGTCA
TAACGAGAAAGTTTACGCCAAACGTGCTAGGGTTGACACCTGGCCTTGTCTGATGCCTAGTAACCTCCGCATACCAG
CCACCCGCACGCCCGCTGGTGCCAAGCTCCAACGTGGGAGCAAGTAGGCGCGCTCAGCGATTGGCCTCATCCCGCTC
GCGCTCACACACCTCAAGGCACGGGCCTCCCACCAGCACGGATTCGCCCCAGGCGAACGAGCGCGCCAAAGCAGCCC
CCTCAACAGCAGCAGCCGAGCTAGCAGACCCG

>SEQ ID NO: 52

ATATATATATATATATATATATATATATATATATATATATATATATATATATATATATATATATATATATATATATA
TATATATATATATATATATATATATATATATATATATATATATATATATATATATATATATATATATATATATATAT
ATATATATATATATATATATATATATATATATA

>SEQ ID NO: 53

TTGGTATGCAGATCAACCAAATCGATACTGTGTGCGCACTTAGGCATGCATAGTCGCAATCGTTACGCACAAGGGCT
GATGGATTTGAGCCAAGCATACCGATGGGGCA

>SEQ ID NO: 54

TGTCAACCTCTCCAATTTGAGCCCCGCTTTCCACAGCGCCAAGCCCTAATATCAGGCGAGGCCTGGCGAGGTTTTGC
CCGCACCCCCGTCCGCTTAGGAGTACGGCAGAGCCCCGGAATCTATGTCCTTGCGCGTCCGCTTGGCATGCAGGTCT
GTACCCTGTGAAGCTTAGGTGACCTGGTGACTAGCTGGGCTTGGTTGGACGGCCAAAGCCCCTTGTCTCGCGTTGTG
CCCCCACATGCGAACACACCTTGGAGTGTCCTAGCGCCCGGGCTCTTGCTATGGTGAAAGCGCTACGTTTGATTTCT
GTTGGATGCGGGTGGCGTGGGCAGGGTGCGTGTGTGGGGCAACATGCGACAATGGACAAGGCGAAGTTCGGTCAAG
GGCTTTTGGATGGCCCTGCGCCTTCTGGGCCATATGCATATATGCATATAGATTGTGGAAAGTGGGGCGGGCGGGTT
CGGAGGTGCGCTTATGGGGTCGGAATGGGGGCTCCGGATGTGGGGGTCGGTTCGAGCTGGTGAGCTTAAGTGCGGCG
AGAGGCCGTAGCGAGGCGTTACTGGACCCGCGTTTACTTAAACATGGCGCGCACTATACTTGTCCATAATTAACCAT
TAGCTTACCAAGTCTGGAAGCTATTGCGCTTTGTTTCGCTGCCTTGCTCGCTGCGTAGTTGCCACAAACGGGCTTGG
GGTCGAGGAGGTGCGAAATCCCGAACTCGCACAGACTTCTGCAGCGGAGTGAAGGGAGGCGCAGCTTCGCAGTTAGG
GCTGCGCTTGGCCTCCCCGCGGCCTCACGACATACAGAAGGTCAAAGTGAACGCGACGGAGCACAGCGGCCGGGCTC
AGGAGCGTCCTACGAGGAGTCGGCATCAGCGGCATTTCGAATCTGCCCTCTCCGCGCTCGCACCTGGAGCGTCGCCG
TAACCCGCTGCTGAGCGCGCTGGGTTTAGCTATATCATAGGTGTATTGGGCTCTCAGGCACCTGCGAAAATCGTGCC
GGTGAGAAGCTTCGGCTTGCACAGGCACGGCGTGCCTCCTGAACCCAGCTTGGTCCCGCGCCCACCACCTCCCTTTC
CCCTCGCACCCCGCATCCGCCCCTCCCCACACTGCTGCCATCCGTCGATTCCATCATGTGTTGTGGCAATCATCACC
TCCTCAAAAACCGCTTCATTTGCCCCTCATCCTCGCCACGCACTGTCAACCTGGCCGCCTCAATGGTCGTCCTCTTC
AGTGCAGCCCTGCAGTACAACTCGCTGCTGGCCGCCAGTGGCCAGGAGGATGCGTTGCCTCCACGCGCTCCTTCAGG
GCACGGCCTGCAGCTGCAGATTAGTGCGCGCTAAGCTCACTAGTCTTCTTGTTCTTGATTGTAGCCTGGGCTTGCAG
CGCACAGTTGCGAGCCATTAGACAGCAGACACGGCGGCGCTCAGACTCCCGCACCGCCACGGCCTCGGGGAGGCTTG

TABLE 6-continued

Sequences Corresponding to Frequency Peaks (SEQ ID NOs 21-167)

GGGTTGCCCTTGGGTTTCGTGCCGGTGCTGGGCGTGCTGGGGTTGGGCTCCATGGATCCGGCCTGCACGTGTCGAAC

CCGAGTTCAAATCCCGTCAGGCTGTCGTCCCCTTCACTCCGCTGCAGAAGTCTGTGCGAGTTCGGCCGAGACCCTCA

TCGGCGCCCCTGCCCAGCCGCACGTTTCGCCCCCAAACTTGATGTCAACCTCTCCAATTTGAGCCCCGCTTTCCACA

GCGCCAAGCCCTAATATCAGGCGAGGCCTGGCGAGGTTTTGCCCGCACCCCCGTCCGCTTAGGAGTACGGCAGAGCC

CCGGAATCTATGTCCTTGCGCGTCCGCTTGGCATGCAGGTCTGTACCCTGTGAAGCTTAGGTGACCTGGTGACTAGC

TGGGCTTGGTTGGACGGCCAAAGCCCCTTGTCTCGCGTTGTGCCCCCACATGCGAACACACCTTGGAGTGTCCTAGC

GCCCGGGCTCTTGCTATGGTGAAAGCGCTACGTTTGATTTCTGTTGGATGCGGGTGGCGTGGGCAGGGTGCGTGTGT

GGGGGCAACATGCGACAATGGACAAGGCGAAGTTCGGTCAAGGGCTTTTGGATGGCCCTGCGCCTTCTGGGCCATAT

GCATATATGCATATAGATTGTGGAAAGTGGGGCGGGCGGGTTCGGAGGTGCGCTTATGGGGTCGGAATGGGGGCTCC

GGATGTGGGGGTCGGTTCGAGCTGGTGAGCTTAAGTGCGGCGAGAGGCCGTAGCGAGGCGTTACTGGACCCGCGTTT

ACTTAAACATGGCGCGCACTATACTTGTCCATAATTAACCATTAGCTTACCAAGTCTGGAAGCTATTGCGCTTTGTT

TCGCTGCCTTGCTCGCTGCGTAGTTGCCACAAACGGGCTTGGGGTCGAGGAGGTGCGAAATCCCGAACTCGCACAGA

CTTCAGCAGCGGAGTGAAGGGAGGCGCAGCTTCGCAGTTAGGGCTGCGCTTGGCCTCCCCGCGGCCTCACGACATAC

AGAAGGTCAAAGTGAACGCGACGGAGCACAGCGGCCGGGCTCAGGAGCGTCCTACGAGGAGTCGGCATCAGCGGCAT

TTCGAATCTGCCCTCTCCGCGCTCGCACCTGGAGCGTCGCCGTAACCCGCTGCTGAGCGCGCTGGGTTTAGCTATAT

CATAGGTGTATTGGGCTCTCAGGCACCTGCGAAAATCGTGCCGGTGAGAAGCTTCGGCTTGCACAGGCACGGCGTGC

CTCCTGAACCCAGCTTGGTCCCGCGCCCACCACCTCCCTTTCCCCTCGCACCCCGCATCCGCCCCTCCCCACACTGC

TGCCATCCGTCGATTCCATCATGTGTTGTGGCAATCATCACCTCCTCAAAAACCGCTTCATTTGCCCCTCATCCTCG

CCACGCACTGTCAACCTGGCCGCCTCAATGGTCGTCCTCTTCAGTGCAGCCCTGCAGTACAACTCGCTGCTGGCCGC

CAGTGGCCAGGAGGATGCGTTGCCTCC

>SEQ ID NO: 55

GAGGCCTGGCGAGGTTTTGCCCGCACCCCCGTCCGCTTAGGAGTACGGCAGAGCCCCGGAATCTATGTCCTTGCGCG

TCCGCTTGGCATGCAGGTCTGTACCCTGTGAAGCTTAGGTGACCTGGTGACTAGCTGGGCTTGGTTGGACGGCCAAA

GCCCCTTGTCTCGCGTTGTGCCCCCACATGCGAACACACCTTGGAGTGTCCTAGCGCCCGGGCTCTTGCTATGGTGA

AAGCGCTACGTTTGATTTCTGTTGGATGCGGGTGGCGTGGGCAGGGTGCGTGTGTGGGGGCAACATGCGACAATGGA

CAAGGCGAAGTTCGGTCAAGGGCTTTTGGATGGCCCTGCGCCTTCTGGGCCATATGCATATATGCATATAGATTGTG

GAAAGTGGGGCGGGCGGGTTCGGAGGTGCGCTTATGGGGTCGGAATGGGGGCTCCGGATGTGGGGGTCGGTTCGAGC

TGGTGAGCTTAAGTGCGGCGAGAGGCCGTAGCGAGGCGTTACTGGACCCGCGTTTACTTAAACATGGCGCGCACTAT

ACTTGTCCATAATTAACCATTAGCTTACCAAGTCTGGAAGCTATTGCGCTTTGTTTCGCTGCCTTGCTCGCTGCGTA

GTTGCCACAAACGGGCTTGGGGTCGAGGAGGTGCGAAATCCCGAACTCGCACAGACTTCTGCAGCGGAGTGAAGGGA

GGCGCAGCTTCGCAGTTAGGGCTGCGCTTGGCCTCCCCGCGGCCTCACGACATACAGAAGGTCAAAGTGAACGCGAC

GGAGCACAGCGGCCGGGCTCAGGAGCGTCCTACGAGGAGTCGGCATCAGCGGCATTTCGAATCTGCCCTCTCCGCGC

TCGCACCTGGAGCGTCGCCGTAACCCGCTGCTGAGCGCGCTGGGTTTAGCTATATCATAGGTGTATTGGGCTCTCAG

GCACCTGCGAAAATCGTGCCGGTGAGAAGCTTCGGCTTGCACAGGCACGGCGTGCCTCCTGAACCCAGCTTGGTCCC

GCGCCCACCACCTCCCTTTCCCCTCGCACCCCGCATCCGCCCCTCCCCACACTGCTGCCATCCGTCGATTCCATCAT

GTGTTGTGGCAATCATCACCTCCTCAAAAACCGCTTCATTTGCCCCTCATCCTCGCCACGCACTGTCAACCTGGCCG

CCTCAATGGTCGTCCTCTTCAGTGCAGCCCTGCAGTACAACTCGCTGCTGGCCGCCAGTGGCCAGGAGGATGCGTTG

CCTCCACGCGCTCCTTCAGGGCACGGCCTGCAGCTGCAGATTAGTGCGCGCTAAGCTCACTAGTCTTCTTGTTCTTG

ATTGTAGCCTGGGCTTGCAGCGCACAGTTGCGAGCCATTAGACAGCAGACACGGCGGCGCTCAGACTCCCGCACCGC

TABLE 6-continued

Sequences Corresponding to Frequency Peaks (SEQ ID NOs 21-167)

CACGGCCTCGGGGAGGCTTGGGGTTGCCCTTGGGTTTCGTGCCGGTGCTGGGCGTGCTGGGGTTGGGCTCCATGGAT

CCGGCCTGCACGTGTCGAACCCGAGTTCAAATCCCGTCAGGCTGTCGTCCCCTTCACTCCGCTGCAGAAGTCTGTGC

GAGTTCGGCCGAGACCCTCATCGGCGCCCCTGCCCAGCCGCACGTTTCGCCCCCAAACTTGATGTCAACCTCTCCAA

TTTGAGCCCCGCTTTCCACAGCGCCAAGCCCTAATATCAGGCGAGGCCTGGCGAGGTTTTGCCCGCACCCCCGTCCG

CTTAGGAGTACGGCAGAGCCCCGGAATCTATGTCCTTGCGCGTCCGCTTGGCATGCAGGTCTGTACCCTGTGAAGCT

TAGGTGACCTGGTGACTAGCTGGGCTTGGTTGGACGGCCAAAGCCCCTTGTCTCGCGTTGTGCCCCCACATGCGAAC

ACACCTTGGAGTGTCCTAGCGCCCGGGCTCTTGCTATGGTGAAAGCGCTACGTTTGATTTCTGTTGGATGCGGGTGG

CGTGGGCAGGGTGCGTGTGTGGGGGCAACATGCGACAATGGACAAGGCGAAGTTCGGTCAAGGGCTTTTGGATGGCC

CTGCGCCTTCTGGGCCATATGCATATATGCATATAGATTGTGGAAAGTGGGGCGGGCGGGTTCGGAGGTGCGCTTAT

GGGGTCGGAATGGGGGCTCCGGATGTGGGGGTCGGTTCGAGCTGGTGAGCTTAAGTGCGGCGAGAGGCCGTAGCGAG

GCGTTACTGGACCCGCGTTTACTTAAACATGGCGCGCACTATACTTGTCCATAATTAACCATTAGCTTACCAAGTCT

GGAAGCTATTGCGCTTTGTTTCGCTGCCTTGCTCGCTGCGTAGTTGCCACAAACGGGCTTGGGGTCGAGGAGGTGCG

AAATCCCGAACTCGCACAGACTTCTGCAGCGGAGTGAAGGGAGGCGCAGCTTCGCAGTTAGGGCTGCGCTTGGCCTC

CCCGCGGCCTCACGACATACAGAAGGTCAAAGTGAACGCGACGGAGCACAGCGGCCGGGCTCAGGAGCGTCCTACGA

GGAGTCGGCATCAGCGGCATTTCGAATCTGCCCTCTCCGCGCTCGCACCTGGAGCGTCGCCGTAACCCGCTGCTGAG

CGCGCTGGGTTTAGCTATATCATAGGTGTATTGGGCTCTCAGGCACCTGCGAAAATCGTGCCGGTGAGAAGCTTCGG

CTTGCACAGGCACGGCGTGCCTCCTGAACCCAGCTTGGTCCCGCGCCCACCACCTCCCTTTCCCCTCGCACCCCGCA

TCCGCCCCTCCCCAC

>SEQ ID NO: 56

GGTGCGCTTATGGGGTCGGAATGGGGGCTCCGGATGTGGGGGTCGGTTCGAGCTGGTGAGCTTAAGTGCGGCGAGAG

GCCGTAGCGAGGCGTTACTGGACCCGCGTTTACTTAAACATGGCGCGCACTATACTTGTCCATAATTAACCATTAGC

TTACCAAGTCTGGAAGCTATTGCGCTTTGTTTCGCTGCCTTGCTCGCTGCGTAGTTGCCACAAACGGGCTTGGGGTC

GAGGAGGTGCGAAATCCCGAACTCGCACAGACTTCTGCAGCGGAGTGAAGGGAGGCGCAGCTTCGCAGTTAGGGCTG

CGCTTGGCCTCCCCGCGGCCTCACGACATACAGAAGGTCAAAGTGAACGCGACGGAGCACAGCGGCTGGGCTCAGGA

GCGTCCTACGAGGAGTCGGCATCAGCGGCATTTCGAATCTGCCCTCTCCGCGCTCGCACCTGGAGCGTCGCCGTAAC

CCGCTGCTGAGCGCGCTGGGTTTAGCTATATCATAGGTGTATTGGGCTCTCAGGCACCTGCGAAAATCGTGCCGGTG

AGAAGCTTCGGCTTGCACAGGCACGGCGTGCCTCCTGAACCCAGCTTGGTCCCGCGCCCACCACCTCCCTTTCCCCT

CGCACCCCGCATCCGCCCCTCCCCACACTGCTGCCATCCGTCGATTCCATCATGTGTTGTGGCAATCATCACCTCCT

CAAAAACCGCTTCATTTGCCCCTCATCCTCGCCACGCACTGTCAACCTGGCCGCCTCAATGGTCGTCCTCTTCAGTG

CAGCCCTGCAGTACAACTCGCTGCTGGCCGCCAGTGGCCAGGAGGATGCGTTGCCTCCACGCGCTCCTTCAGGGCAC

GGCCTGCAGCTGCAGATTAGTGCGCGCTAAGCTCACTAGTCTTCTTGTTCTTGATTGTAGCCTGGGCTTGCAGCGCA

CAGTTGCGAGCCATTAGACAGCAGACACGGCGGCGCTCAGACTCCCGCACCGCCACGGCCTCGGGGAGGCTTGGGGT

TGCCCTTGGGTTTCGTGCCGGTGCTGGGCGTGCTGGGGTTGGGCTCCATGGATCCGGCCTGCACGTGTCGAACCCGA

GTTCAAATCCCGTCAGGCTGTCGTCCCCTTCACTCCGCTGCAGAAGTCTGTGCGAGTTCGGCCGAGACCCTCATCGG

CGCCCCTGCCCAGCCGCACGTTTCGCCCCCAAACTTGATGTCAACCTCTCCAATTTGAGCCCCGCTTTCCACAGCGC

CAAGCCCTAATATCAGGCGAGGCCTGGCGAGGTTTTGCCCGCACCCCCGTCCGCTTAGGAGTACGGCAGAGCCCCGG

AATCTATGTCCTTGCGCGTCCGCTTGGCATGCAGGTCTGTACCCTGTGAAGCTTAGGTGACCTGGTGACTAGCTGGG

CTTGGTTGGACGGCCAAAGCCCCTTGTCTCGCGTTGTGCCCCCACATGCGAACACACCTTGGAGTGTCCTAGCGCCC

GGGCTCTTGCTATGGTGAAAGCGCTACGTTTGATTTCTGTTGGATGCGGGTGGCGTGGGCAGGGTGCGTGTGTGGGG

TABLE 6-continued

Sequences Corresponding to Frequency Peaks (SEQ ID NOs 21-167)

GCAACATGCGACAATGGACAAGGCGAAGTTCGGTCAAGGGCTTTTGGATGGCCCTGCGCCTTCTGGGCCATATGCAT
ATATGCATATAGATTGTGGAAAGTGGGGCGGGCGGGTTCGGAGGTGCGCTTATGGGGTCGGAATGGGGGCTCCGGAT
GTGGGGGTCGGTTCGAGCTGGTGAGCTTAAGTGCGGCGAGAGGCCGTAGCGAGGCGTTACTGGACCCGCGTTTACTT
AAACATGGCGCGCACTATACTTGTCCATAATTAACCATTAGCTTACCAAGTCTGGAAGCTATTGCGCTTTGTTTCGC
TGCCTTGCTCGCTGCGTAGTTGCCACAAACGGGCTTGGGGTCGAGGAGGTGCGAAATCCCGAACTCGCACAGACTTC
TGCAGCGGAGTGGTTGAAAAAATCGACGTCTGTCGCCAAGCCAGCGAAAGAACGAAGCTTTGATAAAGTTCAACAGT
TGGAGTGTATTTTGCGCTGGATTTGCCAGCAAGTAAAACGCCTTGAGCACGCCCTCGTGACCAAGATGGAATCGCCC
GCCACGGCGCCACCCGCGTAAACGACGCTCAACGTCGTCCGTTAGCACAACCTCCTGTACATGCCCATCCTGCGACG
CCCCATTTGAGCCAACCTACAGGCTCGTGTGCACCGAATTTGCAGTCTGTCCGCAGTGCCCATACCTGCACCCGC

>SEQ ID NO: 57

AGCCGCCCAGGGTGTGCGTGCCACCGTCGTCGCCGCGGCACAGGGGGCATTCGCCGCCTGCGCAGCCGGGCATGGGG
TGTTTTACTCTTGCGGCCCGCTTGGCATTCCAGGAGAGGCCCCAGCGGTATTTGAACGCGCAGCAGGCCTCTTCAAA
TGAGAACTTGTCGAACAGGTTTAGGCCGTAGCGTTCGTCGATGTGCTTCCTCGCTGCCTCCCATAGTTCCGCGTACA
GTCCTGATTTGGTATAACCGGTCGCGGTGGATTTACGGGCCATTTTCTTCAGGTCGCGATTGAGGTCGTTGGCGTAG
CGTAACCGTTCTTCCAAATTGCCATTGTGCTCCACAGTTTCCTTCTGGGCAATCCATCCCTCTAAGGGTTCATATGG
GTGCGAGTATAGAGTTTCTGTCGCATCCGGCTGCACTGTTCTGGTGGCCACAGCCTGTGCCGCTTCATCCGCTTTCT
GATTTCCTACGCATGTGTCTGTCTGGTGCGACCTTACGTGATAAAATGATGTCTTGTGTCCAGCTAGGGCACGTTCC
GCAAGTTGGTCGACTATGGTCCCAAACATCTCGCGGTGCTTGCTTACGTGGAGTGACTCGGGCTCCATAATGGCGCG
GCGGAGGATGAACAGACTGACAAGACTGTCGGTGTAGACCCGTAGGTGAGGTGTGTCTCGATGGAGGCATCGACCAC
GGCAGAGGTTGCTTAGCGATAAGTTGGTGTGTAACGTCGGTTCAGACCCGAGTTCGATCCTCCCCAAATTCGGTACA
GGGGAAACCTCCGTGCGTATTCAAATCACGCACAGGCGCTCCACAGGGACCGCACGGCTCTTCAGTCGTGTCCTTGT
CATCCGTGGCTAACGTCAGATAAGAGAGCGGTCGTGAAGTGCCGGCAAAGGGGCCGGACTCTGGAGCGATCCAGAGT
TTCAGTTGAGATGTTGCCCGACAGTCGGCATTACCTGATCCCCCGATCTCAGGTACCAAAAGCCGTGAGGGTAGATC
ATCCGAGCTGAACATGGATAGGACACCAGGGGCTTAATCCACCCCGCTCCCACCGGTGGGCAGGACCGGCAAATGAT
AAGGTGGTCGTGGTGACTTCCCGCCTTCTCTCGAACTGGGTTGAGAGATGATCAGCGAAGGCGTTGCCCCGTTAATA
CATGCTAGGCCCTATGGGCCAGCGTTGGGATTATTATTATTATTATTATTATTATTATTATTATTATTATTATTATT
ATTATTATTATTATTATTATTATTATTATTATTATTATTATTATTATTATTATTATTATTATTATTATTATTATTAT
TATTATTATTATTATTATTATTATTATTATTATTATTATTATTATTATTATTATTATTATTATTATTATTATTATTC
TCGATGGAGGCGGAGCGCCGTGCGTATGGCGGATGATTCACACCGAAGGATGGTGCTCAGGGGTGTGTTGAAGGCGA
TGTCTTCATCAATGTGCGTGGCGCGGTTGTCGCTGGCGTCCCAGACCGCCGCTCCCAGGCCAGTGTACTCTCGTGTG
TGTGGTACTTTGCTCCCGTCGGTAAAGACCGCGGAGCCTCGTGTGTGTGCGAGCGGGACATAAGCGCGGTAGAGGGT
TGCAAGCTCCGTAGGGGATGGTAGGGTGGGGCATCGCGAGGGGGCTGGGCTGGGCGTCTGGCTGCTCTGGGCGA
GGATGCGCCGTTTTAACTTCCGG

>SEQ ID NO: 58

ATCAGGGTTTTAAGGGGTTTTGCAGGGTTTGAAAAGTGTGACATGTCACAAATGATTGGCACAGTATAATTCAGCTA
ATTATAACCAGAATGATTGTTTGAACCCCTTGTGGATGACCGTGATGAGATTTGGGCACACAGCAATGACTTCGTAC
TCCCACTGTTTACTCGCCACAGCACACACAAGTATGAAGAAGGAATCACACTCCCAGAGTTCCACATACACACATTG
GGGCTTCTGGGTTGATGTTGCTTGCCTCACGCCTAGCGCCGTAGCTTCTACGCTGCAGTGCATCACGCCTCCTGTCC
CTCCCTCCCTCCCTCCCATACATGTCGTGCTGGGCACCGGTGGCGCTGGTGTTCTCCAGGTTGGTTTTGGGCGCATC

TABLE 6-continued

Sequences Corresponding to Frequency Peaks (SEQ ID NOs 21-167)

CTTTCTGGTAGTCCGAAGGCCAGCCCGGCCGGCGTCGTCCAGCCCAGCCATCCCGATACAGCAGCCACCTTCCATCA
GCCAGCTATGGGCGTGACCATCCACAGTGTTTACCGTTGGTTACGAGGTAACATGTGCTTTCGCAACTTGCGCTACT
GACTGCCTACTCTCATGCCGCCTGCAAGCCCACTCCGCCTTCCGCTCTGGTCTAAGTACGCATTAGTTCCGCAACAC
TCGTCAATCTCACTTGCCAAATATAACTGAGCCTTGTACTGTGCTGTGGTGCACTTTGACATGTGAGGCATGCATGG
TATGCAAGTGCATACCACTCAGTCCCCTTGTCCCCACGGGGGGGGGTGCAGCCAGCCATCCAATCACACACCCCGC
CTGTTACTCTCAGCCCTGTGGGAGTTCTTTCACATCTTCATGTGTCCATGTTGCAGGACATGTTTGTGATGCATCCG
CAAGCTGGCAGCCAGGGTGCCAGCCCTTGCAGCCCATCAAGTGGCTCTGCATATCAGGACAAGTGTGCATTCCTCCC
CTCCCCTGTAGTGGGTCAGGGCCTGCTGGTATCATGCAGGCTGTCAAGTAATGTGCAGCCATGCTGAAGACATTTTA
TTTGCACCACTTGTGAACGATGGCCTTTGGGAGCGCAAGCGAAAGCAGCCATGGCAGTGGCGCATCAAGTCCTCTTG
CAGGCCTGCAAAGTGCAGACCACACCAGTGGCGACAAGTCTGCAACCGCTGCACCTCAGCGAGGTCCAGCTCATGCT
AGCAATACAACGGCAGTCGCTATATGTATATAATCAATAGCCAGGCCAAACGGCTGCGTGGCTGGACTGCTGCACTC
ACTCACGTGGCCCCTGGTGGCAGGGTGGCCTAAATCAGGGTTTTAAGGGGTTTTGCAGGGTTTGAAAAGTGTGACAT
GTCACAAATGATTGGCACAGTATAATTCAGCTAATTATAACCAGAATGATTGTTTGAACCCCTTGTGGATGACCGTG
ATGAGATTTGGGCACACAGCAATGACTTCGTACTCCCACTGTTTACTCGCCACAGCACACACAAGTATGAAGAAGGA
ATCACACTCCCAGAGTTCCACATACACACATTGGGGCTTCTGGGTTGATGTTGCTTGCCTCACGCCTAGCGCCGTAG
CTTCTACGCTGCAGTGCATCACGCCTCCTGTCCCTCCCTCCCTCCCTCCCATACATGTCGTGCTGGGCACCGGTGGC
GCTGGTGTTCTCCAGGTTGGTTTTGGGCGCATCCTTTCTGGTAGTCCGAAGGCCAGCCCGGCCGGCGTCGTCCAGCC
CAGCCATCCCGATACAGCAGCCACCTTCCATCAGCCAGCTATGGGCGTGACCATCCACAGTGTTTACCGTTGGTTAC
GAGGTAACATGTGCTTTCGCAACTTGCGCTACTGACTGCCTACTCTCATGCCGCCTGCAAGCCCACTCCGCCTTCCG
CTCTGGTCTAAGTACGCATTAGTTCCGCAACACTCGTCAATCTCACTTGCCAAATATAACTGAGCCTTGTACTGTGC
TGTGGTGCACTTTGACATGTGAGGCATGCATGGTATGCAAGTGCATACCACTCAGTCCCCTTGTCCCCACGGGGGGG
GGGGTGCAGCCAGCCATCCAATCACACACCCCGCCTGTTACTCTCAGCCCTGTGGGAGTTCTTTCACATCTTCATGT
GTCCATGTTGCAGGACATGTTTGTGATGCATCCGCAAGCTGGCAGCCAGGGTGCCAGCCCTTGCAGCCCATCAAGTG
GCTCTGCATATCAGGACAAGTGTGCATTCCTCCCCTCCCCTGTAGTGGGTCAGGGCCTGCTGGTATCATGCAGGCTG
TCAAGTAATGTGCAGCCATGCTGAAGACATTTTATTTGCACCACTTGTGAACGATGGCCTTTGGGAGCGCAAGCGAA
AGCAGCCATGGCAGTGGCGCATCAAGTCCTCTTGCAGGCCTGCAAAGTGCAGACCACACCAGTGGCGACAAGTCTGC
AACCGCTGCACCTCAGCGAGGTCCAGCTCATGCTAGCAATACAACGGCAGTCGCTATATGTATATAATCAATAGCCA
GGCCAAACGGCTGCGTGGCTGGACTGCTGCACTCACTCACGTGGCCCCTGGTGGCAGGGTGGCCTAAATCAGGGTTT
TAAGGGGTTTTGCAGGGTTTGAAAAGTGTGACATGTCACAAATGATTGGCACAGTATAATTCAGCTAATTATAACCA
GAATGATTGTTTGAACCCCTTGTGGATGACCGTGATGAGATTTGGGCACACAGCAATGACTTCGTACTCCCACTGTT
TACTCGCCACAGCACACACAAGTATGAAGAAGGAAT

>SEQ ID NO: 59

GGGTGGCCAAGATGCACGCTGTTGTCCAACACAGCCGACTGGTGGGCTGCGACTAGCCCGAAGCCACCACCGATGGA
CTGCATGTGCTCCCACACGGCACGCGTGGTCATACCGCGGACAACAAGCCGCCGTAAATACGCCGCTGCCAGGTACC
GTTCCGCCTTGGGGAGCCCACTTGCGATAGCATGGAAAGCGCACTCCCCATTCTCCGGTGTTTCCTCGGGCTTTGCC
GCCGCTAAGCCGATATCTACAATGCCAGCGGGCAGCGACATTATACCTAGCCTTTCATCGCGACTGAATAACGCTTG
GCCAAATTGGATGGGTACCACGCAACGCTTTCACGCACTATGGTGTAGCGTCAGCACAGTTCAACCATTCAAGGTGA
AATACATACATGTTCGATTCCTGTGTCCGAGTCGCCGCAACATTCGTGCACTTGGCGCAGTCTGAATTACATGGACA
ACCTCATGACTTCGAACGACCGCGCCCGTCGCGCTCTCTGCTCGCTGTTTCCTAAATATTGATTTAATCGCTAACAT

TABLE 6-continued

Sequences Corresponding to Frequency Peaks (SEQ ID NOs 21-167)

GTATTGTACTCGGTAATTACTTCCTGATTAACGCGCGGGGAGCGAGCGCCGCGCTCGCGCGCCCGCTACGCTCGCAT

TTCCTCTCTGGTGCGCTTGCCGTGTATTAGTTTCATTGTTAAGTGTCGTTTAAAAGTCCGCGCGTAGGTCTGCAGCG

CTCATAGAGTTCGCTTGTGTGGCGAGTCCCAGCGCTCGCTGCGCTCGCGTTTTGCAAGGGTTAAGCGAGCGTTGTGA

TTCATTTCCGCGTGCCCTACCGTGTGGCGTTGCGGGCGGGTGCGTAACGCGTGCCTGTGCGTTGCGGTCTCCGCTGC

CTACGTCCGGTCCTACGGGTGGGCTGCGCTGGGG

>SEQ ID NO: 60

TTGGGCTTTTCTTGCGTAGCCTAGGTGGGAGTCTATGAAGAATACCTTCCGGGGTC

>SEQ ID NO: 61

TCACGAGATCGCTTCTGATTGTCCCAACCATTGTATTACGTGTGAGCCACGGC

>SEQ ID NO: 62

TCGGTTTGGAAAGATTTTGGCTCGTTTTGACAATATTGAGAGGCACTGAAGCAGTTGAGACGCCTCTAAATATTCAG

TGGGATCTGGTTGAATGAGAAGCCACAGTGGTGCAAGTATGCAGGACCATGAAAGTCGCATCCCTTCCACCTAGTCT

GTGCACTGTGGCAAGGAGCAGTGGGACACATCATTGTTATGTGCCCTCGTCCCATCACAGTCACCCACAAGCAACTC

CAGTGATCTTCCTAGGTATATTTATGCTATTTATGCTGTGCAAATCATTTCTGACATGTCACACTTCTCAAACCCCG

CAAAACCCCTTAAAACCCCCATTTAGGCGACCCACGGGCCAGGGGCCACGTGAGTGAGTGCAGCAGTCCAGCCACGC

CACCGTTTGGCTTGGCTATCGATTATATACATATAGCGACTGCCGTTGTATGGTTGGCACAAGCTGAAGCTCGCTGG

GGTGGAGCGATTGCGAACTTGGTGACACCGCTGTTGTCCCAGGCCTGCAAGGGGCAGGAGGCATACTGGTCTTGCCA

TGCCAACGTGCTGTGGCCGCTTCAGCGTGCACCTGCAACGCTAACATTCGCAAATGCCACTGACTGATTGTGCTGAG

CATGGCTGCACATTACTTGACAGCCTGCATGATACCTGACCCTGAGAGGGGAAGGGAGGGGGGCACACCTGTCCTGA

TGTGCAGAGCCACATGGGCACTGCAAGGGCTGGTACCACCGCGCCGAACTTGTGGTTGCATTACAAACAGGTCAAG

CAGCATGTGCATACCTAAGTGTGGAAGGGTCTTGCACAGGGGTGAGTGAGGCAGGCAGGTTGGATGGTTGGTCAGGC

AGCACAGCCCCGAGTGTGGGACAAGGGGGATGGGTACCATGCGCTTGCACACCATGCATGTGCAACCTGTCTACAT

GCCACATAGCATCATGAAGCATTCAGTGGGATCTGGTTGAATGAGAAGCCACAGTGGTGCAAGTATGCAGGACCATG

AAAGTCGCATCCCTTCCACCTAGTCTGTGCACTGTGGCAAGGAGCAGTGGGACACATCATTGTTATGTGCCCTCGTC

CCATCACAGTCACCCACAAGCAACTCCAGTGATCTTCCTAGGTATATTTATGCTATTTATGCTGTGCAAATCATTTC

TGACATGTCACACTTCTCAAACCCCGCAAAACCCCTTAAAACCCCCATTTAGGCGACCCACGGGCCAGGGGCCACGT

GAGTGAGTGCAGCAGTCCAGCCACGCCACCGTTTGGCTTGGCTATCGATTATATACATATAGCGACTGCCGTTGTAT

GGTTGGCACAAGCTGAAGCTCGCTGGGGTGGAGCGATTGCGAACTTGGTGACACCGCTGTTGTCCCAGGCCTGCAAG

GGGCAGGAGGCATACTGGTCTTGCCATGCCAACGTGCTGTGGCCGCTTCAGCGTGCACCTGCAACGCTAACATTCGC

AAATGCCACTGACTGATTGTGCTGAGCATGGCTGCACATTACTTGACAGCCTGCATGATACCTGACCCTGAGAGGGG

AAGGGAGGGGGGCACACCTGTCCTGATGTGCAGAGCCACATGGGCACTGCAAGGGCTGGTACCACCGCGCCGAGCT

TGTGGTTGCATTACAAACAGGTCAAGCAGCATGTGCATACCTAAGTGTGGAAGGGTCTTGCACAGGGGTGAGTGAGG

CAGGCAGGTTGGATGGTTGGTCAGGCAGCACAGCCCCGAGTGTGGGACAAGGGGGATGGGTACCATGCGCTTGCAC

ACCATGCATGTGCAACCTGTCTACATGCCACATAGCATCATGAAGCATTCAGTGGGATCTGGTTGAATGAGAAGCCA

CAGTGGTGCAAGTATGCAGGACCATGAAAGTCGCATCCCTTCCACCTAGTCTGTGCACTGTGGCAAGGAGCAGTGGG

ACACATCATTGTTATGTGCCCTCGTCCCATCACAGTCACCCACAAGCAACTCCAGTGATCTTCCTAGGTATATTTAT

GCTATTTATGCTGTGCAAATCATTTCTGACATGTCACACTTCTCAAACCCCGCAAAACCCCTTAAAACCCCCATTTA

GGCGACCCACGGGCCAGGGGCCACGTGAGTGAGTGCAGCAGTCCAGCCACGCCACCGTTTGGCTTGGCTATCGATTA

TATACATATAGCGACTGCCGTTGTATGGTTGGCACAAGCTGAAGCTCGCTGGGGTGGAGCGATTGCGAACTTGGTGA

TABLE 6-continued

Sequences Corresponding to Frequency Peaks (SEQ ID NOs 21-167)

CACCGCTGTTGTCCCAGGCCTGCAAGGGGCAGGAGGCATACTGGTCTTGCCATGCCAACGTGCTGTGGCCGCTTCAG
CGTGCACCTGCAACGCTAACATTCGCACTGTCCTGATGTGCAGAGCCACATGGGGCACTGCAAGGGCTGGTACCACC
GCGCCGAGCTTGTGGTTGCATTACAAACAGGTCAAGCAGCATGTGCATACCTAAGTGTGGAAGGGTCTTGCACAGGG
GTGAGTGAGGCAGGCAGGTTGGATGGTTGGTCAGGCAGCACAGCCCCGAGTGTGGGGACAAGGGGGATGGGTACCAT
GCGCTTGCACACCATGCATGTGCAACCTGTCTACATGCCACATAGCATCATGAAGCATTCAGTGGGATCTGGTTGAA
TGAGAAGCCACAGTGGTGCAAGTATGCAGGACCATGAAAGTCGCATCCCTTCCACCTAGTCTGTGCACTGTGGCAAG
GAGCAGTGGGACACATCATTGTTATGTGCCCTCGTCCCATCACAGTCACCCACAAGCAACTCCAGTGATCTTCCTAG
GTATATTTATGCTATTTATGCTGTGCAAATCATTTCTGACATGTCACACTTCTCAAACCCCGCAAAACCCCTTAAAA
CCCCCATTTAGGCGACCCACGGGCCAGGGGCCACGTGAGTGAGTGCAGCAGTTCAGCCACGCCACCGTTTGGCTTGG
CTATCGATTATATACATATAGCGACTGCCGTTGTATGGTTGGCACAAGCTGAAGCTCGCTGGGGTGGAGCGATTGCG
AACTTGGTGACACCGCTGTTGTCCCAGGCCTGCAAGGGGCAGGAGGCATACTGGTCTTGCCATGCCAACGTGCTGTG
GCCGCTTCAGCGTGCACCTGCAACGCTAACATTCGCAAATGCCACTGACTGATTGTGCTGAGCATGGCTGCACATTA
CTTGACAGCCTGCATGATACCTGACCCTGAGAGGGGAAGGGAGGGGGCACACCTGTCCTGATGTGCAGAGCCACAT
GGGGCACTGCAAGGGCTGGTACCACCGCGCCGAGCTTGTGGTTGCATTACAAACAGGTCAAGCAGCATGTGCATACC
TAAGTGTGGAAGGGTCTTGCACAGGGGTGAGTGAGGCAGGCAGGTTGGATGGTTGGTCAGGCAGCACAGCCCCGAGT
GTGGGGACAAGGGGGATGGGTACCATGCGCTTGCACACCATGCATGTGCAACCTGTCTACATGCCACATAGCATCAT
GAAGCATTCAGTGGGATCTGGTTGAATGAGAAGCCACAGTGGTGCAAGTATGCAGGACCATGAAAGTCGCATCCCTT
CCACCTAGTCTGTGCACTGTGGCAAGGAGCAGTGGGACACATCATTGTTATGTGCCCTCGTCCCATCACAGTCACCC
ACAAGCAACTCCAGTGATCTTCCTAGGTATATTTATGCTATTTATGCTGTGCAAATCATTTCTGACATGTCACACTT
CTCAAACCCCGCAAAACCCCTTAAAACCCCCATTTAGGCGACCCACGGGCCAGGGGCCACGTGAGTGAGTGCAGCAG
TCCAGCCACGCCACCGTTTGGCTTGGCTATCGATTATATACATATAGCGACTGCCGTTGTATGGTTGGCACAAGCTG
AAGCTCGCTGGGGTGGAGCGATTGCGAACTTGGTGACACCGCTGTTGTCCCAGGCCTGCAAGGGGCAGGAGGCATAC
TGGTCTTGCCATGCCAACGTGCTGTGGCCGCTTCAGCGTGCACCTGCAACGCTAACATTCGCAAATGCCACTGACTG
ATTGTGCTGAGCATGGCTGCACATTACTTGACAGCCTGCATGATACCTGACCCTGAGAGGGGAAGGGAGGGGGCAC
ACCTGTCCTGATGTGCAGAGCCACATGGGGCACTGCAAGGGCTGGTACCACCGCGCCGAGCTTGTGGTTGCATTACA
AACAGGTCAAGCAGCATGTGCATACCTAAGTGTGGAAGGGTCTTGCACAGGGGTGAGTGAGGCAGGCAGGTTGGATG
GTTGGTCAGGCAGCACAGCCCCGAGTGTGGGGACAAGGGGGATGGGTACCATGCGCTTGCACACCATGCATGTGCAA
CCTGTCTACATGCCACATAGCATCATGAAGCATTCAGTGGGATCTGGTTGAATGAGAAGCCACAGTGGTGCAAGTAT
GCAGGACCATGAAAGTCGCATCCCTTCCACCTAGTCTGTGCACTGTGGCAAGGAGCAGTGGGACACATCATTGTTAT
GTGCCCTCGTCCCATCACAGTCACCCACAAGCAACTCCAGTGATCTTCCTAGGTATATTTATGCTATTTATGCTGTG
CAAATCATTTCTGACATGTCACACTTCTCAAACCCCGCAAAACCCCTTAAAACCCCCATTTAG

>SEQ ID NO: 63

TTGATCTCACACCACACAAGCAATCTTTGTGGCGTTGCGCACGCGCATACGCATACACACACGCATGCACTATTCAT
GGTGGCACATCCCTAACTTTGGCCTGCTGTGATAAATCGTCTCATCTATAGTCTCATGGGATGCTTGGCCACAATGC
GTAGACATACGTCTCACCTCATACCGTATACAACATTTGCGTGCCGGCGCGGGCACCAGCAGCTCGCTTGCAGACGA
CCTTGCAATACACCCGTACACATGAAACCCAGCCACCCTCGCACATTCAGAAGTAAGCCCACCTGCACAACCATTGG
TTGTCAACCAACAGGGCTCTGTGAGGCAAGCTTTTCTCTCCACCCCAGCAGCAGTACTGCTTGCCATACATCGCCGC
ATTTATGCAATCCCTCTTGCTTGCGGGGTGGTAGCTCAATCACATTCTAGTGATGACCTAGTTGGATGGACGCCAAG
TATCGCCTTCGCTAGGGTTGCCTGGCGAGCGCGCGATGTATAACGCATTCCGATGGGTCGATTATTGTACGGTAATG

TABLE 6-continued

Sequences Corresponding to Frequency Peaks (SEQ ID NOs 21-167)

CAATAATGCATGAACTGCAAGTACAGCAGGTATGGCTTAGCCCAGCGGCAAACTCGCCATCATTTTATGTCTGCCGC
CTGTGCAGCTTGCAGAAGGGTGCGCGACTGATGTATGCTGTATCATGATTGGCAACAGCAGCGACGGGCACACCTGC
CTGACTGTCCAAGCCAGCATGGCTAGTTGCTTGAGCAGTAAAGACACAGTGGCCATGCTACTGCGCCTAGCTTGTTT
GCTTGCTTGCTGCACGAGTCAGCTAGCCATAAACGCTCTGTGCATGTAACGAAAGCGCCTGCCTTGCTTTGCAGCTA
TCAACCAATTGCGTTGCAACGGCAGCATAAAATGGTTGCGGTTGCGGACTTACGCAGCCAGCCAAGAAGATGCTAGC
AGGCACACGCTTGAAGCAAGCAAGCACGCACAAACACACGTAGGTGCGTATGTATTCGTCTATTTAAATATATAGAG
CATACATGTATGCCCATCTAATGAGGCATGTCGTCCATGCGTGCAACCATCGCTCAGACTGCTGCATTAGACCGTTG
ATGGCTAACGCAAATGCCGCACGTACCTACATACAGATACGGATAGTGCAGCAGGCTGCTTTAGCTGCTTGCACGAA
CGTGCGCATGCACGCAGCGCTGAACATGCATGTATGCATGCAAATAGCTGCTAGTTGGCATTCATTCGGCAATTAAT
CAAGCAGCAGCACAGACTTCATAGCTGGTATGATTGCATCGATGAACTTCATCTGCGTACGTACGCCCGCCCTGCTA
TATTTGTAGTAAATGGTTAACGCAAGCCTGCTTGACAGCAGGTCGCTGTACATTCCACGTGCGTGAATGCGTGCATG
GTGGCAGCCGCAAGCAAGGCCACCAGTAGGATGCGCAGACTAGTAATGCTAGCAATCTAGTACGTGGTGGCGTTTCA
TCAAGCTATCTGCCATCCGTAATCTCCAGCACGTTCACGCCCACGCCCACGCCATCGCCGCCGCCTGCACTGGCATC
CTCCAGTGCGGCCGCTGTACCTGCTACTGTCACCACGGGTAGCAGCATACGCTGCTGTTGCTCCAGCAGTTGCTCCG
GGCTTGGCTCCGGTAGCCCTGTCCCCTGAACGACGGTTGGGCGCAACCGCCCGAAGCCACCGCCGGGGTCAGCGCTG
TCGTGCGCCGCTGCTGCTGCAGTTTCTGCTGTTGCGGCGGCAGCCGCTGCCACACCACCTCCGGCACCATATCCGTA
GCAGCTGTCTCCGCGCTGCTGTTGCTCTAGTTGAGCATCGAGGCCGTTATCGAATGCGGTAACACGCGCCGCCACCT
CCCGGATTGCATCAATCAGAAATGCGCGCTGTGCACCCTCGTCATACACACTGAATGGCGGCACATGAATGAAGAGC
GAGT

>SEQ ID NO: 64

GTCCGCCACAGCCGAGCGGCAGCGGCGCCTTCCCTGTTGAGTCGGCTGCCGCCCCCGCCACGGCCTCATCCATCCAT
ACGCAGCTGTCCACCTGTGAGGTAGGCAAACAAACAGGACACGTGCGCGGATGTACGGCGGGATGCTCGCTCGCGTC
AAACTGCTGCCGGTCGAGTCAAACTCTACCTATCGACAGCAGCAGGGCGTGTTGCTGGGGGGAGTGTGAATCTTTAA
TATTATGGCTCCTGCACGTAGCTAGCGATGGGTAATAATAATAATAATAATAATAATAATAATAATAATAATAATAA
TAATAATAATAATAATAATAATAATAATAATAATAATAATAATAATAATAATAATAATAATAATAATAATAATAATA
ATAATAATAATAATAATAATAATAATAATAATAATAATAATAATAATAATAATAATAATAATAATAATAATAATAAT
AATAATAATAATAATAATAATAATAATAATAATAATAATAATAATAATAATAATAATAATAATAATAATTACAATGC
CGGCCCATAGGGCCTGGCATGGATTAACGGGGTAAGGTGACTAGGGCGAGAGGGCCCGCCCCCCTCACGCTGACGCC
TCACCACAAAAGAGTCACGACCTCCGAAACTACAACCTCCAAGTCCTAGGCCGCTCTTCAAAGTCCACTACATCCGA
GCCTGCACACCTAGCATATCGAGCTAGGGAAACACCGTGTTATAGTAGTGGAGCACTACCAGTTCGTGCAAACCGAG
GAGCCATGGTGCTCCTCCTCGAGCCTTGGATCTTGAGCCTTGTCTTGAACCTTGGACCACTAAATTGGACTTCTGCA
CCACGACCTTTCTAGGTTGTGAACTGCGGGCATAAGCCCGCAATTGCCACTAAGGGCAATTACCTATCGTTCGTGGG
ATCACCAATCGGTTTCGCACCAATCTTTCGCCTTTGGCATAATTGGGCTTTTATCCGGATTCGTACCCGGGTCCCTT
CTGCCGTAAGGACGAGTCATATCGCTAACTCAGTTA

>SEQ ID NO: 65

GTGGAAGCTATCTTAAGGCAGTGGCGCATGTGTGCTGGGTGGGTGGGTGGGTGGGTCGAGGTTAGGTAGGGTAGGGC
AAGGTGGGTCGGTCGGTAGGTAAAGGTTCCGTGGTGCTGTTTGATTTTAGATAGTCCAGTGGGTGGCGTTTATGTAT
GTGGAAATCGCTTTTCAGGATTGGGTATAGCTCCAGGGAGGGTGAGTGGGTTGGAGTGTGTTGGGAGCCCTTGCCG
TGTCACTGGGCCTGTTGGGCCAAGGTACCAGCACTTGGGTGGCGTGGGCCATAGCTGGTTGTCAAACGGGGTTTGAA

TABLE 6-continued

Sequences Corresponding to Frequency Peaks (SEQ ID NOs 21-167)

```
GGGGTTTTACGGGGTTTTAGCGGGGTTATAACGCCGGCCGTCCCTAGAGGGGTCAGTAAACTCTACCAACGTGCTGG
ACAGACCTCCTGTGACATGGGAACCTTAGTGGGGGTGGTGGGTGGGGGTTTGGGTGGGTTGGGCACCTTGGGTGTTT
GAACCCCGGGGGTTTTCGGGGTTATCGGGGTTTTAGCCGTAGCGTGCAGTATGACATGAGGAAAAGTGCGCTGACTG
GCCAGGCGTGCTTGGGGTGGTGTAGGGGTGATGTGGGTTGATTTTTAGGGTGAGTTGATGCCTGGAGGGGGTGGTCA
CCTTGGGAGGGGTTTTGGGGGGTTTTACGCGTGCACCCCGACGTGGGGCGGTTGGATTATGTGTATTAAACATGCTT
AATTAACGTAATTAGAATGGTTTAGGGTTATGGGGTTCCCCCCTTAGGGTTTTTGGGGTCGGGGTGTGTGGTCGGG
GGTGTGGGGTTTTGGTCAAACGTTGGTCAAACGTAGCTTGGTCAAAGTTTGACCGGCCTTAGTCAGCGCGTTGTTGG
TCCGATTTGCTCCTGTCTTTTTCTTATGTGTCTTATGTGTTGTGTTAGATAAGGTTTCTTATGTGTGTGTGTGGC
TGTTGGGTTAGATAAGACATATAAGGGTTTCGGGGTTTTGGTGCCCTGTGCCTTGTCCCGCGGGTCCCAACGTGTCC
CCCTTGTGCTGGCATGGTGTTGGGAGTGTGTGCGATGTGTTGGAAGCGTTGGGGGTGCTTGGAGTGCAGTTTGGTGT
GTGTGGTGTGGTGTGGAGTTGGTCAAGGGTGTCAGTCCCCTTGGCACGCTAGCAACCCTACCCCATATCCACCCCCT
GGCCAGCTCTGCCACCCTCGCCCACGCGCATGCACTCACAGCACGTCAAACGAGTTCCCATTTCACTTTGGCATGTA
TGGGGAGGCATGGGGCAGCTCCGGGCGGGGATGGCACCATGGCGGTGGTGGTACCGTGTGCTCGGGTCCTGCCTTTG
GCTCTGCTTGTCCATGACGTACGGCTCTGGGTATCTTCCATGCCCGTAAGTTATGGCCCTAAGGTACCCCAAGGTAC
CCTAAGGTACCCACGCGTGTGCCCTCTAGGGTACAGGGGTAACACTTGCGCATACACACACGCGCGCACACACGCAC
ACACACGCGCACACACTCCCCCCTGCCAACCCCACTCTCACCCCCGCGTCCCCCCGCCCCCCTGCGTGTGCGTGTGT
GTGCCACGACGTGCGTACGGCAAAGTGTGGCCAAGGCCCCCCCTTGCGAGTGGGGGAACCCCCCTAGCCCCTAGGCC
CTAGCCCCCAACCCCTAGACAGCCAGCCCAAACGGAAACAGGTGTGGTGTCATGTATCTGGGGTAGGCGTGAAGAGA
AGCGAAAGCAAGCAATTGCAAAGCTTCGAATCATAACAACACAATCCGAAGAATGAGCTAAGCAATTAGGTCTAGTA
ACTCGGTGAGTGGCAGTGAACTCAAGTAGGCTCTGCCGGGTCAGGTAACTGGTCCTGGCTAGCCCTGCTTGAACTGG
TTCAATCAATGCGTCAATTGGCGGTCAAACGCTGGTTGATTGTTGCCCAAATCTATTGATGGTTTGAGTTGCAACGA
GTGTTGAGAGAGCTTGTATTAATACGCGATGCGTATGCTTATGAACCAAGTGGACCTGCTAGGACAGTAGGTGCAAG
GCCAGTGTAACAGCTGTGCTTTGTTATCTGCCGGCTAGCATTGAAGCTCTGCTTGCGGGAAGCCGCATGCCTGAGTG
TTCGCTAGGTGGTCTGAGCTTATGCCTAACCCGTGTAAGACTCAGCCAATCCGCGATACTTGGTTGCGTTGCTTCCG
GAGCGCTGGTTCAGAGCTGGGAGAACGTTCAGAGAGGCCTCGTGGCAAGAGCTCTTCTGACTCGATTCGTCTTCGGA
CAGTCGTGTTCAGTCGACTCTCGAGTGCTTTCTCAACGGATAGCGCTTCTTAATTGATTCAATTCCTGCGTATCCTT
TGTGATACGCGCCGGAATACTGTGGCATGCGTATGCTCTCGTGGCGTATGTGTGCTGCAGTTTCAATTAAAGGCAGC
TACCTGGTTGATCCTGCCAGTAGTCATATGCTTGTCTCAAAGATTAAGCCATGCATGTCTAAGTATAAACTGCTTAT
ACTGTGAAACTGCGAATGGCTCATTAAATCAGTTATAGTTTATTTGATGGTACCTACTACTCGGATAACCGTAGTAA
TTCTAGAGCTAATACGTGCGCACAACCGACTTCTGGAAGGGTCGTATTTATTAGATAAAAGGCCAGCCGGGCTCTGC
CCGACCTGCGGTGAATCATGATAACTTCACGAATCGTATGGGCTCGTCCCGACGATGTTTCATTCAAATTTCTGCCC
TATCAACTTTCGATGGTAGGATAGAGGCCTACCATGGTGGTAACGGGTGACGGAGGATTAGGGTTCGATTCCGGAGA
GGGAGCCTGAGAGATGGCTACCACATCCAAGGAAGGCAGCAGGCGCGCAAATTACCCAATCCCGACACGGGGAGGTA
GTGACAATAAATAACAATACCGGGCGCTTCGCGTCTGGTAATTGGAATGAGTACAATCTAAATCCCTTAACGAGGAT
CCATTGGAGGGCAAGTCTGGTGCCAGCAGCCGCGGTAATTCCAGCTCCAATAGCGTATATTTAAGTTGTTGCAGTTA
AAAAGCTCGTAGTTGGATTTCGGGTGGGGTGGTGCGGTCCGCCTCTGGTGTGCACTGCTCTGCTCCACCTTCCTGCC
GGGGACGGGCTCCTGGGCTTCACTGTCTGGGACTCGGAGTCGGCGAGGTTACTTTGAGTAAATTAGAGTGTTCAAAG
CAGGCCTACGCTCTGAATACATTAGCATGGAATAACACGATAGGACTCTGGCCTATCTGTTGGTCTGTGGGACCGGA
GTAATGATTAAGAGGGGTAGTCGGGGGCATTCGTATTCCGTTGTCAGAGGTGAAATTCTTGGATTTACGGAAGACGA
```

TABLE 6-continued

Sequences Corresponding to Frequency Peaks (SEQ ID NOs 21-167)

ACATCTGCGAAAGCATTTGCCAAGGATACTTTCATTGATCAAGAACGAAAGTTGGGGGCTCGAAGACGATTAGATAC

CGTCGTAGTCTCAACCATAAACGATGCCGACTAGGGATTGGCAGATGTTCTTTTGATGACTCTGCCAGCACCTTATG

AGAAATCAAAGTTTTTGGGTTCCGGGGGAGTATGGTCGCAAGGCTGAAACTTAAAGGAATTGACGGAAGGGCACCA

CCAGGCGTGGAGCCTGCGGCTTAATTTGACTCAACACGGGGAAACTTACCAGGTCCAGACACGGGAAGGATTGACAG

ATTGAGAGCTCTTTCTTGATTCTGTGGGTGGTGGTGCATGGCCGTTCTTAGTTGGTGGGTTGCCTTGTCAGGTTGAT

TCCGGTAACGAACGAGACCTCAGCCTGCTAAATAGTCAGCATCGCACCTGCGGTGCGCCGACTTCTTAGAGGGACTA

TTGGCGTTTAGCCAATGGAAGTATGAGGCGATAACAGGTCTGTGATGCCCTTAGATGTTCTGGGCCGCACGCGCGCT

ACACTGACGCGACCAACGAGCCTATCCTTGGCCGAGAGGCCCGGGTAATCTTGTAAACCGCGTCGTGATGGGGATAG

ATTATTGCAATTATTAGTCTTCAACGAGGAATGCCTAGTAAGCGCGAGTCATCAGCTCGCGTTGATTACGTCCCTGC

CCTTTGTACACACCGCCCGTCGCTCCTACCGATTGGGTGTGCTGGTGAAGTGTTCGGATTGAGCTTGGCTGGGGCAA

CCTGGCCTTGCTTGAGAAGTTCATTAAACCCTCCCACCTAGAGGAAGGAGAAGTCGTAACAAGGTTTCCGTAGGTGA

ACCTGCGGAAGGATCATTGAATCTATCACAATCCACACCGCGAACTAACACTGTTGGCCTCCGTCTGTATAAAAGCA

AACGGGCCAGGTCTGGGCGCAATGTAAAAGTTACGCCTGGCCTGGGTTGCCGCAAGGCATCGGTCTCTTATACTAAC

CAACCAACACCAAACCAAAACTAAATTAAAACCGAGTATCTAGCTTAGAGCTAGTGCTCACTAACCAAGACAACTCT

CAACAACGGATATCTTGGCTCTCGGATCGATGAAGAACGCAGCGAAATGCGATACGTAGTGTGAATTGCAGAAATAC

GTGAATCATCGAATCTTTGAACGCATATTGCGCTCGAGGCTTCGGCCAAGAGCATGTCTGCCTCAGCGTCGGGTTAA

TACTCGCCCTACTCCAACATACACTTGTGTGTTTGGAGCAAGAGCGGACCTGGCTGTCTCGGTGTTTGATTTTCGGA

TCAGACGCCGGGTCAGCTGAAGTACAGAGGTTGATGCATGGACCCGCTTATGGGCCTCTACTGGGTAGGCAACTCGT

TGCTAATGCTTTAGTAGATGGCTTGGAGCTGTGCTTGTCGACCCAAACCAGGAACTTTGGCCCTGTGCCGAAGCAAA

CCCCTATTTTCTCGACCTGAGCTCAGGCAAGATTACCCGCTGAACTTAAGCATATCAATAAGCGGAGGAAAAGAAAC

TAACAAGGATTCCCCTAGTAACGGCGAGCGAACCGGGAATAGCCCAACTTGAAAATCTCCCTTTGGAGAATTGTAGT

CTAGAGAAGCGCTTTCTAGGGCTGGCGGAACTCAAGTCGGATCGAATGCCGCGTCAGAGAGGGTGATAACCCCGTCG

GTTCCTGCTTAGTCCTTCCACGAAGTGCTTTCCACGAGTCGGGTTGTTTGGGAATGCAGCCCTAATTTGGAGGTAAA

TCCCTTCTAAGGCTAAATACTGCCGAGAGACCGATAGCGAACAAGTACCGTGAGGGAAAGATGAAAAGAACTTTGAA

AAGAGAGTTAAAAGTGCTTGAAATTGTTGAGAGGGAAGCGATTGGCGCTCGTAGGTGCGCCCAGGCTTAAGCGGTCC

TAACGGCCCGTTGAATGTGCTGGGTGCTGGTCAGAATGGGTTGAGTTGGCGGGACAAAAGCTGGGTCCACCCAGGTA

ACCCGGCCGATGCCGCCGACTCGACCAAGGCGTAAAGAGTACCTTGTCCTTCGGGATCTGTGCTCTAAAGATTCTGG

CAGAAGAGCGTCAATCGACCCGTCTTGAAACACGGACCAAGGAGTCTAACATGTATGCGAGTTGGCGGGTGGAAAAC

CCGTAAGCGCAAGTAACCTGACTGGTGGGATGGGTAAAACCCTGCACCATCGACCGACCATGTTGTTTCTACGAAA

GGTTTGAGTGCGAGCATACCTGTTGGGACCCGAAAGATGGTGAACTATGCCTGAGCAGGGTGAAGCCAGAGGAAACT

CTGGTGGAGGCTCGTAGATGTGCTGACGTGCAAATCGCTTTTCAGACTTGGGTATAGGGGCGAAAGACTAATCGAAC

CATCTAGTAGCTGGTTCCCTCCGAAGTTTCCCCCAGGATAGCTGGAGCTTGATCAGTTTTATCGGGTAAAGCGAATG

ATTAGAGGTTCGGGGATGAAACATCCTTCACCTATTCTCAAACTTTAAATAGGTAAGACGTGTCGGTTGCTTAATTG

AACCGGCACATTCAATGTGAGCTCCAAGTGGGCCATTTTTGGTAAGCAGAACTGGCGATGCGGGATGAACCGATAGT

CGAGTTAAGGTGCCAAACTACGCGCTAACCTAGATCCCACAAAGGGTGTTGATTGATATAAACAGCAGGACGGTGGT

CATGGAAGTCGAAATCCGCTAAGGAGTGTGTAACAACTCACCTGCCGAATCAATTAGCCCCGAAAATGGATGGCGCT

TAAGCGCGTGACCTATACTCGGCCATGGAAGCAAGTGCGACGCTTCCATGAGTAGGAGGGCGTGGGTGTCGAGACTA

AGCCTCTGGCGTGAGCCTGGGTGAATCGGCATCTAGTGCAGATCTTGGTGGTAGTAGCAAATATTCAAATGAGAACT

TTGAAGACTGAAGTGGAGAAAGGTTCCATGTGAACAGCAATTGGACATGGGTTAGTCGATCCTAAGAGATGGGGTAA

TABLE 6-continued

Sequences Corresponding to Frequency Peaks (SEQ ID NOs 21-167)

TCCTGTGTGAAGAGCGCGATTCGCGCTGCCCATCGAAAGGGAAAAGGGTTAAGATTCCCTTACTTGGACAAGGCGGC

TGGCGGTAACGCAAGCGAGCCCGGAGACATCGGCATCGGCCCTGGGAAGAGTTCTCTTTTCTTTTTAACAACGCGAA

GGCCCTGGAATCGAATCATTCGGAGATAGGGCTCAGACGTTGGTAAAGCACCGCACTTCTCGCGGTGTCCGGCGCGC

CGTTGACGGTCCTTGAAAATCCGGGGAGCATTCCCGATCTTGCCAAGTCGTACTCATAACCGCATCAGGTCTCCAA

GGTGAACAGCCTCTAGTCGATAGAACAATGTAGATAAGGGAAGTCGGCAAAATGGATCCGTAACTTCGGGAAAAGGA

TTGGCTCTGAGGGCTGGGCCTAGGGGTCTGCAGCTGCGAAGCTCGGGACTGCGGTGGTCTACCCAGCTGGAAACGGC

TGGGCGGACTGCTGCGTGTCCTGGGTGGACGGCTGTAGAAGCTTCGGCGTTCCCTAGGCGACGAACAGCCAACTCAG

AACTGGTACGGACAAGGGGAATCCGACTGTTTAATTAAAACAAAGCATTGTGATGGTCCTAAAGGATGTTGACACAA

TGTGATTTCTGCCCAGTGCTCTGAATGTCAAAGTGAAGAAATTCAACCAAGCGCGGGTAAACGGCGGGAGTAACTAT

GACTCTCTTAAGGTAGCCAAATGCCTCGTCATCTAATTAGTGACGCGCATGAATGGATTAACGAGATTCCCACTGTC

CCTATCTACTATCTAGCGAAACCACAGCCAAGGGAACGGGCTTGGAATAAACAGCGGGGAAAGAAGACCCTGTTGAG

CTTGACTCTAGTCCGACTTTGTGAAATAACTTAAGAGGTGTAGAATAAGTGGGAGCTTCGGCGACGGTGAAATACCA

CTACTTTTAACGTTGTTTTACTTATTCCATTACTTGGAGGCGGGACTCTGTCCCTGCTTCTAGCTCTAAGACGGCTT

TTGCACGTCGATCCAGGTGGAAGACATTGTCAGGTGGGGAGTTTGGCTGGGCGGCACATCTGTTAAAAGATAACGC

AGGTGTCCTAAGATGAGCTCAACGAGAACAGAAATCTCGTGTAGAACAAAAGGGTAAAAGCTCATTTGATTTTGATT

TTCAGTACGAATACAAACTGTGAAAGCATGGCCTATCGATCCTTTAGCCTTTCGGGATTTGAAGCTAGAGGTGTCAG

AAAAGTTACCACAGGGATAACTGGCTTGTGGCAGCCAAGCGTTCATAGCGACGTGCTTTTGATCCTTCGATGTCGCT

CTCCT

>SEQ ID NO: 66

TTGTGAAATTACTTAGAGGTGTAGAATAAGTGGGAGCTTCGGCGACGGTGAAATACCACTACTTTTAACGTGTTTTA

CTTATTCCATTACTTGGAGGCGGGACTCTGTCCCTGCTTCTAGCTCTAAGACGGCTTTTGCACGTCGATCCAGGTGG

AAGACATTGTCAGGTGGGGAGTTTGGCTGGGCGGCACATCTGTTAAAAGATAACGCAGGTGTCCTAAGATGAGCTC

AACGAGAACAGAAATCTCGTGTAGAACAAAAGGGTAAAAGCTCATTTGATTTTGATTTTCAGTACGAATACAAACTG

TGAAAGCATGGCCTATCGATCCTTTAGCCTTTCGGGATTTGAAGCTAGAGGTGTCAGAAAAGTTACCACAGGGATAA

CTGGCTTGTGGCAGCCAAGCGTTCATAGCGACGTTGCTTTTTGATCCTTCGATGTCGGCTCTTCCTATCATTGTGAA

GCAGCATTCACCAAGCGTTGGATTGTTCACCCACTAATAGGGAACGTGAGCTGGGTTTAGACCGTCGTGAGACAGGT

TAGTTTTACCCTACTGTTGGACCGATTCCGCCATAGTAATTCGGCTCAGTACGAGAGGAACCGCCGAGTCAGATAAT

TGGTAATGCCCTTGTCTGAAAAGACAATGGGGCGAAGCTAACATCTGTAGTCTAATGACTGAACGCCTCTAAGTCAG

AAGACGTGCTAGGTGCGGAGTCACTTACCCAATGATGTCACCCGACTAAGGATACATCCGCCTGTGCGGATGCTGGA

GCATACCCGTTGGTTCCCCTGTTAGGTCCACATGGCCGAAGCAGGCGCCAAGCATGACAATTCCACTCGTCATTGGG

GTAAATCCTCTGTAGACGACTTTGTTGCAACTGGGTATTGTAAGTGGTAGAGTGGCCTTGCTGCTACGATCCACTGA

GATTCATCCCGTGTTGCTAAGATTTGTCACTGCCCTTCGGGGCAACCCCTCCTCCTCTCGGAGCGACAGCTCCAGGG

AGGGCCCTCTCTCTCTTCCAAGTGGTGTAGCTGAGCTGAGCGCGTGCCAACGCCGCCGAATCCGTCTAAGTGCCC

ACATGCGTGTGCATGCACTGCCCCTCCTCCCCCACACAGCCAAAGTGCTCAAGGTACCTTCCCTGTGTGTGCGAG

TGAGAGCAACAGCATGCATGTGCCCTTACTTAGGCGGCCTAGTGTGGTATGTGTGTATGCGTGTGGCTTAGTGGCCA

GTTCGACTCTGGCGTGGAAGCTATCTTCTAAGGCAGTGGCGCATGTGTGCTGGGTGGGTGGGTGGGTGGGTAGAGGT

TAGGTAGGGTAGGGCAAGGTGGGTAGGTCGGTAGGTAAAGGTTCCGTGGTGCTGTTTGATTTTAGATAGTCCAGTGG

GTGGCGTTTATGTATGTGGAAATCGCTTTTCAGGATTGGGTATAGCTCCAGGGAGGGTGAGTGGGTTGGGAGTGTGT

TGGGAGCCCTTGCCGTGTCACTGGGCCTGTTGGGCCAAGGTACCAGCACTTGGGTGGCGTGGGCCATAGCTGGTTGT

TABLE 6-continued

Sequences Corresponding to Frequency Peaks (SEQ ID NOs 21-167)

CAAACGGGGTTTGAAGGGGTTTTACGGGGTTTTAGCGGGGTTATAACGCCGGCCGTCCCTAGAGGGGTCAGTAAACT

CTACCAACGTGCTGGACAGACCTCCTGTGACATGGGAACCTTAGTGGGGGTGGTGGGTGGGGGTTTGGGTGGGTTGG

GCACCTTGGGTGTTTGAACCCCGGGGGTTTTCGGGGTTATCGGGGTTTTAGCCGTAGCGTGCAGTATGACATGAGGA

AAAGTGCGCTGACTGGCCAGGCGTGCTTGGGGTGGTGTAGGGGTGACGTGGGTTGATTTTTAGGGTGAGTTGATGCC

TGGAGGGGGTGGTCACCTTGGGAGGGGTTTTGGGGGGTTTTACGCGTGTACCACGACGTGGGGCGGTCGGATTACGT

GTATTAAACATGCTTAATTAACGTAATTAGTTTGGTTTAGGGTTGTGGGGTTCCCCCCTTAGGGTTTTTGGGGTCGG

GGGTGTGTGGGTGGGGGGGTGTGGGGTTTTGGTCAAACGTTGGTCAAACGTTGCCTGGTCAAAGTTTGACCGGCCTT

AGTCAGCGCGTTGTTGTGCCAATAGGCTCCTGTCTTTTTCTTATGTGTCTTATGTGTTGTGTTAGATAAGGTTTCTT

ATGTGTGTGTGTGTGGCTGTTGGGTTAGATAAGACATATAAGGGTTTCGGGGTTTTGGTGCCCTGTGCCTTGTTCCG

CGGGTCCCAACGTGTCCCCCTTGTGCTGGCATGGTGTTGGGAGTGTGTGCGATGTGTTGGAAGCGTTGGGGGTGCTT

GGAGTGCAGTTTGGTGTGTGTGGTGTGGTGTGGAGTTGGTCAAGGGTGTCAGTCCCCTTGGCACGCTAGCAACCCTA

CCCCATATCCACCCCCTGGCCAGCTCTGCCACCCTCGCCCACGCGCATGCACTCACAGCACGTCAAACGAGTTCCCA

TTTCACTTTGGCATGTATGGGGAGGCATGGGGCAGCTCCGGGCGGGGATGGCACCATGGCGGTGGTGGTACCGTGTG

CTCGGGTCCTGCCTTTGGCTCTGCTTGTCCATGACGTACGGCTCTGGGTATCTTCCATGCCCGTAAGTTATGGCCCT

AAGGTACCCTAAGGTACCCTAAGGTACCCACGCGTGTGCCCTCTAGGGTACAGGGGTAACACTTGCGCATACACACA

CGCGCGCACACACGCACACACACGCACACACTCCCAACA

>SEQ ID NO: 67

TATCAACTTTCGATGGTAGGATAGAGGCCTACCATGGTGGTAACGGGTGACGGAGGATTAGGGTTCGATTCCGGAGA

GGGAGCCTGAGAGATGGCTACCACATCCAAGGAAGGCAGCAGGCGCGCAAATTACCCAATCCCGACACGGGGAGGTA

GTGACAATAAATAACAATACCGGGCGCTTCGCGTCTGGTAATTGGAATGAGTACAATCTAAATCCCTTAACGAGGAT

CCATTGGAGGGCAAGTCTGGTGCCAGCAGCCGCGGTAATTCCAGCTCCAATAGCGTATATTTAAGTTGTTGCAGTTA

AAAAGCTCGTAGTTGGATTTCGGGTGGGGTGGTGCGGTCCGCCTCTGGTGTGCACTGCTCTGCTCCACCTTCCTGCC

GGGGACGGGCTCCTGGGCTTCACTGTCTGGGACTCGGAGTCGGCGAGGTTACTTTGAGTAAATTAGAGTGTTCAAAG

CAGGCCTACGCTCTGAATACATTAGCATGGAATAACACGATAGGACTCTGGCCTATCTGTTGGTCTGTGGGACCGGA

GTAATGATTAAGAGGGGTAGTCGGGGGCATTCGTATTCCGTTGTCAGAGGTGAAATTCTTGGATTTACGGAAGACGA

ACATCTGCGAAAGCATTTGCCAAGGATACTTTCATTGATCAAGAACGAAAGTTGGGGGCTCGAAGACGATTAGATAC

CGTCGTAGTCTCAACCATAAACGATGCCGACTAGGGATTGGCAGATGTTCTTTTGATGACTCTGCCAGCACCTTATG

AGAAATCAAAGTTTTTGGGTTCCGGGGGGAGTATGGTCGCAAGGCTGAAACTTAAAGGAATTGACGGAAGGGCACCA

CCAGGCGTGGAGCCTGCGGCTTAATTTGACTCAACACGGGGAAACTTACCAGGTCCAGACACGGGAAGGATTGACAG

ATTGAGAGCTCTTTCTTGATTCTGTGGGTGGTGGTGCATGGCCGTTCTTAGTTGGTGGGTTGCCTTGTCAGGTTGAT

TCCGGTAACGAACGAGACCTCAGCCTGCTAAATAGTCAGCATCGCACCTGCGGTGCGCCGACTTCTTAGAGGGACTA

TTGGCGTTTAGCCAATGGAAGTATGAGGCGATAACAGGTCTGTGATGCCCTTAGATGTTCTGGGCCGCACGCGCGCT

ACACTGACGCGACCAACGAGCCTATCCTTGGCCGAGAGGCCCGGGTAATCTTGTAAACCGCGTCGTGATGGGGATAG

ATTATTGCAATTATTAGTCTTCAACGAGGAATGCCTAGTAAGCGCGAGTCATCAGCTCGCGTTGATTACGTCCCTGC

CCTTTGTACACACCGCCCGTCGCTCCTACCGATTGGGTGTGCTGGTGAAGTGTTCGGATTGAGCTTGGCTGGGGCAA

CCTGGCCTTGCTTGAGAAGTTCATTAAACCCTCCCACCTAGAGGAAGGAGAAGTCGTAACAAGGTTTCCGTAGGTGA

ACCTGCGGAAGGATCATTGAATCTATCACAATCCACACCGCGAACTAACACTGTTGGCCTCCGTCTGTGTAAAAGCA

AACGGGCCAGGTCTGGGCGCAATGTAAAAGTTACGCCTGGCCTGGGTTGCCGCAAGGCATCGGTCTCTTATACTAAC

CAACCAACACCAAACCAAAACTAAATTAAAACCGAGTATCTAGCTTAGAGCTAGTGCTCACTAACCAAGACAACTCT

TABLE 6-continued

Sequences Corresponding to Frequency Peaks (SEQ ID NOs 21-167)

```
CAACAACGGATATCTTGGCTCTCGGATCGATGAAGAACGCAGCGAAATGCGATACGTAGTGTGAATTGCAGAAATAC
GTGAATCATCGAATCTTTGAACGCATATTGCGCTCGAGGCTTCGGCCAAGAGCATGTCTGCCTCAGCGTCGGGTTAA
TACTCGCCCTACTCCAACATGTTTGGAGCAAGAGCGGACCTGGCTGTCTCGGTGTTTGATTTTCGGATCAGACGCCG
GGTCAGCTGAAGTACAGAGGTTGATGCATGGACCCGCTTATGGGCCTCTACTGGGTAGGCAACTCGTTGCTAATGCT
TTAGTAGATGGCTTGGAGCTGTGCTTGTCGACCCAAACCAGGAACTTTGGCCCTGTGCCGAAGCAAACCCCTATTTT
CTCGACCTGAGCTCAGGCAAGATTACCCGCTGAACTTAAGCATATCAATAAGCGGAGGAAAAGAAACTAACAAGGAT
TCCCCTAGTAACGGCGAGCGAACCGGGAATAGCCCAACTTGAAAATCTCCCTTTGGAGAATTGTAGTCTAGAGAAGC
GCTTTCTAGGGCTGGCGGAACTCAAGTCGGATCGAATGCCGCGTCAGAGAGGGTGATAACCCCGTCGGTTCCTGCTT
AGTCCTTCCACGAAGTGCTTTCCACGAGTCGGGTTGTTTGGGAATGCAGCCCTAATTTGGAGGTAAATCCCTTCTAA
GGCTAAATACTGCCGAGAGACCGATAGCGAACAAGTACCGTGAGGGAAAGATGAAAAGAACTTTGAAAAGAGAGTTA
AAAGTGCTTGAAATTGTTGAGAGGGAAGCGATTGGCGCTCGTAGGTGCGCCCAGGCTTAAGCGGTCCTAACGGCCCG
TTGAATGTGCTGGGTGCTGGTCAGAATGGGTTGAGTTGGCGGGACAAAAGCTGGGTCCACCCAGGTAACCCGGCCGA
TGCCGCCGACTCGACCAAGGCGTAAAGAGTACCTTGTCCTTCGGGATCTGTGCTCTAAAGATTCTGGCGAAGAGCG
TCAATCGACCCGTCTTGAAACACGGACCAAGGAGTCTAACATGTATGCGAGTTGGCGGGTGGAAAACCCGTAAGCGC
AAGTAACCTGACTGGTGGGATGGGGTAAAACCCTGCACCATCGACCGACCATGTTGTTTCTACGAAAGGTTTGAGTG
CGAGCATACCTGTTGGGACCCGAAAGATGGTGAACTATGCCTGAGCAGGGTGAAGCCAGAGGAAACTCTGGTGGAGG
CTCGTAGATGTGCTGACGTGCAAATCGCTTTTCAGACTTGGGTATAGGGGCGAAAGACTAATCGAACCATCTAGTAG
CTGGTTCCCTCCGAAGTTTCCCCCAGGATAGCTGGAGCTTGATCAGTTTTATCGGGTAAAGCGAATGATTAGAGGTT
CGGGGGATGAAACATCCTTCACCTATTCTCAAACTTTAAATAGGTAAGACGTGTCGGTTGCTTAATTGAACCGGCAC
ATTCAATGTGAGCTCCAAGTGGGCCATTTTTGGTAAGCAGAACTGGCGATGCGGGATGAACCGATAGTCGAGTTAAG
GTGCCAAACTACGCGCTAACCTAGATCCCACAAAGGGTGTTGATTGATATAAACAGCAGGACGGTGGTCATGGAAGT
CGAAATCCGCTAAGGAGTGTGTAACAACTCACCTGCCGAATCAATTAGCCCCGAAAATGGATGGCGCTTAAGCGCGT
GACCTATACTCGGCCATGGAAGCAAGTGCGACGCTTCCATGAGTAGGAGGGCGTGGGTGTCGAGACTAAGCCTCTGG
CGTGAGCCTGGGTGAATCGGCATCTAGTGCAGATCTTGGTGGTAGTAGCAAATATTCAAATGAGAACTTTGAAGACT
GAAGTGGAGAAAGGTTCCATGTGAACAGCAATTGGACATGGGTTAGTCGATCCTAAGAGATGGGGTAATCCTGTGTG
AAGAGCGCGATTCGCGCTGCCCATCGAAAGGGAAAAGGGTTAAGATTCCCTTACTTGGACAAGGCGGCTGGCGGTAA
CGCAAGCGAGCCCGGAGACATCGGCATCGGCCCTGGGAAGAGTTCTCTTTTCTTTTTAACAACGCGAAGGCCCTGGA
ATCGAATCATTCGGAGATAGGGCTCAGACGTTGGTAAAGCACCGCACTTCTCGCGGTGTCCGGCGCGCCGTTGACGG
TCCTTGAAAATCCGGGGGAGCATTCCCGATCTTGCCAAGTCGTACTCATAACCGCATCAGGTCTCCAAGGTGAACAG
CCTCTAGTCGATAGAACAATGTAGATAAGGGAAGTCGGCAAAATGGATCCGTAACTTCGGGAAAAGGATTGGCTCTG
AGGGCTGGGCCTAGGGGTCTGCAGCTGCGAAGCTCGGGACTGCGGTGGTCTACCCAGCTGGAAACGGCTGGGCGGAC
TGCTGCGTGTCCTGGGTGGACGGCTGTAGAAGCTTCGGCGTTCCCTAGGCGACGAACAGCCAACTCAGAACTGGTAC
GGACAAGGGGAATCCGACTGTTTAATTAAAACAAAGCATTGTGATGGTCCTAAAGGATGTTGACACAATGTGATTTC
TGCCCAGTGCTCTGAATGTCAAAGTGAAGAAATTCAACCAAGCGCGGGTAAACGGCGGGAGTAACTATGACTCTCTT
AAGGTAGCCAAATGCCTCGTCATCTAATTAGTGACGCGCATGAATGGATTAACGAGATTCCCACTGTCCCTATCTAC
TATCTAGCGAAACCACAGCCAAGGGAACGGGCTTGGAATAAACAGCGGGGAAAGAAGACCCTGTTGAGCTTGACTCT
AGTCCGACTTTGTGAAATAACTTAAGAGGTGTAGAATAAGTGGGAGCTTCGGCGACGGTGAAATACCACTACTTTTA
ACCTTGTTTTACTTATTCCATTACTTGGAGGCGGGACTCTGTCCCTGCTTCTAGCTCTAAGACGGCTTTTGCACGTC
GA
```

TABLE 6-continued

Sequences Corresponding to Frequency Peaks (SEQ ID NOs 21-167)

>SEQ ID NO: 68

AGGGTGTCAGTCCCCTTGGCACGCTAGCAACCCTACCCCATATCCACCCCCTGGCCAGCTCTGCCACCCTCGCCCAC
GCGCATGCACTCACAGCACGTCAAACGAGTTCCCATTTCACTTTGGCATGTATGGGGAGGCATGGGGCAGCTCCGGG
CGGGGATGGCACCATGGCGGTGGTGGTACCGTGTGCTCGGGTCCTGCCTTTGGCTCTGCTTGTCCATGACGTACGGC
TCTGGGTATCTTCCATGCCCGTAAGTTATGGCCCTAAGGTACCCTAAGGTACCCTAAGGTACCCACGCGTGTGCCCT
CTAGGGTACAGGGGTAACACTTGCGCATACACACACGCGCGCACACACGCACACACACGCACACACTCCCCCCTGCC
AACCCCACTCTCACCCCCGCGTCCCCCCGCCCCCCTGCGTGTGCGTGTGTGTGCCACGACGTGCGTACGGCAAAGTG
TGGCCAAGGCCCCCCCTTGCGAGTGGGGGAACCCCCCTAGCCCCTAGGCCCTAGCCCCCAACCCCTAGACAGCCAGC
CCAAACGGAAACAGGTGTGGTGTCATGTATCTGGGGTAGGCGTGAAGAGAAGCGAAAGCAAGCAATTGCAAAGCTTC
GAATCATAACAACACAATCCGAAGAATGAGCTAAACAATTAGTTCTAGTAACTCGGTGAGTGGCAGTGAACTCAAGT
AGGCTCTGCCGGGTCAGGTAACTGGTCCTGGCTAGCCCTGCTTGAACTGGTTCAATCAATGCGTCAATTGGCGGTCA
AACGCTGGTTGATTGTTGCCCAAATCTATTGATGGTTTGAGTTGCAACGAGTGTTGAGAGAGCTTGTATTAATACGC
GATGCGTATGCTTATGAACCAAGTGGACCTGCTAGGACAGTAGGTGCAAGGCCAGTGTAACAGCTGTGCTTTGTTAT
CTGCCGGCTAGCATTGAAGCTCTGCTTGCGGGAAGCCGCATGCCTGAGTGTTCGCTAGGTGGTCTGAGCTTATGCCT
AACCCGTGTAAGACTCAGCCAATCCGCGATACTTGGTTGCGTTGCTTCCGGAGCGCTGGTTCAGAGCTGGGAGAACG
TTCAGAGAGGCCTCGTGGCAAGAGCTCTTCTGACTCGATTCGTCTTCGGACAGTCGTGTTCAGTCGACTCTCGAGTG
CTTTCTCAACGGATAGCGCTTCTTAATTGATTCAATTCCTGCGTATCCTTTGTGATACGCGCCGGAATACTGTGGCA
TGCGTATGCTCTCGTGGCGTATGTGTGCTGCAGTTTCAATTAAAGGCAGCTACCTGGTTGATCCTGCCAGTAGTCAT
ATGCTTGTCTCAAAGATTAAGCCATGCATGTCTAAGTATAAACTGCTTATACTGTGAAACTGCGAATGGCTCATTAA
ATCAGTTATAGTTTATTTGATGGTACCTACTACTCGGATAACCGTAGTAATTCTAGAGCTAATACGTGCGCACAAAC
CGACTTCTGGAAGGGTCGTATTTATTAGATAAAAGCGCCAGCCGGGCTCTGCCCGACCTGCGGTGAATCATGATAAC
TTCACGAATCGTATGGGCTCGTCCCGACGATGTTTCATTCAAATTTCTGCCCTATCAACTTTCGATGGTAGGATAGA
GGCCTACCATGGTGGTAACCGGGTGACGGAGGATTAGGGTTCGATTCCGGAGAGGGAGCCTGAGAGATGGCTACCAC
ATCCAAGGAAGGCAGCAGGCGCGCAAATTACCCAATCCCGACACGGGGAGGTAGTGACAATAAATAACAATACCGGG
CGCTTCGCGTCTGGTAATTGGAATGAGTACAATCTAAATCCCTTAACGAGGATCCATTGGAGGGCAAGTCTGGTGCC
AGCAGCCGCGGTAATTCCAGCTCCAATAGCGTATATTTAAGTTGTTGCAGTTAAAAAGCTCGTAGTTGGATTTCGGG
TGGGGTGGTGCGGTCCGCCTCTGGTGTGCACTGCTCTGCTCCACCTTCCTGCCGGGACGGGCTCCTGGGCTTCACT
GTCTGGGAC

>SEQ ID NO: 69

TGTATGGGAGGCATGGGGCAGCTCCGGGCGGGATGGCACCATGGGCGGTGGTGGTACCGTGTGCTCGGGTCCTGC
CTTTGGCTCTGCTTGTCCATGACGTACGGCTCTGGGTATCTTCCATGCCCGTAAGTTATGGCCCTAAGGTACCCTAA
GGTACCCTAAGGTACCCACGCGTGTGCCCTCTAGGGTACAGGGGTAACACTTGCGCATACACACACGCGCGCACACA
CGCACACACACGCACACACTCCCCCCTGCCAACCCCACTCTCACCCCCGCGTCCCCCCGCCCCCCTGCGTGTGCGTG
TGTGTGCCACGACGTGCGTACGGCAAAGTGTGGCCAAGGCCCCCCCTTGCGAGTGGGGGAACCCCCCTAGCCCCTAG
GCCCTAGCCCCCAACCCCTAGACAGCCAGCCCAAACGGAAACAGGTGTGGTGTCATGTATCTGGGGTAGGCGTGAAG
AGAAGCGAAAGCAAGCAATTGCAAAGCTTCGAATCATAACAACACAATCCGAAGAATGAGCTAAGCAATTAGTTCTA
GTAACTCGGTGAGTGGCAGTGAACTCAAGTAGGCTCTGCCGGGTCAGGTAACTGGTCCTGGCTAGCCCTGCTTGAAC
TGGTTCAATCAATGCGTCAATTGGCGGTCAAACGCTGGTTGATTGTTGCCCAAATCTATTGATGGTTTGAGTTGCAA
CGAGTGTTGAGAGAGCTTGTATTAATACGCGATGCGTATGCTTATGAACCAAGTGGACCTGCTAGGACAGTAGGTGC

TABLE 6-continued

Sequences Corresponding to Frequency Peaks (SEQ ID NOs 21-167)

AAGGCCAGTGTAACAGCTGTGCTTTGTTATCTGCCGGCTAGCATTGAAGCTCTGCTTGCGGGAAGCCGCATGCCTGA

GTGTTCGCTAGGTGGTCTGAGCTTATGCCTAACCCGTGTAAGACTCAGCCAATCCGCGATACTTGGTTGCGTTGCTT

CCGGAGCGCTGGTTCAGAGCTGGGAGAACGTTCAGAGAGGCCTCGTGGCAAGAGCTCTTCTGACTCGATTCGTCTTC

GGACAGTCGTGTTCAGTCGACTCTCGAGTGCTTTCTCAACGGATAGCGCTTCTTAATTGATTCAATTCCTGCGTATC

CTTTGTGATACGCGCCGGAATACTGTGGCATGCGTATGCTCTCGTGGCGTATGTGTGCTGCAGTTTCAATTAAAGGC

AGCTACCTGGTTGATCCTGCCAGTAGTCATATGCTTGTCTCAAAGATTAAGCCATGCATGTCTAAGTATAAACTGCT

TATACTGTGAAACTGCGAATGGCTCATTAAATCAGTTATAGTTTATTTGATGGTACCTACTACTCGGATAACCGTAG

TAATTCTAGAGCTAATACGTGCGCCACCCGACTTCTGGAAGGGTCGTATTTATTAGATAAAAGGCCAGCCGGGCTCT

GCCCGACCTGCGGTGAATCATGATAACTTCACGAATCGTATGGGCTCGTCCCGACGATGTTTCATTCAAATTTCTGC

CCTATCAACTTTCGATGGTAGGATAGAGGCCTACCATGGTGGTAACGGGTGACGGAGGATTAGGGTTCGATTCCGGA

GAGGGAGCCTGAGAGATGGCTACCACATCCAAGGAAGGCAGCAGGCGCGCAAATTACCCAATCCCGACACGGGGAGG

TAGTGACAATAAATAACAATACCGGGCGCTTCGCGTCTGGTAATTGGAATGAGTACAATCTAAATCCCTTAACGAGG

ATCCATTGGAGGGCAAGTCTGGTGCCAGCAGCCGCGGTAATTCCAGCTCCAATAGCGTATATTTAAGTTGTTGCAGT

TAAAAAGCTCGTAGTTGGATTTCGGGTGGGGTGGTGCGGTCCGCCTCTGGTGTGCACTGCTCTGCTCCACCTTCCTG

CCGGGGACGGGCTCCTGGGCTTCACTGTCTGGGACTCGGAGTCGGCGAGGTTACTTTGAGTAAATTAGAGTGTTCAA

AGCAGGCCTACGCTCTGAATACATTAGCATGGAATAACACGATAGGACTCTGGCCTATCTGTTGGTCTGTGGGACCG

GAGTAATGATTAAGAGGGGTAGTCGGGGGCATTCGTATTCCGTTGTCAGAGGTGAAATTCTTGGATTTACGGAAGAC

GAACATCTGCGAAAGCATTTGCCAAGGATACTTTCATTGATCAAGAACGAAAGTTGGGGCTCGAAGACGATTAGAT

ACCGTCGTAGTCTCAACCATAAACGATGCCGACTAGGGATTGGCAGATGTTCTTTTGATGACTCTGCCAGCACCTTA

TGAGAAATCAAAGTTTTTGGGTTCCGGGGGGAGTATGGTCGCAAGGCTGAAACTTAAAGGAATTGACGGAAGGGCAC

CACCAGGCGTGGAGCCTGCGGCTTAATTTGACTCAACACGGGGAAACTTACCAGGTCCAGACACGGGAAGGATTGAC

AGATTGAGAGCTCTTTCTTGATTCTGTGGGTGGTGGTGCATGGCCGTTCTTAGTTGGTGGGTTGCCTTGTCAGGTTG

ATTCCGGTAACGAACGAGACCTCAGCCTGCTAAATAGTCAGCATCGCACCTGCGGTGCGCCGACTTCTTAGAGGGAC

TATTGGCGTTTAGCCAATGGAAGTATGAGGCGATAACAGGTCTGTGATGCCCTTAGATGTTCTGGGCCGCACGCGCG

CTACACTGACGCGACCAACGAGCCTATCCTTGGCCGAGAGGCCCGGGTAATCTTGTAAACCGCGTCGTGATGGGGAT

AGATTATTGCAATTATTAGTCTTCAACGAGGAATGCCTAGTAAGCGCGAGTCATCAGCTCGCGTTGATTACGTCCCT

GCCCTTTGTACACACCGCCCGTCGCTCCTACCGATTGGGTGTGCTGGTGAAGTGTTCGGATTGAGCTTGGCTGGGGC

AACCTGGCCTTGCTTGAGAAGTTCATTAAACCCTCCCACCTAGAGGAAGGAGAAGTCGTAACAAGGTTTCCGTAGGT

GAACCTGCGGAAGGATCATTGAATCTATCACAATCCACACCGCGAACTAACACTGTTGGCCTCCGTCTGTATAAAAG

CAAACGGGCCAGGTCTGGGCGCAATGTAAAAGTTACGCCTGGCCTGGGTTGCCGCAAGGCATCGGTCTCTTATACTA

ACCAACCAACACCAAACCAAAACTAAATTAAAACCGAGTATCTAGCTTAGAGCTAGTGCTCACTAACCAAGACAACT

CTCAACAACGGATATCTTGGCTCTCGGATCGATGAAGAACGCAGCGAAATGCGATACGTAGTGTGAATTGCAGAAAT

ACGTGAATCATCGAATCTTTGAACGCATATTGCGCTCGAGGCTTCGGCCAAGAGCATGTCTGCCTCAGCGTCGGGTT

AATACTCGCCCTACTCCAACATACACTTGTGTGTTTGGAGCAAGAGCGGACCTGGCTGTCTCGGTGTTTGATTTTCG

GATCAGACGCCGGGTCAGCTGAAGTACAGAGGTTGATGCATGGACCCGCTTATGGGCCTCTACTGGGTAGGCAACTC

GTTGCTAATGCTTTAGTAGATGGCTTGGAGCTGTGCTTGTCGACCCAAACCAGGAACTTTGGCCCTGTGCCGAAGCA

AACCCCTATTTTCTCGACCTGAGCTCAGGCAAGATTACCCGCTGAACTTAAGCATATCAATAAGCGGAGGAAAAGAA

ACTAACAAGGATTCCCCTAGTAACGGCGAGCGAACCGGGAATAGCCCAACTTGAAAATCTCCCTTTGGAGAATTGTA

GTCTAGAGAAGCGCTTTCTAGGGCTGGCGGAACTCAAGTCGGATCGAATGCCGCGTCAGAGAGGGTGATAACCCCGT

TABLE 6-continued

Sequences Corresponding to Frequency Peaks (SEQ ID NOs 21-167)

```
CGGTTCCTGCTTAGTCCTTCCACGAAGTGCTTTCCACGAGTCGGGTTGTTTGGGAATGCAGCCCTAATTTGGAGGTA

AATCCCTTCTAAGGCTAAATACTGCCGAGAGACCGATAGCGAACAAGTACCGTGAGGGAAAGATGAAAAGAACTTTG

AAAAGAGAGTTAAAAGTGCTTGAAATTGTTGAGAGGGAAGCGATTGGCGCTCGTAGGTGCGCCCAGGCTTAAGCGGT

CCTAACGGCCCGTTGAATGTGCTGGGTGCTGGTCAGAATGGGTTGAGTTGGCGGGACAAAAGCTGGGTCCACCCAGG

TAACCCGGCCGATGCCGCCGACTCGACCAAGGCGTAAAGAGTACCTTGTCCTTCGGGATCTGTGCTCTAAAGATTCT

GGCAGAAGAGCGTCAATCGACCCGTCTTGAAACACGGACCAAGGAGTCTAACATGTATGCGAGTTGGCGGGTGGAAA

ACCCGTAAGCGCAAGTAACCTGACTGGTGGGATGGGGTAAAACCCTGCACCATCGACCGACCATGTTGTTTCTACGA

AAGGTTTGAGTGCGAGCATACCTGTTGGGACCCGAAAGATGGTGAACTATGCCTGAGCAGGGTGAAGCCAGAGGAAA

CTCTGGTGGAGGCTCGTAGATGTGCTGACGTGCAAATCGCTTTTCAGACTTGGGTATAGGGGCGAAAGACTAATCGA

ACCATCTAGTAGCTGGTTCCCTCCGAAGTTTCCCCCAGGATAGCTGGAGCTTGATCAGTTTTATCGGGTAAAGCGAA

TGATTAGAGGTTCGGGGGGATGAAACATCCTTCACCTATTCTCAAACTTTAAATAGGTAAGACGTGTCGGTTGCTTA

ATTGAACCGGCACATTCAATGTGAGCTCCAAGTGGGCCATTTTTGGTAAGCAGAACTGGCGATGCGGGATGAACCGA

TAGTCGAGTTAAGGTGCCAAACTACGCGCTAACCTAGATCCCACAAAGGGTGTTGATTGATATAAACAGCAGGACGG

TGGTCATGGAAGTCGAAATCCGCTAAGGAGTGTGTAACAACTCACCTGCCGAATCAATTAGCCCCGAAAATGGATGG

CGCTTAAGCGCGTGACCTATACTCGGCCATGGAAGCAAGTGCGACGCTTCCATGAGTAGGAGGGCGTGGGTGTCGAG

ACTAAGCCTCTGGCGTGAGCCTGGGTGAATCGGCATCTAGTGCAGATCTTGGTGGTAGTAGCAAATATTCAAATGAG

AACTTTGAAGACTGAAGTGGAGAAAGGTTCCATGTGAACAGCAATTGGACATGGGTTAGTCGATCCTAAGAGATGGG

GTAATCCTGTGTGAAGAGCGCGATTCGCGCTGCCCATCGAAAGGGAAAAGGGTTAAGATTCCCTTACTTGGACAAGG

CGGCTGGCGGTAACGCAAGCGAGCCCGGAGACATCGGCATCGGCCCTGGGAAGAGTTCTCTTTTCTTTTTAACAACG

CGAAGGCCCTGGAATCGAATCATTCGGAGATAGGGCTCAGACGTTGGTAAAGCACCGCACTTCTCGCGGTGTCCGGC

GCGCCGTTGACGGTCCTTGAAAATCCGGGGGAGCATTCCCGATCTTGCCAAGTCGTACTCATAACCGCATCAGGTCT

CCAAGGTGAACAGCCTCTAGTCGATAGAACAATGTAGATAAGGGAAGTCGGCAAAATGGATCCGTAACTTCGGGAAA

AGGATTGGCTCTGAGGGCTGGGCCTAGGGGTCTGCAGCTGCGAAGCTCGGGACTGCGGTGGTCTACCCAGCTGGAAA

CGGCTGGGCGGACTGCTGCGTGTCCTGGGTGGACGGCTGTAGAAGCTTCGGCGTTCCCTAGGCGACGAACAGCCAAC

TCAGAACTGGTACGGACAAGGGGAATCCGACTGTTTAATTAAAACAAAGCATTGTGATGGTCCTAAAGGATGTTGAC

ACAATGTGATTTCTGCCCAGTGCTCTGAATGTCAAAGTGAAGAAATTCAACCAAGCGCGGGTAAACGGCGGGAGTAA

CTATGACTCTCTTAAGGTAGCCAAATGCCTCGTCATCTAATTAGTGACGCGCATGAATGGATTAACGAGATTCCCAC

TGTCCCTATCTACTATCTAGCGAAACCACAGCCAAGGGAACGGGCTTGGAATAAACAGCGGGGAAAGAAGACCCTGT

TGAGCTTGACTCTAGTCCGACTTTGTGAAATAACTTAAGAGGTGTAGAATAAGTGGGAGCTTCGGCGACGGTGAAAT

ACCACTACTTTTAACGTTGTTTTACTTATTCCATTACTTGGAGGCGGGACTCTGTCCCTGCTTCTAGCTCTAAGACG

GCTTTTGCACGTCGATCCAGGTGGAAGACATTGTCAGGTGGGAGTTTGGCTGGGCGGCACATCTGTTAAAAGATA

ACGCAGGTGTCCTAAGATGAGCTCAACGAGAACAGAAATCTCGTGTAGAACAAAAGGGTAAAAGCTCATTTGATTTT

GATTTTCAGTACGAATACAAACTGTGAAAGCATGGCCTATCGATCCTTTAGCCTTTCGGGATTTGAAGCTAGAGGTG

TCAGAAAAGTTACCACAGGGATAACTGGCTTGTGGCAGCCAAGCGTTCATAGCGACGTTGCTTTTTGATCCTTCGAT

GTCGGCTCTTCCTATCATTGTGAAGCAGCATTCACCAAGCGTTGGATTGTTCACCCACTAATAGGGAACGTGAGCTG

GGTTTAGACCGTCGTGAGACAGGTTAGTTTTACCCTACTGTTGGACCGATTCCGCCATAGTAATTCGGCTCAGTACG

AGAGGAACCGCCGAGTCAGATAATTGGTAATGCCCTTGTCTGAAAAGACAATGGGGCGAAGCTAACATCTGTAGTCT

AATGACTGAACGCCTCAAGTCAGAAGACGTGCTAGGTGCGGAGTCACTTACCCAATGATGTCACCCGACTAAGGAT

ACATCCGCCTGTGCGGATGCTGGAGCATACCCGTTGGTTCCCCTGTTAGGTCCACATGGCCGAAGCAGGCGCCAAGC
```

TABLE 6-continued

Sequences Corresponding to Frequency Peaks (SEQ ID NOs 21-167)

ATGACAATTCCACTCGTCATTGGGGTAAATCCTCTGTAGACGACTTTGTTGCAACTGGGTATTGTAAGTGGTAGAGT
GGCCTTGCTGCTACGATCCACTGAGATTCATCCCGTGTTGCTAAGATTTGTCACTGCCCTTCGGGGCAACCCCTCCT
CCTCTCGGAGCGACAGCTCCAGGGAGGGCCCTCTCTCTCTCTTCCAAGTGGTGTAGCTGAGCTGAGCGCGTGCCAAC
GCCGCCGAATCCGTCTAAGTGCCCACATGCGTGTGCATGCACTGCCCCTCCTCCCCCACACAGCCAAAGTGCTCAAG
GTACCTTCCCTGTGTGTGTGCGAGTGAGAGCAACAGCATGCATGTGCCCTTACTTAGGCGGCCTAGTGTGGTATGTG
TGTATGCGTGTGGCTTAGTGGCCAGTTCGACTCTGGCGTGAAGCAT

>SEQ ID NO: 70

CTTGATTCTGTGGGTGGTGGTGCATGGCCGTTCTTAGTTGGTGGGTTGCCTTGTCAGGTTGATTCCGGTAACGAACG
AGACCTCAGCCTGCTAAATAGTCAGCATCGCACCTGCGGTGCGCCGACTTCTTAGAGGGACTATTGGCGTTTAGCCA
ATGGAAGTATGAGGCGATAACAGGTCTGTGATGCCCTTAGATGTTCTGGGCCGCACGCGCGCTACACTGACGCGACC
AACGAGCCTATCCTTGGCCGAGAGGCCCGGGTAATCTTGTAAACCGCGTCGTGATGGGGATAGATTATTGCAATTAT
TAGTCTTCAACGAGGAATGCCTAGTAAGCGCGAGTCATCAGCTCGCGTTGATTACATCCCTGCCCTTTGTACACACC
GCCCGTCGCTCCTACCGATTGGGTGTGCTGGTGAAGTGTTCGGATTGAGCTTGGCTGGGGCAACCTGGCCTTGCTTG
AGAAGTTCATTAAACCCTCCCACCTAGAGGAAGGAGAAGTCGTAACAAGGTTTCCGTAGGTGAACCTGCGGAAGGAT
CATTGAATCTATCACAATCCACACCGCGAACTAACACTGTTGGCCTCCGTCTGTGTAAAAGCAAACGGGCCAGGTCT
GGGCGCAATGTAAAAGTTACGCCTGGCCTGGGTTGCCGCAAGGCATCGGTCTCTTATACTAACCAACCAACACCAAA
CCAAAACTAAATTAAAACCGAGTATCTAGCTTAGAGCTAGTGCTCACTAACCAAGACAACTCTCAACAACGGATATC
TTGGCTCTCGGATCGATGAAGAACGCAGCGAAATGCGATACGTAGTGTGAATTGCAGAAATACGTGAATCATCGAAT
CTTTGAACGCATATTGCGCTCGAGGCTTCGGCCAAGAGCATGTCTGCCTCAGCGTCGGGTTAATACTCGCCCTACTC
CAACATGTTTGGAGCAAGAGCGGACCTGGCTGTCTCGGTGTTTGATTTTCGGATCAGACGCCGGGTCAGCTGAAGTA
CAGAGGTTGATGCATGGACCCGCTTATGGGCCTCTACTGGGTAGGCAACTCGTTGCTAATGCTTTAGTAGATGGCTT
GGAGCTGTGCTTGTCGACCCAAACCAGGAACTTTGGCCCTGTGCCGAAGCAAACCCCTATTTTCTCGACCTGAGCTC
AGGCAAGATTACCCGCTGAACTTAAGCATATCAATAAGCGGAGGAAAAGAAACTAACAAGGATTCCCCTAGTAACGG
CGAGCGAACCGGGAATAGCCCAACTTGAAAATCTCCCTTTGGAGAATTGTAGTCTAGAGAAGCGCTTTCTAGGGCTG
GCGGAACTCAAGTCGGATCGAATGCCGCGTCAGAGAGGGTGATAACCCCGTCGGTTCCTGCTTAGTCCTTCCACGAA
GTGCTTTCCACGAGTCGGGTTGTTTGGGAATGCAGCCCTAATTTGGAGGTAAATCCCTTCTAAGGCTAAATACTGCC
GAGAGACCGATAGCGAACAAGTACCGTGAGGGAAAGATGAAAAGAACTTTGAAAAGAGAGTTAAAAGTGCTTGAAAT
TGTTGAGAGGGAAGCGATTGGCGCTCGTAGGTGCGCCCAGGCTTAAGCGGTCCTAACGGCCCGTTGAATGTGCTGGG
TGCTGGTCAGAATGGGTTGAGTTGGCGGGACAAAAGCTGGGTCCACCCAGGTAACCCGGCCGATGCCGCCGACTCGA
CCAAGGCGTAAAGAGTACCTTGTCCTTCGGGATCTGTGCTCTAAAGATTCTGGCAGAAGAGCGTCAATCGACCCGTC
TTGAAACACGGACCAAGGAGTCTAACATGTATGCGAGTTGGCGGGTGGAAAACCCGTAAGCGCAAGTAACCTGACTG
GTGGGATGGGTAAAACCCTGCACCATCGACCGACCATGTTGTTTCTACGAAAGGTTTGAGTGCGAGCATACCTGTT
GGGACCCGAAAGATGGTGAACTATGCCTGAGCAGGGTGAAGCCAGAGGAAACTCTGGTGGAGGCTCGTAGATGTGCT
GACGTGCAAATCGCTTTTCAGACTTGGGTATAGGGGCGAAAGACTAATCGAACCATCTAGTAGCTGGTTCCCTCCGA
AGTTTCCCCCAGGATAGCTGGAGCTTGATCAGTTTTATCGGGTAAAGCGAATGATTAGAGGTTCGGGGGATGAAACA
TCCTTCACCTATTCTCAAACTTTAAATAGGTAAGACGTGTCGGTTGCTTAATTGAACCGGCACATTCAATGTGAGCT
CCAAGTGGGCCATTTTTGGTAAGCAGAACTGGCGATGCGGGATGAACCGATAGTCGAGTTAAGGTGCCAAACTACGC
GCTAACCTAGATCCCACAAAGGGTGTTGATTGATATAAACAGCAGGACGGTGGTCATGGAAATCGAAATCCGCTAAG
GAGTGTGTAACAACTCACCTGCCGAATCAATTAGCCCCGAAAATGGATGGCGCTTAAGCGCGTGACCTATACTCGGC

TABLE 6-continued

Sequences Corresponding to Frequency Peaks (SEQ ID NOs 21-167)

CATGGAAGCAAGTGCGACGCTTCCATGAGTAGGAGGGCGTGGGTGTCGAGACTAAGCCTCTGGCGTGAGCCTGGGTG

AATCGGCATCTAGTGCAGATCTTGGTGGTAGTAGCAAATATTCAAATGAGAACTTTGAAGACTGAAGTGGAGAAAGG

TTCCATGTGAACAGCAATGGACATGGTTAGTCGATCCTAAGAGAT

>SEQ ID NO: 71

CGGGCCTTGTCTGCCCGCGCCTGAGCTGCCTCCTCTTCAGCGTGGACCCGCCGCAGCTCTGCCTCCATCTCCGCTGA

CAGGGCTGGCGGTGGGATGGGAATGGTCTTGTCCTCACTCCACGCGCCAGCTGTGGGGTGGCATGAGGTCAGGTTGG

AGATGAGGTAAGGTGAGGAGTGGTTGCCATGGGACAGGGTAAGGGGCAAGTGTGTGGCGTACACGTGTCCCGTGGTG

TGCACATCGGAGGTGTTGCGTCCGGACCCCAAGCCTACCCTTCTTCTCATGTTGATCCCCCTCCGCCTTCTCGAAGT

AATTGGAGCCATTGCGGTTGAACTGAGCCTGCAACCGCGTCATGCACCTGTTTGACAATGGCCACCATGAAAGGCCC

TGGCGGGATGCAGGCCTGCAGGCGGTGCCGTATGGCGGTTTCTCGGGCAAGGCGGAGGCGTCCAGCTTGCCGCCCAA

GCTGTCACGGATCACAGTCCAACTCCTGTAATCTGATGTGAGATTTAGTGAGCAATACTCCTCCTGCGGCTGAAGGC

CCACGAGGGCAGCGGCAAATTTACATCTGCAGCCGCGCTGGAGCAGGGTGGGCCCGCTGCTGCTGCCGCTGCTGCT

GCTCGCCCCGATCTCTTGCTGCTGCGCGCAGATGCTTGCATTGCGCTATGGTAGCATAATGGTAGCAAAAAAAGGAG

TGGACAGAAGAGGAGTGACGAGCGCAGTCGGGAAAGGCGAATTTTTTAAAATTGTTGATACCAGCGCACGGCTTGGT

TTATTATCATGAACTGCAATCGCACTGAAAGAACAAAAGTTGTAGCTGACAAGACGCAAAATATTGATACTAACCGC

GACCTGGTGGGCGAAAATTGGGCAAACGGTCGCCCCATTCCCACAACCGTGGTGTTGCGTCCGGACCCCAAGCCTAC

CCTTCTTCTCATGTTGATCCCCCTCCGCCTTCTCGAAGTAATTGGAGCCATTGCGGTTGAACTGAGCCTGCAACCGC

GTCATGCACCTGTTTGACAATGGCCACCATGAAAGGCCCGGGCGGGTGATAGATGTCAGCGCATTCCCACAACCGCA

GCCACGGCGAAATAAAAGGCCGCCCCTCCCATTACTTGCTAACCCAATACCTATCATAACAACTTTTAAGAGCACGC

CAATCTACTGTGCAAGCAAGTTATTAGCGCCGAGCAAACCGTATGGAGTCCGGTTGGCAACGCGAAACAGCCCCGCG

AGCAGGGCTGCAGCGCGGTAACTTATTGGTAAGCTAAACCAATATGTTTTACAAGCGCCGCTATTGCTGCTTAGCTT

TCTTGTTGCAACACGCGGTTGCATGCCATGCAAATGTCAACAGTGCCGCTGAAACCTGAGCGCGAATACCTTGCGGG

CGCTGCCATAACCCTCTTCAGCATTGAAAAGAACTTACAGCATGACACCGGCTGCAAAATCCACTACAGGGCCAGCC

AGCCCAATGTCCAAGGGGCTCGGGTCGACCGTTGGCCCGCTCCGCCGCCACAGGGGGCGCCGCGCCGGCCTCGTCG

TCCTTCGAAGGGTGAGTGCTAGGGCTCCGCTGGTCAGGCATCACAGTGTTTGCATTGCCTAGCAAACGTATGCACGT

TCCAGGTGGACAGTGCGAAGGGGGCAGCAAACTTTGGTAGAACAGGCAGTGGGAGGGGCCCTCGTGGCCACGGCCA

GGACTCCTGCCCCTCCCTGGTCCGCCCCAGCGGCTGGAACGGAGCCTCGTCCTCTCCACGGATCCTAGACAGCAAAA

TACCGCACTGCACGCATTCAGAAGGGGTCCCATCCAAACCCTACCCAAAACCCGTGTCAAGGGGTTTCCAAGCGTGC

GAACGGATGCCTGTCCGTATGGGCTCTTATCCGTTACGTGCAGCACTAGGGGCTGGGTGGGAGGGGTGGGCTGGG

TCAGCTGGGCCGGCT

>SEQ ID NO: 72

CCACACCAAAGTACGCACAGTTAAGCTCACACCAGTACACAGCCGAGGCATTCTTGTAAATTACTCTGTCCTTACCC

ATACCTTCACTGCGGCCATTGGTTGAGTAGGTTCCTAGGGTAATGTGGGTGTTGTTGATGCAGTTCTTCTCCTCACA

CGTATGCTGCACACACACGACTCTCCTGCTTCCGCGACCCCTCCTCACGCAGCGGGTGGAATTGTCCAGTTGTCC

GCTCCAGCGTGGGCTCACCATGAACAACAAAAGCTATCAGCCTGTGCACCGACCACGTAACCCTGGACCACTCTCTC

TCACTCCCAGCGGGGTTGGCCGTATGCCCCACCAGCACGGCTGGGTAACCCCCACCGCCCTGGAACACACAAGTACC

ACCACGCCCCACACGATGGACTGGATTCAAGTAAGGCACCACGTGAATCATGTCCGCTCCCACGCCCAGCTCAACGG

TCGCGCTGCTAAACTCTGCAATGTACTGGCCACCCTGAGCAGCGGGCTTCCTCTCAGTACACACCGTGGGGATGCGC

CCCTGTGGCCACACCTCCAGCCCGTAGCGGGTCCGCTCTGACACCAACGGCACGCACAGCGTGTGAAATGGCTTATC

TABLE 6-continued

Sequences Corresponding to Frequency Peaks (SEQ ID NOs 21-167)

ATACACAATCCCATGGTTTCGCATAAAGCCATGCATGGCCTGCACATGCTCGCGGATGGGTTGCGGGCCCTGGTTGG

GTCCCACATGTGCTGGCAGGTACCGCTCCTTCCCTGCCCACTTGGGTGCCGTGGGGTCCACCGGCAGCTGATCAGGT

GGGCCGTCAACACCACCTACTGGAAACACAGCCAGCACATACAGTGTAATCAGGGCATTTGCCGCCACGGAAACAGG

CACTCTGAGTTCTACGCTCCATGATCTCACCAAGTCAGTGAATGCTTGGAGGTCATGAGCAGGCACCACACGAAATT

TGGGGTAAACATGCGTGCCAATGTTGGCCAGTGCAAGAAAGAATGAACGTGCCGCTGCATAGCCATAATCCTTACGC

ACGTCGGCAGGAATGCGACTGTCAGCACACCTCTTGCCAAAGTTCTGCGCCACCTGCTTCAGGTCCACAGAGAACAG

GCCACCCACACCAAGTGCCTGCTCCTCCCTGGCCTCGCTATCCCTATGCAGTCCACACACAGTCCTCAGCGCCTGGG

GATAGAATAACTGCATCACATCAACAAATGCAAACCCCTGTACCTCAGCCTGCAGGGTATCTATCTTCGCAATCTGC

TTAGGCAACCGAGGATCCTGTGCCTCCCTAAAGGCCTTGTGCAGGCGACGCAGCCCCAGGAGCTTTGCAGGGCCCAC

ACGCGCCAGCTTCTCAAGCTGTGCTGCCGTGAATGGAACCTCAGGGTCCTCTGCGTCTGCCCAGAGGTCCGCTTCCG

GATTGTTGGTCGCCATTGACTACTAGGAGGGCTGGGGTGGGGGGGGGGAGAGGTTGGGCTGGGGTTGGGGCGTGCT

GCCGCACCGTGCCACCCACCCACCCACCCCCTTCTCCTCCTCCTCCTCCCTGGCTGGCTGTTGACGACACGTTGCTA

CACAACCAGCTGTGTGCTATACGTGGCGTTACGAGTACTGTAGTTTGGGGGGCAGCGCGTGGTGGGGCGGAGATCCT

GCGGCCGGAGGGCGGGCAGGAAGGCAGGGAGGGTGGGGGCCACAGGAGGTCAGGACACACACCAAGGGTAGCCCCAA

GGAAAGGACCCGCCGCGCATGGCTATAAGCATATTTCACAGCGACTTTCGGCGCAGGCAGTCTGTGTACATGTCCCC

TAGTAGGCTAGTGCGGGCGCCGGGGTGAATACGGTTTGTCTTCGAGGCCTCGGCCACCTACGAAGCCACAGGGGGCC

CGGCGCCGGGCGTGCCGCAAGCACCCCCCACACCGGCTGAGACCGGTGGTCCTCCAGAGTCCAATTCGCCGCAACCT

CTCCATGCCACATTACGAAGAGGTCACTTCAGTAAGCCCAGGAACTCACCGCAGGTTAAAGCGACGACGTATGAAAA

ATCCCGGCGATGGAGAAGCCGACGGTCAACGAGTAGTTGTTTCTTCTCGCTGGGATTCACTCGACAAGGCCCAGCAT

AGTATCCCAGTAGGCGCCCGGGCGTGGCCGGCAGGCGCAACAAAGATAGCCTTGAAGCCCTCAGCGCACAGACTCCT

CGCAGAAGCAGCACTGACAATATGCTAAGAAGCTAAATATAAGGGATAGAGAACAAGAACAGGGCCTGGAAACGCCG

GGTGGGAACAACGGTGTTGGGCCATCGGCGCCGCGCATACTACCACGGTATGGTTGCTAGCAAAGCGGTTATGTACT

TGCAAGCAAAGTAGTATGTAGTATCTAAAGACAGGTGTCCAGGGTGGGGCGGCTTGCAAAACCAAGTCTTAGTGCGA

TGCGCCGCGCGCAGAGAAAAGGCGCGCCCGCGGTCGGACGCACCGGGCGGGGCCCCACCTGTGAACTCAACCCCC

GGCCAAGCCAGCCCTGCATTTCTCAAAGAAATCTATTGTTTGCACTGGCGCCCGCGCTTGTAACCGTTTGTAGTACA

GAAATTTCACCCCATTTTGGGAGTGTGTATTCACCCCTTGGAAAGCGCCCGCACCCAGGCCACCGGAACGCAGCACA

GACGCGCAGCGGAGACCCCGCCCCCAGCCCAGAATTGCTATACTACACCAGCATGAGGCGTCTATGCGGGGGGGCGC

GGGGGAATCACAGGGGAACGTCAAGTCCGGAGGGGTGCCTGGGGGCCACTTCGGCTGGTGACCAAGGGCTGGCCAAG

GGGTGGCAGGGGGGACGACAAGGGGTCCATACACACGCAATTCGCTGACCGCTGGCGTCATTTGGCACACTGATGAC

ATGACTACATATATGATGACATTTGGG

>SEQ ID NO: 73

GTGGTCTGGAATGCAGCGAATTGGCCAGCTGATAAATTACATGTTTAAATGATCAGTTGTATTATATATTTGCATCG

AGTCACCAGGTAAACACTGCACTGACTTAGCGAACTCGCTCCGGACTTCGCCGTCCCCCTCTCCCCTCCTGCTCTCC

CCCCCCGGCGCGGCCGCATGCCCTCGCACGCCTCTTCCCTCATCGCTTCTACCGCCCCGCGCCCGCGCAAACCCTT

CATTACTTCATAATCAAATGCTTAATCATAGGCACAGTATGTTCTTGACACTTTGCAATGCATCATGAATGAATGT

GGGCACACACGCCTCTGCCTCTGCCTCTGCCTCTGCCGCTGCCTCTGCCGCTGCCTCCGCCTCAACTCCACTCCACT

CCCTTCCTGCCTGCCTGCCTCCTCCTCCTTCTCTGCTGCTACAGAACATCTTGCTCGCTCGCTACGAGAAGCCAAAC

CTCTGGGGCGGCCTCCTGTCCCTCTCTCCCTTGCCCTCTGCGACAGACAGCTTATACTTCCGCGCCTCCTCCGCCAG

CGCCGCCTGGTACAGCGCGTGCATCCACTCAATGCGCGGGGGACGGGCAGGTGCGGCTGGTGGACGTAGGGGCGT

TABLE 6-continued

Sequences Corresponding to Frequency Peaks (SEQ ID NOs 21-167)

AGTCCACCAGCTTCTCCTCCGGCAGCTCCCTGTACACTGCGCCGGGCTTCTTGAACACCCACACTTGCTTCTGGGAG

TTGCTGCCGTACATGCGCACAGCAAACTGCTTCACCAGCTCCAGTGGCCCAAACCCGTGCTGTCCTAGCTGCCGCTC

CATGAGCACTCCTGCTCCTTTGTCCACGACCGCAATGCCCACGGTTGTGGACGAGGCCGCAAACATGGCCCCCAGCG

CATCCTTTGCTGAGGCGGGGATGCCCTGCCAGAACGTGAACACGTGCGTGACGCCCTCCAGGCCTTGGGGTACCTTG

GCCATGTCCTGTTCGAGGGGCAGAGCAGAGAGGGAGGGCAGGGAAGAAGGGAGGATGTGTGTACGTGTGTGGGGGGA

AGGGAGGAAGGGGGAGAAGGGGGAGGCGTGGGGCAGGTACCCACGCCAGCTCCACACACCCCACACACCCCATACAC

CCACGCACCCACGCACCCACCCGCCCACCCACGCACCCACCCCACCACACACCCCACCTCCATTGTCATGGCGAAGA

CAGCAGGTCGCCGCGCCAGGAACTGGGCAGTCACATTCACGCCCTTGCTCTTGATGAACTCCACGAACATGCGCATG

AACTTGATGGCCTTGTCCACCCTGGACGGGCAGGAGTCGTTGCCGTACGCGTATGCGCACAGGCCCCGAGTGAAGGC

CGCCACCAGTGGCCTGCCCAGGCCCACACCAGCATCAAACATCACAGGCCAGGCAAAGGCGCCGCTCAGGATGCCGA

ACAGCACCAAGAAGATCTGCATGGTGCAGGCAGCGTTGATGGTGCCGTAGAAGCCCGTCCCAGTGATGGTCTCGCCG

CCACCGACGTTGTTCTGTTTGGGAAGTGAGGGAGTCATTGGATGGGGAGTGAGGAGTGGATGATGGGTGAGGGGAGG

GGAGGGCACAGCGTTGGGGTGGGGTGGGGTGGGGTGGGGTGGGGAGGGCGGGCAGGTGGGCAGGCGGGGCGGGCAGG

AAAGGTGACAAGACACTGACACAGACGACAACAGCATACTCACTTCCCCAGGGTTCAGGGCGGCGTCGATGTGCTGA

GACTCAACCAGCCGAGGGAACGAAGGCTCAACAGCACCCGGCGCTGCTGCTGCTGCTGCCGCTGCTGTGGTCTC

CCCACCCTCCTCCGTGGCCTCCGTGGCTGCCGTGCCCCCCTCCTCCGCCGCTGCCTCCTCCTCCTCCTCCTCCTCCT

CTGCTGCTGCTGCCTCGTGCTTCAGGTCGTAGAACACATCGGCTGCGTCAGCAACCTCTGCCTGGGACATGCTACCC

TCGAACAGCTGGCTGCTGGGGTCCAGAGGCAGCGGTGGCGGCGGCAGCAGCACCTGTGGTGGTGGTAGGCACGCCGC

CGCCTCATCACCACTCCCTCCCTCCTCCTTACCCTCCCCACCCGACGCCTCCTCCTCCCCCTCCTCTTCCCGCTGCT

GTGGCGGCGCCTGCTGCGACAGCCCTGGGGATAGGGGCTGGGAGCCATGAAGCCCCGCCGCCATCGGGTTCCCCCCT

GCTGCTGCAAACCCAGCAGCCACACCAAGCCCCTGCTGCTGAGTCTGCAGCAAGTTAGTGGCACTGCCGCTGCACCG

CAGCGAGCCACCCGCACACCTGCTACTGACCCCAGCCGACGCCGCCAGCGCCTCAGGCGACACACTGCCTCCCGA

>SEQ ID NO: 74

TCGCCGATGCTGGTGTGGCTGCTGCCCGCCTGGGCTGCCTCCCCTTCAGCGCGGGCCTTGTCTGCCCGCGCCTGAGC

TGCCTCCTCTTCAGCGTGGACCCGCCGCAGCTCTGCCTCCATCTCCGCTGACAGGGCTGGCGGTGGGATGGGAATGG

TCTTGTCCTCACTCCACGCGCCAGCTGTGGGGTGGCATGAGGTCAGGTTGGAGATGAGGTAAGGTGAGGAGTGGTTG

CCATGGGACAGGGTAAGGGGCAAGTGTGTGGCGTACACGTGTCCCGTGGTGTGCACATCGGAGGTGTTGCGTCCGGA

CCCCAAGCCTACCCTTCTTCTCATGTTGATCCCCCTCCGCCTTCTCGAAGTAATTGGAGCCATTGCGGTTGAACTGA

GCCTGCAACCGCGTCATGCACCTGTTTGACAATGGCCACCATGAAAGGCCCTGGCGGGATGCAGGCCTGCAGGCGGT

GCCGTATGGCGGTTTCTCGGGCAAGGCGGAGGCGTCCAGCTTGCCGCCCAAGCTGTCACGGATCACAGTCCAACTCC

TGTAATCTGATGTGAGATTTAGTGAGCAATACTCCTCCTGCGGCTGAAGGCCCACGAGGGCAGCGGCAAATTTACAT

CTGCAGCCGCGCTGGAGCAGGGTGGGCCCGCTGCTGCTGCCGCTGCTGCTCCTCGCCCCGATCTCTTGCTGCTGCG

CGCAGATGCTTGCATTGCGCTATGGTAGCATAATGGTAGCAAAAAAAGGAGTGGACAGAAGAGGAGTGACGAGCGCA

GTCGGGAAAGGCGAATTTTTTAAAATTGTTGATACCAGCGCACGGCTTGGTTTATTATCATGAACTGCAATCGCACT

GAAAGAACAAAAGTTGTAGCTGACAAGACGCAAAATATTGATACTAACCGCGACCTGGTGGGCGAAAATTGGGCAAA

CGGTCGCCCCATTCCCACAACCGTGGTGTTGCGTCCGGACCCCAAGCCTACCCTTCTTCTCATGTTGATCCCCCTCC

GCCTTCTCGAAGTAATTGGAGCCATTGCGGTTGAACTGAGCCTGCAACCGCGTCATGCACCTGTTTGACAATGGCCA

CCATGAAAGGCCCGGGCGGGTGATAGATGTCAGCGCATTCCCACAACCGCAGCCACGGCGAAATAAAAGGCCGCCCC

TCCCATTACTTGCTAACCCAATACCTATCATAACAACTTTTAAGAGCACGCCAATCTACTGTGCAAGCAAGTTATTA

TABLE 6-continued

Sequences Corresponding to Frequency Peaks (SEQ ID NOs 21-167)

GCGCCGAGCAAACCGTATGGAGTCCGGTTGGCAACGCGAAACAGCCCCGCGAGCAGGGCTGCAGCGCGGTAACTTAT
TGGTAAGCTAAACCAATATGTTTTACAAGCGCCGCTATTGCTGCTTAGCTTTCTTGTTGCAACACGCGGTTGCATGC
CATGCAAATGTCAACAGTGCCGCTGAAACCTGAGCGCGAATACCTTGCGGGCGCTGCCATAACCCTCTTCAGCATTG
AAAAGAACTTACAGCATGACACCGGCTGCAAAATCCACTACAGGGCCAGCCAGCCCAATGTCCAAGGGGCTCGGGTC
GACCGTTGGCCCGCTCCGCCGCCACAGGGGGGCGCCGCGCCGGCCTCGTCGTCCTTCGAAGGGTGAGTGCTAGGGCT
CCGCTGGTCAGGCATCACAGTGTTTGCATTGCCTAGCAAACGTATGCACGTTCCAGGTGGACAGTGCGAAGGGGCA
GCAAACTTTGGTAGAACAGGCAGTGGGAGGGGCCCTCGTGGCCACGGCCAGGACTCCTGCCCCTCCCTGGTCCGCC
CCAGCGGCTGGAACGGAGCCTCGTCCTCTCCACGGATCCTAGACAGCAAAATACCGCACTGCACGCATTCAGAAGGG
GTCCCATCCAAACCCTACCCAAAACCCGTGTCAAGGGGTTTCCAAGCGTGCGAACGGATGCCTGTCCGTATGGGCTC
TTATCCGTTACGTGCAGCACTAGGGGCTGGGTGGGAGGGGTGGGCTGGGTCAGCTGGGCCGGCTGGGT

>SEQ ID NO: 75

GCTGCTGCTGCTGTTGCTGCTGCTTCTGCTGCTGCTGCTAATGGTGGTGCTGCGGGCGTTGGAGCTGGTGGTGGTAG
CGCTGGAGCTGGTGGCTCTGGCTGGCGTGTGATGGGCACAGAGATGGTGCCGGTGGGTGTGGGAGCGGCAGGGGTAA
AACGCCCCTCGGATGTGTGGGGTGGTGGTGGCGCTTATGGTGGTGGTGGTGGTGGTGGCGCTTATGGTGGCGGTGGT
GGCGCTTATGGTGGCGGTGGTGGCACTGGTGGTGGTGGCGCTGGTGGTGGTGGTGGTGGTGGTGGTGGGAAGAC
GAGGAAGAAGAGCAAGGTGGCGAAGCAGCCGTTCCAGCCGTTCTGAGCTTGTCTGTTACATGTTGATTGCAAGCAGC
GGCGGCATTAGGCCATAGTCTGCCAGGAATTAAATGATTAATTGGCATTGGCAGCAGGTGGGAGTAGGTCATGCTGG
TCCACTGCTGTGAGACGCACGGCAACACCCGCCAGTGGGCGGGCGTCTCCCACACCAAAGTACGCACAGTTAAGCTC
ACACCAGTACACAGCCGAGGCATTCTTGTAAATTACTCTGTCCTTACCCATACCTTCACTGCGGCCATTGGTTGAGT
AGGTTCCTAGGGTAATGTGGGTGTTGTTGATGCAGTTCTTCTCCTCACACGTATGCTGCACACACACACGACTCTCC
TGCTTCCGCGACCCCTCCTCACGCAGCGGGTGGAATTGTCCAGTTGTCCGCTCCAGCGTGGGCTCACCATGAACAAC
AAAAGCTATCAGCCTGTGCACCGACCACGTAACCCTGGACCACTCTCTCTCACTCCCAGCGGGGTTGGCCGTATGCC
CCACCAGCACGGCTGGGTAACCCCCACCGCCCTGGAACACACAAGTACCACCACGCCCCACACGATGGACTGGATTC
AAGTAAGGCACCACGTGAATCATGTCCGCTCCCACGCCCAGCTCAACGGTCGCGCTGCTAAACTCTGCAATGTACTG
GCCACCCTGAGCAGCGGGCTTCCTCTCAGTACACACCGTGGGGATGCGCCCCTGTGGCCACACCTCCAGCCCGTAGC
GGGTCCGCTCTGACACCAACGGCACGCACAGCGTGTGAAATGGCTTATCATACACAATCCCATGGTTTCGCATAAAG
CCATGCATGGCCTGCACATGCTCGCGGATGGGTTGCGGGCCCTGGTTGGGTCCCACATGTGCTGGCAGGTACCGCTC
CTTCCCTGCCCACTTGGGTGCCGTGGGGTCCACCGGCAGCTGATCAGGTGGGCCGTCAACACCACCTACTGGAAACA
CAGCCAGCACATACAGTGTAATCAGGGCATTTGCCGCCACGGAAACAGGCACTCTGAGTTCTACGCTCCATGATCTC
ACCAAGTCAGTGAATGCTTGGAGGTCATGAGCAGGCACCACACGAAATTTGGGGTAAACATGCGTGCCAATGTTGGC
CAGTGCAAGAAAGAATGAACGTGCCGCTGCATAGCCATAATCCTTACGCACGTCGGCAGGAATGCGACTGTCAGCAC
ACCTCTTGCCAAAGTTCTGCGCCACCTGCTTCAGGTCCACAGAGAACAGGCCACCCACACCAAGTGCCTGCTCCTCC
CTGGCCTCGCTATCCCTATGCAGTCCACACACAGTCCTCAGCGCCTGGGGATAGAATAACTGCATCACATCAACAAA
TGCAAACCCCTGTACCTCAGCCTGCAGGGTATCTATCTTCGCAATCTGCTTAGGCAACCGAGGATCCTGTGCCTCCC
TAAAGGCCTTGTGCAGGCGACGCAGCCCCAGGAGCTTTGCAGGGCCCACACGCGCCAGCTTCTCAAGCTGTGCTGCC
GTGAATGGAACCTCAGGGTCCTCTGCGTCTGCCCAGAGGTCCGCTTCCGGATTGTTGGTCGCCATTGACTACTAGGA
GGGCTGGGGTGGGGGGGGGGAGAGGTTGGGCTGGGGTTGGGGCGTGCTGCCGCACCGTGCCACCCACCCACCC

TABLE 6-continued

Sequences Corresponding to Frequency Peaks (SEQ ID NOs 21-167)

>SEQ ID NO: 76

GTGGTCTGGAATGCAGCGAATTGGCCAGCTGATAAATTACATGTTTAAATGATCAGTTGTATTATATATTTGCATCG
AGTCACCAGGTAAACACTGCACTGACTTAGCGAACTCGCTCCGGACTTCGCCGTCCCCCTCTCCCCTCCTGCTCTCC
CCCCCCGGCGCGGCCGCATGCCCTCGCACGCCTCTTCCCTCATCGCTTCTACCGCCCCGCGCCCGCGCAAACCCTT
CATTACTTCATAATCAAAATGCTTAATCATAGGCACAGTATGTTCTTGACACTTTGCAATGCATCATGAATGAATGT
GGGCACACACGCCTCTGCCTCTGCCTCTGCCGCTGCCTCTGCCGCTGCCTCCGCCTCAACTCCACTCCACTCCCTTC
CTGCCTGCCTGCCTCCTCCTCCTTCTCTGCTGCTACAGAACATCTTGCTCGCTCGCTACGAGAAGCCAAACCTCTGG
GGCGGCCTCCTGTCCCTCTCTCCCTTGCCCTCTGCGACAGACAGCTTATACTTCCGCGCCTCCTCCGCCAGCGCCGC
CTGGTACAGCGCGTGCATCCACTCAATGCGCGGGGGGACGGGCAGGTGCGGCTGGTGGACGTAGGGGGCGTAGTCCA
CCAGCTTCTCCTCCGGCAGCTCCCTGTACACTGCGCCGGGCTTCTTGAACACCCACACTTGCTTCTGGGAGTTGCTG
CCGTACATGCGCACAGCAAACTGCTTCACCAGCTCCAGTGGCCCAAACCCGTGCTGTCCTAGCTGCCGCTCCATGAG
CACTCCTGCTCCTTTGTCCACGACCGCAATGCCCACGGTTGTGGACGAGGCCGCAAACATGGCCCCCAGCGCATCCT
TTGCTGAGGCGGGGATGCCCTGCCAGAACGTGAACACGTGCGTGACGCCCTCCAGGCCTTGGGGTACCTTGGCCATG
TCCTGTTCGAGGGGCAGAGCAGAGAGGGAGGGCAGGGAAGAAGGGAGGATGTGTGTACGTGTGTGGGGGGAAGGGAG
GAAGGGGAGAAGGGGGAGGCGTGGGGCAGGTACCCACGCCAGCTCCACACACCCCACACACCCCATACACCCACGC
ACCCACGCACCCACCCGCCCACCCACGCACCCACCCCACCACACACCCCACCTCCATTGTCATGGCGAAGACAGCAG
GTCGCCGCGCCAGGAACTGGGCAGTCACATTCACGCCCTTGCTCTTGATGAACTCCACGAACATGCGCATGAACTTG
ATGGCCTTGTCCACCCTGGACGGGCAGGAGTCGTTGCCGTACGCGTATGCGCACAGGCCCCGAGTGAAGGCCGCCAC
CAGTGGCCTGCCCAGGCCCACACCAGCATCAAACATCACAGGCCAGGCAAAGGCGCCGCTCAGGATGCCGAACAGCA
CCAAGAAGATCTGCATGGTGCAGGCAGCGTTGATGGTGCCGTAGAAGCCCGTCCCAGTGATGGTCTCGCCGCCACCG
ACGTTGTTCTGTTTGGGAAGTGAGGGAGTCATTGGATGGGGAGTGAGGAGTGGATGATGGGTGAGGGGAGGGGAGGG
CACAGCGTTGGGGTGGGGTGGGGTGGGGTGGGGTGGGAGGGCGGGCAGGTGGGCAGGCGGGGCGGGCAGGAAAGGT
GACAAGACACTGACACAGACGACAACAGCATACTCACTTCCCCAGGGTTCAGGGCGGCGTCGATGTGCTGAGACTCA
ACCAGCCGAGGGAACGAAGGCTCAACAGCACCCGGCGCTGCTGCTGCTGCTGCCGCTGCTGTGGTCTCCCCACC
CTCCTCCGTGGCCTCCGTGGCTGCCGTGCCCCCTCCTCCGCCGCTGCCTCCTCCTCCTCCTCCTCCTCTGCTG
CTGCTGCCTCGTGCTTCAGGTCGTAGAACACATCGGCTGCGTCAGCAACCTCTGCCTGGGACATGCTACCCTCGAAC
AGCTGGCTGCTGGGGTCCAGAGGCAGCGGTGGCGGCGGCAGCAGCACCTGTGGTGGTGGTAGGCACGCCGCCGCCTC
ATCACCACTCCCTCCCTCCTCCTTACCCTCCCCACCCGACGCCTCCTCCTCCCCCTCCTCTTCCCGCTGCTGTGGCG
GCGCCTGCTGCGACAGCCCTGGGGATAGGGGCTGGGAGCCATGAAGCCCGCCGCCATCGGGTTCCCCCCTGCTGCT
GCAAACCCAGCAGCCACACCAAGCCCCTGCTGCTGAGTCTGCAGCAAGTTAGTGGCACTGCCGCTGCACCGCAGCGA
GCCACCCGCACACCTGCTACTGACCCCAGCCGACGCCGCCAGCGCCTCAGGCGACACACTGCCTCCCGA

>SEQ ID NO: 77

TCGCCGATGCTGGTGTGGCTGCTGCCCGCCTGGGCTGCCTCCCCTTCAGCGCGGGCCTTGTCTGCCCGCGCCTGAGC
TGCCTCCTCTTCAGCGTGGACCCGCCGCAGCTCTGCCTCCATCTCCGCTGACAGGGCTGGCGGTGGGATGGGAATGG
TCTTGTCCTCACTCCACGCGCCAGCTGTGGGGTGGCATGAGGTCAGGTTGGAGATGAGGTAAGGTGAGGAGTGGTTG
CCATGGGACAGGGTAAGGGGCAAGTGTGTGGCGTACACGTGTCCCGTGGTGTGCACATCGGAGGTGTTGCGTCCGGA
CCCCAAGCCTACCCTTCTTCTCATGTTGATCCCCCTCCGCCTTCTCGAAGTAATTGGAGCCATTGCGGTTGAACTGA
GCCTGCAACGCGTCATGCACCTGTTTGACAATGGCCACCATGAAAGGCCCTGGCGGGATGCAGGCCTGCAGGCGGT
GCCGTATGGCGGTTTCTCGGGCAAGGCGGAGGCGTCCAGCTTGCCGCCCAAGCTGTCACGGATCACAGTCCAACTCC

TABLE 6-continued

Sequences Corresponding to Frequency Peaks (SEQ ID NOs 21-167)

TGTAATCTGATGTGAGATTTAGTGAGCAATACTCCTCCTGCGGCTGAAGGCCCACGAGGGCAGCGGCAAATTTACAT

CTGCAGCCGCGCTGGAGCAGGGTGGGGCCCGCTGCTGCTGCCGCTGCTGCTCCTCGCCCCGATCTCTTGCTGCTGCG

CGCAGATGCTTGCATTGCGCTATGGTAGCATAATGGTAGCAAAAAAAGGAGTGGACAGAAGAGGAGTGACGAGCGCA

GTCGGGAAAGGCGAATTTTTTAAAATTGTTGATACCAGCGCACGGCTTGGTTTATTATCATGAACTGCAATCGCACT

GAAAGAACAAAAGTTGTAGCTGACAAGACGCAAAATATTGATACTAACCGCGACCTGGTGGGCGAAAATTGGGCAAA

CGGTCGCCCCATTCCCACAACCGTGGTGTTGCGTCCGGACCCCAAGCCTACCCTTCTTCTCATGTTGATCCCCCTCC

GCCTTCTCGAAGTAATTGGAGCCATTGCGGTTGAACTGAGCCTGCAACCGCGTCATGCACCTGTTTGACAATGGCCA

CCATGAAAGGCCCGGGCGGGTGATAGATGTCAGCGCATTCCCACAACCGCAGCCACGGCGAAATAAAAGGCCGCCCC

TCCCATTACTTGCTAACCCAATACCTATCATAACAACTTTTAAGAGCACGCCAATCTACTGTGCAAGCAAGTTATTA

GCGCCGAGCAAACCGTATGGAGTCCGGTTGGCAACGCGAAACAGCCCCGCGAGCAGGGCTGCAGCGCGGTAACTTAT

TGGTAAGCTAAACCAATATGTTTTACAAGCGCCGCTATTGCTGCTTAGCTTTCTTGTTGCAACACGCGGTTGCATGC

CATGCAAATGTCAACAGTGCCGCTGAAACCTGAGCGCGAATACCTTGCGGGCGCTGCCATAACCCTCTTCAGCATTG

AAAAGAACTTACAGCATGACACCGGCTGCAAAATCCACTACAGGGCCAGCCAGCCCAATGTCCAAGGGGCTCGGGTC

GACCGTTGGCCCGCTCCGCCGCCACAGGGGGGCGCCGCGCCGGCCTCGTCGTCCTTCGAAGGGTGAGTGCTAGGGCT

CCGCTGGTCAGGCATCACAGTGTTTGCATTGCCTAGCAAACGTATGCACGTTCCAGGTGGACAGTGCGAAGGGGCA

GCAAACTTTGGTAGAACAGGCAGTGGGAGGGGCCCTCGTGGCCACGGCCAGGACTCCTGCCCCTCCCTGGTCCGCC

CCAGCGGCTGGAACGGAGCCTCGTCCTCTCCACGGATCCTAGACAGCAAAATACCGCACTGCACGCATTCAGAAGGG

GTCCCATCCAAACCCTAAGTGCCCCATGCGGCTCTGCACATGTGTGCTCCCCTTCCCTTTCATGGGTCAGGGCTAGG

TACCATTCATGCAGTCAAGTAATGTGCAGCCATGCTGAGCACAATCAGTTTGTGCCATATGTGAATGACAGCTTTGC

AGGTGCAAGCTGAAGCAGCCACAGCATGGTGGCGTGGCAAGACCAGTATGCCTCATGCCCTTTGCAGGCCTGGGACA

ACAGCGGCGGCACCAAGTCAGCAATCGCTTCACCCCAGCAAGCTCCGGATGGTACCAGCCATACAACGGCAGTCGCT

ATATGTATTGAATCAAAAGCCAGGCCAAACGGCTGCGTGGCTGGACTGCTGCACTCACTCACGTGGCCCCTGGCAGC

AGGGTGACCTAAATCAGGGTTTGGGGGGGTTTTGAGGGGTTTGAAAAGTTTGACATGTCAGAAACGATTTGCACAGC

ATAATTTGCATAATTACAACTAGAATGATTGTTGGGATCACTTGTGGGTGACCGCAATGTGATTTGGGGACATAGCA

ATGACTTTGCATGCCCCATTGCTTCCTTGTCACCACACATGAGTAGGTGGGAAGGGATGGGACTTCCATTGCCCCGC

ATACTTGCACCACTGTGGCCTGCCATTCACCCAGATCCAACTGTATACTGTATTGTGCTGTGTTACATGTTGACACA

TGCATGGTGTGCAAGCACATGCTGCTCAGTCCCCTTGGCCGCCACACAAGGGGCTGTGCTGCCTAACCCCCCATCC

AACCTGCCTGCCCCACTCACCCCTGTGCAAGACCCTTCAGGTGCATGTGTGCAAATGTTGCCTGACATGTCTGTATT

GCAACCACAAGCTAGGAGCCGTGGTGCCAGCCCTTGCAGTGCCCCATGCGGCTCTGCACATGTGTGCTCCCCTTCCC

TTTCATGGGTCAGGGCTAGGTACCATTCATGCAGTCAAGTAATGTGCAGCCATGCTGAGCACAATCAGTTTGTGCCA

TATGTGAATGACAGCTTTGCAGGTGCAAGCTGAAGCAGCCACAGCATGGTGGCGTGGCAAGACCAGTATGCCTCATG

CCCTTTGCAGGCCTGGGACAACAGCGGCGGCACCAAGTCAGCAATCGCTTCACCCCAGCAAGCTCCGGATGGTACCA

GCCATACAACGGCAGTCGCTATATGTATTGAATCAAAAGCCAGGCCAAACGGCTGCGTGGCTGGACTGCTGCACTCA

CTCACGTGGCCCCTGGCAGCAGGGTGACCTAAATCAGGGTTTGGGGGGTTTTGAGGGGTTTGAAAAGTTTGACATG

TCAGAAACGATTTGCACAGCATAATTTGCATAATTACAACTAGAATGATTGTTGGGATCACTTGTGGGTGACCGCAA

TGTGATTTGGGGACATAGCAATGACTTTGCATGCCCCATTGCTTCCTTGTCACCACACATGAGTAGGTGGGAAGGGA

TGGGACTTCCATTGCCCCGCATACTTGCACCACTGTGGCCTGCCATTCACCCAGATCCAACTGTATACTGTATTGTG

CTGTGTTACATGTTGACACATGCATGGTGTGCAAGCACATGCTGCTCAGTCCCCTTGGCCGCCACACAAGGGGCTG

TGCTGCCTAACCCCCCATCCAACCTGCCTGCCCCACTCACCCCTGTGCAAGACCCTTCAGGTGCATGTGTGCAAATG

TABLE 6-continued

Sequences Corresponding to Frequency Peaks (SEQ ID NOs 21-167)

TTGCCTGACATGTCTGTATTGCAACCACAAGCTAGGAGCCGTGGTGCCAGCCCTTGCAGTGCCCCATGCGGCTCTGC

ACATGTGTGCTCCCCTTCCCTTTCATGGGTCAGGGCTAGGTACCATTCATGCAGTCAAGTAATGTGCAGCCATGCTG

AGCACAATCAGTTTGTGCCATATGTGAATGACAGCTTTGCAGGTGCAAGCTGAAGCAGCCACAGCATGGTGGCGTGG

CAAGACCAGTATGCCTCATGCCCTTTGCAGGCCTGGGACAACAGCGGCGGCACCAAGTCAGCAATCGCTTCACCCCA

GCAAGCTCCGGATGGTACCAGCCATACAACGGCAGTCGCTATATGTATTGAATCAAAAGCCAGGCCAAACGGCTGCG

TGGCTGGACTGCTGCACTCACTCACGTGGCCCCTGGTGGTGAGAGCAAACAGTTATCTTTCTATCCAGGCCGAGTTT

GGGGACTCTAATTATTGTAATGAATAAGTAGAAAGAATTAATACAAGTTTAGCTCTTCAAATCGGGCAGATCGTGGC

GGAAGGTGAAGGTCTGCATGCGAGCCCGCAAGCGAGGTTGCAGCCATGTTGACTCGCTGACTCGCCAACCAAGTCAG

CGCTTCTAAACGATGTTTACAATTGATAACTTTAATTGGTTATATGCAAGTCTTAGCTGCCACTATGCCTGTCTGTA

ACAGCTGTCAAAAACAAGTTGACGTTTCTCACACCGAGGTCGGACCTTACTTGTTGACTGCTCTACATCCTGCGCCC

ACAGATTC

>SEQ ID NO: 78

ATGACGATGGTGGAAAAGGGGGGAGGGCGGCATGCAAGTAGTAGAACTCGAACTCCCGTAATTTAAATCACGTGGT

TGGCCATGGCAGGTAGGGTGTCTCTATTTCCATTCTTTTTCTGCCAGCTGAAGGCGCACGCAAACACATACATGTGG

GGATGGCGACGTTAGTAACGGTTCGTTGGATAGGATCAGGGTTGATTGGGCGGTTGGGGACAGTACCATACATATAA

CAAATACATGTGTGGGAGCCCAGGGCAGATAGCGGCTCGATCGCAATTGCTGCGCACGTGCACGATGTGGCAAGTCA

TTGAATGACTACCGTACTAAACATACTAAATAAAAGTGTAAATATGTCGAGATGCACAAATGCCCAACAACTAACAC

GAGTCCGTCGCTTGCATAGCGGCCTGCGCCGCTGCTGGCCACGTTTGCTGTATTTGCTGCCGCGACCGAGCGTAGAT

TGATTGCATCACGGATTGCATGCACGTGTCTATCTCGGTAGTTGCCTGGCGGATGAATCACCTATTTTCTGCATATT

TGCTGTCTAAGTGCGAGTCACTCATCATGATCAACGCAACGCACGCATAGAGCATGCGCCGCAGCTAGCTCAATCGA

ACAGCGCTTGCGTACATGGTGGATGGGGCCAGCTGTTGGTGATACAGCTGTGATAGACCGAATATTTTCATAGCTAG

TTATCTGGGTCCTTGCATGATTGTTTATGATATGCCGTTGTGAAATTAGCGCAGCGTAATTACGCGGACAAACTGCT

CGTGGTGAAAGGCATAAACCATGCATGCATCTTACTTGCGGCGGGTCCATCCATTAATGCTGCTACGTCGTCCCGCC

CGCCCCCCACACTCATGCACACGCACGTACGCGTACTCGAATCCTGCTGCTGGCTAGTTACACATCCCATTGAGACT

TGCGTCAACCCAAGCCTGCCAAGCGCGTGGTTCGTGCCAAGCACGCACCCATCCAAATGATATTTACAGCAGCATAA

AATTATCAGTAGTTCAGGTTTATGTAGCCGTGCGTAGCGAATGGATTCGCGCCAGAGGTGTGCTGCACACTTCTCGA

TCGCTGCTGTGCTAGTGCATACCGTATATGTGTCTCGCCTGGTTCCCACACGCTCTGAATATATCCTAATTACCGCA

TTCTGCATTCGCGCAGCAAAGTTTAAGCTGCTGTACATACCATTTACCGTGTATTCGTATACGCGCGCTAGGCCTTG

GCCGTACCTGCTACGTCTTTTGTAGCGGCGTGCTCCTGCAGAGCCGCTTTAATGACTCTGTCGCGTGATCTGACTGC

TATTTGTCTTGACTTTATATCCTGCCTGGCTGGCGGAGTGCGGGCTTGTCCCGCCCGCCCGCCTACCGCCCATGCTC

GGTAGTAGGGGCGTGCAGGAGGCGGCGGGCCTGACCCGTCTCCTCATCTCCCCCAACTCCCTTAGTAATAACACCAC

TTGCCGACGGCAGGGTGTATCCATTCTATTTCTACTACTCTTCGCGCCTGGCAATGAAACGATACCGTACTCACTGT

GCGCGCATAGTCCCTGACCGTACCCGCTCTCTACGAGCCATCCAGCAGACGATAATAAACGTACCATCCAATCAATT

TGCTGTTCGCACATTACTGGCACGCATGACTGGCCTGCACGCTATTTATTACACCGCGGACAAGCTTATGCCTGCCG

GTCTTCCATTTGTGCCGCAGTGTACAACGTTATCTCGGCGCCTGGCTACTCGGGGCTGTTTTCTTCAGCCCGATGG

AATACGCCAACCTGACAGCGGCTGGTCTCGGGCCAGCAGGAGGCAACGGCGGCAGGCCAGCAGGAGGGACAGGTGCG

TGCGTGGGAAGGATAGCGCATAACATGAAGCTCGATGCATTGCGTCATCATTTGTCTGTGCTGTATAATAAGCTGCA

AGCATGCTCTTGAACTAACATGCTTTAATATGCACCTATCTAGTCGCACGATCTAGTCGTGGCTTCATTTTTACTTT

ATTCACAGCCACGTCCCATATGAAAGCCTTAGCCTTGCGTGCCAGCTAGGCGACTATACGTGATCAGTAAAACTGCG

TABLE 6-continued

Sequences Corresponding to Frequency Peaks (SEQ ID NOs 21-167)

TGTTGCGTTGCCCACGTATTTTATGATAATCGACGACCGACGCAAGTGAGCTTTACGTAAGCGCTTACGTAAAGCTC

ACTTGTCTCCTAGCTACACAGTTGTCCGTCGCATCAACTTCAACACCGCAACACGTGTGGCATTCAGTGCGCTTAGT

CCTTGCTTGCGTTTGGCTAGGCCGGCTGCTGCAAGAGCGCGCGCTTGTGCTTGCTGCGCACGCAGCTGCTGTGCTCG

CTATCCGCGCGCAGTGCGTGGAATTCAGCAGCCGCTGCTGCTGTACGCAACACGGGCGTTGCCGGAAATAATCGCTT

ACGTGGGTATATGTACCTTCTGGGATATGCTGCCCGCGTCTATATATATCTGACAACTGCAGCCCACCTATGCACTA

CTACTCGCGGCTTCGCGCCGCTCTAATAACACTATTTATCTCTTGCGCCACGCATGTCACGTAATATTACAGGTGTC

ATCCAGCTGTCCAGCGGATCCAATCAGCACCAGCTGGGGCAGCACCCACAGCCGCCGC

>SEQ ID NO: 79

GGCCAGGGGCGCCGGACACACGACGACAGGGGTGAATCGATTTGTACCGCTGCACGACATGGGTCTGAGCGCGGATA

CGGATACGGACATGGGTAATGCCCAGGATTAGTGGGACGGGGGCCGGGGAGGCATAAGTGTCTGGGCATGGAACGCT

CACGGACTTCTCACTGGAGGCTCTTGCAAGCTTCACGACCGCAACATCAATAAAGCCGCACGAGCGCACGACATCCT

GGTCATTTCCGAAGCACACCTAACACATCGTGTGCCAGACGGCCGTATAGAACTAGACGGATACGCAGTCTTTCGTG

CACATAGATCGCAAGAAGCTATAAGGTCGGATTTTGGCGGCGTTGCAGTTTATGTGCGTGAGTGTCTGATGGGCGGA

GTGATGCATTTAAGGACAGACGTGAGTCTTACAGGGTGTGAAGTCGTGTGGATGCGGATACGTTCCAAAGATGGAGA

CAGCCTGCTTTTAGGATGTTGTTACCTTGCGCCGGAAACCTCGCGCGTATACAAGGACGGCGGCAAAACGCGTGTGG

CAAGGGAAGCCACAGCTGAGGCCGTCTTTGGAAGGCTCCAGCAGGCTATCTCGGCGATGCGGCAGAACGGCGAAGAG

GTGCTACTAGTAGGTGACCTCAATGCGCGTATGCCGGCAGGGCTTAGAGATATACCGGATCTCGACCAACTAGCAGC

GCTTGAACAAGTGGAGCATATCACGGCACTGGGTGGAGCACTCACGTCGATGCCTAGTCCAGAGGATTACGCGGGGT

TGCCGGCCAGGGCTTCTCAGGATAAGCACGCAAACTGTTTTGGCGAATTTCTAGCGCGTATGTGCCGTTCTCAAGGT

TTTGTGTTACTGAACGGCAGGGCACCAGGGGATGAGTCGGGTCGAATCACCTTCCCAAAAGGGGAGGAGGGGGAAG

CGTCATTGACCTATGCATTGCATCGCCAACTTTATTCCAATCGGTGACGTCAGTAGACGTGGGTGAGCTGCTGAGAT

GGGCGCGCAGGGGCGCCGGTTATGCGAGTGATCACAGGCCTGTTACGCTGACTTTGAGCTGGGAGGTGGAGGGTCAA

GCAAGTACTGAAGGCCAGGCGAAGGCAAAGCGTCCACGCACTGCATTCAATGCGCAGAAGAGTGAGCGCTATAGCAA

TCTTTTCGAACAAGATGAGTCGCCAGTAGTAAGCAAATTAACAGAGCTAAAAGGCCACTTGGAGCAAGGGCGGTACA

GCACTACCGAGGCGGTCGAAGCGTTGAGCAAGTGCCTAAGTGGAGTATTGGAGAAGGCGTTTGGGCAGAGCAGGCCT

GCTCATCTGCGAGAGACCGAGACCCCGTGGTGGAATGAGGAATGTGCGGTGGCGCGTGCCGCGCTCGTCCAGGCGAA

AGTAGCGCTTGGCAAACCAGTTGTGAAGGAAGGAGAAAGGTGGGAAGCGATGCGGGCCGCGAGATCAGTGTACTGCC

GCGCAAAACGCAGGGCTAGAGCCGCCCATGATGCGCAAGTGATGCGGGATAGGGTAGCACGGTGCAGAGCCGACGCT

AAAGCACTGTGGAAGATGATTGAGGAGCGGTGCACGAGCAAATCCCCCATCACGGCAGATGGCTTCCGTGATCACTT

TGCACGGCTACTGAATGATGGGCAGGAACAGTTGACGACAGCGCTGCAAAGCGTTTACTGGCGTACTGCTGTGACG

AAGATGGCTGGCGAGATTCGATGTATGATGACGAGGAATGGGCTGAGTTAGATAGCATATTGAACAGCGATATCTCG

ATAGACGAAGTGACTCATGCTTTAGAGAGGCTACCGAATGGCAAGGCCCCAGGCACGGAAGCCGCGCCATCGGAATG

CTACAAGTACGCAAAGACGCAGGGAGACCCCAGGGCAGACCCCCCCATCCCGCCGGTGAACCGGGTAGCACCTGTTC

TAGAAGTGTTGTTTAACCGCATCTGGCGGGCGCAAGACGGAGATGAAAGTTTTCCGGAACAGTTCACAACCACAGTG

CTGACGCCAATTTACAAGAGAAAGGGCGATGTGAAGACGCCCGGCAACTACAGGGGCATTGCAGTAGGCGGAGCGTT

GGCTAAGTGTTATGCATCTATCCTTCTGAACAGGCTAGCACGAGCAGGCGAGTTGTTCAAGTGGAGGCACCCAGCTC

AGGCTGGTTTCAGGCGGAAATACGGTACTGCCCACCACCTGTTTGTCCTGAGGCACCTGGTGACAAAGCACACACGT

GCAGGAGCACCACCAATGATTGTTGTACAGATTGATTTTGAGAAGGCGTTTGACAAGGTGCCGCGCCCCCTCTTGTG

GCTACGGCTGCGGGAAAAGGGCGTGTCAGGGCGGCTGTTGGAGGCCATACAAGCCGCATATGAAAAGGTCATGATGA

TABLE 6-continued

Sequences Corresponding to Frequency Peaks (SEQ ID NOs 21-167)

CGGTTAAAGCCGATGGCAAACTGAGCGCTGCTTTTGAGGCAACGCAAGGAGTCAAGCAAGGGTGCCCACTGAGCACA

GAGCTGTTCGGGCTCTTTATTGAAACTTTGGCAGAGTATATTGATGCGCACGAGGACTGGTTGGACACTGCAAGCAC

AGCGGGCACCCCTGAGTTAAACGGTAAGAAGCTGTCGCTCCTAATGTACGCTGACGATGTTTCGCTGCTAGCCACCA

CCCCTGAGCGTATGCGGCACCTGTTGTCACTTGTGGATACATTCTGCGAAGCATTTGGTATGAAAGCAAACGTCGCA

AAGTGTGAACGTCTGGTGTTCACTTCAGACGACCAGGAGCGTCGTAGATTGAACGATGAGTGCAGTGGGCTGCGGCT

GGCAGGGCAGCCCATCCCTGCGGTGGACAAGGCACGGTATCTGGGACTAGTCTACGCCCTGGACGTGCTTTTGCCG

CCTGCAGAGAGACGCTATGTGAGGCTGCGCGGCGTGCTATGTACGCGCTTACTAATAGATTAAACCGTTTGAGGATT

TTCTCCCCCGACATACGCATGCGTTGTTTTGAGGTGCAAGTTCGCTCCATCCTAGCATATGGTTGTGAAGTGTGGGG

ACCCGACGTATTAGCGGAAATGCTGGACGGCGGCCCACCACCGCGGCGGCGTGACAGCAATAACCTGGCGCACGGAC

CGTTTGAAGCATGCCTGAAAGACGAGGCCGTCAAATTACAAGTGCAGTACATGAGGATGACAGTGGGTACGAAGCGA

CCATCGCATCGCCTGCTGTTTGCTGAATTAGCACAACTACCACTCCATTTCTTTTTCGCCAAGCTTTGCATTGGATT

CTACAACAGGATTGCCGTGCAGAAGGATAGCCTAGCTCATGATGCACTAATTGATGAAGTACAAGACGCGTTAGTAC

ACCCAGAGGGAGATGGGTGGTGTGCACGGCTTTTCCGTTTTATCTCAGCGCATGGCGTAGACGTATGGCAAGGCCGT

ATGCACATGATCAGGCCGGAAAGGGAGGAGAGCCGAGCAGGTAGCCCGCTGCCTGAAGGGCAAATAGTATCCGCCTT

TCGAGAGAGTCTAATGAAGGCGTGGAAGCACGAGCGGCTGCAGTCTGAGCCAAGCACTTTCCCATCAGACAACAAGC

AACCAGGCGTGCAGATGAGCAAGTACAAGCATTGGATGGGGCTGTGTGCGGAAGGAGCGGCACCACTGACCATGCAA

GGGCACAGTAGAGCATTTATACCAGTTGCGCACCACAAGGCCTTGATGAGGTTCCGCCTATGCTGCTGGCCGCTTAC

TGCCAACCGCGCCTATGGACGACCTAGGGAGGAGAGGATTTGCCCGCTATGTGTTGCAAATGAAGTCGAAGATGAGA

ATCATGTGCTCATGCGGTGTACGGCCTACGACCAGTTGCGTTTGGGTAGCGAGATCGATTTTACAGGCGGAATGCAG

GCCGTCATGCAGAATGCGGACCCAGCCAGGTTAGCCGCGTTACTAGATTCCATTTGGGAGCACAGGAGCATAAGCAC

CCCCATTCGGGGACCAAACTAGCTGCATATATAAGTGTTGCAGGCGTTATAAGGGCCCCCGGCCCGGGCCTAGGTT

TCTACAAGGACAGGAATGCACGTCGTGCTCACCACCTTGTAACCACACACAACAACATGTACCACTACCTAGGTGGA

TTTCACCCCCGCACCTACCGCAACGTGCATCTCCTACGACCCAAAACCCTAGATGACGCTATCGAAGATGCCAGCTA

CGTCAGTGAAGATGCCAGCTACGACTGGGATGATATGCAGGCTAGTACTGGGCGTAACTCCCCTACACCCCCTGAGC

GTAGGGGTGCGGTTCGAAAGAGCGCCCGCCACCTCCTCGCAGCGTACCCTCACCGGCACCCCCCACACCTCCTGAGA

CTGGCAGTTTGTATAGTTATAAGTACGGGTGTTGCGCTTTTAGGCGACATTGACAAGTTACATCCTCAAGTTCCAGA

GCTTCGCGACGGCGGACTTGACAGCGGTTAGATTCGTAGCATCAAGCATGCGCACCATGTGTTCACGACCACGCGAA

GATACTCGCTGACAAACCGAAAGGAACTTCTGGCACCATTGCAAAGTCTCTGGTAAATCGGATGCATCTGGTAGGAG

TGGAATAAAATGCACCCAAGGCAGTAAGCCATTATAATACCAGGCCCGTTGACGAAAAGGAAAGGTATGAATTGCTA

CTGCATGACTTGCCAGAGTGACAGGAAACAATGACTCGGGGCTACTTCCATCGTCAAAAACAACGTAACGTGCATCT

AAAACGTCACCGATATCTGTAAGACGACGAGCCCATGATTCATTCGACCATCGCGCAAAAGATCCTTGAGATATGTA

CACCTGCACTAGAAACATGACGTGTTGTTTACACCCAAATCAATCAAAGAATCCCACCTCACTGCTTTTAGCGATAA

AACTTTTCTCATCAAGAAGGCCCTGTCTTGACAGAATCTCTTGAGGATAATACGGCCACAGAACCGCGTATTCACTG

CCTGAAATAGTATTAATGTGTAAATCCTTAATCAAATTAAAGAAATAACCCACCAGGACTGTATAGCCTTGCAAAAC

TAATGGACACTTCCTGAGCTGCAGCCCCATGGTCAAAATTGATAGGAAATCCATGTTGTTCGTCAAAATAACTTGGT

GGTGCGTGCCTGGTGAAATCGCACAACACGCACATCGCTCTCCAAGGATCCGCAGGTTGAATTTTGCCGTAACGCTT

TTGAACAGCTGCTATTGATGTGTCTCCTGCAGCGAATATAATGCTTGGCCTGCTATTTTTCAGCATATGCAATCTGA

TTAGGCTCCATCGGTGTCTAACAGCAAGGGGATAAAGGTCGCCTAACCAGAACATGACCTGCTCACGAATCCATGCT

GTCTCTTCAGTACTGCTACGCACTACGGGCGCGCAACAATCAAGGGTTGGCAGCGAGTTGCTTTGCACGAAGCAAAA

TABLE 6-continued

Sequences Corresponding to Frequency Peaks (SEQ ID NOs 21-167)

CGTTGTTGGTAGCAACATAATATACAGTGTAATGTGAACAAAATTGCGAACCATATTGACATATGTCGTTGTAGTAA

TTAAGTGGTAATTCACGTATTCTAAACCAAGGGGTGTCAGCTTTGTACAGCTGGAAAATGAGACCTACACGACACTT

AGCCCGCTGATATGCTTGAACATATGCTCCTCACATACCGAGGGTAACGTGCTTTATAGAATTGACAAGGGGTGTCA

GCTTTGTACAGCTGGAAATGGGCTGAGCCCCCGTAC

>SEQ ID NO: 80

GCGTGCGCGGGGGGTTGAAGCTGCCTGGGGCGGGTCGCTGCGGCAGTCCAGATGCCTGCGCCGAGGGATGGCAGATG

CCTGCGCGACCCCGCGCCATCAGCACGGATGCCTGCGCGAGGCATTGCAGATGCCGCGGCGCCCCTGCTAGCACATC

TGAGCTGCCTATTGTAGCCACCTAGTTGCTTGGTAAAACGCCGCAAGAGGGTCTGAAATGGGTAACGGGCAGTGTGT

AGGGGTATGCCAGCACTCCGGCACGCACACACAGCCACACTGCTCAGCCGAGAAGTTAAGGGCTTTGACCATGCTGG

CCTATACTGAGTGCGTGCTGATATTAAAGCAACCATAACACCTTTATAGATACTTCGAGCTGCAGAACTCTGCTGAA

GTTGCGACATTAATGGTCAAGGCTTCCTTCTTTTGGGGCTTGTGGTGCCACAAGAAGGCTACACATAAAGCAGTAGC

AAGTTTAAAAACTACTGGGCAAGCAGGGAAACAAAAGGCTCTCTGCGAACCACTGGTTCGCGGGGCGTGACAGCCAA

CTCGGCGCCGCAGCCAGCTTTCCTAGGGAATACAGCTTGTCACCCAGATAGCAGATATCATGAAATAGATCACAGCA

GGCTCCACGGCTTAAACCCAGCTTTAGCGGCCCCAGACCGTGTTTCCATGTCCGAACCCACAGTCTCCAACTAGTTG

TCACACTGAGTAAATCGCGCTTTGCATCTCTGCGTGTAGAGTATTATTTAGGAAGCAGGCCGGATTGAGCTGCGTGC

TTGCCATGGGCACCGTGGCACACTGGCACCAGCACCAGCACCCACGTGTGTACCGTGCATACCGTGCTTACTGACAT

TCCCGCAATCTAAACTCGGCACGCTTCGTTTCCGGGGTGGAAACCCACGCCAGTCAAGCTGCGGGGCATGGCAGCT

AAGATGCCTGGGCGGACCGCCTCCGGCATCCCAGATGCCTGGGCACGGCAGCTAAGATGCCTGGGCGGACCATCCCC

GCCAGTCGAGATGCGTGGACATGGCACCCCAAGATGCCTGCGCAGGGCTACCCCAGCAATCTCAGCTGCGCGTGCGC

GGGGATCAGGTTGCCTCTGGAACTTAGCTGCCAGACCAGACCCACCCCGCCAGATGCCTGCGCTAGGCAACTTTCCC

ACCCTCCGGCCTGGCCTGCAGGTCTTGAGCGTCGTTCAGGTTTGGGATGCAGGGGTCATGGGTACAGGGCCAGGGTC

GCCGGGGCATAGCCAGTCAGGGTCTGGTTCAGCGGTCATGATCAAATTCAGCGGCCGAGGGAGGTGAGGAGCTCCGG

GACCTTAGCGTGCCCTTACCATAGCTCGGGATGAACTGGCCGCCCATGTCATCAACGATGCTTAAGAATGCGGAACA

GAGAAGCCAAGCGAGCACAACGGTTTAGAGGCCTGGACGCCGGCAGAGCAGAACAGAAAGCGTGAGCAAAGTAGCGA

CAGCAGTTCAATGACAGTTGCCCATCGAGATAATTGCTGCGCAGAAATGGAACGCAGCCGCATGCACCGCTGAAGAG

TGCAGTAACGACGTACTGAAACTTAGCCAGTTCATGAAATAATTGTTTCTTTCTTGTTTTGTTGTTTATCCGAGTGG

TTTTGGTAGTGTATATCAGGCTTTCTTGAGTATTGCTGCCATATTGTCGGAAGCTTGTTCAGAAGGCGTTCTGTCTC

GTGTGAGTGCACTGCTGTAGACTGGTTATCACGTTTGATATACTGATACCTAGCAATCGCTAACGGGCAAGCTTGGG

GGTCATAGAGGGCTTCCGGGAGAGAAGTGTAGCACAATGGCGCCATTTGTTGCCGGCTCCGCCGGAGCTCGGCTGCG

TGAGCCCACCCACGGTCTCCTGTTGTCTGAGACAGCTCACGAGATCGAGACCAGTGGTCTACGAGAGCCCGTGATAC

TCCAGGAGGGTGGATGGGACTCGTCCGCAGCCGTGGGCTGTCCGGCGGGAACTCGTTTGTAAGGCTTATCAAGAGAA

TGATAAGCACCCATTGTAGGGCCATTTTGGGGTTCAACTCTCCGAATTTCCGTCAGCTCTCAACAGAGTGCTTCCAT

GTTGGTATCCGCACGTGTTCGCAGCGAGATATCTTTTACTTCAATAACGTGTATGCCCAAACACCACGCACATGCTG

ACATGCACCGCGTCGGTACGCAAAGAACGTGGCAAGTGCGGTGAATGTTTGTGCGAGGGTGGAGGGAAATGTCAACA

CGGAAACACACAACGTGCCATGCTACCAGCGAGCTTCCGTGTCAGGTGGGCTAGCGTGGGTAAGGGGAAGGGGG

AAGGGGCCCCGACAAACACACAAGGGCGTGGTGCTACCAGCGGGTGGGTGTGGCAAGTGCGGTGAATGTTTGTGCG

AGGGTGGAGGGAAAGGGCAACACGGAAACACACAACGTGCCATGCTACCAGCGAGCTTCCGTGGCAGGTGGGGTACA

GGTTT

TABLE 6-continued

Sequences Corresponding to Frequency Peaks (SEQ ID NOs 21-167)

>SEQ ID NO: 81

ACACCCTCCTCCTCTGGGCGCGAGGCGGGGGAGGGGGTGGGTGTGGGATGCCCCGCGGCCGTGGTTGCCCAGATCCC
GCGCGCCAATGCATGGCCAGCGGTTGGGCGTACAGCGGCGGCAGCAGTAGTGCGCAGCACGCAGGAGTGGACACACG
AGCGGCTGGCTGCAGCACAGCAACGCATGCATGATTACGACCTAGGCGGGCAGTACGCCGCACAGGCACTCGCGCAG
GCGCAGGGAGCAGTGCAGCAGCAGCTGCTGCTTTACAACAGCGGCACTGCAGCAGTGACAGCGAAGCTGGTGCTCAT
CTCGCCATTGGCGGTTACCACAGCCGCCCCAGAGGTGCAGGGCGTCTGGCCCGATGCAGCGAACCCTGGTGCAGAGC
CGCCGTACGTGCTTTGCCCGGAGGACTCGCAGCCGACGCCTGAAGACACAGCGCGGTTATGGAACCTCAGCGATGAC
CAGCAGCAGGCGTTCATGCTGTACGCGCAGCTCCTGCTAGCAGAGGCCGCCGGCGTCCGTCAGCCCCCGTGTGCTC
GGTGCTCACGGGCAAAGCCGGCAGCGGCAAGTCGCGGGTGCTGCAGGCATTGCTGTGGTTTGCATATCAGCACCGCT
GCGAGTCTCTCATTGCCCTCGTGAGCTACACGTGGCGCGCTGCGCTGCATGTGAGTTGTGTGTGGGGTGTGTGGGGT
GTGTGGTGCAAGAGGGGTTCAGTTCGGAGGTGAAGTGTGGCGGTGGTGGACTGGTTTAGCAGCCAGGGAGCCTTACA
TGATCATGCTGTTGACTTCGGCCGCTGCCATCACGGTCCATTTACAGGACTCTACGCCAGGCGTGCTCGGCACCAGC
ACCACGTCCTTCTTTGCGACTGCTGGCACCTTTGGTCCGCCTCACCGCGATCGAGTCGAGCGCAACCTCAATGGTGT
GCGCTTCATTTTCCTAGATGAGTTTAGCACGTGTGGGCTGTCCCACTGGGCGCGCATTTGCATGCATGTGCACGCGG
CACGGAGGCACGTGGGTATAGACAGCACGCACCTATATCACGGGCCGCTGTCAGATCTGCATGGCCTGCTTGTTGGC
GACTTGCGTCAGTTGCCACAGCCACGGCACGTGCCGCTATATAGCGGTGCTGCGGAGGAGAGCTTGCGGCAGCTGCT
GGCGCCGGGCGCGGGGACGGCGGGGCCATGGAGCGCCAGATCCGGCAGCTGGAGCATCCGGAGGGCAGCATGAACC
TCATGGGGCGGGAGCTGTGGAATATGGTGCCGTTCGCGTTCGTTCTCACTCACCAGCATCGGCAGCAAGCAGGCGTA
GGTGACAACAACGAACCTCTCTTCATGCTAGCGGAGAAGTTTGGTGGCGTGCAGGAAATCTCTCAGGCAGATCTGGA
TACAGCGTGCCAGCAGCTCAACGCGCGTGTTTGGCAGCCCCCGAAGCCAGGGATTGACCCCGTGCCCCAGCCCTTTG
CAGTTGTCCAGCGCCATGTTGTGCGGGTTCCACTGGCATTGCAGCTCGTGCAGCTGCATGCGCTCGCGCAGCGTCAG
CAGCTGCTGCTATGGCGTAGCGCGGACTTGTCGCCGGACGGGAGCAGCTTACCTATTTCGCATGTGCATCAATTAGA
GGCGCTTGGCGGGGCCGAGGATGATAGCGGTGTGCCCGCTGTGTGCGCATTCTTTGCTGGCATTCGTTACGTGTTTA
CATCAAATGAGCATGTGCGTCTGTATCACATCAACAACAACAGTGCCACAGGCACCGGCATTGTTCTGCATCCCAAC
GAGCCACCATTGCCAGATGCAAGCATTGCCCCCGTGCATGTCCTCAAGTTCGTGCCCTCGGCTGTAATGGTGCGCCC
CGACGGGCCTGATGCGGGTCGGGTGTCTGTCGATCAGGCCCTGGATGTCGGGGAGATTCCTGTTTTACCGTGCAGTG
CTATGTTCACATCGCAGCATGCAACCCTGCGGTTGCCTGTGATGCGCTGGGGCTTTCGTGTGGAGCTTGCGTATGCA
GTCACCGATTACTTTGCGCAGGGGCAAACTCTGCCAGCGCACGAACTGTGGCTGGTGGATATGTGCAAACCGCAGCA
CGGCAGTTGGCGGCGGGCTTCAATTTACGTAATGCTCACCAGGTTTCGTGGGTTGCATGCCTTACATTTAGTGCGTC
CGCTGTGGGCCTCGCGGGCCGAAGAGCGCCGGCTTAAAAAGGCGCTGCGTACCATGCTAACGCCCGAGGCAGATCTA
GCCGCGGAATGGCAGCGGCTATTGAGGCTCTCGCAGAGCACAGCAGTAGCAGTGCCAGGTATGATTGTGCGCATTCA
GGCCAGCATGGCTGCCTCATAACCAAGGCTTTCAATGCATGCAGTAGTGTTTTTAACATGCGCGAGGTGTACTGACA
GATGACCTGGAAGCGTGGAGTACCTTGTGGGTGGTGAGTGCTGACTGCAATTTACAGCAGTGACTTTCTTGTTGGTG
TTTGGTGTGGTGACCATCATGCTTGGCTTCGCTGGCTGGACGTATGTCACTGAGCTACGTTCGGGTTTAGTTTCTAC
CTGTCCTGTCTCTGCGTGAAGCCGGGGTATTGTTTATCTGCTTGCTTGTCGTGCGTTGGATTGTTGTGTGTTTACAA
CAGGTTGATGTGTGGCGTGGTTAATCCCTTGCACTTTGAGGAGGTTATTGTTAGCCAGCTGGTGTTCGCACAGGAGG
TTGGTGGTCGATGAACAGTCGACCGACAGATGGATCGCGGGATTTGTTTTTGGCATTTACCGCTTGGATTCTATTCG
CAACGTAGCTCGGAATACACGCTTAATATGCATAGTTAGAAGACTTCGGGGACGCAAATCGCTCGGAAATGGAGGAG
GGTCTCAATATGCTCGGCTCGCGATGTCGCGCTCTTGAGCTTGTATTATGCACTGTGCGCAATGCGCGTTCAGCATG

TABLE 6-continued

Sequences Corresponding to Frequency Peaks (SEQ ID NOs 21-167)

CATATTCTTACGAACAACTAGGGACTTGAGTGACGCGGTGTGAAAATCAGTCGGGGTCTCGACATGCTTGGCTCGCC

ATTTCGCGCTCCCGAGCTCGTTGTGTGTGTTCCGAACAATGCACGCTCAGAATTACATGTTCAATATGTCCGTCGCG

ATGTTCGAGCTTGAAAACCGACAAGCATGGTGTATAGATACACCTGGTAGCCTGAATTCCTGTGTTTTTGGTGTATT

TTGTTGATGTTGCATCACGCCGTGCCTTGTCACATTCATGTTTTTTGTACCGGCGTGGCCTTGTTTGTAAATTTCGC

GGCGCCCTGATCTTATCTACTTCTTCGCTGTGATCTGGCAAAAAAAACTGTTCTTGACGGGATTCGAACCTGTGACA

GCATCTCACTAAGCGCCATAATCAGACCCTCCAGAGGAGGGTGTGCACTGAGTTAGCGATCCGGTGATGCAGCCGGG

TATGGGGTGTTTTACACGGGCGGCGCGCTTGGCGTTCCAGGAGAGCCCCCATCGGTATTTGAAGGCACAGCGTGCTT

CT

>SEQ ID NO: 82

GGCGGCAGTAGTGCGCAGCACGCAGGAGTGGACGCACTGGCTGCAGCACAGCAACGCATGCATGATTACGACCTAGG

CGGGCAGTACGCCGCACAGGCGCTCGCGCAGGCGCAGGGAGCAGTGCAGCAGCAGCTGCTGCTTTACAACAGCGGCA

CTGCGGCAGTGACAGCGAAGCTGGTGCTCATCTCGCCATTGGCGGTTACCACAGCCGCCCCAGAGGTGCAGGGCGTC

TGGCCTGACGCAGCGAACCCTGGTGCAGAGCCGCCGTACGTGCTTTGCCCAGAGGACTCGCAGCCGACGCCTGAAGA

CACAGCGCGGTTATGGAACCTCAGCGACGACCAGCAGCAGGCGTTCATGCTGTACGCGCAGCTCCTGCTAACAGAGG

CCGCCGGCGTCCGTCAGCCCCCCGTGTGCTCGGTGCTCACGGGCAAAGCCGGCAGCGGCAAGTCGCGGGTGCTGCAG

GCATTGCTGTGGTTTGCATACCAGCATCGCTGCGAGTCTCTCATTGCCCTCGTGAGCTACACGTGGCGCGCCGCGCT

GCATGTGAGTTGTGTGTGGGGTGTGTGGTGCAAGAGAGGTTCAGTTCAGACGTGAAGTGTGGTGGTGGTGGACTGGT

CCTGGTAGTCCTGCTCGTGCGTGCCGGGGAATTTAGCAGCCAGCGAGCCTTACATGATCGTGCTGTTGGCTTCGGCC

GCTGCCATCATGGTCCATTTACAGGACTCTACGCCAGGCGTGCTCGGCACCAGCACCACGTCCTTCTTTGCAACTGC

TGGCACCTTTGGTCCGCCTCACCGCGATCGAGTGGAGCGCAACCTCAATGGTGTGCGCTTCATTTTCCTAGATGAGT

TTAGCACGTGTGGGCTATCCCACTGGGCGCGCATTTGTATGCATGTGCACGCGGCACGGAGGCACGTGGGTATAGAC

AGCACGCACTTATATCACGGGCCGCTGTCAGATTTGCATGGCCTGCTTGTTGGCGACTTGCGTCAGTTGCCACAGCC

ACGGCACGTGCCGCTATATAGCGGTGCTGCCGAGGAGAGCTTGCGGCGGCTGCTGGCGCCGGGCGTGGGGGACGGTG

GGGCCATGGAGCGCCAGATCCGGCAGCTGGAGCATCCGGAGGGCAGCATGAACCTCATGGGGCGGGAGTTGTGGAAT

ATGGTGCCGTTCGCGTTCGTTCTCACTCACCAGCATCGGCAGCAAGCAGGCGTAGGTGACAGCGACGAACCTCTCTT

CATGCTAGCGGAGAAGTTTGGTGGCGTGCAGGAAATCTCTCAGGCAGACCTGGACACAGCGTGCCAGCAGCTCAATG

CTCGTGTTTGGCAGCCCCCGAAGCCAGGGATTGACCCCGTGCCCCAGCCCTTTGCAGTTGTCCAGCGCCATGTCGTG

CGGGTTCCACTGGCATTGCAGCTCGTGCAGCTGCATGCGCTCGCGCAGCGTCAGCAGCTGCTGCTGTGGCGTAGCGC

GGACTTGTCGCCTGACGGCAGCAGCTTACCTATTTCGCATGTGCATCAATTAGAGGCGCTTGGCGGGCCGAGGATG

ATAGCGGTGTGCCCGCTGTGTGCGCATTCTTTGCTGGTATTCGTTACGTATTTACATCAAATGAGCATGTGCGTCTG

TATCACATCAACAACAACAGTGCCACAGGCACCGGCATTGTTCTGCATCCCAACGAGCCACCATTGCCAGATGCAAG

CATTGCCCCCGTGCATGTCCTCAAGTTCGTGCCCTCAGCTGTAATGGTGCGCCCCGACGGGCCTGATGCGGGTCGGG

TGTCTGTTGATCAGGCCCTGGATGTCGGGGAGATTCCTGTTTTACCGTGCAGTGCTATGTTCACATCGCAGCATGCA

ACCCTGCGGTTGCCTGTGATGCGCTGGGGCTTTCGTGTGGAGCTTGCGTATGCAGTCACCGATTACTTTGCGCAGGG

GCAAACTCTGCCACCGCACGAACTGTGGCTGGTGGATATGTGCAAACCGCAGCACGGTAGTTGGCGGCGGGCTTCCA

TTTACGTAATGCTCACCAGGTTTCGTGGGTTGCATGCCTTGCATTTAGTGCGCCCGCTGTGGGCCTCGCGGGCAGAA

GAGCGCCGGGTTAAAAAGGCGCTGCGTACCATGCTAATGCCCGAGGCAGATCTAGCTGCAGAGTGGCAGCGGCTATT

GAGGCTCTCGCAGAGCACAGCAATAGCGGTGCCAGGTATGATTGAGCGCATTCAGGCGAGCATGGGTGTCTCATAAC

CGAGGCCTTCCATGCATGCATGGTTGCAACATCTGGCATGTGGCGCTGAACGCTGGGTTGTCCTGCGTCCCGGCCAG

TABLE 6-continued

Sequences Corresponding to Frequency Peaks (SEQ ID NOs 21-167)

CACGGATAGCGTAGTGCTTTTAACATGCGCGAGGTGTACTGACAGATGAACTGGAAGCGCGGAGTACCTTGTGGATG

GTGAGTGCTGATTGCAATTTACAGCAGTGACTTTCTTGTTGGTGTTTGGTGTGGTGACCATCATGCTTGGCTTCGCT

GACTGGACGTATGTCACTGAGCTGTTTGACAGGCAGGCGTAGAGTAACGTGTATGTTCGGGTTTAGTTTCTACCTGT

CCTGTCTCTGCGTGAAGCTGGGGTATTGTTTATCTGCTTGCTTGTCGTGCCTTGGATTGTTGCGTGTTTACAACAGG

TTGATGTGTGGCGTGGTTAATCCCTTGCACTTTGATGAGGTTATTGTTAGCCAGCTGGTGTTCGCACAGGAGGTTAG

TGGTCAATGAATAGTCGACCGACAGATGGATCGCGGGATTTGTTTTTGGCATTTATAGTTTGGATTCTATGCGCAAC

GTTGCTTGGAATACACGCTTAATATGCATAGTTGGAAGACTTCCGGGACGCGAATCGCTTGGAAATGGAGGAGGGTC

CCAATATGCTCGGCTCGCGATGTCGCGCTCCTGAGCTTGTATTATGCACTGTGCGCGATGCGTGTTCAGCATGCATA

TTCTTACGAACAACTAGAGACTTGAGTGACGCGGTGTGAAAATCAGTCGGAGTCTTGACATGCTTGGCTCGCCATTT

CGCGCTCCCGAGCTCGTTGTGTGTGTTCCGAGTAATGCACCCTCAAAATACATGTTCAATATGTCCGTGGCAATGTT

GGAGCTTCAAAATCGACAAGCATGGTGTATAGATACACCTGGTAGCCTGAATTCCTGTTTTCCCGGTGTATTCTGTT

GATGTTGTATCACGCCGTGCTTTGTCACATTCTTGGTTATTGCACCGGCGTGGCCTTGTTTGTAAAATTCCGCGGTG

CCCTGATCTTATCTACTTCTTTGCTGTGATCTGGCAAAAAAATATGATCTTGGCGGGATTCGAACCTGAGACCAGCA

CTACGCTAAGCGCCATAATCAGACCCTCCAGGGGAGGGTGTGCACTGAGTTAGCGATCCGGTGATACCGGGTTAACA

CCTCCTCATCTCTGTCACTTGCGTCAGACTCCGCTGATTGCAGGACCCGGGCCGCAGCGGCCCCAGATCGCGCCTGA

GATGCCTACAAGCATCAATGGACGGGTAGGCAATAACAACTGCTTTACCGTACCGTACACGGTAGATGCTCACCTTG

TGGTTGGCACGCTCCTCCTTCCATTCCGCCTCCAACCTGCAAAAAGAAGCCATGTCTACGTGCCGGCAGCAATAGAG

TACAGGCATACTTACTCGGCCACCTTCTGAGCAACGAACGTACTCCGCCGCACCCCCAGCTGATAGCCTCCTTTGCC

TCCTCCTTCCGAAGTTCGTGCTTCATGTAGTCCACCAGCGGCACGTTAGGAAACCCTAACTTCACCCGCGCGTCCAT

GCACGTGCTGCCATCACATGTGCAGGACCCCCCGACTGCAGGAATCCAGCTTGCAATTTTCCCTGCTGACACGCCGT

CATCCTTGCTCCACTTGCCCCCGTTGCACATGTGCACTGTGAATCCTGTATCGTACAGTTCCCGAAGGCCTGGCAGC

ACGGCGTTCTGCACGGCAGGTACGCGTCCTTTAGACAAGTGTGCGCCGTACTCCATAAGAAAGACGCACCTGGTACA

CAAAGCGCAGCGTCTCCCTCACCAGGTAGGACTCTGGCTTGGGTGCTGGCCCTGCGGTGGTGCCAGTCACCTTGGCC

TTGACGATGGTATTGTTGGGCGGGCTGGCGGAGCTGGTGTACTGCGTACGCGCACTTCTCCAGGTGCGTGATGCTC

GGCACGAGCATAGGGTCATCCATGGAGCCGTAAGCATGGACTTCAATGGAGGAGGAGGTGGGGTCGGCGACAATGTA

GATGGCGCCCGGCAGTTGCCTGTGAGTGCGAGTGAACATGACGCACGGTGCATCTCGAGAACATCGCACGGCTTTGT

TATTTTATGAGAGCACTCACTTCAGTTGCGAGCCCTCGAGGTCCTCCACGGCGTTGGCATCAAACAGCGCCGAGAGG

TTGTTGTTCGCAGCGTGTAGGCCATGCCTGATCTTTGCAGCTTTATTTTTCTGCGGGTATTTACATTAGCAAGCCCG

AGCGTCGACTTATAACTTTTGAGTTATGAGGTTACCTGTCGGGCCA

>SEQ ID NO: 83

GATGAAGGCCAAGGAAACGTTGCCGAGGACCACAGTCATGCAAAAGACAGCCGAAAGGAGAACAACCGTAAGGAACT

GCTGCCTACTCCGAATCAGCTTCGACGGAGTCCATTTAAGGCCAGCAAGAATTGATCCGATTGCCGCGCAAGCCAAC

ATGTGTGCTAGCGTTAAGAAAGCTGGGTTATGAAATCCTGTACTTGACAGCAAATACTTATTTAGCAGGAGCACGCC

TATGTTGCTACAATACCAGCATACAATGGCTGCAGTCGTGGACAACCATGCATGGCTTATTCCCGCTTGAGCCATGA

AAATGTGTGGTAAAAGGGGTATTAGTTTACGAGGTCGGTGGCGGCAGCGTGTTATAAGATAACCCGCTCCTTTCGA

GGTTAGAAACAGTAGTTATAAGTATAGTTATAAAAATTATCGGTCACTGTTTATCGGGGCATCTTATTGCAGGGAGC

TGTGTATACAGTATGTCCATTGCCGGAGTATTTTTGTACATCCCGACTTTCCCACGGACGTTCACCCGGTACTGCCC

CGTCGTTTGCACAGGCCACGCATATTCAGAAAACGTGGTTATAACACAGTACAACAGGTCGCAGCGGATTTGTTGAA

AGTTGGAAGGAGGGAGCATGGATGACTGGGTGGCCGCGCCGGCGAGTCCAGCGCAGTTTGACGTGCGTGCAATATTT

TABLE 6-continued

Sequences Corresponding to Frequency Peaks (SEQ ID NOs 21-167)

TGCATTGGCGGATGTAGGCGCAGCGGCTATGCAGGTGGTGGGCGTCGTGGCCAGGACGGGCGCGCCGCGTGCTGCGG

ATGTGCACCGGTCGCGGGGTTACAGGTCCGGACATGCGTGCGGGTACAAGCAGGGGCAAGCAGCAGGTTATAGAGGT

CCAAGGTGCTGTATGGGAAACCCAGCATGGAATCCATGTTGGATTGATGCCAGCTCGCGGCCCATTGCCGGCGCTCA

CCACCCCCCGAGGATGTGCCTGCAGCCCCCGCCACCCTGTCATAGAAGTGTTGTCGCCCCAGCCCCTAATTCCTTT

CCGTCTGTCCCTTAACTGAAGAAGTTGATTTTTCAAGCAAATGCTTCCAAAGGCCGCAGCAGCAACCGCGACCACAG

TCTCAATAACGGCCGCAGCAGCAACCACGGCCACAACAGCACCACGACCTGAGGCCGGCCGGGGCGGGGCGGGGCGG

GGCCACTATAACGACGGGTCCATGCGTTAGAGCCTGCGTTAGCATGCGTGCCGCGTGAAAAGCATGTGCTGTACG

>SEQ ID NO: 84

CCTCTCCTCAACACAGCTGTCCTGCCCGGGGCCAGACACTGCGAACATACTTCTCGCCCGGAATAAGTGCTTACTTC

ATGGCTAGTAACGAAACAGCATTTGAGGTTGCGTTCCTGGAAGAGTGCGAGATGCACATGTTCAGCAACCACGCGTC

CTTCAAGGGATTTGAGACTGTGTATAACCGTACACGCAGCGATCCACAGTTCAAGTTGCCTCTGTTGTGTCGCAAGC

GGCTGACAGAGGCATACTTCCGGTGCGTGGAGCATCCCATCTGTGCTGCGGAGCAATAGCTAATGGTGCATTGCGCA

GGTACATTCTGTGCCTCCACCTGGACTCACACGGACAGCTCGGGGCTACAGTACAGGGCGCCGCTGAGCAGCTAGAC

GCTGACCTGTTGCGATTTCAGGACGAGTACGTGGATACATTCAGCCTGCGTTGGGGGCGTTACCATTTATGTTCCAC

CCCAGGTGCGGAGAGTGCCCTGTGACCATGCTATGTAACTATGACCACAGCAGGAGATGGAGTGTGCACGTGCTTAG

CAGGGACACCGCTGAGAGGATTGCTAAGGGGCCACCAAAGCCGAAGAACCTGTGGAGGCGAGAGGTGCGGGGCACTG

CGGGGTGAGCACGCAGGGAGAAAGCATATACAATGCATGGGTAACATGGGCACCCGGGGCCTTACATTTGGCATGTA

CCAAAAAGTATAGTAGTCACGCTCAATCGTTCGAGGTTGCTTAGCGTGGTGAAGTCGCGCCAGCAGCGCCGGACATG

CAGAACGTTGCCATAGATGACCGAAGAAAGCGCCTGGAGAAGAAAGCAGAATGGCTGTACCAGAATGTGTATACGAG

GAGTGGGGGTAGCGCTGATTTTGGCGCGCAGTCTGGAGCCGTTAGTCGCCAGGAAGAGCAAGACATACATGTCCACA

CGCGCCGGTAAATGTGGCAAGGCTGCTACCAAGAAGCACGCCAAAGTTATGAGTTGCGACCAAAAGCTGTATGACGT

CGAAGACGACGAGCAAGGGCATCGAGATAACGAGCGAGCGGATGAACTTGACCACTTCAGCTGCCGAGAATACCAAT

AGCGTCAAGTCTGTAACAAGTGACCTGCGATATACAAGACATGTATCAAATGCATGAAAATGTCTAGCGTCCCAAGC

GGAAGCCGACCGATACTCACCCTCCCGCGCGCAAGCTGAGGCAAAGAACGTTCGCCTGCAGACGGTGTAAGCAGCGC

TTGATTGTCTGGGATGTCCACAAGATGTTGTGGATAGCGGACACGAACAACACTGGCACGAGGCCGGCGGTCATGGA

AATGGCAAAGCTCCGGGTCCAGTAAACGGCACCTGCACGTATCGTGTTAAGTCACTGTTCCTTCACACGTGGTGGCC

TAAAGCGGTGGTATACGTGCCTGTCCGCGTGTTGAGTTCCTGAAGGGCTCCGCAACTGAGTTCCAGGACAGCGTTGA

CCATAACGCAAGACTGGGCCGAAAAGCCAACCGGTCCGTTGTCAGGGACGAAGAACAACTGAAAGACGTATACGACC

GCGGTGAGGGCCACGGAACACGGTGAAAGGATTCCGCTGGTCGCCATTGAGCGCGGCGGAGCAAGTGGATAGGGCAG

CGAGAAGGGCCACGAATAGCGCAAACTGCGCCATATACCGGCCGAGGCCCACCAGCACGGCGCTCGCGTGCACAATC

CTGGCCGACCGGGCGCTGGTGCTGAAGGGCTCATGCCCAGGCTCCTGCACGTTTTCGACAGTCTCGGTGTTGGGCG

TTTGCGTATGCGTGGCATTTTGTCAGTTGTAATAATGGAAGTGCCAAAGTGAACGTGATTTACACACCGAGGGGTGT

GGGGCCGGGCTTACTTCAACGGTGGGCCAATTTGGATTTCAACTTTGAATCCGGACAGTCAGTCCCCCTGACGGCAT

GTTCCCAGACGCGCCAGTATCCCGGGCTCAGAAGAACGCATGTACTTGCACGCTTATGGAGTTCTAACGTGAGACGA

AACACAGTCGGGACTGAAAGGTCACACATAGAAATGGTTCCTCAACTGGCGGCAGCATTCACAGGGATTCCAGGAGT

ATTGGCGCTGCTCTTGTTCATCGTAACAGTGATTAGGTTTCCACGACCGTTTGCGGACCGGCACAAAATTGTTGCCG

CCATACTGGAGAAATGCGACAGGGACATTTTTGGAGGCAGCTTTCAGCAGGCCGCGACTGCACTGGTATGGAAATTG

AGCTCGTCATTTATGATGCACCGATTGACGCCAGTTGCGCGCAGGGCTGCTTCGACGATTGCTTGAAGGCCGAGGGC

ATCGCTACCGACCAACCACTTGGCACACTGCTCCGTCGCATATTGCGCATGTGCTGCCGCGATGCCAACCAGCCCGA

TABLE 6-continued

Sequences Corresponding to Frequency Peaks (SEQ ID NOs 21-167)

GGCGGTGCTTACTTACAATATTCCGGCATGCGCGGCGGTGAGAAGAAACACCAAATCATGACTGAGGGTTGACACGA
TACTTACGGTACCCCCACCACCCCTCGCTCACAGTGCGGCTCCGGCAACCTGCGTGAAGAGCGGCGTTATCGCGCGA
CCTGCTTCACGCGTGACGAGGGCCCTCTCGACGTGCTTGTGATACTAAAGGCGTGTATACGCACACAGGCACACTAC
TCACACTACTCACACATACATACGCACACATGCACACATGCACACACCAGCACTAACACTAACTAATATAGATACAT
ACTGCTACACTACGCCCAACATACACCAACGAGCTCGGTTTGAATTTCTGAACAAGTGAAATAGGCGAACATAGGAG
CTGTGCATGCCGCAGCAGAATATGGACGTTCTATTTAAAGCCCAAACGAGCAAGGGGACCACTGTGTGCAAAGCCTT
TTGCCGATCCGTCAGTCCCTCGTGGCGGCTGCACCGTGACGGCAATTGTGTACCCACCATAACGGCACCTTGCTCGG
CGGCTGACACTCAGACTATCACAAACGGTGCTATCGTGGAGGGCAAGAAGCAGGGATCGCGACACATGCCAGCGAAG
GCGGGACGCTGGACCAAAGGAATCAGGGGCTGGCTGATGCTGGTGCTGATATTACTAGGCAACTGCGACATTCTCGC
CAAGCAGGGCAGGGAGCGGCAGGCAGGGCAGGGAGCGGCAAACAATGGACTCGACCTGGGAGCCTGCCCGGACGCAG
CCTCACAGACAACTGAAAACGGTAGAGAACTACAAGTGGCTGGGGCTTGTGCTTGGCATAAAGACCGTGTGGTCTAC
GTAAACCCAAATGGATTTGGCTGCACTAACACTATTACACGCGCCGAGCTCGCTGCAATTCGTGCAGCCCTGGAAGA
ATTCGGAGGTGAAACTAGTATGTTCGCGAAGAAAACGCTAACCATTGCCAGTGACTCAGCTGCAAGCTTGTATCTAA
TTAAACGGGCTATTAACGAACCACGCCGCTTACATCTGAGCAAACATAAGGCACTTCTGAGTTCGATCGCCGATTTG
CTCCATGCACGAGCGAAGAGGGACGCACACACCGTTTTCCTCAAAGTCGTTTCTCACACGGGTCTGCACGGTAATGA
AGAAGCCGATAAAGGTGCAGCAGACGTAGCTACAAGCACTAAACCGGCTGACGTCTCGGAGCTCGCTGACAATAACC
CC

>SEQ ID NO: 85

GCGTCCCGTGATCCCTATTTGATGGTTCGCCGTCGAGTAGCTAGTTATGTCATACTTT

>SEQ ID NO: 86

CTGACATCCTGTTCATCCCATCCCTACCACGCTCCAACGTGGGGGCTAGTGGGCCCCGCGGCCTTACAACCGCCGGC
CGACGGCAACACAAAGTTTACCTGATAGAAGTTGGTTACACATCGGACCTCCACCACAGCGAAAAGTGTGACCAGAA
ACAAGCCCAGCACACTCGCCTAGCCGACGCCCTGCGGGATGCAGGCTGGACGTAGTATATAAAAAGGAGCAGATTG
TGACGCTGGGCCACGGCGGCACTGTGTCAAACACCTTGGAACCCCTTCTCCGGTCGCTGGGTGCCACCACCACATCA
GCAAAATCCTGCTGCTCGCGCATACACATGCACAGTGTCATCAGCCTGCGCACCACATCCCTTCTCTACTACCGCCT
TGAGCGCGAAATGGGGATTGTGAACTCACGCCACGTCGGTCCCACTGGCGGCGCCACGGCTGCTGGCCCCAGCCCTC
GCGATCCAGGCTAACTTCCCACCTTTTGACACGGTGGGGTGAGCAAAACTCACTCCTCCTTAAGAAACGCGGCCTCC
TTCGTGAACCGCGTACATATTATTATTATTATTATTATTATTATTATTATTATTATTATTATTATTATTATTATTAT
TATTATTATTATTATTATTATTATTATTATTATTATTATTATTATTATTATTATTATTATTATTATTATTATTATTA
ACCGCGTGTTCATGCAACTCCTTTCGATCGCGCAGCAGGCTTGAAGGGCTGGAGCTGCGGGTTGAGTATAGGCAGGG
CCGAACAGGAGTCCCAGGAAAGGGGCTTCGGGCCGTGAGTTGGTGATGCAGCTGATTATCAGCGTTCACGTCGAATT
TACTACTGCCGGCGTGAGGCGGCGGCAGCAGCTGCTGGCATGGGGCCCGTGGCGGCATACATGCTTGTGGTCATTCC
AACGGGCGCGCAGTGTTGGCCTTGCTTAATTGCTGGCATGTGTTGCCCCGCCGGCCATTACTCCCGCCACGCACGTC
ACCACGCGTACGCTGCCGCCGCCGCCCACATATTCCAGCGCACTATTTGTGCACTATTTGCCGCTTCTGTTACTAAC
TATTCTCGACACTACGGCACCTTTGTGATTTTGCACGGTATGACACGGCGGTACAGTGCCCAGGAGCAAGGATGACC
CCTGCGCC

>SEQ ID NO: 87

TGAATGCACACAGCATTGGGTTCTGGTTGGGCAGGTTCTACGGA

TABLE 6-continued

Sequences Corresponding to Frequency Peaks (SEQ ID NOs 21-167)

>SEQ ID NO: 88

CCTAAAACCCTAAAACCCTAAAACCCTAAAACCCAAAACCCTAAATCGGGGTTTTAAGGGGTTTTGCGGGATTTGAA
AAGTGTGACATGTCAGAAATAATTTGCACAGCATAAATAGCATAATTTCAGCAAGAATAATTGTTAGAGTCACTTGT
GGGTGATCATGATGTGGTTTGGGGGCATAGCAATGACCCAGTGCTTCCTTGTCAGCACGCGTCAGTAGGCGGGAAGG
GATGGGACTTCCATTGCCCCGCATACTAGCACCACTGTGGCATGCCGTTCACCCAGATCCATTTGTATACTATATTG
TGCTGTGTTGACAGATTGCGCATGCATGGTGTGCAAGCACATGCTGCTCAGGCCCCTTGGCATGCCANNNNNNN

>SEQ ID NO: 89

TATCACCCTGAAGATCAAGGAGTTTTACATAAATCCAACAGAGTTTGGTGTTTTCCACCAG

>SEQ ID NO: 90

TATGGAACCTCAGCGATGACCAGCAGCAGGCGTTCATGCTGTACGCGCAGCTCCTGCTAGCAGAGGCCGCCGGCGTC
CGTCAGCCCCCGTGTGCTCGGTGCTCACGGGCAAAGCCGGCAGCGGCAAGTCGCGGGTGCTGCAGGCATTGCTGTG
GTTTGCATATCAGCACCGCTGCGAGTCTCTCATTGCCCTCGTGAGCTACACGTGGCGCGCTGCGCTGCATGTGAGTT
GTGTGTGGGGTGTGTGGGGTGTGTGGTGCAAGAGGGGTTCAGTTCGGAGGTGAAGTGTGGCGGTGGTGGACTGGTTT
AGCAGCCAGGGAGCCTTACATGATCATGCTGTTGACTTCGGCCGCTGCCATCACGGTCCATTTACAGGACTCTACGC
CAGGCGTGCTCGGCACCAGCACCACGTCCTTCTTTGCGACTGCTGGCACCTTTGGTCCGCCTCACCGAGATCGAGTC
GAGCGCAACCTCAATGGTGTGCGCTTCATTTTCCTAGATGAGTTTAGCACGTGTGGGCTGTCCCACTGGGCGCGCAT
TTGCATGCATGTGCACGCGGCACGGAGGCACGTGGGTATAGACAGCACGCACCTATATCACGGGCCGCTGTCAGATC
TGCATGGCCTGCTTGTTGGCGACTTGCGTCAGTTGCCACAGCCACGGCACGTGCCGCTATATAGCGGTGCTGCGGAA
GAGAGCTTGCGGCAGCTGCTGGCGCCGGGCGCGGGGACGGCGGGGCCATGGAGCGCCAGATCCGGCAGCTGGAGCA
TCCGGAGGGCAGCATGAACCTCATGGGCGGGAGCTGTGGAATATGGTGCCGTTCGCGTTCGTTCTCACTCACCAGC
ATCGGCAGCAAGCAGGCGTAGGTGACAACAACGAACCTCTCTTCATGCTAGCGGAGAAGTTTGGTGGCGTGCAGGAA
ATCTCTCAGGCAGATCTGGATACAGCGTGCCAGCAGCTCAACGCGCGTGTTTGGCAGCCCCCGAAGCCAGGGATTGA
CCCCGTGCCCCAGCCCTTTGCAGTTGTCCAGCGCCATGTTGTGCGGGTTCCACTGGCATTGCAGCTCGTGCAGCTGC
ATGCGCTCGCGCAGCGTCAGCAGCTGCTGCTATGGCGTAGCGCGGACTTGTCGCCGGACGGGAGCAGCTTACCTATT
TCGCATGTGCATCAATTAGAGGCGCTTGGCGGGGCCGAGGATGATAGCGGTGTGCCCGCTGTGTGCGCATTCTTTGC
TGGCATTCGTTACGTGTTTACATCAAATGAGCATGTGCGTCTGTATCACATCAACAACAACAGTGCCACAGGCACCG
GCATTGTTCTGCATCCCAACGAGCCACCATTGCCAGATGCAAGCATTGCCCCCGTGCATGTCCTCAAGTTCGTGCCC
TCGGCTGTAATGGTGCGCCCCGACGGGCCTGATGCGGGTCGGGTGTCTGTCGATCAGGCCCTGGATGTCGGGGAGAT
TCCTGTTTTACCGTGCAGTGCTATGTTCACATCGCAGCATGCAACCCTGCGGTTGCCTGTGATGCGCTGGGGCTTTC
GTGTGGAGCTTGCGTATGCAGTCACCGATTACTTTGCGCAGGGGCAAACTCTGCCAGCGCACGAACTGTGGCTGGTG
GATATGTGCAAACCGCAGCACGGCAGTTGGCGGCGGGCTTCAATTTACGTAATGCTCACCAGGTTTCGTGGGTTGCA
TGCCTTACATTTAGTGCGTCCGCTGTGGGCCTCGCGGGCCGAAGAGCGCCGGCTTAAAAAGGCGCTGCGTACCATGC
TAACGCCCGAGGCAGATCTAGCCGCGAATGGCAGCGGCTATTGAGGCTCTCGCAGAGCACAGCAGTAGCAGTGCCA
GGTATGATTGTGCGCATTCAGGCCAGCATGGCTGCCTCATAACCAAGGCTTTCAATGCATGCAGTAGTGTTTTTAAC
ATGCGCGAGGTGTACTGACAGATGACCTGGAAGCGTGGAGTACCTTGTGGGTGGTGAGTGCTGACTGCAATTTACAG
CAGTGACTTTCTTGTTGGTGTTTGGTGTGGTGACCATCATGCTTGGCTTCGCTGGCTGGACGTATGTCACTGAGCTA
CGTTCGGGTTTAGTTTCTACCTGTCCTGTCTCTGCGTGAAGCCGGGGTATTGTTTATCTGCTTGCTTGTCGTGCGTT
GGATTGTTGTGTGTTTACAACAGGTTGATGTGTGGCGTGGTTAATCCCTTGCACTTTGAGGAGGTTATTGTTAGCCA
GCTGGTGTTCGCACAGGAGGTTGGTGGTCGATGAACAGTCGACCGACAGATGGATCGCGGGATTTGTTTTTGGCATT

TABLE 6-continued

Sequences Corresponding to Frequency Peaks (SEQ ID NOs 21-167)

TACCGCTTGGATTCTATTCGCAACGTAGCTCGGAATACACGCTTAATATGCATAGTTAGAAGACTTCGGGGACGCAA

ATCGCTCGGAAATGGAGGAGGGTCTCAATATGCTCGGCTCGCGATGTCGCGCTCTTGAGCTTGTATTATGCACTGTG

CGCAATGCGCGTTCAGCATGCATATTCTTACGAACAACTAGGGACTTGAGTGACGCGGTGTGAAAATCAGTCGGGGT

CTCGACATGCTTGGCTCGCCATTTCGCGCTCCCGAGCTCGTTGTGTGTGTTCCGAACAATGCACGCTCAGAATTACA

TGTTCAATATGTCCGTCGCGATGTTCGAGCTTGAAAACCGACAAGCATGGTGTATAGATACACCTGGTAGCCTGAAT

TCCTGTGTTTTTGGTGTATTTTGTTGATGTTGCATCACGCCGTGCCTTGTCACATTCATGTTTTTTGTACCGGCGTG

GCCTTGTTTGTAAATTTCGCGGCGCCCTGATCTTATCTACTTCTTCGCTGTGATCGGCAAAAAAAACTGTTCTTGA

CGGGATTCGAACCTGTGACAGCATCTCACTAAGCGCCATAATCAGACCCTCCAGAGGAGGGTGTGCACTCCGGTGAT

CGCACTGAACACGGCCTTACCTCCCCGGTACACATTGAACGAGGCACAGTCCAGGGCGACACACTCTCCCCCGTACT

CTTTCTGATGTTTATCGAACCGCTTATATGGTGGCTCCATGTAGGAGGCCGCGGCTACTCCTACGGTTGCTTACCAA

ACCACCTCAACAACAGGTTCCACTGCTCCTCAGCCGCCTACACCGACGACCTGGCGGTGCTTACAAACACCTTGAGC

GACCTACGCATTCAATGCGACAAAATCCACCGCTACTCGGCATGGGCGGGCCTCCAGGTGAACCACGCCAAATGCCG

AGTCACGGGAATCCTGCACCGAAGAGCCCAGCAGGACAAAGGCCTGAACGGTCCCACCTGCAACCGTACCCTCAAAT

CAATGCTCGAAAACAAAATCCACATTGGCGACAAACCTGTGCCTTACCTCCCCGCAACCGAACCCTTCAAATACCTG

GGAGTACAGATAACCATGAACTTGCACTGGGGACCCCAGTTTGCTTACCTATGTGATGCCATCAAAGAAAAAGTGC

CAACCTGCAAACGTCTCTCGCGTCACCAGAACAATGCCTGCGAATTATAAAATCCTGCATACAGTCTATGGCAGCAT

ACAGCTTTGCGGTTATGCCGTACGCAGAGAACGACATCCGCACCCTCGACGCCATGATTGCGCGGCTGGCAAAGAAG

TGTTACCGCCTCACCCCTGGGTTCCC

>SEQ ID NO: 91

GGCGACAAAACCTCGTGGTACCAGCAGTGGTTCGCGGAGTGCCCGTTCGGCCTGCTGGATGTCACCGGGCAGGACGT

GCTGGTGTGTGCCGTGCGGCGCACAGCAGATGGTGGGCTGCAACGCGCGCCGCTCGTCTCTGTAGGGCAGGTGCGAA

TAAGCTGCGGTCCGGGCGCATGTTGTTGCATGTTATCGGTTGTATGGCGGTGTGCGTGTTCAGCATGCTGCTGTCGC

GCTTGCCTGCAGGTGTCGGGCGAGGCGGGGCGCGCTCTGCGCAACAAGGTGGCGCGCACGTGTCAAGAGGTCCACAA

TGGCGACGCCTGGGCTCACATCGACAAGCACTACGACGGCAACTTCTGGATGGCGGGGCTGGCGTCGCCTGCTCGCG

TGGGACACATCATCTGCAGGCAAGAGCACCAGGGGGGTGTTGCATGCGGGCGGCAAGGGTGGCGCGGGCATGGAGGA

GAGGCATGGATGTGCGGTGGGGCCGAGATTGACTGATACGTTGCTGTGCAGGTACGTCAACCAGATCATCTACGAGT

GCGAGGCGGAGCATTATCCATTCAGCATCGAGGAGGCGCTGGAGGAGATGTGTACGCGGTGTGGGAGGCGGCGGTG

CAGGTTGCGCCGTACCTGACCAAGTACAGGTGAGGGCGCCGCGTAGCCGCGGGGCTGCATGCAAGGGCAGTACGTGC

AGGATGGTTGTGTGGGGCGTCGCGTACGTAGCATTGATGTGTGGTGCTGCACGCTCTGGGTCTGCGCGCAGGGATGA

GTTCTTGTCTGCCTGGGGGCGCCAGGCGATGTACGGCGACACGGCAACTAACCTCGTGAGCATGACCAAGAACTGCG

CGGTGTCGTTGCACTTCGACACAACGGACGGTGAGGCTGGTGCGCAGGGGTGTATATCAGGGAAGCGCTGCTTGTGT

ATTTGTGTGTGGGCGGGGGGGGGGGGGGCGGCGGTGGATGGGTGAGTGGGTGTGCGTGCGAGCTGGCTTGT

GTAGATCTGGGAGGGTGGGCGTACTGTGAGGCAAGGTGGTGGTGCTGGTCTGCTATCTGCGTGCTGCTAATGAGTGT

GAATTTCTTCGCGTGGGAATTGACACGCAGGGCCGTACAGCATCATGCTGTGGCGCCACAACGGTGCCGGCAGCCTG

GACGGCGGGCATTTCTTGATGCCTGGCGCCTCCATCAAGGTAAATGGCCAGGTGGTGCATCTCTGCGGGCGGGTGTG

GTTTTGTGTGTCGGCCAGGCGCGCGTATAGTGAGGTCGCGGTGCGGACATGCAAGTCATATGGGCGCTGTTGTTT

GCAGGTGCTGCCGACCGACATGACGATCGTGGTGCTGGCTGCTGGCATGGTCACGCATGGGACGGCGCCCGTGCTGG

AGTCCACTGGCGACGCGCGGCGGTATGGCTACTCGCATTTCCTGCGTGTGCCGGCCATGGAGCGTGTGGCGCGGCTG

ATCAAGGCATCTGGCGGAAAGAAGAAGATGGAGGAGCTGCAGGTACAGGGCATGAAGCGCGTGTTGGCTGCACGTAC

TABLE 6-continued

Sequences Corresponding to Frequency Peaks (SEQ ID NOs 21-167)

AGCAGCGGATCGGAAGGCGCGGCGGGATGAAATCCAGAAGCAGCGGGACGAGCTCCTGAAGAGCGCGCTGGACGGCG
AGGCGCTGCCCGAGGGCGAGCATTTAGCGTTTGCTGTGCGAGGGTTGAAGTGGCACCGGGACATTGTGAAGTGCCTG
GTATGGCAGGACTTCAAGGGCAAGTCCTGAGACCTGTAGCAGGAGGAGCGGGTGGGTAGTAGTGGTTCGTGTAGAGG
CGTGTTGGGCTGTGTAAGTGAGAGGTCATGGGAGTACACAACGCAAATAAAGCAAGAACAGCGGGAGTTTGGTAGGC
AGCGCCAACAGGCGCGAACGCTGCTGGGGAGTTGGTGTGTTGCAGTGGGAGTTGGGCCATGCACGTGAGACAGCGAG
TGGCCGTACAGGTGTTCGCATTTGCATGTTAAAAGGACTGTGCCATTTGCGCCAAGCAAGTGGATGGAGTGGGTGGG
TGATGAACTGGATTGTGGGGTAGAGCTGTGGGCAGGGGCATGCGTTGGGGAACCGGTTTTTCTGTGAGGGCGTGTGG
GTGCGCTAAGGGCAATGTAACAAGACAGCGTGGCTGTAGTCAGGTAGCAGTGTAGGGTTGCGGTTGGGGCTGGGCTG
CAGCGGAAGTAGAAGTAGGGGTAGCTGCTTGTTGTGGTGAAGATGCGCGGGGTGTCGTGCTGGCGAAAGCTTGCAAA
GGTAGTGGGGTGCTGCATTGAGGCGCATGAGGCGCAGTGCATTGGCAGAGGTGCTGGAATGGACAGGAGGCAGCGAG
TGCAATGGCATGAGATGAGCGTTTGTATACAATGAAGGTGTGCAGAACTCGCAACGTTGGCAACGTGCAACATCAAT
GTGTTTGTCGTGGTACCATAAGCAGAACTGCGCCAGGCTGTAAGCACTGAGACTAGGAAATGTCAAGCAGCCGCACA
GAAGATACATCTACGCAACAGCCACAGCTTTTCAATAGCGCATTTGCGCGCACTACCAAGCACTTCACAAACGCCTC
CGTGCACACATGCTGCGCATGAAAGCGAGGAATGCAGGTTGGTTCTAAGCAGAGGTGGAGGCGTAATCAGTCGTGGA
GGAGTAATCAGCATTACGGCAGCTGCGCCTGCACGGTGGCGCCCGCGATAGTCCAACGGCCGATCCGGGCGTGCTGC
GGCTCGTAGCCAGCGGACTGCGCGGCCCAAGCGAGTACGGCGTCCAGCTGCGCTCCGTAGACGACGCGCGCCACATC
AGGCGGCATGGTGACCTTCAAGGTGCGGGAGATGCGAGAGGCATGCATGGTCAGGTGGAGTGCACTCAGGAGATGC
GAGAGGCACGCATGGTGAGGTGGAGTGGCGGGTGGTGGATGGCATGAGCGCAGTCCAGGGAACGCACCAGGGTGCCA
TCGTATGCAGCCAGCGCGGCCGACAGCAGGTAGCCGATGAGGTTGTTGTTGCTGCAGGTAGGCAGGTTTGGATGAAG
CGCAGTGTGGTGAGCAAACTGGTTGGGTGATGCGGGGCCGAGCTTGGCAGGTACGTAGCCCAACCTATATAGGAGGG
TGGCTTGCGCACTTACTCGAGCACCACTGGCATGAAGGCACCATACACCGGCGCGTGGCTGGTGAAGGCGGCCTGGT
CGATGTTGGAGTTGAGCGTGAGCATGTTTTGGTCATGCACCAGGAGCTCGACTAGGATGTGGATCAGGAGCGGAGTG
TCGGGCGTGACGCCCATGATGCCGGTCTCCA

>SEQ ID NO: 92

TCCCTACCTACCTGTCCAAGGCCAAGCCGTGTCAGCTACTGCTGCAAGGGATGTCGAAAGCGGTGACGTTTGGGGCT
GGGGAAGCGTTGTTTCAGGGGTTGACTTTGCAGAACCATCCTGTTGTGTTGCCTGCACTTGAGTCTAGCGTAGCTGT
TTGGTACGCACCGCCCCTGCCTGTTAGCAACGCGAATTCTTCTCCTCATGTCTCTTCGTTGTATCTGACCGCATCCT
CTGCTGTGCCGTCTGCTGCCGCTTCGACCGCAGGGCCTCTGCCTATCGTGCCTGCACGAGTTGGCGGCCTGCGCGTG
TCTGTGCTCGCTGACACTGGAGCTAGTCACGACTTCGTCTCCAAGGCTCTGTGTGACCAGCTGGGACTCAAGTTGTC
GATGGTGGTAAGCAGACCATTCTGGGCCGTGTAGCGTTGCGCGTAGCGTTCGGTTCTGCATTCCTTACGCTCCGTCC
GTTCGTCCTGCCTACCTTCACTGATGCCGCGCAAATGATCATGGGTGCTAGTACTATGTTGCGCGAGGGGGTAGCTG
TAGACATGGGTAAGCACGCTCTGGTGCTGCGAACGGCCAAGCGCACTGTTTCTGTACCGCTCCGGACCATAGGCTTG
CATGCCCTGACTGTAGCGTCCGTTGCGATCGACCAACCCACTGAGAACCTGGCGTTGTCGGCCATTATTGCCATGGC
TCTGCACGCCAAACCCGGTAGTTCTCACTACCTCCCTTAATCGGGAATAGACACGACACCGACGATGGCGCCCTCAG
CGCTGCTGAGCTGCTTGCAGCGCTGGGCAGCGCTGCCAACGGTAAAGCGCTGGGCTCGGATGGGCTGCCTTACAAGG
TGTACAAGGTCTGCGGGACCAGGCTGTCTTCGGGTCTCTGTGCCCAGCAGTAGGGGGTAGCGTGTCTGCCCCTGGT
CAACTCTGTAAGGATGAAGCCTAAAAATAAGTGTTTTGGGCGCTCTCACTCTGGGAAAAGGGGGGGGAAATCCCGG
GAAAAACAGGGGTAGTTCCCCGGAAATATCTTCCCCGCCGTACTGTATGCTTTTCGAAGAAAGTAGGAGTTTGTAC
GGGGAAGTCCTTACGGGGAAGTTCTTACGGGAATAATAATAATAATAATAATAATAATAATAATAATAATAATA

TABLE 6-continued

Sequences Corresponding to Frequency Peaks (SEQ ID NOs 21-167)

ATAATAATAATAATAATAATAATAATAATAATAATAATAATAATAATAATAATAATAATAATAATAAT
AATAATAATAATAATAATAATAATAATAATAATAATAATAATAATAATAATAATAATAATAATCCCAA
CGCTGGCCCATAGGGCCTAGCATGTATTAACGGGGCAACGCCTTCGCTCATCATCTCTCAACCCAGTTCGAGAGAAG
GCGGGAAGTCACCACGACCACCTTATCATTTTCCGGTCCTGCCCACCGGTGGGAGCGGGGTGGATTAAGCCCCTGGT
GTCCTATCCATGTTCAGCTCGGATGATCTACCCTCACCGCTTTCGGTACCTGAGATCGGGGGATCAGGTAATGCCGA
CTGTCGGGCAACATCTCAACTGAAACTCTGGATCGATCCAGAGTCCGGCCCCTTTGCCGGCACTTCACGACCGCTCT
CTTATCTGACGTTAGCCATGGATGACAAGGACACGACTGAAGAGCCGTGCGGTCCCTGCGGAGCGCCTGTGCGTGAT
TTGAATACGCACGGAGGTTTCCCCTGTACCGAATTTGGGGAGGATCGAACCCAGGTCTGAACCGACGTTACACACCA
AC

>SEQ ID NO: 93

TTTAAGGGGTTTTGCAGGGTTTGGAAAGAGTGACATGTCAGTAATGATTTGCATAGCATAGTTCAGCTTATTATAAC
TAGAATGATTGTTTGAACCCCTTGTGGGTGACCATGATGAGGTTCGGGCACATAGCAATGACTTTGCGTGCTTCCTT
GTCACAGCCTTGAGAGCACAAGCACGTGGGAAGGGATGCAACTTCCAAAGCCCTGCATACTCGCACCACTGTGGATT
GCCATTTGCTCAGATGCAGCTGTATACTGTGTTGTGCTGTGTTGCAGGCTTACAGATTGCACAGATGCAAGCCTATG
CCACTCATTCCCCTTGGCCCCACACCGGGGCCCGTGTTGCCCAATCCAGCCTGCCTGCCTTGCTCACCCATGTGCAA
GACTCTTCCACATTCATGTATGCACATGTTGCCTGACCTGTTTGTAATGTAACCACCAGCTAAGCGCAGTGGTGCCA
GCACTTGCAGCGCCCCATATGGCTCTGCACATCACAACAAGTGCCCCTGGCTTGCCTCCCCTCTCCCAGGGGTCAGG
TATCATGCAGGCTGTCAAATAATGTGCTGCCATGCTAAGGACAGTCTAGTCACACCATATGTTAGTGATGGGCTTTG
GGAGTGCAAGCAGAAGCAGCCACAGCACATTGGCATGTCCAGACCCGAATGCCTGGTGCGCCTGCCGACCACACCGG
TGGCGCCAAGTCGGCAACCGCTCCACTCCAGCAAGCTCCAGCTCATGCCAAACATACAACGGCAGCCGCTATATGTA
TATAAGCAATAGCTGTGCCAAACGGCTGCGTGGCTGGACTGCTGCACTCACTCACGTGGCCCCTGGCCCTGGGGTCA
CCTAAATCTGGGTTTTAAGGGGTTTTGCAGGGTTTGGAAAGAGTGACATGTCAGTAATGATTTGCATAGCATAGTTC
AGCTTATTATAACTAGAATGATTGTTTGAACCCCTTGTGGGTGACCATGATGAGGTTCGGGCACATAGCAATGACTT
TGCGTGCTTCCTTGTCACAGCCTTGAGAGCACAAGCACGTGGGAAGGGATGCAACTTCCAAAGCCCTGCATACTCGC
ACCACTGTGGATTGCCATTTGCTCAGATGCAGCTGTATACTGTGTTGTGCTGTGTTGCAGGCTTACAGATTGCACAG
ATGCAAGCCTATGCCACTCATTCCCCTTGGCCCCACACCGGGGCCCGTGTTGCCCAATCCAGCCTGCCTGCCTTGCT
CACCCATGTGCAAGACTCTTCCACATTCATGTATGCACATGTTGCCTGACCTGTTTGTAATGTAACCACCAGCTGAG
CGCAGTGGTGCCAGCACTTGCAGGGCCCCATATGGCTCTGCACATCACAACAAGTGCCCCTGGCTTGCCTCCCCTCT
CCCAGGGTTCAGGTATCATGCTGGCTGTCAAGTAATGTGCTGCCATGCTAAGGACAGTCTAGTCACACCATATGTTA
GTGATGGGCTTTGGGAGTGCAAGCAGAAGCAGCCACAGCACATTGGCATGTCCAGACCCGAATGCCTGGTGTGCCTG
CCGACCACACCGGTGGCGCCAAGTTGGCAACCGCTCCACTCCAGCAAGCTCCAGCTTGCGCCAACCATAGAACGGCA
GCCGCTATATGTATATAAGCAATAGCTGTGCCAAACGGCTGCGTGGCTGGACTGCTGCACTCACTCACGTGGCCCCT
GGCGCAGGGTGGCCTAAATCAGGGTTTTAAGGGGTTTTGCAGGGTTTGGAAAGAGTGACATGTCAGTAATGATTTGC
ATAGCATAGTTCAGCTTATTATAACTAGAATGATTGTTTGAACCCCTTGTGGGTGACCATGATGAGGTTTGGGCACA
TAGCAATGACTTTGCGTGCTTCCTTGTCACAGCCTTGAGAGCACAAGCACGTGGGAATGAACGGATGCAACTTCCAA
AGCCCTGCATACTTGCACCACTGTGGATTGCCATTTGCTCAGATGCAGCTGTATACTGTGTTGTGCTGTGTTGCAGG
CTTACAGATTGCACAGAAGCAAGCCTATGCCGCTCATTCCCCTTGGCCCCACACCGGGGCCCGTGTTGCCCAATCCA
GCCTGCCTGCCTTGCTCACCCATGTGCAAGACTCTTCCACATTCATGTATGCACATGTTGCCTGACCTGTTTGTAAT
GTAACCACCAGCTGAGCGCAGTGGTGCCAGCACTTGCAGGGCCCCATATGGCTCTGCACATCACAACAAGTGCCCCT

TABLE 6-continued

Sequences Corresponding to Frequency Peaks (SEQ ID NOs 21-167)

GGCTTGCCTCCCCTCTCCCAGGGTTCAGGTATCATGCTGGCTGTCAAGTAATGTGCTGCCATGCTAAGGACAGTCTA
GTCACACCATATGTTAGTGATGGGCTTTGGGAGTGCAAGCAGAAGCAGCCACAGCACATTGGCATGTCCAGACCCGA
ATGCCTGGTGCGCCTGCCGACCACACCGGTGGCGCCAAGTTGGCAACCGCTCCACTCCAGCAAGCTCCAGCTTGCGC
CAACCATAGAACGGCAGCCGCTATATGTATATAAGCAATAGCTGTGCCAAACGGCTGCGTGGCTGGACTGCTGCACT
CACTCACGTGGCCCCTGGTGGTGAGAGCAAACATTTATTTTCTTTTACAGGCTGTCTTCCAGGGCGCTGTTAAATGC
AATAGATAAAGATTGGATCATCGAGAAATATACGTCGCTTAAATGCTCCCACCAGCTGGTGTTGGTTGCCTGATCGC
CGCGGTCTACGCGGTCGCTCGCTCACCAGCTCGCCGACGAACTTCCGCGATCAAGGTGGCAGTCAAAGTGTCGAATA
GACAACATTCTCTAGTCGAGGCATGCAGTATAAACATCTTAAATGAAAAAAGCCTTACAAGTTGCAGCTGTCAAACG
AGTCAAATTTCTGCACTTCAGTTGCCTCTTTCGCGCTCGTGGCTGTTTGCCATGTGCACCTTCAGATTTCAGCATAC
ATATGTAGAAATTGGCTCCGACGACGGAGCTGGAGAGAACTCGAAGGGCTGGACCAAATGATTGTCGCTGGAGCGTC
GTTCCAACTTCAGTATGTCACTGCTCCCCTGCATTGGTAAGTGCACAAGCGTGATGAAGACAGGGACACAGA

>SEQ ID NO: 94

AGGGTTTGGAAAGAGTGACATGTCAGTAATGATTTGCATAGCATAGTTCAGCTTATTATAACTAGAATGATTGTTTG
AACCCCTTGTGGGTGACCATGATGAGGTTTGGGCACATAGCAATGACTTTGCGTGCTTCCTTGTCACAGCCTTGAGA
GCACAAGCACGTGGGAATGAACGGATGCAACTTCCAAAGCCCTGCATACTTGCACCACTGTGGATTGCCATTTGCTC
AGATGCAGCTGTATACTGTGTTGTGCTGTGTTGCAGGCTTACAGATTGCACAGAAGCAAGCCTATGCCGCTCATTCC
CCTTGGCCCCACACCGGGGCCCGTGTTGCCCAATCCAGCCTGCCTGCCTTGCTCACCCATGTGCAAGACTCTTCCAC
ATTCATGTATGCACATGTTGCCTGACCTGTTTGTAATGTAACCACCAGCTGAGCGCAGTGGTGCCAGCACTTGCAGG
GCCCCATATGGCTCTGCACATCACAACAAGTGCCCCTGGCTTGCCTCCCCTCTCCCAGGGTTCAGGTATCATGCTGG
CTGTCAAGTAATGTGCTGCCATGCTAAGGACAGTCTAGTCACACCATATGTTAGTGATGGGCTTTGGGAGTGCAAGC
AGAAGCAGCCACAGCACATTGGCATGTCCAGACCCGAATGCCTGGTGCGCCTGCCGACCACACCGGTGGCGCCAAGT
TGGCAACCGCTCCACTCCAGCAAGCTCCAGCTTGCGCCAACCATAGAACGGCAGCCGCTATATGTATATAAGCAATA
GCTGTGCCAAACGGCTGCGTGGCTGGACTGCTGCACTCACTCACGTGGCCCCTGGCGCAGGGTGGCCTAAATCAGGG
TTTTAAGGGGTTTTGCAGGGTTTGGAAAGAGTGACATGTCAGTAATGATTTGCATAGCATAGTTCAGCTTATTATAA
CTAGAATGATTGTTTGAACCCCTTGTGGGTGACCATGATGAGGTTTGGGCACATAGCAATGACTTTGCGTGCTTCCT
TGTCACAGCCTTGAGAGCACAAGCACGTGGGAATGAACGGATGCAACTTCCAAAGCCCTGCATACTTGCACCACTGT
GGATTGCCATTTGCTCAGATGCAGCTGTATACTGTGTTGTGCTGTGTTGCAGGCTTACAGATTGCACAGAAGCAAGC
CTATGCCGCTCATTCCCCTTGGCCCCACACCGGGGCCCGTGTTGCCCAATCCAGCCTGCCTGCCTTGCTCACCCATG
TGCAAGACTCTTCCACATTCATGTATGCACATGTTGCCTGACCTGTTTGTAATGTAACCACCAGCTGAGCGCAGTGG
TGCCAGCACTTGCAGGGCCCCATATGGCTCTGCACATCACAACAAGTGCCCCTGGCTTGCCTCCCCTCTCCCAGGGT
TCAGGTATCATGCTGGCTGTCAAGTAATGTGCTGCCATGCTAAGGACAGTCTAGTCACACCATATGTTAGTGATGGG
CTTTGGGAGTGCAAGCAGAAGCAGCCACAGCACATTGGCATGTCCAGACCCGAATGCCTGGTGCGCCTGCCGACCAC
ACCGGTGGCGCCAAGTTGGCAACCGCTCCACTCCAGCAAGCTCCAGCTTGCGCCAACCATAGAACGGCAGCCGCTAT
ATGTATATAAGCAATAGCTGTGCCAAACGGCTGCGTGGCTGGACTGCTGCACTCACTCACGTGGCCCCTGGCGCAGG
GTGGCCTAAATCAGGGTTTTAAGGGGTTTTGCAGGGTTTGGAAAGAGTGACATGTCAGTAATGATTTGCATAGCATA
GTTCAGCTTATTATAACTAGAATGATTGTTTGAACCCCTTGTGGGTGACCATGATGAGGTTTGGGCACATAGCAATG
ACTTTGCGTGCTTCCTTGTCACAGCCTTGAGAGCACAAGCACGTGGGAATGAACGGATGCAACTTCCAAAGCCCTGC
ATACTTGCACCACTGTGGATTGCCATTTGCTCAGATGCAGCTGTATACTGTGTTGTGCTGTGTTGCAGGCTTACAGA
TTGCACAGAAGCAAGCCTATGCCGCTCATTCCCCTTGGCCCCACACCGGGGCCCGTGTTGCCCAATCCAGCCTGCCT

TABLE 6-continued

Sequences Corresponding to Frequency Peaks (SEQ ID NOs 21-167)

GCCTTGCTCACCCATGTGCAAGACTCTTCCACATTCATGTATGCACATGTTGCCTGACCTGTTTGTAATGTAACCAC
CAGCTGAGCGCAGTGGTGCCAGCACTTGCAGGGCCCCATATGGCTCTGCACATCACAACAAGTGCCCCTGGCTTGCC
TCCCCTCTCCCAGGGTTCAGGTATCATGCTGGCTGTCAAGTAATGTGCTGCCATGCTAAGGACAGTCTAGTCACACC
ATATGTTAGTGATGGGCTTTGGGAGTGCAAGCAGAAGCAGCCACAGCACATTGGCATGTCCAGACCCGAATGCCTGG
TGCGCTGCCGACCACACCGGTGGCGCCAAGTTGGCAACCGCTCCACTCCAGCAAGCTCCAGCTTGCGCCAACCATAG
AACGGCAGCCGCTATATGTATATAAGCAATAGCTGTGCCAAACGGCTGCGTGGCTGGACTGCTGCACTCACTCACGT
GGCCCCTGGCGCAGGGTGGCCTAAATCAGGGTTTTAAGGGGTTTTGCAGGGTTTGGAAAGAGTGACATGTCAGTAAT
GATTTGCATAGCATAGTTCAGCTTATTATAACTAGAATGATTGTTTGAACCCCTTGTGGGTGACCATGATGAGGTTT
GGGCACATAGCAATGACTTTGCGTGCTTCCTTGTCACAGCCTTGAGAGCACAAGCACGTGGGAATGAACGGATGCAA
CTTCCAAAGCCCTGCATACTTGCACCACTGTGGATTGCCATTTGCTCAGATGCAGCTGTATACTGTGTTGTGCTGTG
TTGCAGGCTTACAGATTGCACAGAAGCAAGCCTATGCCGCTCATTCCCCTTGGCCCCACACCGGGGCCCGTGTTGCC
CAATCCAGCCTGCCTGCCTTGCTCACCCATGTGCAAGACTCTTCCACATTCATGTATGCACATGTTGCCTGACCTGT
TTGTAATGTAACCACCAGCTGAGCGCAGTGGTGCCAGCACTTGCAGGGCCCCATATGGCTCTGCACATCACAACAAG
TGCCCCTGGCTTGCCTCCCCTCTCCCAGGGTTCAGGTATCATGCTGGCTGTCAAGTAATGTGCTGCCATGCTAAGGA
CAGTCTAGTCACACCATATGTTAGTGATGGGCTTTGGGAGTGCAAGCAGAAGCAGCCACAGCACATTGGCATGTCCA
GACCCGAATGCCTGGTGCGCCTGCCGACCACACCGGTGGCGCCAAGTTGGCAACCGCTCCACTCCAGCAAGCTCCAG
CTTGCGCCAACCATAGAACGGCAGCCGCTATATGTATATAAGCAATAGCTGTGCCAAACGGCTGCGTGGCTGGACTG
CTGCACTCACTCACGTGGCCCCTGGCGCAGGGTGGCCTAAATCAAGGTTTTAAGGGGTTTTGCAGGGTTTGGAAAGA
GTGACATGTCAGTAATGATTTGCATAGCATAGTTCAGCTTATTATAACTAGAATGATTGTTTGAACCCCTTGTGGGT
GACC

>SEQ ID NO: 95

TGTTTTAACACGTTATGTTCGGTTATGGTGGTAAACTATGGGATTCGTATTTTCCCAGATGAAGCTGTTACTATGCG
TCCTGCTGGTACTCGTTCGGGTA

>SEQ ID NO: 96

ATGTGCTCAGAAAGGCGTCTGAAGCTGCAGTTTCGGAATTGTGGACAAGTTGTTCCGATGACCCCAGAGGTTCTATG
GCTTAATGCACACCCTCCTCTGGAGGGTCTGATTATGGCGCTTAATGAGATGCTGTCACAGGTTCGAATCCCGTCAA
GAACAGTTTTTTTTGCCAGATCACAGCGAAGAAGTAGATAAGATCAGGGCGCCGCGAAATTTACAAACAAGGCCACG
CCGGTACAAAAAACATGAATGTGACAAGGCACGGCGTGATGCAACATCAACAAAATACACCAAAAACACAGGAATTC
AGGCTACCAGGTGTATCTATACACCATGCTTGTCGGTTTTCAAGCTCGAACATCGCGACGGACATATTGAACATGTA
ATTCTGAGCGTGCATTGTTCGGAACACACACAACGAGCTCGGGAGCGCGAAATGGCGAGCCAAGCATGTCGAGACCC
CGACTGATTTTCACACCGCGTCACTCAAGTCCCTAGTTGTTCGTAAGAATATGCATGCTGAACGCGCATTGCGCACA
GTGCATAATACAAGCTCAAGAGCGCGACATCGCGAGCCGAGCATATTGAGACCCTCCTCCATTTCCGAGCGATTTGC
GTCCCCGAAGTCTTCTAACTATGCATATTAAGCGTGTATTCCGAGCTACGTTGCGAATAGAATCCAAGCGGTAAATG
CCAAAAACAAATCCCGCGATCCATCTGTCGGTCGACTGTTCATCGACCACCAACCTCCTGTGCGAACACCAGCTGGC
TAACAATAACCTCCTCAAAGTGCAAGGGATTAACCACGCCACACATCAACCTGTTGTAAACACACAACAATCCAACG
CACGACAAGCAAGCAGATAAACAATACCCCGGCTTCACGCAGAGACAGGACAGGTAGAAACTAAACCCGAACGTAGC
TCAGTGACATACGTCCAGCCAGCGAAGCCAAGCATGATGGTCACCACACCAAACACCAACAAGAAAGTCACTGCTGT
AAATTGCAGTCAGCACTCACCACCCACAAGGTACTCCACGCTTCCAGGTCATCTGTCAGTACACCTCGCGCATGTTA
AAAACACTACTGCATGCATTGAAAGCCTTGGTTATGAGGCAGCCATGCTGGCCTGAATGCGCACAATCATACCTGGC

TABLE 6-continued

Sequences Corresponding to Frequency Peaks (SEQ ID NOs 21-167)

ACTGCTACTGCTGTGCTCTGCGAGAGCCTCAATAGCCGCTGCCATTCCGCGGCTAGATCTGCCTCGGGCGTTAGCAT

GGTACGCAGCGCCTTTTTAAGCCGGCGCTCTTCGGCCCGCGAGGCCCACAGCGGACGCACTAAATGTAAGGCATGCA

ACCCACGAAACCTGGTGAGCATTACGTAAATTGAAGCCCGCCGCCAACTGCCGTGCTGCGGTTTGCACATATCCACC

AGCCACAGTTCGTGCGCTGGCAGAGTTTGCCCCTGCGCAAAGTAATCGGTGACTGCATACGCAAGCTCCACACGAAA

GCCCCAGCGCATCACAGGCAACCGCAGGGTTGCATGCTGCGATGTGAACATAGCACTGCACGGTAAAACAGGAATCT

CCCCGACATCCAGGGCCTGATCGACAGACACCCGACCCGCATCAGGCCCGTCGGGGCGCACCATTACAGCCGAGGGC

ACGAACTTGAGGACATGCACGGGGGCAATGCTTGCATCTGGCAATGGTGACTCGTTGGGATGCAGAACAATGCCGGT

GCCTGTGGCACTGTTGTTGTTGATGTGATACAGACGCACATGCTCATTTGATGTAAACACGTAACGAATGCCAGCAA

AGAATGCGCACACAGCGGGCACACCGCTATCATCCTCGGCCCCGCCAAGCGCCTCTAATTGATGCACATGCGAAATA

GGTAAGCTGCTCCCGTCCGGCGACAAGTCCGCGTACGCCATAGCAGCAGCTGCTGACGCTGCGCGAGCGCATGCAG

CTGCACGAGCTGCAATGCCAGTGGAACCCGCACAACATGGCGCTGGACAACTGCAAAGGGCTGGGGCACGGGGTCAA

TCCCTGGCTTCGGGGGCTGCCAAACACGCGCGTTGAGCTGCTGGCACGCTGTATCCAGATCTGCCTGAGAGATTTCC

TGCACGCCACCAAACTTCTCCGCTAGCATGAAGAGAGGTTCGTTGTTGTCACCTACGCCTGCTTGCTGCCGATGCTG

GTGAGTGAGAACGAACGCGAACGGCACCATATTCCACAGCTCCCGCCCCATGAGGTTCATGCTGCCCTCCGGATGCT

CCAGCTGCCGGATCTGGCGCTCCATGGCCCCGCCGTCCCCGCGCCCGGCGCCAGCAGCTGCCGCAAGCTCTCTTCC

GCAGCACCGCTATATAGCGGCACGTGCCGTGGCTGTGGCAACTGACGCAAGTCGCCAACAAGCAGGCCATGCAGATC

TGACAGCGGCCCGTGATATAGGTGCGTGCTGTCTATACCCACGTGCCTCCGTGCCGCGTGCACATGCATGCAAATGC

GCGCCCAGTGGGACAGCCCACACGTGCTAAACTCATCTAGGAAAATGAAGCGCACACCATTGAGGTTGCGCTCGACT

CGATCGCGGTGAGGCGGACCAAAGGTGCCAGCAGTCGCAAAGAAGGACGTGGTGCTGGTGCCGAGCACGCCTGGCGT

AGAGTCCTGTAAATGGACCGTGATGGCAGCGGCCGAAGTCAACAGCATGATCATGTAAGGCTCCCTGGCTGCTAAAC

CAGTCCACCACCGCCACACTTCACCTCCGAACTGAACCCCTCTTGCACCACACACCCCACACACCCCACACACAACT

CACATGCAGCGCAGCGCGCCACGTGTAGCTCACGAGGGCAATGAGAGACTCGCAGCGGTGCTGATATGCAAACCACA

GCAATGCCTGCAGCACCCGCGACTTGCCGCTGCCGGCTTTGCCCGTGAGCACCGAGCACACGGGGGGCTGACGGACG

CCGGCCGCCTCTGCTAGCAGGAGCTGCGCGTACAGCATGAACGCCTGCTGCTGGTCATCGCTGAGGTTCCATAACCG

CGCTGTGTCTTCAGGCGTCGGCTGCGAGTCCTCCGGGCAAAGCACGTACGGCGGCTCTGCACCAGGGTTCGCTGCAT

CGGGCCAGACGCCCTGCACCTCTGGGGCGGCTGTGGTAACCGCCAATGGCGAGATGAGCACCAGCTTCGCTGTCACT

GCTGCAGTGCCGCTGTTGTAAAGCAGCAGCTGCTGCTGCACTGCTCCCTGCGCCTGCGCGAGTGCCTGTGCGGCGTA

CTGCCCGCCTAGGTCGTAATCATGCATGCGTTGCTGTGCTGCAGCCAGCCGCTCGTGTGTCCACTCCTGCGTGCTGC

GCACTACTGCTGCCGCCGCTGTACGCC

>SEQ ID NO: 97

CCGCCTAACAACGCGCACAAGCTCCCCAGCAGCAGCAGAGGAGCCGCCTGCAGCACCAGCAGCGCCTGCGCTCCAAA

TGCCCCTCGCTCCTGCCGGGTGTCCTTCCGCGCACCTGCATGTACACGCAGTTGGCATGTATCCGCATCACACCCTC

TGGCAACCACAGCTCCCTGTGACCGCCACTACTGGCGCCCCGCGCGTAACTGTCTCATCCGCTTTGCGCACCCAACT

ACCCATGCCGCCGACGATGCTACTCCACCGCAACAACACACCTGGCGCCCACCCACCCCCACCCTGCGCTCACCATG

CTGCCAAGTCATGTACGCCAAATGACCACACCGCTCCACCGCGAAGAAATGCCGCCACCCTCGGAGGCCATGAGACC

ACCGAAGCTCTCCACTCGCTTCGCCGCCGGAGACCGGCAGACCGTCCAAGCGCAAAGCACGCCACTGAGCCTGCCCG

GCGCCCATCCAGCCGCTCGCCAACAGCACAGCCGCCGCGGCTGCCGCTGCCATGAGTACGCTAAGCGCAACGATGAC

GACAGCATCGCGCAGCCTGACAGGCCGCGCCCTGCACAACAGCCACACCCGGATAAATTGAAGGCACAATTCTGCTC

TGCGCCCCAAACCTCCGCTGCACGGCATGCCATGCTTACCATCGCCATGATTGCGCACGCTTGCGTGCCTCCAAGCG

TABLE 6-continued

Sequences Corresponding to Frequency Peaks (SEQ ID NOs 21-167)

CACTGCACGTCGCAGTTCCTCGTAGTTGCCTCGAAGCGACATTGCTGAGCTTCACGCTATGCTACCGTGCGTGTCCA

CTAGCACTCCCATAGTCCACGTATATATTTACTACATCGACGAGCGGCTCGCATTTCCCGCGGGGTGACGCGCCCGA

TGGGTCGAACGCAAATCCGCGATCCACCGTGCCGTGCGGCTCGTTCTAGTGGCTTGTGCTGTCCACCCTACATGCAT

ACGTGAATGCGCATGAGCGCATAATAGCCCGGCCGAATTCAAGCTACACACGCGGAGTCCATCTTATCCCGCATTTC

CGCTTCCATGGCTATTTACAGTTTCGTTGCACAACTTGCTACGTTGAGTACCTGCTCGCCTGCACCCCTTCCTGCCT

TGCACGTGCATGGCGAAGCCACCGTCCAATGCGCAACAAGGACCCGGACCTTGTCTCGGCGCTTTCGGCCACTCCCA

TTCGCGCGCTTGCACACTGGCGCCGCTGCAACGCTGAGGCATACATCTTTTCCGTGCACAGCACGCGTTCGTGCGGC

CCCTTCTCACGCGACCTGCACTCCAACATCCCCACTTCCGGTACTGCTCTGCACACCCACACCCGCGGCGCCTGCAA

ACATGCAGCTGCTCCTGCTGCTGCTAGCGGCGTTTGCCGCTCTCGTCAGCGCGCGCTACGCCCACGCTGACGGGTGA

GCGTCTACCGCCACTGTCGCGCAACCCACCGCTGTTTGCGGCATAACCGTGCTTACGTTTCCTCCGTTGCCGTTTGC

AGGTCCTGCCCGCCCGCTGCGGTGGTCCACTACGCCCATCCTGCTGTCAGGTATGCACCGCTTCATGGTCTCAGCTC

GTCCCACCGGCAATACGCGAGCACCTCTGTACACGACTTGAGCACAACGCTGCTGCCTGTTCACCTCTCACCTATCA

CGCTCGGCACCCCAACAGCACCCCCGGCGCATCGGCGCCCACGCCCACCCCCTTTCACGGCATGCAAGTTCCCCAGC

GGCCACCAACATGCCCAGCCCGAACGTCACAGATACCGCCGTCCTTACCGCGCTTCCCCTCATGCATTCACCTGCGT

ACCCACACCCACTCGACTCCGACGCAGCTGGGCGGCCGGTGCATCTACCCACCCCAGCTTCACCGCCCACACCTGGT

GAGCCAGTGTGCAGTTGTGCGTGTTAGCTCCCGACCCACACGCAGCCGCATCAAGCATGCCACGCTGCCACCCCCAG

CTCGTGTTAGCACTAAATGCTCCACCCTTCCCTTCCTCCGTGCAAGGTCCGCGCTGGCACCCACTCCCGCCTACTAC

ACCATTTCCACGAACAGGTATGCACGCTGCGCCAGCTCGCTGCCCCTGTCATACCCCCCACGCTTTCAGCGCTGGCC

CTTGGATTCCGTCCACGATGTCGCCGCGCCTGCACGCAGGTGCACTTCACTGGACTGCATCAACGCCACCGTCCCCA

CCAACATCAATGACAGGCGAGTTGCCCTGACCTCAACACGCCCGCCCATCAAACCCACACATCCGTGTTTCCGCGCT

TGTCTTGCACCTCCGGTTATCCTACTGTGCCCTCGCTGCTGCTACGCCTATGCTCCTCTCGCACGCCAACCAACCTA

GCCTCCCTGCGCGTCCCTGCCCATGCTTCACGCCCACCTCCACAGCACCGCGCTCGTCAAGCCCACGTACGCTGCTT

ACACCAACATCATCACCATGACGGGCCGCGGCAAGCCTGGCGGTGAGTCGTTCCTATAGCTGCCAGGAGCAAGACAT

CACACAGCCGCGTGCTTTCCTTGCGTGTGTGTGTATGTGTGTGTGTATGTGTGTGTTGCTCTGACAGCCGCGCTGCA

GCACCTCTTCTTGCCGGTATCCATTCTGACTTCTGCTGCGTTCATCCCTGCATACAGGCTCCGCCACGCCTGTGGCC

CCTACCTCCAGCACGCCACCCAGCAAGCCCACCGGGATGTCGCTTGCAGCTGCGCTCGAGAAGCGCATGCAGTCCAC

ATCTCAGCGCTCTACCCGTGTCACCCACGCCCACCTGCCCAGCACTGCGGGCGAGCACAGCCTTTCAGGATGGGTGG

TCACCGTGCTGGCAGGCGCCGCCAACGCCGCGCACCCTGCAATTCACGCCGTGGGCGTCCAGTCTGACCGAGTCCAT

ATCTTAGGTGATGACGGCACCATCC

>SEQ ID NO: 98

GTGGTCTACCCTGTGCGCGCCCCCGCCCGGCCGCCACGTGCGCAGGTGGCTTTGTCGTACGGCCTGACGGGCAGCCG

CATCAGCAGCGGCGTGGCGCTGTACCGCAACTGCACCATAATTTTTAAAAATACTTTTTAATACCTGTAGAATTG

TCACCTTTAGAGCCATCCATATGAGCCGAAGTCATATTATTTTTTGTGTTGCCGAACCACAATCCCGCTCAAGTGCT

TACCATGAGCGGCATGGACACTGCGTGTTTCGGCGTGCGTCGGGTCAGCTGCGGTGCGGGTGTTCGGCCACTGGCAT

ACGCCAACGCGCGTCGGACCCATACATGATGCTTTTGCAGTATGCGGTGTTTTGGTAGCCTCCTAAGCCACTCTGGT

GCCGTCCGCCTTTTTCGCCTGATCGCCCCAAGTCCGGTGCCCTGCCGCCGTGCCGTGCTTGTACTGCAGGCGGCGTT

GGCGTCCTGGGG

TABLE 6-continued

Sequences Corresponding to Frequency Peaks (SEQ ID NOs 21-167)

>SEQ ID NO: 99

GCAGCTAGTTTGGTCCCCGAATGGGGGTGCTTATGCTCCTGTGCTCCCAAATGGAATCTAGTAACGCGGCTAACCTG
GCTGGGTCCGCATTCTGCATGACGGCCTGCATTCCGCCTGTAAAATCGATCTCGCTACCCAAACGCAACTGGTCGTA
GGCCGTACACCGCATGAGCACATGATTCTCATCTTCGACTTCATTTGCAACACATAGCGGGCAAATCCTCTCCTCCC
TAGGTCGTCCATAGGCGCGGTTGGCAGTAAGCGGCCAGCAGCATAGGCGGAACCTCATCAAGGCCTTGTGGTGCGCA
ACTGGTATAAATGCTCTACTGTGCCCTTGCATGGTCAGTGGTGCCGCTCCTTCCGCACACAGCCCCATCCAATGCTT
GTACTTGCTCATCTGCACGCCTGGTTGCTTGTTGTCTGATGGGAAAGTGCTTGGCTCAGACTGCAGCCGCTCGTGCT
TCCACGCCTTCATTAGACTCTCTCGAAAGGCGGATACTATTTGCCCTTCAGGCAGCGGGCTACCTGCTCGGCTCTCC
TCCCTTTCCGGCCTGATCATGTGCATACGGCCTTGCCATACGTCTACGCCATGCGCTGAGATAAAACGGAAAAGCCG
TGCACACCACCCATCTCCCTCTGGGTGTACTAACGCGTCTTGTACTTCATCAATTAGTGCATCGTGAGCTAGGCTAT
CCTTCTGCACGGCAATCCTGTTGTAGAATCCAATGCAAAGCTTGGCGAAAAAGAAATGGAGTGGTAGTTGTGCTAAT
TCAGCAAACAGCAGGCGATGCGATGGTCGCTTCGTACCCACTGTCATCCTCATGTACTGCACTTGTAATTTGACGGC
CTCGTCTTTCAGGCATGCTTCAAACGGTCCGTGCGCCAGGTTATTGCTGTCACGCCGCCGCGGTGGTGGGCCGCCGT
CCAGCATTTCCGCTAATACGTCGGGTCCCCACACTTCACAACCATATGCTAGGATGGAGCGAACTTGCACCTCAAAA
CAACGCATGCGTATGTCGGGGGAGAAAATCCTCAAACGGTTTAATCTATTAGTAAGCGCGTACATAGCACGCCGCGC
AGCCTCACATAGCGTCTCTCTGCAGGCGGCAAAAGCACGTCCAGGGCCGTAGACTAGTCCCAGATACCGTGCCTTGT
CCACCGCAGGGATGGGCTGCCCTGCCAGCCGCAGCCCACTGCACTCATCGTTCAATCTACGACGCTCCTGGTCGTCT
GAAGTGAACACCAGACGTTCACACTTTGCGACGTTTGCTTTCATACCAAATGCTTCGCAGAAAGTATCCACAAGTGA
CAACAGGTGCCGCATACGCTCAGGGGTGGTGGCTAGCAGCGAAACATCGTCAGCGTACATTAGGAGCGACAGCTTCT
TACCGTTTAACTCAGGGGTGCCCGCTGTGCTTGCAGTGTCCAACCAGTCCTCGTGCGCATCAATATACTCTGCCAAA
GTTTCAATAAAGAGCCCGAACAGCTCTGTGCTCAGTGGGCACCCTTGCTTGACTCCTTGCGTTGCCTCAAAAGCAGC
GCTCAGTTTGCCATCGGCTTTAACCGTCATCATGACCTTTTCATATGCGGCTTGTATGGCCTCCAACAGCCGCCCTG
ACACGCCCTTTTCCCGCAGCCGTAGCCACAAGAGGGGCGCGGCACCTTGTCAAACGCCTTCTCAAAATCAATCTGT
ACAACAATCATTGGTGGTGCTCCTGCACGTGTGTGCTTTGTCACCAGGTGCCTCAGGACAAACAGATGGTGGGCAGT
ACCGTATTTCCGCCTGAAACCAGCCTGAGCTGGGTGCCTCCACTTGAACAACTCGCCTGCTCGTGCTAGCCTGTTCA
GAAGGATAGATGCATAACACTTAGCCAACGCTCCGCCTACTGCAATGCCCCTGTAGTTGCCGGGCGTCTTCACATCG
CCCTTTCTCTTGTAAATTGGCGTCAGCACTGTGGTTGTGAACTGTTCCGGAAAACTTTCATCTCCGTCTTGCGCCCG
CCAGATGCGGTTAAACAACACTTCTAGAACAGGTGCTACCCGGTTCACCGGCGGGATGGGGGGTCTGCCCTGGGGT
CTCCCTGCGTCTTTGCGTACTTGTAGCATTCCGATGGCGCGGCTTCCGTGCCTGGGGCCTTGCCATTCGGTAGCCTC
TCTAAAGCATGAGTCACTTCGTCTATCGAGATATCGCTGTTCAATATGCTATCTAACTCAGCCCATTCCTCGTCATC
ATACATCGAATCTCGCCAGCCATCTTCGTCACAGCAGTACGCCAGTAAACGCTTTGCAGCGCTGTCGTCAACTGTTC
CTGCCCCATCATTCAGTAGCCGTGCAAAGTGATCACGGAAGCCATCTGCCGTGATGGGGATTTGCTCGTGCACCGC
TCCTCAATCATCTTCCACAGTGCTTTAGCGTCGGCTCTGCACCGTGCTACCCTATCCCGCATCACTTGCGCATCATG
GGCGGCTCTAGCCCTGCGTTTTGCGCGGCAGTACACTGATCTCGCGGCCCGCATCGCTTCCCACCTTTCTCCTTCCT
TCACAACTGGTTTGCCAAGCGCTACTTTCGCCTGGACGAGCGCGGCACGCGCCACCGCACATTCCTCATTCCACCAC
GGGGTCTCGGTCTCTCGCAGATGAGCAGGCCTGCTCTGCCCAAACGCCTTCTCCAATACTCCACTTAGGCACTTGCT
CAACGCTTCGACCGCCTCGGTAGTGCTGTACCGCCCTTGCTCCAAGTGGCCTTTTAGCTCTGTTAATTTGCTTACTA
CTGGCGACTCATCTTGATCGAAAAGATTGCTATAGCGCTCACTCTTCTGCGCATTGAATGCAGTGCGTGGACGCTTT
GCCTTCGCCTGGCCTTCAGTACTTGCTTGACCCTCCACCTCCCAGCTCAAAGTCAGCGTAACAGGCCTGTGATCACT

TABLE 6-continued

Sequences Corresponding to Frequency Peaks (SEQ ID NOs 21-167)

CGCATAACCGGCGCCCCTGCGCGCCCATCTCAGCAGCTCACCCACGTCTACTGACGTCACCGATTGGAATAAAGTTG

GCGATGCAATGCATAAGTCAATGACG

>SEQ ID NO: 100

ATGCTAAATACCTAGGATCCCCTGCCAGTTTCCGCCCACGCGCACGCTGGGCCGCCAAGCTATCTACAACAGGGTCG

GCAAGTGTGGCGCAACGGCGTTCATTTGGTGATACAGCGCGACCTAGCGCATGCCGTTTGCTGCAATCGCTTCCATG

TCGCGGCGTCTATATGTGATCATTTGGCCAGGGCGCGCGCGCGACTGCGGCGTATGAACGACGCGAGTAACTGCGCT

TCCCTGACAGCTGCAAAAATTTGCGCAGCGATAGAACACAGCGCGATGTACTCGCGGCACAAAATATTTCATATTAA

CGCACATCTATAGCAAAATGTGAATGTCGCTCCAAGCGTCGCAAGCCAGCGACGCAAATTTGCTTCCTCGCGATTCT

TTAGCGGCGCTGTATTCATGGATACCAGTGCTGCTATAATAATAATAATAATAATAATAATAATAATAATAATAATA

ATAATAATAATAATAATAATAATAATAATAATAATAATAATAATATCTACGCAGGGCACAAGTGCCCGCGTGTC

TTAAGGAGGAGTGAGACAAGCTCACCCCACCGTGTAAGACCGACGACCCTCACCCTGGTTTCCGAGGGTGGGGCCCA

CTGGTGGCGCCACCCTGGGTGCGGCCTCCCTGGCTTCCAGAGCGTCGGCGGGCATGGGCAATGCCCATTTCCTGCTC

AAGTTTATAG

>SEQ ID NO: 101

AACACACATACAAAACTTTTGTGGTTTACGCTTTACTGCGCTACCCAGACATCTTTTAAAAGCAAGCGAGAGGAATG

AGCGCTAAGAAGGAGCCCACCATGCAGGAGGCGGCTGCCGCCTGGCGTGAGCGCTCCTGGGCCTCTGGCACTGCCGA

TTGGCATGCTGTTAAGAAGAGGAAACCCTCAGACTTGAACGGGACCATTGAGGAACTGTTTGTGAGACAGAGCTATG

CCGATGCCGCGCTGAGGGAAGTGTTCGCATTAGTGAAGGACTATCCTGAATTAAAGAAGAAGATGGCTGACTTTGAG

GTTAAGCAGACGCTGCTGGAGGAGAGGCTCGCGTCCTCGCAGCAAGCATCCACTCCGCTGCAGAAGTCTGTGCGAGT

TCGGGATTTCGCACCTCCTCGACCCCAAGCCCGTTTGTGGCAACTACGCAGCGAGCAAGGCAGCGAAACAAAGCGCA

ATAGCTTCCAGACTTGGTAAGCTAATGGTTAATTATGGACAAGTATAGTGCGCGCCATGTTTAAGTAAACGCGGGTC

CAGTAACGCCTCGCTACGGCCTCTCGCCGCACTTAAGCTCACCAGCTCGAACCGACCCCCACATCCGGAGCCCCCAT

TCCGACCCCATAAGCGCACCTCCGAACCCGCCCGCCCCACTTTCCACAATCTATATGCATATATGCATATGGCCCAG

AAGGCGCAGGGCCATCCAAAAGCCCTTGACCGAACTTCGCCTTGTCCATTGTCGCATGTTGCCCCCACACACGCACC

CTGCCCACGCCACCCGCATCCAACAGAAATCAAACGTAGCGCTTTCACCATAGCAAGAGCCCGGGCGCTAGGACACT

CCAAGGTGTGTTCGCATGTGGGGGCACAACGCGAGACAAGGGGCTTTGGCCGTCCAACCAAGCCCAGCTAGTCACCA

GGTCACCTAAGCTTCACAGGGTACAGACCTGCATGCCAAGCGGACGCGCAAGGACATAGATTCCGGGGCTCTGCCGT

ACTCCTAAGCGGACGGGGGTGCGGGCAAAACCTCGCCAGGCCTCGCCTGATATTAGGGCTTGGCGCTGTGGAAAGCG

GGGCTCAAATTGGAGAGGTTGACATCAAGTTTGGGGGCGAAACGTGCGGCTGGGCAGGGGCGCCGATGAGGGTCTCG

GCCGAACTCGCACAGACTTCTGCAGCGGAGTGAAGGGGACGACAGCCTGACGGGATTTGAACTCGGGTTCGACACGT

GCAGGCCGGATCCATGGAGCCCAACCCCAGCACGCCCAGCACCGGCACGAAACCCAAGGGCAACCCCAAGCCTCCCC

GAGGCCGTGGCGGTGCGGGAGTCTGAGCGCCGCCGTGTCTGCTGTCTAATGGCTCGCAACTGTGCGCTGCAAGCCCA

GGCTACAATCAAGAACAAGAAGACTAGTGAGCTTAGCGCGCACTAATCTGCAGCTGCAGGCCGTGCCCTGAAGGAGC

GCGTGGAGGCAACGCATCCTCCTGGCCACTGGCGGCCAGCAGCGAGTTGTACTGCAGGGCTGCACTGAAGAGGACGA

CCATTGAGGCGGCCAGGTTGACAGTGCGTGGCGAGGATGAGGGGCAAATGAAGCGGTTTTTGAGGAGGTGATGATTG

CCACAACACATGATGGAATCGACGGATGGCAGCAGTGTGGGAGGGGCGGATGCGGGGTGCGAGGGGAAAGGGAGGT

GGTGGGCGCGGGACCAAGCTGGGTTCAGGAGGCACGCCGTGCCTGTGCAAGCCGAAGCTTCTCACCGGCACGATTTT

CGCAGGTGCCTGAGAGCCCAATACACCTATGATATAGCTAAACCCAGCGCGCTCAGCAGCGGGTTACGGCGACGCTC

CAGGTGCGAGCGCGGAGAGGGCAGATTCGAAATGCCGCTGATGCCGACTCCTCGTAGGACGCTCCTGAGCCCGGCCG

TABLE 6-continued

Sequences Corresponding to Frequency Peaks (SEQ ID NOs 21-167)

CTGTGCTCCGTCGCGTTCACTTTGACCTTCTGTATGTCGTGAGGCCGCGGGGAGGCCAAGCGCAGCCCTAACTGCGA
AGCTGCGCCTCCCTTCACTCCGCTGCAGAAGTCTGTGCGAGTTCGGGATTTCGCACCTCCTCGACCCCAAGCCCGTT
TGTGGCAACTACGCAGCGAGCAAGGCAGCGAAACAAAGCGCAATAGCTTCCAGACTTGGTAAGCTAATGGTTAATTA
TGGACAAGTATAGTGCGCGCCATGTTTAAGTAAACGCGGGTCCAGTAACGCCTCGCTACGGCCTCTCGCCGCACTTA
AGCTCACCAGCTCGAACCGACCCCCACATCCGGAGCCCCCATTCCGACCCCATAAGCGCACCTCCGAACCCGCCCGC
CCCACTTTCCACAATCTATATGCATATATGCATATGGCCCAGAAGGCGCAGGGCCATCCAAAAGCCCTTGACCGAAC
TTCGCCTTGTCCATTGTCGCATGTTGCCCCCACACACGCACCCTGCCCACGCCACCCGCATCCAACAGAAATCAAAC
GTAGCGCTTTCACCATAGCAAGAGCCCGGGCGCTAGGACACTCCAAGGTGTGTTCGCATGTGGGGGCACAACGCGAG
ACAAGGGGCTTTGGCCGTCCAACCAAGCCCAGCTAGTCACCAGGTCACCTAAGCTTCACAGGGTACAGACCTGCATG
CCAAGCGGACGCGCAAGGACATAGATTCCGGGGCTCTGCCGTACTCCTAAGCGGACGGGGGTGCGGGCAAAACCTCG
CCAGGCCTCGC

>SEQ ID NO: 102

GGCCGTATTGGCGCCGTTTCTAGTACTAGACTACCATTTACAAGAATAGGAGGTGTACATTTTACCTTAACTATTAA
AGGAGTGCCTGTCGGCACCCACTTGCGGTGTTCGGTTTCACCGAGCACCCAAGGTCTAGCTACGATTTGCTAC

>SEQ ID NO: 103

AGCTAAAATGTCACTACACGTTCTAGGTTTAGAATTACTTAGGATA

>SEQ ID NO: 104

AAACTCGTTGAAAAACTGGGTAGCAGCGCAGTGTGAGGAGCTCGCGTGCATGCGGACTAGTGTGACTCGTAACGACG
TCACACGGGCGTGTGACAGCACTGATATTGTCCATCAACTGTTTTAAAATTATCATTTTGGAATAAGTTTATTAAAA
ATTTTACGGGTTAATTTTGTGCGACGAATTAAAACATTCCCTGCCACCGTACATCACCTGCAACGAACTCACACACC
ACCGCCCCCACTGCCCTCCACCCGCCCTGCCCTGCCCGCAGCTGCGCTCCGGTGACATGCACCGCGTGCTGTCCGCCC

>SEQ ID NO: 105

CCGAGTGAGTGACTGGATGGTGTGCTTCGGAGCATGTAAACATTCTATATTTATATACTGCGATAAATTTATTTGCT
GCGCTAGTGACTAGCTTGCAACAGGTGGCGGGAGGGG

>SEQ ID NO: 106

TGGCTGGCTTGGGGCGCCAGGCTCTACTGACCGTTACTGGCTGGCCTGAGCGCGGGTGCACGCCACACACGTACACG
TCGTTATGCAAAAGGCGTGAGACGCAGCTCGACACTGCCCGGGCCATGGATGCAGGACGAATCTAGGACAGCCTGTG
GCCCTCCTCGTTTATGGAGTTCAGTCGTTTCACGCCGCCCCTCGCCGCAGGGCTCCGCTGCTCAACGCTCAGCACAC
GCGCCTGCTCATTTCAGATGCGGGTGCTGTTGTGGTGGACAGCGCCCTCCAACGCCCAGTAAGGCCGGTGTGCATCC
GTCGTTGTGAGTTTGGCCCGCCGGGCACTCCAGGGCGCTCGGTGCCCGCTTTTAATAGAAGCTTGAATTTATAAATT
AAAATATTTTTACAATATTTTACGGCGGTGGCGACGCCACGAAACACCTGGTGTATGGTCCATACACACGACCTTGC
CCTGCAAATCCTCTGGAGGTTTGGTGAGGCGAATAATCGTGCACATAATTGTCTTAGTACATCTCATAGCCCATAAC
TCTGGCTCCTTGGCGCCGAAGAACAGTTGTCTTTCGCATAGAGCTCCTTTTACGCGCAACCCTAAACGTACTTTGAG
TTGTGTCACCATATACATCAACCGCAATAAACAGAATGTTGAGGCTTGTCGCCGCAGTATTTCCTCATGCCGACCGC
CTTGCGCCTCTTTGAGCATTATGGCGCGTGGTGCCTTGAAGCTGTAAATTGTCAAGTGTCATACAAAGAATGAAGAA
GGGAAATGCAGGGGGAAAGCAGCTGCGGGTGCTGTCGCTGCTCCCAGGCGCCTCTGACATTGTGCGTGCCCTTGACG
CGGTCAAGCTGTTGGTGGGCCGAACGCACGAGGTGAGCGGCGTAAGCTCACTACCGAGCAATCTACCACAGGGAATG
GGTCAAGGTGACCTCCGGATGCGCAACGGCTCTGCGGGTGTATGCACGCGGGCAAAACCCTGGACGATCGTACAGTG
TGCCGCCGCTTCATGTTGCCTGACCCGCCGCCGCCACCGTCCCGCAACAACGCTAACCCGGGCCTTACGCAGTGCGA

TABLE 6-continued

Sequences Corresponding to Frequency Peaks (SEQ ID NOs 21-167)

CTGGCCCGAGCTCCAGTCCTTACCAGCCTGTACGTCCAATAAACTAGGAGACATGCCGCCTGCGGAAGTTGACCAAG

CAATGGTGGGTGATTGGCTTGACAGCGCCCTAGCCACTGTAGCCCGTGCGTCACGGTACTGGTGTGCGACGCGGGTT

GCTGAACATTCCAGGGAGGCAGGGCCGAGCGGAAGTCGGCACGTGAACGACAGCCCCATGACACGCCTCACTCATGA

AAGGAGGCTGGGCAAACACCAATTCACCAAATGTCACGTTAAG

>SEQ ID NO: 107

CTTTTTTCTCTCTCACTTTCAGGTAGTAACTTGTGAGTGTGTTCTTC

>SEQ ID NO: 108

TGCCAGTACTGGGTGTGTCGCATGTATGAAGTGCCTGATAGCAGCAGAGTCCAGACAACCACGCACGCCGCAGCGCC

CACGGGTGCCACCACATTAATCCGCGGCGGCACCAGGGGGGCGGGTGGGTTGTCACCGTCCCGGCAGAGGGACGAT

CCGAAATACAGTACAGAAGCACAACGGCAGATAAGGCGCCGTGTGCTCCTGACGCGTACAAGACCCAGCTCGGTTCG

GCCCCATGCACAGGCACGTACCCGAGCGTCCTGCGCCGTGCGTGACTCTAACGCAACACGGCAGTTACGTCGCAATA

ACTAGACTTATCTCCACTGCGCTGCGATAAGTCAGCGCTTATTGACTCCTTACTGCCGTGTAGCGTTACAAACCGCC

ACGGCCCCAAACGACAATCCCAATCTCTCAAACCGACAATAGCCTCCACTCATGCCTCAAGCGGCCTAGCAACTCAT

TCGTGGCCCTCAGCGGCCTCCTACCTCCGGCCTCGCAGCTCCCGATAACCCCACCAAGTCCGCCGTGCCCGCCCCAG

CCCGCCCGTGTTGAGGTTGCACTAGTGGCCGAAAGTGCTGCCAGAGTTTGGTAGTAGTCCTCAACGCCGGGAGGTCA

TGGTGCGGGCGACGGCAGCCCTGGTGGCTGGGCTTGATTGGCTTCGCGTATGCAGCTCTTCTCGCAAAGCGCTTGGC

CCAACGCCGGTCATGCAAACCAAGGTGCGGTCGGCGGTGATGGCGGTGGCGTTCGTGCCCTTGCGCTACCGAAATC

ATGTGTCTCGAACACCGCGGAGCGCTCCGCCCATCGCCTAGCTTGCGCACGAACGTACGGTCCTAGTTGCACACTCA

ACAGCGGTCAATAGAACGAGCTTCGTGCTTGGGGATATTGGCTGCACGAGCAGCACCATCACGCGGGGATGAGCGCC

GCCGGAGGCGCCGCCGGCACCTGCTGCAGGCGCAGGGCGACGCCAACGCGGGGCCTGACAGCGCCACACTCCGTCGG

TCATGGGCGGCCAATGGTCACTACCAGAAGACAAGCAGCAATAGGAACACGACTGGCTTTGCAAGGGCCATGATACC

AGACTCACAAACGTATCAGGTGCACCAATGGCCACGACAGAAACACACATGCGTTATCCCGCGTGCGCCAGCCATGC

AGACGACGCCGGGGCGTTACAGGGAAACACATGCATCCTTGTTCAGGTGTGTGGCTTGTGGGCAGCTGTGGCCGTCC

GTGTGCCCAGGAAAGGTAACAGTGCGTGTTGGCACGTGTTGGCACGAACCACTGGAGACCTCGGTACTCTCTACCGG

CCCCCAGGGCCATGCCATAACACGTGTTGACGTTGTAGGCTGCTCGGAACAACCTTGGGAATAATAACAACGTCGTG

ACTCGAAGCTGGGACAGGCTAGCCAACATGCGCCACGCAGGAGAAGGCGCGAGTTGCAACACTAGAGCGGTTTTACG

TACGCGAGTCACGCGCGGCAACCTGCCCTTCGTTCACCCGCGCCGTCGTGGTGTAGGATGCGGGCAGCCATGCCCAG

CCGTGCAGCATGGCCACGAACACTAATTTCTTTCTTGCTAGCTAGGTGCCATGCTTGAGATTTGCAGTGTCTTGCAT

AAGAGTCACTACCAATCAAGCAGTAGGTACACCCATAGATAGCATCACCCCGGCGGACGCAGGACAGGCGCGCACGT

GAATGTTTGCCTCCAAACGCCGCGGGGATGCATGCACACAATGTCCCGTACGTGCCGATACCGTACGCCACGGCAGC

TGTGGGGTGTACCGTAATAGCAGGGAGGGCAACATGAAGGGTAACACCTCAGCAACCCCAGCAAGGCTGGCCTGGTC

GAGCGGCGCGGAGGGGTGAAGGATACCCGGCACGCGTGGAACGCGCAATGTATCTATAGTGATAGAAGGCGTAGTGA

TGGGAGGAAATAAGGAGCACTCGGGGCGCGATGGCGGGTTGGATGCGCCACGGGCCCCGGCCCAGCCAAAGGGAGC

GAACGCTGGGCGGAGCCGGTGGGTGAGCGACTCGAGGGACGTGCCAGTAGTGAACAGCAGTGGCGGATGGGTCATCC

AATGTGAGAGATGATACAGCCACGCCGGCAGCCAAACTCCGCACTCGACCACGTACGGGCACGTCGTGGTACTGCTG

TGAGGAGGCCGGGCTGAGTTGGGATGCCTGCCAAGCCTGGCTACCCACATGTGAGCCTGTGTCGCCATACGCTCTTA

ATAGTAATGACATATAGCACACTGCTCCTAGCACTTCGGTGATAAGTAATTGCCCCGCCGGGTGAAGTAAGGCCGGG

GCTGAAAGGAACCAAGGTTGGTTCCCTAGGCGTCCACTCGCGAGTGGGCAGGCGACACATACAGTTGGCATTGACGT

GCGTTGCGGAACTAATGCGTACGTTGGCTTGGGTCTCTGGTTTCATGAGGCATTGACAGAACACGCTGCCCCTGCTA

TABLE 6-continued

Sequences Corresponding to Frequency Peaks (SEQ ID NOs 21-167)

TGGCTCTGACGAAGTAACATGTATGCATACATGTCCTGAAGGATTGGCAGGGAGCGTGCCGCACCGCACGCAAGCCG

CGTGACTACGGTAAGCATGAGGCCATAACGTGACACAGATGCCGTGCCATACAGGCGG

>SEQ ID NO: 109

ATAGGAGCTATCAGTCTGACTGTGGGGTCGATGCTACCCCGGCATGGATCTGGGTTGAACGGTTGGTGGTACCATCG

CGCGGGCATGGCGGGTCGAGTAGCGTGTTTCATGCACGGCACTCCCGCTAACCAGCTACACACCGCAGTGTACTGGT

TATCCAACAACTACATTCAGACCATTCTGGTATCCCACTCAAACCTGCGCCAAGTGTCAGGAAAAGCGCTTGCCAAG

TCGGCTACCCGCTTTCACAGGATGGCGAGCGGGTGACTGGCATGTGTACAGGCGGGTGGGCCAACAAGAGGGGAGGG

CGGATGGGTGCCGTGACTTGGTGGTGGGCCCCACCGCGAGCAGCAACAGCCCAGCCCAACACACGGGCGCCATCCAA

ACCCACCAGGCAGGCTGTAATCCCAGCTCCGACCGTATCTCGCAACAAAATGTTGGTTGCGCAGGGTCGGGCTCACT

GCGTGACACAGCGTCCGATGCCTGGTGCAGGGCACGAAGGCATGTTTATGCGTCATGCGGTATAGTTATGCGTCATG

CGGTATTGTTATTGGCTGGGCATAGCATGCTGGCCGAACTGCACAAAACTCCACATCGCTCACTGAGGGCGAAATAT

CCGGAAAAACAAATTCGGCACTTGGGCCTAGCGCACACATCGAATGCATATAGGTTGGCTTGGGGTGCGTCAGCCAA

ACTACAAGGGTGGTGCCGCGTGATAGTATGATGTGCGTGCGGACCTCAAGACGTACAGGGTGACGCATGATCACGTA

AGCCCGCTCCGTTGTCAACACGAAGCAATAGCGAGGCGCAGGCTTGCCGTGCACGGTACACTCAAGGCGTATTGCGA

CAGGGCACGCAGCAGGGCACGCAACAAGTCGAAGCGTCCATAACGACAGGGCAGGCAGCATAATTGCATGCGGCACA

CAGGCCATATCGCAAGACACATGATGCGAGGCGCAAAGCCTGTTGCTGGCGGCACACACGCCGTATCCGAACGTGGC

GCTCAGACCACACATTGTCCACAACGCAAAGGCATGTACAACGAAGGCACGTAAGCATTTCAATGCCGTCTATAATC

CACAACGCAAGAGTGTGGGGCCCGTTGCTTGCGGCACACAGGTCGTATCATAAGGGCACGTATGCCATCTATTACCC

AAAAGCAAGGGTGCGAAGCCGTTGCTTGCGGCACACAGGTCACATCATACGGGCACGTATGCCGTGAATTGTCCATA

AAACAAGGGTGCGGAGCCCGTTGCTTGCGGCGCACAGGCCGTATCATAAGAACACGTACGCGGCGCATTGTCCATGA

AGCAAGGGCGCGGAGCCCGTTGCCTGCGGCACACAGGCCGTATCATGAGGGCACGTACGCCGTGAAGTGTCCATGGA

GCAAGGGCGCGGAGCCCGTTGCCTGCGGCGCACAGGCTGTATCATGAGGGCACGTACGCCGTAAATTGTCCATGA

>SEQ ID NO: 110

CCCGTTGCTTGCGGCACACAGGCCGTATCATAAGGGCACGTATGCCGTCCATTGTCCATAAAGCAAGGGCGCGGAGC

CCGTTGCTTGCGGCGCACAGGCCGTATCATAAGGGCACGTATGCCGTCCATTGTCCATAAAGCAAGGGCGCGGAGCC

CATTGCTTGCGGCGCACAGGCCGTATCATAAGGGCACGTATGCCGTCCATTGTCCATAAGGCAAGGGCGCAAAGCCC

GTTGCTTGCGGCGCACAGGCCGGATCCCAACGGCACACACGCCCTTTCCCCAAGGGCACGCGGGCCCTGCGGCCTGG

ATAGGCAGACAGGAGAAGTACCGCGCCAAAAGTCCTGAGGGTCTTGGGGAGGTGGGGGTGGCACAATGGAAGATGTG

GAAAGGTATTGCACAAAGCTGTGAACTGTAAAGCGACGGGTAGACACGAAGGCACGGCAAGCAGGACCGCGCATGGC

AAGCAAGTAGCCCGCCCGCACAGCTGTGCATGCCCTTTTGCTTTCAGTGACTTGCCGAACGCCTTGTCCGCAACGCT

TCGCGCGCCTTTGCTCCGCTTGAAAGCTCCGCTCTGCTCCGATTTGCTCCCGAATGCGGCCCCCGAACCAAAGCGTG

GTTCAAAGCGCCAGAGAAGCTTCGAAGGGCATTCCCTTACGATCAGAGAGCGAGCGTGATCAAGCTAAGGGGTTCCA

TTGAGCAGGATCGCGCAACAAAACGCTGCAACTCCGTCTGAGTATATATTAAACGCTTATTCGGTCCATACATGGTC

AAGTATAGTTAGAACCAGGTATAGGATTGCAAAGAAAGTCCAGAAATGTAGGGAACGTTTAAGTGCGACACACTGAG

GTCACCGTCCCGGCAGAGGGACGATCCGAAATACAGTACAGAAGCACAACGGCAGATAAGGCGCCGTGTGCTCCTGA

CGCGTACAAGACCCAGCTCGGTTCGGCCCCATGCACAGGCACGTACCCGAGCGTCCTGCGCCGTGCGTGACTCTAAC

GCAACACGGCAGTTACGTCGCAATAACTAGACTTATCTCCACTGCGCTGCGATAAGTCAGCGCATATCCCCTCCCCT

CTGTCCCATTGCGCACCATTGCAAGGCCAAGTATGCCGGGAACTTAGCCCCTGAGCCGAGCTACCGGCTATGGGCTC

ATTCCAAACGTCCATTTCAGCGCGCAGTTGTGCGAACGGGGTGGGATGGGGGTGCGGGGGGAGGAATGCCCGGACTG

TABLE 6-continued

Sequences Corresponding to Frequency Peaks (SEQ ID NOs 21-167)

TGCGGGAGGCGCCGGTGAACACAAGCGCGCTGGCGAGCCAAGGCCGTGGGCCGCGATTTCGCGAAATTGCCACCAC

GATAGTATGCACCGTTGATACCACAAAACTCAGCGCTGCTGATGCATCGAGATGAAGCAAACGACGTCGCTGCTTCT

GCCGATCACTCGCATCCACAATGTCTTGTCAAATGTTTATTGCCTTGAGGTATCATCGTCTCTCGAGATACAAGTCC

GCTGACAAGAATTGCAACCCGATGGCGCTATCGAGCGCTGGGATCCTCCAACGCCTCCAATCCCTTCGCCTCTAGTT

ACGTCTTCCTCGCGTTTCCGCAAAGTTATGCATCGCTTGGGACAAATTGAAAGGCGTATTATTTGCACAAGAACTCT

GGCTACGTTCGGGTTTCCCGACGTAACTGCACATAAAACTGGAATAACCGAGGGGGCCCCGCCTGGGACTCGATGCG

ACCGCAATGGCTATTGCCCCTCCCCCTTCGGGGGAAGGGGCAAGCCAACCTGCA

>SEQ ID NO: 111

GGCCCGATTAAACTGCCCACCTGAAACTGTCAAGGGTCCTGATTTAAGGATT

>SEQ ID NO: 112

GGCGGTGTCACCAGCAGCAGCAGCAGCCTGCTGAGCCGCGTCCCTCCCGTTCCCGCATATCCTGGCCCTCATCA

GGTGGACTGCGACGCGTCCAGGATGCAGCAAGGCCCCGCTGATGCCGAAGAGCACAACTATGCAGCTCTATACGCAG

CTGCAACCTGCTTGCCGGAAGTCATTGTGGAGATAAAGGGGCATAGAGCGCGCGTGCTCGGCGGCCACCGGGCTTCA

TGTGCATCAATCTTTGTGCTTCCCGTTGCGGTAAGTACTGGTGTCGACCAGGGCGTCAGGTAACCAGGACAGGGTCT

GCGACGGCGGTATGCCATGAGACAACAGTTGCATGTGCGTGTGCGTATCGTTCACGATTATGAACAGCCGCCACCGC

CACGCACGCAAGGTCAATCAACTAAATCAACCAGCAGCATGCAGCTCTTATAGCGGAATAAAAAGCTGGCATCGCAA

GATATTATCGGATGCATGCAGACGTCGAATGCTTCGACAGAACGCACCAAGCGCCGACATGCATGACGGCAAGCGTC

AACAAGAATTGCACTTCATTCAGCTAGCTAGAGAAAGCTGCTGACTGGAGTGCAATCAATGCATCAGCAGCAGGGCG

CGTGATGGAAGTGCGTGCGATGCAGCACTATATAATACACAAATAAGAAAGCATGGATGTATGTGCGCGCAATGGCT

CACCATTTATCTATCGTGCCGAATGAATCCAGCAGGAATGGCAGCAGCCGCCACTACGTATACAGCGACGTGCCTCC

ATGCGTACATGCATGAAATTGAAGATAAATACATACCTGCACTGCTCACAGGCGGACACTGTTCCAAAACATTCGCC

TCTGGAGTTGCAATGCAATTACGAAATCGTCAATGGGGGCAGTACTGCTGGCGACGCTTCGCGGCCGGTGAAGCGGC

TACCCATACCCCTACCAACTTCAGGTTACAGCGCATTGTCGCTGCTCGAGTTTTGGTGAGTACGTTGGAAGAACAAT

TATCCTTACACACGGGCTATAACCTCTACATATGGCAGGTGATGGGGCGGGCCGTGCGTGCGCGGTACACCACTGCA

TGATGACATACAGCAGCAGGCTAGATGTCCGCCGGCGTCTCGGCTACATGTATACATGAACAGATCAAATGCTCATC

ACCACAATACATGCTTAGTTTCATGTTCAGCCGCATACAACCATATTATCTGTAGCAGCGCTCGCTGCAGCAAGCTC

TCTTCCGCCGTCGCCATCCATGTATGGATGTATGGATGTACGTGGCATTTCGCTCCCTGTGACTCTTGAGCCAGCCT

GCGCCTATGTATCCTACTTTTTGACAGAGAGCATCTGGCTTGGGCAAAATGCTTTGGTGCCGCACACAGACGTCTGC

ATGCGCACTTCATGTATATAATGTATATTATATATGTTAATTATATATATATATATGCGCACGATGTCAACTTGGGT

GCATGCATAACTCCTTGCTGTCAGCACTTACTTCTATCTGGTGCATGCGGCGGCCTTGAGCACTTTACATTGCCGCA

GCGCGCATGCTACTAGCCGCCTTCTCTATCTTCTCAACGCAGCAAGGGGAAAACGTTGTGCTACAACAGATGGGCTG

GTACTTGTTGACAATGTTTCTTCCTGGTGTGTCTTCCTAGCTTAATGCTAGATACACATACAGGAGCCCATTAATAT

TTAATTTGTCTTATTGCTGTGTTTTCAACTCCTGCACACATGCAATAATGCATTGAAGGATTACTACACGCAGCCTG

CAGATCGAGCGAGTGCCGCAGCTATACGACAGCTAGATAGCTGGTGAATGCAATCAGATGGGTGTATTTATATTCAT

GCGCGTGGTGTACCCTCCGCTCTCTCCGCTGCGTGCTACTTGCCACGTATACGTTATTATTGGCTGGCATCATACCG

TAGTAATTACTGGTTTTACGCTGCTGCTTTTTCGGGGACCAACATGCATACTTGGTAATTAAAAGGAATGAGGCTCA

CTTGTATAGCTTGCACTCACCATGCAGGCGTCGCATGTGCATCTATCTACACCTGTATGCGGCATATGCTGCATCTA

CCTGCCCCTAGCTAGCTATGGCCGCGTTGACCTTCATGCGTTGGACGGATTTGCCCGCATATTGCTCACAGGGATGT

GCAAACACACAAAGCGCGGCAGAACAGGGACGAGCCCCAGCCGCGCACAGGCGAGCAGCTGGACCAGCTGTGCAGGC

TABLE 6-continued

Sequences Corresponding to Frequency Peaks (SEQ ID NOs 21-167)

AGGAGCTGGTGGTGGTCGAGCCCAACGGCAAGGTGCGCAACGATTGCATTGTTGTTTTGAACTATACTTGCACTGTC

TTCAGTTGTTTGGTGTCCTTTGGTGCAGCTGCGTGCTATCATTTGCAAGGACTCCCACCCACAGCTATTAGTTGAGC

AGCCCGTGTCATCGTGCGTTGCTGCGCGCGTGCGCTGTGCTCCCTTACTTTCCTGCAATAATTGGATGATATACTTG

AAGTTTCTTAGTGCGTGGGCACAACTGGCGTGGCTGGGCTTCTTGATAAGGTGGCCGAGTGTGCGATGGTACACCAC

GGGACGTGCCCGGGTGCACGTACGGGGTGTTGACATATACTCGGCAGCTCGCGCCCGCGACCTCAACTCTATGTATA

ACTAACTATAGATAGAAAGTGCTTTAACACATCGACTTATATCCTGTATGTCCTGGATTTTGCTAACTGGTGATGAC

ACAATACAATGCCCGTACGCAGGCCGCAATGAGCCTAGCAGATTTCCTGCAGGCGGCTGGCGCGATCCTGGGCGGAC

AGCAGCTGGCTGGACGCCTGCTCCGCGTGCTTTGGTGAGTGGATGTAGCCATACATCCTTATTGGGCGTCGTCATGA

CAATCCTGGACAGGGGAAGGCTCCTCGCTCCCCCCCTCCTCCCTTCCTGACCAAGCTCAGGAACCAAAGGGAACCCC

GCCCTTCCTCAAGCTTGCTTCCAACCGTCCTGAACGAATGCTACGCACAGCAAGGCGAAGCCAAATAAACCGTAGCG

CGCCTACGCCAAATGGTTGATTGCGTAGCATCGTAGCAACCTTCATCTGAAGTCTGCGCACGAGCGACAGGCTGTCT

GCAGGGTTGCAAAAATTAGGATACAGCAAGCAAGGTCAAGCCGTACACCGTATACTTCATCCAGCCAGTGCCGCGAC

AGCATCTCATCTTGCTTGCAGCAGTCTCGTCCCAAGACGTCAGTAGTCATTACACCCCGACACCAGTCACACCCCAA

CACAGGGCAGCGCCCCCACTTTCTGTGCTTGGGAATAATTGTATGTGTTAGGGAATATGAGTTTCGGAACTGACCAT

CCGTGTGATGCCGCAAGCGTGTGCACGCGTATGATGATGATTGGACACAGCGAAACTGCGTATGTATGTGGGTTGGT

GGGGTCTGTTGTCGAAACCAGCAAGCGGTGGGAGTGGGTGTGCATACCTGGCTTGGCGTCGGGGCAGTACTGCTGTA

ACTGCTGCATATCTGGTGTGCAGGTGGGA

>SEQ ID NO: 113

GGTATCCGTGAACCAGTTTCTTACGGTTCTCTTCTTTACGGTAACAACATCATTG

>SEQ ID NO: 114

CGAAGATGGCCCCTCGCGGCGTGGGTACGGCGTGCCCCGCTTGTCGGGCTGTCCCTTCACTTGTAATCCGCATCCA

TAAGCGCCAATGCTACCCACAAACGCAGTGAACAATATCAATACACCAGAGAAGTCATGGTGCCACCAGAAAATGAA

CAAGCTCAATTGTGGAGAGAGACATACGGTAGTGCTAGGCTTGGAAGCAGCCACTGTGCTTGGAATGCGTAATAGCT

CACTGGTCTAGCAGTCTAGCAGTGTCTAGCAGTACTCCGCTTATCTATTGCAGAGGGGTGGCATGGGGTACCGATCC

TCTGGTCACCCCAGGTCCCCGAGGTCCGGGTTCCATTCCCTGCCGTCCCGA

>SEQ ID NO: 115

TCGTATGCGTCCCCGTCCCAGCAGTCGGGTGAGGGGCCTCCCCGGTAGCTCAATTGGTAGAGCATGCCGCTGTCACA

TGGCAGACCCAGGTTCGATTCACGGATTCGGCCGGGTTGAGGCTGACAAGTATAGATGCAGGTTCGGATTCTGCCCG

GGGAACCAAGTCAGTATTCCAGTATGGAGTCCGCGGTACTGACGGAAGCGTTGTAGCGACTCTCTGGGTTCGGATCC

CATTGTTGCAACGTGGAAACTTCACGATGGCCGAATTTGGAGAGTTGGTAGGCCGATAGGTCCAGAACTTTGGTTCC

TATGGACTGAGTGAAGGTGGATGCGTGGGGAGCCTCGTGCCAAGGTCCCACAGAGATACGGTAGGGTTACCCTCGAT

GGGACTCCCTTAAGGCACGCGGGACCTTGGTCTTATTATTATTATTATTATTATTATTATTATTATTATTATTATTA

TTATTATTATTATTATTATTATTATTATTATTATTATTATTATTATTATTATTATTATTATTATTATTATTATTGCC

CCCGCTCTTATATGCCCCGTTAGATTTTTTGGGTTACT

>SEQ ID NO: 116

ATCTTCGTGCAGTGGTCAGGCTTGCCCGAATCCAGCCATCACCCCAATCTCGTACGGTAATGGCCTCACAACTCCCA

ATTACGACTTCCTCCACCATCATTTGTCTTCATGCAGATTAAGATAGGGGCCAGAGTGGTGCTTACGTTCGACCGAG

TATCTATCTACACCCCTTACAGCGACAATATAACGAGGGTGCGTGAGCAATTTAAACAGCGGGCTGCGCTGACCTGC

ACAGCGGTGTTTTGGGTTTCGCGCATGGTCGACCAGCCCAGTTAGGCGCTGACTTATCGCAGCGCAGTGGAGATAAG

TABLE 6-continued

Sequences Corresponding to Frequency Peaks (SEQ ID NOs 21-167)

TCTAGTTATTGCGACGTAACTGCCGTGTTGCGTTAGAGTCACGCACGGCGCAGGACGCTCGGGTACGTGCCTGTGCA

TGGGGCCGAACCGAGCTGGGTCTTGTACGCGTCAGGAGCACACGGCGCCTTATCTGCCGTTGTGCTTCTGTACTGTA

TTTCGGATCGTCCCTCTGCCGGGACGGTGACCTCAGTGTGTCGCACTTAAACGTTCCCTACATTTCTGGACTTTCTT

TGCAATCCTATACCTGGTTCTAACTATACTTGACCATGTATGGACCGAATAAGCGTTTAATATATACTCAGACGGAG

TTGCAGCGTTTTGTTGCGCGATCCTGCTCAATGGAACCCCTTAGCTTGATCACGCTCGCTCTCTGATCGTAAGGGAA

TGCCCTTCGAAGCTTCTCTGGCGCTTTGAACCACGCTTTGGTTCGGGGGCCGCATTCGGGAGCAAATCGGAGCAGAG

CGGAGCTTTCAAGCGGAGCAAAGGCGCGCGAAGCGTTGCGGACAAGGCGTTCGGCAAGTCACTGAAAGCAAAAGGGC

ATGCACAGCTGTGCGGGCGGGCTACTTGCTTGCCATGCGCGGTCCTGCTTGCCGTGCCTTCGTGTCTACCCGTCGCT

TTACAGTTCACAGCTTTGTGCAATACCTTTCCACATCTTCCATTGTGCCACCCCCACCTCCCCAAGACCCTCAGGAC

TTTTGGCGCGGTACTTCTCCTGTCTGCCTATCCAGGCCGCAGGGCCCGCGTGCCCTTGGGGAAGGGGCGTGTGTGCC

GTTGGGATCCGGCCTGTGCGCCGCAAGCAACGGGCTTTGCGCCCTTGCCTTATGGACAATGGACGGCATACGTGCCC

TTATGATACGGCCTGTGTGCCGCAAGCAATGGGCTCCGCGCCCTTGCTTTATGGACAATGGACGGCATACGTGCCCT

TATGATACGGCCTGTGCGCCGCAAGCAACGGGCTCCGCGCCCTTGCTTTATGGACAATGGACGGCATACGTGCCCTT

ATGATACGGCCTGTGTGCCGCAAGCAACGGGCT

>SEQ ID NO: 117

CATGGACAATTTACGGCGTACGTGCCCTCATGATACAGCCTGTGCGCCGCAGGCAACGGGCTCCGCGCCCTTGCTCC

ATGGACACTTCACGGCGTACGTGCCCTCATGATACGGCCTGTGTGCCGCAGGCAACGGGCTCCGCGCCCTTGCTTCA

TGGACAATGCGCCGCGTACGTGTTCTTATGATACGGCCTGTGCGCCGCAAGCAACGGGCTCCGCACCCTTGTTTTAT

GGACAATTCACGGCATACGTGCCCGTATGATGTGACCTGTGTGCCGCAAGCAACGGCTTCGCACCCTTGCTTTTGGG

TAATAGATGGCATACGTGCCCTTATGATACGACCTGTGTGCCGCAAGCAACGGGCTCCACACTCTTGCGTTGTGGAT

TATAGACGGCATTGAAATGCTTACGTGCCTTCGTTGTACATGCCTTTGCGTTGTGGACAATGTGTGGTCTGAGCGCC

ACGTTCGGATACGGCGTGTGTGCCGCCAGCAACAGGCTTTGCGCCTCGCATCATGTGTCTTGCGATATGGCCTGTGT

GCCGCATGCAATTATGCTGCCTGCCCTGTCGTTATGGACGCTTCGACTTGTTGCGTGCCCTGCTGCGTGCCCTGTCG

CAATACGCCTTGAGTGTACCGTGCACGGCAAGCCTGCGCCTCGCTATTGCTTCGTGTTGACAACGGAGCGGGCTTAC

GTGATCATGCGTCACCCTGTACGTCTTGAGGTCCGCACGCACATCATACTATCACGCGGCACCACCCTTGTAGTTTG

GCTGACGCACCCCAAGCCAACCTATATGCATTCGATGTGTGCACTAGGCCCAAGTGCCGAATTTGTTTTTCCGGATA

TTTCGCCCTCAGTGAGCGATGTGGAGTTTTGTGCAGTTCGGCCAGCATGCTATGCCCAGCCAATAACAATACCGCAT

GACGCATAACTATACCGCATGACGCATAAACATGCCTTCGTGCCCTGCACCAGGCATCGGACGCTGTGTCACGCAGT

GAGCCCGACCCTGCGCAACCAACATTTTGTTGCGAGATACGGTCGGAGCTGGGATTACAGCCTGCCTGGTGGGTTTG

GATGGCGCCCGTGTGTTGGGCTGGGCTGTTGCTGCTCGCGGTGGGGCCCACCACCAAGTCACGGCACCCATCCGCCC

TCCCCTCTTGTTGGCCCACCCGCCTGTACACATGCCAGTCACCCGCTCGCCATCCTGTGAAAGCGGGTAGCCGACTT

GGCAAGCGCTTTTCCTGACACTTGGCGCAGGTTTGAGTGGGATACCAGAATGGTCTGAATGTAGTTGTTGGATAACC

AGTACACTGCGGTGTGTAGCTGGTTAGCGGGAGTGCCGTGCATGAAACACGCTACTCGACCCGCCATGCCCGCGCGA

TGGTACCACCAACCGTTCAACCCAGATCCATGCCGGGTAGCATCGACCCCACAGTCAGACTGATAGCTCCTATCCA

GGTGTCAGGCGCCATGTATGTATCTGTGGACGCGTCAAGCTGGCTTGTGCCGTAGCGTTGGCCGCCTGTATGGCACG

GCATCTGTGTCACGTTATGGCCTCATGCTTACCGTAGTCACGCGGCTTGCGTGCTGTGCGGCACGCTCCCTGCCAAT

CCTTCAGGACATGTATGCATACATGTTACTTCGTCAGAGCCATAGCAGGGGCAGCGTGTTCTGTCAATGCCTCATGA

ACCCAGAGACCCAAGCCAACGTACGCATTAGTTCCGCAACGCACGTCAATGCCAACTGTATGTGTCGCCTGCCCACT

CGCGAGTGGACGCCTAGGGAACCAACCTTGGTTCCTTTCAGCCCCGGCCTTACTTCACCCGGCGGGGCAATTACTTA

TABLE 6-continued

Sequences Corresponding to Frequency Peaks (SEQ ID NOs 21-167)

TCACCGAAGTGCTAGGAGCAGTGTGCTATATGTCATTACTATTAAGAGCGTATGGCGACACAGGCTCACATGTGGGT

AGCCAGGCTTGGCAGGCATCCCAACTCAGCCCGGCCTCCTCACAGCAGTACCACGACGTGCCCGTACGTGGTCGAGT

GCGGAGTTTGGCTGCCGGCGTGGCTGTATCATCTCTCACATTGGATGACCCATCCGCCACTGCTGTTCACTACTGGC

ACGTCCCTCGAGTCGCTCACCCACCGGCTCCGCCCAGCGTTCGCTCCCTTTGGCTGGGCCGGGGCCCGTGGCGCATC

CAACCCGCCATCGCGGCCCCGAGTGCTCCTTATTTCCTCCCATCACTACGCCTTCTATCACTATAGATACATTGCGC

GTTCCACGCGTGCCGGGTATCCTTCACCCCTCCGCGCCGCTCGACCAGGCCAGCCTTGCTGGGGTTGCTGAGGTGTT

ACCCTTCATGTTGCCCTCCCTGCTATTACGGTACACCCCACAGCTGCCGTGGCGTACGGTATCGGCACGTACGGGAC

ATTGTGTGCATGCATCCCCGCGGCGTTTGGAGGCAAACATTCACGTGCGCGCCTGTCCTGCGTCCGCCGGGGTGATG

CTATCTATGGGTGTACCTACTGCTTGATTGGTAGTGACTCTTATGCAAGACACTGCAAATCTCAAGCATGGCACCTA

GCTAGCAAGAAAGAAATTAGTGTTCGTGGCCATGCTGCACGGCTGGGCATGGCTGCCCGCATCCTACACCACGACGG

CGCGGGTGAACGAAGGGCAGGTTGCCGCGCGTGACTCGCGTACGTAAAACCGCTCTAGTGTTGCAACTCGCGCCTTC

TCCTGCGTGGCGCATGTTGGCTAGCCTGTCCCAGCTTCGAGTCACGACGTTGTTATTATTCCCAAGGTTGTTCCGAG

CAGCCTACAACGTCAACACGTGTTATGGCATGGCCCTGGGGGCCGGTAGAGAGTACCGAGGTCTCCAGTGGTTCGTG

CCAACACGTGCCAACACGCACTGTTACCTTTCCTGGGCACACGGACGGCCACAGCTGCCCACAAGCCACACACCTGA

ACAAGGATGCATGTGTTTCCCTGTAACGCCCCGGCGTCGTCTGCATGGCTGGCGCACGCGGGATAACGCATGTGTGT

TTCTGTCGTGGCCATTGGTGCACCTGATACGTTTGTGAGTCTGGTATCATGGCCCTTGCAAAGCCAGTCGTGTTCCT

ATTGCTGCTTGTCTTCTGGTAGTGACCATTGGCCGCCCATGACCGACGGAGTGTGGCGCTGTCAGGCCCCGCGTTGG

CGTCGCCCTGCGCCTGCAGCAGGTGCCGGCGGCGCCTCCGGCGGCGCTCATCCCCGCGTGATGGTGCTGCTCGTGCA

GCCAATATCCCCAAGCACGAAGCTCGTTCTATTGACCGCTGTTGAGTGTGCAACTAGGACCGTACGTTCGTGCGCAA

GCTAGGCGATGGGCGGAGCGCTCCGCGGTGTTCGAGACACATGATTTCGGTAGCGCAAGGGCACGAACGCCACCGCC

ATCACCGCCGACCGCACCTTGGTTTGCATGACCGGCCGTTGGGCCAAGCGCTTTGCGAGAAGAGCTGCATACGCGAA

GCCAATCAAGCCCAGCCACCAGGGCTGCCGTCGCCCGCACCATGACCTCCCGGCGTTGAGGACTACTACCAAACTCT

GGCAGCACTTTCGGCCACTAGTGCAACCTCAACACGGGCGGGCTGGGCGGGCACGGCGGACTTGGTGGGGTTATCG

GGAGCTGCGAGGCCGGAGGTAGGAGGCCGCTGAGGGCCACGAATGAGTTGCTAGGCCGCTTGAGGCATGAGTGGAGG

CTATTGTCGGTTTGAGAGATTGGGATTGTCGTTTGGGGCCGTGGCGGTTTGTAACGCTACACGGCAGTAAGGAGTCA

ATAAGCGCTGACTTATCGCAGCGCAGTGGAGATAAGTCTAGTTATTGCGACGTAACTGCCGTGTTGCGTTAGAGTCA

CGCACGGCGCAGGACGCTCGGGTACGTGCCTGTGCATGGGGCCGAACCGAGCTGGGTCTTGTACGCGTCAGGAGCAC

ACGGCGCCTTATCTGCCGTTGTGCTTCTGTACTGTATTTCGGATCGTCCCTCTGCCGGGACGGTGACAACCCACCCG

CCCCCCCTGGTGCCGCCGCGGATTAATGTGGTGGCACCCGTGGGCGCTGCGGCGTGCGTGGTTGTCTGGACTCTGCT

GCTATCAGGCACTTCATACATGCGACACACCCAGTACTGGCAGCACTTTCGGCCACTAGTGCAACCTCAACACGGGC

GGGCTGGGCGGGCACGGCGGACTTGGTGGGGTTATCGGGAGCTGCGAGGCCGGAGGTAGGAGGCCGCTGAGGGCCA

CGAATGAGTTGCTAGGCCGCTTGAGGCATGAGTGGAGGCTATTGTCGGTTTGAGAGATTGGGATTGTCGTTTGGGGC

CGTGGCGGTTTGTAACGCTACACGGCAGTAAGGAGTCAATAACTCATGTGC

>SEQ ID NO: 118

CTCCCTCCCTCCCTCCCTTATGCAAGACCCTTCACATTCATGTATGCACATGCTGCCTGACCCGTTTGTAATGGAAC

CACAAGCTAACCGCGCTGGAGCCAGCCCATGCAGTGCCCCATGCGGGTCTGCACATCAGGACAAGAGCGCCTCCCCT

CTTATGGGTAAGGGTCAGGTATCATGAGGACATTCACTTTGCACCAGATGTCGGGTGGCTTTGTGAATGCAAGTGGA

AGCAGCGATGGCATGTTGGCGTGTCCAGACCTGAATGCCCAGTGCACCTTGCATGGCCGTGGCGCCAAGTCGGCAAC

TABLE 6-continued

Sequences Corresponding to Frequency Peaks (SEQ ID NOs 21-167)

CGCTCCACCCCAGCAAGCTCCAGCTCATACCAANNNNNNNNNNNNNNNNNNNNNNNNNNNNNNNNNNNNNNNN

NNNNNNNNNNNNNNNNNNNNNNNNNNNNNNNNNNNNNNNNNNNNNNNNNNNNNNNNNC

>SEQ ID NO: 119

CTTCCGCAGCTCCGCACTCGCAAGCTCGAGTCCTTGTGAGTGCTCGAGCGCCTGCCAGGTCGACACGATAGCAAGCG

GGTACGTCGCCGCAAGCGCTATTACCGAGCCAACAGCCCCTCCCACTGCTTCAATTGCTGCGGCCTCGCTGGCCATT

TGTAAACTTTGTGTCTTCGGAATGTCTGTTTCTACATGCCGTGTGATACGTTCAAGCTACCACAGAAAGCTAGCACA

AATGAAGAAGGGCAAGGGCTAAACAAACCGTACACCAGTTTGGCGCAAATGCACTTGATCCCACAATTCCAGCGACT

TTTGCGACCGGCTCTCCACCGACCGCTTGGATGCTTGCGCCCGGTCGCTGCCCCAGCTACTTCCGCGGTGAAATAAC

AACGGTGAGCACTCTCAACCACTGCGAGGACAGCCCTAGCAACCGCACTGCGTAAGAAGTACAGCATCGATTTGCTG

CATGTTGATTTTGGCGCAAATGGGGGGTGCAAGCAGTTTGTTTCTCTCAGACGCGAGCTAGCGCCCAAGCGCGCGAT

ATGGGGGCGAGGAGCCACTATGTAGCTGTAACGATTGCATGAGTGGCGAATTTTACTTCGAGGGTCTAGGGTGCGAG

CGGAGTGGGATTACCCCCCGAGGGGCACGCCATGCGCGCAGGCCCCATGCAACAGAAATTCGCCGGGCACCAACCCA

CGCACAGATAATTCATAGGACTACACCATAGCCATCAGAGACCGGCCGGGAACAAGCCCCGCAAGCGGGGCAGCATG

GGCGCGACACCACCCTGCCGCGCCAACTCACCCCAAACACGCCCCAACCACTTGTGCGACACAAGGGCTACCATACA

GTAGCGCGCGACACCTAATCGCGTGCGCCGGAGTGTGCGAGCAAACATTGTACGGCTAAGCTCGTTTGGGCCCTAGG

ACGCAGGGCCTGGCCTGGCATTTGGTGCATTCAATAGAGCATAGAAAACCGAGGCCACATATGTGCTGGGGTGCGCA

AAGGTCGGCGGAATTGTGGGATCAAGTGACGTGGAAATGGATCTGGGGGACTGCGGGGTTTTGGGGTGTGTTGGGTT

GGTGGCGTGAAGGGTGTGATTTGTGAGGAATTTATCGATGCATGCCAAGTTGCACGCCTTTCCCCTGTGTTTCCTAC

ATGCCCCTGAACCCTCCCTTTGCTGGCTGCAGGCGAAGCGACAAGTGGTACCGCTGGTACCACCCACGGGGCCTTG

TGCCCAGGCCGTGGTGGCGCATGGTAACTATACACGTGGCGGTCATCGACATTGCTTTGTGCCGGCGCGCAGCACCC

AGGATGTGCGGCAATCGCTGAAATGCAGTTGTGGGGTCCACACTCATACGGCACCCACGCCCCACAAAGCACTGATG

CAGGGCTCCTGCAGCCGTCACGCCATGGGAATCAGCACATGGGCAGTGGCCTGTGCATACTTCTCTGTGGCCTGGCG

GGGCATCTGGCCAGGGCGTTTGACTAGCGGCATGGGGCCTGCACGCCGGTACGGGGCGCAGGCCCAAAATGATGCA

AGGAAGCTGATGTGTTGCGTGAGGTGCGCAGCGGTTCCTGATGGACGTGGGTGCTGTCATGCGTATGTATGTTGGCT

ATGTGTGTTGTTCTTTGCGCCAGGGTGGTGTCGCCGCGCAGCGGAGCATTGGCGTTGATGCACGGGCGTGAACATT

GGGGCCCGCAATTGGGTTCGCGCCGGCACGGTCGCGGGCATCGCTGAAGATATGTTGGCGCGACCGGTCGCTTATGG

TGCACGCTAATACCCGCATACTGTGCGTAAGCACCGATTGCAATTATAAGTTGCGCATGTAGATATCGGTCTTCTCC

CGACATGCGCTCTGATGACGGGTCCATTTCCGCCAACTTAGGGTGAGAGTTAAGAGCCGGAGCCCTGTTGCCACCTG

CAAAATGCCTTAGCAGCATGTGGCAACTATCTGCCCGAAGCAAGTTGCAAGCCAGCCCAGTTCAGGTTGCCACATGC

CATGCTGGGTATTCCCAGCGCGCTAGCGCACCTGCTTGGGCAGCTCGCTATGGCTGCCGTCGACAGTTGACCCTGGT

ATGCCATCGCTAGAGTCGCAGCCCGCTCCGGCCAACCTCGCTCCTCCGCAACCGACACACGAACCCGACGTCACTTG

ATCCCACAATTCCAGCGACTTTTGCGACCGGCTCTCCACCGACCGCTTGGATGCTTGCGCCCGGTCGCTGCCCCAGC

TACTTCCGCGGTGAAATAACAACGGTGAGCACTCTCAACCACTGCGAGGACAGCCCTAGCAACCGCACTGCGTAAGA

AGTACAGCATCGATTTGCTGCATGTTGATTTTGGCGCAAATGGGGGGTGCAAGCAGTTTGTTTCTCTCAGACGCGAG

CTAGCGCCCAAGCGCGCGATATGGGGGCGAGGAGCCACTATGTAGCTGTAACGATTGCATGAGTGGCGAATTTTACT

TCGAGGGTCTAGGGTGCGAGCGGAGTGGGATTACCCCCCGAGGGGCACGCCATGCGCGCAGGCCCCATGCAACAGAA

ATTCGCCGGGCACCAACCCACGCACAGATAATTCATAGGACTACACCATAGCCATCAGAGACCGGCCGGGAACAAGC

CCCGCAAGCGGGGCAGCATGGGCGCGACACCACCCTGCCGCGCCAACTCACCCCAAACACGCCCCAACCACTTGTGC

GACACAAGGGCTACCATACAGTAGCGCGCGACACCTAATCGCGTGCGCCGGAGTGTGCGAGCAAACATTGTACGGCT

TABLE 6-continued

Sequences Corresponding to Frequency Peaks (SEQ ID NOs 21-167)

AAGCTCGTTTGGGCCCTAGGACGCAGGGCCTGGCCTGGCATTTGGTGCATTCAATAGAGCATAGAAAACCGAGGCCA

CATATGTGCTGGGGTGCGCAAAGGTCGGCGGAATTGTGGGATCAAGTGACGTGGAAATGGATCTGGGGGACTGCGGG

GTTTTGGGGTGTGTTGGGTTGGTGGCGTGAAGGGTGTGATTTGTGAGGAATTTATCGATGCATGCCAAGTTGCACGC

CTTTCCCCTGTGTTTCCTACATGCCCCTGAACCCTCCCTTTGCTGGCTGCAGGCGAAGCGACAAGTGGTACCGCTGG

TACCACCCACGGGGGCCTTGTGCCCAGGCCGTGGTGGCGCATGGTAACTATACACGTGGCGGTCATCGACATTGCTT

TGTGCCGGCGCGCAGCACCCAGGATGTGCGGCAATCGCTGAAATGCAGTTGTGGGGTCCACACTCATACGGCACCCA

CGCCCCACAAAGCACTGATGCAGGGCTCCTGCAGCCGTCACGCCATGGGAATCAGCACATGGGCAGTGGCCTGTGCA

TACTTCTCTGTGGCCTGGCGGGGCATCTGGCCAGGGCGTTTGACTAGCGGCATGGGGCCTGCACGCCGGTACGGGGG

CGCAGGCCCAAAATGATGCAAGGAAGCTGATGTGTTGCGTGAGGTGCGCAGCGGTTCCTGATGGACGTGGGTGCTGT

CATGCGTATGTATGTTGGCTATGTGTGTTGTTCTTTGCGCCAGGGTGGTGTCGCCGCGCAGCGGAGCATTGGCGTTG

ATGCACGGGCGTGAACATTGGGGCCCGCAATTGGGTTCGCGCCGGCACGGTCGCGGGCATCGCTGAAGATATGTTG

GCGCGACCGGTCGCTTATGGTGCACGCTAATACCCGCATACTGTGCGTAAGCACCGATTGCAATTATAAGTTGCGCA

TGTAGATATCGGTCTTCTCCCGACATGCGCTCTGATGACGGGTCCATTTCCGCCAACTTAGGGTGAGAGTTAAGAGC

CGGAGCCCTGTTGCCACCTGCAAAATGCCTTAGCAGCATGTGGCAACTATCTGCCCGAAGCAAGTTGCAAGCCAGCC

CAGTTCAGGTTGCCACATGCCATGCTGGGTATTCCCAGCGCGCTAGCGCACCTGCTTGGGCAGCTCGCTATGGCTGC

CGTCGACAGTTGACCCTGGTATGCCATCGCTAGAGTCGCAGCCCGC

>SEQ ID NO: 120

GTGAAGGGTGTGATTTGTGAGGAATTTATCGATGCATGCCAAGTTGCACGCCTTTCCCCTGTGTTTCCTACATGCCC

CTGAACCCTCCCTTTGCTGGCTGCAGGCGAAGCGACAAGTGGTACCGCTGGTACCACCCACGGGGGCCTTGTGCCCA

GGCCGTGGTGGCGCATGGTAACTATACACGTGGCGGTCATCGACATTGCTTTGTGCCGGCGCGCAGCACCCAGGATG

TGCGGCAATCGCTGAAATGCAGTTGTGGGGTCCACACTCATACGGCACCCACGCCCCACAAAGCACTGATGCAGGGC

TCCTGCAGCCGTCACGCCATGGGAATCAGCACATGGGCAGTGGCCTGTGCATACTTCTCTGTGGCCTGGCGGGGCAT

CTGGCCAGGGCGTTTGACTAGCGGCATGGGGCCTGCACGCCGGTACGGGGGCGCAGGCCCAAAATGATGCAAGGAAG

CTGATGTGTTGCGTGAGGTGCGCAGCGGTTCCTGATGGACGTGGGTGCTGTCATGCGTATGTATGTTGGCTATGTGT

GTTGTTCTTTGCGCCAGGGTGGTGTCGCCGCGCAGCGGAGCATTGGCGTTGATGCACGGGCGTGAACATTGGGGCC

CGCAATTGGGTTCGCGCCGGCACGGTCGCGGGCATCGCTGAAGATATGTTGGCGCGACCGGTCGCTTATGGTGCACG

CTAATACCCGCATACTGTGCGTAAGCACCGATTGCAATTATAAGTTGCGCATGTAGATATCGGTCTTCTCCCGACAT

GCGCTCTGATGACGGGTCCATTTCCGCCAACTTAGGGTGAGAGTTAAGAGCCGGAGCCCTGTTGCCACCTGCAAAAT

GCCTTAGCAGCATGTGGCAACTATCTGCCCGAAGCAAGTTGCAAGCCAGCCCAGTTCAGGTTGCCACATGCCATGCT

GGGTATTCCCAGCGCGCTAGCGCACCTGCTTGGGCAGCTCGCTATGGCTGCCGTCGACAGTTGACCCTGGTATGCCA

TCGCTAGAGTCGCAGCCCGCTCCGGCCAACCTCGCTCCTCCGCAACCGACACACGAACCCGACGTCACTTGATCCCA

CAATTCCAGCGACTTTTGCGACCGGCTCTCCACCGACCGCTTGGATGCTTGCGCCCGGTCGCTGCCCCAGCTACTTC

CGCGGTGAAATAACAACGGTGAGCACTCTCAACCACTGCGAGGACAGCCCTAGCAACCGCACTGCGTAAGAAGTACA

GCATCGATTTGCTGCATGTTGATTTTGGCGCAAATGGGGGTGCAAGCAGTTTGTTTCTCTCAGACGCGAGCTAGCG

CCCAAGCGCGCGATATGGGGCGAGGAGCCACTATGTAGCTGTAACGATTGCATGAGTGGCGAATTTTACTTCGAGG

GTCTAGGGTGCGAGCGGAGTGGGATTACCCCCGAGGGGCACGCCATGCGCGCAGGCCCCATGCAACAGAAATTCGC

CGGGCACCAACCCACGCACAGATAATTCATAGGACTACACCATAGCCATCAGAGACCGGCCGGGAACAAGCCCCGCA

AGCGGGGCAGCATGGGCGCGACACCACCCTGCCGCGCCAACTCACCCCAAACACGCCCCAACCACTTGTGCGACACA

AGGGCTACCATACAGTAGCGCGCGACACCTAATCGCGTGCGCCGGAGTGTGCGAGCAAACATTGTACGGCTAAGCTC

TABLE 6-continued

Sequences Corresponding to Frequency Peaks (SEQ ID NOs 21-167)

```
GTTTGGGCCCTAGGACGCAGGGCCTGGCCTGGCATTTGGTGCATTCAATAGAGCATAGAAAACCGAGGCCACATATG
TGCTGGGGTGCGCAAAGGTCGGCGGAATTGTGGGATCAAGTGACGTGGAAATGGATCTGGGGGACTGCGGGGTTTTG
GGGTGTGTTGGGTTGGTGGCGTGAAGGGTGTGATTTGTGAGGAATTTATCGATGCATGCCAAGTTGCACGCCTTTCC
CCTGTGTTTCCTACATGCCCCTGAACCCTCCCTTTGCTGGCTGCAGGCGAAGCGACAAGTGGTACCGCTGGTACCAC
CCACGGGGGCCTTGTGCCCAGGCCGTGGTGGCGCATGGTAACTATACACGTGGCGGTCATCGACATTGCTTTGTGCC
GGCGCGCAGCACCCAGGATGTGCGGCAATCGCTGAAATGCAGTTGTGGGGTCCACACTCATACGGCACCCACGCCCC
ACAAAGCACTGATGCAGGGCTCCTGCAGCCGTCACGCCATGGGAATCAGCACATGGGCAGTGGCCTGTGCATACTTC
TCTGTGGCCTGGCGGGGCATCTGGCCAGGGCGTTTGACTAGCGGCATGGGGCCTGCACGCCGGTACGGGGGCGCAGG
CCCAAAATGATGCAAGGAAGCTGATGTGTTGCGTGAGGTGCGCAGCGGTTCCTGATGGACGTGGGTGCTGTCATGCG
TATGTATGTTGGCTATGTGTGTTGTTCTTTGCGCCAGGGTGGTGTCGCCGCGCAGCGGAGCATTGGCGTTGATGCAC
GGGGCGTGAACATTGGGGCCCGCAATTGGGTTCGCGCCGGCACGGTCGCGGGCATCGCTGAAGATATGTTGGCGCGA
CCGGTCGCTTATGGTGCACGCTAATACCCGCATACTGTGCGTAAGCACCGATTGCAATTATAAGTTGCGCATGTAGA
TATCGGTCTTCTCCCGACATGCGCTCTGATGACGGGTCCATTTCCGCCAACTTAGGGTGAGAGTTAAGAGCCGGAGC
CCTGTTGCCACCTGCAAAATGCCTTAGCAGCATGTGGCAACTATCTGCCCGAAGCAAGTTGCAAGCCAGCCCAGTTC
AGGTTGCCACATGCCATGCTGGGTATTCCCAGCGCGCTAGCGCACCTGCTTGGGCAGCTCGCTATGGCTGCCGTCGA
CAGTTGACCCTGGTATGCCATCGCTAGAGTCGCAGCCCGCTCCGGCCAAACCTCGCTCCTCCGCAACCGACACACGA
ACCCGACGTCACTTGATCCCACAATTCCAGCGACTTTTGCGACCGGCTCTCCACGACCGCTTGGATGCTTGCGCCCG
GTCGCTGCCCCAGCTACTTCCGCGGTGAAATAACAACGGTGAGCACTCTCAACCACTGCGAGGACAGCCCTAGCAAC
CGCACTGCGTAAGAAGTACAGCATCGATTTGCTGCATGTTGATTTTGGCGCAAATGGGGGGTGCAAGCAGTTTGTTT
CTCTCAGACGCGAGCTAGCGCCCAAGCGCGCGATATGGGGGCGAGGAGCCACTATGTAGCTGTAACGATTGCATGAG
TGGCGAATTTTACTTCGAGGGTCTAGGGTGCGAGCGGAGTGGGATTACCCCCGAGGGGCACGCCATGCGCGCAGGC
CCCATGCAACAGAAATTCGCCGGGCACCAACCCACGCACAGATAATTCATAGGACTACACCATAGCCATCAGAGACC
GGCCGGGAACAAGCCCCGCAAGCGGGGCAGCATGGGCGCGACACCACCCTGCCGCGCCAACTCACCCCAAACACGCC
CCAACCACTTGTGCGACACAAGGGCTACCATACAGTAGCGCGCGACACCTAATCGCGTGCGCCGGAGTGTGCGAGCA
AACATTGTACGGCTAAGCTCGTTTGGGCCCTAGGACGCAGGGCCTGGCCTGGCATTTGGTGCATTCAATAGAGCATA
GAAAACCGAGGCCACATATGTGCTGGGGTGCGCAAAGGTCGGCGGAATTGTGGGATCAAGTGATGGCAATCCTGAAC
CAAAACCGGGCTGTGCACAGCTTAAACCGGATACAATCGTTTGGTGCTTAGACACAGTGCTCAGTCAGTTTAAGCAG
TGAAAGCTTTTTGCCGCGAACAGGTTTTTGCATGGCTTCTGCTCCGACTGCTCGTGCTGTGTGATCTAGAAATAGC
ATTGTAGCTTCAAACCAGGTCTTCTGGCAAGGCTGGCTCAACTTGAGCTCTAGCAAAGGCGGAATCGGTCGGGGCTT
GGCCCCGCACCGTCAGGCGCTCTCCAACACTGCCTAGCCTGGCG
```

>SEQ ID NO: 121
```
ACCTAGCTAGCTAGGAGGTTGTTGCTGCTGACGTGGAATTGGCGTTTAGCCAATGGAAGTATGAGGCGATAACAGGT
CTGTGATGCCCTTAGATGTTCTGGGCCGCACGCGCGCTACACTGACGCGACCAACGAGCCTATCCTTGGCCGAGAGG
CCCGGGTAATCTTGTAAACCGCGTCGTGATGGGGATAGATTATTGCAATTATTAGTCTTCAACGAGGAATGCCTAGT
AAGCGCGAGTCATCAGCTCGCGTTGATTACGTCCCTGCCCTTTGTACACACCGCCCGTCGCTCCTACCGATTGGGTG
AGCTGGTGAAGTGTTCGGATTGAGCTTGGCTGGGGCAACCTGGCCTTGCTTGAGAAGTTCATTAAACCCTCCCACCT
AGAGGAAGGAGAAGTCGTAACAAGGTTTCCGTAGGTGAACCTGCGGAAGGATCATTGAATCTATCACAATCCACACC
GCGAACTAACACTGTTGGCCTCCGTCTGTGTAAAAGCAAACGGGCCAGGTCTGGGCGCAATGTAAAAGTTACGCCTG
GCCTGGGTTGCCGCAAGGCATCGGTCTCTTATACTAACCAACCAACACCAAACCAAAACTAAATTAAAACCGAGTAT
```

TABLE 6-continued

Sequences Corresponding to Frequency Peaks (SEQ ID NOs 21-167)

CTAGCTTAGAGCTAGTGCTCACTAACCAAGACAACTCTCAACAACGGATATCTTGGCTCTCGGATCGATGAAGAACG

CAGCGAAATGCGATACGTAGTGTGAATTGCAGAAATACGTGAATCATCGAATCTTTGAACGCATATTGCGCTCGAGG

CTTCGGCCAAGAGCATGTCTGCCTCAGCGTCGGGTTAATACTCGCCCTACTCCAACACACTTGTGTGTTTGGAGCAA

GAGCGGACCTGGCTGTCTCGGTGTTTGATTTTCGGATCAGACGCCGGGTCAGCTGAAGTACAGAGGTTGATGCATGG

ACCCGCTTATGGGCCTCTACTGGGTAGGCAACTCGTTGCTAATGCTTTAGTAGATGGCTTGGAGCTGTGCTTGTCGA

CCCAAACCAGGAACTTTGGCCCTGTGCCGAAGCAAACCCCTATTTTCTCGACCTGAGCTCAGGCAAGATTACCCGCT

GAACTTAAGCATATCAATAAGCGGAGGAAAAGAAACTAACAAGGATTCCCCTAGTAACGGCGAGCGAACCGGGAATA

GCCCAACTTGAAAATCTTCCCAGGGCCGATGCCGATGTCTCCGGGCTCGCTTGCGTTACCGCCAGCCGCCTTGTCCA

AGTAAGGGAATCTTAACCCTTTTCCCTTTCGATGGGCAGCGCGAATCGCGCTCTTCACACAGGATTACCCCATCTCT

TAGGATCGACTAACCCATGTCCAATTGCTGTTCACATGGAACCTTTCTCCACTTCAGTCTTCAAAGTTCTCATTTGA

ATATTTGCTACTACCACCAAGATCTGCACTAGATGCCGATTCACCCAGGCTCACGCCAGAGGCTTAGTCTCGACACC

CACGCCCTCCTACTCATGGAAGCGTCGCACTTGCTTCCATGGCCGAGTATAGGTCACGCGCTTAAGCGCCATCCATT

TTCGGGGCTAATTGATTCGGCAGGTGAGTTGTTACACACTCCTTAGCGGATTTCGACTTCCATGACCACCGTCCTGC

TGTTTATATCAATCAACACCCTTTGTGGGATCTAGGTTAGCGCGTAGTTTGGCACCTTAACTCGACTATCGGTTCAT

CCCGCATCGCCAGTTCTGCTTACCAAAAATGGCCCACTTGGAGCTCACATTGAATGTGCCGGTTCAATTAAGCAACC

GACACGTCTTACCTATTTAAAGTTTGAGAATAGGTGAAGGATGTTTCATCCCCCGAACCTCTAATCATTCGCTTTAC

CCGATAAAACTGATCAAGCTCCAGCTATCCTGGATGGAAGGTAGGATGGGTGTGAGCCTGCCGCGTGGGACCTGGCG

GTGTGCGTCGAGGGCGCGAGTGTGCTCAGTTCCTCTTGAATTGGTATGTTTAGCTAGAATGGTGAGGCCGAAGCCAG

ATGAAAATTGTTGCTGTATTATATTCTTTGCATTCGCATTTGGCCAGACTTCGGAGGCTGCACAACTGCAGTGAGAT

GTCGATGTATAACAACAGACGTGCGCGAACGTATATGGGGGGCTGGATAGAGTTCGAGAAGTCAAAGATTTTACGGA

GAAGGGGTGGGACTGGGCAGTTCTGACGGCACCTGTTGACGCAAACTGGCGGCCAGCCGGCCACAGTCGAATGTGGT

TCGACCGTGGGCGACGGTGGGCGTGTGCGGCATGTGTGCCGGCGCCCCGTACGCCTCGCCTGCGTGCCCTGCGGCTT

TCGATGCAAAGCAGGGCGGGATGAGGCCACGAGGGGGA

>SEQ ID NO: 122

GGCTCCTGTCTTTTTCTTATGTGTCTTATGTGTTGTGTTAGATAAGGTTTCTTATGTGTGTGTGTGGCTGTTGGG

TTAGATAAGACATATAAGGGTTTCGGGGTTTTGGTGCCCTGTGCCTTGTTCCGCGGGTCCCAACGTGTCCCCCTTGT

GCTGGCATGGTGTTGGGAGTGTGTGCGATGTGTTGGAAGCGTTGGGGGTGCTTGGAGTGCAGTTTGGTGTGTGTGGT

GTGGTGTGGAGTTGGTCAAGGGTGTCAGTCCCCTTGGCACGCTAGCAACCCTACCCCATATCCACCCCCTGGCCAGC

TCTGCCACCCTCGCCCACGCGCATGCACTCACAGCACGTCAAACGAGTTCCCATTTCACTTTGGCATGTATGGGGAG

GCATGGGCAGCTCCGGGCGGGATGGCACCATGGCGGTGGTGGTACCGTGTGCTCGGGTCCTGCCTTTGGCTCTGC

TTGTCCATGACGTACGGCTCTGGGTATCTTCCATGCCCGTAAGTTATGGCCCTAAGGTACCCTAAGGTACCCTAAGG

TACCCACGCGTGTGCCCTCTAGGGTACAGGGGTAACACTTGCGCATACACACACGCGCGCACACACGCACACACACG

CACACACTCCCCCCTGCCAACCCCACTCTCACCCCCGCGTCCCCCGCCCCCCTGCGTGTGCGTGTGTGCCACGA

CGTGCGTACGGCAAAGTGTGGCCAAGGCCCCCCCTTGCGAGTGGGGAACCCCCCTAGCCCCTAGGCCCTAGCCCCC

AACCCCTAGACAGCCAGCCCAAACGGAAACAGGTGTGGTGTCATGTATCTGGGGTAGGCGTGAAGAGAAGCGAAAGC

AAGCAATTGCAAAGCTTCGAATCATAACAACACAATCCGAAGAATGAGCTAAGCAATTAGTTCTAGTAACTCGGTGA

GTGGCAGTGAACTCAAGTAGGCTCTGCCGGGTCAGGTAACTGGTCCTGGCTAGCCCTGCTTGAACTGGTTCAATCAA

TGCGTCAATTGGCGGTCAAACGCTGGTTGATTGTTGCCCAAATCTATTGATGGTTTGAGTTGCAACGAGTGTTGAGA

GAGCTTGTATTAATACGCGATGCGTATGCTTATGAACCAAGTGGACCTGCTAGGACAGTAGGTGCAAGGCCAGTGTA

TABLE 6-continued

Sequences Corresponding to Frequency Peaks (SEQ ID NOs 21-167)

ACAGCTGTGCTTTGTTATCTGCCGGCTAGCATTGAAGCTCTGCTTGCGGGAAGCCGCATGCCTGAGTGTTCGCTAGG

TGGTCTGAGCTTATGCCTAACCCGTGTAAGACTCAGCCAATCCGCGATACTTGGTTGCGTTGCTTCCGGAGCGCTGG

TTCAGAGCTGGGAGAACGTTCAGAGAGGCCTCGTGGCAAGAGCTCTTCTGACTCGATTCGTCTTCGGACAGTCGTGT

TCAGTCGACTCTCGAGTGCTTTCTCAACGGATAGCGCTTCTTAATTGATTCAATTCCTGCGTATCCTTTGTGATACG

CGCCGGAATACTGTGGCATGCGTATGCTCTCGTGGCGTATGTGTGCTGCAGTTTCAATTAAAGGCAGCTACCTGGTT

GATCCTGCCAGTAGTCATATGCTTGTCTCAAAGATTAAGCCATGCATGTCTAAGTATAAACTGCTTATACTGTGAAA

CTGCGAATGGCTCATTAAATCAGTTATAGTTTATTTGATGGTACCTACTACTCGGATAACCGTAGTAATTCTAGAGC

TAATACGTGCGCACAACCCGACTTCTGGAAGGGTCGTATTTATTAGATAAAAGGCCAGCCGGGCTCTGCCCGACCTG

CGGTGAATCATGATAACTTCACGAATCGTATGGGCTCGTCCCGACGATGTTTCATTCAAATTTCTGCCCTATCAACT

TTCGATGGTAGGATAGAGGCCTACCATGGTGGTAACGGGTGACGGAGGATTAGGGTTCGATTCCGGAGAGGGAGCCT

GAGAGATGGCTACCACATCCAAGGAAGGCAGCAGGCGCGCAAATTACCCAATCCCGACACGGGGAGGTAGTGACAAT

AAATAACAATACCGGGCGCTTCGCGTCTGGTAATTGGAATGAGTACAATCTAAATCCCTTAACGAGGATCCATTGGA

GGGCAAGTCTGGTGCCAGCAGCCGCGGTAATTCCAGCTCCAATAGCGTATATTTAAGTTGT1GCAGTTAAAAAGCTC

GTAGTTGGATTTCGGGTGGGGTGGTGCGGTCCGCCTCTGGTGTGCACTGCTCTGCTCCACCTTCCTGCCGGGGACGG

GCTCCTGGGCTTCACTGTCTGGGACTCGGAGTCGGCGAGGTTACTTTGAGTAAATTAGAGTGTTCAAAGCAGGCCTA

CGCTCTGAATACATTAGCATGGAATAACACGATAGGACTCTGGCCTATCTGTTGGTCTGTGGGACCGGAGTAATGAT

TAAGAGGGGTAGTCGGGGGCATTCGTATTCCGTTGTCAGAGGTGAAATTCTTGGATTTACGGAAGACGAACATCTGC

GAAAGCATTTGCCAAGGATACTTTCATTGATCAAGAACGAAAGTTGGGGGCTCGAAGACGATTAGATACCGTCGTAG

TCTCAACCATAAACGATGCCGACTAGGGATTGGCAGATGTTCTTTTGATGACTCTGCCAGCACCTTATGAGAAATCA

AAGTTTTTGGGTTCCGGGGGGAGTATGGTCGCAAGGCTGAAACTTAAAGGAATTGACGGAAGGGCACCACCAGGCGT

GGAGCCTGCGGCTTAATTTGACTCAACACGGGGAAACTTACCAGGTCCAGACACGGGAAGGATTGACAGATTGAGAG

CTCTTTCTTGATTCTGTGGGTGGTGGTGCATGGCCGTTCTTAGTTGGTGGGTTGCCTTGTCAGGTTGATTCCGGTAA

CGAACGAGACCTCAGCCTGCTAAATAGTCAGCATCGCACCTGCGGTGCGCCGACTTCTTAGAGGGACTATTGGCGTT

TAGCCAATGGAAGTATGAGGCGATAACAGGTCTGTGATGCCCTTAGATGTTCTGGGCCGCACGCGCGCTACACTGAC

GCGACCAACGAGCCTATCCTTGGCCGAGAGGCCCGGGTAATCTTGTAAACCGCGTCGTGATGGGGATAGATTATTGC

AATTATTAGTCTTCAACGAGGAATGCCTAGTAAGCGCGAGTCATCAGCTCGCGTTGATTACGTCCCTGCCCTTTGTA

CACACCGCCCGTCGCTCCTACCGATTGGGTGTGCTGGTGAAGTGTTCGGATTGAGCTTGGCTGGGGCAACCTGGCCT

TGCTTGAGAAGTTCATTAAACCCTCCCACCTAGAGGAAGGAGAAGTCGTAACAAGGTTTCCGTAGGTGAACCTGCGG

AAGGATCATTGAATCTATCACAATCCACACCGCGAACTAACACTGTTGGCCTCCGTCTGTGTAAAAGCAAACGGGCC

AGGTCTGGGCGCAATGTAAAAGTTACGCCTGGCCTGGGTTGCCGCAAGGCATCGGTCTCTTATACTAACCAACCAAC

ACCAAACCAAAACTAAATTAAAACCGAGTATCTAGCTTAGAGCTAGTGCTCACTAACCAAGACAACTCTCAACAACG

GATATCTTGGCTCTCGGATCGATGAAGAACGCAGCGAAATGCGATACGTAGTGTGAATTGCAGAAATACGTGAATCA

TCGAATCTTTGAACGCATATTGCGCTCGAGGCTTCGGCCAAGAGCATGTCTGCCTCAGCGTCGGGTTAATACTCGCC

CTACTCCAACATGTTTGGAGCAAGAGCGGACCTGGCTGTCTCGGTGTTTGATTTTCGGATCAGACGCCGGGTCAGCT

GAAGTACAGAGGTTGATGCATGGACCCGCTTATGGGCCTCTACTGGGTAGGCAACTCGTTGCTAATGCTTTAGTAGA

TGGCTTGGAGCTGTGCTTGTCGACCCAAACCAGGAACTTTGGCCCTGTGCCGAAGCAAACCCCTATTTTCTCGACCT

GAGCTCAGGCAAGATTACCCGCTGAACTTAAGCATATCAATAAGCGGAGGAAAAGAAACTAACAAGGATTCCCCTAG

TAACGGCGAGCGAACCGGGAATAGCCCAACTTGAAAATCTCCCTTTGGAGAATTGTAGTCTAGAGAAGCGCTTTCTA

GGGCTGGCGGAACTCAAGTCGGATCGAATGCCGCGTCAGAGAGGGTGN

TABLE 6-continued

Sequences Corresponding to Frequency Peaks (SEQ ID NOs 21-167)

>SEQ ID NO: 123

```
TGGCCTCCGTCTGTGTAAAGCAAACGGGCCAGGTCTGGGCGCAATGTAAAAGTTACGCCTGGCCTGGGTTGCCGCAA
GGCATCGGTCTCTTATACTAACCAACCAACACCAAACCAAAACTAAATTAAAACCGAGTATCTAGCTTAGAGCTAGT
GCTCACTAACCAAGACAACTCTCAACAACGGATATCTTGGCTCTCGGATCGATGAAGAACGCAGCGAAATGCGATAC
GTAGTGTGAATTGCAGAATACGTGAATCATCGAATCTTTGAACGCATATTGCGCTCGAGGCTTCGGCCAAGAGCAT
GTCTGCCTCAGCGTCGGGTTAATACTCGCCCTACTCCAACATGTTTGGAGCAAGAGCGGACCTGGCTGTCTCGGTGT
TTGATTTTCGGATCAGACGCCGGGTCAGCTGAAGTACAGAGGTTGATGCATGGACCCGCTTATGGGCCTCTACTGGG
TAGGCAACTCGTTGCTAATGCTTTAGTAGATGGCTTGGAGCTGTGCTTGTCGACCCAAACCAGGAACTTTGGCCCTG
TGCCGAAGCAAACCCCTATTTTCTCGACCTGAGCTCAGGCAAGATTACCCGCTGAACTTAAGCATATCAATAAGCGG
AGGAAAAGAAACTAACAAGGATTCCCCTAGTAACGGCGAGCGAACCGGGAATAGCCCAACTTGAAAATCTCCCTTTG
GAGAATTGTAGTCTAGAGAAGCGCTTTCTAGGGCTGGCGGAACTCAAGTCGGATCGAATGCCGCGTCAGAGAGGGTG
ATAACCCCGTCGGTTCCTGCTTAGTCCTTCCACGAAGTGCTTTCCACGAGTCGGGTTGTTTGGGAATGCAGCCCTAA
TTTGGAGGTAAATCCCTTCTAAGGCTAAATACTGCCGAGAGACCGATAGCGAACAAGTACCGTGAGGGAAAGATGAA
AAGAACTTTGAAAAGAGAGTTAAAAGTGCTTGAAATTGTTGAGAGGGAAGCGATTGGCGCTCGTAGGTGCGCCCAGG
CTTAAGCGGTCCTAACGGCCCGTTGAATGTGCTGGGTGCTGGTCAGAATGGGTTGAGTTGGCGGGACAAAAGCTGGG
TCCACCCAGGTAACCCGGCCGATGCCGCCGACTCGACCAAGGCGTAAAGAGTACCTTGTCCTTCGGGATCTGTGCTC
TAAAGATTCTGGCAGAAGAGCGTCAATCGACCCGTCTTGAAACACGGACCAAGGAGTCTAACATGTATGCGAGTTGG
CGGGTGGAAAACCCGTAAGCGCAAGTAACCTGACTGGTGGGATGGGTAAAACCCTGCACCATCGACCGACCATGTT
GTTTCTACGAAAGGTTTGAGTGCGAGCATACCTGTTGGGACCCGAAAGATGGTGAACTATGCCTGAGCAGGGTGAAG
CCAGAGGAAACTCTGGTGGAGGCTCGTAGATGTGCTGACGTGCAAATCGCTTTTCAGACTTGGGTATAGGGGCGAAA
GACTAATCGAACCATCTAGTAGCTGGTTCCCTCCGAAGTTTCCCCCAGGATAGCTGGAGCTTGATCAGTTTTATCGG
GTAAAGCGAATGATTAGAGGTTCGGGGATGAAACATCCTTCACCTATTCTCAAACTTTAAATAGGTAAGACGTGTC
GGTTGCTTAATTGAACCGGCACATTCAATGTGAGCTCCAAGTGGGCCATTTTTGGTAAGCAGAACTGGCGATGCGGG
ATGAACCGATAGTCGAGTTAAGGTGCCAAACTACGCGCTAACCTAGATCCCACAAAGGGTGTTGATTGATATAAACA
GCAGGACGGTGGTCATGGAAGTCGAAATCCGCTAAGGAGTGTGTAACAACTCACCTGCCGAATCAATTAGCCCCGAA
AATGGATGGCGCTTAAGCGCGTGACCTATACTCGGCCATGGAAGCAAGTGCGACGCTTCCATGAGTAGGAGGGCGTG
GGTGTCGAGACTAAGCCTCTGGCGTGAGCCTGGGTGAATCGGCATCTAGTGCAGATCTTGGTGGTAGTAGCAAATAT
TCAAATGAGAACTTTGAAGACTGAAGTGGAGAAAGGTTCCATGTGAACAGCAATTGGACATGGGTTAGTCGATCCTA
AGAGATGGGTAATCCTGTGTGAAGAGCGCGATTCGCGCTGCCCATCGAAAGGGAAAAGGGTTAAGATTCCCTTACT
TGGACAAGGCGGCTGGCGGTAACGCAAGCGAGCCCGGAGACATCGGCATCGGCCCTGGGAAGAGTTCTCTTTTCTTT
TTAACAACGCGAAGGCCCTGGAATCGAATCATTCGGAGATAGGGCTCAGACGTTGGTAAAGCACCGCACTTCTCGCG
GTGTCCGGCGCGCCGTTGACGGTCCTTGAAAATCCGGGGAGCATTCCCGATCTTGCCAAGTCGTACTCATAACCGC
ATCAGGTCTCCAAGGTGAACAGCCTCTAGTCGATAGAACAATGTAGATAAGGGAAGTCGGCAAAATGGATCCGTAAC
TTCGGGAAAAGGATTGGCTCTGAGGGCTGGGCCTAGGGGTCTGCAGCTGCGAAGCTCGGGACTGCGGTGGTCTACCC
AGCTGGAAACGGCTGGGCGGACTGCTGCGTGTCCTGGGTGGACGGCTGTAGAAGCTTCGGCGTTCCCTAGGCGACGA
ACAGCCAACTCAGAACTGGTACGGACAAGGGGAATCCGACTGTTTAATTAAAACAAAGCATTGTGATGGTCCTAAAG
GATGTTGACACAATGTGATTTCTGCCCAGTGCTCTGAATGTCAAAGTGAAGAAATTCAACCAAGCGCGGGTAAACGG
CGGGAGTAACTATGACTCTCTTAAGGTAGCCAAATGCCTCGTCATCTAATTAGTGACGCGCATGAATGGATTAACGA
GATTCCCACTGTCCCTATCTACTATCTAGCGAAACCACAGCCAAGGGAACGGGCTTGGAATAAACAGCGGGGAAAGA
```

TABLE 6-continued

Sequences Corresponding to Frequency Peaks (SEQ ID NOs 21-167)

AGACCCTGTTGAGCTTGACTCTAGTCCGACTTTGTGAAATAACTTAAGAGGTGTAGAATAAGTGGGAGCTTCGGCGA

CGGTGAAATACCACTACTTTTAACGTTGTTTTACTTATTCCATTACTTGGAGGCGGGACTCTGTCCCTGCTTCTAGC

TCTAAGACGGCTTTTGCACGTCGATCCAGGTGGAAGACATTGTCAGGTGGGGAGTTTGGCTGGGGCGGCACATCTGT

TAAAAGATAACGCAGGTGTCCTAAGATGAGCTCAACGAGAACAGAAATCTCGTGTAGAACAAAAGGGTAAAAGCTCA

TTTGATTTTGATTTTCAGTACGAATACAAACTGTGAAAGCATGGCCTATCGATCCTTTAGCCTTTCGGGATTTGAAG

CTAGAGGTGTCAGAAAAGTTACCACAGGGATAACTGGCTTGTGGCAGCCAAGCGTTCATAGCGACGTTGCTTTTTGA

TCCTTCGATGTCGGCTCTTCCTATCATTGTGAAGCAGCATTCACCAAGCGTTGGATTGTTCACCCACTAATAGGGAA

CGTGAGCTGGGTTTAGACCGTCGTGAGACAGGTTAGTTTTACCCTACTGTTGGACCGATTCCGCCATAGTAATTCGG

CTCAGTACGAGAGGAACCGCCGAGTCAGATAATTGGTAATGCCCTTGTCTGAAAAGACAATGGGGCGAAGCTAACAT

CTGTAGTCTAATGACTGAACGCCTCTAAGTCAGAAGACGTGCTAGGTGCGGAGTCACTTACCCAATGATGTCACCCG

ACTAAGGATACATCCGCCTGTGCGGATGCTGGAGCATACCCGTTGGTTCCCTGTTAGGTCCACATGGCCGAAGCAG

GCGCCAAGCATGACAATTCCACTCGTCATTGGGGTAAATCCTCTGTAGACGACTTTGTTGCAACTGGGTATTGTAAG

TGGTAGAGTGGCCTTGCTGCTACGATCCACTGAGATTCATCCCGTGTTGCTAAGATTTGTCACTGCCCTTCGGGCA

ACCCCTCCTCCTCTCGGAGCGACAGCTCCAGGGAGGGCCCTCTCTCTCTCTCTTCCAAGTGGTGTAGCTGAGCTG

AGCGCGTGCCAACGCCGCCAAATCCGTCTAAGTGCCCACATGTGTGTGCATGCCCTGCCCCTCCTCCCCCACACAGC

CAAAGTGCTCAAGGTACCTTCCCTGTGTGTGTGCAAGTGAGAGCAACAGCATGCATGTGCCCTTACTTAGGCGGCCT

AGTGTGGTATGTG

>SEQ ID NO: 124

AAACGTTGGTCAAACGTAGCTTGGTCAAAGTTTGACCGGCCTTAGTCAGCGCGTTGTTGGTCCGATTTGCTCCTGTC

TTTTTCTTATGTGTCTTATGTGTTGTGTTAGATAAGGTTTCTTATGTGTGTGTGTGGCTGTTGGGTTAGATAAGA

CATATAAGGGTTTCGGGGTTTTGGTGCCCTGTGCCTTGTCCCGCGGGTCCCAACGTGTCCCCCTTGTGCTGGCATGG

TGTTGGGAGTGTGTGCGATGTGTTGGAAGCGTTGGGGGTGCTTGGAGTGCAGTTTGGTGTGTGTGGTGTGGTGTGGA

GT1GGTCAAGGGTGTCAGTCCCCTTGGCACGCTAGCAACCCTACCCCATATCCACCCCCTGGCCAGCTCTGCCACCC

TCGCCCACGCGCATGCACTCACAGCACGTCAAACGAGTTCCCATTTCACTTTGGCATGTATGGGGAGGCATGGGCA

GCTCCGGGCGGGATGGCACCATGGCGGTGGTGGTACCGTGTGCTCGGGTCCTGCCTTTGGCTCTGCTTGTCCATGA

CGTACGGCTCTGGGTATCTTCCATGCCCGTAAGTTATGGCCCTAAGGTACCCTAAGGTACCCTAAGGTACCCACGCG

TGTGCCCTCTAGGGTACAGGGGTAACACTTGCGCATACACACACGCGCGCACACACGCACACACACGCACACACTCC

CCCCTGCCAACCCCACTCTCACCCCCGCGTCCCCCCGCCCCCCTGCGTGTGCGTGTGTGCCACGACGTGCGTACG

GCAGTGTGGCCAAGGCCCCCCCTTGCGAGTGGGGAACCCCCTAGCCCCTAGGCCCTAGCCCCAACCCCTAGACA

GCCAGCCCAAACGGAAACAGGTGTGGTGTCATGTATCTGGGGTAGGCGTGAAGAGAAGCGAAAGCAAGCAAT

>SEQ ID NO: 125

AAGACATATAAGGGTTTCGGGGTTTTGGTGCCCTGTGCCTTGTTCCGCGGGTCCCAACGTGTCCCCCTTGTGCTGGC

ATGGTGTTGGGAGTGTGTGCGATGTGTTGGAAGCGTTGGGGGTGCTTGGAGTGCAGTTTGGTGTGTGTGGTGTGGTG

TGGAGTTGGTCAAGGGTGTCAGTCCCCTTGGCACGCTAGCAACCCTACCCCATATCCACCCCCTGGCCAGCTCTGCC

ACCCTCGCCCACGCGCATGCACTCACAGCACGTCAAACGAGTTCCCATTTCACTTTGGCATGTATGGGGAGGCATGG

GGCAGCTCCGGGCGGGATGGCACCATGGCGGTGGTGGTACCGTGTGCTCGGGTCCTGCCTTTGGCTCTGCTTGTCC

ATGACGTACGGCTCTGGGTATCTTCCATGCCCGTAAGTTATGGCCCTAAGGTACCCTAAGGTACCCTAAGGTACCCA

TABLE 6-continued

Sequences Corresponding to Frequency Peaks (SEQ ID NOs 21-167)

CGCGTGTGCCCTCTAGGGTACAGGGGTAACACTTGCGCATACACACACGCGCGCACACACGCACACACACGCGCACA
CACTCCCCCCTGCCAACCCCACTCTCACCCCCGCGTCCCCCCGCCCCCCTGCGTGTGCGTGTGTGCCACGACGTG
CGTACGGCAAAGTGTGGCCAAGGCCCCCCCTTGCGAGTGGGGGAACCCCCCTA

>SEQ ID NO: 126

TCTGCGGCGGTTGTGTGGTGGTTGCGGGCTGCAGCAGCCGGTGCCTTTGCAAGCAGCAGTCCTGCCGCCGCCAGGCT
TCTGCTGTCGCTGTTGCTCTTGCTGTTGCTGGGCGCTGCAGTTGCTGCTGGCTGCTGCTGTTGCTGCAGCTGCTGAG
CACCGGCGGCCACCATTGCCAGATAGTGTGGCTGCGGCGGTTGATATGCAGCTGCTGGCAGCTGCTGCGCATATACC
CGCGACTGTTTCTTCTGCGAGGGCACGGGCTGCTGCTGCTGTGCGCTATTTGCAGTAGTTGATGCCGCGACATG
CGAGGGCGGAAGCAGCTTGCTGCTACTGCCGCCGCCGCCGCCGCTGCAGAGACCTGCGGCGGCCGCCGTTGATG
ACCTGCCACCTCTGGTGCTGGCTTGCGTCTTAAAGCCCTTGCTCCGCTGCCTCTCCTCCTTCAGCTTGATGAGCAAG
GCAGGAATATTGCTCGCTGCGTACACGTACGAGATAGGCATGATGTATGAGCGAGATAGACCGTGCATCAGCATCTT
GTTGCGTACGTACGTGCGCACACGCGGGCGACTTATCTATCTATCTATCTATCTGCTGCATGCTGCTAAGCCAGCGA
AACAGGCAAAACGAATTGTCGTGTGCGTAGCTAGCCGAATGCCAGCCACGCGTGCGTCCGTAATACGTATTTACGGC
GGATGAGCAGTAGTGGCATTGCAGGTGGAAATGCGCTTGATTGCTTCCGTGCTTCCGTGTGTCAATACGCACAAACA
TGTTATGCCCGCCCGGGCACATCAATTTATTGTCCAGATAGACAAACGGTCTCAATGGGTTCGCTGCACCAAGCATC
ACGCGTGCGTGCCGCACCCAGCTACTTACCAACCAGCTCGTGCCACTCGCCATCGTAGTCCTCGTGTGGGAAGTTGG
TGATGGCTTGCCGGCCCAACTTGCAGATGCATGCGCGGTCGAACACACGCGCGGCCTCCTCTTCCTGCATTGCAGAA
GTTAAGTGTAACGATGCGAAAAGGCCCTGAACAGAAGTTGCCGAAACGGGAGATACTCGTGTTACATTCGGGTGACT
TGACCGGCAGTTATTTCGCTGGGTTGTGTGCATTTGCAGCGCGGCGCAGCAGCGCAAGCAAGTGCAATTTTCAACAT
ATATGTACACTGTTGTGCTGCGTTACCCTCACAGTAAAAGGACCAGCTAGCAGGTGTCAGCCCACCGTTTCCGCAAC
ACGGCACTACACACAGCTAGTCAGCAGATTCTGTCGCCAGCAGCCGTGCAAACAAGCAAGCCAGCAGTGACTTGG
TAATAAGGCTGAACCCGCCCAAATAAAGCGCTAGCTAGCTCATCACGCGTACTTACACGTGTGTAGTCGCCAAGTGT
TACTGTCCGTCCACCATGAGATATCTGATGGATGGGATGCATGGGCGCGCGGGACAATTATTATCAGTGCAAATGGA
TGGTATTAGCAGCAGCAGCACAAACGGCAAGTAAAGGATAGGCTCATACGCCAACGGCAATTCATACACATGCAAGC
ATGGAGCTAGCTAGCTAGCACCGTGCGTGCGTGCTCAATGTACCGCATGTGGAGCTTTCATTAGAAATAATACCTTC
CATCCGTGCAAACAACAAATAACGCACGTGCGTGGCCTTCTGAGGTTGTCATCTGAGATGTATCTCTAGACACTATG
TACAGGCTGCATTGCTGCTGGCGTGCGTTATCTCCTACGGGACGGAGGGATATGCATGCGCGTGCGTGCCCAACTAC
TCCTGCTGGACGCTATGTACATGGCCGCACTCGCCCCGCCCTTGCTCCTGCTGGCGGTTCTGCTAGGATTCGGCCCG
ACCGTCCACGGCGTTTACCGTCGGTTACGAGCGAGGTAACATGTGAATTCGCAACTTGCGCTACTGACTGCCTGCTC
TCGTGCCGCCTGCAAGCCCACTCCGCCTTCCGCTCTGGCCTACGTACGCATAACTAGTTCCGCAACGCACGTCAATT
GCTTGAGAACGTAGGTAGGGATGTGTTTGACCCCTGTGCGCTAGCGCAAGCAAGTACGTTTCCGAACATCGTATGTA
AGTAAGCGTTGCCCGCGAGATACATACCGCCAGTTTTAGATAGATCGGGCGGGATTACTATTGCGCGTGTTCGGGAT
CAAGCTAGCGGATGCAGCTGCTGTATGACTACAGTGTAACCCTGCCTGTTGGCGAGGCGTACGTGTGTAAACAATTG
ATCCCGCCATGTCAAGATGATGCATAACATATATACAGTGATGCAGATGTCGCCAGCACGCAAAACCCACACAGCTG
CTAATGCACTTGAATTATCAATTGCAATTGCTGCCGCTGCTGTCCTACGTAATATAAGCTGGCTAGCTAGCTGCTGT
TCCATCCCACACAATAATGCATGGCGTACGTTGATAGCTAGCTAGCCGCACAAGCTAGTTGCAACGGGCGGCAATGA
CGTGCAGGGCTGACGGGATTGGGCATCAATTGCGGTAGTTCAGCAGGCGCATGCGTTTTGAAGCTACATGGTAGTAG
TGCCGTTGGCCGCTTATCGTTTATGCGCATGGTACATTTTTATCATGCATGAATACTTGTGAAACGAATGAACTTGA
CGTGCTGCCAAACGCGGCCTGTATCTAGCTGCTCACCCGCCCCTCATCCAGCCGTCCAGTCCTGCTTGTATACGCGC

TABLE 6-continued

Sequences Corresponding to Frequency Peaks (SEQ ID NOs 21-167)

GCTACCGGGGATAATCGGTCAGCTAGGTCGCGCGCGCTGCACATTATGTATGTATGGCCTGCCCCGCTGCGCCCGGG

CCCTAGATAC

>SEQ ID NO: 127

GCGAAGCTTTGAACCACTGGATTACTGTGCTGATAGAAAGCTTGCCGGTTTTTGTCAGAGCATGAGCGACCGTGCTT

TCGCTTGCAGCTGAGTTTTATTCAGAGCGTGAGACACAGGACTGTGGCCTCTCATGTGATAGAAATGTGCTCACTTG

TCTTCGAGTTCTGAATTAAGAAAGCAACAACGCCCAGAGGCTTCGCAGCCTGAGGAGACAAAGCAGAAGACAGCTAC

TGAATGAATGAAAGGATAGCCTTATGTAATTAAAAACATAACAGACCCGACTGGGTTCTGCACAAACGCGTGCAGGA

AATGCGGTGTCGAGTTTGGGTGGGCTGGTGCGCACATCGCGATGGGGCTAAAGCATACAGACATGATCCATTTAATG

CATTGTCATACAGTTTCAGATCTGCGAGTACTTCAGTGGAATGTGCATGGATTCGCTGCGTGGAAGCAGGAGCAGAC

TAGTGTGATGCGAATGTTGCTGAGCTACGACATTGTTGCGCTAACTGAGACTCACCTGCAAGGCGATGCAATGTTGC

GTGCGATCATGCCGCAGGGCTCACAGCTCCACACGTTGGACGGAGCAGGTCGGAAGGGAGGCGTGGCGCTGTGGATA

AGCGCAAAGATGGCTGATAAGGTGGAGTTGTTAGGCAAGTCTCAGCTGCCAAGGGGCAGCCAGAGTATCTGGGTGCG

GTTTCGTGGGAACGCACTGGCGTTGGGAGGGAAGAGCATAGTGATAGGAGCATGCTACGCGGCCCCCGCTAGCTCTA

AGCGGTATGCAAGGGCACGTGTGCAGGCTGGCGTGACACGCACAGCGGGAGATAGGGTTTTCGGCAAGCTAAGAGCA

CTGATAAATCGTTTTTGCACTGCTAACGACGAGCTGTTGCTTATGGGAGATATGAATGCACGGGTTGCCAATTTGCA

AGAAGTCCTAGGCGCGGAGGCGGATGGTGAGATTGCTGCACACACGGGCACGAATGCATCGAGCCTATTGGCGGCCA

TACCGGAGAGGAAAAGCATGGACCAAAAGCAAGGCCATGCGCACGGCCAGCTACTTGTGAATCTGTGCCGTGAGCTG

GGACTATGTATCCTAAACGGGCGGGTTGAGGGTGACGCGGACGGAGAATGCACGTTCACAGGAGGCACGGGGAAGAG

CATGATTGATCTCTACGTTACCACACCGGCACTTTACTTCAAGGCACGGCAACTGGAGGTGTGCAACATTCCTGAAG

GCGAGGACGAGATCCATCTAGGTGACTTGATGAGCGATCATTGCCCTGTTAAGCTCACGCTTGGGGTTGGCAGATGG

GATCAAGCTGCGAAGCAGCACGGCGGCAAGGCTCGCTTTGATATGCGTAGACGGGGCGCGTACTCATCGATTTATCA

GGATCCGGAGTGCGCAGAGCTGCGGAGGATAGCCGATGTCATGTGTCGTCTGGGGCGCAGTGCAGAAAATGGCGGTA

TCACCAGCACGGAGGCGGTGGACCGGCTTGGCAAAGTGCTATACCGTGCGATGGATAAGGCTTTTGGACGAACTGGG

ACCGACACGCGCAAGGTACGTGGGCAGGATGACGCACCCTGGTGGACGGAGGAGCTAGCGGCTGCGCGACGGGATAT

GTTAGGACAGAAAGCTCAGATGAGAGCTACTGGCACCTTGCAAGATGAGGCTGCACGGGCCGAATTTTCGAGGCTAA

GGACGCGGTACCAGCGCATGCGACGAGAGGCCAAGGAACGATATAAGGTTACGTTTTTCACAGAGTTTTTGGATGAG

TGCAAGGCGGACCCACGTGCCCTATGGCAGCGTCTGAACGATGGGGTTGTCCCCTCCTGCCCGCTCACATCGGTCAC

GGATTGGACGTCCTTCTTTGACACACTCTATAATGGCTCACTGAATGCGTTTGACAATGTGACTGCGGACGAGATTC

TTTCCATGATTAATAGAAGGCCCGGCGTAGGTACGCGCAGATGGGCAGTAGAGGATGCACAGACGCAGGAAGATGAG

CCTAGCGCACGGCACGCACGAGTTGTGGCAGCTGCGTCCTTGAACATACCTTTCTCGCTGAGCGAGGTTGAAGAGGC

GCTACGGTGTCTAAAAAATCACAAGTCTGGCGGGCTAGACCGCGTACCTGCAGAGTGCTACAAGTACGCCACGCGGG

AAATTGAAGACGGAAAAGAGTTTAATGTGCTTGCGCCGTTTTTGCTGACACTCTTTGAGCACATACGCATTAGCGGC

GACTACCCTAGGCAGTTTTGTGAGACGTCCTTAACGCCCATCCACAAGAAGGGTGACGTTTCGGACATGTCCAATTA

CCGCGGACTGGCGGTGGGAGGAGCGCTGGCCAAGTGCTACGCCTTCCTGTTGGAGCGGCGTCTCAGTACGTGGGGGG

AAACCTGTGATGCGCGTTGTGCTTATCAAGGCGGCTTCCGCAGAAAGAGGGGCACGATTCACAATTTGTTTGTGCTA

CGACACCTCACGGACAAGTACAAAACGACACAATTGGGCAGGGGGCAAGCATTATTCGTGTGTCAGATCGATTTTGA

AAAGGCGTTTGACAGAGTGCCGAGGGATTTGTTGTGGCAAAGACTGGAAGAGAGAGGAGTACACGGCGCCATGCTGG

AAGCGTTGAAGAAAGCTTACGAGAAAGTGATGTTACGCGTACGCGTAGATGGACGTACCGGTGACCCTTTTGAGTCA

ACGGCTGGCGTGAAACAAGGCTGTCCATTGAGCCCCACACTTTTTGGGCTGTTTGTTGAGGCATACGCAGACTATCT

TABLE 6-continued

Sequences Corresponding to Frequency Peaks (SEQ ID NOs 21-167)

GGCAGCCAAAGACGAATTAGATCCTGCCATGATGGCGGCCGGGGATTGCCCAGTAGTTGACGGACATCGTTTGCCCT
TGCTCTTTTACGCTGATGATCTAAGCTTGTTTGCGACAACACACCGTCGGATGCTCCAGATGCTGACAACACTACGT
GAGTTCTGTGAGGCTTTCGGAATGCGTGTGAATGTTACAAAGTCAGAAGTGCTGGGTGTGCATTCGTCAGCCACCTT
TCGGCGTTATTTACGGCAGGAGCCAAGCCCCATGCCGGTGTACATGCGGGAATACCAGCAAGGACTGGAAGCACTTC
GCTTCTTTCCCTGGAAGCGTAGAGCGCGGTACCTTGGCCTGTATTACGGCCCCAGTTTTAAGTTTGAATCTTGTTGC
AAAGAGTTACGTGCATCGGGTGAGCGAGCTATGCATGCACTACGACGGAAGTTACGCAAGAAGGGGCTTATGGTCCC
TGCGGTAGCTATGCGGTGCTTTAACGCTCAGGTGCGTGCGGTATTATCTTACGGTGCACAAGTGTGGGCACCAGACG
CGCTTCTCCAAGTGTTCAATGCGTCCCCAGTTGACGGTCAAAGATATGGAGCGTTTGATCGAGCACTAGAGCATGGC
ATGGTTCGCATTCAGATGGATTTCATGAAGGAAGTGGTGGGAGCCCAGAAACCAACACATGAACTGCTCTTTCGAGA
GCTTGGGTGCATGCCACTACACGTGCATTGGGCTGAGCTTGTTTTCCGTTTTTGGAACCAACTGGTTAAGGCAACCG
GCACTGTTTACCATCAGGCGTTTAAGGAGGAGATACGAGCGGTGTTGAGCAACCTACCGACGCCGCCCACGCACACG
TGGGGGGCTAAAGTTCTGCGGTTATTGATGGTTGGCCTTGGCTACCGTTTCAGTGGAGAGGCAGCTGATATCGAGGC
CAATATTACACGCATTACTACGCAAGAACTGGATGTTGCCTCCCTCATGGGGAAGGTACGCGAGAAGTTTGAGGAGG
ACTGGGCTAGCAACAGGTTAGAGGTTAATCCACGGGATTTTGTGACGCAAGCAGGGGTCAAGCCTGGCGTGAAGATA
TGTCGTTACAAGCATTGGATGGGGGAAACACGGCACACGCAAATCTACATTCCTCGAGCATGGCATGTCTCCATGAT
GAGATTCAGGATGGGCGTGTGGATGATTGAGGCTAACAACCCACGCGGTGCGCAGGGTGCGCACAGGGAGAGAGCAC
AGAGAGTATGTCCGCTTTGCCACGCTGATGGGGAGGAGCATGTAGAGGATGAGAGGCATGTGCTGCTTGAGTGCAAG
GCGTACGATGATATCAGAAGCACGCTGTGGGAGGTGATTCCCGCGACTATGATGGACGCGATGGCCAGTGGTGACCA
GAGGGGTTTAGCGCGTGTCATTCACGCGATAAGGCTGCGACGTAACGACCTTACGGCGCGACCAATTTAGATATATT
ATTGCATGAACTGTTTTGCTTTTTGAATAATCCTTTTGAGACTAGTTTTGGCGGTCCATGAGCTTCCTGGCTCGTTT
GGACCAATCTACGAGCATGAACTTGTAACATCAATCAATCAATCAGTCATACAGAATATTACTACCTTTAACTGTCC
TAAATGCATGCCCCGCCCCGAATTGCTGTTGAAATGCTGGCCGAGTCGCCATGAGCTTATCAACATGCCCCAATCTT
ACGTTCTGTTTTAATACCTACGTGCACACTTGTACATGCATCTCAAAAACGGGCATAGGGGTTGGTTCCAGAAGTC
GGGGCCCACTCGCCCAAAGCATATGATAGGTGACATATATGTTATGCTTTGACGTATGCCCTACACGCAAGTAGTGT
TCAGGCTCTGGGTTTGTGCATGAAGAATCAGCTTAATAAACAACGCCTCGTCTTCCCTCTTGGGCAAGCGGCAGCTG
TCCATACTGGCAGCAATACCAATCACCGAGCATTCAATCTTGCATGAGACCAGCTTCCGTCTCTGAGACCGCAACGC
GAGATGGACCTGTTACCGCGTGAGCAGGTTGCACGCTTC

>SEQ ID NO: 128

TGCGGAGAGGCGCGTGTAGGGAGTGTAGGCACCTGGCGAGCGGGTGCTGGGGTTGGGTACGGCGGGGAGCCGCATTG
GCCTCCCGCTCGCCCGCAACCCCGGCACGCCTGCGCCTAAAGGGCCTAGCCCAACCCAACCCTTGGGTCGCCGGCAC
TGTTGTCAAAGTATTGAGGCTGGTGGTTGCTGCTGGACTTCAACTTGGTCAAAGCTGATACGCAGAGAGAGCGCTGC
GAATGTGGCACCACAGGCCCATCACACGCCGTAACCTATACCGTACGTTTAGTAGAGAGAAGTGAAGGCCCCGGGTT
CCTCCTTGCTGATAAGGGTGTGATGCGTGTGTCCTGGCTTCTTCAGGGCCCGTGCACGTCTCGTCGTTTGTGGCTAT
TCATGTGTTCTTGTGGACGACGAGCGATGGCGGGACACAAATGGAACGTCACGTTGGTAATCGTTTAGATATTCCAT
TGGTGGCTGCCCCTGCTTTGAAGAACGAGTCTTGGCCTGTAACGGCTAGACACGGAGATGCAAGCAAGGGACCCTGC
CGTACAAACGGCGTAACGAAACTGAACTCGCCAGAAGTGAACACGCACGCACAAGGAGAACACGCAGCGGCTGTTTT
AGACTTAAACAACGTCTTGCGTTTGCTATCAATGAACGCAGTCGGGTTTCGATGCATGTATCTTGGCGCCGCCGCAC
ACGCCACATACAAATGCGGGCTTGAGTACCCTAGAGTGGAAGTTGCGTGGGGCGCACTTGGCTCGGCCCGGCCATA
CAATTGCATTTCCTCGCCACCTGCGGCTGTAGGCA

TABLE 6-continued

Sequences Corresponding to Frequency Peaks (SEQ ID NOs 21-167)

>SEQ ID NO: 129

TGTTCTAGAAGTGTTGTTTAACCGCATCTGGCGGGCGCAAGACGGAGATGAAAGTTTTCCGGAACAGTTCACAACCA
CAGTGCTGACACCAATTTACAAGAGAAAGGGCGATGTGAAGACGCCCGGCAACTACAGGGGCATTGCAGTAGGCGGA
GCGTTGGCTAAGTGTTATGCATCTATCCTTCTGAACAGGCTAGCATGAGCAGGCGAGTTGTTCAAGTGGAGGCACCC
AGCTCAGGCTGGTTTCAGGCGGAAATACGGTACTGCCCACCACCTGTTTGTCCTGAGGCACCTGGTGACAAAGCACA
CACGTGCAGGAGCACCACCAATGATTGTTGTACAGATTGATTTTGAGAAGGCGTTTGACAAGGTGCCGCGTCCCCTC
TTGTGGCTACGGCTGCGGGAAAAGGGCGTGTCAGGGCGGCTGTTGGAGGCCATACAAGCCGCATATGAAAAGGTCAT
GATGACGGTTAAAGCCGATGGCAAACTGAGCGCTGCTTTTGAGGCAACGCAAGGAGTCAAGCAAGGGTGCCCACTGA
GCACAGAGCTGTTCGGGCTCTTTATTGAAACTTTGGCAGAGTATATTGATGCGCACGAGGACTGGTTGGACACTGCA
AGCACAGCGGGCACCCCTGAGTTAAACGGTAAGAAGCTGTCGCTCCTAATGTATGCTGACGATGTTTCGCTGCTAGC
CACCACCCCTGAGCGTATGCGGCACCTGTTGTCACTTGTGGATACTTTCTGCGAAGCATTTGGTATGAAAGCAAATG
TCGCAAAGTGTGAACGTCTGGTGTTCACTTCAGACGACCAGGAGCGTCGTAGATTGAACGATGAGTGCAGTGGGCTG
CGGCTGGCAGGGCAGCCCATCCCTGCGGTGGACAAGGCACGGTATCTGGGACTAGTCTACGGCCCTGGACGTGCTTT
TGCCGCCTGCAGAGAGACGCTATGTGAGGCTGCGCGGCGTGCTATGTACGCGCTTACTAATAGATTAAACCGTTTGA
GGATTTTCTCCCCCGACATACGCATGCGTTGTTTTGAGGTGCAAGTTCGCTCCATCTTAGCATATGGTTGTGAAGTG
TGGGGACCCGACGTATTAGCGGAAATGCTGGACGGCGGCCCACCACCGCGGCGGCGTGACAGCAATAACCTGGCGCA
CGGACCGTTTGAAGCATGCCTGAAAGACGAGGCCGTCAAATTACAAGTGCAGTACATGAGGATGACAGTGGGTACGA
AGCGACCATCGCATCGCCTGCTGTTTGCTGAATTAGCACAACTACCACTCCATTTCTTTTTCGCCAAGCTTTGCATT
GGATTCTACAACAGGATTGCCGTGCAGAAGGATAGCCTAGCTCACGATGCACTAATTGATGAAGTACAAGACGCGTT
AGTACACCCAGAGGGAGATGGGTGGTGTGCACGGCTTTTCCGTTTTATCTCAGCGCATGGCGTAGACGTACGGCAAG
GCCGTATGCACATGATCAGGCCGGAAAGGGAGGAGAGCCGAGCAGGTAGCCCGCTGCCTGAAGGGCAAATAGTATCC
GCCTTTCGAGAGAGTCTAATGAAGGCGTGGAAGCACGAGCGGCTGCAGTCTGAGCCAAGCACTTTCCCATCAGACAA
CAAGCAACCAGGCGTGCAGATGGGCAAGTATAGCAAGTACAAGCATTGGATGGGGCTGTGTGCGGAAGGAGCGGCAC
CACTGACCATGCAAGGGCACAGTATCACCGGATTGCTAACTCAGTTAGCGATTTGACTCGTCTTTACGGCAGAAGGG
ACCCAGGTACGAATCCAGATAAAAGCCCAATTATGCAAAAGGCGAAAGATTGGTGCGAAACTGATTGGTGATCCCAC
GAACGATAGGTAATTGCCCTTAGTGGCAATTGCGGGCTTATGCCCGCTGCAACCTAGAAAGGTCGTGGTGCAGAAGT
CCGATTTAGTGGCGAGGTCCAAGGTTCAAGACAAGGCTCAAGATCCAAGGCTCGAGGAGGAGCGCCATGGCTCCTCG
GTTTGCACGAACTGGCAGTGCTCCACTACTATAATGCGGCGTTTCCCTAGCTCGATATGCTAGGTGTGCAGGCTTGG
ATGTAGTGGACTTTGAAGAGTGGCCTAGGACTTGGAGGTTGTAGTTTCGGAGGTTGTGACTCTTTCGTGGTGAGGCG
TCAGCGTGAGGGGGCGGGCCCTCTCGCCCAGTCACCTTGCCCCGTTAATCCATGCCAGGCCCTATGGGCCGGCGT
TGTAATTATTATTATTATTATTATTATTATTATTATTATTATTATTATTATTATTATTATTATTATTATTATTATTA
TTATTATTATTATTATTATTATTATTATTATTATTATTATTATTATTATTATTATTATTATTATTATTATTATTATT
ATTATTATTATTATTATTATTATTATTATTATTATTATTCCTATACCATAAGAAGAATAATAATAGAAACCGGA
CTTAGCCGCGCGGGCGATCCTCCGAGGGTGTGGGGAGGGCCGGGGCCCCGGGCGTGAGGGACCCAGCTTTGTTGCG
AGGAGCGTCGCGCGTGCTCGCGACGTAGCTGGGGCCGCATACTGGAGTGCGCTCCGTGGCGTTTGTGTCGGAGCCGC
GGCCATTTGCTGTCCGGGCAGCCGCGAGGGACCCAGTTGTGTAAATACAGCGCACAGAATTCGGCCCCCCACTTAAG
AACGCCGTGTCGCCGAGTTGAGTATCGGGTTTGCGCGAGCACCGGTGTGGGGCCGCGTGGCCCCATAAAAGGGACCC
AGAATTATAAATAGCAATTAATAGGCAGCATGCGCCTCAGGCAC

TABLE 6-continued

Sequences Corresponding to Frequency Peaks (SEQ ID NOs 21-167)

>SEQ ID NO: 130

GCTAAGACTTATAAGATCCATATAACGTCAACTTTTGCATGTGCCCCCACAGTGCCCCAAAGCCCTGAAAGCTCGAT
TGCCCCCGATTGCCGAAAAACACTGCACCGCCTGTTTCCGGGGGTTTATTCACTTTGAACTTGAACGCTGATTACTT
GAAAAGTCAGCTGTGGCTGTCGCTGTGCGCTCGCACTGCATGGCCTTCAACATCATCAATCCGCCTGATTTCCTGAA
CTAATCCTATTGTATTGCCTTATACCTATATTTTGAAGCCGTCGGCGTCCTCAAAAACTGCCTATAACAAAAAACGT
TGTTTGCTCTCACCACCAGGGGCCACGTGAGTGAGTGCAGCAGTCCAGCCACGCAGCCGTTTGGCCCGGCTTTTGAT
TATATACATATAGCGACTGCCGTTCTATGGTTGGCACAAGCTGGAGGTCGCCAGAGTGAAGCGGTTGTCAACTTGCG
CCACCGCAGGCAAGGGGCAGGGGGCATGCTGACCTTGACATGCCAACCTGTTGTGGCTGATTCTTCTGGCACTTCCA
AAGCCCATTATTTACATATAATCCACAGCATGGCTGCACATTACTTGACAGCCTGAATGATACCTGACCCTGACCCA
TGAGAGGGGAGGGGAGTGGAGCACACATGTTGTGTGTGGTTACAAGGTGGTGAGCACGACGTGCATTCCTGTCCTTG
TGCACATGTGCAGAGCCGCATGGGGCACTGAAGGGCTGGCACCAAGGCCTAGCTGGTGGTTGCATTACAAGCATGTC
AGGCAACATGTGCGTGCATAGATGTGAAAGGGTCTTGCACAGGTGTGAGTGAGGCAGGCAGGTTGGATGGTGGGCTG
GGCAGCACAGCCCCCAGTGTGGTGTGCCAATGGGAAAGAGCAGCATGTGCTTGCACACCATGCATGTGCAATCTGTC
AACATGCAACACAGCACAATACAGTATATAAATGGATCACATTGAATGGCAAGCCACAGTGATGTGAGTATGCGGGG
CCATGAATGTCCCATCCCTTCCCGCCTACTCATGCTTGATGACAAGGAAGCTGTGGGGCACACTACGTGCCCAAATC
ACATCACGGTCACCCACAAGTTGTTTCAATAATCATTCTAGCTTTTCTTATGCTTACTTAGCTTAGCACATCTTTCC
TGACATGTCACACTTTCCAAACCCCACAAAACCCCTTAAAACCCCCATTTAGGGTTT

>SEQ ID NO: 131

TTGCGGTGTGCCCAAATCTCGTCAGGGTCACCCACAAGTGGTTCAAGCAATCATTTTAGTCATAGTAAGCTGAATTA
TACTGTGCAAATCATTTCTGACATGTCACTCTTTCCAAACCCTGCAAAACCCCTTGAAACCCTGACTTAGGCCACCC
TGCGCCAGGGGCCACGTGAGTGAGTGCAGCAGTCCAGCCACGCAGCCGTTTGGCCTGGCTATTGACTATATACATAC
AGCGGCTGCCGTTGTATGGTTGGCAGAGCTGGAGGTCGCCAGAGTGCAGCGGTTGTCAACTTGGTGCCACCGCAGGC
CTGCAAGCGGCAGGAGGCATGCCTGTCTGGACATGCCACATGTTGTGGCTGATGCTGCTTGCAATTTCAAAGCCCAT
CATACACATATAATGCAAGCAGAATGTGCTCAACATGGCTGCACATTACTTGACAGCGTGAATGATGCCTGGCCCTG
ACCGATGAGAGGGGAGGGGAGCAGAGCAGAGCCACATGGGAGACTGCAAGGGCTGGCACCACGGCTCCTAGCTTGTG
GTTGCATTACAAGCATGTCAGCCAACATGTGCATATGTGAATACCAGTATAAAAGGTCTTGCACAGGGGTGAGTGAG
GCAGGCAGGTTGAATGGTGGGTTGGGCAGCACAGCCCCCAGCATGGGACAAGGGGAATGAGCAGCATATGTTTGCA
CACCATGCATGTGCAATCTGCCAACATACAACACAGCACAATACAGTGTAGAGATGGATCAGGGAGAATGACAAGCC
ACAGTGGTGCGAGTATGCAGGGCCATGGAAGTCGCATCCCTTCCTGCCTGTTCATGCATAGTGACAAGGGAGCAGTG
GGACACGCAAAGCCATTGCGGTGTGCCCAAATCTCGTCAGGGTCACCCACAAGTGGTTCAAGCAATCATTTTAGTCA
TAGTAAGCTGAATTATACTGTGCAAATCATTTCTGACATGTCACTCTTTCCAAACCCTGCAAAACCCCTTGAAACCC
TGACTTAGGCCACCCTGCGCCAGGGGCCACGTGAGTGAGTGCAGCAGTCCAGCCACGCAGCCGTTTGGCCTGGCTAT
TGACTATATACATACAGCGGCTGCCGTTGTATGGTTGGCAGAGCTGGAGGTCGCCAGAGTGCAGCGGTTGTCAACTT
GGTGCCACCGCAGGCCTGCAAGCGGCAGGAGGCATGCCTGTCTGGACATGCCACATGTTGTGGCTGATGCTGCTTGC
AATTTCAAAGCCCATCATACACATATAATGCAAGCAGAATGTGCTCAACATGGCTGCACATTACTTGACAGCGTGAA
TGATGCCTGGCCCTGACCGATGAGAGGGGAGGGGAGCAGAGCAGAGCCACATGGGAGACTGCAAGGGCTGGCACCAC
GGCTCCTAGCTTGTGGTTGCATTACAAGCATGTCAGCCAACATGTGCATATGTGAATA

TABLE 6-continued

Sequences Corresponding to Frequency Peaks (SEQ ID NOs 21-167)

>SEQ ID NO: 132

GTGGGATGGGAATGGTCTTGTCCTCACTCCACGCGCCAGCTGTGGGGTGGCATGAGGTCAGGTTGGAGATGAGGTAA
GGTGAGGAGTGGGTTGCCATGGGACAGGGTAAGGGGCAAGTGTGGCGTACACGTGTCCCGTGGTGTGCACATCGGAG
GTGTTGCGTCCGGACCCCAAGCCTACCCTTCTTCTCATGTTGATCCCCCTCCGCCTTCTCGAAGTAATTGGAGCCAT
TGCGGTTGAACTGAGCCTGCAACCGCGTCATGCACCTGTTTGACAATGGCCACCATGAAAGGCCCTGGCGGGATGCA
GGCCTGCAGGCGGTGCCGTATGGCGGTTTCTCGGGCAAGGCGGAGGCGTCCAGCTTGCCGCCCAAGCTGTCACGGAT
CACAGTCCAACTCCTGTAATCTGATGTGAGATTTAGTGAGCAATACTCCTCCTGCGGCTGAAGGCCCACGAGGGCAG
CGGCAAATTTACATCTGCAGCCGCGCTGGAGCAGGGTGGGGCCCGCTGCTGCTGCCGCTGCTGCTGCTCGCCCCGAT
CTCTTGCTGCTGCGCGCAGATGCTTGCATTGCGCTATGGTAGCATAATGGTAGCAAAAAAGGAGTGGACAGAAGAG
GAGTGACGAGCGCAGTCGGAAAGGCGAATTTTTTAAAATTGTTGATACCAGGGCACGGCTTGGTTTATTATCTTGA
ACTGCAATCGCACTGAAAGAACAAAGGTTGTAGCTACAAGACGCAAAATATTGATACTAACCGCGACCTGGTGGGCG
AAAATTGGGCAAACGGTCGCCCCATTCCCACAACCGTGGTGTTGCGTCCGGACCCCAAGCCTACCCTTCTTCTCATG
TTGATCCCCCTCCGCCTTCTCGAAGTAATTGGAGCCATTGCGGTTGAACTGAGCCTGCAACCGCGTCATGCACCTGT
TTGACAATGGCCACCATGAAAGGCCCGGGCGGGTGATAGATGTCAGCGCATTCCCACAACCGCAGCCACGGCGAAAT
AAAAGGCCGCCCCTCCCATTACTTGCTAACCCAATACCTATCATAACAACTTTTAAGAGCACGCCAATCTACTGTGC
AAGCAAGTTATTAGCGCCGAGCAAACCGTATGGAGTCCGGTTGGCAACGCGAAACAGCCCCGCGAGCAGGGCTGCAG
CGCGGTAACTTATTGGTAAGCTAAACCAATATGTTTGACAAGCGCCGCTATTGCTGCTTAGCTTTCTTGTTGCAACA
CGCGGTTGCATGCCATGCAAATGTCAACAGTGCCGCTGAAACCTGAGCGCGAATACCTTGCGGGCGCTGCCATAACC
CTCTTCAGCATTGAAAAGAACTTACAGCATGACACCGGCTGCAAAATCCACTACAGGGCCAGCCAGCCCAATGTCCA
AGGGGCTCGGGTCGACCGTTGGCCCGCTCCGCCGCCACAGGGGGCGCCGCGCCGGCCTCGTCGTCCTTCGAAGGGT
GAGTGCTAGGGCTCCGCTGGTCAGGCATCACAGTGTTTGCAATGCCTAGCAAACGTATGCACGTTCCAGGTGGACAG
TGCGAAGGGGCAGCAAACTTTGGTAGAACAGGCAGTGGGAGGGGCCCTCGTGGCCACGGCCAGGACTCCTGCCCC
TCCCTGGTCCGCCCCAGCGGCTGGAACGGAGCCTCGTCCTCTCCACGGATCC

>SEQ ID NO: 133

AAGGGGAATGAGCAGCATGTGCATGCGCACCATGCATGCGCAATCAGTCAGCATGCACCATAGCATATTGCACTATT
CAGTATGACCTGGGCGAATCAGAAGCCACACTGGTGCAAGTATGCAGTACAATGAAAGTTGCATTCCTTCCCCCAAC
TTGTCACCTGTGGTAAGGAGG

>SEQ ID NO: 134

GAGTGCAAGGAAGCAGCCACAGCATGTTGGCGTGTCCGGACCTGAGGCCTGCCGACCACACTGGTGGCGCCAAGTCA
GCAACCGCTCCACCCCAGCAAGCTCCAGCTAATGCCAACCATACAACGGCAGTCGCTATATGCATATAAGCAATAGC
CGGGCCAAACGGTTGCGTGGCTGGACTGCTGCACTCACTCACGTGGCCCCTGGCCCGTGGGTCGCCTAAATGGGGGT
TTTAAGGGGTTTTGCGGGGTTTGAGAAGTTTGACATGTCAGAAATGTTTTGTATAGTGTAATTTACACAATTATAGC
TAGAAGGATTGTTGGAACCACATGTGGTTGACCGTGATGTGATTTGGGCACATAGCCATGACTTTGCATGTCACACC
GCTTCCTTGTCACAGTGCACAAGTCAGCAGACAGGATGCGACTCATATGGTACTGCATACTTGCACCACTGTGGCTT
CTCATTCACCCAGGTCATACTGAATACTGCATTGTGCTGTGGTGCATGCTGACAGGTTGCACATGCATTGTGTGCAT
GCACATGCTGCTCATTCCCCTTGTCCCTGCACTGGGGGGCTGTGCTGCGACCCACCATCCAACCTGCCTGCCTCACT
CACCCGTGTGCAAGACCCTTTCACATTTGTATATGCACATGTTGCCTGACCCGTTTGTAATGCAGCCACAAGCTAAA
CGTGGTGGTGCCAGCCCTTGCAGTGCCCCATGCGGCTCTGCACATCAGGACAAGTGTTCCCCGCTTGCCTCCCCTCT
CATGGGTGAGGGTCAGGTATCATGCAGGCTATCAGGTAATGTGCTGCCATGCTGAGGATATTCAATTTGCACCATAT

TABLE 6-continued

Sequences Corresponding to Frequency Peaks (SEQ ID NOs 21-167)

GTCAATGGGCTTTGGGAGTGCAAGGAAGCAGCCACAGCATGTTGGCGTGTCCGGACCTGAGGCCTGCCGACCACACT
GGTGGCGCCAAGTCAGCAACCGCTCCACCCCAGCAAGCTCCAGCTAATGCCAACCATACAACGGCAGTCGCTATATG
CATATAAGCAATAGCCGGGCCAAACGGTTGCGTGGCTGGACTGCTGCACTCACTCACGTGGCCCCTGGCCCGTGGGT
CGCCTAAATGGGGGTTTTAAGGGGTTTTGCGGGGTTTGAGAAGTTTGACATGTCAGAAATGTTTTGTATAGTGTAAT
TTACACAATTATAGCTAGAAGGATTGTTGGAACCACATGTGGTTGACCGTGATGTGATTTGGGCACATAGCCATGAC
TTTGCATGTCACACCGCTTCCTTGTCACAGTGCACAAGTCAGCAGACAGGATGCGACTCATATGGTACTGCATACTT
GCACCACTGTGGCTTCTCATTCACCCAGGTCATACTGAATACTGCATTGTGCTGTGGTGCATGCTGACAGGTTGCAC
ATGCATTGTGTGCATGCACATGCTGCTCATTCCCCTTGTCCCTGCACTGGGGGGCTGTGCTGCGACCCACCATCCAA
CCTGCCTGCCTCACTCACCCGTGTGCAAGACCCTTTCACATTTGTATATGCACATGTTGCCTGACCCGTTTGTAATG
CAGCCACAAGCTAAACGTGGTGGTGCCAGCCCTTGCAGTGCCCCATGCGGCTCTGCACATCAGGACAAGTGTTCCCC
GCTTGCCTCCCCTCTCATGGGTGAGGGTCAGGTATCATGCAGGCTATCAGGTAATGTGCTGCCATGCTGAGGATATT
CAATTTGCACCATATGTCAATGGGCTTTGGGAGTGCAAGGAAGCAGCCACAGCATGTTGGCGTGTCCGGACCTGAGG
CCTGCCGACCACACTGGTGGCGCCAAGTCAGCAACCGCTCCACCCCAGCAAGCTCCAGCTAATGCCAACCATACAAC
GGCAGTCGCTATATGCATATAAGCAATAGCCGGGCCAAACGGTTGCGTGGCTGGACTGCTGCACTCACTCACGTGGC
CCCTGGTGGTGAGAGCAAACATTTTACTTACGATACAGGCCGTGGTTGACGATGCTGTTTATTGCATTGGGTAGGCA
TGATAGATTATTATCGGCTCAGCCACTTGAAGCGGGCTGATCGATGATTGGAACCATGGAAAGCCGGGCTCGCGAGC
AGGCCGGCGAGCTGTTGACTTGGCCACGCCGAAGTCAGCTGCTTATTATTGGTAGTTTGTACTATCGCCCTATCTCA
AGA

>SEQ ID NO: 135

GGCACTTCAGCTGTATTCTTAGTTTACCCTATTGGCCAAGGG

>SEQ ID NO: 136

ATGCACCCCTGGTTGAATATTGCCTGGAGCATGTGAGGATCCATCTTCGCACCGACCGATTGTATGTTAATGCTTGC
GATGCTTACTGGCGGATTGCGTTTGTGCGCGAGTTGCTAGGAGATGGCTGATGTCGGTGCGGTAGTGGCGCAGGTGT
TGGGGATGAGAGTTGGTTGCCGTTGACGTGTGTGCGCGGAGCACTATGGGCTATAAATTCAGCAGGCGGAAAAATCG
CTCTGTTATTACTTTGCTAGTCACACCGTTAAGCCTCCCATGACACCTTTGGGGGCCTAAAAAGGAGCAGATTGTTA
CGCTGGGCCACGGCGGCACTGTATCAAACACCTTGGAACCCCTCCTTCGGTCGCTGGGTGCCACCACCACATCAGCA
AAATCCTGCTGCTCGCGCATACACATGCACAGTGTCATCAGCCTGCGCACTACATCCTTTCTCTACTACCGCCTTGA
GCGCGAAATGGGGATTGTGAACTCACGCCATGTCGGTCCCACTGGCGGCGCCACGGCTGCTGGCCCCAGCCCTCGCG
ATCCCTCGCTAACTTTCCACCTTTTGACACGGTGGGGTGAGCAAAACTCACTCCTCCTTAAGAAACGCGGCCTTCGT
GAACCGCGTACATATTATTATTATTATTATTATTATTATTATTATTATTATTATTATTATTATTATTATTATTATTA
TTATTATTATTATTATTATTATTATTATTATTATTATTATTATTATTATTATTATTATTATTATTATTATTATTATT
ATTATTATTATTATTATTATTATTATTATTATTGCCCCCGCTCTTAAGGGTCTCGCTACACGTTTTGGGTT
ACGGCGCCATAGACGCCGCGCCGCGCCCTCGTTCGTGCGCCCGGCGCGCTAGTCTGAAAGCCCGCAGCCCCGCGCAC
CTATAACCCCGCG

>SEQ ID NO: 137

GCAGCTGGGCGGGCCTGGGCCGCAGCACGGTAACCAAGCGGTCACTGCAAGGTAACCAGTTGGTCCGACACTGGTTA
CCACGCGGTCTGTTAACCGCTGGTAACCAGTGAGGCGGTCTATTAACCGTCGGTTAGCGGCCTCAAGCCCAAATAAA
CCGATGGTAACCTGAGTGCCAAACCGGCCATTTCTCCCGGGATAACCGCTGGGTAACCAGCGATTAACCGATGGTTT
AATAATAATAATAATAATAATAATAATAATAATAATAATAATAATAATAATAATAATAATAATAATAATAATAATAA

TABLE 6-continued

Sequences Corresponding to Frequency Peaks (SEQ ID NOs 21-167)

TAATAATAATAATAATAATAATAATAATAATAATAATAATAATAATAATAATAATAATAATAATAATAATAATAATA

ATAATAATAATAATTACAACGCCGGCCCATAGGGCCTGGCATGGATTAACGGGGCAAGGTGACTAGGGCGAGAGGGC

CCGCCCCCCTCACGCTGACGCCTCACCACGAAAGAGTCACAACCTCCGAAACTACAACCTCCAAGTCCTAGGCCGCT

CTTCAAAGTCCACTACATCCAAGCCTGCACACCTAGCATATCGAGCTAGGGAAACGCCGCGTTATAGTAGTGGAGCA

CTGCCAGTTCGTGCAAACCGAGGAGCCATGGCGCTCCTCCTCGAGCCTTGGATCTTGAGCCTTGTCTTGAACCTTGG

ACCTCGCCACTAAATCGGACTTCTGCACCACGACCTTTCTAGGTTGCAGCGGGCATAAGCCCGCAATTGCCACTAAG

GGCAATTACCTATCGTTCGTGGGATCACCAATCGGTTTCGCACCAATCTTTCGCCTTTTGCATAATTGGGCTTTTAT

CCGGATTTGTACCCAGGTCCCTTCTGCCGTAAGGACGAGTTAAATCGCTAACTGAGTTAGCGATCCGGTGATAACCG

ATGGTTAAATAGGGGCTGGAACGGTAGGGGATGGAAGTATGAAGGGGTGGGACCGAGTC

>SEQ ID NO: 138

GTGGCGGAGTCTGTATCCCGCTCTGCGTTTTGTTTGGGGCGCCGTCTCCTGGCCTCCTCGCTCAACTGGCGGGTTTG

GCTTGAAAACCCCCTGATATATTGTCCTTCAGTTAGGGACGGCGTGGTGGCATCCTTAAAGAACTATCTATCAGGGG

TTTTTGGGTGCCGTCAGGTGGGCGCCTCCCTGGGGACACGATTTGTCCTGGAGTGGGAGAGGGTGCAATGTCCCCAT

AGGCCGACAATGCAATCTAGCATGCAGGGGGCTAGGAAGGGACCAATGCAATCTAGAACCACCGGCGGTCCCTTGAC

ACCCTTAGGGGCACGCCCCATGGATCGCATGGCGGTCCGCCGGGTGGAGGTGGCTGGACGCGTGTGCGTGCACTCGT

GCATGCCGTGCTGCGGCCGGGCATGCGGGCTTCAGGGTGGGTCTGGTGCCGAAGCCGAATATTATTATTATTAT

TATTATTATTATTATTATTATTATTATTATTATTATTATTATTATTATTATTATTATTATTATTATTATTATTA

TTATTATTATTATTATTATTATTATTATTATTATTATTATTATTATTATTATTATTATTATTATTATTATTATT

CCTATATCATAAGAAGAATAATAATAGAAACCGGACTTAGTCGCGCGGGCGATCCTCCGAGGGTGTGGGGGAGGGCC

GGGGCCCCGGGCGTGAGGGACCCAGCTTTGTTGCGAGGAGCGTCGCGCGTGCTCGCGACGTCGCTGGGGCCGCATAC

GGGAGTGCGCTCCGTGGCGTTTATGTCGGAGCCGCGGCCATTTGCTGTCCGGGCAGCCGCGAGGGACCCAGT

>SEQ ID NO: 139

TATTGACTCCTTACTGCCGTGTAGCGTTACAAACCGCCACGGCCCCAAACGATAATCCCAATCTCTCAAACCGACAA

TAGCCTCCACTCATGCCTCAAGCGGCCTAGCAACTCATTCGTGGCCCTCAGCGGCCTCCTACCTCCGGCCTCGCAGC

TCCCGATACCCCACCAAGTCCGCCGTGCCCGCCCCAGCCCGCCCGTGTTGAGGTTGCACTAGTGGCCGAAAGTGCTG

CCAGTACTGGGTGTGTCGCATGTATGAAGTGCCTGATAGCAGCAGAGTCCAGACAACCACGCACGCCGCAGCGCCCA

CGGGTGCCACCACATTAATCCGCGGCGGCACCAGGGGGGGCGGGTGGGTTGTCACCGTCCCGGCAGAGGGACGATCC

GAAATACAGTACAGAAGCACAACGGCAGATAAGGCGCCGTGTGCTCCTGACGCGTACAAGACCCAGCTCGGTTCGGC

CCCATGCACAGGCACGTACCCGAGCGTCCTGCGCCGTGCGTGACTCTAACGCAACACGGCAGTTACGTCGCAATAAC

TAGACTTATCTCCACTGCGCTGCGATAAGTCAGCGCTTATTGACTCCTTACTGCCGTGTAGCGTTACAAACCGCCAC

GGCCCCAAACGATAATCCCAATCTCTCAAACCGACAATAGCCTCCACTCATGCCTCAAGCGGCCTAGCAACTCATTC

GTGGCCCTCAGCGGCCTCCTACCTCCGGCCTCGCAGCTCCCGATACCCCACCAAGTCCGCCGTGCCCGCCCCAGCCC

GCCCGTGTTGAGGTTGCACTAGTGGCCGAAAGTGCTGCCAGAGTTTGGTAGTAGTCCTCAACGCGGGGAGGTCATGG

TGCGGGCGACGGCAGCCCTGGTGGCTGGGCTTGATTGGCTTCGCGTATGCAGCTCTTCTCGCAAAGCGCTCGGCCCA

ACGGCCGGTCACGCAAACCAAGGTGCGGTCGGCGGTGATGGCGGCGGCGTTCGTGCCCTTGCGCTACCGAAATCATG

TGTCTCGAACACCGCGGAGCGCTCCGCCCATCGCCTTGCTTGCGCACGAACGTACGGTCCTAGTTGCACACTCGACA

GCGGTCGATAGAACGAGCTTCGTGCTTGGGGATATTGGCTGCACGAGCAGCACCATCACATGGGGATGAGCGCCGCC

GGAGGCGCCGCCGGCACCTGCTGCAGGCGGCGCAGGGCGACGCCAACGCGGGGCCTGACAGCGCCACACTCCGTCGG

TCATGGGCGGTCAATGGTCACTACCAGAAGACAAGCAGCAATAGGAACACGACTGGCGTTGCAAGGGCCATGATACC

TABLE 6-continued

Sequences Corresponding to Frequency Peaks (SEQ ID NOs 21-167)

AGACTCACAAACGTATCAGGTGCACCAATGGCCACGACAGAAACACACATGCATTGTCCCGCGTGCGCCAGCCACGC

AGACGACGCCGGGGCGTTACAGGGAAACACATGCATCCTTGTTCAGGTGTGTGGCTTCTGGGCAGCTGTGGCCGTCC

GTGTGCCTAGGAAAGGTAACAGTGCGTGTTGGCACGTGTTGGCACGAAGCACTGGAGACCTCGCTCGGTACTCTCTA

CCGGCCCCCAGGGCCATGCCATAACACGTGTTGACGTTGTAGGCTGCTCGGAACAACCTTGGGAATAATAACAACTT

CGTGACTCGAAGCTGGGACAGACTAGCCAACATGAGCCACGCAGGAGAAGGCGCGAGGTGCAACACTAGAGCGGTTT

TACGTACGCGAGTCACGCGCGGCAACCTGCCCTTCACCCGCGCCGTCGTGGTGTAGGATGCGGGCAGCCATGCCCAG

CCGTGCAGCATGGCCACGAACACTAATTTCTTTCTTGCTAGCTAGGTGCCATGCTTGAGATTTGCAGTGTCTTGCAT

AAGAGTCACTACCAATCAAGCAGTAGGTACACCCATAGATAGCATCACCCCGGCGGACGCAGGACAGGCGCGCACGT

GAATGCCTCCAAACGCCGCGGGGATGCATGCACACAATGTCCCGTACGTGCCGATACCGTACGCCACGGCGGCTGTG

GGGTGTACCGTAATAGCAGGGAGGGCAACATGAAGGGTAACACCTCAGCAACCCCAGCAAGGCTGGCCTGGTCGAGC

GGCGCGGAGGGGTGAAGGATACCCGGCACGCGTGGAACACGCAATGTATCTATAGTGATAGAAGGCGTAGTGATGGG

AGGAAATAAGGAGCACTCGGGGCCGCGATGGCGGGTTGGATGCGCCACGGGCCCCGGCCCAGCCAAAGGGAGCGAAC

GCCGGGCGGAGCCGGTGGGTGAGCGACTCGAGGGACGTGCCAGTAGTGAACCCATCGCAGTGGCGGATGGGTCATCC

AATGTGAGAGATGATACAGCCACGCCGGCAGCCAAACTCCGCACTCGCCCACGTACGGGCACGTTGTGGTACTGCTG

TGAGGAGGCCGGGCTGAGTTGGGATGCCTGCCGACTGCCAAGCCCGCAGGGCACTGTCGGCCTGGCTACCCACATGT

GAGCCTGTGTCGCCATACGCTCTTAATAGTAATGACATATAGCACACTGCTCCTAGCACTTCGGTGATAAGTAATTG

CCCCGCCGGGTGAAGTAAGGCCGGGGCTGAAAGGAACCAAGGCTGGTTCCCTAGGCGTCCACTGGCGAGTGGGCAGG

CGACACATTCAGTTGGCATTGACGTGCAGGGGTTCCTGTTGACGTGCGTTGCGGAACTAATGCGTACGTTGGCTTGG

GTCTCTGGGTTCATGAGGCATTGACAGAACACGCTGCCCCTGCTATGGTTCTGACCAAGGAACATGTATGCATACAT

GTCCTGAAGGATTGGCAGGGAGCGTGCCGCACAGCACGCAAGCCGCGTGACTACGGTAAGCATGACGCCATAACGTG

ACACAGATGCCGGGCATGCCATACAGGCGGCCAACGCTACGGCACAAGCCAGCTTGACGCGTCCACAGATACATACA

TGGCGCCTGACACCTGGATAGGAGCTATCAGTCTGACTGTGGGTCGATGCTACCCCGGCATGGATCTGGGTTGAACG

GTTGGTGGTACCATCGCGCGGGCGTGGCGGGTCGAGTAGCGTGTTTCATGCACGGCACTCCCGCTAACCAGCTACAC

ACCGCAGTGTACTGGTTATCCAACAACTACATTCAGACCATTCTGGTATCCCACTCAAACCTGCGCCAAGTGTCAGG

AAAAGCGCTTGCCAAGTCGGCTACCCGCTTTCACAGGATGGCGAGCGGGTGGCTGGCATGTGTACAGGCGGGTGGGC

CAACAAGAGGGGAGGGCGGATGGGTGCCGTGACTCGGTGGTGGGCCCCACCGCGAGCAGCAACAGCCCAGCCCAACA

CACGGGCGCCATCTAAACCCACCAAGCAGGCTGTGATCCCAGCTCCGACCGTATCTCGCAACAAAATGTTGGTTGGG

CAGGGTCGGGCTCACTGCGTGACACAGCGTCCGATGCCTGGTGCAGGGCTGCACGAAGGCATGTTTATGCGTCATGC

GGTATTGTTATGCGTCATGCGTATTGTTATTGGCAATAGCATGCTGGCCGAACTGCACAAAACTCCACAATTCGGC

ACTTGGGCCTAGCGCACACATCGAATGCATATAGGTTGGCTTGGGGTGCGTCAGCCAAACTACAATGGTGATGCCGC

GTGATAGTATGATGTGCGTGCGGACCTCAAGACGTACAGGGTGACGCATGATCACGTAAGCCCGCTCCGTTGTCAAC

ACGAAGCAATAGCGAGGCGCAGGCTTGCCGTGCACGGCACACTCAAGGCGTATTGCGACAGGGCACGCAGCAGGGCA

CGCAACAAGTCGAAGCGTCCATAACGACAGGGCAGGCAGCATAATTGCATGCGGCACACGGGCAATATCGCAAGACA

CATGATGCGAGGCGCAAAGCCTGTTGCTGGCGGCACACACGCCGTATCCGAACGTGGCGCTCAGACCACACATTGTC

CACAACGCAAAGGCATGTACAACGAAGGCACGTAAGCATTTCAATGCCGTCTATAATCCACAACGCAAGAGTGTGGA

GCCCGTTGCTTGCGGCACACAGGTCGTATCATAAGGGCACGTATGCCATCTATTACCCAAAAGCAAGGGTGAGCTGT

TGCTTGCGGCACACAGGTCACATCATACGGGCACGTATGCCGTGAATTGTCCATAAAACAAGGGTGCAGAGCCCGTT

GCTTGCGGCGCACAGGCCGTATCATAAGAACACGTACGCGGCGCATTGTCCATGAAGCAAGGGCGCGGAGCCCGTTG

TABLE 6-continued

Sequences Corresponding to Frequency Peaks (SEQ ID NOs 21-167)

CCTGCGGCACACAGGCCGTATCATGAGGGCACGTACGCCGTGAAGTGTCCATGAAGCAAGGGCGCGGAGCCCGTTGC

CTGCGGCGCACAGGCCGTATTATGAGGGCACGTACGCCGTAAATTGTCCATGTAGCAAGG

>SEQ ID NO: 140

ACACAGGCCGTATCATAAGGGCACGTATGCCGTCCATTGTCCATAAAGCAAGGGCGCGGAGCCCGTTGCTTGCGGCG

CACAGGCCGTATCATAAGGGCACGTATGCCGTCCATTGTCCATAAAGCAAGGGCGCGGAGCCCATTGCTTGCGGCAC

ACAGGCCGTATCATAAGGGCACGTATGCCATCCATTGTCCATAAGGCAAGGGCGCAAAGCCCGTTGCTTGCGGCGCA

CAGGCCGGATCCCAACGGCACACACGCCCTTTCCCCAAGGGCACGCGGGCCCTGCGGCCTGGATAGGCAGACAGGAG

AAGTACCGCGCCAAAAGCCCTGAGGTCTTGGGGAGGTGGGGGTGGCACGATGGAAGATGAAAGGTATTGCACAAAGC

TGTGAACTGTAAAGCGACGGGTAGACACGAAGGCACGGCAAGCAGGACCGCGCATGGCAAGCAAGTAGCCCGCCCGC

ACAGCTGTGCATGCCCTTTTGCTTTCAGTGACTTGCCGAACGCCTTGTCCGCAACGCTTCGCGCGCCTTTGCTCCGC

TTGAAAGCTCCGCTCTGCTCCGATTTGCTCCCGAATGCGGCCCCCGAACCAAAGCGTGGTCCAAAGCGCCAGAGAAG

CGTCGAAGGGCATTCCCTTACGATCAGAGAGCGAGCGTGATCAAGCTAAGGGGTTCCATTGAGCAGGATCGCGCAAC

AAAGCGCTGCAACTCCGTCTGAGTGTATATTAAACGCTTATTCGGTCCAGACATGGTAAAGTATAGTTAGAACCAGG

TATAGGATTGCAAAGAAAGTCCAGAAATGTAGGGAACGTTTAAGTGCGACACACTGAGGTCACCGTCCCGGCAGAGG

GACGATCCGAAATACAGTACAGAAGCACAACGGCAGATAAGGCGCCGTGTGCTCCTGACGCGTACAAGACCCAGCTC

GGTTCGGCCCCATGCACAGGCACGTACCCGAGCGTCCTGCGCCGTGCGTGACTCTAACGCAACACGGCAGTTACGTC

GCAATAACTAGACTTATCTCCACTGCGCTGCGATAAGTCAGCGCTTAACAGGAAGTCACTTCGC

>SEQ ID NO: 141

ATGGACAATTTACGGCGTACGTGCCCTCATGATACAGCCTGTGCGCCGCAGGCAACGGGCTCCGCGCCCTTGCTCCA

TGGACACTTCACGGCGTACGTGCCCTCATGACACGGCCTGTGTGCCGCAGGCAACGGGCTCCGCGCCCTTGCTTCAT

GGACAATGCGCCGCGTACGTGTTCTTATGATACGGTCTGTGCGCCGCAAGCAACGGGCTCCGCACCCTTGTTTTATG

GACAATTCACGGCATACGTGCCCGTATGATGTGACCTGTGTGCCGCAAGCAACGGCTTCGCACCCTTGCTTTTGGGT

AATAGATGGCATACGTGCCCTTATGATACGACCTGTGTGCCGCAAGCAACGGGCTCCACACTCTTGCGTTGTGGATT

ATAGACGGCATTGAAATGCTTACGTGCCTTCGTTGTACATGCCTTTGCGTTGTGGACAATGTGTGGTCTGAGCGCCA

CGTTCGGATACGGCGTGTGTGCCGCCAGCAACAGGCTTTGCGCCTCGCATCATGTGTCTTGCGATATGGCCTGTGTG

CCGCATGCAATTATGCTGCCTGCCCTGTCGTTATGGACGCTTCGACTTGTTGCGTGCCCTGCTGCGTGCCCTGTCGC

AATACGCCTTGAGTGTACCGTGCACGGCAAGCCTGCGCCTCGCTATTGCTTCGTGTTGACAACGGAGCGGGCTTACG

TGATCATGCGTCACCCTGTACGTCTTGAGGTCCGCACGCACATCATACTATCACGCGGCATCACCCTTGTAGTTTGG

CTGACGCACCCCAAGCCAACCTATATGCATTCGATGTGTGCGCTAGGCCCAAGTGCCGAATTTGTTTTTCCGGATAT

TTCGCCCTCAGTGAGCGATGTGGAGTTTTGTGCAGTTCGGCCAGCATGCTATGCCCAGCCAATAACAATACCGCATG

ATGCATAACTATACCGCATGACGCATAACTATACCGCATGACGCATAAACATGCCTTCGTGCCCTGCACCAGGCATC

GGACGCTGTGTCACGCAGTGAGCCCGACCCTGCGCAACCAACATTTTGTTGCGAGATACGGTCGGAGCTGGGATTAC

AGCCTGCCTGGTGGGTTTGGATGGCGCCCGTGTGTTGGGCTGGGCTGTTGCTGCTCGCGGTGGGGCCCACCACCAAG

TCACGGCACCCATCCGCCCTCCCCTCTTGTTGGCCCACCCGCCTGTACACATGCCAGTCACCCGCTCGCCATCCTGT

GAAAGCGGGTAGCCGACTTGGCAAGCGCTTTTCCTGACACTTGGCGCAGGTTTGAGTGGGATACCAGAATGGTCTGA

ATGTAGTTGTTGGATAACCAGTACACTGCGGTGTGTAGCTGGTTAGCGGGAGTACCGTGCATGAAACACGCTACTCG

ACCCGCCATGCCCGCGCGATGGTACCACCAACCGTTCAACCCAGATCCATGCCGGGTAGCATCGACCCCACAGTCA

GACTGATAGCTCCTATCCAGGTGTTAGGCGCCATGTATGTATCTGTGGACGCGTCAAGCTGGCTTGTGCCGTAGCGT

TGGCCGCCTGTATGGCACGGCATCTGTGTCACGTTATGGCCTCATGCTTACCGTAGTCACGCGGCTTGCGTGCTGTG

TABLE 6-continued

Sequences Corresponding to Frequency Peaks (SEQ ID NOs 21-167)

CGGCACGCTCCCTGCCAATCCTTCAGGACATGTATGCATACATGTTACTTCGTCAGAGCCATAGCAGGGGCAGCGTG
TTCTGTCAATGCCTCATGAACCCAGAGACCCAAGCCAACGTACGCATTAGTTCCGCAACGCACGTCAATGCCAACTG
TATGTGTCGCCTGCCCACTC

>SEQ ID NO: 142

GACCTGCGGTGCCACGCTCTGGGTCAGATCCGCGGCTGCGCTGGGTGTGGGCACAGAGACCACATTTGTCTCGAACC
CATGTAAATGCTCATGCTCATGCTCATGGCTGAGCATGCCAGCAATGACCGCCACAGCTTCCTCCTCGCCGTACTCT
TCCTTCACCTCCTGGAAGTGGCCGAGTGCCTCCTCCTGCAGCGTTGCAAGTATCAGCAAACTACCCGTAGCCGCCCT
AGCATGTGCACTTACCTGCGTCGGCGTGAGCTTGCCCCATTTCAAGCTGGCATCCCGCAGCGCCCTGGCCAGGGCTG
CCTATAGCCTTCTTCCTTCAGCACCTGCAGCAGCGAGCCCTCCCCAGCCCCCTTCCCATCCATGTTGAAGCGCTCAA
AATGCGTCTGCAGGAGCTGCTGGCTGAGTGCAGTTGCACCTGTTGCATAGGGGATGAAAGGAGTTAATGGGAGCTTG
GCACGCAACCGTGCACACGAGGCTTGCACACCTTGCGGCTTGCGGACCTTGCGAGCCGCCACCACCGGGTTGACAAT
AATAATAATAATAATAATAATAATAATAATAATAATAATAATAATAATAATAATAATAATAATAATAATAATAATAA
TAATAATAATAATTACAACGCCGGCCCATAGGGCCTGGCATGGATTAACGGGGCAAGGTGACTAAGGCGAGAGG
GCCCGCCCCCTCACGCTGACGCCTCACCACGAAAGAGTCACAACCTCCGAAACTACAACCTCCAAGTCCTAGGCCG
CTCTTCAAAGTCCACTACATCCAAACCTGCACACCTAGCATATCGAGCTAGGGAAACGCCACGTTATAGTAGTGGAG
CACTGCCAGTTCGTGCAAACCGAGGAGCCATGGCGCTCCTCTTCGAGCCTTGGATCTTGAGCCTTGTCTTGAACCTT
GGACCTCGCCACTAAATCGGACTTCTGCACCGCGACCTTTCTAGTTTGCAGCGGCATAAGCCCGCAATTGCCACTAA
GGGCAATTACCGTGGGATCACCAATCGGTTTCGCACCAATCTTTCGCCTTTTGCATAGTTGGGCTTTTATCCGGA

>SEQ ID NO: 143

TTTGTCGGTAGTTGGGTAGTCTGTCGGGCGAACATAGTGGAGAGGGCCCTTTGGGTGGGGCCTCGTTTGGGTTTGGT
TTGATTCGGGGCGGCGGTGTTGGTGGTTGCGGCGGCGGCGGTAGGTTTGGAATTGTTGGGTATGTCCTTGGGTCAA
GCGGCATGTCTAGGTGGTAGGGGTGTAAGCAGAATATGTCGCCTTTCACTGCTTGCCAGAGGTCCGGTGTCATAGGT
TTACGCCCAATGTGTACAAAGGATTCGACTAGAAACCAGCTGTCTTCTTCCTTGCGGATTGCGTAGGCGTGTCTCCC
ATCGTGCACCATACACCCCATGTTCCGGGAGCATTCTGGGAGTAGGCCTAGAATTGTGTCCTGAGAGTGGCCTGGGT
CAAGGTTAGGGGCGGCTAAGCGTAGAAGCAGGCGTGTTCCCGTAGTGTCGATTGGCGCTGGGCGGTGGCGGAGGTAG
TGGTTGATGGCGGCTTCATGGAAAAGCCCATTGTGTTTGAAGTGATGGCCCCAGGTCGCTTGTAGTTCGGGTGTGTC
GGCCAGCGCAATGTGCACGACTTGGCAGAAAGCAAGCACGGCATGGGCCCTTAGCCACGGTGCTCCCAGCATGTTAT
TGATAGCGTGTATCGTACAGAAATTGAGGTGTTGTTGTTCGCGGAAGTATGTGCTTGGTATTTGTCTGGGCCAGCTT
AGTGGTACTGGGATATGCCCGTTTTCGGCTGCTGGTGTAGTAGTCCGCTCTGTGTTATTTCCGCCTCGTAGCGGATG
TGAGGGTGACGTTAAATCGGGTTGCTGTTGTCCAGGCTGCGTGCCGATTTGTAGAGTCATTGGGTTGCTACTCATGA
TGTGCGAGTAGGCCGCAAGGTTGGTGATAAGGTTGATCGTTGCGTCGTGAGGGTGTGCGTGTGTTTGGGATAGGAGT
AGGGTGGTGGTGACGGTGGTGATGTTGAGGCTTGGCGGGCCAGGGACGTGCGGGAGGATTGCAAGGCCAACGGGGT
CGTAACTGGTGCTAGTTGGGGGAGTGGGCAGTGGTTTGTAGGTTCATGAGGAGCAGGATGATAGTGGTCAATGTGC
ATATAGAGAAGGTAGGTTTCAGGATTATACCGCGGCCAAGCCCATATAGCGGAAGCCCCAGGATTGCAGGTACCGCG
CCGCGCGTTGTTTTGATAATGCTGTATACCGCGCACGTTGTCGCTAGTAGCGTAATGATGGTTGTGGTGTGCTGGTA
TGTCATGATCAGGAGGATTAAAGGCTGGGCTAGAAGAAAGGCTGCAGGGATGGTGAAAATCAGGTTTTTCGCCCGTG
CTGGTGTGGGGTGAGCTAGCAGGTTGCGTGATGCGTGGTTGAGTTGCGCAACGCCGGCGATAGTTAGGATGAGCGTG
GGGATCCATAGTGATGCCTGCGACGTGACTTGCCAGCCGCTCAGGCCTAGCTGCACAGCGCTGGTGGCCGAGTGGGA
TAGTGTGTGTGCGAGGAGGATTCGCAGCCAGGCGACGGTGTGGCGCAGGAGTGTACAGGTTCCGTGGAATATGCCTA

TABLE 6-continued

Sequences Corresponding to Frequency Peaks (SEQ ID NOs 21-167)

CGGTGACCCAGAGAAGTGTGCTGGCGGTGTGAGCAGAGACATAGCTGGCTGTCGTTATGAGCGTGTCTGTTTCGTTG

TTCAGTAGCAGCTGTGTGATGGGGTATGGTCCCATTATCTGGCACCAGTGGCTGGGGTCGCGGCTGTAGGCGGTGTT

GTGGTGGCAGAGGACGGTACAGGCAAATGTGTTGCAGTTTGCTTGTTCGGCGTGCGCCGCGTTGTCTCGCTCCGGGG

GTCCGTCGTTCCCCGCGCTGAGTTCTTCGTCTCTTGCCACTTTACCATAGGTGACCGCTGCGTCGGCGGTCTTGCTA

CTCTCCGCGTGCGCATAGCTCCCACTACTTATGTCCTCACCTATATTGCTCGCTGCTATCCTAGGGCCCATAGCATC

CTCCATCTTGTCCTGCAGTTGGCGCCAGCAGACATTAAATCCGATACATTTAGAAAAGCTGTCTCTCTGCAGTTCGA

GGCTCTCAGGCAAGCGATACCCATCGGCGTCTACGCCCATGTTGCTGAAAATTGCAGCCGCACTGTGCGTGCACCGC

TCAGTTCTATCGGCAGTCTCACACCACATCCTCTGCTCTCTCTTTCCGGCAGCGGGTTTGCTCCGCATTGTCCTT

GTTGCTGGCAGCCGTGTGGGTTGTAGAGCTCCTCGGCCCGTGTTGGGCGGTTAGGCTACGGGGGGCAGATTGGTGGG

AAGGGTGGTGTTGGAT

>SEQ ID NO: 144

CAATGTATGTGAATGATGGATGGGCTTTGGAAGTGCAAGAACAATCAGCCACAACAGGTTGGCGTGCCAAAGGTCCT

TCAGCGGGCCTCCTGCCCCTCGCAGGCCTGCGATAGCGCCAAGTTGACAACCGCTTCACTCTGGCAACCTCCAGCTC

ATGCCAACCATACAACGGCAGTCGTTATATGTATATAAGCAACATCCTGGCCAAACAGTTGCGTGGCTGGACTGCTG

CCCTCACTCACGTGGCCCCTGGTAGCGGGGTGGCCTAAAGGGGGGTTTTATCGGGTTTTGCAGGTTTTGGAAAGGTA

AGACATGTCAGAAATGATGTACTAAGTTCTATAAGCATAATTGAAGCCAGAAAGATTGCTAGAACCACTTGGAGGTG

GGCACAATGTGAGTTGGGCACGTGGCAAAGACTTTGCATGCCCTACTGCTGCTCCCTTGTCATCACGCACAAGTAGG

CATGAAGGGATGGGATTCTCATGGCCCCACATACTCGCATCAATGTGCCTTGCCATTCACCAAGATGTATTTGTATG

CTGTCCTGTGCTGTGTTGCATGTTGACAGACTGCACATGCATGGTGTATTGGTGTGCCAGCACATGCTGCCCTTTCT

CCTTCGTGTGCCACACTGGGGGCTGTGCTGCCCAACCCAGCATCCAACCTGCCTGCCTGACTCACCCCTTCACATCT

ATGTACGCACATGTGGCCTGACATTCAATTTGCAATGTATGTGAATGATGGATGGGCTTTGGAAGTGCAAGAACAAT

CAGCCACAACAGGTTGGCGTGCCAAAGGTCCTTCAGCGGGCCTCCTGCCCCTCGCAGGCCTGCGATAGCGCCAAGTT

GACAACCGCTTCACTCTGGCAACCTCCAGCTCATGCCAACCATACAACGGCAGTCGTTATATGTATATAAGCAACAT

CCTGGCCAAACAGTTGCGTGGCTGGACTGCTGCCCTCACTCACGTGGCCCCTGGTAGCGGGGTGGCCTAAAGGGGGG

TTTTATCGGGTTTTGCAGGTTTTGGAAAGGTAAGACATGTCAGAAATGATGTACTAAGTTCTATAAGCATAATTGAA

GCCAGAAAGATTGCTAGAACCACTTGGAGGTGGGCACAATGTGAGTTGGGCACGTGGCAAAGACTTTGCATGCCCTA

CTGCTGCTCCCTTGTCATCACGCACAAGTAGGCATGAAGGGATGGGATTCTCATGGCCCCACATACTCGCATCAATG

TGCCTTGCCATTCACCAAGATGTATTTGTATGCTGTCCTGTGCTGTGTTGCATGTTGACAGACTGCACATGCATGGT

GTATTGGTGTGCCAGCACATGCTGCCCTTTCTCCTTCGTGTGCCACACTGGGGGCTGTGCTGCCCAACCCAGCATCC

AACCTGCCTGCCTGACTCACCCCTTCACATCTATGTACGCACATGTGGCCTGACATTCAATTTGCAATGTATGTGAA

TGATGGATGGGCTTTGGAAGTGCAAGAACAATCAGCCACAACAGGTTGGCGTGCCAAAGGTCCTTCAGCGGGCCTCC

TGCCCCTCGCAGGCCTGCGATAGCGCCAAGTTGACAACCGCTTCACTCTGGCAACCTCCAGCTCATGCCAACCATAC

AACGGCAGTCGTTATATGTATATAAGCAACATCCTGGCCAAACAGTTGCGTGGCTGGACTGCTGCCCTCACTCACGT

GGCCCCTGGTAGCGGGGTGGCCTAAAGGGGGGTTTTATCGGGTTTTGCAGGTTTTGGAAAGGTAAGACATGTCAGAA

ATGATGTACTAAGTTCTATAAGCATAATTGAAGCCAGAAAGATTGCTAGAACCACTTGGAGGTGGGCACAATGTGAG

TTGGGCACGTGGCAAAACTTTGCATGCCCTACTGCTGCTCCCTTGTCATCACGCACAAGTAGGCATGAAGGGATGG

GATTCTCATGGCCCCACATACTCGCATCAATGTGCCTTGCCATTCACCAAGATGTATTTGTATGCTGTCCTGTGCTG

TGTTGCATGTTGACAGACTGCACATGCATGGTGTATTGGTGTGCCAGCACATGCTGCCCTTTCTCCTTCGTGTGCCA

CACTGGGGGCTGTGCTGCCCAACCCAGCATCCAACCTGCCTGCCTGACTCACCCCTTCACATCTATGTACGCACATG

TABLE 6-continued

Sequences Corresponding to Frequency Peaks (SEQ ID NOs 21-167)

TGGCCTGACATTCAATTTGCAATGTATGTGAATGATGGATGGGCTTTGGAAGTGCAAGAACAATCAGCCACAACAGG

TTGGCGTGCCAAAGGTCCTTCAGCGGGCCTCCTGCCCCTCGCAGGCCTGCGATAGCGCCAAGTTGACAACCGCTTCA

CTCTGGCAACCTCCAGCTCATGCCAACCATACAACGGCAGTCGTTATATGTATATAAGCAACATCCTGGCCAAACAG

TTGCGTGGCTGGACTGCTGCCCTCACTCACGTGGCCCCTGGTAGCGGGGTGGCCTAAAGGGGGGTTTTATCGGGTTT

TGCAGGTTTTGGAAAGGTAAGACATGTCAGAAATGATGTACTAAGTTCTATAAGCATAATTGAAGCCAGAAAGATTG

CTAGAACCACTTGGAGGTGGGCACAATGTGAGTTGGGCACGTGGCAAAGACTTTGCATGCCCTACTGCTGCTCCCTT

GTCATCACGCACAAGTAGGCATGAAGGGATGGGATTCTCATGGCCCCACATACTCGCATCAATGTGCCTTGCCATTC

ACCAAGATGTATTTGTATGCTGTCCTGTGCTGTGTTGCATGTTGACAGACTGCACATGCATGGTGTATTGGTGTGCC

AGCACATGCTGCCCTTTCTCCTTCGTGTGCCACACTGGGGGCTGTGCTGCCCAACCCAGCATCCAACCTGCCTGCCT

GACTCACCCCTTCACATCTATGTACGCACATGTGGCCTGACATTCAATTTGCAATGTATGTGAATGATGGATGGGCT

TTGGAAGTGCAAGAACAATCAGCCACAACAGGTTGGCGTGCCAAAGGTCCTTCAGCGGGCCTCCTGCCCCTCGCAGG

CCTGCGATAGCGCCAAGTTGACAACCGCTTCACTCTGGCAACCTCCAGCTCATGCCAACCATACAACGGCAGTCGTT

ATATGTATATAAGCAACATCCTGGCCAAACAGTTGCGTGGCTGGACTGCTGCCCTCACTCACGTGGCCCCTGGTAGC

GGGGTGGCCTAAAGGGGGGTTTTATCGGGTTTTGCAGGTTTTGGAAAGGTAAGACATGTCAGAAATGATGTACTAAG

TTCTATAAGCATAATTGAAGCCAGAAAGATTGCTAGAACCACTTGGAGGTGGGCACAATGTGAGTTGGGCACGTGGC

AAAAACTTTGCATGCCCTACTGCTGCTCCCTTGTCATCACGCACAAGTAGGCATGAAGGGATGGGATTCTCATGGCC

CCACATACTCGCATCAATGTGCCTTGCCATTCACCAAGATGTATTTGTATGCTGTCCTGTGCTGTGTTGCATGTTGA

CAGACTGCACATGCATGGTGTATTGGTGTGCCAGCACATGCTGCCCTTTCTCCTTCGTGTGCCACACTGGGGCTGT

GCTGCCCAACCCAGCATCCAACCTGCCTGCCTGACTCACCCCTTCACATCTATGTACGCACATGTGGCCTGACATTC

AATTTGCAATGTATGTGAATGATGGATGGGCTTTGGAAGTGCAAGAACAATCAGCCACAACAGGTTGGCGTGCCAAA

GGTCCTTCAGCGGGCCTCCTGCCCCTCGCAGGCCTGCGATAGCGCCAAGTTGACAACCGCTTCACTCTGGCAACCTC

CAGCTCATGCCAACCATACAACGGCAGTCGTTATATGTATATAAGCAACATCCTGGCCAAACAGTTGCGTGGCTGGA

CTGCTGCCCTCACTCACGTGGCCCCTGGTGGTGAGAGCAAACAATTATATTTCAATACAGGCCGTCTTCCAGGGCGG

TAATAAGTGCAACAGATAAAGAAATAACCAAAGAGTAGTATGCACTGCTTATATGCTTCCGCTAGCTGGTGTTGGTG

GCCTGATCGCCGTGCTCGGCGAGGTCTGCTCGGCGGTCATGGTCAAGGTCACGCCAAGTTGAAATAGACCACAATCG

CAATCGAGATATGCAGTATAATCATCTTGACCGAGGGAAGCCTTACA

>SEQ ID NO: 145

TGGACTGCTGCACTCACTCACGTGGCCCCTGGTAGCGGGGTGGCCTAAATCAGGGTTTTGAGGGGTTTTACAGGGTT

TGGAAAGAGTGACATGTCAGAAATGATTTGCATAGCATAGATCAGCTTATTTCAACTAGAATGATTGTTTGAACCCC

TTGTGGGTGACCATGATGAGGTTTGGGCACATAGCAATGACTTGCATGCTTCCTTGTCCCAGTGTACGAGTCAGTGG

ACGGGACGTGACTCCTATGGTCCTGCATGCTTGCACCACTGTGGCTTCTCATTCACCCAGGTCATACTGAATACTGC

ATTGTGCTGTGGTGCATGCTGGCAGGTTGCATTGTGTGCATGCACATGCTGCTCATTCCCCTTGTCCCTGCACTGGG

GGCTGTGCTGCCTGGCCCACCATCCACCAACCTGCCTGCCTCACTCACTCACCCCTGTGCAAGACCCTTTCTCATTA

ATATATGCACATGTTGCCTGATCCATTGGTAATGCTGGCACAAGCCACAAGGTGGTGCCAGCCCTTGCAGTGCCCCA

TGTGGCAAGCTCAGGACTAGTGTGTTGGGCTTGCCTCCCCTCTCATTGGTCAGGGCAAGGGTCAGGGTCAGGCATCA

TGCAGGCTGTCAAGTATTGTGCTGCCATGCTGAGGACATTCAATTTGCACCATATGTGAGCGATAGCCTTTGAGTGT

GCAAGCAGAAGCAGCCACAGCACATTGGCTTGTCCAGACCCATGGCAGGCCTGCCGACCACACTGGTGGCGCCAAGT

CGGCAACCGCCCCACCCCAGCAAGCTCCAGCTCATGCCAACCATACAACGGCAGTCGCTATATGGATATAAGCAATC

GCCGGACCAAACGGCTGCGTGGCTGGACTGCTGCACTCACTCACGTGGCCCCTGGTAGCGGGGTGGCCTAAATCAGG

TABLE 6-continued

Sequences Corresponding to Frequency Peaks (SEQ ID NOs 21-167)

GTTTTGAGGGGTTTTACAGGGTTTGGAAAGAGTGACATGTCAGAAATGATTTGCATAGCATAGATCAGCTTATTTCA
ACTAGAATGATTGTTTGAACCCCTTGTGGGTGACCATGATGAGGTTTGGGCACATAGCAATGACTTGCATGCTTCCT
TGTCCCAGTGTACGAGTCAGCGGACGGGACGTGACTCCTATGGTCCTGCATGCTTGCACCACTGTGGCTTCTCATTC
ACCCAGGTCATACTGAATACTGCATTGTGCTGTGGTGCATGCTGGCAGGTTGCATTGTGTGCATGCACATGCTGCTC
ATTCCCCTTGTCCCTGCACTGGGGGCTGTGCTGCCTGGCCCACCATCCACCAACCTGCCTGCCTCACTCACTCACCC
CTGTGCAAGACCCTTTCTCATTAATATATGCACATGTTGCCTGATCCATTGGTAATGCTGGCACAAGCCACAAGGTG
GTGCCAGCCCTTGCAGTGCCCCATGTGGCAAGCTCAGGACTAGTGTGTTGGGCTTGCCTCCCCTCTCATTGGTCAGG
GCAAGGGTCAGGGTCAGGCATCATGCAGGCTGTCAAGTATTGTGCTGCCATGCTGAGGACATTCAATTTGCACCATA
TGTGAGCGATAGCCTTTGAGTGTGCAAGCAGAAGCAGCCACAGCACATTGGCTTGTCCAGACCCATGGCAGGCCTGC
CGACCACACTGGTGGCGCCAAGTCGGCAACCGCCCCACCCCAGCAAGCTCCAGCTCATGCCAACCATACAACGGCAG
TCGCTATATGGATATAAGCAATCGCCGGACCAAACGGCTGCGTGGCTGGACTGCTGCACTCACTCACGTGGCCCCTG
GTAGCGGGGTGGCCTAAATCAGGGTTTTGAGGGGTTTTACAGGGTTTGGAAAGAGTGACATGTCAGAAATGATTTGC
ATAGCATAGATCAGCTTATTTCAACTAGAATGATTGTTTGAACCCCTTGTGGGTGACCATGATGAGGTTTGGGCACA
TAGCAATGACTTGCATGCTTCCTTGTCCCAGTGTACGAGTCAGCGGACGGGACGTGACT

>SEQ ID NO: 146

TAAGAATGGTGAGCATTGTGTGCTTGGCGAGAAAGGGGAGGATTGCGGTGTGTTAAGAATGCGGATGTTACAGAGGG
GACAGTCCCAGCACCCGAAAACGCCGAGCCATCACATGCTATCAGGGCCCAACTTGACTCCACCAACCACGACTTTG
CTGCAAACCCTCCCGCGGGCAAAGTCCGTGTGACTCCGCGCACAGTGAGTCCTAGCCAAGCCTCAACCCGCCAGAGC
CCCACCGCTGTGCCTCAATGCCACAAGCCTAGGCACCGGGGTGCCGGGAAACGTCTAGGCCACAGGACACACGCACA
GCGCACGCACTAACCAGGGCGCAAGCGTCCACCGTCCAGGTACTAGAACGGTCGCCCACACGTGCATCCTGTCCACA
CACAAAGCTACCAACCACGCACAACCTCTCACGGCGAGGGAGGCGGGGAATCAGCGTCATGCGGCAAGCGCAATACA
CGCAGGGGCCGCATCTTGTTTTACAACTTGGCTAACAATACCGAAAGCTGGCAAGATCAAAATGTAGACCTCAGGGT
GACCAAAGAACCAGAACAAGTGCTGATACAAAATCAAATCACCGAGACTCACAGAAGTAAGCAGTGTTGATGTTACGG
TCAGTCAGCAACATAACCAAAGCGGCAGCCAATACTGGTACGGCCAAAATGACCAATACAGCAGTCAAAGCAATGGC
CCATACGAACAATGGCATGTGCAACAGTTTCATACCTGGGGCACGCAAACCAGCTACAGTGACCGACATGTTGACAG
CACCCAAGATAGAGCTCAAACCGTTCAAGTGCAAGCTCAAAATAGCCAAATCTACGCTAGTACCGCTGTGTTGTACG
CTTAGTGGTGGATAAGCGGCAAGCGCAAAACCACGCCGTCACTAACAGCCCGAGATATGAAAGGATGCGCAAACGGC
ACAGCGTCCCAACCCTTTGGCCTGATACCCAAAGTCACAAACGTCTGGAGACGACCCCAGACGTCAGCTACGACGGC
AAGTC

>SEQ ID NO: 147

CCACGAACGAAAGGTAATTGCCCTTAGTGGCAATTGCGGGCTTATGCCCGCTGCAACCTAGAAAGGTCGTGGTGCAG
AAGTCCGATTTAGTGGCGAGGTCCAAGGTTCAAGACAAGGCTCAAGATCCAAGGCTCGAGGAGGAGCGCCATGGCTC
CTCGGTTTGCACGAACTGGCAGTGCTCCACTACTATAACGCGGCGTTTCCCTAGCTCGATATGTTAGGTGTGCAGGC
TCGGATGTAGTGGACTTTGAAGAGCGGCCTAGGACTTGGAGGTTGTAGTTTCGGAGGTTGTGACTCTTTCGTGGTGA
GGTGTCAGCGTGAGGGGGCGGGCCCTCTCGCCCTAGTCACCTTGCCCCGTTAATCCATGCCAGGCCCTATGGGCCG
GCGTTGTAATTATTATTATTATTATTATTATTATTATTATTATTATTATTATTATTATTATTATTATTATTATTATT
ATTATTATTATTATTATTATTATTATTATTATTATTATTATTATTATTATTATTATTATTATTATTATTATTATTGG
GGGAGGGGCGCGTGGAGTGACGGGGAGGGATGGGGAGGGGCGGGGCGATGGGTGGCAGAGGAACCGTGGCGGGAT
GCCATGAGGAAGTCAGGAGGGGTGCTGGGCGGATGGGCGCCCCTGAGGTGTACTGGCGAGGTGTGGTGCCTGGATGA

TABLE 6-continued

Sequences Corresponding to Frequency Peaks (SEQ ID NOs 21-167)

AGCGGGAAGAAGCGGGGAAGAAGGCGCCTGGTTCCCAGAGTGGGAATGGAGGGAATTCCCTTACAATCGTGCATAC
GAGTGCAACCCAGCAGGTGTGGTCCGCAAAACGTCCACCAAGCAGGTGATAAAAGGCAAACAGCGGCGTAATACCTG
GTGGTTTCGGCTAGGTGGTGTCGACGTGCGACGAGCCCACGTTGTCGCGGTGTGCTGGTTAGTGCAAGCACCCTTGT
TGCGCCTGGGGGCGGGTGGAAGGTCAAACCCAGATGATGGGCGACCCGTGACGCACGTGATTAGGTACAAGGACGGC
AACACGCTGAACGACAATGCGTCCAACCTGGAGGTGAAGA

>SEQ ID NO: 148

CACATCTGGTGGGGTCCACCGGCCCTGTCGCTGGGCTGGTGACAGGTGTGAGTCGCGGGGTGGGGAGGCGTAGGCT
CGCTAGGGGGTTTGGATAGTCGTTGGAGGTGGGCAGCGTGCGCGGCGTGCCATCCCTGCAGTGTAGGGCATTTGCTA
GCGGGCTCGCTAGTGACGTTCCAGTGCATGTGTACAAAGTAACGGCTGCATCTCTGCCCGTAGGCAAGGTGAGCGTG
TGGTGTTCCCGTGTATTTCATGATCGTATAGGCCGTAGCGGCTCCGCGCACAATGGTGGTCGGCTTCCAGGCCACTT
CATAGTATAGGGCAGTTTGAGATCACCGGATCGCTAACTCAGTGCACACCCTCCTCTGGAGGGTCTGATTATGGCGC
TTAGTGAGATGCTGTCACAGGTTCGAATCCCGTCAAGAACAGTTTTTTTTGCCAGATCACAGCGAAGAAGTAGATAA
GATCAGGGCGCCGCGAAATTTACAAACAAGGCCACGCCGGTACAAAAAACATGAATGTGACAAGGCACGGCGTGATG
CAACATCAACAAAATACACCAAAAACACAGGAATTCAGGCTACCAGGTGTATCTATACACCATGCTTGTCGGTTTTC
AAGCTCGAACATCGCGACGGACATATTGAACATGTAATTCTGAGCGTGCATTGTTCGGAACACACACAACGAGCTCG
GGAGCGCGAAATGGCGAGCCAAGCATGTCGAGACCCCGACTGATTTTCACACCGCGTCACTCAAGTCCCTAGTTGTT
CGTAAGAATATGCATGCTGAACGCGCATTGCGCACAGTGCATAATACAAGCTCAAGAGCGCGACATCGCGAGCCGAG
CATATTGAGACCCTCCTCCATTTCCGAGCGATTTGCGTCCCCGAAGTCTTCTAACTATGCATATTAAGCGTGTATTC
CGAGCTACGTTGCGAATAGAATCCAAGCGGTAAATGCCAAAAACAAATCCCGCGATCCATCTGTCGGTCGACTGTTC
ATCGACCACCAACCTCCTGTGCGAACACCAGCTGGCTAACAATAACCTCCTCAAAGTGCAAGGGATTAACCACGCCA
CACATCAACCTGTTGTAAACACACAACAATCCAACGCACGACAAGCAAGCAGATAAACAATACCCCGGCTTCACGCA
GAGACAGGACAGGTAGAAACTAAACCCGAACGTAGCTCAGTGACATACGTCCAGCCAGCGAAGCCAAGCATGATGGT
CACCACACCAAACACCAACAAGAAAGTCACTGCTGTAAATTGCAGTCAGCACTCACCACCCACAAGGTACTCCACGC
TTCCAGGTCATCTGTCAGTACACCTCGCGCATGTTAAAAACACTACTGCATGCATTGAAAGCCTTGGTTATGAGGCA
GCCATGCTGGCCTGAATGCGCACAATCATACCTGGCACTGCTACTGCTGTGCTCTGCGAGAGCCTCAATAGCCGCTG
CCATTCCGCGGCTAGATCTGCCTCGGGCGTTAGCATGGTACGCAGCGCCTTTTTAAGCCGGCGCTCTTCGGCCCGCG
AGGCCCACAGCGGACGCACTAAATGTAAGGCATGCAACCCACGAAACCTGGTGAGCATTACGTAAATTGAAGCCCGC
CGCCAACTGCCGTGCTGCGGTTTGCACATATCCACCAGCCACAGTTCGTGCGCTGGCAGAGTTTGCCCCTGCGCAAA
GTAATCGGTGACTGCATACGCAAGCTCCACACGAAAGCCCCAGCGCATCACAGGCAACCGCAGGGTTGCATGCTGCG
ATGTGAACATAGCACTGCACGGTAAAACAGGAATCTCCCCGACATCCAGGGCCTGATCGACAGACACCCGACCCGCA
TCAGGCCCGTCGGGGCGCACCATTACAGCCGAGGGCACGAACTTGAGGACATGCACGGGGGCAATGCTTGCATCTGG
CAATGGTGACTCGTTGGGATGCAGAACAATGCCGGTGCCTGTGGCACTGTTGTTGTTGATGTGATACAGACGCACAT
GCTCATTTGATGTAAACACGTAACGAATGCCAGCAAAGAATGCGCACACAGCGGGCACACCGCTATCATCCTCGGCC
CCGCCAAGCGCCTCTAATTGATGCACATGCGAAATAGGTAAGCTGCTCCCGTCCGGCGACAAGTCCGCGCTACGCCA
TAGCAGCAGCTGCTGACGCTGCGCGAGCGCATGCAGCTGCACGAGCTGCAATGCCAGTGGAACCCGCACAACATGGC
GCTGGACAACTGCAAAGGGCTGGGGCACGGGTCAATCCCTGGCTTCGGGGCTGCCAAACACGCGCGTTGAGCTGC
TGGCACGCTGTATCCAGATCTGCCTGAGAGATTTCCTGCACGCCACCAAACTTCTCCGCTAGCATGAAGAGAGGTTC
GTTGTTGTCACCTACGCCTGCTTGCTGCCGATGCTGGTGAGTGAGAACGAACGCGAACGGCACCATATTCCACAGCT
CCCGCCCCATGAGGTTCATGCTGCCCTCCGGATGCTCCAGCTGCCGGATCTGGCGCTCCATGGCCCCGCCGTCCCCC

TABLE 6-continued

Sequences Corresponding to Frequency Peaks (SEQ ID NOs 21-167)

GCGCCCGGCGCCAGCAGCTGCCGCAAGCTCTCTTCCGCAGCACCGCTATATAGCGGCACGTGCCGTGGCTGTGGCAA

CTGACGCAAGTCGCCAACAAGCAGGCCATGCAGATCTGACAGCGGCCCGTGATATAGGTGCGTGCTGTCTATACCCA

CGTGCCTCCGTGCCGCGTGCACATGCATGCAAATGCGCGCCCAGTGGGACAGCCCACACGTGCTAAACTCATCTAGG

AAAATGAAGCGCACACCATTGAGGTTGCGCTCGACTCGATCGCGGTGAGGCGGACCAAAGGTGCCAGCAGTCGCAAA

GAAGGACGTGGTGCTGGTGCCGAGCACGCCTGGCGTAGAGTCCTGTAAATGGACCGTGATGGCAGCGGCCGAAGTCA

ACAGCATGATCATGTAAGGCTCCCTGGCTGCTAAACCAGTCCACCACCGCCACACTTCACCTCCGAACTGAACCCCT

CTTGCACCACACACCCCACACACCCCACACACAACTCACATGCAGCGCAGCGCGCCACGTGTAGCTCACGAGGGCAA

TGAGAGACTCGCAGCGGTGCTGATATGCAAACCACAGCAATGCCTGCAGCACCCGCGACTTGCCGCTGCCGGCTTTG

CCCGTGAGCACCGAGCACACGGGGGGCTGACGGACGCCGGCGGCCTCTGCTAGCAGGAGCTGCGCGTACAGCATGAA

CGCCTGCTGCTGGTCATCGCTGAGGTTCCATAACCGCGCTGTGTCTTCAGGCGTCGGCTGCGAGTCCTCCGGGCAAA

GCACGTACGGCGGCTCTGCACCAGGGTTCGCTGCATCGGGCCAGACGCCCTGCACCTCTGGGGCGGCTGTGGTAACC

GCCAATGGCGAGATGAGCACCAGCTTCGCTGTCACTGCTGCAGTGCCGCTGTTGTAAAGCAGCAGCTGCTGCTGCAC

TGCTCCCTGCGCCTGCGCGAGTGCCTGTGCGGCGTACTGCCCGCCTAGGTCGTAATCATGCATGCGTTGCTGTGCTG

CAGCCAGCCGCTCGTGTGTCCACTCCTGCGTGCTGCGCACTACTGCTGCCGCCGCTGTACGCCCAACCGCTGGCCAT

GCATTGGCGCGCGGGATCTGGGCAACCACGGTGGTCGCCTCTGTAGTCAGACCGCCACCCAGGCCGCCGTGCACAAT

GCGCTGCAGCAGCCCTGCGCGTTCCGTCTCCGATAGCGCACAACCCTGCCAGAGCTCCGCTGCGGGCGCTGCGCTGC

GCCTAACATCGGGTTCCTCATCATCCTGCGGCTCTGCCTCCAGGTCGTCCATGCCCTCCAACGGCACGCCCTCCAAC

AGTGCCTCCTCTGCCACATCCTCAGCGGTGCCCTCCGCCTCCGCCTGCAGCTGCCGCCGCTCCTCCGCCCGCATTCG

CACGCGCGCAAGCCCATCCACGTGATCAAGCATACGACACGCGATGCGCACATGCAGCGACTGGCCATCCGCCGGCT

GTGCAAAGCACCGCTGATAAGCTGCCCATGCGCCGTTGCTGAGATCGAGCATGTCGTCACAGCTGTAGGCGGCGAAG

TTCGCGAGCGCAAACACTGCATAGCGCTCCAGCACCTGCGGATCGCCCACGCCGTCCGCAGGCCGCACAACGGGGTC

ACACACCGGCTGCGGCACGTACGGCCGCAGCCGGCGTCGCCACACGCATTTACTGTACTCTGGGTGCGCGGGATGCA

AGCGCAGATGGTGCCCTTGCGCTCCATCTGGCCCGGCCGAGTGCTGCGGGGTGGTGGGCACACATACAGTTCTTTGC

TGCTGGGCCGTGCCGAAGTGCTGCTGCAAGACATTATAACGCATGCGAGCCTACGGACTCAACACCCCGTAACTCCA

GGCGTGCAAGCTGCCGCGCACACAACCTCGTACCTTATAAAACAACATCGCCATCATCATAGGAGACAGCTCGCGCA

GCGCCTCGCCGCGGTACAGGTAATCTTTCAGGTAGCTTGATGACCGGTAACGAGCAGGTGCGACGGCGGGCTGCTCT

AGCTGCTGTACGCTTCCGCTGGGCCCGGGATCTGGGACATCGCTAGCGATTGTGCTGGCGGCCGGAAGCTGGCCTTC

CCCTGTCGGACTCCCGCCCGCTCCAACGCTGCCCATTGTACACACGAGCCGCAGCTGGGTGTCTCTGGGCCTGAGCT

CCGGGTCCGCGCGCTTCAGCTGCGACTGCACATGCTGCGAGAACATCCTGTAATCGATGGCCCTGAACTGGTGGCTT

TCGTGCGCGTCGGTGCCCCGCATC

>SEQ ID NO: 149

CTTCCACGTACGCCTCTGCAGGTGCCCTCGCTTCGTGTGCCCATCAACTTCCTTACACCCCTCCATGCCGTGTTCAA

CGAGAACCTCATCGTCATCCCTCCCCGTCTTCCTGCTGCCGCCGCTGACCCTGCGCTACCTGCCATTGCTGAGGATG

CTGGTGCCGTCGGTGCCACTGCTGGTGCAGCCGCTGCTGCTGACGCTGCGCCCGCCGCCATCGCTGGCGCTATGCTG

CAGCCGCCAGCAGGAGATGACGATGGTGACTTACAGCTCGAGGACGTCCCAATCTTCTACGCAGGCCTCCTCAACGC

CCTGGTGCGCCGCCCCTCTGTCACGGCCCAGGTGAGCCTACGCAGCTGTGCTCCACAACAACCTCTTAGTCGTACTC

CACCTCCATACCATTGTATCTGCACTCCCCAGCCTCCCTCGCTTTGCACGGTGTCCATACATACCACTGCCACCCCC

CTTCTCCACTGGCCCCTCCCCACTCGTCCGTGCCTCAGATCGTCCTCTCGCTCCGCACACCCACCTCGCGCCGCGCC

ATCCTGAACAAGCTGCGCGAGCCCACGGCCGGCCGCCGTGCTCTGTTCCTGATGGCCGCGCAAAACCGCGGCGAGGA

TABLE 6-continued

Sequences Corresponding to Frequency Peaks (SEQ ID NOs 21-167)

GATAACCGCGACAATGGAGACCGGTATCATGGGCGTCACGCCCGACACTCCGCTCCTGATCCACATCCTAGTCGAGC

TCCTGGTGCATGACCAAAACATGCTCACGCTCAACTCCAACATCGACCAGGCCGCCTTCACCAGCCACGCGCCGGTG

TATGGTGCCTTCATGCCAGTGGTGCTCGAGTAAGTGCGCAAGCCGCCCTCCTATATAGGTTGGGCTACGTACCTGCC

AAGCTCGGCCCCGCATCACCCAACCAGTTTGCTCACCACACTGCGCTTCATCCAAACCTGCCTACCTGCAGCAACAA

CAACCTCATCGGCTACCTGCTGTCGGCCGCGCTGGCTGCATACGATGGCACCCTGGTGCGTTCCCTGGACTGCGCTC

ATGCCATCCACCACCCGCCACTCCACCTCACCATGCGTGCCTCTCGCATCTCCTGAGTGCACTCCACCTGACCATGC

ATGCCTCTCGCATCTCCCCGCACCTTGAAGGTCACCATGCCGCCTGATGTGGCGCGCGTCGTCTACGGAGCGCAGCT

GGACGCCGTACTCGCTTGGGCGCGCAGTCCGCTGGCTACGAGCCGCAGCACGCCCGGATCGGCCGTTGGACTATCG

CGGGCGCCACCGTGCAGGCGCAGCTGCCGTAATGCTGATTACTCCTCCACGACTGATTACGCCTCCACCTCTGCTTA

GAACCAACCTGCATTCCTCGCTTTCATGCGCAGCATGTGTGCACGGAGGCGTTTGTGAAGTGCTTGGTAGTGCGCGC

AAATGCGCTATTGAAAAGCTGTGGCTGTTGCGTAGATGTATCTTCTGTGCGGCTGCTTGACATTTCCTAGTCTCAGT

GCTTACAGCCTGGCGCAGTTCTGCTTATGGTACCACGACAAACACATTGATGTTGCACGTTGCCAACGTTGCGAGTT

CTGCACACCTTCATTGTATACAAACGCTCATCTCATGCCATTGCACTCGCTGCCTCCTGTCCATTCCAGCACCTCAG

CCAATGCACTGCGCCTCATGCGCCTCAATGCAGCACCCCACTACCTTTGCAAGCTTTCGCCAGCACGACACCCCGCG

CATCTTCACCACAACAAGCAGCTACCCCTACTTCTACTTCCGCTGCAGCCCAGCCCCAACCGCAACCCTACACTGCT

ACCTGACTACAGCCACGCTGTCTTGTTACATTGCCCTTAGCGCACCCACACGCCCTCACAGAAAAACCGGTTCCCCA

ACGCATGCCCTGCCCACAGCTCTACCCCACAATCCAGTTCATCACCCACCCACTCCATCCACTTGCTTGGCGCAAA

TGGCACAGTCCTTTTAACATGCAAATGCGAACACCTGTACGGCCACTCGCTGTCTCACGTGCATGGCCCAACTCCCA

CTGCAACACACCAACTCCCCAGCAGCGTTCGCGCCTGTTGGCGCTGCCTACCAAACTCCCGCTGTTCTTGCTTTATT

TGCGTTGTGTACTCCCATGACCTCTCACTTACACAGCCCAACACGCCTCTACACGAACCACTACTACCCACCCGCTC

CTCCTGCTACAGGTCTCAGGACTTGCCCTTGAAGTCCTGCCATACCAGGCACTTCACAATGTCCCGGTGCCACTTCA

ACCCTCGCACAGCAAACGCTAAATGCTCGCCCTCGGGCAGCGCCTCGCCGTCCAGCGCGCTCTTCAGGAGCTCGTCC

CGCTGCTTCTGGATTTCATCCCGCCGCGCCTTCCGATCCGCTGCTGTACGTGCAGCCAACACGCGCTTCATGCCCTG

TACCTGCAGCTCCTCCATCTTCTTCTTTCCGCCAGATGCCTTGATCAGCCGCGCCACACGCTCCATGGCCGGCACAC

GCAGGAAATGCGAGTAGCCATACCGCCGCGCGTCGCCAGTGGACTCCAGCACGGGCGCCGTCCCATGCGTGACCATG

CCAGCAGCCAGCACCACGATCGTCATGTCGGTCGGCAGCACCTGCAAACAACAGCGCCCATATGACTTGCATGTCCG

CACCGCGACCTCACTATACGCGCGCCTGGCCGACACACACAAAACCACACCCGCCCGCAGAGATGCACCACCTGGCC

ATTTACCTTGATGGAGGCGCCAGGCATCAAGAAATGCCCGCCGTCCAGGCTGCCGGCACCGTTGTGGCGCCACAGCA

TGATGCTGTACGGCCCTGCGTGTCAATTCCCACGCGAAGAAATTCACACTCATTAGCAGCACGCAGATAGCAGACCA

GCACCACCACCTTGCCTCACAGTACGCCCACCCTCCCAGATCTACACAAGCCAGCTCGCACGCACACCCACTCACCC

ATCCACCGCCCGCCCCCCCCCCCCCCCCGCCCACACACACAAATACACAAGCAGCGCTTCCCTGATATACACCCC

TGCGCACCAGCCTCACCGTCCGTTGTGTCGAAGTGCAACGACACCGCGCAGTTCTTGGTCATGCTCACGAGGTTAGT

TGCCGTGTCGCCGTACATCGCCTGGCGCCCCAGGCAGACAAGAACTCATCCCTGCGCGCAGACCCAGAGCGTGCAG

CACCACACATCAATGCTACGTACGCGACGCCCACACAACCATCCTGCACGTACTGCCCTTGCATGCAGCCCCGCGG

CTACGCGGCGCCCTCACCTGTACTTGGTCAGGTACGGCGCAACCTGCACCGCCGCCTCCCACACCGCCGTACACATC

TCCTCCAGCGCCTCCTCGATGCTGAATGGATAATGCTCCGCCTCGCACTCGTAGATGATCTGGTTGACGTACCTGCA

CAGCAACGTATCAGTCAATCTCGGCCCCACCGCACATCCATGCCTCTCCTCCATGCCCGCGCCACCCTTGCCGCCCG

CATGCAACACCCCCTGGTGCTCTTGCCTGCAGATGATGTCCCACGCGAGCAGGCGACGCCAGCCCCGCCATCCA

GAAGTTGCCGTCGTAGTGCTTGTCGATGTGAGCCCAGGCGTCGCCATTGTGGACCTCTTGACACGTGCGCGCCACCT

TABLE 6-continued

Sequences Corresponding to Frequency Peaks (SEQ ID NOs 21-167)

TGTTGCGCAGAGCGCGCCCCGCCTCGCCCGACACCTGCAGGCAAGCGCGACAGCAGCATGCTGAACACGCACACCGC

CATACAACCGATAACATGCAACAACATGCGCCCGGACCGCAGCTTATTCGCACCTGCCCTACAGAGACGAGCGGCGC

GCGTTGCAGCCCACCATCTGCTGTGCGCCGCACGGCACACACCAGCACGTCCTGCCCGGTGACATCCAGCAGGCCGA

ACGGGCACTCCGCGAACCACTGCTGGTACCACGAGGTTTTGTCGCCGC

>SEQ ID NO: 150

CTGCAACCTAGAAAGGTCGTGGTGCAGAAGTCCGATTTAGTGGCGAGGTCCAAGGTTCAAGACAAGGCTCAAGATCC

AAGGCTCGAGGAGGAGCGCCATGGCTCCTCGGTTTGCACGAACTGGCAGTGCTCCACTACTATAACGCGGCGTTTCC

CTAGCTCGATATGCTAGGTGTGCAGGCTTGGATGTAGTGGACTTTGAAGAGCGGCCTAGGACTTGGAAGATGTAGTT

TCGGAGGTTGTGACTCTTTCGTGGTGAGGCGTCAGCGTGAGGGGGCGGGCCCTCTCGCCCTAGTCACCTTGCCCCG

TTAATCCATGCCAGGCCCTATGGGCCGGCGTTGTAATTGTAATTATTATTATTATTATTATTATTATTATTATTATT

ATTATTATTATTATTATTATTATTATTATTATTATTATTATTATTATTATTATTATTATTATTATTATTATGATTAT

TATGATGCACCCGAGTCGGCGCACGCCGCCACAGGCACCCATGTATGCAACTAAATGTCCTGAGGCTGCTGCGTGGG

CTTGCACCGTCAAGGCAGGTGGCGCAGGCGCGAGGGTGCCGTGGCGGCGGGCTGGTGGGGAGG

>SEQ ID NO: 151

CACACACACACACACACACACACACACGTGCCGTGCAGGCTGGTAGACATGTCCCCCTCCATCCCCCCTCCCCCCTC

GGTGTCATTTCGCCTGCACAAGCCTCCAAAGGCTACACATGCCTTGTACAGACACATGAACGTGCCGTGCAGGCTGG

TAGACATGCCCGCCTCTACCCTCCCTCCCCCCTCGCTGTCAATTCGCCTGCACAAGCCTCCAAAGGCTACCCATGCC

TTGTACAGACACATGAACGTGCCGTGCAGGCTGGTAGACATGCCCGCCTCCATCCCCCCTACCCCCCTCGCTGTCAA

TTCGCCTGCACAAGCCTCCAAAGGCTACACATGCCTTGTACAGACACATGAACGTGCCGTGCAGGCTGGTAGACATG

CCCGCCTCTACCCCCCCCTCCCCCCCTCGCTGTT

>SEQ ID NO: 152

CTCACAAGTCTCCAAAGGCTACCCATGCCCTGTACAGACACAAGAACGTGCCGTGCAGGCTGGTAGACATGCCCCCC

TCCATCCCCCCTCCCCTTCTCGCTGTCAATTCGCCTGCACAAGCCTCCAAAGGCTACACATGCCTTGTACAGACACA

TGAACGTGCCGTGCAGGCTGGTAGACATGCCCCCCTCCATCCCCCCTCCCCCCCTCACTGTTAATTCGCCTGCACA

AGCCCCCGCAGGCTATCCATGCCTTGTACAGACACATGAACG

>SEQ ID NO: 153

TGGCCGCAACAGAAAATCTGGAAATTTGGGCAAGGCTAAACTCAAGTGTTCTTGCTCAGGTTGCGTGGGCAGACTCG

TAAGTAACCCGCAGAATGAGTGTGCCGCTGCATGGGTGGACTGTCAACCATATTGTGTGATGCAGGATCCTGGGCAC

CTGGATTCATCAGCATAATCATGGCCAGCATGGTGACATTTTAATTGGTTGGGACAAGCGTGGCCTACACTACCGAG

CATTGTTGGCTTTCCTTGTAAACATTGCAGACCTTAAGAGTGTGCGGTCTGGGGCAATCCCCCAGTCACCCAGTGAG

CCGGTTGAGGGCTACTGTGTGAGCACTACTCTGGTTGGGTTTCTGCGGTGCCTAGATATACTGCACCGGCTGCGCGG

CTTCACCATGTGTCCAAATGTACGGCGAGGGCTACGGGAGTACGTCCTGCGAGTGCTGCGTAAAATGGTGAGCCCTC

GGTCTTTAAACTGCTGAGGGGATTGTCGCCTGACCCCATGCATGTGATTCATACGCAGTATCCTCATGTCATACGGA

CTGCAAAGCCGGTTCTTCCAACGGTACTTGCTGACATGCAGCATGTTAGCGAGCTGAAGCCTATGAAGGCATCTTTG

GACCATAACACACACACCCGTTACATGGCAGACTACAGTCATAAGTGGGCAACCATCCGCATGATGGTTCACATGGC

GTGGGCTGGACGTCGAATGGGGCATGTGATGAGGCTTAAGCTGGGGGACTTGCAGTTTCAGTACTGCTCCTCATGTA

CTGTCAGCACTTCCAGCACGGCAACATCATCATGGTACCTGAAGCTGCGCATTGCATTTGCCAAGAACAAGTGTACT

GACGGCAGCTTTCAGAGTGTCATACTAAACTCAGAGAATAATAATAATAATAATAATAATAATAATAATAATAATAA

TAATAATAATAATAATAATAATAATAATAATAATAATAATAATAATAATAATAATAATAATAATAATAATAATAATA

TABLE 6-continued

Sequences Corresponding to Frequency Peaks (SEQ ID NOs 21-167)

ATAATAATAATAATAATAATAATAATAATAATAATAATAATTACAACGCCGGCCCATAGGTAACGGGGCAAGGT
GACTAGGGCGAGAGGGCCCACCCCCCTCACGCTGACGCCTCACCACGAAAGAGTCACAACCTCCGAAACAACAACCT
CCATGTCCTAGGCCGCTCTTCAAAGTCCACTACATCCGAGCCTGCACACCTAACATATCGTGCTAGGGAAACGCCGC
GTTAAAGTAGTGGAGCACTGCCAGTTCGTGCAATCCGAGGAGCCATGGCGCTCCTCCTCAAGCCTTGGATCTTGAGC
CTTGTCTTGAACCTTGGACCTCGCCGCTAAATCGGACTTCTGCACCACGACCTTTCTAGGTTGCACCGGGCATAAGC
CCGCAATTGCCACTATGGGCAATTACCTTCATTCGTGGGATCACCAATCGGTTTCGCACCAATCTTTCACCTTTTGC
ATAATTGGGCTTTTATCCGGATTTGTGCCCGGGTCCCTTCTGCCGTAAGGACGAGTCAAATCGCTAAACTAGTTAGC
AATCCGGTGATGTACTAAACTCAGAGCATTATCAGCACAGCATGTTGCAGCAGGAATTTGATGAGCGGTGAAGGCCT
GTCCAGGGGTTGAGCGGCGAGGAAGAGGGAGTCAGTGACGCGTTTGCAGAGGTTATACTTGCTAGACGCAGGGTAAA
AGCAAGGTGGAGCCGGCGGAAGGCAGAAGCGGGGTAGGGCCGGACGCGGGTGCGAGGGGGTGTGTGAGATGGGACA
GGGTTCAGGCAGGTTGGCGAGGTCCCATAGGGTGCAGCTGACGCCCGTACCCCAAGCAGACAGTAAACAGTTTGCAG
CGGCAGAGCAGGAGTGCATGGCTGGTCGAACGCCGGAGTTAC

>SEQ ID NO: 154

ATATGTTAGGTGTGCAGGCTCGGATGTAGTGGACTTTGAAGAGCGGCCTAGGAATTGGAGGTTGTAGTTTCGGAGGT
TGTGACTCTTTCGTGGTGAGGCGTCAGCGTGAGGGGGTGGGCCCTCTCACCCTAGTCACCTTGCCCCGTTAATCCA
TGCCAGGCCCTATGGGCCGGCGTTGTAATTATTATTATTATTATTATTATTATTATTATTATTATTATTATTATC

>SEQ ID NO: 155

TAGGCGCAGGATGTAGAGCCGTCAAGTAAGGTCCGACCTCGGTGTGAGAAACTTCAACTTGTTTTTGACAGCTGTTA
CAGGCATAGTGACAGCTAAGACTTCGCATATAACCAATTGAAGATATTAGTCGTCAACATCGACTAGAAGCGCTGAC
TTGGTTCGCGAGTCAGCGAGTCAACATGGCTGCAAGCTCACTTGCGGGCTCGCATGCAGACCTTCACCATCCGCCGC
GATCTGCCCGATTTGAAGAGCTAAACTTATATTAATTCGTTCTACTTATTCATTACAATAATTGGAGTTCTCAAACT
CGGCCTGAATAGAAAGATAAATGTTTGCTCTCACCACCAGGGGCCACGTGAGTGAGTGCAGCAGTCCAGCCACGCAG
CCGTTTGGCCTGGCTTTCGATTTAATACATATAGCGACTGCCGTTGTATGGCTGGTACCATCCGGCGCTTGCTGGGG
TGAAGCGATTGCTGACTTGGTGCCACCGCTGTTGTCCTAGGCCTGCAAAGGGCATGAGGCATACCTGTCTTGCCATG
CCACCGTGCTGTGGCTGCTTCAGCTTGCACCTGCAAAGCTGTCATTCACATATGGTACATACTGATTGTGCCCAGCA
TGGCTGCACATCACTTGACAGCATGCATGATACCTGACCCTGGCCCATGAGAGGGAAGGGGAGCGGAGCACACATGT
GCAGAGCCGCATGGGGCACTGCAAGGGCTGGCACCACGGCTCCCAGCTTGTGGTTGCATTACAGACATGTCAGGCAA
CATGCGCATACATGCACCTGAAGGGTCTTGCACAGGGGTGAGTGGGGCAGGCAGGTTGGATGGTGGGTTAGGCAGCA
CAGCCCCCCTGTGTGGCGTGCCAAGGGGAATGAGCAGCATGTGCTTGCACACCGTGCATGTGCAATCTGTCAACATG
CAACACAGCACAATATAGTATACAATTGGATCTGGGTGAATGGCAGGCCACAGTGGTACGAGTATGCGGGCAATGG
AAGTCCCACCCCGTACCACCTACTCATGCTTGGTAACAAGGAAGCAATGGGGCATGCAACATCATTGCTACGTCCCC
AAATCACATTGTGGTCACCCACAAGTGATTCCAACAATCAATCTAGCTGTTATTATGCTATTTATGCTGTGCAAACC
CTTTCTGACATGTAACACATTTCAAACCTGTCAAAACCCCTCAAAACCCCCCTTTAGGGTT

>SEQ ID NO: 156

GCGGTTGCGCGGGGTTATAGGTGCGCGGGGTTGCGGGCTTTCAGACTAGCGCGCCGGGCGCGCGAACAAGGGCGCGG
CGCGGCGTCTATGCGCCGAAAGCCAAAAAATCTAGCGAGACCCTTAAGAGCGGGGGCAATAATAATAATAATAATAA
TAATAATAATAATAATAATAATAATAATAATAATAATAATAATAATAATAATAATAATAATAATAATAATAATAATA
ATAATAATAATAATAATAATAATAATAATAAGAGG

TABLE 6-continued

Sequences Corresponding to Frequency Peaks (SEQ ID NOs 21-167)

>SEQ ID NO: 157

CGGGGTTGCGGGCTTTCAGACTTGCGCGCCGGGCGCGCGAACGAGGGCGCGGCGCGGCGTCTATGGCGCCGAAAGCC
AAAAAATCTAGCGAGACCCTTAAAAGCGGGGGCAAATAATAATAATAATAATAATAATAATAATAATAATAATAATA
ATAATAATAATAATAATAATAATAATAATAATAATAATAATAATAATAATAATAATAATAATAATAATAATAATAAT
AATAATAATAATAATAATAATAATAATAATAATAATAATAATAATAATAATAATAATAATAATATTATTCAACT
TCGGCACCAGACCCACCCTGAAGCCCGCATGCCCGGCCGCAGCACGGCATGCACGAGTGCACGCACACGCGTCCAGC
CACCTCCACCCGGCGGACCGCCATGCGATCCATGGGGCGTGCCCCTAAGGGTGTCAAGGGACCGCCGGTGGTTCTAG
ATTGCATTGGTCCCTTCCTAGCCCCCTGCATGCTAGATTGCATTGTCGGCCTATGGGACATTGCACCCTCTCCCAC
TCCAGGACAAATCGTGTCCCCAGGGAGGCGCCCACCTGACGGCACCCAAAACCCCCTGATAGATAGTTCTTTAAGGA
TGCCACCACGCCGTCCCTAACTGAAGGACAATATATCAGGGGGTTTTCAAGCCAAACCCGCCAGTTGAGGAGGCCAG
GAGACGGTGCCCCAAACAAAACGCAGAGCGGGATACAGACTCCGCCACTCAATGTATATGTTACATGCAATCTATTG
TAGCAATAGCGCTTGACGGCAGGCTAAAACGTGCTCGCCGACGCTCAAGTCACGACATTGACCGACCAACATCGGCG
TTGTTTTGGGGCGTGATCAATTGCCGTCAACACAGATATCTGCATAGATGTAATCAGGCTACTATCT

>SEQ ID NO: 158

CATCCCAAAGTAACCCAAAAAATCTAACGGGGCATATAGGAGCGGGGGCAAATAATAATAATAATAATAATAATAAT
AATAATAATAATAATAATAATAATAATAATAATAATAATAATAATAATAATAATAATAATAATAATAATAATAATAA
TAATAATAATAATAATAATAATAATAATAATAATAATAATAATAATATTATTATTATTATTCGGCTTTGGC
ACCAGACCCACCCTGAAGCCCGCATGCCCGGCCGCAGCACGGCATGCACGAGTGCATGCACACGCGTCCAGCCACCT
CCACCCGGCGGACCGCCATGCGATCCATGGGCGTGCCCCTAAGGGTGTCAAGGGACCGCCGGTGGTTCTAGATTGC
ATTGGTCCCTTCCTAGCCCCCTGCATGCTAGATTGCATTGTCGGCCTATGGGACATTGCACCCTCTCCCACTCCAG
GACAAATCGTGTCCCCAGGGAGGCGCCCACCTGACGGCACCCAAAACCCCCTGATAGATAGTTCTTTAAGGATGCCA
CCACGCCGTCCCTAACTGAAGGACAATATATCAGGGGGTTTTCAAGCCAAACCCGCCAGTTGAGGAGGCCAGGAGAC
GGTGCCCCAAACAAAACGCAGAGCGGGATACAGACTCCGCCACTCAATGTATATGTTACATGCAATCTATTGGAGCA
ATAGCGCTTGACGGCAGGCTAAAACGTGCTCGCCGACGCTCAAGTCACGACATTGACCGACCAACATCGGCGTTGTT
TTGGGGCGTGATCAATTGCCGTCAACACAGATATCTGCATAGATGTAATCAGGCTACTATCTGGCCTGATATGGCGT
GTCCTGGCGAACGCGACTGTCACATGTAGATGTTTGAGGTCGGCCCCGGCTCAATGAAGTGCCCCGGAGTTACTCTA
ATGCGGTAGTAGATGTTATACGAATGGTACTTGGCTGGGACACGACCGGCCCGTAGGGCCGTGCGCGAGTTAGACG
TTGCCGACCAACCTCGCAGCGCCACCTTGCCGGTTCCTGAGGCGCATGTAATTGCTATATATAAATATGGGTCCCTT
TTATGGGGACACGCGGCCACACACCGGTGCTCGCGCAGATCCGGACCTCAACTCGGCGACGCAGCGTTCTTAAGTGG
GGGGCCAAATTCTGTGCGCTGTATTTACAAAACTGGGTCCCTCACGGCTGCCCGGACAGCAAATGGCCGCGGTTCCG
ACACA

>SEQ ID NO: 159

TGTCTTCAGCTCTGCTAACTCTGCTGGGCCAGTAGGTCAGCGATGGCCCCGAACATTTCGCGGTGATTGTTTACGTG
TAGGGACTCGGGTTCTAGAATTGACAGCGCACGGGTGCGGACACATAGGTCATGCATGCGTTAGCACAATGCAGACA
TCATACTCGGCTATCTGATACCTCATCTTATTGGTCTTATGAGCTGAACACTTCACCATGTCGTAACCCAAAGACAT
CAGATAATCAAAATACTTCTGATGCATGGATGGATGCGTGAGGTATAGCTTCTTGGGTGTCATCAGGAACGGAACAA
GGGTGGCCTCCGGCGACCGCAAATATGAAAACATGGCATCCGAAACGCCGACCCAGGAGTCGGAGAGAATGTCATCG
ACTGAAACAATGCCGCCGGGGTGCAGGCTGCAGGCTGCAAGTTTAGTGTCTCGTAGAGCCGCATCATAAAAATGTCC
GCCGTCTACACTGAAAAAACGGAACTGAGGAATGGACCTTGTTGAAAACGTTTTCACCGTAATATCCATGGAGTTCC

TABLE 6-continued

Sequences Corresponding to Frequency Peaks (SEQ ID NOs 21-167)

CTTCAATAACAGTAAAATTAGTGTGAGGGGAAAATCGTCGGGCGTTGTTAAGAAATATCTGCAGATCTCCTCGCCCA

GAGCCGTCTAAATTCTGTGTTTGATGACCAAATAAATCCATAGCAATTACCGGCTCTTCCGGAGCAGCAGACAATCA

GAGGCCAATGATGTATTTACCGTGATGTACTCCGATTTCACCAATGGAACCGTAAATATTGTTCTGATGCTGATACC

TTGTTAGAAGTATACTGACATTCAAATCAAATGTAGTCAGCCAGCCACCAAGTCTTGACATTCCAGTTTGGTACTCG

AGGATGAGTTTGTCTTGCATAGAAATATCAGGCAACGTATTACTATCGAGTTTTGAAAGTCTTGCATCGCAAATGAC

AGCCGACTGGCAAGGGCCAGACAGCAACAGCATCGTACATAAGTAAAGGTATATTAGTCTGACCATCTCTCAAGAGG

CGAACGTAATCCGGAACCTTCCGGAAATTTCACTGCGAAACCATCACCGCCAACCCCCACCCTGTGCGCAGCACCCG

TAAAAACCCGGGAATTATAAAAACTTTTGCGCTGTAACGCGGGCTGTCACTGAGGCACTGGCCACGATGCAGCTGTG

TGACGGCAGGCCTGCACCGCATTGACCTTCCCAGCGTATGAGCACGGAGCGTGGAGAGGCTGGACGGCCACCACACC

CGACCCTGTGTACCAGCAGCTGTCCTGGGCACTTGCGGGGTGATTAAGATGCGCCTGCGGTGATCACAGCAATAGTC

GGAGGTACCAGATGTGTGGTCGGGAGATGATTCAGTCGAATATACCAGGAGGCAGGAGAACCTGTAAAGGAAAGAAG

TAGGAAGGGAGAAAAGGGGAAGAGACTTGGCGGCCGGCTGGCCGGACCTGCACGGGAGAAGGCGGGGATAGAAGCCG

TGGCCTCAGGCAGAGCCTGGGCGTAGTTGTTAGGGCGTGTAGAACGCCAGAGGTATTGGATAGGAGGGAAGAGCGGG

ACTACCCTATAAGGCTGAGTAACCGCTGGTGTCGTACGCGCCGCTGATGCGCAACCCGGCTGAACTGAGCAAGCTGG

GCTCCCTGGCAAGCAAGTCGATACAACAGGTGTGTGCTCCGCTCACAGGCAAGCAATCCGATGCGAATGCTACAGGC

TGCACGCACAGGCAGGCAAGTCGGTGCAACAGATACGAGTTGCTTACACCCAAGGCTGGTGGATACAGTATGCAGAC

CAGATGGCTGGTAGAAGAGAGCAGGAGTCGGGAGCGGTAGTCTGTCGCAATCCCGAAGGGAAACCGGAAGGGGGGA

GTAGGGAGACAGTAGGCTGGATCGGTC

>SEQ ID NO: 160

AGGCTTGGTGCGACCTAGTTGTGAGGGGGGGCGGCTACCGCTAGCGTCTCTGGCTGCTTAGTCGTAGACTTAGGCT

TCCTAAGGCAGGTGCTGTGCAGCTGTGGGAGTCGACCTGGAATGTTCGTCAGGCCCCTAGATTGACTAGTGTTGCGG

AACTAATGCGTACGTAGACCAGAGCGGAAGGCGGAGTGGGCTTGCAGGCGGCACGAGAGTAGGCAGTCAGTAGCGCA

AGTTGTGAATTCACATGTTACCTCGTAACCGACGGTAAACGCTGTGGACGTTCGCGCCCATGGCTGGCTGACGGAAG

GTGGCTGCTGTATTGGGATGGCTGGGCTGGACGACGGCGGCCGGGCTGGCGTCGGGACTACCAGAAAGGATGCGCGC

GAAAACCGCAATGCGCGTTCAGCATGCATATTCTTACGAACAACTAGGGACTTGAGTGACGCGGTGTGAAAATCAGT

CGGGGTCTCGACATGCTTGGCTCGCCATTTCGCGCTCCCGAGCTCGTTGTGTGTGTTCCGAACAATGCACGCTCAAA

ATACATGTTCAATATGTCCGTCGCGATGTTCGGCAAATAGGCCAATGCGCAACGGAGTGCGCGCTTGCGGACCCAA

AGGCGGTGCCGGGTGTGCCGTGGCGAGTGTGTAGAGGACGAGAGGCACGTCTTGCTCGAATGTGGAGCTTACACAGA

GCTAAGAGTGGCATATGGAATCAATAGTAATTGTGTGAAGGAAGTCATGCTTAGCACAGAGGTTAGAAAATTAGCCG

CGTTCCTGTACTCAGTGCAGGCTCTGCGTGCTAGCATTCTGCGGGCGATTGAGCGGACTGAACCTGCTTTGTTCTG

CTATATGCGCCTCCGGACTCAAAGGAGTTAGTGGGGCCGCATGGACTACGACGCCATGTAAATGCTCATGCTCATGC

GATGTTGGAGCTTGAAAACCGACAAGCATGGTGTATAGATACACCTGGTAGCCTGAATTCCTGTTTTTTCGCGATGT

CGGTGTATTCTGTTGATGTTGCATCATGTCGTGCTTTATCGCATTCTTGGTTTCTGCACCCGCGTGGCCTTGTTTGT

AAAATTTCGCGGCGCCCTGATCTTATCTTGTTCTTCGTTGTGATCGTGTGTCAAAAATTTGTTTTTGGCGGGATTCG

AACCTGTGAGCACTACGCTAAGCTCCATAATCAGACCCTCCAGAGGAGGGTGTGCAAACTAGTTAGCGATCCGGTGA

TTCGGGCGGCGATACTCCTTAGCTTGGATGTGACAGACGGCGGTACTCCTTAGCTTAGACTTCTTGGCAATGCAACT

GTACGGGCGTACGACGGGGCCCTCGCCATGAGTATAAAAGCAGCCCTCTTCCAGCCGTTACAGGTAGACCCAGACT

TGAGCAAGCGCGCAAGACCCAGACTTGACACGCCAATACGCACAACCAAGTCATCCGGTGAACTCTAATACTGACTC

CTGTTTCCCTCGCTCTACGCGAGCCTTTGTAAAGAACCGTGTGCCCTTCTCGCTCCTCTGTCCCTCTGCCCCGGTTC

TABLE 6-continued

Sequences Corresponding to Frequency Peaks (SEQ ID NOs 21-167)

CCTTGGCCATAGCGCCCATCACAGCCCGCAGGGCTCTCTCACGGCAGCTGGACAGCCATCTGCGCACAGCCTCTCCG

TCGCCCCAACGTCTCTCTCTTACAGGCTCGCAGGAACCAAGCCAAGGCCCCGGTCGCCCCAGTGCACCCCGCCTTTC

CCTCGTCTCCCCAGCGAGCGAGTGGACTACCCACGAGCGCAGTACTCGCGGACGAACGTGTGACAGCCGTGTCCTGT

CACCTGCGCCCTGCGCCGCCTCTCCCTCTTCCCAACCTCTCCCGCAGGCGCTCCTTCTCCCTCAACGTGCCGCCCCA

CTGCAGCACGATTACGACAGCTCTCTGGCCTTCCCCAGCGAGCGAGTGAATAACACGAGTGAGCCCTCGTGTGCCTA

CGTGTGACGGCCCTGCCTGTCACTGGCTTCTCTCCCTCTTTCTCCTCTCTCCCTCTCTCTACCGCCCGCCGCAGCGT

GTCCTCCCACCTGCATCACGGCCCCTGCCTCCGTTTACGCAGACTTCCGCTGTAAGACGCATCTCGATTAACTCAAC

AACGCTTCCGCACTTATCTCTCAAAAGCTAAAACAGCCTCCAGCACACACACATACGGTATCGTGATCAGAGAGCTT

CCGCTCTACTGTCGCTTCCGCAGCCTCAGCCGAGTGACACACGCGCTCTGTCCTCACACAGACACGTGTTACAGGTT

ATACAACGATCCTTGGGCACGCCGGCATACGTAGCCTCCGCGAAAAAAATTATGTCGTGGACGCGTTCCGCGCAGGC

CCGGCGGGCTGGCTGCACACTAATACCTTGCAGCTGTGCCGAGATAGGCCTTCATCGCCGAGTTCGCCGACTTCCCC

GTCTCGCCGGCTTCACCGACGCTGGCGTTCCAGGCTCGCACGCTCAGTACTTTGCATTACATGCTATTCTTTGCAGT

GGCCTGCATGTGCGAAGCGCGAAACTGGCGCGACATAACTTTCTTCCTTCAATGCCTGCCGCGCTCGTGTTTCGCGT

GTAACCCTACCGCTGTTGCAATTCACTGCATTACATGCTATAGTGTGGCGCTGCGTGTGTGCGTGTAACGCGTGTGT

GCGAGAAGCCGTGCGAGAAGCCGGTCCAGGGTACGGTCCGGGGTACGCTGGGCGCTAAGTGGTGTAGTCCTCCGCTC

TGCTCTACGCTACGCTTCGAGGAGCTACGGCGATCCGCTCTGCTCTACGCTACGCTTCGAGGAGCTACGGCGATAAC

CGGAGGGCCCCGCTGCGGGAACTCGATGCGACCGCAAGGGCTCTTGCCCCTCCCCCTTCGGGGGAAGGGGCAAGCCA

ACCAGGGTGGCTGCCTAGCTGTGGCCGGGCTGACGCGAAGGCTGACGGGCTGCTGTAAATGGTGAGCCGAGACTGGT

ATGAAAGGCTGG

>SEQ ID NO: 161

TGAGATTTGGGCACATAGCAATGACTTTGCATGCCCCACTGCTCCCTCACCGCCTCCCAGGATACGGCATGTGACTT

TAATGGCCCTGGATACTTGCACCACTGAGGCTTCTCATTCGCCCAAGTCATACTGAATACTGCATTGTGCTATGGTG

CAGGCTGACAGATTGCACATGCATGCTGTGCATGCACATGCTGCTCATTCCCCTTGTCCCCACACTGGAGGCTGAGC

TGCCCAACCCAGAATCCAACATGCCTGCCTCGCTCAACCCTGTGCAGGACCCTTTCACATGCATGTATGCACATGTT

GCCTGACCTGTTAGCAACATAAGCTAAGTGCCGTGGTGCTAGCACCTGCAGTGCCTAATGCGGCTCTGCACATCAGG

GCAAGTGTGCACGGCTTGCCTCTTCCCTCATGGGTGAGGGTCAGCTGGTCAGGTATCATGTAGGCTGTCAAGTAATG

TGCAGCCATGCTGACGGCATTCAATGTGAGTGATGGGCTTTGGGAGTGCAAGCAGAATCAGCTGTAACAGGTTGGTG

CGTCAAGATCGGCATGCCTCCTGCCCGGTGCAGGCCTGTGGTGGCACCAAGTTGACAACCGCTTCACACCAGCGAGC

TCCAGCTTGCACCAATCATAAAACGGCAGTCGTTATATGTATACAATCGATAGCCAGGCCAAACGGCTGCGTGGCTG

GACTGCTGCACTCACTCACGTGGCCCCTGGTAGCAGGGTGCCCTAAATGGGGGTTTTAAGGGGTTTTGCACGGTTTG

AAAAGTGTGACATGTCAGAAATGATCTGCACAGTATAATTCAGCTAATAATGACTAGAATGATTGTTTGAACCCCTT

GTGGGTGACTGTGATGAGATTTGGGCACATAGCAATGACTTTGCATGCCCCACTGCTCCCTCACCGCCTCCCAGGAT

ACGGCATGTGACTTTAATGGCCCTGGATACTTGCACCACTGAGGCTTCTCATTCGCCCAAGTCATACTGAATACTGC

ATTGTGCTATGGTGCAGGCTGACAGATTGCACATGCATGCTGTGCATGCACATGCTGCTCATTCCCCTTGTCCCCAC

ACTGGAGGCTGAGCTGCCCAACCCAGAATCCAACATGCCTGCCTCGCTCAACCCTGTGCAGGACCCTTTCACATGCA

TGTATGCACATGTTGCCTGACCTGTTAGCAACATAAGCTAAGTGCCGTGGTGCTAGCACCTGCAGTGCCTAATGCGG

CTCTGCACATCAGGGCAAGTGTGCACGGCTTGCCTCTTCCCTCATGGGTGAGGGTCAGCTGGTCAGGTATCATGTAG

GCTGTCAAGTAATGTGCAGCCATGCTGACGGCATTCAATGTGAGTGATGGGCTTTGGGAGTGCAAGCAGAATCAGCT

GTAACAGGTTGGTGCGTCAAGATCGGCATGCCTCCTGCCCGGTGCAGGCCTGTGGTGGCACCAAGTTGACAACCGCT

TABLE 6-continued

Sequences Corresponding to Frequency Peaks (SEQ ID NOs 21-167)

TCACACCAGCGAGCTCCAGCTTGCACCAATCATAAAACGGCAGTCGTTATATGTATACAATCGATAGCCAGGCCAAA
CGGCTGCGTGGCTGGACTGCTGCACTCACTCACGTGGCCCCTGGTGGTGAGAGCAAACGTTTATCTTTCTATACAGG
CCACGTTTGAGGACGCTGTTAAAAGCAATAGATAAAGGATAGAACATTTAGTAGTATGCGTTGCTTATACGCTCCCG
CCAGCTCTTGTTGGTGGCGTGATCGCGGCACTTGGCGAGATCGAAGTCTCGGCGGTCATGGTCAAAGTCGCGCCAAG
GTCAAATAGACAACATTCAATAGTTGAGATTTGCAGTCATCGTGACTGAGGAAAGCCTTACAAGTTGCAGCTGTCAA
AAAGAGTCAATTCTGCAATTCGCTTGAGCCTTTCTTGCTCGCGGCTGTTTACCTTGTGACCCTGCATGCATACAAGC
ATACGTATGTTAGGATTGGCTCCGACGGCGGGGCTGGAGAGAACTCGAAGGACTGGACCAAACGAATGTCGCTGGAG
CGTCGTGCTAACTTCACTTTGCCACTGCTCCTCTGAGCCGGTAGGAGTCGGCAGGCGCACAAGCGCGATGGAGACAG
GGAGACAAGGTGGGAGACAATGAGGGGGAGGGACACAGGGAGGGACCCAGGCAGAGGCAGGGATGGAGGGTTATGTG
CACGAGCCCAATAAGTCCCACAAGTCAAGGTTGGGAGTCGTCGCCCAACCCAGAAAGAGGGAGGGAG

>SEQ ID NO: 162

CGTTTTGATAACGAGGCTCGGTCTAAACCGTGTGAATATGAAGCAGGGCTCCTATCTTAATGTCTCCAGACATTAAA
CGGCCATTTTGGCCATTTTCCAGACAAACGGAGGGGGGGGTTCACGCACGCTTTTGAACAAAACAAGCGGTGTCTGA
GGAGAGGCAAACTCTACCATAGTGACATATATATTTTGTGGAAAGTGAGGGAATGTCATGGTCTTTTAGGAGATTTT
CGGCGATCTGACGAGGATGAAGGATACCTCGATCAAATCTTCCCTTTTGCAGATGCGCAGAGCCGGTGACGAGGATT
TGCCGGGGATGCCGCATTTTCAGTCACGCAGAGTTGTCAGGGGTGCAAAGCCCGCTGCAACTCCTTCCACAGTCCAT
GGTCCAGCTAACCCGCGCACAGTGAAGAAAAGCTGAGACGATAGAGGTCAGGAATGAACAGAAGTCAGGGATGGACC
CCGTGCACGGGCGGAACCGTGGAGCTGCGGAGGGGTTGAAGAAAACAGGCAGGGACGAGGCGCGCGGGAGAGGGGGT
ATACAGCAGCCTTGACAGCAGCTTCGTATTGGAGTGCACTGAACCACTCGCACTCAGGGCGGGGCTGCTGTCAAGCT
CAACCATGCTACTCCTCCATGCGTAGGGGAATCAACAAGAACGGGACCTGGGAAAGGACCGGGGAAAGGACCGGGGA
AAGGACCGGTGAAAAGGACCAGGGAATTGACCGAGGAATGGGGAGCCATCACGGGACATTGACTAGGACACAGTGAT
ATTAAGAATTCAACATGAAACACATTACATTCTGCCGTCGGCACACAACAAATGGAGAAGTGGGGCACAAAATTATG
AGCAAACGATAATGTTTTCGTGAGTAGCTGCGGGCTACTACTGACTTATCGCAGCGCAGTGGAGATAAGTCTAGTT
ATTGCGACGTAACTGCCGTGTTGCGTTAGAGTCACGCACGGCGCAGGACGCTCGGGTACGTGCCTGTGCATGGGGCC
GAACCGAGCTGGGTCTTGTACGCGTCAGGAGCACACGGCGCCTTATCTGCCGTTGTGCTTCTGTACTGTATTTCGGA
TCGTCCCTCTGCCGGGACGGTGACCTCAGTGTGTCGCACTTAAACGTTCCCTACATTTCTGGACTTTCTTTGCAATC
CTATACCTGGTTCTAACTATACTTGACCATGTATGGACCGAATAAGCGTTTAATATATACTCAGACGGAGTTGCAGC
GTTTTGTTGCGCGATCCTGCTCAATGGAACCCCTTAGCTTGATCACGCTCGCTCTCTGATCGTAAGGGAATGCCCTT
CGAAGCTTCTCTGGCGCTTTGAACCACGCTTTGGTTCGGGGCCGCATTCGGGAGCAAATCGGAGCAGAGCGGAGCT
TTCAAGCGGAGCAAAGGCGCGCGAAGCGTTGCGGACAAGGCGTTCGGCAAGTCACTGAAAGCAAAAGGGCATGCACA
GCTGTGCGGGCGGGCTACTTGCTTGCCATGCGCGGTCCTGCTTGCCGTGCCTTCGTGTCTACCCGTCGCTTTACAGT
TCACAGCTTTGTGCAATACCTTTCCACATCTTCCATTGTGCCACCCCCACCTCCCCAAGACCCTCAGGACTTTTGGC
GCGGTACTTCTCCTGTCTGCCTATCCAGGCCGCAGGGCCCGCGTGCCCTTGGGGAAAGGGCGTGTGTGCCGTTGGGA
TCCGGCCTGTGCGCCGCAAGCAACGGGCTTTGCGCCCTTGCCTTATGGACAATGGACGGCATACGTGCCCTTATGAT
ACGGCCTGTGTGCCGCAAGCAATGGGCTCCGCGCCCTTGCTTTATGGACAATGGACGGCATACGTGCCCTTATGATA
CGGCCTGTGCGCCGCAAGCAACGGGCTCCGCGCCCTTGCTTTATGGACAATGGACGGCATACGTGCCCTTATGATAC
GGCCTGTGTGCCGCAAGCAACGGG

TABLE 6-continued

Sequences Corresponding to Frequency Peaks (SEQ ID NOs 21-167)

>SEQ ID NO: 163

CATGGACAATTTACGGCGTACGTGCCCTCATGATACAGCCTGTGCGCCGCAGGCAACGGGCTCCGCGCCCTTGCTCC
ATGGACACTTCACGGCGTACGTGCCCTCATGATACGGCCTGTGTGCCGCAGGCAACGGGCTCCGCGCCCTTGCTTCA
TGGACAATGCGCCGCGTACGTGTTCTTATGATACGGCCTGTGCGCCGCAAGCAACGGGCTCCGCACCCTTGTTTTAT
GGACAATTCACGGCATACGTGCCCGTATGATGTGACCTGTGTGCCGCAAGCAACGGCTTCGCACCCTTGCTTTTGGG
TAATAGATGGCATACGTGCCCTTATGATACGACCTGTGTGCCGCAAGCAACGGGCTCCACACTCTTGCGTTGTGGAT
TATAGACGGCATTGAAATGCTTACGTGCCTTCGTTGTACATGCCTTTGCGTTGTGGACAATGTGTGGTCTGAGCGCC
ACGTTCGGATACGGCGTGTGTGCCGCCAGCAACAGGCTTTGCGCCTCGCATCATGTGTCTTGCGATATGGCCTGTGT
GCCGCATGCAATTATGCTGCCTGCCCTGTCGTTATGGACGCTTCGACTTGTTGCGTGCCCTGCTGCGTGCCCTGTCG
CAATACGCCTTGAGTGTACCGTGCACGGCAAGCCTGCGCCTCGCTATTGCTTCGTGTTGACAACGGAGCGGGCTTAC
GTGATCATGCGTCACCCTGTACGTCTTGAGGTCCGCACGCACATCATACTATCACGCGGCACCACCCTTGTAGTTTG
GCTGACGCACCCCAAGCCAACCTATATGCATTCGATGTGTGCGCTAGGCCCAAGTGCCGAATTTGTTTTTCCGGATA
TTTCGCCCTCAGTGAGCGATGTGGAGTTTTGTGCAGTTCGGCCAGCATGCTATGCCCAGCCAATAACAATACCGCAT
GACGCATAACTATACCGCATGACGCATAAACATGCCTTCGTGCCCTGCACCAGGCATCGGACGCTGTGTCACGCAGT
GAGCCCGACCCTGCGCAACCAACATTTTGTTGCGAGATACGGTCGGAGCTGGGATTACAGCCTGCCTGGTGGGTTTG
GATGGCGCCCGTGTGTTGGGCTGGGCTGTTGCTGCTCGCGGTGGGGCCCACCACCAAGTCACGGCACCCATCCGCCC
TCCCCTCTTGTTGGCCCACCCGCCTGTACACATGCCAGTCACCCGCTCGCCATCCTGTGAAAGCGGGTAGCCGACTT
GGCAAGCGCTTTTCCTGACACTTGGCGCAGGTTTGAGTGGGATACCAGAATGGTCTGAATGTAGTTGTTGGATAACC
AGTACACTGCGGTGTGTAGCTGGTTAGCGGGAGTGCCGTGCATGAAACACGCTACTCGACCCGCCATGCCCGCGCGA
TGGTACCACCAACCGTTCAACCCAGATCCATGCCGGGTAGCATCGACCCCACAGTCAGACTGATAGCTCCTATCCA
GGTGTCAGGCGCCATGTATGTATCTGTGGACGCGTCAAGCTGGCTTGTGCCGTAGCGTTGGCCGCCTGTATGGCACG
GCATCTGTGTCACGTTATGGCCTCATGCTTACCGTAGTCACGCGGCTTGCGTGCTGTGCGGCACGCTCCCTGCCAAT
CCTTCAGGACATGTATGCATACATGTTACTTCGTCAGAGCCATAGCAGGGGCAGCGTGTTCTGTCAATGCCTCATGA
ACCCAGAGACCCAAGCCAACGTACGCATTAGTTCCGCAACGCACGTCAATGCCAACTGTATGTGTCGCCTGCCCACT
CGCGAGTGGACGCCTAGGGAACCAACCTTGGTTCCTTTCAGCCCCGGCCTTACTTCACCCGGCGGGGCAATTACTTA
TCACCGAAGTGCTAGGAGCAGTGTGCTATATGTCATTACTATTAAGAGCGTATGGCGACACAGGCTCACATGTGGGT
AGCCAGGCTTGGCAGGCATCCCAACTCAGCCCGGCCTCCTCACAGCAGTACCACGACGTGCCCGTACGTGGTCGAGT
GCGGAGTTTGGCTGCCGGCGTGGCTGTATCATCTCTCACATTGGATGACCCATCCGCCACTGCTGTTCACTACTGGC
ACGTCCCTCGAGTCGCTCACCCACCGGCTCCGCCCAGCGTTCGCTCCCTTTGGCTGGGCCGGGGCCCGTGGCGCATC
CAACCCGCCATCGCGGCCCCGAGTGCTCCTTATTTCCTCCCATCACTACGCCTTCTATCACTATAGATACATTGCGC
GTTCCACGCGTGCCGGGTATCCTTCACCCCTCCGCGCCGCTCGACCAGGCCAGCCTTGCTGGGGTTGCTGAGGTGTT
ACCCTTCATGTTGCCCTCCCTGCTATTACGGTACACCCCACAGCTGCCGTGGCGTACGGTATCGGCACGTACGGGAC
ATTGTGTGCATGCATCCCCGCGGCGTTTGGAGGCAAACATTCACGTGCGCGCCTGTCCTGCGTCCGCCGGGGTGATG
CTATCTATGGGTGTACCTACTGCTTGATTGGTAGTGACTCTTATGCAAGACACTGCAAATCTCAAGCATGGCACCTA
GCTAGCAAGAAAGAAATTAGTGTTCGTGGCCATGCTGCACGGCTGGGCATGGCTGCCCGCATCCTACACCACGACGG
CGCGGGTGAACGAAGGGCAGGTTGCCGCGCGTGACTCGCGTACGTAAAACCGCTCTAGTGTTGCAACTCGCGCCTTC
TCCTGCGTGGCGCATGTTGGCTAGCCTGTCCCAGCTTCGAGTCACGACGTTGTTATTATTCCCAAGGTTGTTCCGAG
CAGCCTACAACGTCAACACGTGTTATGGCATGGCCCTGGGGGCCGGTAGAGAGTACCGAGGTCTCCAGTGGTTCGTG
CCAACACGTGCCAACACGCACTGTTACCTTTCCTGGGCACACGGACGGCCACAGCTGCCCACAAGCCACACACCTGA

TABLE 6-continued

Sequences Corresponding to Frequency Peaks (SEQ ID NOs 21-167)

ACAAGGATGCATGTGTTTCCCTGTAACGCCCCGGCGTCGTCTGCATGGCTGGCGCACGCGGGATAACGCATGTGTGT
TTCTGTCGTGGCCATTGGTGCACCTGATACGTTTGTGAGTCTGGTATCATGGCCCTTGCAAAGCCAGTCGTGTTCCT
ATTGCTGCTTGTCTTCTGGTAGTGACCATTGGCCGCCCATGACCGACGGAGTGTGGCGCTGTCAGGCCCCGCGTTGG
CGTCGCCCTGCGCCTGCAGCAGGTGCCGGCGGCGCCTCCGGCGGCGCTCATCCCCGCGTGATGGTGCTGCTCGTGCA
GCCAATATCCCCAAGCACGAAGCTCGTTCTATTGACCGCTGTTGAGTGTGCAACTAGGACCGTACGTTCGTGCGCAA
GCTAGGCGATGGGCGGAGCGCTCCGCGGTGTTCGAGACACATGATTTCGGTAGCGCAAGGGCACGAACGCCACCGCC
ATCACCGCCGACCGCACCTTGGTTTGCATGACCGGCCGTTGGGCCAAGCGCTTTGCGAGAAGAGCTGCATACGCGAA
GCCAATCAAGCCCAGCCACCAGGGCTGCCGTCGCCCGCACCATGACCTCCCGGCGTTGAGGACTACTACCAAACTCT
GGCAGCACTTTCGGCCACTAGTGCAACCTCAACACGGGCGGGCTGGGGCGGGCACGGCGGACTTGGTGGGGTTATCG
GGAGCTGCGAGGCCGGAGGTAGGAGGCCGCTGAGGGCCACGAATGAGTTGCTAGGCCGCTTGAGGCATGAGTGGAGG
CTATTGTCGGTTTGAGAGATTGGGATTGTCGTTTGGGGCCGTGGCGGTTTGTAACGCTACACGGCAGTAAGGAGTCA
ATAAGCGCTGACTTATCGCAGCGCAGTGGAGATAAGTCTAGTTATTGCGACGTAACTGCCGTGTTGCGTTAGAGTCA
CGCACGGCGCAGGACGCTCGGGTACGTGCCTGTGCATGGGGCCGAACCGAGCTGGGTCTTGTACGCGTCAGGAGCAC
ACGGCGCCTTATCTGCCGTTGTGCTTCTGTACTGTATTTCGGATCGTCCCTCTGCCGGGACGGTGACAACCCACCCG
CCCCCCCTGGTGCCGCCGCGGATTAATGTGGTGGCACCCGTGGGCGCTGCGGCGTGCGTGGTTGTCTGGACTCTGCT
GCTATCAGGCACTTCATACATGCGACACACCCAGTACTGGCAGCACTTTCGGCCACTAGTGCAACCTCAACACGGGC
GGGCTGGGGCGGGCACGGCGGACTTGGTGGGGTTATCGGGAGCTGCGAGGCCGGAGGTAGGAGGCCGCTGAGGGCCA
CGAATGAGTTGCTAGGCCGCTTGAGGCATGAGTGGAGGCTATTGTCGGTTTGAGAGATTGGGATTGTCGTTTGGGGC
CGTGGCGGTTTGTAACGCTACACGGCAGTAAGGAGTCAATAAGA

>SEQ ID NO: 164

ATTCTATTCACACCATATGTTAGTGATGGGCTTTGGGAGGAGTGCAAGCAGAAGCAGCCACAGCACATTGGCATGTC
CAGACCCGAATGCCTGGTGCGCCTGCCGACCACACCTGTGGCGCCAAGTCGGCAACCGCTCCACTCCAGCAAGCTCC
AGCTCATGCCAAACATACAATGGCAGCCGCTATATGTATATAAGCAATAGCTGTGCCAAACGGCTGCGTGGCTGGAC
TGCTGCACTCACTCACGTGGCCCCTGGCGCAGGGTGGCCTAAATCAGGGTTTCAAGGGGTTTTGCAGGGTTTGGAAA
GAGTGACATGTCAGTAATGATCTGCATAGCATAATGCAGCTTATTATAACTAGAATGATTGTTTGAAACCCTTGCGG
GTGACCATGATGAGGTTTGGGCACATAGCAATGACTTTGTGTGCTTCCTTGTCACAGCCTTGAGAGCACAAGCACGT
GGGAAGGGATGCAACTTCCAAAGCCCTGCATACTCGCACCACTGCGGAATGCCATTTGCTCAGATCCAGCTGTATAC
TGTGTTGTGCTGTGTTGCAGGCTTACAGATTGCACAGATGCAAGCCTATGCCGCTCATTCCCCTTGGCCCCACACCG
GGGCCCGTGTTGCCCAATCCAGGCTGCCTGCCTCGCTCACCCATGTGCAAGACTCTTCCAGATTCATGTATGCACAT
GTTGCCTGACCTGTTTGTAATGTAACCACCAGCTAAGCGCAGTGGTGCCAGCACTTGCAGCGCCCCATATGGCTCTG
CACATCACAACAAGTGCCCCTGGCTTGCCTCCCCTCTCCCAGGGGTCAGGTATCATGCAGGCTGTCAAGTTATGTGC
TGCCATGCTAAGGACATTCTATTCACACCATATGTTAGTGATGGGCTTTGGGAGGAGTGCAAGCAGAAGCAGCCACA
GCACATTGGCATGTCCAGACCCGAATGCCTGGTGCGCCTGCCGACCACACCTGTGGCGCCAAGTCGGCAACCGCTCC
ACTCCAGCAAGCTCCAGCTCATGCCAAACATACAACGGCAGCCGCTATATGTATATAAGCAATAGCTGTGCCAAACG
GCTGCGTGGCTGGACTGCTGCACTCACTCACGTGGCCCCTGGCGCAGGGTGGCCTAAATCAGGGTTTCAAGGGGTTT
TGCAGGGTTTGGAAAGAGTGACATGTCAGTAATGATCTGCATAGCATAATGCAGCTTATTATAACTAGAATGATTGT
TTGAAACCCTTGCGGGTGACCATGATGAGGTTTGGGCACATAGCAATGACTTTGTGTGCTTCCTTGTCACAGCCTTG
AGAGCACAAGCACGTGGGAAGGGATGCAACTTCCAAAGCCCTGCATACTCGCACCACTGCGGAATGCCATTTGCTCA
GATCCAGCTGTATACTGTGTTGTGCTGTGTTGCAGGCTTACAGATTGCACAGATGCAAGCCTATGCCGCTCATTCCC

TABLE 6-continued

Sequences Corresponding to Frequency Peaks (SEQ ID NOs 21-167)

```
CTTGGCCCCACACCGGGGCCCGTGTTGCCCAATCCAGGCTGCCTGCCTCGCTCACCCATGTGCAAGACTCTTCCAGA

TTCATGTATGCACATGTTGCCTGACCTGTTTGTAATGTAACCACCAGCTAAGCGCAGTGGTGCCAGCACTTGCAGCG

CCCCATATGGCTCTGCACATCACAACAAGTGCCCCTGGCTTGCCTCCCCTCTCCCAGGGGTCAGGTATCATGCAGGC

TGTCAAGTTATGTGCTGCCATGCTAAGGACATTCTATTCACACCATATGTTAGTGATGGGCTTTGGGAGGAGTGCAA

GCAGAAGCAGCCACAGCACATTGGCATGTCCAGACCCGAATGCCTGGTGCGCCTGCCGACCACACCTGTGGCGCCAA

GTCGGCAACCGCTCCACTCCAGCAAGCTCCAGCTCATGCCAAACATACAACGGCAGCCGCTATATGTATATAAGCAA

TAGCTGTGCCCAACGGCTGCGTGGCTGGACTGCTGCACTCACTCACGTGGCCCCTGGCGCAGGGTGGCCTAAATCAG

GGTTTCAAGGGGTTTTGCAGGGTTTGGAAAGAGTGACATGTCAGTAATGATCTGCATAGCATAATGCAGCTTATTAT

AACTATAATGATTGTTTGAAACCCTTGCGGGTGACCATGATGAGGTTTGGGCACATAGCAATGACTTTGTGTGCTTC

CTTGTCACAGCCTTGAGAGCACAAGCACGTGGGAAGGGATGCAACTTCCAAAGCCCTGCATACTCGCACCACTGCGG

AATGCCATTTGCTCAGATCCAGCTGTATACTGTGTTGTGCTGTGTTGCAGGCTTACAGATTGCACAGATGCAAGCCT

ATGCCGCTCATTCCCCTTGGCCCCACACCGGGGCCCGTGTTGCCCAATCCAGGCTGCCTGCCTCGCTCACCCATGTG

CAAGACTCTTCCAGATTCATGTATGCACATGTTGCCTGACCTGTTTGTAATGTAACCACCAGCTAAGCGCAGTGGTG

CCAGCACTTGCAGCGCCCCATATGGCTCTGCACATCACAACAAGTGCCCCTGGCTTGCCTCCCCTCTCCCAGGGGTC

AGGTATCATGCAGGCTGTCAAGTTATGTGCTGCCATGCTAAGGACATTCTATTCACACCATATGTTAGTGATGGGCT

TTGGGAGGAGTGCAAGCAGAAGCAGCCACAGCACATTGGCATGTCCAGACCCGAATGCCTGGTGCGCCTGCCGACCA

CACCTGTGGCGCCAAGTCGGCAACCGCTCCACTCCAGCAAGCTCCAGCTCATGCCAAACATACAACGGCAGCCGCTA

TATGTATATAAGCAATAGCTGTGCCCAAACGGCTGCGTGGCTGGACTGCTGCACTCACTCACGTGGCCCCTGGCGCAG

GGTGGCCTAAATCAGGGTTTCAAGGGGTTTTGCAGGGTTTGGAAAGAGTGACATGTCAGTAATGATCTGCATAGCAT

AATGCAGCTTATTATAACTAGAATGATTGTTTGAAACCCTTGCGGGTGACCATGATGAGGTTTGGGCACATAGCAAT

GACTTTGTGTGCTTCCTTGTCACAGCCTTGAGAGCACAAGCACGTGGGAAGGGATGCAACTTCCAAAGCCCTGCATA

CTCGCACCACTGCGGAATGCCATTTGCTCAGATCCAGCTGTATACTGTGTTGTGCTGTGTTGCAGGCTTACAGATTG

CACAGATGCAAGCCTATGCCGCTCATTCCCCTTGGCCCCACACCGGGGCCCGTGTTGCCCAATCCAGGCTGCCTGCC

TCGCTCACCCATGTGCAAGACTCTTCCAGATTCATGTATGCACATGTTGCCTGACCTGTTTGTAATGTAACCACCAG

CTAAGCGCAGTGGTGCCAGCACTTGCAGCGCCCCATATGGCTCTGCACATCACAACAAGTGCCCCTGGCTTGCCTCC

CCTCTCCCAGGGGTCAGGTATCATGCAGGCTGTCAAGTTATGTGCTGCCATGCTAAGGACATTCTATTCACACCATA

TGTTAGTGATGGGCTTTGGGAGGAGTGCAAGCAGAAGCAGCCACAGCACATTGGCATGTCCAGACCCGAATGCCTGG

TGCGCCTGCCGACCACACCTGTGGCGCCAAGTCGGCAACCGCTCCACTCCAGCAAGCTCCAGCTCATGCCAAACATA

CAACGGCAGCCGCTATATGTATATAAGCAATAGCTGTGCCCAACGGCTGCGTGGCTGGACTGCTGCACTCACTCACG

TGGCCCCTGGCGCAGGGTGGCCTAAATCAGGGTTTCAAGGGGTTTTGCAGGGTTTGGAAAGAGTGACATGTCAGTAA

TGATCTGCATAGCATAATGCAGCTTATTATAACTATAATGATTGTTTGAAACCCTTGCGGGTGACCATGATGAGGTT

TGGGCACATAGCAATGACTTTGTGTGCTTCCTTGTCACAGCCTTGAGAGCACAAGCACGTGGGAAGGGATGCAACTT

CCAAAGCCCTGCATACTCGCACCACTGCGGAATGCCATTTGCTCAGATCCAGCTGTATACTGTGTTGTGCTGTGTTG

CAGGCTTACAGATTGCACAGATGCAAGCCTATGCCGCTCATTCCCCTTGGCCCCACACCGGGGCCCGTGTTGCCCAA

TCCAGGCTGCCTGCCTCGCTCACCCATGTGCAAGACTCTTCCAGATTCATGTATGCACATGTTGCCTGACCTGTTTG

TAATGTAACCACCAGCTAAGCGCAGTGGTGCCAGCACTTGCAGCGCCCCATATGGCTCTGCACATCACAACAAGTGC

CCCTGGCTTGCCTCCCCTCTCCCAGGGGTCAGGTATCATGCAGGCTGTCAAGTTATGTGCTGCCATGCTAAGGACAT

TCTATTCACACCATATGTTAGTGATGGGCTTTGGGAGGAGTGCAAGCAGAAGCAGCCACAGCACATTGGCATGTCCA

GACCCGAATGCCTGGTGCGCCTGCCGACCACACCTGTGGCGCCAAGTCGGCAACCGCTCCACTCCAGCAAGCTCCAG
```

TABLE 6-continued

Sequences Corresponding to Frequency Peaks (SEQ ID NOs 21-167)

CTCATGCCAAACATACAATGGCAGCCGCTATATGTATATAAGCAATAGCTGTGCCAAACGGCTGCGTGGCTGGACTG

CTGCACTCACTCACGTGGCCCCTGGCGCAGGGTGGCCTAAATCAGGGTTTCAAGGGGTTTTGCAGGGTTTGGAAAGA

GTGACATGTCAGTAATGATCTGCATAGCATAATGCAGCTTATTATAACTAGAATGATTGTTTGAAACCCTTGCGGGT

GACCATGATGAGGTTTGGGCACATAGCAATGACTTTGTGTGCTTCCTTGTCACAGCCTTGAGAGCACAAGCACGTGG

GAAGGGATGCAACTTCCAAAGCCCTGCATACTCGCACCACTGCGGAATGCCATTTGCTCAGATCCAGCTGTATACTG

TGTTGTGCTGTGTTGCAGGCTTACAGATTGCACAGATGCAAGCCTATGCCGCTCATTCCCCTTGGCCCCACACCGGG

GCCCGTGTTGCCCAATCCAGGCTGCCTGCCTCGCTCACCCATGTGCAAGACTCTTCCAGATTCATGGAATCTGAAAT

GTTTGCCCGCGGTGCGGGCAAACATTTCTTTTCCTATCCAGGGCGTCTTACAGGGCGCTGTGCAATGCAATAGATAA

AAGATAAAGGTTAGTAGTATATGTTGTTTACACGCTCCCGCCAGCTGTTGTTGGTGGTGTGATCGCCGCACTCGGCG

AGGTCGCTGACCAGCTCGCCGAGGCGAAGGGCTTCGGCGGTCATGGTCAAGGTCGCGCCAAGGTCCAATGGACAACA

TTCAATAGTCGAGACCTGCAGTATAAACTATAAACACATCTTGACTGAGGAAAACCTTAGTTGCAGCTGGTCAAAAG

AGTCAAATTCTACAATTCGCTTGAGCCTTTCGCGCTTGCGGCTGTTTGCCTTGTAAACCTGCATGCATACAAGCATA

CTAATGTTAGGACTGGCTCCGACGGCGGGACTGGAGAGAACTCGAGGGACTGGACCAAATGATTGTCGCTGGAGCGT

CCTGCAAACTTCACTTTGCCACTGCTGCCCTGAGTCGGTAGGTGCACAAGCGTGATGGAGACAGG

>SEQ ID NO: 165

TCCTGCTCGTGCGTGCGGGGGGGTTTAGCAGCCAGGGAGCCTTACATGATCATGCTGTTGACTTCGGCCGCTGCCAT

CACGGTCCATTTACAGGACTCTACGCCAGGCGTGCTCGGCACCAGCACCACGTCCTTCTTTGCGACTGCTGGCACGT

TTGGTCCGCCTCACCGCGATCGAGTCGAGCGCAACCTCAATGGTGTGCGCTTCATTTTCCTAGATGAGTTTAGCACG

TGTGGGCTGTCCCACTGGGCGCGCATTTGCATGCATGTGCACGCGGCACGGAGGCACGTGGGTATAGACAGCACGCA

CCTATATCACGGGCCGCTGTCAGATCTGCATGGCCTGCTTGTTGGCGACTTGCGTCAGTTGCCACAGCCACGGCACG

TGCCGCTATATAGCGGTGCTGCGGAGGAGAGCTTGCGGCGGCTGCTGGCGCCGGGCGCGGGGACGGTGGGGCCATG

GAGCGCCAGATCCGGCAGCTGGAGCATCCGGAGGGCAGCATGAACCTCATGGGGCGGGAGCTGTGGAATATGGTGCC

GTTCGCGTTCGTTCTCACTCACCAGCATCGGCAGCAAGCAGGCGTAGGTGACAACAACGAACCTCTCTTCATGCTAG

CGGAGAAGTTTGGTGGCGTGCAGGAAATCTCTCAGGCAGATCTGGACACAGCGTGCGAGCAGCTCAACGCGCGTGTT

TGGCGGCCCCCGAAGCCAGGGATTGACCCCGTGCCCCAGCCCTTTGCAGTTGTCCAGCGCCATGTCGTGCGGGTTCC

ACTGGCATTGCAGCTCGTGCAGCTGCATGCGCTCGCGCAGCGTCAGCAGCTGCTGCTGTGGCGTAGCGCGGACTTGT

CGCCTGACGGGAGCAGCTTACCTATTTCGCATGTGCATCAATTAGAGGCGCTTGGCGGGGCCGACGATGATAGCGGT

GTGCCCGCTGTGTGCGCATTCTTTGCTGGCATTCGTTACGTGTTTACATCAAATGAGCATGTGCGTCTGTATCACAT

CAACAACAACAGTGCCACAGGCACCGGCATTGTTCTGCATCTCAACGAGCCACCATTGCCAGATGCAAGCATTGCCC

CCGTGCATGTCCTCAAGTTCGTGCCCTCGGCTGTAATGGTGCGCCCTGACGGGCCTGATGCGGGTCGGGTGTCTGTC

GATCAGGCCCTGGATGTCGGGGAGATTCCTGTTTTACCGTGCAGTGCTATGTTCACATCGCAGCATGCAGCCCTGCG

GTTGCCTGTGATGCGCTGGGGCTTTCGTGTGGAGCTTGCATATGCAGTCACCGATTACTTTGCGCAGGGGCAAACTC

TGCCACCGCACGAACTGTGGCTGGTGGATATGTGCAAACCGCAGCACGGCAGTTGGCGGCGGGCTTCAATTTACGTA

ATGCTCACCAGGTTTCGTGGGTTGCATGCGTTACATTTAGTGCGCCCGCTGTGGGCCTCGCGGGCCGAAGAGCGCCG

GCTTAAAAAGGCGCTGCGTACCATGCTAACGCCCGAGGCAGATCTAGCTGCTGAATGGCAGCGGCTATTGAGGCTCT

CGCAGAGCACAGCAGTAGCGGTGCCAGGTATGATTGTGCGCATTCAGGCTAGCATGGCTGCCTCATAACCAAGGCCT

TCAATGCATGCATGGTTGCAACATCTGGCATGTGGCGGTAAACACTGGGTTGTCCTGCGTCCCGGCCAGCAAGGATA

GCGTAGTGTTTTTAACATGCGCGAGGTGTACTGACAGATGACCTGGAAGCGTGGAGTACCTTGTGGGTGGTGAGTGC

TGACTGCAATTTACAGCAGTGACTTTCTTGTTGGTGTTTGGTGTGGTGACCATCATGCTTGGCTTCGCTGGCTGGAC

TABLE 6-continued

Sequences Corresponding to Frequency Peaks (SEQ ID NOs 21-167)

GTATGTCACTGAGCTGTTTGACAGACAGGCGTAGGGCAACGTGTACGTTCGGGTTTAGTTTCTACCTGTCCTGTCTC

TGCGTGAAGCCGGGGTATTGTTTATCTGCTTGCTTGTCGTGCTTTGGATTGTTGCGTGTTTACAACAGGTTGATGTG

TGGCCTGGTTAATCCCTTGCACTTTGATGAGGTTATTGTTAGCCAGCGGGTGTTCGCACACGCGGGTACCACCAGGC

GGCTGGATGGGGTGTACGGGAGCCCCTTCTTCCGCGGGCCTTTTCACTATTAGCAATAACTCGTACAAGGATGCTGA

CCCGACCTATCCGCTATTGCCCGTGGTGAAAACTGGGCTGCCGTCCGGGGGGTGCGTTTTCCCAGCCAAACCCGCAC

GTTGGACGTTGCCCCGGGGCAAATCCTACCGCACGGATTAGACAACGCCTTTCTGTAGGTACATAACCAACATCATC

ATCAGCCAGAAGTGGTCGGCAAAGGTCCAAATTATGCTTATCAGGGCTCAAGTCGCGAAATTGACCGAAGCCCATAC

CTCGCATATGCGCTGTTTGGGGCCTGAATCTATTGCCGTCGACATTAATTCTCGTATAGATGTAATCAAAATAGCTT

CAGGCTAAGTTGGCGGGGTCCTGGCGAGCGCGACATATAGCATTTCAACTTGAGCTCTCGCTCAAAATTATGCCCGA

GCACCATCCAGGGACCTTATTATGTGTAATGGGATGTCAATTCATGATCGGGGCGACAGTCTGGGCATAGACCTGGC

GATCCCGCCCTTGACTCCCGGAGTGGTACCCGCGTGCCGACAGATGGATCGCGGGATTTGTTTTGGCATTTACCGC

TTGGATTCTATTCGCAACGTAGCTCGGAATACACGCTTAATATGCATAGTCAGAAGACTTTGGGGACGCAAATCGCT

TGGAAATGGAGGAGGGTCTCAATATGCTCGGCTCGCGATGTCGCGCTCCTGAGCTTGTATTATGCACTGCGCGCAAT

ACGCGTTCAGCATGCATATTCTTACGAACAACTAGGGACTTGAGTGATGCGGTGTGAAAATCAGTCGGTGTCTCGAC

ATGCTTGGCTCGCCATTTCGCGCTCACGAGCTCGTTGTGTGTGTTCCGAACATTGCACGCTCAAAATACATGTTCAA

TATGTCCGTCGCGATGTTGGAGCTTCAAAACCGACAAGCATGGTGTATAGATACACCTGGTAGCCTGAATTCCTGTT

TTTTCGCAATGTCGGTGCATTTTGTTGATGTTGCATCATGTCGTGCTTCATCGCATTCTTGATTTCTGCACCGGCGT

GGTCTTGTTTGTAAAATTCCGCGGTGCCCTGATCTTATTTTGTTCTTCGTTGTGATCGTGTGTCAAAAATTTGTTTT

TGGCGGGATTCGAACCTGTGAGCACTACGCTAAGCGCCATAATCAGACCCTCCAGAGGAGGGTGTGCAAACTAGCGA

CCCGGTGATACCGTGGCAAGGGAGCCATAAAAACACCTAGTAAGGGAGGCAGCAGACAGTCACTAGTTGTAGGCGGG

GGCTCCACCAGACAACCCAACACAGTGCGAGAAGATGAACCATGCACACTGGCTTGCGAGGTACCACTAGGTTCAAC

GCATCCATCGTCATTCAACCTG

>SEQ ID NO: 166

GACATGTCCCCCTCCATCCTACCTCCCCCCCTCGCTGTCAATTCGCCTGCACAAGCCTCCAAAGGCTACACATGCCT

TGTACAGACACATGAACGTGCCGTGCAGGCTGGTAGACATGCCCGCCTCTACCACCCCTCCCCCCCTCGCTGTCAAT

TCGCCTGCACAAGCCTCCAAAGGCTACCCAGGCCCTGTACAGACACACGAACGTGCCGTGCAGGCTGGTAGACATGC

CCGCCTCCACCCCCCTCCCCCCTCGCTGTTACTTTGCCCTCACAAGCCTCCAAAGGCTACCCATGCCTTGTACAGA

CACATAAACGTGCCGTGCAGGCTGGTAGACATGCCCGCCTCTATCACCCCTCCCCCCCTCGCTGTCAATTCGCCTGC

ACAAGCCTCCAAAGGCTACCCATGCCTAGTACAGACACATGAACGTGCCGTGCAGGCTGGTAGACATGCCCGCCTCT

ACCCCCCCTCCCCCCCTCACTGT

>SEQ ID NO: 167

GGCAGGCGCGCGAATGAAAACCCACATGTGCCCAACTGCCGCCGCATCGGCCCACTTTAGTTCCACAAACGCCCA

CCGACTGCTGCATGCATCATGAGTGTGTTGCAGCTACCTCGCCAGCGCCGGGTCCGATGCGATGCACTGCGCTTGTG

TTTATTGGTTCGACTGCAAATGAACAGCGGCAGACATGCGCCAGGGAAAAGCCAAATGTGCGCAACTACTGCTGCCG

GCCAACTAACTGCCCAAACGCCAAGTGTGCTGCAGTTACTCGGCCAGCTCCTATGCGGTGCACTGCGTGTGCGCGTT

TGTGTTTTGTTTATGCCGGTGTCTGACTGCTAGCATATCACTACATGTGTTTATACTCGCATGTATACTTGCTGCAC

CATCGATCACTAGCCGCGTGTCGTTGCAAAACCGGCCGCAAACCGCTCAGGGCAGCGGCCGCCTTGCCCCGCCCGCT

GCCCCGCCACGCTAGGCTGCCATGGCCGGTCCAGCTGGGCTGCGCCTGCAGCATCGCAACCAAATTGCTTTGGAGTG

CGAGTGCGAGTGGAAGGCGTGTGCCAGTACAACGCCCCAACTGCTGCCGCCTGACTGCCCAACTGCCAAGTGTGCTT

TABLE 6-continued

Sequences Corresponding to Frequency Peaks (SEQ ID NOs 21-167)

CAGTTGCTCCGCCAGCTCCTATGCGATACACTGCATTTGTTTGCACTGTTCTTATGTCGGTGCTTAAATTGTAAAT

CATGAAAAACATTGCAGTAATATGCGGCTGCCTCGTGCACCATGTGCGCTGTCATGTGCAAGTGTGGTTGTGCAGTG

GGCTCAACAGCCAAGCAGAACCAGCAATTACACGCCCTCGCTCCCACTTTCCAACACGGGTGCCCACTCTATGCACA

AGCCAGCACGAATGCATGATGCTATCATTTCTGAGCAGTAAGCGCCACAGCTTAGTGCACCTGGCTCCAGTGCAACC

CCTCGCAGCGCAACAGAGGCGCAACCTTTTAGCTGCATCCAAGCAAGCAATCTGCGCTCCGCGCATGCCGTAAACTG

TGCCACACAGCACGTGCGGGTGGAGTCAGTTCATGTCCGTGCAACAATTGTGTGCAACCATCCCAGCAATGCAGTTC

CAGCCGGCGTCCTCGCCTTCCTCCCATCCAAACGTTCCGTTAGCCGGTGCATGTATTACGGTAGGCTCCCTTCTCAC

CCATACCCTAGCCACCATTTCCCACCGGGGGCTCCGGGGGCGCCCCCCTGTCAAAGAGAAGCGACGGGCCGCGAGGG

GGGCGGGTAATAATCCCTACCCGCCACACCCACCCCCATCATCATCACAGATCCTTTGCGCTGCATACCAGGGGGGT

CGACAGGGGGGCGCCGCCCCCCTGTCCATTTCCGGGGGGTGCAGGGGGGCTGGCCCCCCTGCGGGGGAAAAATGAGA

TGCTTCCATAGTTGCTCCCTTCTCCTCCTTCTCCCCCGCCTGTCATCCCACTGCCTCCCCTTGGGGGCGCGCGGGGG

CATGTGGATCTAAGGGCCTCATTATCATTATTATCGTTATTAATTATATTATTATTATTATTATTATTATTATTATT

ATTATTATTATTATTATTATTATTATTATTATTATTATTATTATTATTATTATTATTATTATTATTATTATTATTAT

TATTATTATTATTATTATTATTATTATTATTCCTATATCATAAGAAGAATAATAATAGAAACCGGACTTAG

CCGCGCGGGCGATCCTCCGAGGGTGGGGGGGGGGCCGGGGCCCCGGGCGTGAGGGACCCAGCTTTGTTGTGAGGAGC

GTCGCGCGTGCTCGCGACATAGCTGGGGCCGCATACGGGAGTGCGCTCCGTGGCGTTTGTGTCGGAGCCGCGGCCAT

TTGCTGTCCGGGCAGCCGCGAGGGACCCAGTTGTGTAAATACAGCGCACAGAATTCGGCCCCCCACTTAAGAACGCC

GCGTCGCCGAGTTGAGTATCGGGTTTGCGCGAGCACCGGTGTGTGGCCGCGTGGCCCCATAAAAGGGACCCAGAATT

ATGAATAGCAATTAATAGGCAGCATGCGCCTCAGGCACCGGCAAGGTGGCGCTGCGAGGTCGGTCGGCAACGTCCAA

CTACGGGCCGGTCGTGTCCCCAGCCCAGTACCATTCCTATAGCATCTACTACAACAT

Sequences of high sequence-coverage peaks, including sequences occurring within high sequence coverage peaks, can be assayed for centromere function using any assay for centromere function, such as any of those described in the present application. Sequences capable of de novo centromere formation can be used in artificial chromosomes constructs. Repeat sequences, including stretches of di- or tri-nucleotide repeats, other common sequence motifs, A/T-rich or G/C-rich sequences, or repeats or combinations of sequences that are found to occur within the sequences identified as high sequence-coverage peaks, may be contributors to centromere function and de novo centromere formation activity associated with any of the listed sequences. They can be used in any combination for the synthesis of artificial chromosomes, such as artificial chromosomes for use in algal species such as *Chlamydomonas reinhardtii*.

The sequences of Table 6 were analyzed by Tandem Repeat Finder available at (tandem.bu.edu/trf/trf.html). Tandem repeats of 184 bp (SEQ ID NO:168, SEQ ID NO:169, SEQ ID NO:170) and 112 bp and 111 bp (SEQ ID NO:171, SEQ ID NO:172, SEQ ID NO:173, SEQ ID NO:174, SEQ ID NO:175, or SEQ ID NO:176) were found to be present in multiple copies and in multiple loci within the peak coverage regions.

TABLE 7

184 base pair motifs

SEQ ID NO: 168
CCTGGACAAGGCGGGTGGGGTCCACACCGCCCAGCCATCACCACACACCC
CACCTGCCACACCCACCCTTGTGCACTGTTGTTTCACATTTTCATATGTG
CATGTTGCCTGACCTATTTGCAATGCAGACACGAGCAGGGAGCCATGTTG
CCAGCCCTCACAGTGCCTTCAGTGCCCCTGCACG

SEQ ID NO: 169
CCTGGACAAGGCGGGTGGGGTCCACACCGCCCAGCCATCACCAGACACCC
CACCTGCCACACCCACCCTTGTGCACTGTTGTTTCACATTTTCATATGTG
CATGTTGCCTGACCTATTTGCAATGCAGACACGAGCAGGGAGCCATGTTG
CCAGCCCTCACAGTGCCTTCAGTGCCCCTGCACG

SEQ ID NO: 170
CCTGGACAAGGCGGGTGGGGTCCACACAGCCCAGCCATCACCAGACACCC
CACCTGCCACACCCACCCTTGTGCACTGTTGTTTCACATTTTCATATGTG
CATGTTGCCTGACCTATTTGCAATGCAGACACGAGCAGGGAGCCATGTTG
CCAGCCCTCACAGTGCCTTCAGTGCCCCTGCACG

TABLE 8

112 and 111 base pair motifs

SEQ ID NO: 171
ACGTGCCGTGCAGGCTGGTAGACATGCCCGCCTCTACCACCCCTCCCCCC
CTCGCTGTCAATTCGCCTGCACAAGCCTCCAAAGGCTACCCATGCCCTGT
ACAGACACATGA

TABLE 8-continued

112 and 111 base pair motifs

SEQ ID NO: 172
ACGTGCCGTGCAGGCTGGTAGACATGCCCCCCTCCATCCCCCCCTCCCCC
CCTCACTGTCAATTCGCCTGCACAAGCCTCCAAAGGCTACCATGCCTTGT
ACAGACACATGA

SEQ ID NO: 173
ACGTGCCGTGCAGGCTGGTAGACATGCCCCCCTCCATCCCCCCTCCCCCC
CTCACTGTCAATTCGCCTACACAAGCCCCAAAGGCTACACATGCCTTGT
ACAGACACACGA

SEQ ID NO: 174
ACGTGCCGTGCAGGCTGGTAGACATGCCCGCCTCCATCCCCCCTCCCCCC
TCGCTGTCAATTCGCCTGCACAAGCCTCCAAAGGCTACACATGCCTTGTA
CAGACACATGA

SEQ ID NO: 175
ACGTGCCGTGCAGGCTGGTAGACATGCCCCCTCCATCCCCCCTACCCCCC
TCGCTGTCAATTCGCCTAGCACAAGCCTCCAAAGGCTACCCATGCCTTGT
ACAGACACACG

SEQ ID NO: 176
ACGTGCCGTGCAGGCTGGTAGACATGCCCCCCTCCATCCCCCCTCCCCCC
CTCACTGTCAATTCGCCTGCACAAGCCCCAAAGGCTACCATGCCTTGTA
CAGACACATGA

Also found within the identified sequences of Table 6 were 13 di- and tri-nucleotide repeats, as provided in Table 9.

TABLE 9

Dinucleotide and Trinucleotide Repeats

| Sequence | Length | Copy no | Loci | Copy/locus | Max copy |
|---|---|---|---|---|---|
| GA/TC | 2 | 427.5 | 6 | 71 | 85 |
| AT/TA | 2 | 145 | 2 | 73 | 96 |
| CT/AG | 2 | 56 | 1 | 56 | 56 |
| CA/TG | 2 | 32 | 2 | 16 | 18.5 |
| GT/AC | 2 | 17 | 1 | 17 | 17 |
| AAT/ATT | 3 | 664 | 14 | 47 | 67 |
| TAT/ATA | 3 | 301.3 | 8 | 38 | 66 |
| TAA/TTA | 3 | 185.3 | 3 | 62 | 89 |
| CAA/TTG | 3 | 89.7 | 1 | 90 | 89 |
| CCA/TGG | 3 | 71.3 | 2 | 36 | 37 |
| GCT/AGC | 3 | 42.7 | 4 | 11 | 13 |
| AGG/CCT | 3 | 31.3 | 3 | 10 | 14 |
| CTG/CAG | 3 | 16.7 | 1 | 16.7 | 16.7 |

All publications and patent applications mentioned in this specification are herein incorporated by reference to the same extent as if each individual publication or patent application was specifically and individually indicated to be incorporated by reference.

---

What is claimed is:

1. A method of identifying a centromere sequence, comprising:
   (a) immunoprecipitating protein-DNA complexes from fragmented chromatin derived from at least one cell using an antibody to a centromere-associated protein, wherein the antibody is raised against and binds to SEQ ID NO: 1 or 2;
   (b) determining nucleic acid sequences of individual nucleic acid molecules of a population of nucleic acid molecules isolated from the protein-DNA complexes;
   (c) mapping the determined sequences of said individual nucleic acid molecules onto a reference genome of said cell, and calculating
      (i) a sequence coverage score across the reference genome by counting the number of determined sequences that map to a nucleotide in the reference sequence; and
      (ii) a baseline frequency of occurrence in said population of nucleic acid molecules by mapping the sequences onto the reference genome and computing the average sequence coverage, excluding peaks of nucleotide sequences occurring at a frequency at least 2-fold above the average sequence coverage score; and
   (d) identifying a nucleic acid sequence corresponding to a high sequence-coverage peak on the reference genome of at least 2-fold above the baseline frequency of occurrence as a centromere sequence.

2. The method of claim 1, wherein determining nucleic acid sequences of individual nucleic acid molecules is performed using a machine that isolates single nucleic acid molecules of a population of nucleic acid molecules prior to sequencing.

3. The method of claim 1, wherein determining nucleic acid sequences of individual nucleic acid molecules is performed by a high-throughput parallel sequencing machine.

4. The method of claim 3, wherein the high throughput parallel sequencing is performed using a high-throughput parallel sequencing machine that performs at least 10,000 sequencing reactions simultaneously.

5. The method of claim 1, further comprising, prior to step (b), separately amplifying individual nucleic acid molecules of a population of nucleic acid molecules isolated from the protein-DNA complexes.

6. The method of claim 5, wherein separately amplifying individual nucleic molecules of a population of nucleic acid molecules isolated from the protein-DNA complexes is performed using a machine that isolates single nucleic acid molecules from a population of nucleic acid molecules prior to amplification.

7. The method of claim 6, wherein said machine isolates single nucleic acid molecules from a pool of nucleic acid molecules prior to amplification, performs amplification reactions on the isolated individual nucleic acid molecules to generate isolated amplification products of the individual nucleic acid molecules of the pool, and performs parallel sequencing reactions on the isolated amplification products of the individual nucleic acid molecules of the pool to provide sequences of the individual molecules of the pool.

8. The method of claim 1, wherein at least one cell is at least one fungal, algal, or protist cell.

9. The method of claim 8, wherein at least one cell is at least one algal cell.

10. The method of claim 9, wherein at least one algal cell is of the Chlorophyceae, Pluerastrophyceae, Ulvophyceae, Micromonadophyceae, or Charophytes class.

11. The method of claim 10, wherein at least one algal cell is a cell of an alga of the Chlorophyceae class.

12. The method of claim 11, wherein at least one algal cell is a cell of an alga of the Dunaliellale, Volvocale, Chloroccale, Oedogoniale, Sphaerolpleale, Chaetophorale, Microsporale, or Tetrasporale orders.

13. The method of claim 12, wherein at least one algal cell is a cell of an *Amphora, Ankistrodesmus, Asteromonas, Botryococcus, Chaetoceros, Chlamydomonas, Chlorococcum, Chlorella, Cricosphaera, Crypthecodinium, Cyclotella, Dunaliella, Emiliania, Euglena, Haematococcus, Halocafeteria, Isochrysis, Monoraphidium, Nannochloris, Nannochloropsis, Navicula, Neochloris, Nitzschia, Ochromonas, Oedogonium, Oocystis, Ostreococcus, Pavlova, Phaeodactylum, Pleurochrysis, Pleurococcus, Pyramimonas, Scenedesmus, Skeletonema, Stichococcus, Tetraselmis, Thalassiosira* or *Volvox* species.

14. The method of claim 1, further comprising performing one or more assays to evaluate the centromere sequence.

15. The method of claim 14, wherein at least one assay is an assay for stable heritability of an artificial chromosome comprising the centromere sequence.

16. The method of claim 14, wherein at least one assay detects the presence of a selectable or nonselectable marker on an artificial chromosome comprising the centromere sequence.

17. The method of claim 14, wherein at least one assay detects the presence of the centromere sequence or a nucleic acid sequence linked thereto on an artificial chromosome.

18. The method of claim 1, wherein said high sequence-coverage peak has nucleotide sequence occurring at a frequency being between 2 and 5-fold above the baseline frequency.

19. The method of claim 1, wherein said high sequence-coverage peak has nucleotide sequence occurring at a frequency being between 5 and 10-fold above the baseline frequency.

20. The method of claim 1, wherein said high sequence-coverage peak has nucleotide sequence occurring at a frequency being more than 10 fold above the baseline frequency.

21. The method of claim 1 wherein the method does not include a step of hybridizing nucleic acid molecules isolated from the immunoprecipitated protein-DNA complexes to one or more known centromere sequences.

22. The method of claim 1 wherein the antibody binds SEQ ID NO: 1.

23. The method of claim 1 wherein the antibody binds SEQ ID NO: 2.

* * * * *

SEQUENCE LISTING

<160> NUMBER OF SEQ ID NOS: 176

<210> SEQ ID NO 1
<211> LENGTH: 45
<212> TYPE: PRT
<213> ORGANISM: Chlamydomonas reinhardtii

<400> SEQUENCE: 1

Gln Ser Lys Pro Ala Arg Pro Gly Arg Lys Ala Gln Ala Glu Ala Ala
1               5                   10                  15

Thr Pro Thr Lys Ser Lys Arg Pro Ser Gly Ala Ala Ala Thr Pro Thr
            20                  25                  30

Arg Gly Gly Arg Ser Pro Gly Gly Gly Thr Pro Thr Gly
        35                  40                  45

<210> SEQ ID NO 2
<211> LENGTH: 18
<212> TYPE: PRT
<213> ORGANISM: Chlamydomonas reinhardtii

<400> SEQUENCE: 2

Arg Thr Lys Gln Ser Pro Ala Arg Pro Gly Arg Lys Ala Gln Ala Glu
1               5                   10                  15

Ala Cys

<210> SEQ ID NO 3
<211> LENGTH: 1096
<212> TYPE: DNA
<213> ORGANISM: Chlamydomonas reinhardtii
<220> FEATURE:
<221> NAME/KEY: misc_feature
<222> LOCATION: 1009
<223> OTHER INFORMATION: n = A,T,C or G

<400> SEQUENCE: 3
gaggcaggtg atttaatcag tctccttata ggcgatgatt tagcggccgc gaattcgccc      60

```
tttggcatg gcgacgggaa agctacgaca gtgtgtactg gagtcacatg ttttattgcc      120
cgggcatgcg acagcttcat acctcaaatt ctgccactgc atagtgcaca gcgtctgact    180
gtggtaaaac cggtctcacc tgcccgcaca gatgatgaag ctgcagcgga agctgcaggg    240
cggcgcggcc gctggcccgt aaacccctgc tgtacggtgc tgaaggcttc agtgtgcggt   300
tggatatggt ggactgcagc acttgatttc atcatggcgc ccattcctgt acaaagcgac   360
ggcccgtggc cgcatggtgg gcagggccgc agcactggct gagcctattt gagttgaggg   420
cggacagcgt ggcgtgcttg ggagcggagg tgctgcactc acaggcgtgc acgggcccaa   480
aatgacactg gggcgaggcg cacacagaca ggtccacagg ttaagtgcgt gcgtggtcga   540
cgagcggacg agcggtcagg ccaaaggctg ggggaggata gggcgatgcg tgcccgatgt   600
gaacccagct aggccaattc tggttgttct gggcgatgaa gacggctggt ttgatcttgc   660
aaggcgtgaa gttgcaggga cttgtggccg tcatgcgctc atgggatgtt gagggcttgg   720
agcgtgaagg cggttgatac gttcggtacg gccatgtagg tggagcacag tttgacggtg   780
ttggggttca gccatacggt aagcaatgaa atgtgatgcg ccaattgtgc ctctgcctca   840
ccgcgacttg taaatgaact ggtgtgcagc ccaaggtgca gcccttgtcc ctgcctacgt   900
accgcgccaa ctcgggcggc cccccaattc aatctgtgct atcagccgca gtcacacagc   960
agtggtgcac actctcgaca aagggcgaat tcgtttaayc tgcaggctng tccctttagt   1020
gagggttatt ctgagctggc gtatcatggt caaactgttt ctcggtggaa ttgtttcccc   1080
tccaatcccc cactac                                                   1096
```

<210> SEQ ID NO 4
<211> LENGTH: 1007
<212> TYPE: DNA
<213> ORGANISM: Chlamydomonas reinhardtii
<220> FEATURE:
<221> NAME/KEY: misc_feature
<222> LOCATION: 710, 749, 802
<223> OTHER INFORMATION: n = A,T,C or G

<400> SEQUENCE: 4

```
ctcagtattc accctcacta aaggagacta gtcctgcagg tttaaacgaa ttcgcctttg     60
cactggtgga ggactgcgtg gtaaagcagg gcgcggtggg tcgactcata cggcaactgg    120
acgcggcggc atcggcgtca gaggtggcaa gctggcgggt ggcggatgct gagggccgct   180
acaggtgcgg cggaggcacg ggcgtgcagc agcacactgt gtgggtcttg tgtgcgtgta   240
tttgagcggt gtagtgggtg gtgcctgatg gaccgccagc tgccctgtgc tctacacgca   300
gggctgcaaa cgacgacaac gcaaagctgc ggcagctgct gcacgaggaa aaggaggtgc   360
gcgcgtgctg tccccgtgcc tggctccgcc tccttgccca aggggccgga gcccgtgccg   420
gctacttgtc aacttagttg acggtacaga ctgcttaagc tcaccctcct tcccctcgct   480
ccttcgttcc ccgtaccggt ccatctatgc ttcaggcctg gcggataccc cagctgctgc   540
cggacgccgc cggcctcagc cgggacgagc tggtggagag gtgggtggtg gtgggttggt   600
tggcgggggg tgtttgtaat gaccgagggc agtccaaggg ttggcatgta ggggacgggg   660
tggttgagcg caggcacgaa tgcatggggg cgggcataca caagcagccn cacccttcg   720
tcgttcaacc ttgccccat ccgccttcnc ggtcccgccc ctgccgtgct cgacccatca   780
cccgccatac gccacccacg cnaggtgtga gagcgccatg gcggcgtacg gccgagagcg   840
ccgccgcaac gccgagctgg tgcaccgcct gcagcaaagg gcgaattcgc ggccggctaa   900
atcgattcac ctatagtgag tcgtatacag ttctctggac gtcgttttac aacgtcatga   960
```

```
ctgggaaacc atggcgtacg caggtaatct gcgtagagca ggtcatc         1007
```

<210> SEQ ID NO 5
<211> LENGTH: 643
<212> TYPE: DNA
<213> ORGANISM: Chlamydomonas reinhardtii

<400> SEQUENCE: 5

```
cagaattaac cctcactaaa gggactagtc ctgcaggttt aaacgaattc gcccttaca    60
ctggacgtgc gggcaacaga tgcagacagc gcattgctca cacgggccta cgggcattgc   120
ggcataggcc gtgggcattg tgcatggcca gaacgaaagg gcagaagttg ccctctcatg   180
agggcaccgg cggggcatgc gtttgtgtgg gctcgctgcc gtgcagagaa ggttgcatga   240
gcttaagggc gtgccgtgag gcggcttgtc gcttgtgttc aggtcctgcg acttcatggc   300
tggttggtgt gctgcttcag ttgtcctgcg ttgtgcaatg atcaggagcg ctgcgcatga   360
tcgcctatgg ctagcaatgc cagctttggt acagcaatgc gccccagacg caggtgcgcc   420
tggcatggtg caaatgcgtt gactgctgag agtaaatgag tgacatgact aggtattctt   480
ggctgtgtac ctgtgctgat gacgctgctc gtgatccgtc ctattaagac ccggaaaact   540
tggcactttc tattgattct tccctataga ttctcctctt cctcccttgt ccattgattt   600
ctccgcatct tcctcaccaa gggcgaattc gcggccgcta aat                    643
```

<210> SEQ ID NO 6
<211> LENGTH: 993
<212> TYPE: DNA
<213> ORGANISM: Chlamydomonas reinhardtii

<400> SEQUENCE: 6

```
atacgactca ctatagggcg aattgaattt agcggccgcg aattcgccct tcccaccgat    60
ttggcgcact gctctgagac cacataagca cacgccaggt tagaggggtc cgaggtggtg   120
ggatagccgc ccgcctgcag caccaaatcg gtgcgaccgc ggaaagcccc ccacacaggg   180
cccccctacca tcttgaccgt gacggtgtag gtgcccggaa tgatgggccg ggtgtccacc   240
ggcacgtgaa ccgtgaggac agcctgaccg cgctggagcg gtaccgccag cggtgacctg   300
cgcatgagct ccgctgtgaa ggctgctttg ctggcgctgg tcgcgcgccg gctgaaggcc   360
agccccgcaa acgtgcggga ggggcggcct gtgctgtgca gagagtggcc ctgcaagagc   420
tgcggctggt tgccctgcct gcacagggtg tccagcactg acaaggcagc gctggtcact   480
tcccggacgc cggctgagga cagctgctcg ccctctggga gccccgtggt ggcacccacc   540
agaaggactg ggtaggtagg caggctgggg ccctgaggct gcgtcgtcag gtcctgcacg   600
ccgtgcgcca cgctatgcgt ggacagggca aggtggagct gcagcccggg gctgaagaac   660
gggctggcaa agggcgaatt cgtttaawct ctrcagract agtcccttta gtgagggtta   720
attctgagct tggcgtaatc atggtcatag ctgtttcctg tgtgaaattg ttatccgctc   780
acaattccac acaacatacg agccggaagc ataaagtgta aagcctgggg tgcctaatga   840
gtgagctaac tcacattaat tgcgttcgc tcactgcccg ctttccagtc gggaaacctg   900
tcgtgccagc tgcattaatg aatcggcaac gcgcggggag aggcggtttg cgtattgggc   960
gctcttccgc ttctcgctca ctgactcgct gcg                                993
```

<210> SEQ ID NO 7
<211> LENGTH: 1034
<212> TYPE: DNA

<213> ORGANISM: Chlamydomonas reinhardtii

<400> SEQUENCE: 7

```
ctagtctgca ggtttaaacg aattcgcctt cgctgggtac ggccggctaa tgcaggaata      60
agggatgtca gttagaagcg ggtgcttcac gagtgtaaaa ctacggtact cgaaaggtct     120
ccagcatcaa ggcacgccat tccatgctct ggcgcgggtt ggcagggtgc atgcctgcca     180
caacgtcgat aatagtacta gatcggggct gggggggtgg tgtgggccag gatgtaggtt     240
gcttatctcc aagtgcacac ggccacgcca tgcttctgcg gcatcgcaca gggtgtgctg     300
gcttgcaaca gcatagcatg cgctgatttg cttcggcaac cgcacctcaa catacggtag     360
caagactccg agcgacatat gcacccgggg aggtgcctgc actgctcgtg tacggcaccc     420
acacgcgctg caagtctgca ccgacagtct ccggcgcggg cgtcgtcgt tcaattatcg      480
tccatgcctg ggctgggtgc agtctgtttc tcgggactca actatgtcag ccacttgctt     540
cccttgcgat gtcccaccgc acccacggct tgcaccgtat cacgccatat caggcaggtg     600
tcagggaagc ccgggggggcc atgtcgagct cttcctcggg aaacaacgcc cgccgcaata     660
ataataataa tgcaaacgcc ggcccatggg gcctggcgtg gattatcggg ggtaaggtgg     720
gctaggggcg aggaggccca ccccctcgc gctgccacct cgccacgcac tccgaggagg      780
gtgtgggggg agccgtggct cacccgcctc tcggtttgag taaggcgaa ttcgcggccg      840
ctaatacktc aattcgccct atagtgagtc gtatacattc actggccgtc gtttacacgt     900
cgtgactggg aaaccctggc gtacccactt atcgcttgca gcacatcccc ttcgcagctg     960
ggtaatacga aaagccgccc gatcgccttc ccacagtggc agctatacgt cgggagttaa    1020
gttatcttaa aaaa                                                       1034
```

<210> SEQ ID NO 8
<211> LENGTH: 1034
<212> TYPE: DNA
<213> ORGANISM: Chlamydomonas reinhardtii

<400> SEQUENCE: 8

```
gattcccccct caatagaggg actagtcctg caggtttaaa cgaattcgcc ttattctctt      60
tcaacttatt atatgttata agaaaacaca gctgcagtgc ggagagcagc catggttcgc     120
gaacttcgac ggacatcctt tccagcaccc ctcgcgcccc tcgccccgcc acggcgctgc     180
cacggcccac cctgctggtt tccccagcac aacgtatttt caaacgtact agccgacgag     240
ggcagcgtac agtacgtagt acagtacgta gtacatagta cgcgtactac gaactacgca     300
accctgccgc gcgcaggaca cacgcacagc gcacgcacta accagggcgc aagcgtccag     360
gtactagaac ggtcgcccac acgtgcatcc tgcccacaca caaagccacc aaccacgcac     420
aacctctcgc ggcgagggag gcggggaatc agcgtcatac ggcaagcgca aaaccatgcc     480
gtcaccaaca gcccgagata ggaaaggatg cgcaaacggc acaacgtccc aaccctttgg     540
cctgataccc aaagtcacaa acgtctggag acgaccccag aagtcagcta cgacggcaag     600
tccaatccgc ggttttatgg acaaaccact gggccctgct actgtacgta atccagcttc     660
cgcaatgtgt ggccggcccc tggtcgctct gcccccctt gctttgtggt ctcgccgctt      720
gatcgtgtgg gggtgtgtct ggggggtggtt gtgttccctc ggccttgtct ttcgcgcgtg     780
cggtgtgggg actgtgggggc tctgcccaat gtttaggcta gtactgtgcc tgtggcacgt     840
gaagtggagg ctttgccttg tgttgggcct tcggggcttg aagggcgaa ttcgcggccg      900
ctaatagttc aatcgcccta tagtgagtcg tattacattc actggccgtc gttttacaac     960
```

| | |
|---|---|
| gtcgtgactg ggaaaccctg gcgtacccac taatcgcctt gcagcacatc cccttcctca | 1020 |
| gctggcgtta tagc | 1034 |

<210> SEQ ID NO 9
<211> LENGTH: 812
<212> TYPE: DNA
<213> ORGANISM: Chlamydomonas reinhardtii

<400> SEQUENCE: 9

| | |
|---|---|
| accctcacta aagggactag tcctgcaggt ttaaacgaat tcgcccttga gcaggtgttc | 60 |
| atcgtcggcg gcacaggcaa ttacgtgaag gacctgggcg agaagggtga gcttggcggg | 120 |
| gacctgaaat ctttgactgg gaacagggcc gtttgtttgc gccttggcgc tccccggcat | 180 |
| tcatgcagct gcagatctcg acgcgagtct gacagcacgc tatgataggt agagttgcct | 240 |
| gcttgtcgcc tggcggcctt cagcgcgttg acattgccgc ctgccttgac tttgccctct | 300 |
| gacgcctcac tgacttcgct actgctgcca ctgccgtctg tgtgatgcag ggttcataga | 360 |
| cgcctgcaag accaccagcg ctacccggat cttccccgac acgcagcatc acaatgtgct | 420 |
| cggcttgccc ttcaccggga tgagcaacgt cgctggcgtc aatggcccag acgcgctgtc | 480 |
| acccttcgct atcgtcacgg acaaggacat cgaccgcgct gacaacgacc ccaaccacat | 540 |
| tttcgtgcgg cccgaccatc ccggcgtcac ccttccacat cctcgcacta cccatggcgg | 600 |
| tggcggccga cgacacttyc cgcggcgcgg sgcctggcgg tcggcacgac gccggcgccc | 660 |
| aacggcgcgc tgcaccggtc ccacaccccc gccagccccc tggcgaccct gacgaccccc | 720 |
| ggcatgctca gggtcggcgc tcgtgrggcc acggtggcca ggccgtcgag acggaggtct | 780 |
| gaagggcgaa ttcgcggccg ctaaattcaa tt | 812 |

<210> SEQ ID NO 10
<211> LENGTH: 1127
<212> TYPE: DNA
<213> ORGANISM: Chlamydomonas reinhardtii

<400> SEQUENCE: 10

| | |
|---|---|
| cgtactcgaa ggtttacgat tcgcccttgg gtgcaccgtg gccgcccgc acgcccgcac | 60 |
| cttggttccg ctcccggatg gcctkgarga atgtytcgag ttgcagcacg tcgcaatcct | 120 |
| tcagtcgctc cgcgtcatgg ccatccgcaa tgcttcgcgt aacaacagac gcaacgcggc | 180 |
| gagcggcagg cctcccgctg caggcaacgt tgcaggccaa cagagccgcc ggtccygaaa | 240 |
| ccccaagtcc acgaggtgta gcacgcgccc ttgtgattac agcaggatat cttccacttg | 300 |
| tgctagggct actcgccgag ctagccaacg agccgctggg ccccgaagga agagaattcg | 360 |
| tcatttgatt gaaacgcgtg caggcccgat tcgaccttac aaactacaga ctgataaata | 420 |
| aaagcttaaa agatggtgca atttagatca cagcccaaaa tagcagggcg tttgcgtggt | 480 |
| cgcttatgcg tgcgacgtgt tttgctgcgt gcgtatcaag ttggctgaat atgcaagca | 540 |
| aactttggag gagaacaagt ttaaggttgg aaagcagccg gagggttaag aagagctcgc | 600 |
| agaaggccty tgkggggttg ggggccaaaa ggccctgccc atgcagcggt ccatgaagcg | 660 |
| gtcttcagcg cagccaaagc tcttacagta cactttatac ccttgtttat atcagcattc | 720 |
| agctggaggc taacacgcaa agaaaagtcc cttcacgatg gcttccagag agggcacttc | 780 |
| aggcaccctc aagccatttta cctcaccaag caagagctag ggaggagtca accatatgga | 840 |
| cgtttgcagt cccccatgccc acacacatca gacaagtacc ggcccaacca tccgagccat | 900 |

```
cctccaggcc atctcgcctg cgcggcgcag catcatacat ccgccggccg tgtgttgcgc      960
agcgatgtat cacatggggc ttggaacctc ttgcacaccc cgcaacctca agtcaaaaga     1020
cacatattcg tagcaccaac catactctgg ccccataccg cgtatgcgct ctgaacaccc     1080
ggcccgcttt gcgggtcaaa gggcgaatcg cggccggctc tacctag                  1127
```

<210> SEQ ID NO 11
<211> LENGTH: 1281
<212> TYPE: DNA
<213> ORGANISM: Chlamydomonas reinhardtii

<400> SEQUENCE: 11

```
cctatagcgg cgcgattcgc cctttggtat gcttgcacct gacggcgctt gcctcgttta       60
actccctgcg cagaatcacg tgtacttcac ggatgtcagt aagtaggggc gttgggtcag      120
ctgtgccctg tcaggatcag ctgcggaata ccctggcagc actgctgcac cgcacgcata      180
cggcacccaa tgtgccaatc tctgcccccc cttcctcaac taatcatgat tgcaacccca      240
cccgccatgc ctgtaactcc gtcccgcgcc ttaaacccag tgtgcttggc gatgccgcac      300
atcctgcact tgagcgtggc ggggtcacc gcgttcctgt tcttcgccat cacagccttc       360
atgtgagttg gcaaacgggg ggcatgggtg ccctttaagt accgtatcca tacttgggct      420
gtgtgctccg tgcttgtgat acggtatggc agagatcgcg cccacccggg gccccttycc      480
tcaggtgctc cccgctcttg ctgtggagac ctgtctctca tctaaacccc ttcctgctcc      540
atccatcagg gtcatcgcct cgtcagacct caaccctgta tcgcgtgggt acttagcctc      600
gcccgctgct gtcacgcgac tgaagatcct gtgcgcaaaa gccatctacg tcgtaagtct      660
gcacaccgct gttgccgtag tttatgcaac cccgccccat tcgacaggcg ggcctgaacg      720
caagcaaggg cactgacacg tgtgcgtgtc gctgccctgc cgcccgcaga ttgtggctga      780
cgatatgcag agctggccca accccaggc cattatcatc ctcctcagcg tcctcctcat       840
ctggtggtgg aacttccgaa gggtgggtgc ggtggcgggt tcgtttgcgg cgttgcgctc      900
tcaggtggta aagggccgcg ggcttttggg ttgcggaact tgtatccgcc gctcagagtt      960
ggaccgtgag cacccsccga ggtaggcttg agaggaggca cgcgcttact tcgtttagtc     1020
gcgtcgctgc actcccgcgg agctgctcgt gttcgtacat ggcacgtgac actctcagag     1080
ggcgcatcag ggagtatctg ggttagtcat gttcacctgc ggcttctccc atgcaagact     1140
tgttcccagc acttgctgga acacgctctc atcccatgac gaccaactgc ctgcagttgc     1200
ccttctaccg accggtcgtc aacgtggtgt ggtgttccat gtggtcgggc atccaagggc     1260
gaatcgtaac tgcagatttc g                                              1281
```

<210> SEQ ID NO 12
<211> LENGTH: 1360
<212> TYPE: DNA
<213> ORGANISM: Chlamydomonas reinhardtii

<400> SEQUENCE: 12

```
gcaggtacag ggcgtgcggc agaacttatc tttgcatttc tagcgcgacg gacctttgcg       60
aaagtcgctc accgagtggc ccaaagtcgc cactttcctg cgtcggttc ctccattacc       120 ctatcaacac ataggttggc cccaatgatc gtaaataagc ggccttcaag tgggggtagc      180
ccgaatccta gcgaaatgcg cactcgccga acatgccggc atgcccgcac gcgcgcctgg      240
ggtgcgctcc aaggccagct agcttactcc tggcgtgcct atgcagtcat atgtgtgaaa      300
gagccaggcc tgctcatttg tagggccgcc gcttgggcgc tgggcccggc catcggcacg      360
```

```
cccacgtgcc tacctccctg acgcctgacc cccatgtgcc cagaccacga ctcgcttggg    420
cggcccgagt gctggcattg catgccgact agtatggctt ggtatagcgg gccgggcggg    480
cgcgtcacac agactccagg gcactggagc ggaccccaca tcgccgcaac aggcgcgcgc    540
cgtgcgtcac cyyatcacgc agcctgtacc cgcggccgca cccgcttgcc acacactccc    600
cgccgagctc gtcaccacgt agctggacac gtcagaagca cctggtcacg acatcaggcc    660
tcggacctgc acccaggctc acacctggcc cgaacagtgc gtgtgcggtr tgccgtgtgc    720
agcgggtggc tgtgggtagg ggtgaggact gaggggcgca ggtgctggac tgtcacgcat    780
ccgctgcgcc gagtatttct ggcgccctcg atgcacctat gacacgcacc acggccatgg    840
cggcgtgtgc tgcccgcccc ggtggccgct gttggctccg gtcagtgtct cagggtgtgc    900
agacacaccg gggctgagcg ccgcctcagg ggcgcccatg tgcggcccgc tgtccttgtg    960
agcggcccta atggccgctg tccgtgtgga tgaaagcaaa cgggtgttgg ggggcccacg   1020
tcggaggcat cagggtaggc ctggcgggcc cgggatagcc cgcgtgggcg gccaggagca   1080
ccgtgccata ccgcggcgag gtgcacctcc gtgcttgtgc tggcgacctt tgcgtataat   1140
tataaataca agtatattag cgagccacgg aagtcgcgga tcacgcagta caggcgtgcg   1200
gcagacttat ctttgcattt ctagcgcgac ggactttgcg aagtcgctca cgagtggccc   1260
aagtcgcact ttcctggcgt cggtcctcat accctatcaa cacatagtgg ccccatgatc   1320
gtaataagcg gccttcaggg gggtagccga tctacgaatg                         1360

<210> SEQ ID NO 13
<211> LENGTH: 1103
<212> TYPE: DNA
<213> ORGANISM: Chlamydomonas reinhardtii
<220> FEATURE:
<221> NAME/KEY: misc_feature
<222> LOCATION: 384
<223> OTHER INFORMATION: n = A,T,C or G

<400> SEQUENCE: 13
ttatacggca ggttttccag tcagacgtgt aaacgacggc cagtgaattg tatgcgactc     60
agatagggcg actgmtwtag cggcssgawt cgcccttcct gcctcccagc tagcccgctg    120
cccacctgaa kgttccgggc cgctcccact caagcaaggc cgccaatgtg cygcycaggc    180
tgtgacccat gcagaaggcg cctgcgtgtg tgtgtgtagg gaagtgcagg ggggcaggtg    240
aggtgcaggt ggaaaccccca cacgcggc ggcygcatgc ggcgtcctcc cctgctggtc     300
caggagagaa tctcctcctc ctcccctgat ggtacgacac ccacactcca gaccacgacc    360
ccagaccatg tgctactcaa gtancccct cccccagtcc ccttkcaacg ctccctgctt     420
cgttgggctc gggcacataa tccccactg actccccgcc tcaccccgca cgccctcccg     480
ctccacgtaa tcctgaactg ctgcgaccag gtctgcctcg ctgatgggcc ctgttggcgc    540
gggggcctgg ccgtggccag gcaggtcgag agctacgcaa cgaaagtgct tggagagcag    600
gggcacctgc agcgagcgac gcccagccat gtcatggatg aaatgtcaat tacgcggaac    660 tcggggggctg ggttgactgc cgctgttttgt tatttgatgt attaatttga tacaagttgc   720
tcaccattgg caagaagatg cgaccgtgaa agccattcgc gtgcagcagc agaagcaaag    780
ggccgctgcc gcccaactcg tgcgccacga cgctaagttt tggcatcctg ctgagttaaa    840
gatacttaag tacaacgggc agcaacatat tgcattctct ttcgctaacg caggcggacc    900
tgcatgggta ggggcgcgtg caggccagcg cacaccggcc cccccactct cccaggcgat    960
```

```
cgtttaactg cagactagtc cctttagtga ggtatctgag ctgcgtatca tgtcatagct   1020
gttctgtgtg aatgtatcgc tccatccacc aactacagcg agcataatgt aagctgggtg   1080
ctatgatggc tactcaatat gct                                           1103

<210> SEQ ID NO 14
<211> LENGTH: 1153
<212> TYPE: DNA
<213> ORGANISM: Chlamydomonas reinhardtii

<400> SEQUENCE: 14
ggctgtagtt ggtggattgg agggataaca tcacacagaa acagctatga catgatacgc     60
cagctcagaa tacctcataa gggactakct ckrcrgttwa cgaattcsyc yttcaaggcc    120
atgcccaccc ggtcacctac cggcgaacwt cgtcatgacc tcgatatgtt ggctgyctct    180
cccgcctgca ggtgcaccag gtgctgcagc gagtggcgcy cgacctgcyc gccgcctggt    240
gggaccgctg gagcyycgac gcgcyyyagt cctrccggct gccgcagcag ccgctgccgc    300
aggtgcaggc gcaggcgcag gcgccgcagc cagacctagc agctgataca ggtgcgagca    360
tgtcggcagc ggcagcagta actccagcyc caggtgtagg ccaggcatta gggggcggc     420 ggagcycggg gtttcgctat aggtggtggg aaggggtctg gcggcgcgac ctgcagcatg    480
gccaccttgt tcctgcagca ctacctcgac agcctgggct ccctcaacac gttcgggtag    540
ggcgctctcc ggcagccgca tgtgacgcct gcgtcatcac cggagcgtgt aatgaatgtg    600
atgggactga ttctgttcac tgcgtacatg cggtggcaga cgtgagcgtg ttgctgtgtc    660
aattgtgatt ggactggact ggagaggggt gatgtgacaa gcaaatatga gagagtcagw    720
gggcacgtac atgaagggca gcaagaaaga aatgtggccg aggtgcctgt gccccggctg    780
gcagggcgtc accgtacata cagatgaaga ggtatgagag cgtggcgaga tgtaaccgca    840
gttgcgcctg cagaaggcgt acgcatttat cgaacactgt tctttcttc tcccggccga     900 tatgaaggtt tgtgaagctt tccsggcaga taccgtagga tcttcaagct tgtcagatag    960
acgtagccgc tggtaaggcg cggcaacaat gagcggcccc tgasgtgggg cgagttggsc   1020
gaacttcctg ggkraagggc gaaatcscgg ccggctsatm rtccccctata ataggcgata   1080 aattacggcg gcgtttaaac tctgccggga agacaggcgt accacattat gcttggaata   1140
ctttcactgc ttt                                                      1153

<210> SEQ ID NO 15
<211> LENGTH: 965
<212> TYPE: DNA
<213> ORGANISM: Chlamydomonas reinhardtii
<220> FEATURE:
<221> NAME/KEY: misc_feature
<222> LOCATION: (165)...(188)
<223> OTHER INFORMATION: n = A,T,C or G

<400> SEQUENCE: 15
gtcgcatrgy arwasrattc gcccttcmcc gaatygttgk gattgggcgt aatgacgtct     60
gcgcacgagc amcagaaggt gaaggttcaa cacggcgtac cgtgcatgct tactgcggtg    120
ggggctgcat ggctgctgcc tgcgtgcggc agactgctcc ttgtnnnnnn nnnnnnnnnn    180
nnnnnnnnag ccaggtcatt tgttccgggc cgccagcgcc ggctgcccaa acatatgaga    240
tttggccatg catgcttgaa aaaagcagca gcagcaatca tgtagaccca cccaggaagt    300
ggtctgccgg gttctcgtgc aggggcagg gaaatccgga gcggtcgaaa agtccaggg     360 cgtcatgcgc cgggccctgg tacacgatcg agccgcggtt gagcagcagc agctggtcaa    420
```

```
acagcgcgaa gatcttggcc tggggcctgc agcggcggaa gcagaaacag gagcatgggt    480
caggcgggcg cggatgcgga cgtgcgtgca catgtatgtg tgcttgcgct tgctgcttgg    540
gaatatgagc atgcaaggcg ctgcgacata gctgcgggcg tatgagcacc cgcccatctg    600
ctgctgggag ttcgtgctag ctaaatgcga gctgtagcgc tgcaacagca ggctggccac    660
caacagcagg cctacgcggc tgcctcactc actggtggat ggtggtgacg acggtgcaaa    720
ggcggctcat ggcgaggcgg cgcagcaggc ggcacagcga cagcgctgca cgcacgaaca    780
cgcacacgtc gggtaggcag gttagggagc aggttggggt gacgtgcgtg gtgaagcagc    840
ggcaagaggg atggacrgac cgcagcgact gacgctgcac atcgagcgct acgcacggta    900
cgaagtacga agagcgcgaa accctcaagc aagcaasgac gtggccmact tgggatggca    960
tgact                                                               965
```

<210> SEQ ID NO 16
<211> LENGTH: 1035
<212> TYPE: DNA
<213> ORGANISM: Chlamydomonas reinhardtii

<400> SEQUENCE: 16

```
ttaaaaccga agtatctagc ttagagctag tgctcactaa ccaagacaac tctcaacaac     60
ggatatcttg gctctcggat cgatgaagaa cgcagcgaaa tgcgatacgt agtgtgaatt    120
gcagaaatac gtgaatcatc gaatctttga acgcatattg cgctcgaggc ttcggccaag    180
agcatgtctg cctcagcgtc gggttaatac tcgcyctact ccaacatgtt tggagcaaga    240
gcggacctgg ctgtctcggt gtttgatttt cggatcagac gccgggtcag ctgaagtaca    300
gaggttgatg catggacccg cttatgggcc tctactgggt aggcaactcg ttgctaatgc    360
tttagtagat ggcttggagc tgtgcttgtc gacccaaacc aggaactttg gccctgtgcc    420
gaagcaaacc cctattttct cgacctgagc tcaggaagac ttaccccgctg aacttaagca    480 tatcaataag cggaggaaaa gaaactaaca aggatttccc ctagtaacgg cgagcgaacc    540
gggaatagcc caacttgaaa atctcccttt ggagaatttg tagtctagag aaagcgcttt    600
ctagggctgg gcggaactca agtcggatcg aatgcccgcg tcagwarrgg gtgawaaccc    660
ccgtcggttc ctgccytagt ccttccacga agtgctttcc acgagtcggg ttgttttggg    720
aatgcagccc taatttggag gtaaatccct tctaaggcta atactgccg agagaccgat    780 agcgaacaag taccgtgagg gaaagatgaa aagaactttg aaagagagtt aaagtgcttg    840
aaattgttga gagggagcga tggcgctaag gcgattcttt aaactgcagg ctagtccttt    900
aatgagggta atctgagctg gcgtatcacg tcatactgtt ctcgtgggat tgtatccctc    960 catccccac aacacgaaca aaagtaagct gtccatgata caccataatg gtggtctccc   1020
ctcctcggac gcgca                                                    1035
```

<210> SEQ ID NO 17
<211> LENGTH: 818
<212> TYPE: DNA
<213> ORGANISM: Chlamydomonas reinhardtii

<400> SEQUENCE: 17

```
aatttagcgg ccgcgaattc gcccttgtgg ggacggagag tgcgctgagc tgctcggggg     60
tgcagtcatt aagtccaggg ccgcaaggcg taagaacgcg tgcccatgc atgtgtatga    120 agccctgagc agtttattct gctggcccaa tctgcgcaaa cagattctgc cgggcatcgg    180
```

| | |
|---|---|
| cggcacggtg cgcaagcata cgggcctgct gtccggcatc tccaccctcc tgcgagggct | 240 |
| gggcgtcggc gggggcaaaa acccgcgtgc gcgcggcggc cgggcacgcg cacagagcgg | 300 |
| cgctggcgac aaggcgcagc ggaggctgct gggactcgac gggtggtgga gcaggtggca | 360 |
| gtcgcaggag ggcgcacgca gctcagcgca caggcgtgg gtgtgrgagg agccggagag | 420 |
| cgaggaggcg cagctgcgcg rgcggcggac gctggccggc gccatgyagg acgatgagcg | 480 |
| cattgcggcg cgrgaggact rrgccggraa ggtggagcrg ctgctgtcgc grgcgatgcg | 540 |
| gtccgtgcgg crggcgctgc cgrgctggcr gtgaggtaac ggcgaacgtg agtattgtag | 600 |
| gcgtgtgcgc rcgtgrrrrc ragtgcrtgt gcrtgcagtg rrcragrrrc tgmgatcggc | 660 |
| gcagractga cggcygctga ctgaaccggc aagagacccr gattggtagt gcctagrcag | 720 |
| acgaagaacg gaccagacct gtgagggata gttgtattga tgtcaaaggg cgaattcgtt | 780 |
| taaacctgca ggactagtcc ctttagtgag ggtaattc | 818 |

<210> SEQ ID NO 18
<211> LENGTH: 746
<212> TYPE: DNA
<213> ORGANISM: Chlamydomonas reinhardtii

<400> SEQUENCE: 18

| | |
|---|---|
| aaacacgcag ttacgattcg cccttcacct gaccccaaag tgctgcgcca gctcgtccag | 60 |
| ctgctgctgc gggtcgtcgc tgcccagcac gtgcggcgcc gccacgtcac gccgctctgc | 120 |
| caggcgctgg tcgcgggtca ggaacacgcg ccctcggag gcggcgcgcg cggtcagctg | 180 |
| gaggcgggga ggcgcagggt gtggaggggt gaagggatt gagggaggcg aacggagatg | 240 |
| aggggcaggt gggggcaagg aacgactgcg atgtcgccat ggaattcccc gctgccgctg | 300 |
| cccctggcgc tgtttcacgc acccgcgcca gctcctgttt gccgggcgag gtgcggccca | 360 |
| cgtactcggc gtccagcccc aggcagcgca gccacctgca cccacccacg tgcgcgtcac | 420 |
| gtgttgcacc gcgatgcgaa tgatactgca atgccgtgag tgttacccc atcaaggaga | 480 |
| tagggtggc agtgaggtcc acgacacagt gcaaactgcg cggtgccggc tagccagccg | 540 |
| tgtgcctagt atctcaggag gcgaatgctg gggctgtgcc gagcgccgtg acttgacggg | 600 |
| gtgtgacgcc gcccgcacct gcacagccgc cctagcatgg agtccagcag gaagcggctg | 660 |
| ggcggcccgg cagtagccac tgccgcagcc gggcggcctg tagcagccgc gtcgccggca | 720 |
| ccggcagtag caggagcgcc agcggt | 746 |

<210> SEQ ID NO 19
<211> LENGTH: 906
<212> TYPE: DNA
<213> ORGANISM: Chlamydomonas reinhardtii

<400> SEQUENCE: 19

| | |
|---|---|
| cctatagcgg cgcgattcgc ccttgctagg gccgctgggg ccagggccgc cgtgcgctga | 60 |
| cgtccgcagc gcactcggcg ccacgcctgg tgacgccgcc gcgctgacgt gccggttaga | 120 |
| cacggagcgg gaggggtagg tggcgaggtc gaccggctca tcatcaatga ccaccctgcc | 180 |
| ggcggcgctg acacgccggc ccgcgctgcc cggcgcgtgt aagcaccccg ccaccgccgc | 240 |
| tgctggcgac gccgctgcgg ccgctaacgg actggcgctg tggccgcgcc ggtgtcgtgg | 300 |
| ctgagctgct gttcagcatg gcgtcacggg cggtgcggac acggccaggc ggcgcgctgg | 360 |
| cggcggcaac ggcgcccacg cccgcggcac ccgccgcagg cgaaatgcct gcgggcgtgt | 420 |
| cgcgtggcgg cacggccatg gctgacgtgt tgattgtggc gcggttggcg gcgcccttga | 480 |

```
agaagtccgc ggcggttcgc actgcgggca tgtcggacgg cagcgcccgc tcatcctctg   540
ctgcggcgtt ccgcggccgt cctttggtgc cgccagacac cggcaccacg gttgaggcaa   600
agtagtccag cgcggtgccg agggcgggag gcaggccgtc ggccacgggc ggcggcaccg   660
tctgagtggc agtctccacc ttgctggtgg aggcggggga ggagggcgtg cccacggcgg   720
cggggcgcgg cgagagggag gaagaggtgt agggctcaag cggcggagag ctggttagcg   780
tgcctgcgct ctgcgcgtgc gcgagcgagg ctgcggcgcc gccagcgggc ggagcgcgga   840
tggcgcggac aggtgctgac gtggcagcag tggctgcgtg aagggcgaat tcgttaaccg   900
catatg                                                              906

<210> SEQ ID NO 20
<211> LENGTH: 996
<212> TYPE: DNA
<213> ORGANISM: Chlamydomonas reinhardtii

<400> SEQUENCE: 20
tatcatgcgg ttacgattcg cccttggccg ccgcccgccc gtgggctttg tatgcgggtg    60
gtcttgcgcc acgatgccgg agttgggtgc cgtagtcaca tcaaggtcgc aagatcgaaa   120
cccatcagga acggttcggc tccgttacct gtgttggcac tgaacatact tgtgccgaac   180
ttccccgaac gagcgccatc tcggccttcc taggtcgctg ctctacgggt gaggacgctg   240
gtgcggcggg ttctgatggt ttccccgcga gagctatcct gctttctaga agccggtctg   300
cgagccagtt ggcgctgatg cgccggggca ggaggaggcc cctgattagg gaatgcgcgt   360
cacccagcgc cgatctgcga gcccgtgttt cgaggcgtta ccgtggccca gtatggccga   420
tggttgcaga caaccccccct ccccaaaatt cgctaaccgg gcttcgggct gcacccaaca   480
gtgtgagggc cctgccctgt tggtgctggt gttttggggt aggagttgca ctttgcaaag   540
tggcagtcag tctgacgccg acccgcggct taggtgagca gcgctagcgt ttgcggtgag   600
ccttgctcgg ggttcctccc ctcctttagt gaggcgagga gcatgggggt cattcgaggt   660
tctctcctcg agtgtgcgta cgtgtctcgt gcgtttatga agcccctggct tgcccgcggc   720 tgtcatccca catgtaacct ctattcgcta accgcatggg ggtcattcgg ggatctctcc   780
tcgggtgagc gtgcgtgtct cgtacgttttt tggggccctg gctagtccac ggctgtcgtc   840
ccacatgtaa cctctatcag ctaaccgcca tatcagctat actcgtctac tccgctgggt   900
gtgcgttaag gcgcctcggc gccctgacct tcaaggcgaa tcgcggccgc taattcaatc   960
gccctataag gagtcgtatt accattcact gcgtct                             996

<210> SEQ ID NO 21
<211> LENGTH: 3047
<212> TYPE: DNA
<213> ORGANISM: Chlamydomonas reinhardtii

<400> SEQUENCE: 21
atacccaatc ctgaaaagcg atttccacat acataaacgc cacccactgg actatctaaa    60
atcaaacagc accacggaac ctttacctac cgacctaccc accttgccct acccaccta   120 acctctaccc acccacccac ccacccagga cacatgcgcc actgccttac aagatagctt   180
ccagcgccag agtcgaactg gccactaagc cacacgcata cacacatacc acactaggcc   240
gcctaagtaa gggcacatgc atgctgttgc tctcactcgc acacacacag gaaggtacc   300 cttgagcact ttggctgtgt gggggaggag gggcagtgca tgcacacgca tgtgggcact   360
```

| | |
|---|---|
| tagacggatt cggcggcgtt ggcacgcgct cagctcagct acaccacttg gaagagagag | 420 |
| agagggccct ccctggagct gtcgctccga gaggaggagg ggttgcccg aagggcagtg | 480 |
| acaaatctta gcaacacggg atgaatctca gtggatcgta gcagcaaggc cactctacca | 540 |
| cttacaatac ccagttgcaa caaagtcgtc tacagaggat ttaccccaat gacgagtgga | 600 |
| attgtcatgc ttggcgcctg cttcggccat gtggacctaa caggggaacc aacgggtatg | 660 |
| ctccagcatc cgcacaggcg gatgtatcct tagtcgggtg acatcattgg gtaagtgact | 720 |
| ccgcacctag cacgtcttct gacttagagg cgttcagtca ttagactaca gatgttagct | 780 |
| tcgccccatt gtcttttcag acaagggcat taccaattat ctgactcggc ggttcctctc | 840 |
| gtactgagcc gaattactat ggcggaatcg gtccaacagt agggtaaaac taacctgtct | 900 |
| cacgacggtc taaacccagc tcacgttccc tattagtggg tgaacaatcc aacgcttggt | 960 |
| gaatgctgct tcacaatgat aggaagagcc gacatcgaag gatcaaaaag caacgtcgct | 1020 |
| atgaacgctt ggctgccaca agccagttat ccctgtggta acttttctga cacctctagc | 1080 |
| ttcaaatccc gaaaggctaa aggatcgata ggccatgctt tcacagtttg tattcgtact | 1140 |
| gaaaatcaaa atcaaatgag cttttaccct tttgttctac acgagatttc tgttctcgtt | 1200 |
| gagctcatct taggacacct gcgttatctt ttaacagatg tgccgcccca gccaaactcc | 1260 |
| ccacctgaca atgtcttcca cctggatcga cgtgcaaaag ccgtcttaga gctagaagca | 1320 |
| gggacagagt cccgcctcca agtaatggaa taagtaaaac aacgttaaaa gtagtggtat | 1380 |
| ttcaccgtcg ccgaagctcc cacttattct acacctctta agttatttca caaagtcgga | 1440 |
| ctagagtcaa gctcaacagg gtcttctttc cccgctgttt attccaagcc cgttcccttg | 1500 |
| gctgtggttt cgctagatag tagataggga cagtgggaat ctcgttaatc cattcatgcg | 1560 |
| cgtcactaat tagatgacga ggcatttggc taccttaaga gagtcatagt tactcccgcc | 1620 |
| gtttacccgc gcttggttga atttcttcac tttgacattc agagcactgg gcagaaatca | 1680 |
| cattgtgtca acatccttta ggaccatcac aatgctttgt tttaattaaa cagtcggatt | 1740 |
| cccccttgtcc gtaccagttc tgagttggct gttcgtcgcc tagggaacgc cgaagcttct | 1800 |
| acagccgtcc acccaggaca cgcagcagtc cgcccagccg tttccagctg ggtagaccac | 1860 |
| cgcagtcccg agcttcgcag ctgcagaccc ctaggcccag ccctcagagc caatccttt | 1920 |
| cccgaagtta cggatccatt ttgccgactt cccttatcta cattgttcta tcgactagag | 1980 |
| gctgttcacc ttggagacct gatgcggtta tgagtacgac ttggcaagat cgggaatgct | 2040 |
| cccccggatt ttcaaggacc gtcaacggcg cgccggacac cgcgagaagt gcggtgcttt | 2100 |
| accaacgtct gagccctatc tccgaatgat tcgattccag ggccttgcgc ttgttaaaaa | 2160 |
| gaaaagagaa ctcttcccag ggccgatgcc gatgtctccg ggctcgcttg cgttaccgcc | 2220 |
| agccgccttg tccaagtaag ggaatcttaa ccctttccc tttcgatggg cagcgcgaat | 2280 |
| cgcgctcttc acacaggatt accccatctc ttaggatcga ctaacccatg tccaattgct | 2340 |
| gttcacatgg aacctttctc cacttcagtc ttcaaagttc tcatttgaat atttgctact | 2400 |
| accaccaaga tctgcactag atgccgattc acccaggctc acgccagagg cttagtctcg | 2460 |
| acacccacgc cctcctactc atggaagcgt cgcacttgct tccatggccg agtataggtc | 2520 |
| acgcgcttaa gcgccatcca ttttcggggc taattgattc ggcaggtgag ttgttacaca | 2580 |
| ctccttagcg gatttcgact tccatgacca ccgtcctgct gtttatatca atcaacaccc | 2640 |
| tttgtgggat ctaggttagc gcgtagtttg gcacttaaac tcgactatcg gttcatcccg | 2700 |
| catcgccagt tctgcttacc aaaaatggcc cacttggagc tcacattgaa tgtgccggtt | 2760 |

| | |
|---|---|
| caattaagca accgacacgt cttacctatt taaagtttga gaataggtga aggatgtttc | 2820 |
| atcccccgaa cctctaatca ttcgctttac ccgataaaac tgatcaagct ccagctatcc | 2880 |
| tggggaaac ttcggaggga accagctact agatggttcg attagtcttt cgcccctata | 2940 |
| cccaagtctg aaaagcgatt tgcacgtcag cacatctacg agcctacgag gcattcttgt | 3000 |
| gacaatctcg tgcggctgct ggccctctgg aatgcctttg gaaattc | 3047 |

<210> SEQ ID NO 22
<211> LENGTH: 365
<212> TYPE: DNA
<213> ORGANISM: Chlamydomonas reinhardtii

<400> SEQUENCE: 22

| | |
|---|---|
| cacgcggccg gccggtggcc gtaggtcacg tagactacgc ttttgctagc gtacaacacc | 60 |
| taatgactga tgtaccttct ggtatgatct tgcgttacgc tcacgctaac ggcgccagct | 120 |
| tgttctttat tgtagtctat ttgcacgtat tgcgtggtat gtactacggt agcggcgctc | 180 |
| agccacgtga gatcgtctgg atcagtggtg tcgttatctt gttggtaatg attatcaccg | 240 |
| ccttcattgg ttatgtacta ccatggggcc aaatgtcttt ctgggtgct accgtaatta | 300 |
| ctagtttggc tactgccatt ccagtagtag gtaaacacat catgtactgg ttggccggcc | 360 |
| gaccg | 365 |

<210> SEQ ID NO 23
<211> LENGTH: 4404
<212> TYPE: DNA
<213> ORGANISM: Chlamydomonas reinhardtii

<400> SEQUENCE: 23

| | |
|---|---|
| ggacaattta cggcgtacgt gccctcatga tacagcctgt gcgccgcagg caacgggctc | 60 |
| cgcgcccttg ctccatggac acttcacggc gtacgtgccc tcatgatacg gcctgtgtgc | 120 |
| cgcaggcaac gggctccgcg cccttgcttc atggacaatg cgccgcgtac gtgttcttat | 180 |
| gatacggcct gtgcgccgca agcaacgggc tccgcaccct tgttttatgg acaattcacg | 240 |
| gcatacgtgc ccgtatgatg tgacctgtgt gccgcaagta acggcttcgc acccttgctt | 300 |
| ttgggtaata gatggcatac gtgcccttat gatacgacct gtgtgccgca agcaacgggc | 360 |
| tccacactct tgccgttgtgg attatagacg gcattgaaat gcttacgtgc cttcgttgta | 420 |
| catgcctttg cgttgtggac aatgtgtggt ctgagcgcca cgttcggata cggcgtgtgt | 480 |
| gccgccagca acaggctttg cgcctcgcat catgtgtctt gcgatatggc ccgtgtgccg | 540 |
| catgcaatta tgctgcctgc cctgtcgtta tggacgcttc gacttgttgc gtgccctgct | 600 |
| gcgtgccctg tcgcaatacg ccttgagtgt accgtgcacg gcaagcctgc gcctcgctat | 660 |
| tgcttcgtgt tgacaacgga gcgggcttac gtgatcatgc gtcaccctgt acgtcttgag | 720 |
| gtccgcacgc acatcatact atcacgcggc atcacccttg tagtttggct gacgcacccc | 780 |
| aagccaacct atatgcattc gatgtgtgcg ctaggcccaa gtgccgaatt tgttttttccg | 840 |
| gatatttcgc cctcagtgag cgatgtggag ttttgtgcag ttcggccagc atgctattgc | 900 |
| ccagccaata acaataccgc atgacgcata agcatgcctt cgtgccctgc accaggcatc | 960 |
| ggacgctgtg tcacgcagtg agcccgaccc tgcgcaacca acattttgtt gcgagatacg | 1020 |
| gtcggagctg ggattacagc ctgcctggtg gttttgatg gcgcccgtgt gttcggctgg | 1080 |
| gctgttgctg ctcgcggtgg ggcccaccac caagtcacgg cacccatccg ccctcccctc | 1140 |

```
ttgttggccc acccgcctgt acacatgcca gtcacccgct cgccatcctg tgaaagcggg  1200
tagccgactt ggcaagcgct tttcctgaca cttggcgcag gtttgagtgg gataccagaa  1260
tggtctgaat gtagttgttg gataaccagt acactgcggt gtgtagctgg ttagcgggag  1320
tgccgtgcat gaaacacgct actcgacccg ccatgcccgc gcgatggtac caccaaccgt  1380
tcaacccaga tccatgccgg ggtagcatcg accccacagt cagactgata gctcctatcc  1440
aggtgtcagg cgccatgtat gtatctgtgg acgcgtcaag ctggcttgtg ccgtagcgtt  1500
ggccgcctgt atggcacgcc cggcatctgt gtcacgttat ggcctcatgc ttaccgtagt  1560
cacgcggctt gcgtgctgtg cggcacgctc cctgccaatc cttcaggaca tgtatgcata  1620
catgttactt cgtcagagcc atagcagggg cagcgtgttc tgtcaatgcc tcatgaaccc  1680
agagacccaa gccaacgtac gcattagttc cgcaacgcac gtcaatgcca actgtatgtg  1740
tcgcctgccc actcgcgagt ggacgcctag ggtaccaacc ttggttccct tcagcccgg   1800
ccttacttca cccggcgggg caattactta tcaccgaagt gctaggagca gtgtgctata  1860
tgtcattact attaagtaag agcgtatggc gacacaggct cacatgtggg tagccaggct  1920
gacagtgccc tgcgggcttg gcagtcggca ggcatcccaa ctcagcccgg cctcctcaca  1980
gcagtaccac gacgtgcccg tacgtggtcg agtgcggagt tggctgccg gcgtggctgt   2040
atcatctctc acattggatg acccatccgc cactgctgtt cagtactggc acgtccctcg  2100
agtcgctcac ccaccggctc cgcccagcgt tcgctccctt tcgctgggcc ggggcccgtg  2160
gcgcatccaa cccgccatcg cggccccgag tgctccttat ttcctcccat cactacgcct  2220
tctatcacta tagatacatt gcgcgttcca cgcgtgccgg gtatccttca ccctccgcg   2280
ccgctcgacc aggccagcct tgctgggtt gctgaggtgt tacccttcat gttgccctcc   2340
ctgctattac ggtacacccc acagccgccg tggcgtacgg tatcggcacg tacgggacat  2400
tgtgtgcatg catccccgcg gcgtttggag gcaaacattc acgtgcgcgc ctgtcctgcg  2460
tccgccgggg tgatgctatc tatgggcgta cctactgctt gatgggtagt gactcttatg  2520
caagacactg caaatctcaa gcatggcacc tagctagcaa gaaagaaatt agtgttcgtg  2580
gccatgctgc acggctgggc atggctgccc gcatcctaca ccacgacggc gcgggtgaag  2640
ggcaggttgc cgcgcgtgac tcgcgtacgt aaaaccgctc tagtgttgca actcgcgcct  2700
tctcctgcgt ggcgcatgtt ggctagcctg tcccagcttc gagtcacgac gttgttatta  2760
ttcccaaggt tgttccgagc agcctaaacg tcaacacgtg ttatggcatg ccctggggg   2820
ccggtagaga gtaccgaggt ctccagtggt tcgtgccaac acgtgccaac acgcactgtt  2880
acctttcctg ggcacacgga cggccacagc tgcccagaag ccacacacct gaacaaggat  2940
gcatgtgttt ccctgtaacg ccccggccgtc gtctgcatgg ctggcgcacg cgggacaacg  3000
catgtgtgtt tctgtcgtgg ccattggtgc acctgatacg tttgtgagtc tggtatcatg  3060
gcccttgcaa agccagtcgt gttcctattg ctgcttgtct tctggtagtg accattggcc  3120
gcccatgacc gacggagtgt ggcgctgtca ggccccgcgt tggcgtcgcc ctgcgcctgc  3180
agcaggtgcc ggcggcgcct ccggcggcgc tcatccccgc gtgatggtgc tgctcgtgca  3240
gccaatatcc ccaagcacga agctcgttct attgaccgct gtcgagtgtg caactaggac  3300
cgtacgttcg tgcgcaagct aggcgatggg cggagcgctc cgcggtgttc gagacacatg  3360
atttcggtag cgcaagggca cgaacgccac cgccatcacc gccgaccgca ccttggtttg  3420
catgaccggc cgttgggccg agcgctttgc gagaagagct gcatacgcga agccaatcaa  3480
gcccagccac cagggctgcc gtcgcccgca ccatgacctc ccggcgttga ggactactac  3540
```

```
caaactctgg cagcactttc ggccactagt gcaacctcaa cacgggcggg ctggggcggg    3600
cacggcggac ttggtggggt tatcgggagc tgcgaggccg gaggtaggag gccgctgagg    3660
gccacgaatg agttgctagg ccgcttgagg catgagtgga ggctattgtc ggtttgagag    3720
attgggattg tcgtttgggg ccgtggcggt ttgtaacgct acacggcagt aaggagtcaa    3780
taagcgctga cttatcgcag cgcagtggag ataagtctag ttattgcgac gtaactgccg    3840
tgttgcgtta gagtcacgca cggcgcagga cgctcgggta cgtgcctgtg catggggccg    3900
aaccgagctg ggtcttgtac gcgtcaggag cacacggcgc cttatctgcc gttgtgcttc    3960
tgtactgtat ttcggatcgt ccctctgccg ggacggtgac aacccacccg cccccccctgg   4020 tgccgccgcg gattaatgtg gtggcacccg tgggcgctgc ggcgtgcgtg gttgtctgga    4080
ctctgctgct atcaggcact tcatacatgc gacacaccca gtactggcag cactttcggc    4140
cactagtgca acctcaacac gggcgggctg gggcgggcac ggcggacttg gtggggttat    4200
cgggagctgc gaggcggag gtaggaggcc gctgagggcc acgaatgagt tgctaggccg     4260
cttgaggcat gagtggaggc tattgtcggt ttgagagatt gggattgtcg tttggggccg    4320
tggcggtttg taacgctaca cggcagtaag gagtcaataa gatactaata gcggatgtcc    4380
gtggctcgac aggtcgactc accc                                          4404

<210> SEQ ID NO 24
<211> LENGTH: 214
<212> TYPE: DNA
<213> ORGANISM: Chlamydomonas reinhardtii

<400> SEQUENCE: 24
gggacgggca gaggaggcag ttgcctgcca actgcctagg caagtaaggt ggctgtatgg      60
cgtggcgtca cgatgaacat gacgtacgag tgtgtggctg gagcggagca agatcatttg    120
tacgcatgcg tggtgaagga tctcttgtct gcagccgacc atctcaaacc gcgatcaaga    180
tgagccgcac gccgcgtgcc ttactcgtgt cgct                                214

<210> SEQ ID NO 25
<211> LENGTH: 503
<212> TYPE: DNA
<213> ORGANISM: Chlamydomonas reinhardtii

<400> SEQUENCE: 25
atcccgaagg ggacaaattt atttattgtc ccgtaaggga aagtcgtgga gtatttaata     60
cagctttagt tgaaatcttc ggtgatgacg catgtcgtca aggtcaaagg acggcatggc    120
ccgcccggcg ttgtgcaccc tccctgctg tgcacagacg ctgttgcagt gaggagtgcc     180
actgtgccgg gtgcgccgcc gcagtaatgg ggtcccgcag ctccaggtac gagcgtcagc    240
ttcagcggcc agctgacgtg cgagcccagt agccattccc ctggactata atctgtgcgt    300
ctggcacgat ttcctcgtaa agcgcaaaat tctgccagcc catcctcctc aatcaggatc    360
gtcctggcca cgtgggttca ttcctgcctt tctacctcgt gcacccgcag ccctgcgaca    420
aagctcacag ctccagggcg ctgatgcctg cgtgcagttg ctccgcggcc tgctgctgcg    480
ggcccgagca cgcaaaaggg ggg                                           503

<210> SEQ ID NO 26
<211> LENGTH: 2690
<212> TYPE: DNA
<213> ORGANISM: Chlamydomonas reinhardtii
```

```
<400> SEQUENCE: 26
aagaacatgc cactcaggcg ccttgtcaca tggggggtgc cacccagcca accgcacacc      60
acgcctgtca ctctcagccc tgtgtggacc tctttcacat cttcacatgt ccctttttgtc    120 aaacatgttt gtgatgcaac cgcaagctgg cagctgcagt gccaccacag cccttgcagt     180
ccaacaagtg gctttgcatg tcaggacaag tgcgcattcc cccccgccct cccctctagt     240
ggggcagggc ctgctagtat catgcaaact gtcaagtaat gtgcagccat gctgagcaca     300
ttcaatttgc accatatgtg aaacgatggg ctttgggagt gcaagcagca gcagccacag    360
catgttggcg agtcaagtcc tcttgcaggc ctgcagacca ccagtcat gacaagtccg       420 caacatctgc acctcagcga ggtccagctc atgccagcaa tacaacagca gtcgctatat    480
gtattgaacc gattgccggg cctaacggct gcgtggctgg actgctgcac tcactcacgt    540
ggcccctggt gcagggtggc ctaaatcagg gttttcaaggg gttttgcagg gtttggaaag   600
agtgacatgt cagaaatgat ttgtacagtg tatttaggtg ttttatatct tagatgatca    660
ttggaagcat tggtgggtga ctgggaggag gtttgggcac ataagtctga ctttgtgcac    720
cccatgactt acttggcaca gtgcacataa gtatgcagac agcctagcac ttccatggtc    780
ccgcacccca ctggggcttc tctttcacca ggcctaactg agccttgtac tgtgctgtgg    840
tgtagattta cttgttaggc atgcatggta tgcaagaaca tgccactcag gcgccttgtc    900
acatgggggg tgccacccag ccaaccgcac accacgcctg tcactctcag ccctgtgtgg   960
acctctttca catcttcaca tgtccctttt gtcaaacatg tttgtgatgc aaccgcaagc    1020
tggcagctgc agtgccacca cagcccttgc agtccaacaa gtggctttgc atgtcaggac    1080
aagtgcgcat tccccccccgc cctccctct agtggggcag ggcctgctag tatcatgcaa    1140
actgtcaagt aatgtgcagc catgctgagc acattcaatt tgcaccatat gtgaaacgat    1200
gggctttggg agtgcaagca gcagcagcca cagcatgttg gcgagtcaag tcctcttgca    1260
ggcctgcaga ccacaccagt catgacaagt ccgcaacatc tgcacctcag cgaggtccag    1320
ctcatgccag caatacaaca gcagtcgcta tatgtattga accgattgcc gggcctaacg    1380
gctgcgtggc tggactgctg cactcactca cgtggcccct ggtgcagggt ggcctaaatc    1440 agggttttcaa ggggttttgc agggtttgga aagagtgaca tgtcagaaat gatttgtaca    1500
gtgtatttag gtgttttata tcttagatga tcattggaag cattggtggg tgactgggag    1560
gaggtttggg cacataagtc tgactttgtg caccccatga cttacttggc acagtgcaca    1620
taagtatgca gacagcctag cacttccatg gtcccgcacc ccactggggc ttctctttca    1680
ccaggcctaa ctgagccttg tactgtgctg tggtgtagat ttacttgtta ggcatgcatg    1740
gtatgcaaga acatgccact caggcgcctt gtcacatggg gggtgccacc cagccaaccg    1800
cacaccacgc ctgtcactct cagccctgtg tggacctctt tcacatcttc acatgtccct    1860
tttgtcaaac atgtttgtga tgcaaccgca agctggcagc tgcagtgcca ccacagccct    1920
tgcagtccaa caagtggctt tgcatgtcag gacaagtgcg cattcccccc cgccctcccc    1980
tctagtgggg cagggcctgc tagtatcatg caaactgtca gtaatgtgc agccatgctg     2040 agcacattca atttgcacca tatgtgaaac gatgggcttt gggagtgcaa gcagcagcag    2100
ccacagcatg ttggcgagtc aagtcctctt gcaggcctgc agaccacacc agtcatgaca    2160
agtccgcaac atctgcacct cagcgaggtc cagctcatgc cagcaataca acagcagtcg    2220
ctatatgtat tgaaccgatt gccgggccta acggctgcgt ggctggactg ctgcactcac    2280
tcacgtggcc cctggtggtg cgggcaaaca ttttatttttt cacacagacc gtgttcgagg    2340
```

| | |
|---|---|
| attcagtgta agtcttagga aaagttagaa gataatacat aagattagct tcacttatcg | 2400 |
| ggaaaatctg agaaggtgac gtccatgctc ggcgagttga ccagcgagca gtcgcaacca | 2460 |
| ttctggctcg gtgtctggta aacgtatcgg catttaaaat cattcaatgc attaaatatg | 2520 |
| tgcccgcaat catgcatata tgctctgtgc agctgtcaaa aacgatttca atggagtttc | 2580 |
| tttcacttag gtcaatcctt tctcgcggct cctttatcaa ctgttaatag catgagattt | 2640 |
| caatgccaaa ccgcgttttg gcggctggac tggaagctga agggcagacc | 2690 |

<210> SEQ ID NO 27
<211> LENGTH: 2887
<212> TYPE: DNA
<213> ORGANISM: Chlamydomonas reinhardtii

<400> SEQUENCE: 27

| | |
|---|---|
| ttgactcgtt tgacagctgc aacttgtaag gcttacctca gccaagataa ttacactgca | 60 |
| tgtatcgact gtgaatgtgg catatttcaa cttggcgtga ccttgaccat gaccgccgaa | 120 |
| gctcctcggc caacttcgcc gagcgaggcg atgtcacacc caccaacacc agctagcggg | 180 |
| agcacgtaag cactgcatac cattcattgg tctctttttt atctgttgcg tttattaccg | 240 |
| ccatgtaaga tggcctgtat caaaatataa ttgtttgctc tcaccaccag gggccacgtg | 300 |
| agtgagtgca gcagtccagc cacgcagctg tttggcctag ctattgatta tatacatata | 360 |
| gcgactgccg ttgtattgct ggcatgagct ggacctcgct gaggtgcagc ggttgccgac | 420 |
| ttgtcgccac tggtgtagtc tgcaggcctg caagaggact tgatgcacca gtgccgtggc | 480 |
| tgctttcact tgtgctccca agcccatcg ttcacatgtg gtgcaaatga atgtcttca | 540 |
| gcatggctgc acattacttg acagcctgca tgataccagc aggccctgac ccactagagg | 600 |
| ggaggggagg aatgcacact tgtcctgata tgcagagcca cttgatgggc tgcaagggct | 660 |
| ggcaccctgg ctgccagctt gtggttgcat cacaaacatg tccggcaaca tggacacttg | 720 |
| aagatgtgaa agagctccca cagggctgag actgacaggg ggtgtgtgtg attggctggg | 780 |
| ctgcacccgt cccctgtggg gacaagggga ctgagtggta tgtgcgtgca taccatgcat | 840 |
| gcctcacatg tcaaagtgca ccacagcaca gtacaaggct cagttatacc tggcaagtga | 900 |
| gaagccccag tgtgtgtatg tggaaccctg ggagtgtgat tccttctgca tacttgtgtg | 960 |
| tgctgtgcgt ggcaagtaag cagtgggagc acaaagtcat tgctatgtgc ccaaatctca | 1020 |
| tcacggtcac ccacaaggag ttcaaacaat tattctagtt atagttagct gaattatact | 1080 |
| gtgcaaatca tttcggacat gtcacacttt ccaaatcctg caaaaccccca taaaaccctg | 1140 |
| atttaggcca ccctgctacc aggggccacg tgagtgagtg cagcagtcca gccacgcagc | 1200 |
| tgtttggcct agctattgat tatatacata tagcgactgc cgttgtattg ctggcatgag | 1260 |
| ctggacctcg ctgaggtgca gcggttgccg acttgtcgcc actggtgtag tctgcaggcc | 1320 |
| tgcaagagga cttgatgcac cagtgccgtg gctgctttca cttgtgctcc caagcccat | 1380 |
| cgttcacatg tggtgcaaat gaaatgtctt cagcatggct gcacattact tgacagcctg | 1440 |
| catgatacca gcaggccctg acccactaga ggggagggga ggaatgcaca cttgtcctga | 1500 |
| tatgcagagc cacttgatgg gctgcaaggg ctggcaccct ggctgccagc ttgtggttgc | 1560 |
| atcacaaaca tgtccggcaa catggacact tgaagatgtg aaagagctcc cacagggctg | 1620 |
| agactgacag gcggtgtgtg tgattggctg ggctgcaccc gtccctgtg gggacaaggg | 1680 |
| gactgagtgg tatgtgcgtg cataccatgc atgcctcaca tgtcaaagtg caccacagca | 1740 |

```
cagtacaagg ctcagttata cctggcaagt gagaagcccc agtgtgtgta tgtggaaccc    1800
tgggagtgtg attccttctg catacttgtg tgtgctgtgc gtggcaagta agcagtggga    1860
gcacaaagtc attgctatgt gcccaaatct catcacggtc acccacaagg agttcaaaca    1920
attattctag ttatagttag ctgaattata ctgtgcaaat catttcggac atgtcacact    1980
ttccaaatcc tgcaaaaccc cataaaaccc tgatttaggc caccctgcta ccaggggcca    2040
cgtgagtgag tgcagcagtc cagccacgca gctgtttggc ctagctattg attatataca    2100
tatagcgact gccgttgtat tgctggcatg agctggacct cgctgaggtg cagcggttgc    2160
cgacttgtcg ccactggtgt agtctgcagg cctgcaagag gacttgatgc accagtgccg    2220
tggctgcttt cacttgtgct cccaaagccc atcgttcaca tgtggtgcaa atgaaatgtc    2280
ttcagcatgg ctgcacatta cttgacagcc tgcatgatac cagcaggccc tgacccacta    2340
gaggggaggg gaggaatgca cacttgtcct gatatgcaga gccacttgat gggctgcaag    2400
ggctggcacc ctggctgcca gcttgtggtt gcatcacaaa catgtccggc aacatggaca    2460
cttgaagatg tgaaagagct cccacagggc tgagactgac aggcggtgtg tgtgattggc    2520
tgggctgcac ccgtcccctg tggggacaag gggactgagt ggtatgtgcg tgcataccat    2580
gcatgcctca catgtcaaag tgcaccacag cacagtacaa ggctcagtta cctggcaa     2640 gtgagaagcc ccagtgtgtg tatgtggaac cctgggagtg tgattccttc tgcatacttg    2700
tgtgtgctgt gcgtggcaag taagcagtgg gagcacaaag tcattgctat gtgcccaaat    2760
ctcatcacgg tcacccacaa ggagttcaaa caattattct agttatagtt agctgaatta    2820
tactgtgcaa atcatttcgg acatgtcaca ctttccaaat cctgcaaaac cccataaaac    2880
cctgatt                                                               2887
```

<210> SEQ ID NO 28
<211> LENGTH: 2541
<212> TYPE: DNA
<213> ORGANISM: Chlamydomonas reinhardtii

<400> SEQUENCE: 28

```
actccggcga cctccagctt atgccaagca tacaacggca gtcactgtat gtatataatc      60
gatagccggg ccaaacggct gcgtggctgg actgctgcac tcactcacgt ggcccctggc     120
cccggggtcg cctaaatggg ggttttaagg ggttttgagg gttttgacaa gtgacacatg     180
tcggaaatga tcggcacagt gtatttaagt gtattatatc taagatgatc attggaagca     240
ttggtgagtg actgggatga ggttggggca cataagtctg gctttgtgca ccccacggct     300
tacttggcac agtgcacata agtatgtaga cagcccagca cttccatggt cccacatgca     360
caccccactg gggcttctct cttgccaggc ctaatctagc cttgtactgt gctgtggtgt     420
aaattgacat gttaggcatg catggtatgc aagcacatgc cacttaggcc ccttgtcccc     480
acatgggcgg tgccacccag ccaaccgcac accctgcctg tcactgtcag ccctgtgtgg     540
aactctttca catcttcaca tgtccattat gtctaacatg tttgtgatgc aaccgcaagc     600
cggcagctgg ggtgccaccg cagcccttgc agttcatcaa gtggctttgc atgtcaggac     660
aagtgcgcat tcctcccctc ccctctagtg gggcagggcc tgctaggatc atgcaagctg     720
tcaagtaatg tgcagccatg ctgagcacat tcagtttgca ccctatgtga atgatgggct     780
ttgggagtgc aagtggaatc agccacagac caatgccaag aggggcatgc ctcctgcccc     840
ttgcaggcct gcggaggcgc caagtgtgcg accgcttcac tccggcgacc tccagcttat     900
gccaagcata caacggcagt cgctgtatgt atataatcga tagccgggcc aaacggctgc     960
```

```
gtggctggac tgctgcactc actcacgtgg cccctggccc cggggtcgcc taaatggggg   1020
ttttaagggg ttttgagggt tttgacaagt gacacatgtc ggaaatgatc ggcacagtgt   1080
atttaagtgt attatatcta agatgatcat tggaagcatt ggtgagtgac tgggatgagg   1140
ttggggcaca taagtctggc tttgtgcacc ccacggctta cttggcacag tgcacataag   1200
tatgtagaca gcccagcact tccatggtcc cacatgcaca ccccactggg gcttctctct   1260
tgccaggcct aatctagcct tgtactgtgc tgtggtgtaa attgacatgt taggcatgca   1320
tggtatgcaa gcacatgcca cttaggcccc ttgtccccac atgggcggtg ccacccagcc   1380
aaccgcacac cctgcctgtc actgtcagcc ctgtgtggaa ctctttcaca tcttcacatg   1440
tccattatgt ctaacatgtt tgtgatgcaa ccgcaagccg gcagctgggg tgccaccgca   1500
gcccttgcag ttcatcaagt ggcttttgcat gtcaggacaa gtgcgcattc ctcccctccc   1560
ctctagtggg gcagggcctg ctaggatcat gcaagctgtc aagtaatgtg cagccatgct   1620
gagcacattc agtttgcacc ctatgtgaat gatgggcttt ggagtgcaa gtggaatcag    1680 ccacagacca atgccaagag gggcatgcct cctgccccctt gcaggcctgc ggaggcgcca   1740
agtgtgcaac cgcttcactc cggcgacctc cagcttatgc caagcataca acggcagtcg   1800
ctgtatgtat ataatcgata gccgggccaa acggctgcgt ggctggactg ctgcactcac   1860
tcacgtggcc cctggccccg ggtcgccta aatgggggtt ttaaggggtt ttgagggttt    1920
tgacaagtga cacatgtcgg aaatgatcgg cacagtgtat ttaagtgtat tatatctaag   1980
atgatcattg gaagcattgg tgagtgactg ggatgaggtt ggggcacata agtctggctt   2040
tgtgcacccc acggcttact tggcacagtg cacataagta tgtagacagc ccagcacttc   2100
catggtccca catgcacacc ccactggggc ttctctcttg ccaggcctaa tctagccttg   2160
tactgtgctg tggtgtaaat tgacatgtta ggcatgcatg gtatgcaagc acatgccact   2220
taggcccctt gtccccacat gggcggtgcc acccagccaa ccgcacaccc tgcctgtcac   2280
tgtcagccct gtgtggaact cttttcacatc ttcacatgtc cattatgtct aacatgtttg   2340
tgatgcaacc gcaagccggc agctggggtg ccaccgcagc ccttgcagtt catcaagtgg   2400 cttttgcatgt caggacaagt gcgcattcct cccctcccct ctagtggggc agggcctgct   2460
aggatcatgc aagctgtcaa gtaatgtgca gccatgctga gcacattcag tttgcaccct   2520
atgtgaatga tgggctttgg g                                              2541
```

<210> SEQ ID NO 29
<211> LENGTH: 2270
<212> TYPE: DNA
<213> ORGANISM: Chlamydomonas reinhardtii

<400> SEQUENCE: 29

```
cgacctccag cttatgccaa gcatacaacg gcagtcgctg tatgtatata atcgatagcc    60
gggccaaacg gctgcgtggc tggactgctg cactcactca cgtggcccct ggccccgggg   120
tcgcctaaat gggggtttta aggggttttg agggttttga caagtgacac atgtcggaaa   180
tgatcggcac agtgtattta agtgtattat atctaagatg atcattggaa gcattggtga   240
gtgactggga tgaggttggg gcacataagt ctggctttgt gcaccccacg gcttacttgg   300
cacagtgcac ataagtatgt agacagccca gcacttccat ggtcccacat gcacacccca   360
ctggggcttc tctcttgcca ggcctaatct agccttgtac tgtgctgtgg tgtaaattga   420
catgttaggc atgcatggta tgcaagcaca tgccacttag gccccttgtc cccacatggg   480
```

-continued

```
cggtgccacc cagccaaccg cacaccctgc ctgtcactgt cagccctgtg tggaactctt    540
tcacatcttc acatgtccat tatgtctaac atgtttgtga tgcaaccgca agccggcagc    600
tggggtgcca ccgcagccct tgcagttcat caagtggctt tgcatgtcag acaagtgcg     660
cattcctccc ctcccctcta gtggggcagg gcctgctagg atcatgcaag ctgtcaagta    720
atgtgcagcc atgctgagca cattcagttt gcaccctatg tgaatgatgg gctttgggag    780
tgcaagtgga atcagccaca gaccaatgcc aagaggggca tgcctcctgc ccttgcagg     840
cctgcggagg cgccaagtgt gcaaccgctt cactccggcg acctccagct tatgccaagc    900
atacaacggc agtcgctgta tgtatataat cgatagccgg ccaaacggc tgcgtggctg     960
gactgctgca ctcactcacg tggcccctgg ccccggggtc gcctaaatgg gggttttaag   1020
gggttttgag ggttttgaca agtgacacat gtcggaaatg atcggcacag tgtatttaag   1080
tgtattatat ctaagatgat cattggaagc attggtgagt gactgggatg aggttggggc   1140
acataagtct ggctttgtgc accccacggc ttacttggca cagtgcacat aagtatgtag   1200
acagcccagc acttccatgg tcccacatgc acaccccact ggggcttctc tcttgccagg   1260
cctaatctag ccttgtactg tgctgtggtg taaattgaca tgttaggcat gcatggtatg   1320
caagcacatg ccacttaggc cccttgtccc cacatgggcg tgccaccca gccaaccgca   1380
caccctgcct gtcactgtca gccctgtgtg gaactctttc acatcttcac atgtccatta   1440
tgtctaacat gtttgtgatg caaccgcaag ccggcagctg ggtgccacc gcagcccttg   1500
cagttcatca gtggctttg catgtcagga caagtgcgca ttcctcccct cccctctagt   1560
ggggcagggc ctgctaggat catgcaagct gtcaagtaat gtgcagccat gctgagcaca   1620
ttcagtttgc accctatgtg aatgatgggc tttgggagtg caagtggaat cagccacaga   1680
ccaatgccaa gaggggcatg cctcctgccc cttgcaggcc tgcggaggcg ccaagtgtgc   1740
aaccgcttca ctccggcgac ctccagctta tgccaagcat acaacggcag tcgctgtatg   1800
tatataatcg atagccgggc caaacggctg cgtggctgga ctgctgcact cactcacgtg   1860
gcccctggtg gtgagagcaa acatttatat tttgatacag gccgtgtttg aggccgctgt   1920
taattgcagt aaataatcaa gaattcaaag catacgatca gcctctcaag tcttgcatat   1980
cgatcatggt aaggcatgct tagcagcgag ctcacggcca tgttgactcg gtcgcgcggg   2040
gtcaactgat cagcattcta agttctttc tatcgctctt atcgtcaatc attcgttctt   2100
tatatgcggc tgttgtgact atgcagctgt caaattgaca aaacgagcat aaaattgtct   2160
cagccgagct tggcctttct cagtcgccgc ttttcatttc ctgccaatcg tcagcattta   2220
tccaagtaac agatcttcgt tatactcgac aggattgtgg gcaacaaggg               2270
```

<210> SEQ ID NO 30
<211> LENGTH: 40
<212> TYPE: DNA
<213> ORGANISM: Chlamydomonas reinhardtii

<400> SEQUENCE: 30

```
cagtcatgag accttcaggc gttgaaacca taacaacaca                            40
```

<210> SEQ ID NO 31
<211> LENGTH: 224
<212> TYPE: DNA
<213> ORGANISM: Chlamydomonas reinhardtii

<400> SEQUENCE: 31

```
caggaaggca cccaacacga gtaacgtcag caggaccacg tggcaaacca tgtacaacac    60
```

```
ggttgaaagc ccggaagccg taagcagcac ctagtacttg catacgcag aacacgtaag    120 caagcaactc gtgtacagcg aagatgctta ccatgcacaa tacctcggca atgaagttag   180
ggaatagtgg gaaggccaag ttacccaaag taaacaggaa gacg                    224
```

<210> SEQ ID NO 32
<211> LENGTH: 5623
<212> TYPE: DNA
<213> ORGANISM: Chlamydomonas reinhardtii

<400> SEQUENCE: 32

```
gcgcggcagg gtggtgtcgc gcccatgctg ccccgcttgc ggggcttgtt cccggccggt    60
ctctgatggc tatggtgtag tcctatgaat tatctgtgcg cgggttggtg cccggcgaat   120
ttctgttgca tggggcctgc gcgcatggcg tgcccctcgg ggggtaatcg cgctcggatc   180
acataagggc cgctcgaact aaaatttgcc actcatacaa taattacagc tactgtatgt   240
ctactcgccc atgtgtagca cgcttgggcg ctagctcgca tttgagagaa ccaacaccct   300 tgctccccc attttcgtca aaccaacat tctgcaaatt gatactgtag ttctcactct     360
gagtagcagc tacggctgtc gttcccgtgg ttgagagccc ttaccgttgt ggttctactg   420
tggaggcagc gggcgtagcg accgggcgca agcagccgag cgggcggtgg agaaccagtc   480
gcaaaagtct gcggaattgt gggatccagt gaaggcgggt tcgtgtgtcg gttgtgacag   540
agcgaggtga gcccgagcgc gaagcccagc tggcgctaca acctttgggt caaaagtcaa   600
cgatagccgc tgcgggccag gcgcgtggcc tcgctgggtc gctggttgca cccagcatgg   660
cgtttcgcaa gcttaactgg ttttggttgc aagttccttc gcggcgatgc tccaattgcg   720
ccctatgcac tggttgcagg tcgtcggcgg tgttccggcg tcatgcttcc gtggcaaaat   780
gtatgatgcg ctccggtcat cgagtcgcat gtgccggagg gaccaatagc aggcagcgca   840
gcttagaatt gcaatcggtg agtatatgta gacagccact actaacgtgt atcattagcg   900
accagtcata cttgtggcgc gtcggcacgc cgcacgcgtg cccgccgtca ctcacccca    960 aggggtctgt tcccgacact cgcgccagcc gtaccgatgc gccagcattt cgcgcaacca  1020
taccatctga cggagcgcta tgcgcaatca tcgcttaccg aatgccggct caggttccta  1080
tccgcaactg ctccatcccc actaagttac ggtactcact tcccctcctt cacaccctt   1140 cctgcctgcc tccaccctca gcgaaacttc ttggccggcc agtgcccgcc cgccttcagc  1200
accgccggca acgtgtgtgc cagcatccgc ttcatacagt cacgcacaaa ctgtggcgtg  1260
atgaccttct gaaccaccct tctccatctcg tccaggtagg gctgcagggg gtcctcgcca  1320
gcctcggtgg gccgccgtgc gttgcagaac tgccgcatga cgagggcaac ggccgcgtgc  1380
gactgctcca ctgggcagtg catgtcgccg ctgtacgtgg gaagcttcat gaaattggcc   1440
ttagtgacgc ccacaccacg gaagtcagca atctcgccgt tgccgtggca tgccgggttg   1500
tcccatgaca cgtagggctt gatagggcc acgggcgggg gtggcggcgg cttcctctta   1560
ccccgccggc cctgcttctg cgcggccttc accgccgcgg tttgctttgc agccagcctt  1620
gcagccttct cccggaacgc gcccagcatg cgccctatgt acttaacaaa ctccgccttc   1680
gtgatgaacc ttgcatcctt ccccgccagg gtctgcggtg gtgacaggca gtggcgggcg   1740
gcagcttgag catggcgcgt ggaggacaca accggcggcg cttcccaccc tctgtggcag   1800
cgcgatacag ccccctgaac cgggagccgc taaacgcacg ggggacagat gaccggcggc   1860
ccgtgctgtg gaggctgcag tgtgggtgct ttgtctacaa ggcacggcac acagtggcta  1920
```

```
acagtattcg gcgatgtgcc ccgcacgcac ccagctgctt caactgcacc tatcacacct    1980
ccggccgagg tgcaagtgag gccgcacagc gcgcgtttcg catgctgatt gaccttgcgc    2040
ggcggctggg ggaggcgtgt acggtggtgt gggaggcgcg ggtggttgag gggtgtggcc    2100
ccttcgactt ttggctgtgg gagtgggggtg tggtggttga agtggatggc atgcagcaca    2160
cggataccce gcatcacggc acggaagcgc aagcacagtg gctggtggat cggtggaagg    2220
aagcagctgc tgttcgcaag cggctgcatg tggcgcggtt gcatgtgatg gacatggtgt    2280
gctgggaggc cgtggttgcg cgtgcactgt gtgctgctcg taacggcatt ccgccgtgcg    2340
tgcactacag cgactactac ctgcggcctg tgattacaca gtcatgagct cccaacgcac    2400
ctggtactgt agctcgggtg gcggcgtgta ggccctgcct gtggtgccgg caacaggctc    2460
ccatcgcacg acgccgaagg cagggcacac ggtgatgatg tacttgatgg tgttgggtcg    2520
tgatgatccg cagcggtagt cctcaatggt gatgctctgc ccgcgcgggc ctgcagtcca    2580
ggcggtgtag tcggttgggt tgcagatgaa ggtcttttcg tcggtcatgg cgaaaccgtt    2640
gaagatggtt aagttgagcc atgcgtcgct ttcaaactcc gctgtgccaa tgtctggtgg    2700
caagggaaag gcgccatcgc tgacaccgta ctccctttca gcctccacgg ctgagaccat    2760
cttcacgcct ggagcattgg ggttgacaag cttgcgcaac cacgctgctg agcggtccag    2820
ccggtcaccc cactgctcgg ggctgaggaa ggggcggtgc tccacctta agttctttg    2880
gagggttgga tcgtagtgtt gcatggagcg ccacagggga ttgaaagtga tcttgtggga    2940
tttgagaacg tcttgaaagg gcgcgtcgtg ctcgtacttg gcggcagagt catagtggac    3000
gctcttgacg tggtcgacca gggttttcag gatggggtcc gacaccgtgc gcggccggcc    3060
tgggcgtggc ttgggctctg tcccgccagt gtgcacgtag cgcacgtacc acttcttaat    3120
ctgctctgcc atatgcttgg gtgatgcctc ccatggtgtg taatcaactg gctgcgggaa    3180
gatctctggg catgcctcgc gtgccttgaa ctccgccacg gcaatggggc cccagcgctg    3240
aggtgtggtg ccacgtgtgg taagcccaga acgtaacag gcctgaatgg caatggcggc    3300
tactagcgca gctaccattc gccgccatgc gtccgttgac aggttggaat agatggtgcc    3360
agtggtagca tccatccttt cacctgtgtg cgtcggtgat ggggtttgcg ggtgcgtggt    3420
gagagagggg gacaggtgca cgctatcatg aaccaggcta aattcgtaat aattcgcccc    3480
ccatgcgcca caaaccccac ccaacctgaa accccttagt tccccagatc catttccacg    3540
tcactgtgtc gcacaattcc gccgaccttt gcgcaccca gcatatgtgt gcccgcggtt    3600
tccaatgctc tattgaatgc accaaaagcc agcccaggcc ctgcgtccta gggcccaaac    3660
gagctcctcc gtacaatgtt tgctcgcaca ctccggcgca cgcgattagg tgtcgcgcgc    3720
tactgtatgg tagcccttgt gtcgcacaag tggttggagc gtgtttgggg tgagttggcg    3780
cggcagggtg gtgtcgcgcc catgctgccc cgcttgcggg gcttgttccc ggccggtctc    3840
tgatggctat ggtgtagtcc tatgaattat ctgtgcgcgg gttggtgccc ggcgaatttc    3900
tgttgcatgg ggcctgcgcg catggcgtgc ccctcggggg gtaatcgcgc tcggatcaca    3960
taagggccgc tcgaactaaa atttgccact catacaataa ttacagctac tgtatgtcta    4020
ctcgcccatg tgtagcacgc ttgggcgcta gctcgcattt gagagaacca acacccttgc    4080
tcccccatt ttcgtcaaaa ccaacattct gcaaattgat actgtagttc tcactctgag    4140
tagcagctac ggctgtcgtt cccgtggttg agagccctta ccgttgtggt tctactgtgg    4200
aggcagcggg cgtagcgacc gggcgcaagc agccgagcgg gcggtggaga accagtcgca    4260
aaagtctgcg gaattgtggg atccagtgaa ggcgggttcg tgtgtcggtt gtgacagagc    4320
```

| | |
|---|---|
| gaggtgagcc cgagcgcgaa gcccagctgg cgctacaacc tttgggtcaa aagtcaacga | 4380 |
| tagccgctgc gggccaggcg cgtggcctcg ctgggtcgct ggttgcaccc agcatggcgt | 4440 |
| ttcgcaagct taactggttt tggttgcaag ttccttcgcg gcgatgctcc aattgcgccc | 4500 |
| tatgcactgg ttgcaggtcg tcggcggtgt tccggcgtca tgcttccgtg gcaaaatgta | 4560 |
| tgatgcgctc cggtcatcga gtcgcatgtg ccggagggac caatagcagg cagcgcagct | 4620 |
| tagaattgca atcggtgagt atatgtagac agccactact aacgtgtatc attagcgacc | 4680 |
| agtcatactt gtggcgcgtc ggcacgccgc acgcgtgccc gccgtcactc accccaaagg | 4740 |
| ggtctgttcc cgacactcgc gccagccgta ccgatgcgcc agcatttcgc gcaaccatac | 4800 |
| catctgacgg agcgctatgc gcaatcatcg cttaccgaat gccggctcag gttcctatcc | 4860 |
| gcaactgctc catccccact aagttacggt actcacttcc cctccttcac acccttcct | 4920 |
| gcctgcctcc accctcagcg aaacttcttg gccggccagt gcccgcccgc cttcagcacc | 4980 |
| gccggcaacg tgtgtgccag catccgcttc atacagtcac gcacaaactg tggcgtgatg | 5040 |
| accttctgaa ccaccttctc catctcgtcc aggtagggct gcaggggggtc ctcgccagcc | 5100 |
| tcggtgggcc gccgtgcgtt gcagaactgc cgcatgacga gggcaacggc cgcgtgcgac | 5160 |
| tgctccactg ggcagtgcat gtcgccgctg tacgtgggaa gcttcatgaa attggcctta | 5220 |
| gtgacgccca caccacggaa gtcagcaatc tcgccgttgc cgtggcatgc cgggttgtcc | 5280 |
| catgacacgt agggcttgat aggggccacg ggcgggggtg gcggcggctt cctcttaccc | 5340 |
| cgccggccct gcttctgcgc ggccttcacc gccgcggttt gctttgcagc cagccttgca | 5400 |
| gccttctccc ggaacgcgcc cagcatgcgc cctatgtact aacaaactc cgccttcgtg | 5460 |
| atgaaccttg catccttccc cgccagggtc tgcggtggtg acaggcagtg gcgggcggca | 5520 |
| gcttgagcat ggcgcgtgga ggacacaacc ggcggcgctt cccaccctct gtggcagcgc | 5580 |
| gatacagccc cctgaaccgg gagccgctaa acgcacgggg gac | 5623 |

<210> SEQ ID NO 33
<211> LENGTH: 2347
<212> TYPE: DNA
<213> ORGANISM: Chlamydomonas reinhardtii

<400> SEQUENCE: 33

| | |
|---|---|
| catctgatgt attatctcct agcgtactga gatattgaca aagcatcctc aaacacggct | 60 |
| tgtacagaaa tataaatgtt tgcccgcacc accaggggcc acgtgagtga gtgcagcagt | 120 |
| ccagccacgc aaccgtttga ccaatctatt gcttatacgc atatagcaac tgccgttgta | 180 |
| tggttggcat gagctggagc ttgctggggt ggagcggttg ccaacttggc accacagcag | 240 |
| gcgacacgcc aacatgctgt ggctgcttcc agttgcatcc ccaaggccaa tcaacatctg | 300 |
| gtgcatgaga ggggaggcaa gctgggcaca cttgtcctgt tgtgcagagc tgcatggggc | 360 |
| actgcaaggg ctggcaccac cacgcttagc ttgtggttgc atcacaaaca gtcaggcaac | 420 |
| atgtacatac acgaatatgc aagggtcttg cacacgggtg agtgaggcag gcaggttgga | 480 |
| tggttagttg tgcagcatgg ccccaacatg agaacaaggg gaatgggcag cacatgcatg | 540 |
| cacaccatgg ttgcgtgatc tgtcaacatg caccatagca caatgcagta ttcagtataa | 600 |
| tctgggtgaa tgagaagcca cagtggtgca aggtcacagg accatataag ccgcattcct | 660 |
| tccccctactt gcgccctgca actgtaacaa gaggattgtc gcctaggttg acaagggagc | 720 |
| gagtctcccg ttacagtcct cccccccctgg aagcgaacgt cctcgtgaga ccaccagcgc | 780 |

| | |
|---|---|
| atccgtagat gttataggct cactgcaggc gcggggtggg tttactgcct ttggcccagt | 840 |
| tgcgctgttg cctcgctctc acgggtcatc cacctcaggg caaggagggt ttaaccctct | 900 |
| tgtgcactag ttcggaccca tgcacccatc cgggatcgaa cccgggacct aacagtcag | 960 |
| ggtgactcct ggcattttgc accaatgtaa caagaaaatt gtcgcctagg ttgacaaggg | 1020 |
| agcgagtctc ccgttacagc aacaaggaag cagtggggca cacaaagtca ttgctatctg | 1080 |
| cccaaatcac accatgccac ccccacaagt gcttccacca atcattctag ctataattat | 1140 |
| gctaattata cggtctatac aatttctgac atgtcacaca tttcaaacct ttcaaaaccc | 1200 |
| ctcaaaaccc ccctttaggc caccccgcta ccagggcca cgtgagtgag tgcagcagtc | 1260 |
| cagccacgca accgtttgac caatctattg cttatacgca tatagcgact gccgttgtat | 1320 |
| ggttggcatg agctggagct tgctggggtg gagcggttgc caacttggca ccacagcagg | 1380 |
| cgacacgcca acatgctgtg gctgcttcca gttgcatccc caaggccaat caacatctgg | 1440 |
| tgcatgagag gggaggcaag ctgggcacac ttgtcctgtt gtgcagagct gcatggggca | 1500 |
| ctgcaagggc tggcaccacc acgcttagct tgtggttgca tcacaaacag tcaggcaaca | 1560 |
| tgtacataca cgaatatgca agggtcttgc acacgggtga gtgaggcagg caggttggat | 1620 |
| ggttagttgt gcagcatggc cccaacatga gaacaagggg aatgggcagc acatgcatgc | 1680 |
| acaccatggt tgcgtgatct gtcaacatgc accatagcac aatgcagtat tcagtataat | 1740 |
| ctgggtgaat gagaagccac agtggtgcaa ggtcacagga ccatataagc cgcattcctt | 1800 |
| cccctacttg cgccctgcaa ctgtaacaag aggattgtcg cctaggttga caagggagcg | 1860 |
| agtctcccgt tacagtcctc ccccctgga agcgaacgtc ctcgtgagac caccagcgca | 1920 |
| tccgtagatg ttataggctc actgcaggcg cggggtgggt ttactgcctt tggcccagtt | 1980 |
| gcgctgttgc ctcgctctca cgggtcatcc acctcagggc aaggagggtt taaccctctt | 2040 |
| gtgcactagt tcggacccat gcacccatcc gggatcgaac ccggacctc aacagtcagg | 2100 |
| gtgactcctg gcattttgca ccaatgtaac aagaaaattg tcgcctaggt tgacaaggga | 2160 |
| gcgagtctcc cgttacagca acaaggaagc agtggggcac acaaagtcat tgctatctgc | 2220 |
| ccaaatcaca ccatgccacc cccacaagtg cttccaccaa tcattctagc tataattatg | 2280 |
| ctaattatac ggtctataca atttctgaca tgtcacacat ttcaaacctt tcaaaacccc | 2340 |
| tcaaaac | 2347 |

<210> SEQ ID NO 34
<211> LENGTH: 675
<212> TYPE: DNA
<213> ORGANISM: Chlamydomonas reinhardtii

<400> SEQUENCE: 34

| | |
|---|---|
| cgaacgaggg cgcggcgcgg cgtctatggc gccgtaaccc aaaatgtgta gcgagaccct | 60 |
| taagagcggg ggcaataata ataataataa taataataat aataataata ataataataa | 120 |
| taataataat aataataata ataataataa taataataat aataataata ataataataa | 180 |
| taataataat aataataata ataataggaa taataataat aataataatt acaatgccgg | 240 |
| cccatagggc ctggcatgga ttaacggggc aaggtgacta gggcgagagg gcccgcccca | 300 |
| gtgtttccaa aaccgggtac tagtacccat tcgggtactg agaaaataat tcgccgaaat | 360 |
| tgacgcgggt actggaaact aattattggg gcctcgagta cccacacggg taccaaaaat | 420 |
| ttaatccgcc ggaccctata ctacccggcc cctgttcagc acgaggcaa tcgaccacgc | 480 |
| gagctctgtc ttagaggctg ctgcatctgg caccgtgacg ctgccgcagg gcagcttcgt | 540 |

```
ggcgttctgg caatcgctga ctcgcgcgca gtacattgcc gacagctgca gtgagttcgt      600
gcgcctggcc aagctggcgg ctaccattgt acccggatca gtggaggcgg agcgtgtgtt      660
cagcaccatg agcta                                                      675

<210> SEQ ID NO 35
<211> LENGTH: 2715
<212> TYPE: DNA
<213> ORGANISM: Chlamydomonas reinhardtii

<400> SEQUENCE: 35
cagcccggtg gtggcacgtg cgtgtcaagc cgccgaggtc gcaccacgtc cttctttgcg       60
actgctggca cctttggtcc gcctcaccgc gatcgagtcg agcgcaacct caatggtgtg      120
cgcttcattt tcctagatga gtttagcacg tgtgggctgt cccactgggc gcgcatttgc      180
atgcatgtgc acgcggcacg gaggcacgtg ggtatagaca gcacgcacct atatcacggg      240
ccgctgtcag atctgcatgg cctgcttgtt ggcgacttgc gtcagttgcc acagccacgg      300
cacgtgccgc tatatagcgg tgctgcggaa gagagcttgc ggcagctgct ggcgccgggc      360
gcgggggacg gcggggccat ggagcgccag atccggcagc tggagcatcc ggagggcagc      420
atgaacctca tggggcggga gctgtggaat atggtgccgt tcgcgttcgt tctcactcac      480
cagcatcggc agcaagcagg cgtaggtgac aacaacgaac ctctcttcat gctagcggag      540
aagtttggtg gcgtgcagga aatctctcag gcagatctgg atacagcgtg ccagcagctc      600
aacgcgcgtg tttggcagcc cccgaagcca gggattgacc ccgtgcccca gcccctttgca      660 gttgtccagc gccatgttgt gcgggttcca ctggcattgc agctcgtgca gctgcatgcg      720
ctcgcgcagc gtcagcagct gctgctatgg cgtagcgcgg acttgtcgcc ggacgggagc      780
agcttaccta tttcgcatgt gcatcaatta gaggcgcttg gcggggccga ggatgatagc      840
ggtgtgcccg ctgtgtgcgc attctttgct ggcattcgtt acgtgtttac atcaaatgag      900
catgtgcgtc tgtatcacat caacaacaac agtgccacag gcaccggcat tgttctgcat      960
cccaacgagt caccattgcc agatgcaagc attgcccccg tgcatgtcct caagttcgtg     1020
ccctcggctg taatggtgcg ccccgacggg cctgatgcgg tcgggtgtc tgtcgatcag      1080 gccctggatg tcggggagat tcctgtttta ccgtgcagtg ctatgttcac atcgcagcat     1140
gcaaccctgc ggttgcctgt gatgcgctgg ggctttcgtg tggagcttgc gtatgcagtc     1200
accgattact ttgcgcaggg gcaaactctg ccagcgcacg aactgtggct ggtggatatg     1260
tgcaaaccgc agcacggcag ttggcggcgg gcttcaattt acgtaatgct caccaggttt     1320
cgtgggttgc atgccttaca tttagtgcgt ccgctgtggg cctcgcgggc cgaagagcgc     1380
cggcttaaaa aggcgctgcg taccatgcta acgcccgagg cagatctagc gcggaatgg      1440 cagcggctat tgaggctctc gcagagcaca gcagtagcag tgccaggtat gattgtgcgc     1500
attcaggcca gcatggctgc ctcataacca aggcttccaa tgcatgcagt agtgttttta     1560
acatgcgcga ggtgtactga cagatgacct ggaagcgtgg agtaccttgt gggtggtgag     1620
tgctgactgc aatttacagc agtgactttc ttgttggtgt ttggtgtggt gaccatcatg     1680
cttggcttcg ctggctggac gtatgtcact gagctacgtt cgggtttagt ttctacctgt     1740
cctgtctctg cgtgaagccg gggtattgtt tatctgcttg cttgtcgtgc gttggattgt     1800
tgtgtgttta caacaggttg atgtgtggcg tggttaatcc cttgcacttt gaggaggtta     1860
ttgttagcca gctggtgttc gcacaggagg ttggtggtcg atgaacagtc gaccgacaga     1920
```

```
tggatcgcgg gatttgtttt tggcatttac cgcttggatt ctattcgcaa cgtagctcgg    1980
aatacacgct taatatgcat agttagaaga cttcggggac gcaaatcgct cggaaatgga    2040
ggagggtctc aatatgctcg gctcgcgatg tcgcgctctt gagcttgtat tatgcactgt    2100
gcgcaatgcg cgttcagcat gcatattctt acgaacaact agggacttga gtgacgcggt    2160
gtgaaaatca gtcggggtct cgacatgctt ggctcgccat ttcgcgctcc cgagctcgtt    2220
gtgtgtgttc cgaacaatgc acgctcagaa ttacatgttc aatatgtccg tcgcgatgtt    2280
cgagcttgaa aaccgacaag catggtgtat agatacacct ggtagcctga attcctgtgt    2340 tttggtgta ttttgttgat gttgcatcac gccgtgcctt gtcacattca tgttttttgt    2400
accggcgtgg ccttgtttgt aaatttcgcg gcgccctgat cttatctact tcttcgctgt    2460
gatctggcaa aaaaaactgt tcttgacggg attcgaacct gtgacagcat ctcactaagc    2520
gccataatca gaccctccag aggagggtgt gcactgagtt agcgatccgg tgatgaagca    2580
tctgccaaca tgtgccccac cctcagcaac cgcaccctcg ccagctccac caggcacccc    2640
tggctggtca agcaaatact ctacgcccgc tatggctacc tcttcaacgc acagcttaaa    2700
cggcgctacc gcctg                                                     2715

<210> SEQ ID NO 36
<211> LENGTH: 1504
<212> TYPE: DNA
<213> ORGANISM: Chlamydomonas reinhardtii

<400> SEQUENCE: 36
atggggcagg taggacaagc gtaagcgttt ggaaaatgga gggcttgaat gtctgagctc      60
atccatgtgt acaagaacag aaatactgtc aagttttgtg tcattgattg ctgattcgtt     120
tgtggtattg ttcaattatt gttgttcggg cattgcatcg cactcgaggg gctgggtggt     180
tcattggggt tgggaccggg tatcccagct tgtatcccag gggttgtgcg cggggagcaa     240
gcggcggggg ctgcagatgc tgaagcgcgt gctaggctgc ctatctgtct cgaagatgct     300
tcaagactgt gtgaacgttg cttcacgata ttatggggtg gtttatgctg gctgcacgca     360
ccatacacca tacagctact aacattcgtc acacttgcac ccaagtgtgc gcgagggaat     420
ccatgtaaca atatcttggc ttgatatgcg ctgacttatc gcagcgcagt ggagataagt     480
ctagttattg cgacgtaact gccgtgttgc gttagagtca cgcacggcgc aggacgctcg     540
ggtacgtgcc tgtgcatggg gccgaaccga gctgggtctt gtacgcgtca ggagcacacg     600
gcgccttatc tgccgttgtg cttctgtact gtatttcgga tcgtccctct gccgggacgg     660
tgacctcagt gtgtcgcact taaacgttcc ctacatttct ggactttctt tgcaatccta     720
tacctggttc taactatact ttaccatgtc tggaccgaat aagcgtttaa tatacactca     780
gacggagttg cagcgctttg ttgcgcgatc ctgctcaatg gaaccccta gcttgatcac     840 gctcgctctc tgatcgtaag ggaatgccct tcgacgcttc tctggcgctt tggaccacgc     900
tttggttcgg gggccgcatt cgggagcaaa tcggagcaga gcggagcttt caagcggagc     960
aaaggcgcgc gaagcgttgc ggacaaggcg ttcggcaagt cactgaaagc aaagggcat    1020 gcacagctgt gcgggcgggc tacttgcttg ccatgcgcgg tcctgcttgc cgtgccttcg    1080
tgtctacccg tcgctttaca gttcacagct tgtgcaata cctttcatct tccatcgtgc    1140
cacccccacc tccccaagac ctcagggctt tggcgcgggt acttctcctg tctgcctatc    1200
caggccgcag ggcccgcgtg cccttgggga aagggcgtgt gtgccgttgg atcggcct     1260 gtgcgccgca agcaacgggc tttgcgccct tgccttatgg acaatggatg gcatacgtgc    1320
```

```
ccttatgata cggcctgtgt gccgcaagca atgggctccg cgcccttgct ttatggacaa   1380
tggacggcat acgtgccctt atgatacggc ctgtgcgccg caagcaacgg gctccgcgcc   1440
cttgctttat ggacaatgga cggcatacgt gcccttatga tacggcctgt gtgccgcaag   1500
caat                                                                1504

<210> SEQ ID NO 37
<211> LENGTH: 2736
<212> TYPE: DNA
<213> ORGANISM: Chlamydomonas reinhardtii

<400> SEQUENCE: 37
ttgctacatg gacaatttac ggcgtacgtg ccctcataat acggcctgtg cgccgcaggc     60
aacgggctcc gcgcccttgc ttcatggaca cttcacggcg tacgtgccct catgatacgg    120
cctgtgtgcc gcaggcaacg ggctccgcgc ccttgcttca tggacaatgc cgcgtacg     180 tgttcttatg atacgcctg tgcgccgcaa gcaacgggct ctgcacccct tgttttatgga    240 caattcacgg catacgtgcc cgtatgatgt gacctgtgtg ccgcaagcaa cagctcaccc    300
ttgcttttgg gtaatagatg gcatacgtgc ccttatgata cgacctgtgt gccgcaagca    360
acgggctcca cactcttgcg ttgtggatta tagacggcat tgaaatgctt acgtgccttc    420
gttgtacatg cctttgcgtt gtggacaatg tgtggtctga cgccacgtt cggatacggc    480 gtgtgtgccg ccagcaacag gctttgcgcc tcgcatcatg tgtcttgcga tattgcccgt    540
gtgccgcatg caattatgct gcctgccctg tcgttatgga cgcttcgact tgttgcgtgc    600
cctgctgcgt gccctgtcgc aatacgcctt gagtgtgccg tgcacggcaa gcctgcgcct    660
cgctattgct tcgtgttgac aacggagcgg gcttacgtga tcatgcgtca ccctgtacgt    720
cttgaggtcc gcacgcacat catactatca cgcggcatca ccattgtagt ttggctgacg    780
caccccaagc caacctatat gcattcgatg tgtgcgctag gcccaagtgc cgaattgtgg    840
agttttgtgc agttcggcca gcatgctatt gccaataaca ataccgcatg acgcataaca    900
ataccgcatg acgcataaac atgccttcgt gcagccctgc accaggcatc ggacgctgtg    960
tcacgcagtg agcccgaccc tgcccaacca acatttgtt gcgagatacg gtcggagctg    1020
ggatcacagc ctgcttggtg ggtttagatg gcgcccgtgt gttgggctgg gctgttgctg    1080
ctcgcggtgg ggcccaccac cgagtcacgg cacccatccg ccctccctc ttgttggccc    1140 acccgcctgt acacatgcca gccacccgct cgccatcctg tgaaagcggg tagccgactt    1200
ggcaagcgct tttcctgaca cttggcgcag gtttgagtgg ataccagaa tggtctgaat    1260 gtagttgttg gataaccagt acactgcggt gtgtagctgg ttagcgggag tgccgtgcat    1320
gaaacacgct actcgacccg ccacgcccgc gcgatggtac caccaaccgt tcaacccaga    1380
tccatgccgg ggtagcatcg acccacagtc agactgatag ctcctatcca ggtgtcaggc    1440
gccatgtatg tatctgtgga cgcgtcaagc tggcttgtgc cgtagcgttg gccgcctgta    1500
tggcatgccc ggcatctgtg tcacgttatg gcgtcatgct taccgtagtc acgcggcttg    1560
cgtgctgtgc ggcacgctcc ctgccaatcc ttcaggacat gtatgcatac atgttccttg    1620
gtcagaacca tagcagggc agcgtgttct gtcaatgcct catgaaccca gagacccaag    1680
ccaacgtacg cattagttcc gcaacgcacg tcaacaggaa ccctgcacg tcaatgccaa    1740 ctgaatgtgt cgcctgccca ctcgccagtg gacgcctagg gaaccagcct tggttccttt    1800
cagccccggc cttacttcac ccggcggggc aattactat caccgaagtg ctaggagcag    1860
```

-continued

```
tgtgctatat gtcattacta ttaagagcgt atggcgacac aggctcacat gtgggtagcc      1920
aggccgacag tgccctgcgg gcttggcagt cggcaggcat cccaactcag cccggcctcc      1980
tcacagcagt accacaacgt gcccgtacgt gggcgagtgc ggagtttggc tgccggcgtg      2040
gctgtatcat ctctcacatt ggatgaccca tccgccactg cgatgggttc actactggca      2100
cgtccctcga gtcgctcacc caccggctcc gcccggcgtt cgctcccttt ggctgggccg      2160
gggcccgtgg cgcatccaac ccgccatcgc ggccccgagt gctccttatt tcctcccatc      2220
actacgcctt ctatcactat agatacattg cgtgttccac gcgtgccggg tatccttcac      2280
ccctccgcgc cgctcgacca ggccagcctt gctggggttg ctgaggtgtt acccttcatg      2340
ttgccctccc tgctattacg gtacacccca cagccgccgt ggcgtacggt atcggcacgt      2400
acgggacatt gtgtgcatgc atcccgcgcg cgtttggagg cattcacgtg cgcgcctgtc      2460
ctgcgtccgc cggggtgatg ctatctatgg gtgtacctac tgcttgattg gtagtgactc      2520
ttatgcaaga cactgcaaat ctcaagcatg gcacctagct agcaagaaag aaattagtgt      2580
tcgtggccat gctgcacggc tgggcatggc tgcccgcatc ctacaccacg acggcgcggg      2640
tgaagggcag gttgccgcgc gtgactcgcg tacgtaaaac cgctctagtg ttgcacctcg      2700
cgccttctcc tgcgtggctc atgttggcta gtctgt                                2736

<210> SEQ ID NO 38
<211> LENGTH: 3597
<212> TYPE: DNA
<213> ORGANISM: Chlamydomonas reinhardtii

<400> SEQUENCE: 38
tgcctgacct acttgcaatg cagacacgag cagggagcca tgttgccagc cctcacagtg        60
ccttcagtgc cctgcacgc ctggacaagg cgggtggggt ccacaccgcc cagccatcac       120
cagacacccc acctgccaca cccacccttg tgcactgttg tttcacattt tcatatgtgc       180
atgttgcctg acctatttgc aatgcagaga cgagcaggga gccatgttgc cagccctcac       240
agtgccttcc gtgccctgc acgcctggac aaggcgggtg gggcccctgc cacccagcca       300
tcaccagaca ccccacctgc cacacccacc cttgtgcact gttgtttcac attttcatat       360
gtgcatgttg cctgacctat ttgcaatgca gacacgagca gggagccatg ttgccagccc       420
tcacagtgcc ttccgtgccc ctgcacgcct ggacaaggcg ggtggggtcc acaccgccca       480
gccatcacca cacccccac ctgccacacc cacccttgtg cactgttgtt tcacattttc       540
atatgtgcat gttgcctgac ctatttgcaa tgcagacacg agcagggagc catgttgcca       600
gccctcacag tgccttcagt gcccctgcac gcctggacaa ggcgggtggg gtccacaccg       660
cccagccatc accacacacc ccacctgcca cacccaccct tgtgcactgt tgtttcacat       720
tttcatatgt gcatgttgcc tgacctattt gcaatgcaga cacgagcagg gagccatgtt       780
gccagccctc acagtgcctt cagtgcccct gcacgcctgg acaaggcggg tggggccct        840
gccacccagc catcaccaca cacccccacct gccacaccca cccttgtgca ctgttgtttc      900
acattttcat atgtgcatgt tgcctgacct atttgcaatg cagacacgag caggagcca        960
tgttgccagc cctcacagtg ccttcagtgc cctgcacgc ctggacaagg cgggtggggt       1020
ccacaccgcc cagccatcac cacacaccc acctgccaca cccaccttg tgcactgttg       1080
tttcacattt tcatatgtgc atgttgcctg acctatttgc aatgcagaca cgagcaggga      1140
gccatgttgc cagccctcac agtgccttca gtgcccctgc acgcctggac aaggcgggtg      1200
gggtccctgc cacccagaca tcaccacaca ccccacctgc cacacccacc cttgtgcact      1260
```

```
gttgtttcac attttcatat gtgcatgttg cctgacctat ttgcaatgca gacacgagca    1320
gggagccatg ttgccagccc tcacagtgcc ttcagtgccc ctgcacgcct ggacaaggcg    1380
ggtggggtcc acaccgccca gccatcacca cacccccac ctgccacacc cacccttgtg     1440
cactgttgtt tcacattttc atatgtgcat gttgcctgac ctatttgcaa tgcagacacg    1500
agcagggagc catgttgcca gccctcacag tgccttcagt gccctgcac gcctggacaa     1560
ggcgggtggg gtccacaccg cccagccatc accacacacc ccacctgcca cacccaccct    1620
tgtgcactgt tgtttcacat tttcatatgt gcatgttgcc tgacctattt gcaatgcaga    1680
cacgagcagg gagccatgtt gccagccctc acagtgcctt cagtgcccct gcacgcctgg    1740
acaaggcggg tggggtccac accgcccagc catcaccaca caccccacct gccacaccca    1800
cccttgtgca ctgttgtttc acattttcat atgtgcatgt tgcctgacct atttgcaatg    1860
cagacacgag cagggagcca tgttgccagc cctcacagtg ccttcagtgc cctgcacgc    1920
ctggacaagg cgggtggggt ccacaccgcc cagccatcac cacacacccc acctgccaca    1980
cccacccttg tgcactgttg tttcacattt tcatatgtgc atgttgcctg acctatttgc    2040
aatgcagaca cgagcaggga gccatgttgc cagccctcac agtgccttca gtgcccctgc    2100
acgcctggac aaggcgggtg gggtccacac cgcccagcca tcaccacaca cccccacctgc    2160
cacacccacc cttgtgcact gttgtttcac attttcatat gtgcatgttg cctgacctat    2220
ttgcaatgca gacacgagca gggagccatg ttgccagccc tcacagtgcc ttcagtgccc    2280
ctgcacgcct ggacaaggcg gtggggccc ctgccaccca gccatcaccc cacacccac     2340
ctgccacacc caccccttgtg cactgttgtt tcacattttc atatgtgcat gttgcctgac    2400
ctatttgcaa tgcagacacg agcagggagc catgttgcca gccctcacag tgccttcagt    2460
gccctgcac gcctggacaa ggcgggtggg gcccacaccg cccagccatc accacacacc    2520
ccacctgcca cacccaccct tgtgcactgt tgtttcacat tttcatatgt gcatgttgcc    2580
tgacctattt gcaatgcaga cacgagcagg gagccatgtt gccagccctc acagtgcctt    2640
cagtgcccct gcacgcctgg acaaggcggg tggggtccac accgcccagc catcaccaca    2700
caccccacct gccacaccca cccttgtgca ctgttgtttc acattttcat atgtgcatgt    2760
tgcctgacct atttgcaatg cagacacgag cagggagcca tgttgccagc cctcacagtg    2820
ccttcagtgc cctgcacgc acgcctggac aaggcgggtg gggtccacac cgcccagcca    2880
tcaccacaca ccccacctgc cacacccacc cttgtgcact gttgtttcac attttcatat    2940
gtgcatgttg cctgacctat ttgcaatgca gacacgagca gggagccatg ttgccagccc    3000
tcacagtgcc ttcagtgccc ctgcacgcac gcctggacaa ggcgggtggg gtccacaccg    3060
cccagccatc accacacacc ccacctgcca caccaccct tgtgcactgt tgtttcacat    3120
tttcatatgt gcatgttgcc tgacctattt gcaatgcaga cacgagcagg gagccatgtt    3180
gccagccctc acagtgcctt cagtgcccct gcacgtacgc ctggacaagg cgggtggggt    3240
ccacaccgcc cagccatcac cacacaccc acctgccaca cccaccttg tgcactgttg     3300
tttcacattt tcatatgtgc atgttgcctg acctatttgc aatgcagaca cgagcaggga    3360
gccatgttgc cagccctcac agtgccttca gtgcccctgc acgcacgcct ggacaaggcg    3420
ggtggggtcc acaccgccca gccatcacca cacccccac ctgccacacc cacccttgtg    3480
cactgttgtt tcacattttc atatgtgcat gttgcctgac ctatttgcaa tgcagacacg    3540
agcagggagc catgttgcca gccctcacag tgccttcagt gccctgcac gcctgga       3597
```

<210> SEQ ID NO 39
<211> LENGTH: 5362
<212> TYPE: DNA
<213> ORGANISM: Chlamydomonas reinhardtii

<400> SEQUENCE: 39

| | | | | | |
|---|---|---|---|---|---|
| acacgagcag | ggagccatgt | tgccagccct | cacagtgcct | tcagtgcccc | tgcacgcacg | 60 |
| cctggacaag | gcgggtgggg | tccacaccgc | ccagccatca | ccacacaccc | cacctgccac | 120 |
| acccacccct | gtgcactgtt | gtttcacatt | ttcatatgtg | catgttgcct | gacctatttg | 180 |
| caatgcagac | acgagcaggg | agccatgttg | ccagccctca | cagtgccttc | agtgcccctg | 240 |
| cacgcctgga | caaggcgggt | ggggtccaca | ccgcccagcc | atcaccacac | accccacctg | 300 |
| ccacacccac | ccttgtgcac | tgttgtttca | cattttcata | tgtgcatgtt | gcctgaccta | 360 |
| tttgcaatgc | agacacgagc | agggagccat | gttgccagcc | ctcacagtgc | cttcagtgcc | 420 |
| cctgcacgcc | tggacaaggc | gggtgggtc | cacaccgccc | agccatcacc | acaccccca | 480 |
| cctgccacac | ccaccttgt | gcactgttgt | ttcacattt | catatgtgca | tgtcgcctga | 540 |
| cctattcgca | atgcagacac | gagcagggag | ccatgttgcc | agccctcaca | gtgccttcag | 600 |
| tgcccctgca | cgcctggaca | aggcgggtgg | ggtccacacc | gcccagccat | caccacacac | 660 |
| cccacctgcc | acacccaccc | ttgtgcactg | ttgtttcaca | ttttcatatg | tgcatgttgc | 720 |
| ctgacctatt | tgcaatgcag | acatgagcag | ggagccatgt | tgccagccct | cacagtgcct | 780 |
| tcagtgcccc | tgcacgcctg | acaaggcgg | gtggggtcca | caccgccag | ccatcaccac | 840 |
| acacccacc | tgccacaccc | accttgtgc | actgttgttt | cacattttca | tatgtgcatg | 900 |
| ttgcctgacc | tattcgcaat | gcagacacga | gcagggagcc | atgttgccag | ccctcacagt | 960 |
| gccttcagtg | cccctgcacg | cctggacaag | gcgggtgggg | tccacaccgc | ccagccatca | 1020 |
| ccacacaccc | cacctgccac | acccaccctt | gtgcactgtt | gtttcacatt | ttcatatgtg | 1080 |
| catgttgcct | gacctatttg | caatgcagac | acgagcaggg | agccatgttg | ccagccctca | 1140 |
| cagtgccttc | agtgcccctg | cacgcctgga | caaggcgggt | ggggtccaca | ccgcccagcc | 1200 |
| atcaccacac | accccacctg | ccacacccac | ccttgtgcac | tgttgtttca | cattttcata | 1260 |
| tgtgcatgtc | gcctgaccta | tttgcaatgc | agacacgagc | agggagccat | gttgccagcc | 1320 |
| ctcacagtgc | cttcagtgcc | cctgcacgcc | tggacaaggc | gggtgggtc | cacaccgccc | 1380 |
| agccatcacc | atacacccca | cctgccacac | ccaccttgt | gcactgttgt | ttcacattt | 1440 |
| catatgtgca | tgttgcctga | cctattcgca | atgcagacac | gagcagggag | ccatgttgcc | 1500 |
| agccctcaca | gtgccttcag | tgcccctgca | cgcctggaca | aggcgggtgg | ggtccacacc | 1560 |
| gcccagccat | caccacacac | cccacctgcc | acacccaccc | ttgtgcactg | ttgtttcaca | 1620 |
| ttttcatatg | tgcatgttgc | ctgacctatt | tgcaatgcag | acacgagcag | ggagccatgt | 1680 |
| tgccagccct | cacagtgcct | tcagtgcccc | tgcacgcctg | acaaggcgg | gtggggtcca | 1740 |
| caccgcccag | ccatcaccac | acacccacc | tgccacaccc | accttgtgc | actgttgttt | 1800 |
| cacattttca | tatgtgcatg | tcgcctgacc | tatttgcaat | gcagacacga | gcagggagcc | 1860 |
| atgttgccag | ccctcacagt | gccttcagtg | cccctgcacg | cctggacaag | gcgggtgggg | 1920 |
| tccacaccgc | ccagccatca | ccacacaccc | cacctgccac | acccaccctt | gtgcactgtt | 1980 |
| gtttcacatt | ttcatatgtg | catgtcgcct | gacctatttg | caatgcagac | acgagcaggg | 2040 |
| agccatgttg | ccagccctca | cagtgccttc | agtgcccctg | cacgcctgga | caaggcgggt | 2100 |
| ggggtccaca | ccgcccagcc | atcaccatac | accccacctg | ccacacccac | ccttgtgcac | 2160 |

```
tgttgtttca catttttcata tgtgcatgtt gcctgaccta tttgcaatgc agacacgagc    2220
agggagccat gttgccagcc ctcacagtgc cttcagtgcc cctgcacgcc tggacaaggc    2280
gggtggggc cacaccgccc agccatcacc acacacccca cctgccacac ccaccttgt     2340
gcactgttgt ttcacatttt catatgtgca tgttgcctga cctatttgca atgcagacac    2400
gagcagggag ccatgttgcc agccctcaca gtgccttcag tgcccctgca cgcctggaca    2460
aggcgggtgg ggtccacacc gcccagccat caccacacac cccacctgcc acccaccc     2520
ttgtgcactg ttgtttcaca ttttcatatg tgcatgtcgc ctgacctatt tgcaatgcag    2580
acacgagcag ggagccatgt tgccagccct cacagtgcct tcagtgcccc tgcacgcctg    2640
gacaaggcgg gtggggtcca caccgcccag ccatcaccac acccccacc tgccacaccc    2700
acccttgtgc actgttgttt cacattttca tatgtgcatg tcgcctgacc tatttgcaat    2760
gcagacacga gcagggagcc atgttgccag ccctcacagt gccttcagtg cccctgcacg    2820
cctggacaag gcgggtgggg tccacaccgc ccagccatca ccataccc cacctgccac     2880
acccaccctt gtgcactgtt gtttcacatt ttcatatgtg catgttgcct gacctattcg    2940
caatgcagac acgagcaggg agccatgttg ccagccctca cagtgcgttc agtgcccctg    3000
cacgcacgcc tggacaaggc gggtggggtc cacaccgccc agccatcacc acaccccca    3060
cctgccacac ccaccttgt gcactgttgt ttcacatttt catatgtgca tgttgcctga    3120
cctatttgca atgcagacac gagcagggag ccatgttgcc agccctcaca gtgccttcag    3180
tgcccctgca cgcctggaca aggcgggtgg ggtccacacc gcccagccat caccacacac    3240
cccacctgcc acccaccc ttgtgcactg ttgtttcaca ttttcatatg tgcatgttgc     3300
ctgacctatt tgcaatgcag acacgagcag ggagccatgt tgccagccct cacagtgcct    3360
tcagtgcccc tgcacgcacg cctggacaag gcgggtgggg tccacaccgc ccagccatca    3420
ccacacccc cacctgccac acccaccctt gtgcactgtt gtttcacatt ttcatatgtg    3480
catgttgcct gacctatttg caatgcagac acgagcaggg agccatgttg ccagccctca    3540
cagtgccttc agtgcccctg cacgcctgga caaggcgggt ggggtccaca ccgcccagcc    3600
atcaccacac ccccacctg ccacacccac ccttgtgcac tgttgtttca catttttcata    3660
tgtgcatgtc gcctgaccta tttgcaatgc agacacgagc agggagccat gttgccagcc    3720
ctcacagtgc cttcagtgcc cctgcacgcc tggacaaggc gggtggggtc cacaccgccc    3780
agccatcacc acacccca cctgccacac ccaccttgt gcactgttgt ttcacatttt      3840
catatgtgca tgtcgcctga cctatttgca atgcagacac gagcagggag ccatgttgcc    3900
agccctcaca gtgccttcag tgcccctgca cgcctggaca aggcgggtgg ggtccacacc    3960
gcccagccat caccacacac cccacctgcc acccacccc ttgtgcactg ttgtttcaca    4020
ttttcatatg tgcatgttgc ctgacctatt tgcaatgcag acacgagcag ggagccatgt    4080
tgccagccct cacagtgcct tcagtgcccc tgcacgcctg acaaggcgg gtggggtcca    4140
caccgcccag ccatcaccac acccccacc tgccacaccc accttgtgc actgttgttt    4200
cacattttca tatgtgcatg ttgcctgacc tatttgcaat gcagacacga gcagggagcc    4260
atgttgccag ccctcacagt gccttcagtg cccctgcacg cctggacaag gcgggtgggg    4320
tccacaccgc ccagccatca ccacacaccc cacctgccac acccaccctt gtgcactgtt    4380
gtttcacatt ttcatatgtg catgttgcct gacctatttg caatgcagac acgagcaggg    4440
agccatgttg ccagccctca cagtgccttc agtgcccctg cacgcctgga caaggcgggt    4500
```

| | |
|---|---:|
| ggggcccctg ccacccagcc atcaccacac accccacctg ccacacccac ccttgtgcac | 4560 |
| tgttgtttca catttcata tgtgcatgtt gcctgaccta tttgcaatgc agacacgagc | 4620 |
| agggagccat gttgccagcc ctcacagtgc cttcagtgcc cctgcacgcc tggacaaggc | 4680 |
| gggtggggtc caccgcccc agccatcacc acacacccca cctgccacac ccacccttgt | 4740 |
| gcactgttgt ttcacatttt catatgtgca tgttgcctga cctatttgca atgcagacac | 4800 |
| gagcagggag ccatgttgcc agccctcaca gtgccttcag tgccctgca cgcctggaca | 4860 |
| aggcgggtgg ggtccacacc gcccagccat caccacacac cccacctgcc acacccaccc | 4920 |
| ttgtgcactg ttgtttcaca ttttcatatg tgcatgtcgc ctgacctatt tgcaatgcag | 4980 |
| acacgagcag ggagccatgt tgccagccct cacagtgcct tcagtgcccc tgtacgcctg | 5040 |
| gacaaggcgg gtggggtcca caccgcccag ccatcaccac acccccacc tgccacaccc | 5100 |
| acccttgtgc actgttgttt cacattttca tatgtgcatg tcgcctgacc tatttgcaat | 5160 |
| gcagacacga gcaggagcc atgttgccag ccctcacagt gccttcagtg ccctgcacg | 5220 |
| cctggacaag gcgggtgggg ccctgccacc cagccatcac cacacacccc ctgccaca | 5280 |
| cccaccttg tgcactgttg tttcacattt tcatatgtgc atgttgcctg acctatttgc | 5340 |
| aatgcagaca cgagcaggga gc | 5362 |

<210> SEQ ID NO 40
<211> LENGTH: 2681
<212> TYPE: DNA
<213> ORGANISM: Chlamydomonas reinhardtii

<400> SEQUENCE: 40

| | |
|---|---:|
| actttcatat gtgcatgttg cctgacctat ttgcaatgca gacacgagca gggagccatg | 60 |
| ttgccagccc tcacagtgcc ttcagtgccc ctgcacgcct ggacaaggcg gtgggtcc | 120 |
| acaccgccca gccatcacca cacccccac ctgccacact caccttgtg cactgttgtt | 180 |
| tcacattttc atatgtgcaa gttgcctgac ctatttgcaa tgcagacacg agcagggagc | 240 |
| catgttgcca gccctcacag tgccttcagt gccctgcac gcctggacaa ggcgggtggg | 300 |
| gtccacaccg cccagccatc accacacacc ccacctgcca cacccaccct tgtgcactgt | 360 |
| tgtatcacat tttcatatgt gcatgttgcc tgacctattt gcaatgcaga cacgagcagg | 420 |
| gagccatgtt gccagccctc acagtgcctt cagtgcccct gcacgcctgg acaaggcggg | 480 |
| tggggtccac accgcccagc catcaccaca ccccacct gccacaccca cccttgtgca | 540 |
| ctgttgtttc acattttcat atgtgcatgt tgcctgacct atttgcaatg cagacacgag | 600 |
| cagggagcca tgttgccagc cctcacagtg ccttcagtgc cctgcacgc ctggacaagg | 660 |
| cgggtggggt ccacaccgcc cagccatcac cacacaccc acctgccaca cccacccttg | 720 |
| tgcactgttg tttcacattt tcatatgtgc atgttgcctg acctatttgc aatgcagaca | 780 |
| cgagcaggga gccatgttgc cagccctcac agtgccttca gtgccctgc acgcctggac | 840 |
| aaggcgggtg gggtccctgc cacccagaca tcaccacaca ccccacctgc cacacccacc | 900 |
| cttgtgcact gttgtttcac attttcatat gtgcatgttg cctgacctat ttgcaatgca | 960 |
| gacacgagca gggagccatg ttgccagccc tcacagtgcc ttcagtgccc ctgcacgcct | 1020 |
| ggacaaggcg gtggggtcc acaccgccca gccatcacca cacccccac ctgccacacc | 1080 |
| cacccttgtg cactgttgtt tcacattttc atatgtgcat gttgcctgac ctatttgcaa | 1140 |
| tgcagacacg agcagggagc catgttgcca gccctcacag tgccttcagt gccctgcac | 1200 |
| gcctggacaa ggcgggtggg gtccacaccg cccagccatc accacacacc ccacctgcca | 1260 |

```
cactcaccct tgtgcactgt tgtttcacat tttcatatgt gcatgttgcc tgacctattt    1320
gcaatgcaga cacgagcagg gagccatgtt gccagccctc acagtgcctt cagtgcccct    1380
gcacgcctgg acaaggcggg tggggtccat gccacccagc catcaccaca cacccccacct   1440 gccacaccca cccttgtgca ctgttgtttc acatttctcat atgtgcatgt tgcctgacct   1500
atttgcaatg cagacacgag cagggagcca tgttgccagc cctcacagtg ccttcagtgc    1560
ccctgcacgc ctggacaagg cgggtggggt ccacaccgcc cagccatcac acacacccc     1620 acctgccaca cccacccttg tgcactgttg tttcacattt tcatatgtgc atgtcgcctg    1680
acctatttgc aatgcagaca cgagcaggga gccatgttgc cagccctcac agtgccttca    1740 gtgccctgc acgcctggac aaggcgggtg ggtccacac cgcccagcca tcaccacaca     1800
ccccacctgc cacacccacc cttgtgcact gttgtttcac attttcatat gtgcatgttg    1860
cctgacctat tcgcaatgca gacacgagca gggagccatg ttgccagccc tcacagtgcc    1920
ttcagtgccc ctgcacgcct ggacaaggcg gtgggtcc acaccgccca gccatcacca     1980 cacccccac ctgccacacc caccctgtg cactgttgtt tcacatttc atatgtgcat      2040 gttgcctgac ctatttgcaa tgcagacacg agcaggagc catgttgcca gccctcacag    2100
tgccttcagt gccctgcac gcctggacaa ggcgggtggg gtccacaccg cccagccatc    2160
accacacacc ccacctgcca cacccaccct tgtgcactgt tgtttcacat tttcatatgt    2220
gcatgctgcc tgacctattt gcaatgcaga cacgagcagg gagccatgtt gccagccctc    2280
acagtgcctt cagtgcccct gcacgcctgg acaaggcggg tggggtccac accgcccagc    2340
catcaccaca caccccacct gccacaccca cccttgtgca ctgttgtttc acattttcat    2400
atgtgcatgc tgcctgacct atttgcaatg cagacacgag cagggagcca tgttgccagc    2460
cctcacagtg ccttcagtgc ccctgcacgc ctggacaagg cgggtggggt ccacagcgcc    2520
cagccatcac cacacacccc acctgccaca cccacccttg tgcactgttg tttcacattt    2580
tcatatgtgc atgctgcctg acctatttgc aatgcagaca cgagcaggga gccatgttgc    2640
cagccctcac agtgccttca gtgcccctgc acgcctggac a                        2681
```

<210> SEQ ID NO 41
<211> LENGTH: 5263
<212> TYPE: DNA
<213> ORGANISM: Chlamydomonas reinhardtii

<400> SEQUENCE: 41

```
acccgacctg ccacacccac ccttgtgcac tgttgtttca catttttcata tgtgcatgtt      60 gcctgaccta tttgcaatgc agacacgagc agggagccat gttgccagcc tcacagtgc     120 cttcagtgcc cttgcacgcc tggacaaggc gggtgggggc cctgccaccc agccatcacc    180
acacacccca cctgccacac ccacccttgt gcactgttgt ttcacatttt catatgtgca    240
tgttgcctga cctatttgca atgcagacac gagcagggag ccatgttgcc agccctcaca    300
gtgccttcag tgcccttgca cgcctggaca aggcgggtgg ggcccctgcc acccagccat    360
caccacacac cccacctgcc acacccaccc ttgtgcactg ttgtttcaca ttttcatatg    420
tgcatgtcgc ctgacctatt tgcaatgcag acacgagcag ggagccatgt tgccagccct    480
cacagtgcct tcagtgcccc tgcacgcctg acaaggcgg gtgggccccc tgcctcccag    540
ccatcaccac acaccccacc tgccacaccc accttgtgc actgttgttt cacatttttca   600 tatgtgcatg ttgcctgacc tatttgcaat gcagacacga gcaggagcc atgttgccag    660
```

```
ccctcacagt gccttcagtg ccctgcacg cctggacaag gcgggtgggg tccctgccac      720
ccagccatca ccacacaccc cacctgccac acccacccctt gtgcactgtt gtttcacatt    780
ttcatatgtg catgttgcct gacctatttg caatgcagac acgagcaggg agccatgttg     840
ccagccctca cagtgccttc agtgcccctg cacgcctgga caaggcgggt ggggtccaca     900
ccgcccagcc atcaccacac accccacctg ccacacccac ccttgtgcac tgttgtttca     960
cattttcata tgtgcatgtt gcctgaccta tttgcaatgc agacacgagc agggagccat    1020
gttgccagcc ctcacagtgc cttcagtgcc cctgcacgcc tggacaaggc gggtggggtc    1080
cacaccgccc agccatcacc acacacccca cctgccacac ccaccttgt gcactgttgt     1140
ttcacatttt catatgtgca tgttgcctga cctatttgca atgcagacac gagcagggag    1200
ccatgttgcc agccctcaca gtgccttcag tgcccctgca cgcctggaca aggcgggtgg    1260
ggtccacacc gcccagccat caccacacac cccacctgcc acccacccc ttgtgcactg     1320
ttgtttcaca ttttcatatg tgcatgttgc ctgacctatt tgcaatgcag acacgagcag    1380
ggagccatgt tgccagccct cacagtgcct tcagtgcccc tgcacgcctg acaaggcgg     1440
gtggggtccc tgccacccag acatcaccac acccccacc tgccacaccc accttgtgc      1500
actgttgttt cacattttca tatgtgcatg ttgcctgacc tatttgcaat gcagacacga    1560
gcagggagcc atgttgccag ccctcacagt gccttcagtg ccctgcacg cctggacaag     1620
gcgggtgggg tccacaccgc ccagccatca ccacacaccc cacctgccac acccacccctt   1680
gtgcactgtt gtttcacatt ttcatatgtg catgttgcct gacctatttg caatgcagac    1740
acgagcaggg agccatgttg ccagccctca cagtgccttc agtgcccctg cacgcctgga    1800
caaggcgggt ggggtccaca ccgcccagcc atcaccacac ccccacctg ccacacccac     1860
ccttgtgcac tgttgtttca cattttcata tgtgcatgtt gcctgaccta tttgcaatgc    1920
agacacgagc agggagccat gttgccagcc ctcacagtgc cttcagtgcc cctgcacgcc   1980
tggacaaggc gggtggggtc cacaccgcct agccatcacc acacccccca cctgccacac    2040
ccacccttgt gcactgttgt ttcacatttt catatgtgca tgttgcctga cctatttgca    2100
atgcagacac gagcagggag ccatgttgcc agccctcaca gtgccttcag tgcccctgca    2160
cgcctggaca aggcgggtgg ggtccacacc gcccagccat caccacacac cccacctgcc   2220
acccacccc ttgtgcactg ttgtttcaca ttttcatatg tgcatgttgc ctgacctatt     2280
tgcaatgcag acacgagcag ggagccatgt tgccagccct cacagtgcct tcagtgcccc   2340
tgcacgcctg gacaaggcgg gtggggtcca caccgcccag ccatcaccac accccacc      2400
tgccacaccc acccttgtgc gctgttgttt cacattttca tatgtgcatg ttgcctgacc   2460
tatttgcaat gcagacacga gcagggagcc atgttgccag ccctcacagt gccttcagtg    2520
cccctgcacg cctggacaag gcgggtgggg tccacaccgc cagccatca ccagacaccc     2580
cacctgccac actcacccctt gtgcactgtt gtttcacatt ttcatatgtg catgtcgcct   2640
gacctatttg caatgcagac acgagcaggg agccatgttg ccagccctca cagtgccttc    2700
agtgcccctg cacgcctgga caaggcgggt ggggtccaca ccgcccagcc atcaccagac   2760
accccacctg ccacactcac ccttgtgcac tgttgtttca cattttcata tgtgcatgtt   2820
gcctgaccta tttgcaatgc agacacgagc agggagccat gttgccagcc ctcacagtgc    2880
cttcagtgcc cctgcacgcc tggacaaggc gggtggggtc cacaccgccc agccatcacc   2940
acacccccca cctgccacac ccaccttgt gcactgttgt ttcacatttt catatgtgca     3000
tgttgcctga cctatttgca atgcagacac gagcagggag ccatgttgcc agccctcaca    3060
```

```
gtgccttcag tgcccctgca cgcctggaca aggcgggtgg ggtccacacc gcccagccat    3120
caccacacac cccacctgcc acacccaccc ttgtgcactg ttgtttcaca ttttcatatg    3180
tgcatgctgc ctgacctatt tgcaatgcag acacgagcag ggagccatgt tgccagccct    3240
cacagtgcct tcagtgcccc tgcacgcctg acaaggcgg gtggggtcca caccgcccag    3300
ccatcaccac acacccacc tgccacaccc accttgtgc actgttgttt cacattttca    3360
tatgtgcatg ttgcctgacc tatttgcaat gcagacacga gcaggagcc atgttgccag    3420 ccctcacagt gccttcagtg ccctgcacg cctggacaag gcgggtgggg tccacaccgc    3480
ccagccatca ccacacaccc cacctgccac acccaccctt gtgcactgtt gtttcacatt    3540
ttcatatgtg catgttgcct gacctatttg caatgcagac acgagcaggg agccatgttg    3600
ccagccctca cagtgccttc agtgcccctg cacgcctgga caaggcgggt ggggtccaca    3660
ccgcccagcc atcaccacac accccacctg ccacacccac ccttgtgcac tgttgtttca    3720
cattttcata tgtgcacgtt gcctgaccta tttgcaatgc agacacgagc agggagccat    3780
gttgccagcc ctcacagtgc cttcagtgcc cctgcacgcc tggacaaggc gggtgggggc    3840
cttgccaccc agccatcacc acacacccca cctgccacac ccaccttgt gcactgttgt    3900 ttcacatttt catatgtgca tgtcgcctga cctatttgca atgcagacac gagcagggag    3960
ccatgttgcc agccctcaca gtgccttcag tgcccctgca cgcctggaca aggcgggtgg    4020
ggtccacacc gcccagccat caccacacac cccacctgcc acacccaccc ttgtgcactg    4080
ttgtttcaca ttttcatatg tgcatgtcgc ctgacctatt tgcaatgcag acacgagcag    4140
ggagccatgt tgccagccct cacagtgcct tcagtgccct gcacgcctg acaaggcgg    4200 gtggggccct gccacccagg catcaccaca ccccacct gccacaccca ccttgtgca    4260 ctgttgtttc acattttcat atgtgcatgt tgcctgacct atttgcaatg cagacacgag    4320
cagggagcca tgttgccagc cctcacagtg ccttcagtgc cctgcacgc tggacaagg    4380 cgggtggggt ccacaccgcc cagccatcac cacacacccc acctgccaca cccacccttg    4440
tgcactgttg tttcacattt tcatatgtgc atgttgcctg acctatttgc aatgcagaca    4500
cgagcaggga gccatgttgc cagccctcac agtgccttca gtgccttgc acgcctggac    4560 aaggcgggtg ggtccacac cgcccagcca tcaccacaca ccccacctgc cacacccacc    4620
cttgtgcact gttgtttcac attttcatat gtgcatgttg cctgacctat ttgcaatgca    4680
gacacgagca gggagccatg ttgccagccc tcacagtgcc ttcagtgccc ctgcacgcct    4740
ggacaaggcg ggtggggtcc acaccgccca gccatcacca cacccccac ctgccacacc    4800 caccttgtg cactgttgtt tcacattttc atatgtgcat gttgcctgac ctatttgcaa    4860
tgcagacacg agcagggagc catgttgcca gccctcacag tgccttcagt gcccctgcac    4920
gtacgcctgg acaaggcggg tggggtccac accgcccagc catcaccaca ccccacct    4980 gccacaccca cccttgtgca ctgttgtttc acatttcat atgtgcatgt tgcctgacct    5040
attcgcaatg cagacacgag cagggagcca tgttgccagc cctcacagtg ccttcagtgc    5100
ccctgcacgc ctggacaagg cgggtggggt ccacaccgcc cagccatcac cacacacccc    5160
acctgccaca cccacccttg tgcactgttg tttcacattt tcatatgtgc atgttgcctg    5220
acctatttgc aatgcagaca cgagcaggga gccatgttgc cag                      5263
```

<210> SEQ ID NO 42
<211> LENGTH: 613
<212> TYPE: DNA

<213> ORGANISM: Chlamydomonas reinhardtii

<400> SEQUENCE: 42

```
cgggaaacgt ttccgggcgt agacgccgcg ggcctgaggg catctacaag atacgggcac    60
tggcgcccag gcaggcgagc agcacccacg catgacgtga tctcgctcga tctgcaatat   120
tgtactgtat tacgtattgt acgctgtttt acagggactg tccaggacca aaatgtcgca   180
gattacgttg ggcacgggag ggggggggac cataactcat aagggtcct gggtctgcgc   240
ccagcgtctt gatgtctttg acacagtgcg ccgcacagca tgcccagcac cagttcttaa   300
aactcttttg ggttgcaaag caaccatata ataaccggc gtccttcagg atttgcttac   360
ttccagccca taagtattca ttaatccgcc atggactatg ttgccaagcc gaaacacaca   420
gttgaacccc atgtgcgttt ctaacacatc acatgcgccg tgtggtcacc cctgttgtcc   480
ccctgtcccg agtccctggt cgcgagagtg ggctgtactg tgttggaaat cccaggacgt   540
cgtagtacta ggcgtatcag gaggacaggg tcacgtaccg tattgtgcaa acctgcccct   600
aagcacggga aat                                                      613
```

<210> SEQ ID NO 43
<211> LENGTH: 896
<212> TYPE: DNA
<213> ORGANISM: Chlamydomonas reinhardtii

<400> SEQUENCE: 43

```
ttgccgaaac ttgggtcatc tgagggccga agccctgcct cccgccgct tcggcacccc    60
agccagcatg ccgggtcagc gccccgaacc cgcaccctga tccgccaccg cacgcccggc   120
ccggattaac catagttcat tttgggatcg gaaccaacgc tcctccccac cccactaccc   180
ccggatgtat gctccgtgcc tggcggcgtc ggggataata ataataataa taataataat   240
aataataata ataataataa taataataat aataataata ataataataa taataataat   300
aataataata ataataataa taataataat aataataata ataataataa taataataat   360
aataataata ataataataa taataataat aataataata ataataataa ttacaacgcc   420
ggcccatagg gcctggcatg gattaacggg gcaaggtgac tagggcgaga gggcccgccc   480
ccctcacgct gacgcctcac cacgaaagag tcacaacctc cgaaactaca acctccaagt   540
cctaggccgc tcttcaaagt ccactacatc cgagcctgca cacctagcat atcgagctag   600
ggaaacgccg cgttatagta gtggagcact gccagttcgt gcaaaccgag gagccatggc   660
gctcctcctc gagccttgga tcttgagcct tgtcttgaac cttggacctc gccactaaat   720
cggacttctg caccacgacc tttctaggtt gcagcgggca taagcccgca attgccacta   780
agggcaatta cctatcattc gtgggatcac caatcggttg cgcaccaatc tttcgccttt   840
tgcataattg ggcttttatc cggattcgta cccgggtccc ttctgccgta aggacg       896
```

<210> SEQ ID NO 44
<211> LENGTH: 2361
<212> TYPE: DNA
<213> ORGANISM: Chlamydomonas reinhardtii

<400> SEQUENCE: 44

```
ccacttattg actccttact gccgtgtagc gttacaaacc gccacggccc caaacgataa    60
tcccaatctc tcaaaccgac aatagcctcc actcatgcct caagcggcct agcaactcat   120
tcgtggccct cagcggcctc ctacctccgg cctcgcagct cccgataccc caccaagtcc   180
gccgtgcccg ccccagcccg cccgtgttga ggttgcacta gtggccgaaa gtgctgccag   240
```

```
tactgggtgt gtcgcatgta tgaagtgcct gatagcagca gagtccagac aaccacgcac    300
gccgcagcgc ccacgggtgc caccacatta atccgcggcg gcaccagggg gggcgggtgg    360
gttgtcaccg tcccggcaga gggacgatcc gaaatacagt acagaagcac aacggcagat    420
aaggcgccgt gtgctcctga cgcgtacaag acccagctcg gttcggcccc atgcacaggc    480
acgtacccga gcgtcctgcg ccgtgcgtga ctctaacgca acacggcagt acgtcgcaa     540 taactagact tatctccact gcgctgcgat aagtcagcgc ttattgactc cttactgccg    600
tgtagcgtta caaaccgcca cggccccaaa cgataatccc aatctctcaa accgacaata    660
gcctccactc atgcctcaag cggcctagca actcattcgt ggccctcagc ggcctcctac    720
ctccggcctc gcagctcccg ataccccacc aagtccgccg tgcccgcccc agcccgcccg    780
tgttgaggtt gcactagtgg ccgaaagtgc tgccagagtt tggtagtagt cctcaacgcg    840
gggaggtcat ggtgcgggcg acggcagccc tggtggctgg gcttgattgg cttcgcgtat    900
gcagctcttc tcgcaaagcg ctcggcccaa cggccggtca cgcaaaccaa ggtgcggtcg    960
gcggtgatgg cggcggcgtt cgtgcccttg cgctaccgaa atcatgtgtc tcgaacaccg   1020
cggagcgctc cgcccatcgc cttgcttgcg cacgaacgta cggtcctagt tgcacactcg   1080
acagcggtcg atagaacgag cttcgtgctt ggggatattg gctgcacgag cagcaccatc   1140
acatggggat gagcgccgcc ggaggcgccg ccggcacctg ctgcaggcgg cgcagggcga   1200
cgccaacgcg gggcctgaca cgccacacac ccgtcggtca tgggcggtca atggtcacta   1260
ccagaagaca agcagcaata ggaacacgac tggcgttgca agggccatga taccagactc   1320
acaaacgtat caggtgcacc aatggccacg acagaaacac acatgcattg tcccgcgtgc   1380
gccagccacg cagacgacgc cggggcgtta cagggaaaca catgcatcct tgttcaggtg   1440
tgtggcttct gggcagctgt ggccgtccgt gtgcctagga aaggtaacag tgcgtgttgg   1500
cacgtgttgg cacgaagcac tggagacctc gctcggtact ctctaccggc cccagggcc    1560 atgccataac acgtgttgac gttgtaggct gctcggaaca accttgggaa taataacaac   1620
ttcgtgactc gaagctggga cagactagca aacatgagcc acgcaggaga aggcgcgagg   1680
tgcaacacta gagcggtttt acgtacgcga gtcacgcgcg gcaacctgcc cttcacccgc   1740
gccgtcgtgg tgtaggatgc gggcagccat gcccagccgt gcagcatggc cacgaacact   1800
aatttctttc ttgctagcta ggtgccatgc ttgagatttg cagtgtcttg cataagagtc   1860
actaccaatc aagcagtagg tacacccata gatagcatca ccccggcgga cgcaggacag   1920
gcgcgcacgt gaatgcctcc aaacgccgcg gggatgcatg cacacaatgt cccgtacgtg   1980
ccgataccgt acgccacggc ggctgtgggg tgtaccgtaa tagcagggag gcaacatga    2040 agggtaacac ctcagcaacc ccagcaaggc tggcctggtc gagcggcgcg gagggggtgaa   2100 ggatacccgg cacgcgtgga acacgcaatg tatctatagt gatagaaggc gtagtgatgg   2160
gaggaaataa ggagcactcg gggccgcgat ggcgggttgg atgcgccacg gcccccggcc   2220
cagccaaagg gagcgaacgc cgggcggagc cggtgggtga gcgactcgag ggacgtgcca   2280
gtagtgaacc catcgcagtg gcggatgggt catccaatgt gagagatgat acagccacgc   2340
cggcagccaa actccgcact c                                            2361
```

<210> SEQ ID NO 45
<211> LENGTH: 1916
<212> TYPE: DNA
<213> ORGANISM: Chlamydomonas reinhardtii

<400> SEQUENCE: 45

```
atggacaatt tacggcgtac gtgccctcat gatacagcct gtgcgccgca ggcaacgggc      60
tccgcgccct tgctccatgg acacttcacg gcgtacgtgc cctcatgaca cggcctgtgt     120
gccgcaggca acgggctccg cgccttgct tcatggacaa tgcgccgcgt acgtgttctt     180
atgatacggt ctgtgcgccg caagcaacgg gctccgcacc cttgttttat ggacaattca     240
cggcatacgt gcccgtatga tgtgacctgt gtgccgcaag caacggcttc gcacccttgc     300
ttttgggtaa tagatggcat acgtgccctt atgatacgac ctgtgtgccg caagcaacgg     360
gctccacact cttgcgttgt ggattataga cggcattgaa atgcttacgt gccttcgttg     420
tacatgcctt tgcgttgtgg acaatgtgtg gtctgagcgc cacgttcgga tacggcgtgt     480
gtgccgccag caacaggctt tgcgcctcgc atcatgtgtc ttgcgatatg gcctgtgtgc     540
cgcatgcaat tatgctgcct gccctgtcgt tatggacgct tcgacttgtt gcgtgccctg     600
ctgcgtgccc tgtcgcaata cgccttgagt gtaccgtgca cggcaagcct gcgcctcgct     660
attgcttcgt gttgacaacg gagcgggctt acgtgatcat gcgtcaccct gtacgtcttg     720
aggtccgcac gcacatcata ctatcacgcg gcatcaccct gtagtttgg ctgacgcacc     780
ccaagccaac ctatatgcat tcgatgtgtg cgctaggcc aagtgccgaa tttgttttc     840
cggatatttc gccctcagtg agcgatgtgg agttttgtgc agttcggcca gcatgctatg     900
cccagccaat aacaataccg catgatgcat aactataccg catgacgcat aactataccg     960
catgacgcat aaacatgcct tcgtgccctg caccaggcat cggacgctgt gtcacgcagt    1020
gagcccgacc ctgcgcaacc aacatttgt tgcgagatac ggtcggagct gggattacag    1080
cctgcctggt gggtttggat ggcgcccgtg tgtttgggctg ggctgttgct gctcgcggtg    1140
gggcccacca ccaagtcacg gcacccatcc gccctccct cttgttggcc cacccgcctg    1200
tacacatgcc agtcacccgc tcgccatcct gtgaaagcgg gtagccgact tggcaagcgc    1260
ttttcctgac acttggcgca ggtttgagtg ggataccaga atggtctgaa tgtagttgtt    1320
ggataaccag tacactgcgg tgtgtagctg gttagcggga gtaccgtgca tgaaacacgc    1380
tactcgaccc gccatgcccg cgcgatggta ccaccaaccg ttcaacccag atccatgccg    1440
gggtagcatc gaccccacag tcagactgat agctcctatc caggtgttag gcgccatgta    1500
tgtatctgtg gacgcgtcaa gctggcttgt gccgtagcgt tggccgcctg tatggcacgg    1560
catctgtgtc acgttatggc ctcatgctta ccgtagtcac gcggcttgcg tgctgtgcgg    1620
cacgctcccct gccaatcctt caggacatgt atgcatacat gttacttcgt cagagccata    1680
gcagggggcag cgtgttctgt caatgcctca tgaacccaga gacccaagcc aacgtacgca    1740
ttagttccgc aacgcacgtc aatgccaact gtatgtgtcg cctgcccact cgcgagtgga    1800
cgcctaggga accaaccttg gttcctttca gccccggcct tacttcaccc ggcggggcaa    1860
ttacttatca ccgaagtgct aggagcagtg tgctatatgt cattactatt aagagc        1916
```

<210> SEQ ID NO 46
<211> LENGTH: 552
<212> TYPE: DNA
<213> ORGANISM: Chlamydomonas reinhardtii

<400> SEQUENCE: 46

```
gggggcctga acgctgtggt acggtggggc aagcacaccc ttgccgcaga gcccgaaggg      60
gaaggaggca gtggcggtac cactgccact ggcgtcctcc ttcgggctgg ctgggataca     120
gaccgacacg cgaaccggtg cattattcag ggcttcagct atcgacgcag catagcctac     180
```

| | |
|---|---|
| ttaccatgtc atgctctatc tttttgtttt gcgtccaaag ctggaaggca tctcttagct | 240 |
| cgttaagctc aggcgagtgc ggtggcagct tttttaatcg ctcttcgcag tatggaagac | 300 |
| gtgatagctt aggtagctgg tcgcctgata gatggcccgc cagcacaagc aacagggcaa | 360 |
| ggcctaactg cagccgagcc tgtcgcccgc ggtcacgtgt aattaccata gttggctcag | 420 |
| ttcattttac tatatactgt atgtcatccg tgtgtgctga agcaaaacaa actgcgctct | 480 |
| tactgatgat caacacagct gagtctgagt cccccacgat tggatacaag agaggagtgc | 540 |
| cgagggagat gc | 552 |

<210> SEQ ID NO 47
<211> LENGTH: 4334
<212> TYPE: DNA
<213> ORGANISM: Chlamydomonas reinhardtii

<400> SEQUENCE: 47

| | |
|---|---|
| aggatgtgcg gcgatcgctg aaatgcagtt gtggggtcca cactcatatg gcacccacgc | 60 |
| cccacacagc actgatgcag ggctcctgca gccgtcacgc catgggaatc agcatatggg | 120 |
| cagtggcctg tgcatacttc tctgtggcct ggcggggcat ctggccaggg cgtttgacta | 180 |
| gcggcatggg gcctgcacgc cggtaggggg cgcaggccc aaaatgatgc aaggaagctg | 240 |
| atgtgttgcg tgaggtgcgc agcggttcct gatggacgtg ggtgctttca tgcgtatgta | 300 |
| tattggctat gtgtgttgat cttttgcacca gggtggtgtc gccgcgcagc ggagcattgg | 360 |
| tgttggtgca cggggcgtga acattggggc ccgcagttgg gatcgcgccg gcacggtcgc | 420 |
| gggcaccgct gaagatatgt tggcgcgacc ggtcgcttat ggtgcacgct aatacccgca | 480 |
| tactgtgtgt aagcaccgat gcaattata agttgcgcat gtagatatcg gtcttctccc | 540 |
| gacatgcgct ctgatgacgg ttccatttcc gccaacttag ggtgagagtt aagagccgga | 600 |
| gccctgttgc cacctgcaaa atgccttagc aacatgtggc aactatctgc ccgaagcaag | 660 |
| ttgcaagcca gcccagttca ggttgccaca tgccatgctg ggtattccca gcgcgctagc | 720 |
| gcacctgctt gggcagctcg ctatggctgc cgtcgacagt tgaccctggt atgccatcgc | 780 |
| tagagtcgca gcccgctccg gccaacctcg ctcctccgca accgacacac gaacccgacg | 840 |
| tcacttgatc ccacaattcc agcgactttt gcgaccggct ctccaccgac cgcttggatg | 900 |
| cttgcgcccg gtcgctgccc cagctacttc cgcggtgaaa taacaacggt gagcactctc | 960 |
| aaccactgcg aggacagccc tagcaaccgc actgcgtaag aagtacagca tcgatttgct | 1020 |
| gcatgttgat tttggcgcaa atgggggtg caagcagttt gtttctctca gacgcgagct | 1080 |
| agcgcccaag cgcgcgatat gggggcgagg agccactatg tagctgtaac gattgcatga | 1140 |
| gtggcgaatt ttacttcgag ggtctagggt gcgagcggag tgggattacc ccccgagggg | 1200 |
| cacgccatgc gctcaggccc catgcaacag aaattcgccg ggcaccaacc cacgcacaga | 1260 |
| taattcatag gactacacca tagccatcag agaccggccg ggaacaagcc ccgcaagcgg | 1320 |
| ggcagcatgg gcgcgacacc accctgccgc gccaactcac cccaaacacg ccccaaccac | 1380 |
| ttgtgcgaca caagggctac catacagtag cgcgcgacac ctaatcgcgt gcgccggagt | 1440 |
| gtgcgagcaa acattgtacg gaggagctcg tttgggccct aggacgcagg gcctgggctg | 1500 |
| gcatttggtg cattcaatag agcatagaaa accgaggcca catatgtgct cgggtgcgca | 1560 |
| aaggtcggcg gaattgtggg atcaagtgac gtggaaatgg atctggggga ctgcggggtt | 1620 |
| ttggggtgtg ttgggttggt ggcgtgaagg gtgtgatttg tgaggaattt atcgatgcat | 1680 |

```
gccaagttgc acgcctttcc cctgtgtttc ctacatgccc ctgaaccctc cctttgctgg    1740
ctgcaggcga agcgacaagt ggtaccgctg gtaccaccca cgggggcctt gtgcccaagc    1800
cgtggtggcg catggtaact atacacgtgg cggtcatcga cattgctttg tgccggcgcg    1860
cagcacccag gatgtgcggc gatcgctgaa atgcagttgt ggggtccaca ctcatatggc    1920
acccacgccc cacacagcac tgatgcaggg ctcctgcagc cgtcacgcca tgggaatcag    1980
catatgggca gtggcctgtg catacttctc tgtggcctgg cggggcatct ggccagggcg    2040
tttgactagc ggcatggggc ctgcacgccg taggggggc gcaggcccaa aatgatgcaa    2100
ggaagctgat gtgttgcgtg aggtgcgcag cggttcctga tggacgtggg tgctttcatg    2160
cgtatgtata ttggctatgt gtgttgatct ttgcaccagg gtggtgtcgc cgcgcagcgg    2220
agcattggtg ttggtgcacg gggcgtgaac attgggccc gcagttggga tcgcgccggc    2280
acggtcgcgg gcaccgctga agatatgttg gcgcgaccgg tcgcttatgg tgcacgctaa    2340
tacccgcata ctgtgtgtaa gcaccgattg caattataag ttgcgcatgt agatatcgt     2400
cttctcccga catgcgctct gatgacggtt ccatttccgc caacttaggg tgagagttaa    2460
gagccggagc cctgttgcca ctgcaaaat gccttagcaa catgtggcaa ctatctgccc    2520
gaagcaagtt gcaagccagc ccagttcagg ttgccacatg ccatgctggg tattcccagc    2580
gcgctagcgc acctgcttgg gcagctcgct atggctgccg tcgacagttg accctggtat    2640
gccatcgcta gagtcgcagc ccgctccggc caacctcgct cctccgcaac cgacacacga    2700
acccgacgtc tgacgtggaa atggatctgg gggactgcgg ggttttgggg tgtgttgggt    2760
tggtggcgtg aagggtgtga tttgtgagga atttatcgat gcatgccaag ttgcacgcct    2820
ttcccctgtg tttcctacat gccctgaac cctcccttg ctggctgcag gcgaagcgac    2880
aagtggtacc gctggtacca cccacggggg ccttgtgccc aagccgtggt ggcgcatggt    2940
aactatacac gtggcggtca tcgacattgc tttgtgccgg cgcgcagcac ccaggatgtg    3000
cggcgatcgc tgaaatgcag ttgtggggtc cacactcata tggcacccac gccccacaca    3060
gcactgatgc agggctcctg cagccgtcac gccatgggaa tcagcatatg ggcagtggcc    3120
tgtgcatact tctctgtggc ctggcggggc atctggccag ggcgtttgac tagcggcatg    3180
gggcctgcac gccggtaggg gggcgcaggc ccaaaatgat gcaaggaagc tgatgtgttg    3240
cgtgaggtgc gcagcggttc ctgatggacg tgggtgcttt catgcgtatg tatattggct    3300
atgtgtgttg atctttgcac caggtggtg tcgccgcgca gcggagcatt ggtgttggtg    3360
cacggggcgt gaacattggg gcccgcagtt gggatcgcgc cggcacggtc gcgggcaccg    3420
ctgaagatat gttggcgcga ccggtcgctt atggtgcacg ctaatacccg catactgtgt    3480
gtaagcaccg attgcaatta taagttgcgc atgtagatat cggtcttctc ccgacatgcg    3540
ctctgatgac ggttccattt ccgccaactt agggtgagag ttaagagccg gagccctgtt    3600
gccacctgca aaatgcctta gcaacatgtg gcaactatct gcccgaagca agttgcaagc    3660
cagcccagtt caggttgcca catgccatgc tgggtattcc cagcgcgcta gcgcacctgc    3720
ttgggcagct cgctatggct gccgtcgaca gttgaccctg gtatgccatc gctagagtcg    3780
cagcccgctc cggccaacct cgctcctccg caaccgacac acgaaccga cgtcagacgt    3840
ggaaatggat ctgggggact gcggggtttt ggggtgtgtt gggttggtgg cgtgaagggt    3900
gtgatttgtg aggaatttat cgatgcatgc caagttgcac gcctttcccc tgtgtttcct    3960
acatgccccg aaccctccc tttgctggct gcaggcgaag cgacaagtgg taccgctggt    4020
accacccacg ggggccttgt gcccaagccg tggtggcgca tggtaactat acacgtggcg    4080
```

```
gtcatcgaca ttgctttgtg ccggcgcgca gcacccagga tgtgcggcga tcgctgaaat    4140
gcagttgtgg ggtccacact catatggcac ccacgcccca cacagcactg atgcagggct    4200
cctgcagccg tcacgccatg ggaatcagca tatgggcagt ggcctgtgca tacttctctg    4260
tggcctggcg gggcatctgg ccagggcgtt tgactagcgg catggggcct gcacgccggt    4320
aggggggcac aggc                                                      4334

<210> SEQ ID NO 48
<211> LENGTH: 1498
<212> TYPE: DNA
<213> ORGANISM: Chlamydomonas reinhardtii

<400> SEQUENCE: 48
gatgtgtggg ttgcggagat ggaggccgtg gccgcggaag ggatgagcga tggaagttag      60
gaccatgcac ggaccttccg ccgcgtccct cactcactcc caggtcaacg tgaagtgcga     120
atcagcttgt aacgaggcgc agaagtgtgc acaagccgca gaacctgcga gtgaagccat     180
acccaccacc ctcacctggc gggcgggcgc cttggctagg cctgctgccc accaccagtg     240
ccaaggcagg ccatcgcatc ttctgtgtgg cgccgcggcc ttgacagata tattgaactc     300
agcacgcaaa atgctaatta ccgtctgagc aagataaagc cgcttatgca agaaacacg      360 agtcaacgcg ggctacaaaa gaaaatgctc cgagttgctt ctaaccgtca tcgaacgaat     420
tatttatgcg ctgacttatc gcagcgcagt ggagataagt ctagttattg cgacgtaact     480
gccgtgttgc gttagagtca cgcacggcgc aggacgctcg ggtacgtgcc tgtgcatggg     540
gccgaaccga gctgggtctt gtacgcgtca ggagcacacg gcgccttatc tgccgttgtg     600
cttctgtact gtatttcgga tcgtccctct gccgggacgg tgacctcagt gtgtcgcact     660
taaacgttcc ctacatttct ggactttctt tgcaatccta tacctggttc taactatact     720
tgaccatgta tggaccgaat aagcgtttaa tatatactca gacggagttg cagcgttttg     780
ttgcgcgatc ctgctcaatg gaacccctta gcttgatcac gctcgctctc tgatcgtaag     840
ggaatgccct tcgaagcttc tctggcgctt tgaaccacgc tttggttcgg gggccgcatt     900
cgggagcaaa tcgagcaga gcggagcttt caagcggagc aaaggcgcgc gaagcgttgc     960
ggacaaggcg ttcggcaagt cactgaaagc aaaagggcat gcacagctgt gcgggcgggc    1020
tacttgcttg ccatgcgcgg tcctgcttgc cgtgccttcg tgtctacccg tcgctttaca    1080
gttcacagct ttgtgcaata ccttccaca tcttccattg tgccacccc acctccccaa     1140 gaccctcagg acttttggcg cggtacttct cctgtctgcc tatccaggcc gcagggcccg    1200
cgtgcccttg gggaaagggc gtgtgtgccg ttgggatccg gcctgtgcgc cgcaagcaac    1260
gggctttgcg cccttgcctt atggacaatg gacggcatac gtgcccttat gatacggcct    1320
gtgtgccgca agcaatgggc tccgcgccct tgctttatgg acaatggacg gcatacgtgc    1380
ccttatgata cggcctgtgc gccgcaagca acgggctccg cgcccttgct ttatggacaa    1440
tggacggcat acgtgccctt atgatacggc ctgtgtgccg caagcaacgg gctccgcg       1498

<210> SEQ ID NO 49
<211> LENGTH: 2204
<212> TYPE: DNA
<213> ORGANISM: Chlamydomonas reinhardtii

<400> SEQUENCE: 49
catggacaat ttacggcgta cgtgccctca tgatacagcc tgtgcgccgc aggcaacggg      60
```

| | | |
|---|---|---|
| ctccgcgccc ttgctccatg acacttcac ggcgtacgtg ccctcatgat acggcctgtg | 120 |
| tgccgcaggc aacgggctcc gcgcccttgc ttcatggaca atgcgccgcg tacgtgttct | 180 |
| tatgatacgg cctgtgcgcc gcaagcaacg ggctccgcac ccttgtttta tggacaattc | 240 |
| acggcatacg tgcccgtatg atgtgacctg tgtgccgcaa gcaacggctt cccacccttg | 300 |
| cttttgggta atagatggca tacgtgccct tatgatacga cctgtgtgcc gcaagcaacg | 360 |
| ggctccacac tcttgcgttg tggattatag acggcattga aatgcttacg tgccttcgtt | 420 |
| gtacatgcct ttgcgttgtg acaatgtgt ggtctgagcg ccacgttcgg atacggcgtg | 480 |
| tgtgccgcca gcaacaggct ttgcgcctcg catcatgtgt cttgcgatat ggcctgtgtg | 540 |
| ccgcatgcaa ttatgctgcc tgccctgtcg ttatggacgc ttcgacttgt tgcgtgccct | 600 |
| gctgtgtgcc ctgtcgcaat acgccttgag tgtaccgtgc acggcaagcc tgcgcctcgc | 660 |
| tattgcttcg tgttgacaac ggagcgggct tacgtgatca tgcgtcaccc tgtacgtctt | 720 |
| gaggtccgca cgcacatcat actatcacgc ggcaccaccc ttgtagtttg gctgacgcac | 780 |
| cccaagccaa cctatatgca ttcgatgtgt gcgctaggcc caagtgccga atttgttttt | 840 |
| ccggatattt cgccctcagt gagcgatgtg gagttttgtg cagttcggcc agcatgctat | 900 |
| gcccagccaa taacaatacc gcatgacgca taactatacc gcatgacgca taaacatgcc | 960 |
| ttcgtgccct gcaccaggca tcggacgctg tgtcacgcag tgagcccgac cctgcgcaac | 1020 |
| caacattttg ttgcgagata cggtcggagc tgggattaca gcctgcctgg tgggtttgga | 1080 |
| tggcgcccgt gtgttgggct gggctgttgc tgctcgcggt ggggcccacc accaagtcac | 1140 |
| ggcacccatc cgccctcccc tcttgttggc ccacccgcct gtacacatgc cagtcacccg | 1200 |
| ctcgccatcc tgtgaaagcg ggtagccgac ttggcaagcg cttttcctga cacttggcgc | 1260 |
| aggtttgagt gggataccag aatggtctga atgtagttgt tggataacca gtacactgcg | 1320 |
| gtgtgtagct ggttagcggg agtgccgtgc atgaaacacg ctactcgacc cgccatgccc | 1380 |
| gcgcgatggt accaccaacc gttcaaccca gatccatgcc ggggtagcat cgaccccaca | 1440 |
| gtcagactga tagctcctat ccaggtgtca ggcgccatgt atgtatctgt ggacgcgtca | 1500 |
| agctggcttg tgccgtagcg ttggccgcct gtatggcacg gcatctgtgt cacgttatgg | 1560 |
| cctcatgctt accgtagtca cgcggcttgc gtgctgtgcg gcacgctccc tgccaatcct | 1620 |
| tcaggacatg tatgcataca tgttacttcg tcagagccat agcaggggca gcgtgttctg | 1680 |
| tcaatgcctc atgaacccag agacccaagc caacgtacgc attagttccg caacgcacgt | 1740 |
| caatgccaac tgtatgtgtc gcctgcccac tcgcgagtgg acgcctaggg aaccaacctt | 1800 |
| ggttcctttc agccccggcc ttacttcacc cggcggggca attacttatc accgaagtgc | 1860 |
| taggagcagt gtgctatatg tcattactat taagagcgta tggcgacaca ggctcacatg | 1920 |
| tgggtagcca ggcttggcag gcatcccaac tcagcccggc ctcctcacag cagtaccacg | 1980 |
| acgtgcccgt acgtggtcga gtgcggagtt tggctgccgg cgtggctgta tcatctctca | 2040 |
| cattggatga cccatccgcc actgctgttc actactggca cgtccctcga gtcgctaccc | 2100 |
| caccggctcc gcccagcgtt cgctcccttt ggctgggccg gggcccgtgg cgcatccaac | 2160 |
| ccgccatcgc ggccccgagt gctccttatt tcctcccatc acta | 2204 |

<210> SEQ ID NO 50
<211> LENGTH: 2092
<212> TYPE: DNA
<213> ORGANISM: Chlamydomonas reinhardtii

<400> SEQUENCE: 50

```
ccgcgccgct cgaccaggcc agccttgctg gggttgctga ggtgttaccc ttcatgttgc    60
cctccctgct attacggtac accccacagc tgccgtggcg tacggtatcg gcacgtacgg   120
gacattgtgt gcatgcatcc ccgcggcgtt tggaggcaaa cattcacgtg cgcgcctgtc   180
ctgcgtccgc cggggtgatg ctatctatgg tgtacctac  tgcttgattg gtagtgactc   240
ttatgcaaga cactgcaaat ctcaagcatg gcacctagct agcaagaaag aaattagtgt   300
tcgtggccat gctgcacggc tgggcatggc tgcccgcatc ctacaccacg acggcgcggg   360
tgaacgaagg gcaggttgcc gcgcgtgact cgcgtacgta aaaccgctct agtgttgcaa   420
ctcgcgcctt ctcctgcgtg gcgcatgttg gctagcctgt cccagcttcg agtcacgacg   480
ttgttattat tcccaaggtt gttccgagca gcctacaacg tcaacacgtg ttatggcatg   540
gccctggggg ccgtagaga  gtaccgaggt ctccagtggt cgtgccaac  acgtgccaac   600
acgcactgtt acctttcctg gcacacggaa cggccacagc tgcccacaag ccacacacct   660
gaacaaggat gcatgtgttt ccctgtaacg ccccggcgtc gtctgcatgg ctggcgcacg   720
cgggataacg catgtgtgtt tctgtcgtgg ccattggtgc acctgatacg tttgtgagtc   780
tggtatcatg gcccttgcaa agccagtcgt gttcctattg ctgcttgtct tctggtagtg   840
accattggcc gcccatgacc gacggagtgt ggcgctgtca ggccccgcgt tggcgtcgcc   900
ctgcgcctgc agcaggtgcc ggcggcgcct ccggcggcgc tcatccccgc gtgatggtgc   960
tgctcgtgca gccaatatcc ccaagcacga agctcgttct attgaccgct gttgagtgtg  1020
caactaggac cgtacgttcg tgcgcaagct aggcgatggg cggagcgctc cgcggtgttc  1080
gagacacatg atttcggtag cgcaagggca cgaacgccac cgccatcacc gccgaccgca  1140
ccttggtttg catgaccggc cgttgggcca agcgctttgc gagaagagct gcatacgcga  1200
agccaatcaa gcccagccac cagggctgcc gtcgcccgca ccatgacctc ccggcgttga  1260
ggactactac caaactctgg cagcactttc ggccactagt gcaacctcaa cacgggcggg  1320
ctggggcggg cacggcggac ttggtggggt tatcggggagc tgcgaggccg gaggtaggag  1380
gccgctgagg gccacgaatg agttgctagg ccgcttgagg catgagtgga ggctattgtc  1440
ggtttgagag attgggattg tcgtttgggg ccgtggcggt ttgtaacgct acacggcagt  1500
aaggagtcaa taagcgctga cttatcgcag cgcagtggag ataagtctag ttattgcgac  1560
gtaactgccg tgttgcgtta gagtcacgca cggcgcagga cgctcgggta cgtgcctgtg  1620
catggggccg aaccgagctg ggtcttgtac gcgtcaggag cacacggcgc cttatctgcc  1680
gttgtgcttc tgtactgtat ttcggatcgt ccctctgccg ggacggtgac aacccacccg  1740
cccccctgg  tgccgccgcg gattaatgtg gtggcacccg tgggcgctgc ggcgtgcgtg  1800
gttgtctgga ctctgctgct atcaggcact tcatacatgc gacacaccca gtactggcag  1860
cactttcggc cactagtgca acctcaacac gggcgggctg gggcgggcac ggcggacttg  1920
gtggggttat cggagctgc  gaggccgag  gtaggaggcc gctgagggcc acgaatgagt  1980
tgctaggccg cttgaggcat gagtggaggc tattgtcggt ttgagagatt gggattgtcg  2040
tttggggccg tggcggtttg taacgctaca cggcagtaag gagtcaataa gt          2092
```

<210> SEQ ID NO 51
<211> LENGTH: 1187
<212> TYPE: DNA
<213> ORGANISM: Chlamydomonas reinhardtii

<400> SEQUENCE: 51

```
gcggacgtgg aagcttgggc ggacgtccca gcattgactg ctaccctggg taggtctctg      60
ataaccatgt gctccgggct gtatcagtga atgtgacgcc tctcaatcag caagttctgt     120
gacaccagtc acaccacaat cggtgcaagt aacccgtcac agcgcgcatc aatccccgac     180
cccgccacac aatccccgac acgggagcta cccaccagcg ttaaggacgg ccgcccagca     240
ggcccttcca acattgtttc cgcgcgcgtc agcacaccat agtagtgcgc ttgttaacgc     300
tggatggagc atgcctcagc ccatccaaac acgcagcggc attcccgcca tgcatgcagg     360
tgcacttcga aagcattgcc ccgcctgggt gcaccgacac cagttgtttg tgttggctac     420
tgcccaacct cctcgcagtc caactactgc ccagtcccac tgcaccggaa tcaccaccag     480
cagtcctgcg gctatcatag ctttcaatga agcacgtgta atacctaata caataggttc     540
atgcaagttg gtgataaaat gcacatcatc actctcgtgt ctcgattgtc ttctctgatg     600
cgtgctgtca tcgtgtgcac gccacatctg tagcgactca catctctcac atcttcacgc     660
cgcaccaatt tcacagaatc cacaatcatt ctcaaacccg ccctgcgtgc gccgcctgtg     720
gtacacgtgt gcgtgccgcc cacagcccga ttactcctgc gtccgacatc ctgctcaacc     780
caccctattc gttggctaca cgacttgcgc ttgacaatat gcaatgactg tccctcgctt     840
ctgcgtcttg cctcttttagg acgtacgtca caaacacagt gcgtgcatgg ccatgtgccc     900
tcacactctt ctacactcgt gtcataacga gaaagtttac gccaaacgtg ctagggttga     960
cacctggcct tgtctgatgc ctagtaacct ccgcatacca gccacccgca cgcccgctgg    1020
tgccaagctc caacgtggga gcaagtaggc gcgctcagcg attggcctca tcccgctcgc    1080
gctcacacac ctcaaggcac gggcctccca ccagcacgga ttcgcccccag gcgaacgagc   1140 gcgccaaagc agcccccctca acagcagcag ccgagctagc agacccg                1187
```

<210> SEQ ID NO 52
<211> LENGTH: 191
<212> TYPE: DNA
<213> ORGANISM: Chlamydomonas reinhardtii

<400> SEQUENCE: 52

```
atatatatat atatatatat atatatatat atatatatat atatatatat atatatatat      60
atatatatat atatatatat atatatatat atatatatat atatatatat atatatatat     120
atatatatat atatatatat atatatatat atatatatat atatatatat atatatatat     180
atatatatat a                                                           191
```

<210> SEQ ID NO 53
<211> LENGTH: 109
<212> TYPE: DNA
<213> ORGANISM: Chlamydomonas reinhardtii

<400> SEQUENCE: 53

```
ttggtatgca gatcaaccaa atcgatactg tgtgcgcact taggcatgca tagtcgcaat      60
cgttacgcac aagggctgat ggatttgagc caagcatacc gatggggca                 109
```

<210> SEQ ID NO 54
<211> LENGTH: 2953
<212> TYPE: DNA
<213> ORGANISM: Chlamydomonas reinhardtii

<400> SEQUENCE: 54

```
tgtcaacctc tccaatttga gccccgcttt ccacagcgcc aagccctaat atcaggcgag      60
gcctggcgag gttttgcccg caccccgtc cgcttaggag tacggcagag ccccggaatc     120
```

```
tatgtccttg cgcgtccgct tggcatgcag gtctgtaccc tgtgaagctt aggtgacctg    180
gtgactagct gggcttggtt ggacggccaa agcccttgt ctcgcgttgt gccccacat     240 gcgaacacac cttggagtgt cctagcgccc gggctcttgc tatggtgaaa gcgctacgtt    300
tgatttctgt tggatgcggg tggcgtgggc agggtgcgtg tgtgggggca acatgcgaca    360
atggacaagg cgaagttcgg tcaagggctt ttggatggcc ctgcgccttc tgggccatat    420
gcatatatgc atatagattg tggaaagtgg ggcgggcggg ttcggaggtg cgcttatggg    480
gtcggaatgg gggctccgga tgtggggtc ggttcgagct ggtgagctta agtgcggcga    540
gaggccgtag cgaggcgtta ctggacccgc gtttacttaa acatggcgcg cactatactt    600
gtccataatt aaccattagc ttaccaagtc tggaagctat tgcgctttgt ttcgctgcct    660
tgctcgctgc gtagttgcca caaacgggct tggggtcgag gaggtgcgaa atcccgaact    720
cgcacagact tctgcagcgg agtgaaggga ggcgcagctt cgcagttagg gctgcgcttg    780
gcctccccgc ggcctcacga catacagaag gtcaaagtga acgcgacgga gcacagcggc    840
cgggctcagg agcgtcctac gaggagtcgg catcagcggc atttcgaatc tgccctctcc    900
gcgctcgcac ctggagcgtc gccgtaaccc gctgctgagc gcgctgggtt tagctatatc    960
ataggtgtat tgggctctca ggcacctgcg aaaatcgtgc cggtgagaag cttcggcttg    1020
cacaggcacg gcgtgcctcc tgaacccagc ttggtcccgc gcccaccacc tcccttttccc   1080 ctcgcacccc gcatccgccc ctcccccacac tgctgccatc cgtcgattcc atcatgtgtt   1140
gtggcaatca tcacctcctc aaaaaccgct tcatttgccc ctcatcctcg ccacgcactg    1200
tcaacctggc cgcctcaatg gtcgtcctct tcagtgcagc cctgcagtac aactcgctgc    1260
tggccgccag tggccaggag gatgcgttgc ctccacgcgc tccttcaggg cacggcctgc    1320
agctgcagat tagtgcgcgc taagctcact agtcttcttg ttcttgattg tagcctgggc    1380
ttgcagcgca cagttgcgag ccattagaca gcagacacgg cggcgctcag actcccgcac    1440
cgccacggcc tcggggaggc ttggggttgc ccttgggttt cgtgccggtg ctgggcgtgc    1500 tgggggttggg ctccatggat ccggcctgca cgtgtcgaac ccgagttcaa atcccgtcag   1560
gctgtcgtcc ccttcactcc gctgcagaag tctgtgcgag ttcggccgag accctcatcg    1620
gcgcccctgc ccagccgcac gtttcgcccc caaacttgat gtcaacctct ccaatttgag    1680
ccccgctttc cacagcgcca agccctaata tcaggcgagg cctggcgagg ttttgccccgc   1740 acccccgtcc gcttaggagt acggcagagc cccggaatct atgtccttgc gcgtccgctt    1800
ggcatgcagg tctgtaccct gtgaagctta ggtgacctgg tgactagctg ggcttggttg    1860
gacggccaaa gcccttgtc tcgcgttgtg ccccacatg cgaacacacc ttggagtgtc    1920
ctagcgcccg ggctcttgct atggtgaaag cgctacgttt gatttctgtt ggatgcgggt    1980
ggcgtgggca gggtgcgtgt gtgggggcaa catgcgacaa tggacaaggc gaagttcgt     2040 caagggcttt tggatggccc tgcgccttct gggccatatg catatatgca tatagattgt    2100
ggaaagtggg gcgggcgggt tcggaggtgc gcttatgggg tcggaatggg ggctccggat    2160 gtggggtcg gttcgagctg gtgagcttaa gtgcggcgag aggccgtagc gaggcgttac    2220
tggacccgcg tttacttaaa catggcgcgc actatacttg tccataatta accattagct    2280
taccaagtct ggaagctatt gcgctttgtt tcgctgcctt gctcgctgcg tagttgccac    2340
aaacgggctt ggggtcgagg aggtgcgaaa tcccgaactc gcacagactt cagcagcgga    2400
gtgaagggag gcgcagcttc gcagttaggg ctgcgcttgg cctccccgcg cctcacgac    2460
```

-continued

| | |
|---|---|
| atacagaagg tcaaagtgaa cgcgacggag cacagcggcc gggctcagga gcgtcctacg | 2520 |
| aggagtcggc atcagcggca tttcgaatct gccctctccg cgctcgcacc tggagcgtcg | 2580 |
| ccgtaacccg ctgctgagcg cgctgggttt agctatatca taggtgtatt gggctctcag | 2640 |
| gcacctgcga aaatcgtgcc ggtgagaagc ttcggcttgc acaggcacgg cgtgcctcct | 2700 |
| gaacccagct tggtcccgcg cccaccacct cccttcccc tcgcaccccg catccgcccc | 2760 |
| tccccacact gctgccatcc gtcgattcca tcatgtgttg tggcaatcat cacctcctca | 2820 |
| aaaaccgctt catttgcccc tcatcctcgc cacgcactgt caacctggcc gcctcaatgg | 2880 |
| tcgtcctctt cagtgcagcc ctgcagtaca actcgctgct ggccgccagt ggccaggagg | 2940 |
| atgcgttgcc tcc | 2953 |

<210> SEQ ID NO 55
<211> LENGTH: 2710
<212> TYPE: DNA
<213> ORGANISM: Chlamydomonas reinhardtii

<400> SEQUENCE: 55

| | |
|---|---|
| gaggcctggc gaggttttgc ccgcaccccc gtccgcttag gagtacggca gagccccgga | 60 |
| atctatgtcc ttgcgcgtcc gcttggcatg caggtctgta ccctgtgaag cttaggtgac | 120 |
| ctggtgacta gctgggcttg gttggacggc caaagcccct tgtctcgcgt tgtgccccca | 180 |
| catgcgaaca caccttggag tgtcctagcg cccgggctct tgctatggtg aaagcgctac | 240 |
| gtttgatttc tgttggatgc gggtggcgtg gcagggtgc gtgtgtgggg gcaacatgcg | 300 |
| acaatggaca aggcgaagtt cggtcaaggg cttttggatg ccctgcgcc ttctgggcca | 360 |
| tatgcatata tgcatataga ttgtggaaag tggggcgggc gggttcggag gtgcgcttat | 420 |
| ggggtcggaa tgggggctcc ggatgtgggg gtcggttcga gctggtgagc ttaagtgcgg | 480 |
| cgagaggccg tagcgaggcg ttactggacc cgcgtttact taaacatggc gcgcactata | 540 |
| cttgtccata attaaccatt agcttaccaa gtctggaagc tattgcgctt tgtttcgctg | 600 |
| ccttgctcgc tgcgtagttg ccacaaacgg gcttgggtc gaggaggtgc gaaatcccga | 660 |
| actcgcacag acttctgcag cggagtgaag ggaggcgcag cttcgcagtt agggctgcgc | 720 |
| ttggcctccc cgcggcctca cgacatacag aaggtcaaag tgaacgcgac ggagcacagc | 780 |
| ggccgggctc aggagcgtcc tacgaggagt cggcatcagc ggcatttcga atctgccctc | 840 |
| tccgcgctcg cacctggagc gtcgccgtaa cccgctgctg agcgcgctgg gtttagctat | 900 |
| atcataggtg tattgggctc tcaggcacct gcgaaaatcg tgccggtgag aagcttcggc | 960 |
| ttgcacaggc acggcgtgcc tcctgaaccc agcttggtcc cgcgcccacc acctcccttt | 1020 |
| ccctcgcac cccgcatccg cccctcccca cactgctgcc atccgtcgat tccatcatgt | 1080 |
| gttgtggcaa tcatcacctc tcaaaaacc gcttcatttg ccctcatcc tcgccacgca | 1140 |
| ctgtcaacct ggccgcctca atggtcgtcc tcttcagtgc agccctgcag tacaactcgc | 1200 |
| tgctggccgc cagtggccag gaggatgcgt tgcctccacg cgctccttca gggcacggcc | 1260 |
| tgcagctgca gattagtgcg cgctaagctc actagtcttc ttgttcttga ttgtagcctg | 1320 |
| ggcttgcagc gcacagttgc gagccattag acagcagaca cggcggcgct cagactcccg | 1380 |
| caccgccacg gcctcgggga ggcttggggt tgcccttggg tttcgtgccg gtgctgggcg | 1440 |
| tgctggggtt gggctccatg gatcggcct gcacgtgtcg aacccgagtt caaatcccgt | 1500 |
| caggctgtcg tccccttcac tccgctgcag aagtctgtgc gagttcggcc gagaccctca | 1560 |
| tcggcgcccc tgcccagccg cacgtttcgc ccccaaactt gatgtcaacc tctccaattt | 1620 |

```
gagccccgct ttccacagcg ccaagcccta atatcaggcg aggcctggcg aggttttgcc      1680 cgcaccccg tccgcttagg agtacggcag agccccggaa tctatgtcct tgcgcgtccg       1740
cttggcatgc aggtctgtac cctgtgaagc ttaggtgacc tggtgactag ctgggcttgg      1800
ttggacggcc aaagccccctt gtctcgcgtt gtgccccac atgcgaacac accttggagt      1860
gtcctagcgc ccgggctctt gctatggtga aagcgctacg tttgatttct gttggatgcg      1920
ggtggcgtgg gcagggtgcg tgtgtggggg caacatgcga caatgacaa ggcgaagttc       1980 ggtcaagggc ttttggatgg ccctgcgcct tctgggccat atgcatatat gcatatagat      2040 tgtgaaagt ggggcgggcg ggttcggagg tgcgcttatg gggtcggaat gggggctccg       2100
gatgtggggg tcggttcgag ctggtgagct aagtgcggc gagaggccgt agcgaggcgt       2160
tactggaccc gcgtttactt aaacatggcg cgcactatac ttgtccataa ttaaccatta     2220
gcttaccaag tctggaagct attgcgcttt gtttcgctgc cttgctcgct cgtagttgc      2280 cacaaacggg cttggggtcg aggaggtgcg aaatcccgaa ctcgcacaga cttctgcagc     2340
ggagtgaagg gaggcgcagc ttcgcagtta gggctgcgct tggcctcccc gcggcctcac    2400
gacatacaga aggtcaaagt gaacgcgacg gagcacagcg gccgggctca ggagcgtcct    2460
acgaggagtc ggcatcagcg gcatttcgaa tctgccctct ccgcgctcgc acctggagcg   2520
tcgccgtaac ccgctgctga gcgcgctggg tttagctata tcataggtgt attgggctct   2580
caggcacctg cgaaaatcgt gccggtgaga agcttcggct tgcacaggca ggcgtgcct    2640 cctgaaccca gcttggtccc gcgcccacca cctccctttc ccctcgcacc ccgcatccgc   2700
ccctccccac                                                            2710

<210> SEQ ID NO 56
<211> LENGTH: 2231
<212> TYPE: DNA
<213> ORGANISM: Chlamydomonas reinhardtii

<400> SEQUENCE: 56
ggtgcgctta tggggtcgga atggggctc cggatgtggg ggtcggttcg agctggtgag       60
cttaagtgcg gcgagaggcc gtagcgaggc gttactggac ccgcgtttac ttaaacatgg     120
cgcgcactat acttgtccat aattaaccat tagcttacca agtctggaag ctattgcgct    180
ttgtttcgct gccttgctcg ctgcgtagtt gccacaaacg ggcttggggt cgaggaggtg    240
cgaaatcccg aactcgcaca gacttctgca gcggagtgaa gggaggcgca gcttcgcagt    300
tagggctgcg cttggcctcc ccgcggcctc acgacataca gaaggtcaaa gtgaacgcga    360
cggagcacag cggctgggct caggagcgtc ctacgaggag tcggcatcag cggcatttcg    420
aatctgccct ctccgcgctc gcacctggag cgtcgccgta accgctgct gagcgcgctg    480 ggtttagcta tatcataggt gtattgggct ctcaggcacc tgcgaaaatc gtgccggtga    540
gaagcttcgg cttgcacagg cacggcgtgc ctcctgaacc cagcttggtc ccgcgcccac    600
cacctccctt tcccctcgca ccccgcatcc gccctcccc acactgctgc catccgtcga    660
ttccatcatg tgttgtggca atcatcacct cctcaaaaac cgcttcattt gcccctcatc    720
ctcgccacgc actgtcaacc tggccgcctc aatggtcgtc ctcttcagtg cagccctgca    780
gtacaactcg ctgctggccg ccagtggcca ggaggatgcg ttgcctccac gcgctccttc    840
agggcacggc ctgcagctgc agattagtgc gcgctaagct cactagtctt cttgttcttg    900
attgtagcct gggcttgcag cgcacagttg cgagccatta gacagcagac acggcggcgc    960
```

```
tcagactccc gcaccgccac ggcctcgggg aggcttgggg ttgcccttgg gtttcgtgcc    1020
ggtgctgggc gtgctggggt tgggctccat ggatccggcc tgcacgtgtc gaacccgagt    1080
tcaaatcccg tcaggctgtc gtccccttca ctccgctgca gaagtctgtg cgagttcggc    1140
cgagaccctc atcggcgccc ctgcccagcc gcacgtttcg cccccaaact tgatgtcaac    1200
ctctccaatt tgagccccgc tttccacagc gccaagccct aatatcaggc gaggcctggc    1260
gaggttttgc ccgcaccccc gtccgcttag gagtacggca gagccccgga atctatgtcc    1320
ttgcgcgtcc gcttggcatg caggtctgta ccctgtgaag cttaggtgac ctggtgacta    1380
gctgggcttg gttggacggc caaagcccct tgtctcgcgt tgtgccccca catgcgaaca    1440
caccttggag tgtcctagcg cccgggctct tgctatggta aaagcgctac gtttgatttc    1500
tgttggatgc gggtggcgtg ggcagggtgc gtgtgtgggg gcaacatgcg acaatggaca    1560
aggcgaagtt cggtcaaggg cttttggatg gccctgcgcc ttctgggcca tatgcatata    1620
tgcatataga ttgtggaaag tggggcgggc gggttcggag gtgcgcttat ggggtcggaa    1680
tgggggctcc ggatgtgggg gtcggttcga gctggtgagc ttaagtgcgg cgagaggccg    1740
tagcgaggcg ttactggacc cgcgtttact aaacatggc gcgcactata cttgtccata    1800
attaaccatt agcttaccaa gtctggaagc tattgcgctt tgtttcgctg ccttgctcgc    1860
tgcgtagttg ccacaaacgg gcttggggtc gaggaggtgc gaaatcccga actcgcacag    1920
acttctgcag cggagtggtt gaaaaaatcg acgtctgtcg ccaagccagc gaaagaacga    1980
agctttgata aagttcaaca gttggagtgt attttgcgct ggatttgcca gcaagtaaaa    2040
cgccttgagc acgccctcgt gaccaagatg gaatcgcccg ccacggcgcc accgcgtaa    2100
acgacgctca acgtcgtccg ttagcacaac ctcctgtaca tgcccatcct gcgacgcccc    2160
atttgagcca acctacaggc tcgtgtgcac cgaatttgca gtctgtccgc agtgcccata    2220
cctgcacccg c                                                         2231
```

<210> SEQ ID NO 57
<211> LENGTH: 1717
<212> TYPE: DNA
<213> ORGANISM: Chlamydomonas reinhardtii

<400> SEQUENCE: 57

```
agccgcccag ggtgtgcgtg ccaccgtcgt cgccgcggca caggggggcat tcgccgcctg      60
cgcagccggg catggggtgt tttactcttg cggcccgctt ggcattccag agagggcccc     120
agcggtatttt gaacgcgcag caggcctctt caaatgagaa cttgtcgaac aggtttaggc     180
cgtagcgttc gtcgatgtgc ttcctcgctg cctcccatag ttccgcgtac agtcctgatt     240
tggtataacc ggtcgcggtg gatttacggg ccatttctt caggtcgcga ttgaggtcgt      300
tggcgtagcg taaccgttct tccaaattgc cattgtgctc cacagttttc ttctgggcaa     360
tccatccctc taagggttca tatgggtgcg agtatagagt ttctgtcgca tccggctgca     420
ctgttctggt ggccacagcc tgtgccgctt catccgcttt ctgatttcct acgcatgtgt     480
ctgtctggtg cgaccttacg tgataaaatg atgtcttgtg tccagctagg gcacgttccg     540
caagttggtc gactatggtc ccaaacatct cgcggtgctt gcttacgtgg agtgactcgg     600
gctccataat ggcgcggcgg aggatgaaca gactgacaag actgtcggtg tagacccgta     660
ggtgaggtgt gtctcgatgg aggcatcgac cacggcagag gttgcttagc gataagttgg     720
tgtgtaacgt cggttcagac ccgagttcga tcctccccaa attcggtaca ggggaaacct     780
ccgtgcgtat tcaaatcacg cacaggcgct ccacagggac cgcacggctc ttcagtcgtg     840
```

```
tccttgtcat ccgtggctaa cgtcagataa gagagcggtc gtgaagtgcc ggcaaagggg      900
ccggactctg gagcgatcca gagtttcagt tgagatgttg cccgacagtc ggcattacct      960
gatcccccga tctcaggtac caaaagccgt gagggtagat catccgagct gaacatggat     1020
aggacaccag gggcttaatc cacccgctc ccaccggtgg gcaggaccgg caatgataa       1080
ggtggtcgtg gtgacttccc gccttctctc gaactgggtt gagagatgat cagcgaaggc     1140
gttgccccgt taatacatgc taggccctat gggccagcgt tgggattatt attattatta     1200
ttattattat tattattatt attattatta ttattattat tattattatt attattatta     1260
ttattattat tattattatt attattatta ttattattat tattattatt attattatta     1320
ttattattat tattattatt attattatta ttattattat tattattatt attattatta     1380
ttattctcga tggaggcgga gcgccgtgcg tatggcggat gattcacacc gaaggatggt     1440
gctcaggggt gtgttgaagg cgatgtcttc atcaatgtgc gtggcgcggt tgtcgctggc     1500
gtcccagacc gccgctccca ggccagtgta ctctcgtgtg tgtggtactt tgctcccgtc     1560
ggtaaagacc gcggagcctc gtgtgtgtgc gagcgggaca taagcgcggt agagggttgc     1620
aagctccgta ggggatggta gggtggggc atcgcgaggg ggctggggct ggggcgtctg     1680
gctgctctgg gcgaggatgc gccgttttaa cttccgg                              1717
```

<210> SEQ ID NO 58
<211> LENGTH: 2731
<212> TYPE: DNA
<213> ORGANISM: Chlamydomonas reinhardtii

<400> SEQUENCE: 58

```
atcagggttt taaggggttt tgcagggttt gaaaagtgtg acatgtcaca aatgattggc       60
acagtataat tcagctaatt ataaccagaa tgattgtttg aaccccttgt ggatgaccgt      120
gatgagattt gggcacacag caatgacttc gtactcccac tgtttactcg ccacagcaca      180
cacaagtatg aagaaggaat cacactccca gagttccaca tacacacatt ggggcttctg      240
ggttgatgtt gcttgcctca cgcctagcgc cgtagcttct acgctgcagt gcatcacgcc      300
tcctgtccct ccctccctcc ctcccataca tgtcgtgctg ggcaccggtg gcgctggtgt      360
tctccaggtt ggttttgggc gcatcctttc tggtagtccg aaggccagcc cggccggcgt      420
cgtccagccc agccatcccg atacagcagc caccttccat cagccagcta tgggcgtgac      480
catccacagt gtttaccgtt ggttacgagg taacatgtgc tttcgcaact gcgctactg       540
actgcctact ctcatgccgc ctgcaagccc actccgcctt ccgctctggt ctaagtacgc      600
attagttccg caacactcgt caatctcact tgccaaatat aactgagcct tgtactgtgc      660
tgtggtgcac tttgacatgt gaggcatgca tggtatgcaa gtgcatacca ctcagtcccc      720
ttgtccccac gggggggggg tgcagccagc catccaatca cacacccgc ctgttactct       780
cagccctgtg ggagttcttt cacatcttca tgtgtccatg ttgcaggaca tgtttgtgat      840
gcatccgcaa gctggcagcc agggtgccag cccttgcagc ccatcaagtg gctctgcata      900
tcaggacaag tgtgcattcc tccctccc tgtagtgggt cagggcctgc tggtatcatg        960
caggctgtca agtaatgtgc agccatgctg aagacatttt atttgcacca cttgtgaacg     1020
atggcctttg ggagcgcaag cgaaagcagc catggcagtg gcgcatcaag tcctcttgca     1080
ggcctgcaaa gtgcagacca caccagtggc gacaagtctg caaccgctgc acctcagcga     1140
ggtccagctc atgctagcaa tacaacggca gtcgctatat gtatataatc aatagccagg     1200
```

```
ccaaacggct gcgtggctgg actgctgcac tcactcacgt ggcccctggt ggcagggtgg      1260
cctaaatcag ggttttaagg ggttttgcag ggtttgaaaa gtgtgacatg tcacaaatga      1320
ttggcacagt ataattcagc taattataac cagaatgatt gtttgaaccc cttgtggatg      1380
accgtgatga gatttgggca cacagcaatg acttcgtact cccactgttt actcgccaca      1440
gcacacacaa gtatgaagaa ggaatcacac tcccagagtt ccacatacac acattggggc      1500
ttctgggttg atgttgcttg cctcacgcct agcgccgtag cttctacgct gcagtgcatc      1560
acgcctcctg tccctccctc cctccctccc atacatgtcg tgctgggcac cggtggcgct      1620
ggtgttctcc aggttggttt tgggcgcatc ctttctggta gtccgaaggc cagcccggcc      1680
ggcgtcgtcc agcccagcca tcccgataca gcagccacct ccatcagcc agctatgggc       1740 gtgaccatcc acagtgttta ccgttggtta cgaggtaaca tgtgctttcg caacttgcgc      1800
tactgactgc ctactctcat gccgcctgca agcccactcc gccttccgct ctggtctaag      1860
tacgcattag ttccgcaaca ctcgtcaatc tcacttgcca aatataactg agccttgtac      1920
tgtgctgtgg tgcactttga catgtgaggc atgcatggta tgcaagtgca taccactcag      1980
tccccttgtc cccacggggg gggggtgca gccagccatc caatcacaca ccccgcctgt       2040
tactctcagc cctgtgggag ttctttcaca tcttcatgtg tccatgttgc aggacatgtt      2100
tgtgatgcat ccgcaagctg gcagccaggg tgccagccct tgcagcccat caagtggctc      2160
tgcatatcag gacaagtgtg cattcctccc ctccctgta gtgggtcagg gcctgctggt       2220
atcatgcagg ctgtcaagta atgtgcagcc atgctgaaga cattttattt gcaccacttg      2280
tgaacgatgg cctttgggag cgcaagcgaa agcagccatg gcagtggcgc atcaagtcct      2340
cttgcaggcc tgcaaagtgc agaccacacc agtggcgaca agtctgcaac cgctgcacct      2400
cagcgaggtc cagctcatgc tagcaataca acggcagtcg ctatatgtat ataatcaata     2460
gccaggccaa acggctgcgt ggctggactg ctgcactcac tcacgtggcc cctggtggca     2520
gggtggccta aatcagggtt ttaagggggtt ttgcagggtt tgaaaagtgt gacatgtcac    2580
aaatgattgg cacagtataa ttcagctaat tataaccaga atgattgttt gaaccccttg     2640 tgatgaccg tgatgagatt tgggcacaca gcaatgactt cgtactccca ctgtttactc      2700
gccacagcac acacaagtat gaagaaggaa t                                    2731
```

<210> SEQ ID NO 59
<211> LENGTH: 881
<212> TYPE: DNA
<213> ORGANISM: Chlamydomonas reinhardtii

<400> SEQUENCE: 59

```
gggtggccaa gatgcacgct gttgtccaac acagccgact ggtgggctgc gactagcccg       60
aagccaccac cgatggactg catgtgctcc cacacggcac gcgtggtcat accgcggaca      120
acaagccgcc gtaaatacgc cgctgccagg taccgttccg ccttggggag cccacttgcg      180
atagcatgga aagcgcactc cccattctcc ggtgtttcct cgggctttgc cgccgctaag      240
ccgatatcta caatgccagc gggcagcgac attataccta gcctttcatc gcgactgaat      300
aacgcttggc caaattggat gggtaccacg caacgctttc acgcactatg gtgtagcgtc      360
agcacagttc aaccattcaa ggtgaaatac atacatgttc gattcctgtg tccgagtcgc      420
cgcaacattc gtgcacttgg cgcagtctga attacatgga caacctcatg acttcgaacg      480
accgcgcccg tcgcgctctc tgctcgctgt ttcctaaata ttgatttaat cgctaacatg      540
tattgtactc ggtaattact tcctgattaa cgcgcgggga gcgagcgccg cgctcgcgcg      600
```

```
cccgctacgc tcgcatttcc tctctggtgc gcttgccgtg tattagtttc attgttaagt      660
gtcgtttaaa agtccgcgcg taggtctgca gcgctcatag agttcgcttg tgtggcgagt      720
cccagcgctc gctgcgctcg cgttttgcaa gggttaagcg agcgttgtga ttcatttccg      780
cgtgccctac cgtgtggcgt tgcgggcggg tgcgtaacgc gtgcctgtgc gttgcggtct      840
ccgctgccta cgtccggtcc tacgggtggg ctgcgctggg g                          881
```

<210> SEQ ID NO 60
<211> LENGTH: 56
<212> TYPE: DNA
<213> ORGANISM: Chlamydomonas reinhardtii

<400> SEQUENCE: 60

```
ttgggctttt cttgcgtagc ctaggtggga gtctatgaag aataccttcc ggggtc          56
```

<210> SEQ ID NO 61
<211> LENGTH: 53
<212> TYPE: DNA
<213> ORGANISM: Chlamydomonas reinhardtii

<400> SEQUENCE: 61

```
tcacgagatc gcttctgatt gtcccaacca ttgtattacg tgtgagccac ggc             53
```

<210> SEQ ID NO 62
<211> LENGTH: 4606
<212> TYPE: DNA
<213> ORGANISM: Chlamydomonas reinhardtii

<400> SEQUENCE: 62

```
tcggtttgga aagattttgg ctcgttttga caatattgag aggcactgaa gcagttgaga      60
cgcctctaaa tattcagtgg gatctggttg aatgagaagc cacagtggtg caagtatgca     120
ggaccatgaa agtcgcatcc cttccaccta gtctgtgcac tgtggcaagg agcagtggga     180
cacatcattg ttatgtgccc tcgtcccatc acagtcaccc acaagcaact ccagtgatct     240
tcctaggtat atttatgcta tttatgctgt gcaaatcatt tctgacatgt cacacttctc     300
aaaccccgca aaaccccttta aaaccccat ttaggcgacc cacgggccag ggccacgtg      360 agtgagtgca gcagtccagc cacgccaccg tttggcttgg ctatcgatta tatacatata     420
gcgactgccg ttgtatggtt ggcacaagct gaagctcgct ggggtggagc gattgcgaac     480
ttggtgacac cgctgttgtc ccaggcctgc aaggggcagg aggcatactg gtcttgccat     540
gccaacgtgc tgtggccgct tcagcgtgca cctgcaacgc taacattcgc aaatgccact     600
gactgattgt gctgagcatg gctgcacatt acttgacagc ctgcatgata cctgaccctg     660 agagggaag ggaggggggc acacctgtcc tgatgtgcag agccacatgg ggcactgcaa      720
gggctggtac caccgcgccg aacttgtggt tgcattacaa acaggtcaag cagcatgtgc     780
atacctaagt gtggaagggt cttgcacagg ggtgagtgag gcaggcaggt tggatggttg     840
gtcaggcagc acagccccga gtgtggggac aagggggatg ggtaccatgc gcttgcacac     900
catgcatgtg caacctgtct acatgccaca tagcatcatg aagcattcag tgggatctgg     960
ttgaatgaga agccacagtg gtgcaagtat gcaggaccat gaaagtcgca tcccttccac    1020
ctagtctgtg cactgtggca aggagcagtg ggacacatca ttgttatgtg ccctcgtccc    1080
atcacagtca cccacaagca actccagtga tcttcctagg tatatttatg ctatttatgc    1140
tgtgcaaatc atttctgaca tgtcacactt ctcaaacccc gcaaaacccc ttaaaacccc    1200
```

```
catttaggcg acccacgggc caggggccac gtgagtgagt gcagcagtcc agccacgcca    1260
ccgtttggct tggctatcga ttatatacat atagcgactg ccgttgtatg gttggcacaa    1320
gctgaagctc gctggggtgg agcgattgcg aacttggtga caccgctgtt gtcccaggcc    1380
tgcaaggggc aggaggcata ctggtcttgc catgccaacg tgctgtggcc gcttcagcgt    1440
gcacctgcaa cgctaacatt cgcaaatgcc actgactgat tgtgctgagc atggctgcac    1500
attacttgac agcctgcatg atacctgacc ctgagagggg aagggagggg ggcacacctg    1560
tcctgatgtg cagagccaca tggggcactg caagggctgg taccaccgcg ccgagcttgt    1620
ggttgcatta caaacaggtc aagcagcatg tgcataccta agtgtggaag ggtcttgcac    1680
aggggtgagt gaggcaggca ggttggatgg ttggtcaggc agcacagccc cgagtgtggg    1740
gacaagggggg atgggtacca tgcgcttgca caccatgcat gtgcaacctg tctacatgcc    1800
acatagcatc atgaagcatt cagtgggatc tggttgaatg agaagccaca gtggtgcaag    1860
tatgcaggac catgaaagtc gcatcccttc cacctagtct gtgcactgtg gcaaggagca    1920
gtgggacaca tcattgttat gtgccctcgt cccatcacag tcacccacaa gcaactccag    1980
tgatcttcct aggtatattt atgctattta tgctgtgcaa atcatttctg acatgtcaca    2040
cttctcaaac cccgcaaaac cccttaaaac ccccatttag gcgacccacg gccaggggc    2100
cacgtgagtg agtgcagcag ttcagccacg ccaccgtttg gcttggctat cgattatata    2160
catatagcga ctgccgttgt atggttggca caagctgaag ctcgctgggg tggagcgatt    2220
gcgaacttgg tgacaccgct gttgtcccag gcctgcaagg ggcaggaggc atactggtct    2280
tgccatgcca acgtgctgtg gccgcttcag cgtgcacctg caacgctaac attcgcactg    2340
tcctgatgtg cagagccaca tggggcactg caagggctgg taccaccgcg ccgagcttgt    2400
ggttgcatta caaacaggtc aagcagcatg tgcataccta agtgtggaag ggtcttgcac    2460
aggggtgagt gaggcaggca ggttggatgg ttggtcaggc agcacagccc cgagtgtggg    2520
gacaagggggg atgggtacca tgcgcttgca caccatgcat gtgcaacctg tctacatgcc    2580
acatagcatc atgaagcatt cagtgggatc tggttgaatg agaagccaca gtggtgcaag    2640
tatgcaggac catgaaagtc gcatcccttc cacctagtct gtgcactgtg gcaaggagca    2700
gtgggacaca tcattgttat gtgccctcgt cccatcacag tcacccacaa gcaactccag    2760
tgatcttcct aggtatattt atgctattta tgctgtgcaa atcatttctg acatgtcaca    2820
cttctcaaac cccgcaaaac cccttaaaac ccccatttag gcgacccacg gccaggggc    2880
cacgtgagtg agtgcagcag ttcagccacg ccaccgtttg gcttggctat cgattatata    2940
catatagcga ctgccgttgt atggttggca caagctgaag ctcgctgggg tggagcgatt    3000
gcgaacttgg tgacaccgct gttgtcccag gcctgcaagg ggcaggaggc atactggtct    3060
tgccatgcca acgtgctgtg gccgcttcag cgtgcacctg caacgctaac attcgcaaat    3120
gccactgact gattgtgctg agcatggctg cacattactt gacagcctgc atgatacctg    3180
accctgagag gggaagggag gggggcacac ctgtcctgat gtgcagagcc acatggggca    3240
ctgcaagggc tggtaccacc gcgccgagct tgtggttgca ttacaaacag gtcaagcagc    3300
atgtgcatac ctaagtgtgg aagggtcttg cacaggggtg agtgaggcag gcaggttgga    3360
tggttggtca ggcagcacag ccccgagtgt ggggacaagg gggatgggta ccatgcgctt    3420
gcacaccatg catgtgcaac ctgtctacat gccacatagc atcatgaagc attcagtggg    3480
atctggttga atgagaagcc acagtggtgc aagtatgcag gaccatgaaa gtcgcatccc    3540
ttccacctag tctgtgcact gtggcaagga gcagtgggac acatcattgt tatgtgccct    3600
```

```
cgtcccatca cagtcaccca caagcaactc cagtgatctt cctaggtata tttatgctat   3660
ttatgctgtg caaatcattt ctgacatgtc acacttctca aaccccgcaa aaccccttaa   3720 aaccccatt taggcgaccc acgggccagg ggccacgtga gtgagtgcag cagtccagcc    3780
acgccaccgt ttggcttggc tatcgattat atacatatag cgactgccgt tgtatggttg   3840
gcacaagctg aagctcgctg gggtggagcg attgcgaact tggtgacacc gctgttgtcc   3900
caggcctgca aggggcagga ggcatactgg tcttgccatg ccaacgtgct gtggccgctt   3960
cagcgtgcac ctgcaacgct aacattcgca aatgccactg actgattgtg ctgagcatgg   4020
ctgcacatta cttgacagcc tgcatgatac ctgaccctga gaggggaagg gaggggggca   4080
cacctgtcct gatgtgcaga gccacatggg gcactgcaag ggctggtacc accgcgccga   4140
gcttgtggtt gcattacaaa caggtcaagc agcatgtgca tacctaagtg tggaagggtc   4200
ttgcacaggg gtgagtgagg caggcaggtt ggatggttgg tcaggcagca cagccccgag   4260
tgtggggaca aggggatgg gtaccatgcg cttgcacacc atgcatgtgc aacctgtcta    4320
catgccacat agcatcatga agcattcagt gggatctggt tgaatgagaa gccacagtgg   4380
tgcaagtatg caggaccatg aaagtcgcat cccttccacc tagtctgtgc actgtggcaa   4440
ggagcagtgg gacacatcat tgttatgtgc cctcgtccca tcacagtcac ccacaagcaa   4500
ctccagtgat cttcctaggt atatttatgc tatttatgct gtgcaaatca tttctgacat   4560
gtcacacttc tcaaacccccg caaaacccct aaaaccccc atttag                  4606

<210> SEQ ID NO 63
<211> LENGTH: 1929
<212> TYPE: DNA
<213> ORGANISM: Chlamydomonas reinhardtii

<400> SEQUENCE: 63
ttgatctcac accacacaag caatctttgt ggcgttgcgc acgcgcatac gcatacacac     60
acgcatgcac tattcatggt ggcacatccc taactttggc ctgctgtgat aaatcgtctc    120
atctatagtc tcatgggatg cttggccaca atgcgtagac atacgtctca cctcataccg    180
tatacaacat ttgcgtgccg gcgcgggcac cagcagctcg cttgcagacg accttgcaat    240
acacccgtac acatgaaacc cagccaccct cgcacattca gaagtaagcc cacctgcaca    300
accattggtt gtcaaccaac agggctctgt gaggcaagct tttctctcca ccccagcagc    360
agtactgctt gccatacatc gccgcattta tgcaatccct cttgcttgcg gggtggtagc    420
tcaatcacat tctagtgatg acctagttgg atggacgcca agtatcgcct tcgctagggt    480
tgcctggcga gcgcgcgatg tataacgcat tccgatgggt cgattattgt acggtaatgc    540
aataatgcat gaactgcaag tacagcaggt atggcttagc ccagcggcaa actcgccatc    600
attttatgtc tgccgcctgt gcagcttgca gaagggtgcg cgactgatgt atgctgtatc    660
atgattggca acagcagcga cgggcacacc tgcctgactg tccaagccag catggctagt    720
tgcttgagca gtaaagacac agtggccatg ctactgcgcc tagcttgttt gcttgcttgc    780
tgcacgagtc agctagccat aaacgctctg tgcatgtaac gaaagcgcct gccttgcttt    840
gcagctatca accaattgcg ttgcaacggc agcataaaat ggttgcggtt gcggacttac    900
gcagccagcc aagaagatgc tagcaggcac acgcttgaag caagcaagca cgcacaaaca    960
cacgtaggtg cgtatgtatt cgtctattta aatatataga gcatacatgt atgcccatct   1020
aatgaggcat gtcgtccatg cgtgcaacca tcgctcagac tgctgcatta gaccgttgat   1080
```

```
ggctaacgca aatgccgcac gtacctacat acagatacgg atagtgcagc aggctgcttt    1140
agctgcttgc acgaacgtgc gcatgcacgc agcgctgaac atgcatgtat gcatgcaaat    1200
agctgctagt tggcattcat tcggcaatta atcaagcagc agcacagact tcatagctgg    1260
tatgattgca tcgatgaact tcatctgcgt acgtacgccc gccctgctat atttgtagta    1320
aatggttaac gcaagcctgc ttgacagcag gtcgctgtac attccacgtg cgtgaatgcg    1380
tgcatggtgg cagccgcaag caaggccacc agtaggatgc gcagactagt aatgctagca    1440
atctagtacg tggtggcgtt tcatcaagct atctgccatc cgtaatctcc agcacgttca    1500
cgcccacgcc cacgccatcg ccgccgcctg cactggcatc ctccagtgcg gccgctgtac    1560
ctgctactgt caccacgggt agcagcatac gctgctgttg ctccagcagt tgctccgggc    1620
ttggctccgg tagccctgtc ccctgaacga cggttgggcg caaccgcccg aagccaccgc    1680
cggggtcagc gctgtcgtgc gccgctgctg ctgcagtttc tgctgttgcg gcggcagccg    1740
ctgccacacc acctccggca ccatatccgt agcagctgtc tccgcgctgc tgttgctcta    1800
gttgagcatc gaggccgtta tcgaatgcgg taacacgcgc cgccacctcc cggattgcat    1860
caatcagaaa tgcgcgctgt gcaccctcgt catacacact gaatggcggc acatgaatga    1920
agagcgagt                                                            1929

<210> SEQ ID NO 64
<211> LENGTH: 1037
<212> TYPE: DNA
<213> ORGANISM: Chlamydomonas reinhardtii

<400> SEQUENCE: 64
gtccgccaca gccgagcggc agcggcgcct tccctgttga gtcggctgcc gccccgcca      60 cggcctcatc catccatacg cagctgtcca cctgtgaggt aggcaaacaa acaggacacg    120
tgcgcggatg tacggcggga tgctcgctcg cgtcaaactg ctgccggtcg agtcaaactc    180
tacctatcga cagcagcagg gcgtgttgct gggggggagtg tgaatcttta atattatggc    240
tcctgcacgt agctagcgat gggtaataat aataataata ataataataa taataataat    300
aataataata ataataataa taataataat aataataata ataataataa taataataat    360
aataataata ataataataa taataataat aataataata ataataataa taataataat    420
aataataata ataataataa taataataat aataataata ataataataa taataataat    480
aataataata ataataataa taataataat aataataata ataataataa ttacaatgcc    540
ggcccatagg gcctggcatg gattaacggg gtaaggtgac tagggcgaga gggcccgccc    600
ccctcacgct gacgcctcac cacaaaagag tcacgacctc cgaaactaca acctccaagt    660
cctaggccgc tcttcaaagt ccactacatc cgagcctgca cacctagcat atcgagctag    720
ggaaacaccg tgttatagta gtggagcact accagttcgt gcaaaccgag gagccatggt    780
gctcctcctc gagccttgga tcttgagcct tgtcttgaac cttggaccac taaattggac    840
ttctgcacca cgacctttct aggttgtgaa ctgcgggcat aagcccgcaa ttgccactaa    900
gggcaattac ctatcgttcg tgggatcacc aatcggtttc gcaccaatct ttcgcctttg    960
gcataattgg gctttatcc ggattcgtac ccgggtccct tctgccgtaa ggacgagtca    1020
tatcgctaac tcagtta                                                  1037

<210> SEQ ID NO 65
<211> LENGTH: 7628
<212> TYPE: DNA
<213> ORGANISM: Chlamydomonas reinhardtii
```

<400> SEQUENCE: 65

```
gtggaagcta tcttaaggca gtggcgcatg tgtgctgggt gggtgggtgg gtgggtcgag      60
gttaggtagg gtagggcaag gtgggtcggt cggtaggtaa aggttccgtg gtgctgtttg     120
attttagata gtccagtggg tggcgtttat gtatgtggaa atcgcttttc aggattgggt     180
atagctccag ggagggtgag tgggttggga gtgtgttggg agcccttgcc gtgtcactgg     240
gcctgttggg ccaaggtacc agcacttggg tggcgtgggc catagctggt tgtcaaacgg     300
ggtttgaagg ggttttacgg ggttttagcg gggttataac gccggccgtc cctagagggg     360
tcagtaaact ctaccaacgt gctgacagac ctcctgtga catgggaacc ttagtggggg      420
tggtgggtgg gggtttgggt gggttgggca ccttgggtgt ttgaaccccg ggggttttcg     480
gggttatcgg ggttttagcc gtagcgtgca gtatgacatg aggaaaagtg cgctgactgg     540
ccaggcgtgc ttggggtggt gtaggggtga tgtgggttga ttttagggt gagttgatgc      600
ctggaggggg tggtcacctt gggagggtt ttggggggtt ttacgcgtgc accccgacgt      660
ggggcggttg gattatgtgt attaaacatg cttaattaac gtaattagaa tggtttaggg     720
ttatggggtt cccccttag ggttttggg gtcggggtg tgtggtcggg ggtgtgggt         780
tttggtcaaa cgttggtcaa acgtagcttg gtcaaagttt gaccggcctt agtcagcgcg     840
ttgttggtcc gatttgctcc tgtcttttc ttatgtgtct tatgtgttgt gttagataag      900
gtttcttatg tgtgtgtgtg tggctgttgg gttagataag acatataagg gtttcggggt     960
tttggtgccc tgtgccttgt cccgcgggtc ccaacgtgtc cccttgtgc tggcatggtg     1020
ttgggagtgt gtgcgatgtg ttggaagcgt tgggggtgct tggagtgcag tttggtgtgt    1080
gtggtgtggt gtggagttgg tcaagggtgt cagtcccctt ggcacgctag caaccctacc    1140
ccatatccac cccctggcca gctctgccac cctcgcccac gcgcatgcac tcacagcacg    1200
tcaaacgagt tcccatttca ctttggcatg tatggggagg catggggcag ctccgggcgg    1260
ggatggcacc atggcggtgg tggtaccgtg tgctcgggtc ctgcctttgg ctctgcttgt    1320
ccatgacgta cggctctggg tatcttccat gcccgtaagt tatggcccta aggtacccca    1380
aggtacccta aggtacccac gcgtgtgccc tctagggtac aggggtaaca cttgcgcata    1440
cacacacgcg cgcacacacg cacacacacg cgcacacact cccccctgcc aaccccactc    1500
tcacccccgc gtcccccgc ccccctgcgt gtgcgtgtgt gtgccacgac gtgcgtacgg     1560
caaagtgtgg ccaaggcccc cccttgcgag tgggggaacc cccctagccc ctaggcccta    1620
gccccaacc cctagacagc cagcccaaac ggaaacaggt gtggtgtcat gtatctgggg     1680
taggcgtgaa gagaagcgaa agcaagcaat tgcaaagctt cgaatcataa caacacaatc    1740
cgaagaatga gctaagcaat taggtctagt aactcggtga gtggcagtga actcaagtag    1800
gctctgccgg gtcaggtaac tggtcctggc tagccctgct tgaactggtt caatcaatgc    1860
gtcaattggc ggtcaaacgc tggttgattg ttgcccaaat ctattgatgg tttgagttgc    1920
aacgagtgtt gagagagctt gtattaatac gcgatgcgta tgcttatgaa ccaagtggac    1980
ctgctaggac agtaggtgca aggccagtgt aacagctgtg ctttgttatc tgccggctag    2040
cattgaagct ctgcttgcgg gaagccgcat gcctgagtgt tcgctaggtg gtctgagctt    2100
atgcctaacc cgtgtaagac tcagccaatc cgcgatactt ggttgcgttg cttccggagc    2160
gctggttcag agctgggaga acgttcagag aggcctcgtg gcaagagctc ttctgactcg    2220
attcgtcttc ggacagtcgt gttcagtcga ctctcgagtg ctttctcaac ggatagcgct    2280
```

```
tcttaattga ttcaattcct gcgtatcctt tgtgatacgc gccggaatac tgtggcatgc    2340
gtatgctctc gtggcgtatg tgtgctgcag tttcaattaa aggcagctac ctggttgatc    2400
ctgccagtag tcatatgctt gtctcaaaga ttaagccatg catgtctaag tataaactgc    2460
ttatactgtg aaactgcgaa tggctcatta aatcagttat agtttatttg atggtaccta    2520
ctactcggat aaccgtagta attctagagc taatacgtgc gcacaaccga cttctggaag    2580
ggtcgtattt attagataaa aggccagccg ggctctgccc gacctgcggt gaatcatgat    2640
aacttcacga atcgtatggg ctcgtcccga cgatgtttca ttcaaatttc tgccctatca    2700
actttcgatg gtaggataga ggcctaccat ggtggtaacg ggtgacggag gattagggtt    2760
cgattccgga gagggagcct gagagatggc taccacatcc aaggaaggca gcaggcgcgc    2820
aaattaccca atcccgacac ggggaggtag tgacaataaa taacaatacc gggcgcttcg    2880
cgtctggtaa ttggaatgag tacaatctaa atcccttaac gaggatccat tggagggcaa    2940
gtctggtgcc agcagccgcg gtaattccag ctccaatagc gtatatttaa gttgttgcag    3000
ttaaaaagct cgtagttgga tttcgggtgg ggtggtgcgg tccgcctctg gtgtgcactg    3060
ctctgctcca ccttcctgcc ggggacgggc tcctgggctt cactgtctgg gactcggagt    3120
cggcgaggtt actttgagta aattagagtg ttcaaagcag gcctacgctc tgaatacatt    3180
agcatggaat aacacgatag gactctggcc tatctgttgg tctgtgggac cggagtaatg    3240
attaagaggg gtagtcgggg gcattcgtat tccgttgtca gaggtgaaat tcttggattt    3300
acggaagacg aacatctgcg aaagcatttg ccaaggatac tttcattgat caagaacgaa    3360
agttggggc tcgaagacga ttagataccg tcgtagtctc aaccataaac gatgccgact    3420
agggattggc agatgttctt ttgatgactc tgccagcacc ttatgagaaa tcaaagtttt    3480
tgggttccgg gggagtatg gtcgcaaggc tgaaacttaa aggaattgac ggaagggcac    3540
caccaggcgt ggagcctgcg gcttaatttg actcaacacg gggaaactta ccaggtccag    3600
acacgggaag gattgacaga ttgagagctc tttcttgatt ctgtgggtgg tggtgcatgg    3660
ccgttcttag ttggtgggtt gccttgtcag gttgattccg gtaacgaacg agacctcagc    3720
ctgctaaata gtcagcatcg cacctgcggt gcgccgactt cttagaggga ctattggcgt    3780
ttagccaatg gaagtatgag gcgataacag gtctgtgatg cccttagatg ttctgggccg    3840
cacgcgcgct acactgacgc gaccaacgag cctatccttg gccgagaggc ccgggtaatc    3900
ttgtaaaccg cgtcgtgatg gggatagatt attgcaatta ttagtcttca acgaggaatg    3960
cctagtaagc gcgagtcatc agctcgcgtt gattacgtcc ctgcccttg tacacaccgc    4020
ccgtcgctcc taccgattgg gtgtgctggt gaagtgttcg gattgagctt ggctggggca    4080
acctggcctt gcttgagaag ttcattaaac cctcccacct agaggaagga gaagtcgtaa    4140
caaggtttcc gtaggtgaac ctgcggaagg atcattgaat ctatcacaat ccacaccgcg    4200
aactaacact gttggcctcc gtctgtataa aagcaaacgg gccaggtctg gcgcaatgt    4260
aaaagttacg cctggcctgg gttgccgcaa ggcatcggtc tcttatacta accaaccaac    4320
accaaaccaa aactaaatta aaaccgagta tctagcttag agctagtgct cactaaccaa    4380
gacaactctc aacaacggat atcttggctc tcggatcgat gaagaacgca gcgaaatgcg    4440
atacgtagtg tgaattgcag aaatacgtga atcatcgaat ctttgaacgc atattgcgct    4500
cgaggcttcg gccaagagca tgtctgcctc agcgtcgggt taatactcgc cctactccaa    4560
catacacttg tgtgtttgga gcaagagcgg acctggctgt ctcggtgttt gattttcgga    4620
tcagacgccg ggtcagctga agtacagagg ttgatgcatg gacccgctta tgggcctcta    4680
```

```
ctgggtaggc aactcgttgc taatgctttta gtagatggct tggagctgtg cttgtcgacc    4740
caaaccagga actttggccc tgtgccgaag caaaccccta ttttctcgac ctgagctcag    4800
gcaagattac ccgctgaact taagcatatc aataagcgga ggaaagaaa ctaacaagga     4860
ttcccctagt aacggcgagc gaaccgggaa tagcccaact tgaaaatctc cctttggaga    4920
attgtagtct agagaagcgc tttctagggc tggcggaact caagtcggat cgaatgccgc    4980
gtcagagagg gtgataaccc cgtcggttcc tgcttagtcc ttccacgaag tgctttccac    5040
gagtcgggtt gtttgggaat gcagccctaa tttggaggta aatcccttct aaggctaaat    5100
actgccgaga gaccgatagc gaacaagtac cgtgagggaa agatgaaaag aactttgaaa    5160
agagagttaa aagtgcttga aattgttgag agggaagcga ttggcgctcg taggtgcgcc    5220
caggcttaag cggtcctaac ggcccgttga atgtgctggg tgctggtcag aatgggttga    5280
gttggcggga caaaagctgg gtccacccag gtaacccggc cgatgccgcc gactcgacca    5340
aggcgtaaag agtaccttgt ccttcgggat ctgtgctcta aagattctgg cagaagagcg    5400
tcaatcgacc cgtcttgaaa cacggaccaa ggagtctaac atgtatgcga gttggcgggt    5460
ggaaaacccg taagcgcaag taacctgact ggtgggatgg ggtaaaaccc tgcaccatcg    5520
accgaccatg ttgtttctac gaaaggtttg agtgcgagca tacctgttgg gacccgaaag    5580
atggtgaact atgcctgagc agggtgaagc cagaggaaac tctggtggag gctcgtagat    5640
gtgctgacgt gcaaatcgct tttcagactt gggtataggg gcgaaagact aatcgaacca    5700
tctagtagct ggttccctcc gaagtttccc ccaggatagc tggagcttga tcagttttat    5760
cgggtaaagc gaatgattag aggttcgggg atgaaacatc cttcacctat tctcaaactt    5820
taaataggta agacgtgtcg gttgcttaat tgaaccggca cattcaatgt gagctccaag    5880
tgggccattt ttggtaagca gaactggcga tgcgggatga accgatagtc gagttaaggt    5940
gccaaactac gcgctaacct agatcccaca aagggtgttg attgatataa acagcaggac    6000
ggtggtcatg gaagtcgaaa tccgctaagg agtgtgtaac aactcacctg ccgaatcaat    6060
tagccccgaa aatggatggc gcttaagcgc gtgacctata ctcggccatg gaagcaagtg    6120
cgacgcttcc atgagtagga gggcgtgggt gtcgagacta agcctctggc gtgagcctgg    6180
gtgaatcggc atctagtgca gatcttggtg gtagtagcaa atattcaaat gagaactttg    6240
aagactgaag tggagaaagg ttccatgtga acagcaattg gacatgggtt agtcgatcct    6300
aagagatggg gtaatcctgt gtgaagagcg cgattcgcgc tgcccatcga aagggaaaag    6360
ggttaagatt cccttacttg gacaaggcgg ctggcggtaa cgcaagcgag cccggagaca    6420
tcggcatcgg ccctgggaag agttctcttt tcttttaac aacgcgaagg ccctggaatc      6480
gaatcattcg gagatagggc tcagacgttg gtaaagcacc gcacttctcg cggtgtccgg    6540
cgcgccgttg acggtccttg aaaatccggg ggagcattcc cgatcttgcc aagtcgtact    6600
cataaccgca tcaggtctcc aaggtgaaca gcctctagtc gatagaacaa tgtagataag    6660
ggaagtcggc aaaatggatc cgtaacttcg ggaaaaggat tggctctgag ggctgggcct    6720
aggggtctgc agctgcgaag ctcgggactg cggtggtcta cccagctgga aacggctggg    6780
cggactgctg cgtgtcctgg gtggacggct gtagaagctt cggcgttccc taggcgacga    6840
acagccaact cagaactggt acggacaagg ggaatccgac tgtttaatta aaacaaagca    6900
ttgtgatggt cctaaaggat gttgacacaa tgtgatttct gcccagtgct ctgaatgtca    6960
aagtgaagaa attcaaccaa gcgcgggtaa acggcgggag taactatgac tctcttaagg    7020
```

```
tagccaaatg cctcgtcatc taattagtga cgcgcatgaa tggattaacg agattcccac    7080
tgtccctatc tactatctag cgaaaccaca gccaagggaa cgggcttgga ataaacagcg    7140
gggaaagaag accctgttga gcttgactct agtccgactt tgtgaaataa cttaagaggt    7200
gtagaataag tgggagcttc ggcgacggtg aaataccact acttttaacg ttgttttact    7260
tattccatta cttggaggcg ggactctgtc cctgcttcta gctctaagac ggcttttgca    7320
cgtcgatcca ggtggaagac attgtcaggt ggggagtttg gctggggcgg cacatctgtt    7380
aaaagataac gcaggtgtcc taagatgagc tcaacgagaa cagaaatctc gtgtagaaca    7440
aaagggtaaa agctcatttg attttgattt tcagtacgaa tacaaactgt gaaagcatgg    7500
cctatcgatc ctttagcctt tcgggatttg aagctagagg tgtcagaaaa gttaccacag    7560
ggataactgg cttgtggcag ccaagcgttc atagcgacgt gcttttgatc cttcgatgtc    7620
gctctcct                                                            7628

<210> SEQ ID NO 66
<211> LENGTH: 2734
<212> TYPE: DNA
<213> ORGANISM: Chlamydomonas reinhardtii

<400> SEQUENCE: 66
ttgtgaaatt acttagaggt gtagaataag tgggagcttc ggcgacggtg aataccact      60
acttttaacg tgttttactt attccattac ttggaggcgg gactctgtcc ctgcttctag    120
ctctaagacg gcttttgcac gtcgatccag gtggaagaca ttgtcaggtg gggagtttgg    180
ctggggcggc acatctgtta aaagataacg caggtgtcct aagatgagct caacgagaac    240
agaaatctcg tgtagaacaa aagggtaaaa gctcatttga ttttgatttt cagtacgaat    300
acaaactgtg aaagcatggc ctatcgatcc tttagccttt cgggatttga agctagaggt    360
gtcagaaaag ttaccacagg gataactggc ttgtggcagc caagcgttca tagcgacgtt    420
gcttttgat cttcgatgt cggctcttcc tatcattgtg aagcagcatt caccaagcgt    480
tggattgttc acccactaat agggaacgtg agctgggttt agaccgtcgt gagacaggtt    540
agttttaccc tactgttgga ccgattccgc catagtaatt cggctcagta cgagaggaac    600
cgccgagtca gataattggt aatgcccttg tctgaaaaga caatggggcg aagctaacat    660
ctgtagtcta atgactgaac gcctctaagt cagaagacgt gctaggtgcg gagtcactta    720
cccaatgatg tcacccgact aaggatacat ccgcctgtgc ggatgctgga gcatacccgt    780
tggttcccct gttaggtcca catggccgaa gcaggcgcca agcatgacaa ttccactcgt    840
cattggggta atcctctgt agacgacttt gttgcaactg gtattgtaa gtggtagagt    900
ggccttgctg ctacgatcca ctgagattca tcccgtgttg ctaagatttg tcactgccct    960
tcggggcaac ccctcctcct ctcggagcga cagctccagg gagggccctc tctctctctt   1020
ccaagtggtg tagctgagct gagcgcgtgc caacgccgcc gaatccgtct aagtgcccac   1080
atgcgtgtgc atgcactgcc cctcctcccc cacacagcca aagtgctcaa ggtaccttcc   1140
ctgtgtgtgt gcgagtgaga gcaacagcat gcatgtgccc ttacttaggc ggcctagtgt   1200
ggtatgtgtg tatgcgtgtg gcttagtggc cagttcgact ctggcgtgga agctatcttc   1260
taaggcagtg gcgcatgtgt gctgggtggg tgggtgggtg gtagaggtt aggtagggta    1320
gggcaaggtg ggtaggtcgg taggtaaagg ttccgtggtg ctgtttgatt ttagatagtc   1380
cagtgggtgg cgtttatgta tgtggaaatc gcttttcagg attgggtata gctccaggga   1440
gggtgagtgg gttgggagtg tgttgggagc ccttgccgtg tcactgggcc tgttgggcca   1500
```

| | |
|---|---:|
| aggtaccagc acttgggtgg cgtgggccat agctggttgt caaacggggt ttgaaggggt | 1560 |
| tttacggggt tttagcgggg ttataacgcc ggccgtccct agaggggtca gtaaactcta | 1620 |
| ccaacgtgct ggacagacct cctgtgacat gggaacctta gtgggggtgg tgggtggggg | 1680 |
| tttgggtggg ttgggcacct tgggtgtttg aaccccgggg gttttcgggg ttatcggggt | 1740 |
| tttagccgta gcgtgcagta tgacatgagg aaaagtgcgc tgactggcca ggcgtgcttg | 1800 |
| gggtggtgta ggggtgacgt gggttgattt ttagggtgag ttgatgcctg gaggggtgg | 1860 |
| tcaccttggg aggggttttg ggggttttta cgcgtgtacc acgacgtggg gcggtcggat | 1920 |
| tacgtgtatt aaacatgctt aattaacgta attagtttgg tttagggttg tggggttccc | 1980 |
| cccttagggt ttttgggtc ggggtgtgt gggtggggg gtgtggggtt ttggtcaaac | 2040 |
| gttggtcaaa cgttgcctgg tcaaagtttg accggcctta gtcagcgcgt tgttgtgcca | 2100 |
| ataggctcct gtcttttct tatgtgtctt atgtgttgtg ttagataagg tttcttatgt | 2160 |
| gtgtgtgtgt ggctgttggg ttagataaga catataaggg tttcggggtt ttggtgccct | 2220 |
| gtgccttgtt ccgcgggtcc caacgtgtcc cccttgtgct ggcatggtgt tgggagtgtg | 2280 |
| tgcgatgtgt tggaagcgtt gggggtgctt ggagtgcagt ttggtgtgtg tggtgtggtg | 2340 |
| tggagttggt caagggtgtc agtccccttg gcacgctagc aaccctaccc catatccacc | 2400 |
| ccctggccag ctctgccacc ctcgcccacg cgcatgcact cacagcacgt caaacgagtt | 2460 |
| cccatttcac tttggcatgt atggggaggc atggggcagc tccggcgggg gatggcacca | 2520 |
| tggcggtggt ggtaccgtgt gctcgggtcc tgcctttggc tctgcttgtc catgacgtac | 2580 |
| ggctctgggt atcttccatg cccgtaagtt atggccctaa ggtaccctaa ggtaccctaa | 2640 |
| ggtacccacg cgtgtgccct ctagggtaca ggggtaacac ttgcgcatac acacacgcgc | 2700 |
| gcacacacgc acacacacgc acacactccc aaca | 2734 |

<210> SEQ ID NO 67
<211> LENGTH: 4622
<212> TYPE: DNA
<213> ORGANISM: Chlamydomonas reinhardtii

<400> SEQUENCE: 67

| | |
|---|---:|
| tatcaacttt cgatggtagg atagaggcct accatggtgg taacgggtga cggaggatta | 60 |
| gggttcgatt ccggagaggg agcctgagag atggctacca catccaagga aggcagcagg | 120 |
| cgcgcaaatt acccaatccc gacacgggga ggtagtgaca ataataaca ataccgggcg | 180 |
| cttcgcgtct ggtaattgga atgagtacaa tctaaatccc ttaacgagga tccattggag | 240 |
| ggcaagtctg gtgccagcag ccgcggtaat tccagctcca atagcgtata tttaagttgt | 300 |
| tgcagttaaa aagctcgtag ttggatttcg ggtgggtgg tgcggtccgc ctctggtgtg | 360 |
| cactgctctg ctccaccttc ctgccgggga cgggctcctg ggcttcactg tctgggactc | 420 |
| ggagtcggcg aggttacttt gagtaaatta gagtgttcaa agcaggccta cgctctgaat | 480 |
| acattagcat ggaataacac gataggactc tggcctatct gttggtctgt gggaccggag | 540 |
| taatgattaa gaggggtagt cggggcatt cgtattccgt tgtcagaggt gaaattcttg | 600 |
| gatttacgga agacgaacat ctgcgaaagc atttgccaag atactttca ttgatcaaga | 660 |
| acgaaagttg ggggctcgaa gacgattaga taccgtcgta gtctcaacca taaacgatgc | 720 |
| cgactaggga ttggcagatg ttcttttgat gactctgcca gcaccttatg agaaatcaaa | 780 |
| gtttttgggt tccggggga gtatggtcgc aaggctgaaa cttaaaggaa ttgacggaag | 840 |

```
ggcaccacca ggcgtggagc ctgcggctta atttgactca acacgggaa acttaccagg      900
tccagacacg ggaaggattg acagattgag agctctttct tgattctgtg ggtggtggtg    960
catggccgtt cttagttggt gggttgcctt gtcaggttga ttccggtaac gaacgagacc   1020
tcagcctgct aaatagtcag catcgcacct gcggtgcgcc gacttcttag agggactatt   1080
ggcgtttagc caatggaagt atgaggcgat aacaggtctg tgatgccctt agatgttctg   1140
ggccgcacgc gcgctacact gacgcgacca acgagcctat ccttggccga gaggcccggg   1200
taatcttgta aaccgcgtcg tgatggggat agattattgc aattattagt cttcaacgag   1260
gaatgcctag taagcgcgag tcatcagctc gcgttgatta cgtccctgcc ctttgtacac   1320
accgcccgtc gctcctaccg attgggtgtg ctggtgaagt gttcggattg agcttggctg   1380
gggcaacctg gccttgcttg agaagttcat taaaccctcc cacctagagg aaggagaagt   1440
cgtaacaagg tttccgtagg tgaacctgcg aaggatcat tgaatctatc acaatccaca    1500
ccgcgaacta acactgttgg cctccgtctg tgtaaaagca acgggccag gtctgggcgc    1560
aatgtaaaag ttacgcctgg cctgggttgc cgcaaggcat cggtctctta tactaaccaa   1620
ccaacaccaa accaaaacta aattaaaacc gagtatctag cttagagcta gtgctcacta   1680
accaagacaa ctctcaacaa cggatatctt ggctctcgga tcgatgaaga acgcagcgaa   1740
atgcgatacg tagtgtgaat tgcagaaata cgtgaatcat cgaatctttg aacgcatatt   1800
gcgctcgagg cttcggccaa gagcatgtct gcctcagcgt cgggttaata ctcgccctac   1860
tccaacatgt ttggagcaag agcggacctg gctgtctcgg tgtttgattt tcggatcaga   1920
cgccgggtca gctgaagtac agaggttgat gcatgggccc gcttatgggc ctctactggg   1980
taggcaactc gttgctaatg ctttagtaga tggcttggag ctgtgcttgt cgacccaaac   2040
caggaacttt ggccctgtgc cgaagcaaac ccctattttc tcgacctgag ctcaggcaag   2100
attaccgct gaacttaagc atatcaataa gcggaggaaa agaaactaac aaggattccc     2160
ctagtaacgg cgagcgaacc gggaatagcc caacttgaaa atctcccttt ggagaattgt   2220
agtctagaga agcgctttct agggctggcg gaactcaagt cggatcgaat gccgcgtcag   2280
agagggtgat aaccccgtcg gttcctgctt agtccttcca cgaagtgctt ccacgagtc    2340
gggttgtttg ggaatgcagc cctaatttgg aggtaaatcc cttctaaggc taaatactgc   2400
cgagagaccg atagcgaaca agtaccgtga gggaaagatg aaaagaactt tgaaaagaga   2460
gttaaaagtg cttgaaattg ttgagaggga agcgattggc gctcgtaggt gcgcccaggc   2520
ttaagcggtc ctaacggccc gttgaatgtg ctgggtgctg gtcagaatgg gttgagttgg   2580
cgggacaaaa gctgggtcca cccaggtaac ccggccgatg ccgccgactc gaccaaggcg   2640
taaagagtac cttgtccttc gggatctgtg ctctaaagat tctggcagaa gagcgtcaat   2700
cgacccgtct tgaaacacgg accaaggagt ctaacatgta tgcgagttgg cgggtggaaa   2760
acccgtaagc gcaagtaacc tgactggtgg gatggggtaa aaccctgcac catcgaccga   2820
ccatgttgtt tctacgaaag gtttgagtgc gagcatacct gttgggaccc gaaagatggt   2880
gaactatgcc tgagcagggt gaagccagag gaaactctgg tggaggctcg tagatgtgct   2940
gacgtgcaaa tcgcttttca gacttgggta taggggcgaa agactaatcg aaccatctag   3000
tagctggttc cctccgaagt ttccccccagg atagctggag cttgatcagt tttatcgggt   3060
aaagcgaatg attagaggtt cggggatga aacatccttc acctattctc aaactttaaa    3120
taggtaagac gtgtcggttg cttaattgaa ccggcacatt caatgtgagc tccaagtggg   3180
ccatttttgg taagcagaac tggcgatgcg ggatgaaccg atagtcgagt taaggtgcca   3240
```

```
aactacgcgc taacctagat cccacaaagg gtgttgattg atataaacag caggacggtg  3300
gtcatggaag tcgaaatccg ctaaggagtg tgtaacaact cacctgccga atcaattagc  3360
cccgaaaatg gatggcgctt aagcgcgtga cctatactcg gccatggaag caagtgcgac  3420
gcttccatga gtaggagggc gtgggtgtcg agactaagcc tctggcgtga gcctgggtga  3480
atcggcatct agtgcagatc ttggtggtag tagcaaatat tcaaatgaga actttgaaga  3540
ctgaagtgga gaaaggttcc atgtgaacag caattggaca tgggttagtc gatcctaaga  3600
gatggggtaa tcctgtgtga agagcgcgat tcgcgctgcc catcgaaagg gaaaagggtt  3660
aagattccct tacttggaca aggcggctgg cggtaacgca agcgagcccg gagacatcgg  3720
catcggccct gggaagagtt ctcttttctt tttaacaacg cgaaggccct ggaatcgaat  3780
cattcggaga tagggctcag acgttggtaa agcaccgcac ttctcgcggt gtccggcgcg  3840
ccgttgacgg tccttgaaaa tccggggag cattcccgat cttgccaagt cgtactcata  3900
accgcatcag gtctccaagg tgaacagcct ctagtcgata gaacaatgta gataagggaa  3960
gtcggcaaaa tggatccgta acttcgggaa aaggattggc tctgagggct gggcctaggg  4020
gtctgcagct gcgaagctcg ggactgcggt ggtctaccca gctggaaacg gctgggcgga  4080
ctgctgcgtg tcctgggtgg acggctgtag aagcttcggc gttccctagg cgacgaacag  4140
ccaactcaga actggtacgg acaaggggaa tccgactgtt taattaaaac aaagcattgt  4200
gatggtccta aggatgttg acacaatgtg atttctgccc agtgctctga atgtcaaagt  4260
gaagaaattc aaccaagcgc gggtaaacgg cgggagtaac tatgactctc ttaaggtagc  4320
caaatgcctc gtcatctaat tagtgacgcg catgaatgga ttaacgagat tcccactgtc  4380
cctatctact atctagcgaa accacagcca agggaacggg cttggaataa acagcgggga  4440
aagaagaccc tgttgagctt gactctagtc cgactttgtg aaataactta agaggtgtag  4500
aataagtggg agcttcggcg acggtgaaat accactactt ttaaccttgt tttacttatt  4560
ccattacttg gaggcgggac tctgtccctg cttctagctc taagacggct tttgcacgtc  4620
ga                                                                  4622
```

<210> SEQ ID NO 68
<211> LENGTH: 2011
<212> TYPE: DNA
<213> ORGANISM: Chlamydomonas reinhardtii

<400> SEQUENCE: 68

```
agggtgtcag tcccttggc acgctagcaa ccctacccca tatccacccc ctggccagct   60
ctgccaccct cgcccacgcg catgcactca cagcacgtca aacgagttcc catttcactt  120
tggcatgtat ggggaggcat ggggcagctc cgggcgggga tggcaccatg gcggtggtgg  180
taccgtgtgc tcgggtcctg cctttggctc tgcttgtcca tgacgtacgg ctctgggtat  240
cttccatgcc cgtaagttat ggccctaagg taccctaagg taccctaagg tacccacgcg  300
tgtgccctct agggtacagg ggtaacactt gcgcatacac acacgcgcgc acacacgcac  360
acacacgcac acactccccc ctgccaaccc cactctcacc cccgcgtccc ccgccccccc  420
tgcgtgtgcg tgtgtgtgcc acgacgtgcg tacggcaaag tgtggccaag gcccccccctt  480
gcgagtgggg gaaccccct agcccctagg ccctagcccc caaccctag acagccagcc  540
caaacgaaa caggtgtggt gtcatgtatc tggggtaggc gtgaagagaa gcgaaagcaa  600
gcaattgcaa agcttcgaat cataacaaca caatccgaag aatgagctaa acaattagtt  660
```

```
ctagtaactc ggtgagtggc agtgaactca agtaggctct gccgggtcag gtaactggtc      720
ctggctagcc ctgcttgaac tggttcaatc aatgcgtcaa ttggcggtca aacgctggtt      780
gattgttgcc caaatctatt gatggtttga gttgcaacga gtgttgagag agcttgtatt      840
aatacgcgat gcgtatgctt atgaaccaag tggacctgct aggacagtag gtgcaaggcc      900
agtgtaacag ctgtgctttg ttatctgccg gctagcattg aagctctgct tgcgggaagc      960
cgcatgcctg agtgttcgct aggtggtctg agcttatgcc taacccgtgt aagactcagc     1020
caatccgcga tacttggttg cgttgcttcc ggagcgctgg ttcagagctg ggagaacgtt     1080
cagagaggcc tcgtggcaag agctcttctg actcgattcg tcttcggaca gtcgtgttca     1140
gtcgactctc gagtgctttc tcaacggata gcgcttctta attgattcaa ttcctgcgta     1200
tcctttgtga tacgcgccgg aatactgtgg catgcgtatg ctctcgtggc gtatgtgtgc     1260
tgcagtttca attaaaggca gctacctggt tgatcctgcc agtagtcata tgcttgtctc     1320
aaagattaag ccatgcatgt ctaagtataa actgcttata ctgtgaaact gcgaatggct     1380
cattaaatca gttatagttt atttgatggt acctactact cggataaccg tagtaattct     1440
agagctaata cgtgcgcaca aaccgacttc tggaagggtc gtatttatta gataaaagcg     1500
ccagccgggc tctgcccgac ctgcggtgaa tcatgataac ttcacgaatc gtatgggctc     1560
gtcccgacga tgtttcattc aaatttctgc cctatcaact ttcgatggta ggatagaggc     1620
ctaccatggt ggtaaccggg tgacggagga ttagggttcg attccggaga gggagcctga     1680
gagatggcta ccacatccaa ggaaggcagc aggcgcgcaa attacccaat cccgacacgg     1740
ggaggtagtg acaataaata acaataccgg gcgcttcgcg tctggtaatt ggaatgagta     1800
caatctaaat cccttaacga ggatccattg gagggcaagt ctggtgccag cagccgcggt     1860
aattccagct ccaatagcgt atatttaagt tgttgcagtt aaaaagctcg tagttggatt     1920
tcgggtgggg tggtgcggtc cgcctctggt gtgcactgct ctgctccacc ttcctgccgg     1980
ggacgggctc ctgggcttca ctgtctggga c                                    2011
```

<210> SEQ ID NO 69
<211> LENGTH: 7207
<212> TYPE: DNA
<213> ORGANISM: Chlamydomonas reinhardtii

<400> SEQUENCE: 69

```
tgtatgggga ggcatggggc agctccgggc ggggatggca ccatgggcgg tggtggtacc       60
gtgtgctcgg gtcctgcctt tggctctgct tgtccatgac gtacggctct gggtatcttc      120
catgcccgta agttatggcc ctaaggtacc ctaaggtacc ctaaggtacc cacgcgtgtg      180
ccctctaggg tacaggggta acacttgcgc atacacacac gcgcgcacac acgcacacac      240
acgcacacac tcccccctgc caaccccact ctcacccccg cgtcccccg  cccccctgcg      300
tgtgcgtgtg tgtgccacga cgtgcgtacg gcaaagtgtg gccaaggccc cccttgcga      360
gtgggggaac ccccctagcc cctaggccct agccccaac ccctagacag ccagcccaaa       420
cggaaacagg tgtggtgtca tgtatctggg gtaggcgtga agagaagcga agcaagcaa       480
ttgcaaagct tcgaatcata acaacacaat ccgaagaatg agctaagcaa ttagttctag      540
taactcggtg agtggcagtg aactcaagta ggctctgccg ggtcaggtaa ctggtcctgg      600
ctagccctgc ttgaactggt tcaatcaatg cgtcaattgg cggtcaaacg ctggttgatt      660
gttgcccaaa tctattgatg gtttgagttg caacagtgt tgagagagct tgtattaata      720
cgcgatgcgt atgcttatga accaagtgga cctgctagga cagtaggtgc aaggccagtg      780
```

-continued

```
taacagctgt gctttgttat ctgccggcta gcattgaagc tctgcttgcg ggaagccgca      840
tgcctgagtg ttcgctaggt ggtctgagct tatgcctaac ccgtgtaaga ctcagccaat      900
ccgcgatact tggttgcgtt gcttccggag cgctggttca gagctgggag aacgttcaga      960
gaggcctcgt ggcaagagct cttctgactc gattcgtctt cggacagtcg tgttcagtcg     1020
actctcgagt gctttctcaa cggatagcgc ttcttaattg attcaattcc tgcgtatcct     1080
ttgtgatacg cgccggaata ctgtggcatg cgtatgctct cgtggcgtat gtgtgctgca     1140
gtttcaatta aaggcagcta cctggttgat cctgccagta gtcatatgct tgtctcaaag     1200
attaagccat gcatgtctaa gtataaactg cttatactgt gaaactgcga atggctcatt     1260
aaatcagtta tagtttattt gatggtacct actactcgga taaccgtagt aattctagag     1320
ctaatacgtg cgccacccga cttctggaag ggtcgtattt attagataaa aggccagccg     1380
ggctctgccc gacctgcggt gaatcatgat aacttcacga atcgtatggg ctcgtcccga     1440
cgatgtttca ttcaaatttc tgccctatca actttcgatg gtaggataga ggcctaccat     1500
ggtggtaacg ggtgacggag gattagggtt cgattccgga gagggagcct gagagatggc     1560
taccacatcc aaggaaggca gcaggcgcgc aaattaccca atcccgacac ggggaggtag     1620
tgacaataaa taacaatacc gggcgcttcg cgtctggtaa ttggaatgag tacaatctaa     1680
atcccttaac gaggatccat ggagggcaa gtctggtgcc agcagccgcg gtaattccag     1740
ctccaatagc gtatatttaa gttgttgcag ttaaaaagct cgtagttgga tttcgggtgg     1800
ggtggtgcgg tccgcctctg gtgtgcactg ctctgctcca ccttcctgcc ggggacgggc     1860
tcctgggctt cactgtctgg gactcggagt cggcgaggtt actttgagta aattagagtg     1920
ttcaaagcag gcctacgctc tgaatacatt agcatggaat aacacgatag gactctggcc     1980
tatctgttgg tctgtgggac cggagtaatg attaagaggg gtagtcgggg gcattcgtat     2040
tccgttgtca gaggtgaaat tcttggattt acggaagacg aacatctgcg aaagcatttg     2100
ccaaggatac tttcattgat caagaacgaa agttgggggc tcgaagacga ttagataccg     2160
tcgtagtctc aaccataaac gatgccgact agggattggc agatgttctt ttgatgactc     2220
tgccagcacc ttatgagaaa tcaaagtttt tgggttccgg gggagtatg gtcgcaaggc     2280
tgaaacttaa aggaattgac ggaagggcac caccaggcgt ggagcctgcg gcttaatttg     2340
actcaacacg gggaaactta ccaggtccag acacgggaag gattgacaga ttgagagctc     2400
tttcttgatt ctgtgggtgg tggtgcatgg ccgttcttag ttggtgggtt gccttgtcag     2460
gttgattccg gtaacgaacg agacctcagc ctgctaaata gtcagcatcg cacctgcggt     2520
gcgccgactt cttagaggga ctattggcgt ttagccaatg gaagtatgag gcgataacag     2580
gtctgtgatg cccttagatg ttctgggccg cacgcgcgct acactgacgc gaccaacgag     2640
cctatccttg gccgagaggc ccgggtaatc ttgtaaaccg cgtcgtgatg gggatagatt     2700
attgcaatta ttagtcttca acgaggaatg cctagtaagc gcgagtcatc agctcgcgtt     2760
gattacgtcc ctgccctttg tacacaccgc ccgtcgctcc taccgattgg gtgtgctggt     2820
gaagtgttcg gattgagctt ggctggggca acctggcctt gcttgagaag ttcattaaac     2880
cctcccacct agaggaagga gaagtcgtaa caaggtttcc gtaggtgaac ctgcggaagg     2940
atcattgaat ctatcacaat ccacaccgcg aactaacact gttggcctcc gtctgtataa     3000
aagcaaacgg gccaggtctg ggcgcaatgt aaaagttacg cctggcctgg gttgccgcaa     3060
ggcatcggtc tcttatacta accaaccaac accaaaccaa aactaaatta aaaccgagta     3120
```

```
tctagcttag agctagtgct cactaaccaa gacaactctc aacaacggat atcttggctc    3180
tcggatcgat gaagaacgca gcgaaatgcg atacgtagtg tgaattgcag aaatacgtga    3240
atcatcgaat ctttgaacgc atattgcgct cgaggcttcg gccaagagca tgtctgcctc    3300
agcgtcgggt taatactcgc cctactccaa catacacttg tgtgtttgga gcaagagcgg    3360
acctggctgt ctcggtgttt gattttcgga tcagacgccg ggtcagctga agtacagagg    3420
ttgatgcatg gacccgctta tgggcctcta ctgggtaggc aactcgttgc taatgcttta    3480
gtagatggct tggagctgtg cttgtcgacc caaaccagga actttggccc tgtgccgaag    3540
caaaccccta ttttctcgac ctgagctcag gcaagattac ccgctgaact taagcatatc    3600
aataagcgga ggaaaagaaa ctaacaagga ttccctagt aacggcgagc gaaccgggaa     3660
tagcccaact tgaaaatctc cctttggaga attgtagtct agagaagcgc tttctagggc    3720
tggcggaact caagtcggat cgaatgccgc gtcagagagg gtgataaccc cgtcggttcc    3780
tgcttagtcc ttccacgaag tgctttccac gagtcgggtt gtttgggaat gcagccctaa    3840
tttggaggta aatcccttct aaggctaaat actgccgaga gaccgatagc gaacaagtac    3900
cgtgagggaa agatgaaaag aactttgaaa agagagttaa aagtgcttga aattgttgag    3960
agggaagcga ttggcgctcg taggtgcgcc caggcttaag cggtcctaac ggcccgttga    4020
atgtgctggg tgctggtcag aatgggttga gttggcggga caaaagctgg gtccacccag    4080
gtaacccggc cgatgccgcc gactcgacca aggcgtaaag agtaccttgt ccttcgggat    4140
ctgtgctcta aagattctgg cagaagagcg tcaatcgacc cgtcttgaaa cacggaccaa    4200
ggagtctaac atgtatgcga gttggcgggt ggaaaacccg taagcgcaag taacctgact    4260
ggtgggatgg ggtaaaaccc tgcaccatcg accgaccatg ttgtttctac gaaaggtttg    4320
agtgcgagca tacctgttgg gacccgaaag atggtgaact atgcctgagc agggtgaagc    4380
cagaggaaac tctggtggag gctcgtagat gtgctgacgt gcaaatcgct tttcagactt    4440
gggtataggg gcgaaagact aatcgaacca tctagtagct ggttccctcc gaagtttccc    4500
ccaggatagc tggagcttga tcagttttat cgggtaaagc gaatgattag aggttcgggg    4560
ggatgaaaca tccttcacct attctcaaac tttaaatagg taagacgtgt cggttgctta    4620
attgaaccgg cacattcaat gtgagctcca agtgggccat ttttggtaag cagaactggc    4680
gatgcgggat gaaccgatag tcgagttaag gtgccaaact acgcgctaac ctagatccca    4740
caaagggtgt tgattgatat aaacagcagg acggtggtca tggaagtcga aatccgctaa    4800
ggagtgtgta acaactcacc tgccgaatca attagcccg aaaatggatg gcgcttaagc     4860
gcgtgaccta tactcggcca tggaagcaag tgcgacgctt ccatgagtag gagggcgtgg    4920
gtgtcgagac taagcctctg gcgtgagcct gggtgaatcg gcatctagtg cagatcttgg    4980
tggtagtagc aaatattcaa atgagaactt tgaagactga agtggagaaa ggttccatgt    5040
gaacagcaat tggacatggg ttagtcgatc ctaagagatg gggtaatcct gtgtgaagag    5100
cgcgattcgc gctgcccatc gaaagggaaa agggttaaga ttcccttact tggacaaggc    5160
ggctggcggt aacgcaagcg agcccggaga catcggcatc ggccctggga agagttctct    5220
tttcttttta acaacgcgaa ggccctgaa tcgaatcatt cggagatagg gctcagacgt      5280
tggtaaagca ccgcacttct cgcggtgtcc ggcgcgccgt tgacggtcct tgaaaatccg    5340
ggggagcatt cccgatcttg ccaagtcgta ctcataaccg catcaggtct ccaaggtgaa    5400
cagcctctag tcgatagaac aatgtagata agggaagtcg gcaaaatgga tccgtaactt    5460
cgggaaaagg attggctctg agggctgggc ctaggggtct gcagctgcga agctcgggac    5520
```

```
tgcggtggtc tacccagctg gaaacggctg ggcggactgc tgcgtgtcct gggtggacgg    5580
ctgtagaagc ttcggcgttc cctaggcgac gaacagccaa ctcagaactg gtacggacaa    5640
ggggaatccg actgtttaat aaaacaaag cattgtgatg gtcctaaagg atgttgacac     5700
aatgtgattt ctgcccagtg ctctgaatgt caaagtgaag aaattcaacc aagcgcgggt    5760
aaacggcggg agtaactatg actctcttaa ggtagccaaa tgcctcgtca tctaattagt    5820
gacgcgcatg aatggattaa cgagattccc actgtcccta tctactatct agcgaaacca    5880
cagccaaggg aacgggcttg gaataaacag cggggaaaga agaccctgtt gagcttgact    5940
ctagtccgac tttgtgaaat aacttaagag gtgtagaata agtgggagct tcggcgacgg    6000
tgaaatacca ctactttaa cgttgtttta cttattccat tacttggagg cgggactctg     6060
tccctgcttc tagctctaag acggcttttg cacgtcgatc caggtggaag acattgtcag    6120
gtggggagtt tggctggggc ggcacatctg ttaaaagata acgcaggtgt cctaagatga    6180
gctcaacgag aacagaaatc tcgtgtagaa caaaagggta aaagctcatt tgattttgat    6240
tttcagtacg aatacaaact gtgaaagcat ggcctatcga tcctttagcc tttcgggatt    6300
tgaagctaga ggtgtcagaa aagttaccac agggataact ggcttgtggc agccaagcgt    6360
tcatagcgac gttgcttttt gatccttcga tgtcggctct tcctatcatt gtgaagcagc    6420
attcaccaag cgttggattg ttcacccact aataggaac gtgagctggg tttagaccgt     6480
cgtgagacag gttagtttta ccctactgtt ggaccgattc cgccatagta attcggctca    6540
gtacgagagg aaccgccgag tcagataatt ggtaatgccc ttgtctgaaa agacaatggg    6600
gcgaagctaa catctgtagt ctaatgactg aacgcctcta agtcagaaga cgtgctaggt    6660
gcggagtcac ttacccaatg atgtcacccg actaaggata catccgcctg tgcggatgct    6720
ggagcatacc cgttggttcc cctgttaggt ccacatggcc gaagcaggcg ccaagcatga    6780
caattccact cgtcattggg gtaaatcctc tgtagcgac tttgttgcaa ctgggtattg      6840
taagtggtag agtggccttg ctgctacgat ccactgagat tcatcccgtg ttgctaagat    6900
ttgtcactgc ccttcggggc aacccctcct cctctcggag cgacagctcc agggagggcc    6960
ctctctctct cttccaagtg gtgtagctga gctgagcgcg tgccaacgcc gccgaatccg    7020
tctaagtgcc cacatgcgtg tgcatgcact gcccctcctc ccccacacag ccaaagtgct    7080
caaggtacct tccctgtgtg tgtgcgagtg agagcaacag catgcatgtg cccttactta    7140
ggcggcctag tgtggtatgt gtgtatgcgt gtggcttagt ggccagttcg actctggcgt    7200
gaagcat                                                              7207
```

<210> SEQ ID NO 70
<211> LENGTH: 2663
<212> TYPE: DNA
<213> ORGANISM: Chlamydomonas reinhardtii

<400> SEQUENCE: 70

```
cttgattctg tgggtggtgg tgcatggccg ttcttagttg gtgggttgcc ttgtcaggtt     60
gattccggta acgaacgaga cctcagcctg ctaaatagtc agcatcgcac ctgcggtgcg    120
ccgacttctt agagggacta ttggcgttta gccaatggaa gtatgaggcg ataacaggtc    180
tgtgatgccc ttagatgttc tgggccgcac gcgcgctaca ctgacgcgac caacgagcct    240
atccttggcc gagaggcccg ggtaatcttg taaaccgcgt cgtgatgggg atagattatt    300
gcaattatta gtcttcaacg aggaatgcct agtaagcgcg agtcatcagc tcgcgttgat    360
```

```
tacatccctg cccttttgtac acaccgcccg tcgctcctac cgattgggtg tgctggtgaa    420
gtgttcggat tgagcttggc tggggcaacc tggccttgct tgagaagttc attaaaccct    480
cccacctaga ggaaggagaa gtcgtaacaa ggtttccgta ggtgaacctg cggaaggatc    540
attgaatcta tcacaatcca caccgcgaac taacactgtt ggcctccgtc tgtgtaaaag    600
caaacgggcc aggtctgggc gcaatgtaaa agttacgcct ggcctgggtt gccgcaaggc    660
atcggtctct tatactaacc aaccaacacc aaaccaaaac taaattaaaa ccgagtatct    720
agcttagagc tagtgctcac taaccaagac aactctcaac aacggatatc ttggctctcg    780
gatcgatgaa gaacgcagcg aaatgcgata cgtagtgtga attgcagaaa tacgtgaatc    840
atcgaatctt tgaacgcata ttgcgctcga ggcttcggcc aagagcatgt ctgcctcagc    900
gtcgggttaa tactcgccct actccaacat gtttggagca agagcggacc tggctgtctc    960
ggtgtttgat tttcggatca gacgccgggt cagctgaagt acagaggttg atgcatggac   1020
ccgcttatgg gcctctactg ggtaggcaac tcgttgctaa tgctttagta gatggcttgg   1080
agctgtgctt gtcgacccaa accaggaact ttggccctgt gccgaagcaa accctatt    1140
tctcgacctg agctcaggca agattacccg ctgaacttaa gcatatcaat aagcggagga   1200
aaagaaacta acaaggattc ccctagtaac ggcgagcgaa ccgggaatag cccaacttga   1260
aaatctccct ttggagaatt gtagtctaga gaagcgcttt ctagggctgg cggaactcaa   1320
gtcggatcga atgccgcgtc agagagggtg ataaccccgt cggttcctgc ttagtccttc   1380
cacgaagtgc tttccacgag tcgggttgtt tgggaatgca gccctaattt ggaggtaaat   1440
cccttctaag gctaaatact gccgagagac cgatagcgaa caagtaccgt gagggaaaga   1500
tgaaaagaac tttgaaaaga gagttaaaag tgcttgaaat tgttgagagg gaagcgattg   1560
gcgctcgtag gtgcgcccag gcttaagcgg tcctaacggc ccgttgaatg tgctgggtgc   1620
tggtcagaat gggttgagtt ggcgggacaa aagctgggtc cacccaggta acccggccga   1680
tgccgccgac tcgaccaagg cgtaaagagt accttgtcct tcgggatctg tgctctaaag   1740
attctggcag aagagcgtca atcgacccgt cttgaaacac ggaccaagga gtctaacatg   1800
tatgcgagtt ggcgggtgga aaacccgtaa gcgcaagtaa cctgactggt gggatgggggt   1860
aaaaccctgc accatcgacc gaccatgttg tttctacgaa aggtttgagt gcgagcatac   1920
ctgttgggac ccgaaagatg gtgaactatg cctgagcagg gtgaagccag aggaaactct   1980
ggtggaggct cgtagatgtg ctgacgtgca aatcgctttt cagacttggg tatagggggcg   2040
aaagactaat cgaaccatct agtagctggt tccctccgaa gtttccccca ggatagctgg   2100
agcttgatca gttttatcgg gtaaagcgaa tgattagagg ttcggggggat gaaacatcct   2160
tcacctattc tcaaacttta aataggtaag acgtgtcggt tgcttaattg aaccggcaca   2220
ttcaatgtga gctccaagtg ggccattttt ggtaagcaga actggcgatg cgggatgaac   2280
cgatagtcga gttaaggtgc caaactacgc gctaacctag atcccacaaa gggtgttgat   2340
tgatataaac agcaggacgg tggtcatgga aatcgaaatc cgctaaggag tgtgtaacaa   2400
ctcacctgcc gaatcaatta gcccgaaaa tggatggcgc ttaagcgcgt gacctatact   2460
cggccatgga agcaagtgcg acgcttccat gagtaggagg gcgtgggtgt cgagactaag   2520
cctctggcgt gagcctgggt gaatcggcat ctagtgcaga tcttggtggt agtagcaaat   2580
attcaaaatga gaactttgaa gactgaagtg gagaaaggtt ccatgtgaac agcaatggac   2640
atggttagtc gatcctaaga gat                                           2663
```

<210> SEQ ID NO 71
<211> LENGTH: 1940
<212> TYPE: DNA
<213> ORGANISM: Chlamydomonas reinhardtii

<400> SEQUENCE: 71

```
cgggccttgt ctgcccgcgc ctgagctgcc tcctcttcag cgtggacccg ccgcagctct      60
gcctccatct ccgctgacag ggctggcggt gggatgggaa tggtcttgtc ctcactccac     120
gcgccagctg tggggtggca tgaggtcagg ttggagatga ggtaaggtga ggagtggttg     180
ccatgggaca gggtaagggg caagtgtgtg gcgtacacgt gtcccgtggt gtgcacatcg     240
gaggtgttgc gtccggaccc caagcctacc cttcttctca tgttgatccc cctccgcctt     300
ctcgaagtaa ttggagccat tgcggttgaa ctgagcctgc aaccgcgtca tgcacctgtt     360
tgacaatggc caccatgaaa ggccctggcg ggatgcaggc ctgcaggcgg tgccgtatgg     420
cggtttctcg ggcaaggcgg aggcgtccag cttgccgccc aagctgtcac ggatcacagt     480
ccaactcctg taatctgatg tgagatttag tgagcaatac tcctcctgcg gctgaaggcc     540
cacgagggca gcggcaaatt tacatctgca gccgcgctgg agcagggtgg ggcccgctgc     600
tgctgccgct gctgctgctc gccccgatct cttgctgctg cgcgcagatg cttgcattgc     660
gctatggtag cataatggta gcaaaaaaag gagtggacag aagaggagtg acgagcgcag     720
tcgggaaagg cgaattttt aaaattgttg ataccagcgc acggcttggt ttattatcat     780
gaactgcaat cgcactgaaa gaacaaaagt tgtagctgac aagacgcaaa atattgatac     840
taaccgcgac ctggtgggcg aaaattgggc aaacggtcgc cccattccca caaccgtggt     900
gttgcgtccg gaccccaagc ctacccttct tctcatgttg atccccctcc gccttctcga     960
agtaattgga gccattgcgg ttgaactgag cctgcaaccg cgtcatgcac ctgtttgaca    1020
atggccacca tgaaaggccc gggcgggtga tagatgtcag cgcattccca caaccgcagc    1080
cacggcgaaa taaaaggccg cccctcccat tacttgctaa cccaataacct atcataacaa    1140
cttttaagag cacgccaatc tactgtgcaa gcaagttatt agcgccgagc aaaccgtatg    1200
gagtccggtt ggcaacgcga aacagccccg cgagcagggc tgcagcgcgg taacttattg    1260
gtaagctaaa ccaatatgtt ttacaagcgc cgctattgct gcttagcttt cttgttgcaa    1320
cacgcggttg catgccatgc aaatgtcaac agtgccgctg aaacctgagc gcgaatacct    1380
tgcgggcgct gccataaccc tcttcagcat tgaaaagaac ttacagcatg acaccggctg    1440
caaaatccac tacagggcca gccagcccaa tgtccaaggg gctcgggtcg accgttggcc    1500
cgctccgccg ccacaggggg gcgccgcgcc ggcctcgtcg tccttcgaag ggtgagtgct    1560
agggctccgc tggtcaggca tcacagtgtt tgcattgcct agcaaacgta tgcacgttcc    1620
aggtggacag tgcgaagggg gcagcaaact ttggtagaac aggcagtggg aggggcccct    1680
cgtggccacg gccaggactc ctgcccctcc ctggtccgcc ccagcggctg gaacggagcc    1740
tcgtcctctc cacggatcct agacagcaaa ataccgcact gcacgcattc agaagggtc     1800
ccatccaaac cctacccaaa acccgtgtca aggggtttcc aagcgtgcga acggatgcct    1860
gtccgtatgg gctcttatcc gttacgtgca gcactagggg ctgggtgggg agggggtggg    1920
ctgggtcagc tgggccggct                                                 1940
```

<210> SEQ ID NO 72
<211> LENGTH: 2876
<212> TYPE: DNA
<213> ORGANISM: Chlamydomonas reinhardtii

<400> SEQUENCE: 72

```
ccacaccaaa gtacgcacag ttaagctcac accagtacac agccgaggca ttcttgtaaa      60
ttactctgtc cttacccata ccttcactgc ggccattggt tgagtaggtt cctagggtaa     120
tgtgggtgtt gttgatgcag ttcttctcct cacacgtatg ctgcacacac acacgactct     180
cctgcttccg cgacccctcc tcacgcagcg ggtggaattg tccagttgtc cgctccagcg     240
tgggctcacc atgaacaaca aaagctatca gcctgtgcac cgaccacgta accctggacc     300
actctctctc actcccagcg gggttggccg tatgccccac cagcacggct gggtaacccc     360
caccgccctg gaacacacaa gtaccaccac gccccacacg atggactgga ttcaagtaag     420
gcaccacgtg aatcatgtcc gctcccacgc ccagctcaac ggtcgcgctg ctaaactctg     480
caatgtactg gccaccctga gcagcgggct cctctcagt acacaccgtg gggatgcgcc      540
cctgtggcca cacctccagc ccgtagcggg tccgctctga caccaacggc acgcacagcg     600
tgtgaaatgg cttatcatac acaatcccat ggtttcgcat aaagccatgc atggcctgca     660
catgctcgcg gatgggttgc gggccctggt tgggtcccac atgtgctggc aggtaccgct     720
ccttccctgc ccacttgggt gccgtggggt ccaccggcag ctgatcaggt gggccgtcaa     780
caccacctac tggaaacaca gccagcacat acagtgtaat cagggcattt gccgccacgg     840
aaacaggcac tctgagttct acgctccatg atctccaccaa gtcagtgaat gcttggaggt    900
catgagcagg caccacacga aatttggggt aaacatgcgt gccaatgttg gccagtgcaa     960
gaaagaatga acgtgccgct gcatagccat aatccttacg cacgtcggca ggaatgcgac    1020
tgtcagcaca cctcttgcca aagttctgcg ccacctgctt caggtccaca gagaacaggc    1080
cacccacacc aagtgcctgc tcctccctgg cctcgctatc cctatgcagt ccacacacag    1140
tcctcagcgc ctggggatag aataactgca tcacatcaac aaatgcaaac ccctgtacct    1200
cagcctgcag ggtatctatc ttcgcaatct gcttaggcaa ccgaggatcc tgtgcctccc    1260
taaaggcctt gtgcaggcga cgcagcccca ggagctttgc agggcccaca cgcgccagct    1320
tctcaagctg tgctgccgtg aatggaacct cagggtcctc tgcgtctgcc cagaggtccg    1380
cttccggatt gttggtcgcc attgactact aggagggctg gggtgggggg ggggagagg     1440
ttgggctggg gttggggcgt gctgccgcac cgtgccaccc acccacccac cccttctcc     1500
tcctcctcct ccctggctgg ctgttgacga cacgttgcta cacaaccagc tgtgtgctat    1560
acgtggcgtt acgagtactg tagtttgggg ggcagcgcgt ggtggggcgg agatcctgcg    1620
gccgagggc gggcaggaag gcagggaggg tgggggccac aggaggtcag gacacacacc      1680
aagggtagcc ccaaggaaag gacccgccgc gcatggctat aagcatattt cacagcgact    1740
ttcggcgcag gcagtctgtg tacatgtccc ctagtaggct agtgcgggcg ccggggtgaa    1800
tacggtttgt cttcgaggcc tcggccacct acgaagccac aggggcccg cgccgggcg      1860
tgccgcaagc acccccaca ccggctgaga ccggtggtcc tccagagtcc aattcgccgc      1920
aacctctcca tgccacatta cgaagaggtc acttcagtaa gcccaggaac tcaccgcagg    1980
ttaaagcgac gacgtatgaa aaatcccggc gatggagaag ccgacggtca acgagtagtt    2040
gtttcttctc gctgggattc actcgacaag gcccagcata gtatcccagt aggcgcccgg    2100
gcgtggccgg caggcgcaac aaagatagcc ttgaagccct cagcgcacag actcctcgca    2160
gaagcagcac tgacaatatg ctaagaagct aaatataagg gatagagaac aagaacaggg    2220
cctggaaacg ccggggtggga acaacggtgt tgggccatcg gcgccgcgca tactaccacg    2280
gtatggttgc tagcaaagcg gttatgtact tgcaagcaaa gtagtatgta gtatctaaag    2340
```

```
acaggtgtcc agggtggggc ggcttgcaaa accaagtctt agtgcgatgc gccgcgcgcg    2400
agagaaaagg cgcgcccgcg gtcggacgca ccgggcgggg gccccacctg tgaactcaac    2460
ccccggccaa gccagccctg catttctcaa agaaatctat tgtttgcact ggcgcccgcg    2520
cttgtaaccg tttgtagtac agaaatttca ccccattttg ggagtgtgta ttcacccctt    2580
ggaaagcgcc cgcacccagg ccaccggaac gcagcacaga cgcgcagcgg agacccgcc     2640 cccagcccag aattgctata ctacaccagc atgaggcgtc tatgcggggg ggcgcggggg    2700
aatcacaggg gaacgtcaag tccggagggg tgcctggggg ccacttcggc tggtgaccaa    2760
gggctggcca aggggtggca gggggacga caagggtcc atacacacgc aattcgctga      2820
ccgctggcgt catttggcac actgatgaca tgactacata tatgatgaca tttggg        2876
```

<210> SEQ ID NO 73
<211> LENGTH: 2308
<212> TYPE: DNA
<213> ORGANISM: Chlamydomonas reinhardtii

<400> SEQUENCE: 73

```
gtggtctgga atgcagcgaa ttggccagct gataaattac atgtttaaat gatcagttgt      60
attatatatt tgcatcgagt caccaggtaa acactgcact gacttagcga actcgctccg     120
gacttcgccg tcccctctc ccctcctgct ctcccccccc cggcgcggcc gcatgccctc      180
gcacgcctct tccctcatcg cttctaccgc cccgcgcccg cgcaaaccct tcattacttc     240
ataatcaaaa tgcttaatca taggcacagt atgttcttga cactttgcaa tgcatcatga     300
atgaatgtgg gcacacacgc ctctgcctct gcctctgcct ctgccgctgc ctctgccgct     360
gcctccgcct caactccact ccactccctt cctgcctgcc tgcctcctcc tcttctctg      420 ctgctacaga acatcttgct cgctcgctac gagaagccaa acctctgggg cggcctcctg     480
tccctctctc ccttgccctc tgcgacagac agcttatact tccgcgcctc ctccgccagc     540
gccgcctggt acagcgcgtg catccactca atgcgcgggg ggacgggcag gtgcggctgg     600
tggacgtagg gggcgtagtc caccagcttc tcctccggca gctccctgta cactgcgccg     660
ggcttcttga acacccacac ttgcttctgg gagttgctgc cgtacatgcg cacagcaaac     720
tgcttcacca gctccagtgg cccaaacccg tgctgtccta gctgccgctc catgagcact     780
cctgctcctt tgtccacgac cgcaatgccc acggttgtgg acgaggccgc aaacatggcc     840
cccagcgcat cctttgctga ggcggggatg ccctgccaga acgtgaacac gtgcgtgacg     900
ccctccaggc cttggggtac cttggccatg tcctgttcga gggcagagc agagagggag      960 ggcagggaag aagggaggat gtgtgtacgt gtgtgggggg aagggaggaa ggggagaag     1020 ggggaggcgt gggcaggta cccacgccag ctccacacac cccacacacc ccatacaccc    1080
acgcacccac gcacccaccc gcccacccac gcacccaccc caccacacac cccacctcca    1140
ttgtcatggc gaagacagca ggtcgccgcg ccaggaactg ggcagtcaca ttcacgccct    1200
tgctcttgat gaactccacg aacatgcgca tgaacttgat ggccttgtcc accctggacg    1260
ggcaggagtc gttgccgtac gcgtatgcgc acaggccccg agtgaaggcc gccaccagtg    1320
gcctgcccag gccacacca gcatcaaaca tcacaggcca gcaaaggcg ccgctcagga      1380 tgccgaacag caccaagaag atctgcatgg tgcaggcagc gttgatggtg ccgtagaagc    1440
ccgtcccagt gatggtctcg ccgccaccga cgttgttctg tttgggaagt gagggagtca    1500
ttggatgggg agtgaggagt ggatgatggg tgaggggagg ggagggcaca gcgttgggt     1560
```

```
ggggtggggt ggggtggggt ggggagggcg ggcaggtggg caggcggggc gggcaggaaa    1620
ggtgacaaga cactgacaca gacgacaaca gcatactcac ttccccaggg ttcagggcgg    1680
cgtcgatgtg ctgagactca accagccgag ggaacgaagg ctcaacagca cccggcgctg    1740
ctgctgctgc tgctgccgct gctgtggtct cccacccctc ctccgtggcc tccgtggctg    1800
ccgtgccccc ctcctccgcc gctgcctcct cctcctcctc ctcctcctct gctgctgctg    1860
cctcgtgctt caggtcgtag aacacatcgg ctgcgtcagc aacctctgcc tgggacatgc    1920
taccctcgaa cagctggctg ctggggtcca gaggcagcgg tggcggcggc agcagcacct    1980
gtggtggtgg taggcacgcc gccgcctcat caccactccc tccctcctcc ttaccctccc    2040
cacccgacgc ctcctcctcc ccctcctctt cccgctgctg tggcggcgcc tgctgcgaca    2100
gccctgggga taggggctgg gagccatgaa gccccgccgc catcgggttc cccctgctg     2160 ctgcaaaccc agcagccaca ccaagcccct gctgctgagt ctgcagcaag ttagtggcac    2220
tgccgctgca ccgcagcgag ccacccgcac acctgctact gaccccagcc gacgccgcca    2280
gcgcctcagg cgacacactg cctcccga                                       2308
```

<210> SEQ ID NO 74
<211> LENGTH: 1995
<212> TYPE: DNA
<213> ORGANISM: Chlamydomonas reinhardtii

<400> SEQUENCE: 74

```
tcgccgatgc tggtgtggct gctgcccgcc tgggctgcct cccttcagc gcgggccttg      60 tctgcccgcg cctgagctgc ctcctcttca gcgtggaccc gccgcagctc tgcctccatc    120
tccgctgaca gggctggcgg tgggatggga atggtcttgt cctcactcca cgcgccagct    180
gtggggtggc atgaggtcag gttggagatg aggtaaggtg aggagtggtt gccatgggac    240
agggtaaggg gcaagtgtgt ggcgtacacg tgtcccgtgg tgtgcacatc ggaggtgttg    300
cgtccggacc ccaagcctac ccttcttctc atgttgatcc ccctccgcct tctcgaagta    360
attggagcca ttgcggttga actgagcctg caaccgcgtc atgcacctgt tgacaatgg     420 ccaccatgaa aggccctggc gggatgcagg cctgcaggcg gtgccgtatg gcggtttctc    480
gggcaaggcg gaggcgtcca gcttgccgcc caagctgtca cggatcacag tccaactcct    540
gtaatctgat gtgagattta gtgagcaata ctcctcctgc ggctgaaggc ccacgagggc    600
agcggcaaat ttacatctgc agccgcgctg gagcagggtg gggcccgctg ctgctgccgc    660
tgctgctcct cgccccgatc tcttgctgct gcgcgcagat gcttgcattg cgctatggta    720
gcataatggt agcaaaaaaa ggagtggaca gaagaggagt gacgagcgca gtcgggaaag    780 gcgaatttttt taaaattgtt gataccagcg cacggcttgg tttattatca tgaactgcaa    840
tcgcactgaa agaacaaaag ttgtagctga caagacgcaa atattgata ctaaccgcga    900 cctggtgggc gaaattgggc aaacggtcg ccccattccc acaaccgtgg tgttgcgtcc     960
ggaccccaag cctacccttc ttctcatgtt gatccccctc cgccttctcg aagtaattgg   1020
agccattgcg gttgaactga gcctgcaacc gcgtcatgca cctgtttgac aatggccacc   1080
atgaaaggcc cggcgggtg atagatgtca gcgcattccc acaaccgcag ccacggcgaa   1140
ataaaaggcc gccctccca ttacttgcta acccaatacc tatcataaca acttttaaga   1200
gcacgccaat ctactgtgca agcaagttat tagcgccgag caaaccgtat ggagtccggt   1260
tggcaacgcg aaacagcccc gcgagcaggg ctgcagcgcg gtaacttatt ggtaagctaa   1320
accaatatgt tttacaagcg ccgctattgc tgcttagctt tcttgttgca acacgcggtt   1380
```

```
gcatgccatg caaatgtcaa cagtgccgct gaaacctgag cgcgaatacc ttgcgggcgc    1440
tgccataacc ctcttcagca ttgaaaagaa cttacagcat gacaccggct gcaaaatcca    1500
ctacagggcc agccagccca atgtccaagg ggctcgggtc gaccgttggc ccgctccgcc    1560
gccacagggg ggcgccgcgc cggcctcgtc gtccttcgaa gggtgagtgc tagggctccg    1620
ctggtcaggc atcacagtgt ttgcattgcc tagcaaacgt atgcacgttc caggtggaca    1680
gtgcgaaggg ggcagcaaac tttggtagaa caggcagtgg gagggggccc tcgtggccac    1740
ggccaggact cctgcccctc cctggtccgc cccagcggct ggaacggagc ctcgtcctct    1800
ccacggatcc tagacagcaa ataccgcac tgcacgcatt cagaaggggt cccatccaaa     1860
ccctacccaa aacccgtgtc aaggggtttc caagcgtgcg aacggatgcc tgtccgtatg    1920
ggctcttatc cgttacgtgc agcactaggg gctgggtggg gaggggtgg gctgggtcag     1980 ctgggccggc tgggt                                                     1995
```

<210> SEQ ID NO 75
<211> LENGTH: 1999
<212> TYPE: DNA
<213> ORGANISM: Chlamydomonas reinhardtii

<400> SEQUENCE: 75

```
gctgctgctg ctgttgctgc tgcttctgct gctgctgcta atggtggtgc tgcgggcgtt      60
ggagctggtg gtggtagcgc tggagctggt ggctctggct ggcgtgtgat gggcacagag     120
atggtgccgg tgggtgtggg agcggcaggg gtaaaacgcc cctcggatgt gtggggtggt     180
ggtggcgctt atggtggtgg tggtggtggt ggcgcttatg gtggcggtgg tggcgcttat     240
ggtggcggtg gtggcactgg tggtggtggc gctggtggtg gtggtggtgg tggtggtggt     300
gggaagacga ggaagaagag caaggtggcg aagcagccgt tccagccgtt ctgagcttgt     360
ctgttacatg ttgattgcaa gcagcggcgg cattaggcca tagtctgcca ggaattaaat     420
gattaattgg cattggcagc aggtgggagt aggtcatgct ggtccactgc tgtgagacgc     480
acggcaacac ccgccagtgg gcgggcgtct cccacaccaa agtacgcaca gttaagctca     540
caccagtaca cagccgaggc attcttgtaa attactctgt ccttacccat accttcactg     600
cggccattgg ttgagtaggt tcctagggta atgtgggtgt tgttgatgca gttcttctcc     660
tcacacgtat gctgcacaca cacacgactc tcctgcttcc gcgaccctc ctcacgcagc     720 gggtggaatt gtccagttgt ccgctccagc gtgggctcac catgaacaac aaaagctatc    780
agcctgtgca ccgaccacgt aaccctggac cactctctct cactcccagc ggggttggcc    840
gtatgcccca ccagcacggc tgggtaaccc ccaccgccct ggaacacaca agtaccacca    900
cgccccacac gatggactgg attcaagtaa ggcaccacgt gaatcatgtc cgctcccacg    960
cccagctcaa cggtcgcgct gctaaactct gcaatgtact ggccaccctg agcagcgggc    1020
ttcctctcag tacacaccgt ggggatgcgc cctgtggcc acacctccag cccgtagcgg    1080
gtccgctctg acaccaacgg cacgcacagc gtgtgaaatg cttatcata cacaatccca     1140 tggtttcgca taaagccatg catggcctgc acatgctcgc ggatggggttg cgggccctgg   1200 ttgggtccca catgtgctgg caggtaccgc tccttccctg cccacttggg tgccgtgggg    1260
tccaccggca gctgatcagg tgggccgtca acaccaccta ctggaaacac agccagcaca    1320
tacagtgtaa tcagggcatt tgccgccacg gaaacaggca ctctgagttc tacgctccat    1380
gatctcacca agtcagtgaa tgcttggagg tcatgagcag gcaccacacg aaatttgggg    1440
```

```
taaacatgcg tgccaatgtt ggccagtgca agaaagaatg aacgtgccgc tgcatagcca   1500
taatccttac gcacgtcggc aggaatgcga ctgtcagcac acctcttgcc aaagttctgc   1560
gccacctgct tcaggtccac agagaacagg ccacccacac caagtgcctg ctcctccctg   1620
gcctcgctat ccctatgcag tccacacaca gtcctcagcg cctggggata gaataactgc   1680
atcacatcaa caaatgcaaa cccctgtacc tcagcctgca gggtatctat cttcgcaatc   1740
tgcttaggca accgaggatc ctgtgcctcc ctaaaggcct tgtgcaggcg acgcagcccc   1800
aggagctttg cagggcccac acgcgccagc ttctcaagct gtgctgccgt gaatggaacc   1860
tcagggtcct ctgcgtctgc ccagaggtcc gcttccggat tgttggtcgc cattgactac   1920
taggagggct ggggtggggg ggggggagag gttgggctgg ggttggggcg tgctgccgca   1980
ccgtgccacc cacccaccc                                                1999

<210> SEQ ID NO 76
<211> LENGTH: 2302
<212> TYPE: DNA
<213> ORGANISM: Chlamydomonas reinhardtii

<400> SEQUENCE: 76
gtggtctgga atgcagcgaa ttggccagct gataaattac atgtttaaat gatcagttgt     60
attatatatt tgcatcgagt caccaggtaa acactgcact gacttagcga actcgctccg    120
gacttcgccg tcccctctc ccctcctgct ctccccccc cggcgcggcc gcatgccctc     180
gcacgcctct tccctcatcg cttctaccgc cccgcgcccg cgcaaaccct tcattacttc    240
ataatcaaaa tgcttaatca taggcacagt atgttcttga cactttgcaa tgcatcatga    300
atgaatgtgg gcacacacgc ctctgcctct gcctctgccg ctgcctctgc cgctgcctcc    360
gcctcaactc cactccactc ccttcctgcc tgcctgcctc ctcctccttc tctgctgcta    420
cagaacatct tgctcgctcg ctacgagaag ccaaacctct ggggcggcct cctgtccctc    480
tctcccttgc cctctgcgac agacagctta tacttccgcg cctcctccgc cagcgccgcc    540
tggtacagcg cgtgcatcca ctcaatgcgc ggggggacgg gcaggtgcgg ctggtggacg    600 taggggcgt agtccaccag cttctcctcc ggcagctccc tgtacactgc gccgggcttc     660
ttgaacaccc acacttgctt ctgggagttg ctgccgtaca tgcgcacagc aaactgcttc    720
accagctcca gtggcccaaa cccgtgctgt cctagctgcc gctccatgag cactcctgct    780
cctttgtcca cgaccgcaat gcccacggtt gtggacgagg ccgcaaacat ggcccccagc    840
gcatcctttg ctgaggcggg gatgccctgc cagaacgtga acacgtgcgt gacgccctcc    900
aggccttggg gtaccttggc catgtcctgt tcgagggggca gagcagagag ggagggcagg    960
gaagaaggga ggatgtgtgt acgtgtgtgg ggggaaggga ggaaggggga gaaggggggag   1020 gcgtggggca ggtacccacg ccagctccac acaccccaca caccccatac acccacgcac   1080
ccacgcaccc accccgccac ccacgcaccc acccccaccac acaccccacc tccattgtca   1140
tggcgaagac agcaggtcgc cgcgccagga actgggcagt cacattcacg cccttgctct   1200
tgatgaactc cacgaacatg cgcatgaact tgatggcctt gtccaccctg gacgggcagg   1260
agtcgttgcc gtacgcgtat gcgcacaggc cccgagtgaa ggccgccacc agtgcctgc    1320 ccaggcccac accagcatca aacatcacag gccaggcaaa ggcgccgctc aggatgccga   1380
acagcaccaa gaagatctgc atggtgcagg cagcgttgat ggtgccgtag aagcccgtcc   1440
cagtgatggt ctcgccgcca ccgacgttgt tctgtttggg aagtgaggga gtcattggat   1500
ggggagtgag gagtggatga tggtgaggg ggggaggg cacagcgttg gggtggggtg      1560
```

-continued

```
gggtggggtg gggtggggag ggcgggcagg tgggcaggcg gggcgggcag gaaaggtgac    1620
aagacactga cacagacgac aacagcatac tcacttcccc agggttcagg gcggcgtcga    1680
tgtgctgaga ctcaaccagc cgagggaacg aaggctcaac agcacccggc gctgctgctg    1740
ctgctgctgc cgctgctgtg gtctcccac cctcctccgt ggcctccgtg gctgccgtgc     1800 cccctcctc cgccgctgcc tcctcctcct cctcctcctc ctctgctgct gctgcctcgt     1860
gcttcaggtc gtagaacaca tcggctgcgt cagcaacctc tgcctgggac atgctaccct    1920
cgaacagctg gctgctgggg tccagaggca gcggtggcgg cggcagcagc acctgtggtg    1980
gtggtaggca cgccgccgcc tcatcaccac tccctccctc ctccttaccc tccccacccg    2040
acgcctcctc ctcccctcc tcttcccgct gctgtggcgg cgcctgctgc gacagccctg     2100
gggatagggg ctgggagcca tgaagccccg ccgccatcgg gttccccct gctgctgcaa     2160 acccagcagc acaccaagc ccctgctgct gagtctgcag caagttagtg gcactgccgc     2220
tgcaccgcag cgagccaccc gcacacctgc tactgacccc agccgacgcc gccagcgcct    2280
caggcgacac actgcctccc ga                                            2302
```

<210> SEQ ID NO 77
<211> LENGTH: 4320
<212> TYPE: DNA
<213> ORGANISM: Chlamydomonas reinhardtii

<400> SEQUENCE: 77

```
tcgccgatgc tggtgtggct gctgcccgcc tgggctgcct cccctcagc gcgggccttg      60 tctgcccgcg cctgagctgc ctcctcttca gcgtggaccc gccgcagctc tgcctccatc    120
tccgctgaca gggctggcgg tgggatggga atggtcttgt cctcactcca cgcgccagct    180
gtggggtggc atgaggtcag gttggagatg aggtaaggtg aggagtggtt gccatgggac    240
agggtaaggg gcaagtgtgt ggcgtacacg tgtcccgtgg tgtgcacatc ggaggtgttg    300
cgtccggacc ccaagcctac ccttcttctc atgttgatcc ccctccgcct tctcgaagta    360
attggagcca ttgcggttga actgagcctg caaccgcgtc atgcacctgt ttgacaatgg    420
ccaccatgaa aggccctggc gggatgcagg cctgcaggcg gtgccgtatg gcggtttctc    480
gggcaaggcg gaggcgtcca gcttgccgcc caagctgtca cggatcacag tccaactcct    540
gtaatctgat gtgagattta gtgagcaata tcctcctgc ggctgaaggc ccacgagggc     600
agcggcaaat ttacatctgc agccgcgctg gagcagggtg gggcccgctg ctgctgccgc    660
tgctgctcct cgccccgatc tcttgctgct gcgcgcagat gcttgcattg cgctatggta    720
gcataatggt agcaaaaaaa ggagtggaca aagaggagt gacgagcgca gtcgggaaag     780
gcgaattttt taaaattgtt gataccgcg cacggcttgg tttattatca tgaactgcaa     840
tcgcactgaa agaacaaaag ttgtagctga caagacgcaa atattgata ctaaccgcga     900 cctggtgggc gaaaattggg caaacggtcg ccccattccc acaaccgtgg tgttgcgtcc    960
ggaccccaag cctacccttc ttctcatgtt gatcccctc cgccttctcg aagtaattgg    1020
agccattgcg gttgaactga gcctgcaacc gcgtcatgca cctgtttgac aatggccacc    1080
atgaaaggcc cggcgggtg atagatgtca gcgcattccc acaaccgcag ccacggcgaa    1140
ataaaaggcc gccctccca ttacttgcta acccaatacc tatcataaca actttttaaga   1200 gcacgccaat ctactgtgca agcaagttat tagcgccgag caaaccgtat ggagtccggt    1260
tggcaacgcg aaacagcccc gcgagcaggg ctgcagcgcg gtaacttatt ggtaagctaa    1320
```

```
accaatatgt tttacaagcg ccgctattgc tgcttagctt tcttgttgca acacgcggtt    1380
gcatgccatg caaatgtcaa cagtgccgct gaaacctgag cgcgaatacc ttgcgggcgc    1440
tgccataacc ctcttcagca ttgaaaagaa cttacagcat gacaccggct gcaaaatcca    1500
ctacagggcc agccagccca atgtccaagg ggctcgggtc gaccgttggc ccgctccgcc    1560
gccacagggg ggcgccgcgc cggcctcgtc gtccttcgaa gggtgagtgc tagggctccg    1620
ctggtcaggc atcacagtgt ttgcattgcc tagcaaacgt atgcacgttc caggtggaca    1680
gtgcgaaggg ggcagcaaac tttggtagaa caggcagtgg ggggggccc tcgtggccac     1740 ggccaggact cctgcccctc cctggtccgc cccagcggct ggaacggagc ctcgtcctct    1800
ccacggatcc tagacagcaa ataccgcac tgcacgcatt cagaaggggt cccatccaaa     1860
ccctaagtgc cccatgcggc tctgcacatg tgtgctcccc ttccctttca tgggtcaggg    1920
ctaggtacca ttcatgcagt caagtaatgt gcagccatgc tgagcacaat cagtttgtgc    1980
catatgtgaa tgacagcttt gcaggtgcaa gctgaagcag ccacagcatg gtggcgtggc    2040
aagaccagta tgcctcatgc cctttgcagg cctgggacaa cagcggcggc accaagtcag    2100
caatcgcttc accccagcaa gctccggatg gtaccagcca taacggca gtcgctatat      2160 gtattgaatc aaaagccagg ccaaacggct gcgtggctgg actgctgcac tcactcacgt    2220
ggcccctggc agcagggtga cctaaatcag ggtttggggg ggttttgagg ggtttgaaaa    2280
gtttgacatg tcagaaacga tttgcacagc ataatttgca taattacaac tagaatgatt    2340
gttgggatca cttgtgggtg accgcaatgt gatttgggga catagcaatg actttgcatg    2400
ccccattgct tccttgtcac cacacatgag taggtgggaa gggatgggac ttccattgcc    2460
ccgcatactt gcaccactgt ggcctgccat tcacccagat ccaactgtat actgtattgt    2520
gctgtgttac atgttgacac atgcatggtg tgcaagcaca tgctgctcag tccccttggc    2580
cgccacacaa gggggctgtg ctgcctaacc cccatccaa cctgcctgcc ccactcaccc     2640
ctgtgcaaga cccttcaggt gcatgtgtgc aaatgttgcc tgacatgtct gtattgcaac    2700
cacaagctag gagccgtggt gccagccctt gcagtgcccc atgcggctct gcacatgtgt    2760
gctccccttc cctttcatgg gtcagggcta ggtaccattc atgcagtcaa gtaatgtgca    2820
gccatgctga gcacaatcag tttgtgccat atgtgaatga cagcttttgca ggtgcaagct    2880 gaagcagcca gcatggtg gcgtggcaag accagtatgc ctcatgccct ttgcaggcct     2940
gggacaacag cggcggcacc aagtcagcaa tcgcttcacc ccagcaagct ccggatggta    3000
ccagccatac aacggcagtc gctatatgta ttgaatcaaa agccaggcca aacggctgcg    3060
tggctggact gctgcactca ctcacgtggc cctggcagc agggtgacct aaatcagggt     3120
ttgggggggt tttgagggggt ttgaaaagtt tgacatgtca gaaacgatttt gcacagcata    3180 atttgcataa ttacaactag aatgattgtt gggatcactt gtgggtgacc gcaatgtgat    3240
ttggggacat agcaatgact ttgcatgccc cattgcttcc ttgtcaccac acatgagtag    3300
gtgggaaggg atgggacttc cattgccccg catacttgca ccactgtggc ctgccattca    3360
cccagatcca actgtatact gtattgtgct gtgttacatg ttgacacatg catggtgtgc    3420
aagcacatgc tgctcagtcc ccttggccgc cacacaaggg ggctgtgctg cctaaccccc    3480
catccaacct gcctgcccca ctcacccctg tgcaagaccc ttcaggtgca tgtgtgcaaa    3540
tgttgcctga catgtctgta ttgcaaccac aagctaggag ccgtggtgcc agcccttgca    3600
gtgccccatg cggctctgca catgtgtgct cccctttccct ttcatgggtc agggctaggt    3660
accattcatg cagtcaagta atgtgcagcc atgctgagca caatcagttt gtgccatatg    3720
```

| | |
|---|---|
| tgaatgacag ctttgcaggt gcaagctgaa gcagccacag catggtggcg tggcaagacc | 3780 |
| agtatgcctc atgcccttg caggcctggg acaacagcgg cggcaccaag tcagcaatcg | 3840 |
| cttcacccca gcaagctccg gatggtacca gccatacaac ggcagtcgct atatgtattg | 3900 |
| aatcaaaagc caggccaaac ggctgcgtgg ctggactgct gcactcactc acgtggcccc | 3960 |
| tggtggtgag agcaaacagt tatctttcta tccaggccga gtttggggac tctaattatt | 4020 |
| gtaatgaata agtagaaaga attaatacaa gtttagctct tcaaatcggg cagatcgtgg | 4080 |
| cggaaggtga aggtctgcat gcgagcccgc aagcgaggtt gcagccatgt tgactcgctg | 4140 |
| actcgccaac caagtcagcg cttctaaacg atgtttacaa ttgataactt taattggtta | 4200 |
| tatgcaagtc ttagctgcca ctatgcctgt ctgtaacagc tgtcaaaaac aagttgacgt | 4260 |
| ttctcacacc gaggtcggac cttacttgtt gactgctcta catcctgcgc ccacagattc | 4320 |

<210> SEQ ID NO 78
<211> LENGTH: 2599
<212> TYPE: DNA
<213> ORGANISM: Chlamydomonas reinhardtii

<400> SEQUENCE: 78

| | |
|---|---|
| atgacgatgg tggaaaaggg ggggagggcg gcatgcaagt agtagaactc gaactcccgt | 60 |
| aatttaaatc acgtggttgg ccatggcagg tagggtgtct ctatttccat tcttttctg | 120 |
| ccagctgaag gcgcacgcaa acacatacat gtggggatgg cgacgttagt aacggttcgt | 180 |
| tggataggat cagggttgat tgggcggttg gggacagtac catacatata acaaatacat | 240 |
| gtgtgggagc ccagggcaga tagcggctcg atcgcaattg ctgcgcacgt gcacgatgtg | 300 |
| gcaagtcatt gaatgactac cgtactaaac atactaaata aaagtgtaaa tatgtcgaga | 360 |
| tgcacaaatg cccaacaact aacacgagtc cgtcgcttgc atagcggcct gcgccgctgc | 420 |
| tggccacgtt tgctgtattt gctgccgcga ccgagcgtag attgattgca tcacggattg | 480 |
| catgcacgtg tctatctcgg tagttgcctg gcggatgaat cacctatttt ctgcatattt | 540 |
| gctgtctaag tgcgagtcac tcatcatgat caacgcaacg cacgcataga gcatgcgccg | 600 |
| cagctagctc aatcgaacag cgcttgcgta catggtggat ggggccagct gttggtgata | 660 |
| cagctgtgat agaccgaata ttttcatagc tagttatctg ggtccttgca tgattgttta | 720 |
| tgatatgccg ttgtgaaatt agcgcagcgt aattacgcgg acaaactgct cgtggtgaaa | 780 |
| ggcataaacc atgcatgcat cttacttgcg gcgggtccat ccattaatgc tgctacgtcg | 840 |
| tcccgcccgc cccccacact catgcacacg cacgtacgcg tactcgaatc ctgctgctgg | 900 |
| ctagttacac atcccattga gacttgcgtc aacccaagcc tgccaagcgc gtggttcgtg | 960 |
| ccaagcacgc acccatccaa atgatattta cagcagcata aaattatcag tagttcaggt | 1020 |
| ttatgtagcc gtgcgtagcg aatggattcg cgccagaggt gtgctgcaca cttctcgatc | 1080 |
| gctgctgtgc tagtgcatac cgtatatgtg tctcgcctgg ttcccacacg ctctgaatat | 1140 |
| atcctaatta ccgcattctg cattcgcgca gcaaagtta agctgctgta cataccattt | 1200 |
| accgtgtatt cgtatacgcg cgctaggcct tggccgtacc tgctacgtct tttgtagcgg | 1260 |
| cgtgctcctg cagagccgct ttaatgactc tgtcgcgtga tctgactgct atttgtcttg | 1320 |
| actttatatc ctgcctggct ggcggagtgc gggcttgtcc cgcccgcccg cctaccgccc | 1380 |
| atgctcggta gtaggggcgt gcaggaggcg gcgggcctga cccgtctcct catctcccc | 1440 |
| aactccctta gtaataacac cacttgccga cggcagggtg tatccattct atttctacta | 1500 |

```
ctcttcgcgc ctggcaatga aacgataccg tactcactgt gcgcgcatag tccctgaccg    1560
tacccgctct ctacgagcca tccagcagac gataataaac gtaccatcca atcaatttgc    1620
tgttcgcaca ttactggcac gcatgactgg cctgcacgct atttattaca ccgcggacaa    1680
gcttatgcct gccggtcttc catttgtgcc gcagtgtaca acgttatctc ggcgcctggc    1740
tactcggggc ctgttttctt cagcccgatg gaatacgcca acctgacagc ggctggtctc    1800
gggccagcag gaggcaacgg cggcaggcca gcaggaggga caggtgcgtg cgtgggaagg    1860
atagcgcata acatgaagct cgatgcattg cgtcatcatt tgtctgtgct gtataataag    1920
ctgcaagcat gctcttgaac taacatgctt taatatgcac ctatctagtc gcacgatcta    1980
gtcgtggctt cattttact ttattcacag ccacgtccca tatgaaagcc ttagccttgc    2040
gtgccagcta ggcgactata cgtgatcagt aaaactgcgt gttgcgttgc ccacgtattt    2100
tatgataatc gacgaccgac gcaagtgagc tttacgtaag cgcttacgta aagctcactt    2160
gtctcctagc tacacagttg tccgtcgcat caacttcaac accgcaacac gtgtggcatt    2220
cagtgcgctt agtccttgct tgcgtttggc taggccggct gctgcaagag cgcgcgcttg    2280
tgcttgctgc gcacgcagct gctgtgctcg ctatccgcgc gcagtgcgtg gaattcagca    2340
gccgctgctg ctgtacgcaa cacgggcgtt gccggaaata atcgcttacg tgggtatatg    2400
taccttctgg gatatgctgc ccgcgtctat atatatctga caactgcagc ccacctatgc    2460
actactactc gcggcttcgc gccgctctaa taacactatt tatctcttgc gccacgcatg    2520
tcacgtaata ttacaggtgt catccagctg tccagcggat ccaatcagca ccagctgggg    2580
cagcacccac agccgccgc                                                 2599

<210> SEQ ID NO 79
<211> LENGTH: 5657
<212> TYPE: DNA
<213> ORGANISM: Chlamydomonas reinhardtii

<400> SEQUENCE: 79
ggccaggggc gccggacaca cgacgacagg ggtgaatcga tttgtaccgc tgcacgacat      60
gggtctgagc gcggatacgg atacggacat gggtaatgcc caggattagt gggacggggg     120
ccggggaggc ataagtgtct gggcatggaa cgctcacgga cttctcactg gaggctcttg     180
caagcttcac gaccgcaaca tcaataaagc cgcacgagcg cacgcacatcc tggtcatttc     240 cgaagcacac ctaacacatc gtgtgccaga cggccgtata gaactagacg gatacgcagt     300
ctttcgtgca catagatcgc aagaagctat aaggtcggat tttggcggcg ttgcagttta     360
tgtgcgtgag tgtctgatgg gcggagtgat gcatttaagg acagacgtga gtcttacagg     420
gtgtgaagtc gtgtggatgc ggatacgttc caaagatgga gacagcctgc ttttaggatg     480
ttgttacctt gcgccggaaa cctcgcgcgt atacaaggac ggcggcaaaa cgcgtgtggc     540
aagggaagcc acagctgagg ccgtctttgg aaggctccag caggctatct cggcgatgcg     600
gcagaacggc gaagaggtgc tactagtagg tgaccctcaat gcgcgtatgc cggcagggct     660
tagagatata ccggatctcg accaactagc agcgcttgaa caagtggagc atatcacggc     720
actgggtgga gcactcacgt cgatgcctag tccagaggat tacgcggggt tgccggccag     780
ggcttctcag gataagcacg caaactgttt tggcgaattt ctagcgcgta tgtgccgttc     840
tcaaggtttt gtgttactga acggcagggc accaggggat gagtcgggtc gaatcacctt     900
cccaaaaggg gaggaggggg gaagcgtcat tgacctatgc attgcatcgc caactttatt     960
ccaatcggtg acgtcagtag acgtgggtga gctgctgaga tgggcgcgca ggggcgccgg    1020
```

```
ttatgcgagt gatcacaggc ctgttacgct gactttgagc tgggaggtgg agggtcaagc   1080
aagtactgaa ggccaggcga aggcaaagcg tccacgcact gcattcaatg cgcagaagag   1140
tgagcgctat agcaatcttt tcgaacaaga tgagtcgcca gtagtaagca aattaacaga   1200
gctaaaaggc cacttggagc aagggcggta cagcactacc gaggcggtcg aagcgttgag   1260
caagtgccta agtggagtat tggagaaggc gtttgggcag agcaggcctg ctcatctgcg   1320
agagaccgag accccgtggt ggaatgagga atgtgcggtg gcgcgtgccg cgtcgtcca    1380
ggcgaaagta gcgcttggca aaccagttgt gaaggaagga gaaggtggg aagcgatgcg    1440
ggccgcgaga tcagtgtact gccgcgcaaa acgcagggct agagccgccc atgatgcgca   1500
agtgatgcgg gatagggtag cacggtgcag agccgacgct aaagcactgt ggaagatgat   1560
tgaggagcgg tgcacgagca atcccccat acggcagat ggcttccgtg atcactttgc     1620
acggctactg aatgatgggg caggaacagt tgacgacagc gctgcaaagc gtttactggc   1680
gtactgctgt gacgaagatg gctggcgaga ttcgatgtat gatgacgagg aatgggctga   1740
gttagatagc atattgaaca gcgatatctc gatagacgaa gtgactcatg ctttagagag   1800
gctaccgaat ggcaaggccc caggcacgga agccgcgcca tcggaatgct acaagtacgc   1860
aaagacgcag ggagacccca gggcagaccc ccccatcccg ccggtgaacc gggtagcacc   1920
tgttctagaa gtgttgttta accgcatctg gcgggcgcaa gacggagatg aaagttttcc   1980
ggaacagttc acaaccacag tgctgacgcc aatttacaag agaaagggcg atgtgaagac   2040
gcccggcaac tacaggggca ttgcagtagg cggagcgttg gctaagtgtt atgcatctat   2100
ccttctgaac aggctagcac gagcaggcga gttgttcaag tggaggcacc cagctcaggc   2160
tggtttcagg cggaaatacg gtactgccca ccacctgttt gtcctgaggc acctggtgac   2220
aaagcacaca cgtgcaggag caccaccaat gattgttgta cagattgatt ttgagaaggc   2280
gtttgacaag gtgccgcgcc ccctcttgtg gctacggctg cgggaaaagg gcgtgtcagg   2340
gcggctgttg gaggccatac aagccgcata tgaaaaggtc atgatgacgg ttaaagccga   2400
tggcaaactg agcgctgctt ttgaggcaac gcaaggagtc aagcaagggt gcccactgag   2460
cacagagctg ttcgggctct ttattgaaac tttggcagag tatattgatg cgcacgagga   2520
ctggttggac actgcaagca cagcgggcac ccctgagtta aacggtaaga agctgtcgct   2580
cctaatgtac gctgacgatg tttcgctgct agccaccacc cctgagcgta tgcggcacct   2640
gttgtcactt gtggatacat tctgcgaagc atttggtatg aaagcaaacg tcgcaaagtg   2700
tgaacgtctg gtgttcactt cagacgacca ggagcgtcgt agattgaacg atgagtgcag   2760
tgggctgcgg ctggcagggc agcccatccc tgcggtggac aaggcacggt atctgggact   2820
agtctacggc cctggacgtg cttttgccgc ctgcagagag acgctatgtg aggctgcgcg   2880
gcgtgctatg tacgcgctta ctaatagatt aaaccgtttg aggattttct ccccccgacat  2940
acgcatgcgt tgttttgagg tgcaagttcg ctccatccta gcatatggtt gtgaagtgtg   3000
gggacccgac gtattagcgg aaatgctgga cggcggccca ccaccgcggc ggcgtgacag   3060
caataacctg gcgcacggac cgtttgaagc atgcctgaaa gacgaggccg tcaaattaca   3120
agtgcagtac atgaggatga cagtgggtac gaagcgacca tcgcatcgcc tgctgtttgc   3180
tgaattagca caactaccac tccatttctt tttcgccaag ctttgcattg gattctacaa   3240
caggattgcc gtgcagaagg atagcctagc tcatgatgca ctaattgatg aagtacaaga   3300
cgcgttagta cacccagagg gagatgggtg gtgtgcacgg cttttccgtt ttatctcagc   3360
```

```
gcatggcgta gacgtatggc aaggccgtat gcacatgatc aggccggaaa gggaggagag   3420
ccgagcaggt agcccgctgc ctgaagggca aatagtatcc gcctttcgag agagtctaat   3480
gaaggcgtgg aagcacgagc ggctgcagtc tgagccaagc actttcccat cagacaacaa   3540
gcaaccaggc gtgcagatga gcaagtacaa gcattggatg gggctgtgtg cggaaggagc   3600
ggcaccactg accatgcaag ggcacagtag agcatttata ccagttgcgc accacaaggc   3660
cttgatgagg ttccgcctat gctgctggcc gcttactgcc aaccgcgcct atggacgacc   3720
tagggaggag aggatttgcc cgctatgtgt tgcaaatgaa gtcgaagatg agaatcatgt   3780
gctcatgcgg tgtacggcct acgaccagtt gcgtttgggt agcgagatcg attttacagg   3840
cggaatgcag gccgtcatgc agaatgcgga cccagccagg ttagccgcgt tactagattc   3900
catttgggag cacaggagca taagcacccc cattcgggga ccaaactagc tgcatatata   3960
agtgttgcag gcgttataag ggcccccccgg cccgggccta ggtttctaca aggacaggaa   4020
tgcacgtcgt gctcaccacc ttgtaaccac acacaacaac atgtaccact acctaggtgg   4080 atttcaccccc cgcacctacc gcaacgtgca tctcctacga cccaaaaccc tagatgacgc   4140
tatcgaagat gccagctacg tcagtgaaga tgccagctac gactgggatg atatgcaggc   4200
tagtactggg cgtaactccc ctacacccccc tgagcgtagg ggtgcggttc gaaagagcgc   4260
ccgccacctc ctcgcagcgt accctcaccg gcaccccccca cacctcctga gactggcagt   4320
ttgtatagtt ataagtacgg gtgttgcgct tttaggcgac attgacaagt tacatcctca   4380
agttccagag cttcgcgacg gcggacttga cagcggttag attcgtagca tcaagcatgc   4440
gcaccatgtg ttcacgacca cgcgaagata ctcgctgaca aaccgaaagg aacttctggc   4500
accattgcaa agtctctggt aaatcggatg catctggtag gagtggaata aaatgcaccc   4560
aaggcagtaa gccattataa taccaggccc gttgacgaaa aggaaaggta tgaattgcta   4620
ctgcatgact tgccagagtg acaggaaaca atgactcggg gctacttcca tcgtcaaaaa   4680
caacgtaacg tgcatctaaa acgtcaccga tatctgtaag acgacgagcc catgattcat   4740
tcgaccatcg cgcaaaagat ccttgagata tgtacacctg cactagaaac atgacgtgtt   4800
gtttacaccc aaatcaatca aagaatccca cctcactgct tttagcgata aaacttttct   4860
catcaagaag gccctgtctt gacagaatct cttgaggata atacggccac agaaccgcgt   4920
attcactgcc tgaaatagta ttaatgtgta aatccttaat caaattaaag aaataaccca   4980
ccaggactgt atagccttgc aaaactaatg gacacttcct gagctgcagc cccatggtca   5040
aaattgatag gaaatccatg ttgttcgtca aaataacttg gtggtgcgtg cctggtgaaa   5100
tcgcacaaca cgcacatcgc tctccaagga tccgcaggtt gaattttgcc gtaacgcttt   5160
tgaacagctg ctattgatgt gtctcctgca gcgaatataa tgcttggcct gctatttttc   5220
agcatatgca atctgattag gctccatcgg tgtctaacag caagggata aaggtcgcct   5280 aaccagaaca tgacctgctc acgaatccat gctgtctctt cagtactgct acgcactacg   5340
ggcgcgcaac aatcaagggt tggcagcgag ttgctttgca cgaagcaaaa cgttgttggt   5400
agcaacataa tatacagtgt aatgtgaaca aaattgcgaa ccatattgac atatgtcgtt   5460
gtagtaatta agtggtaatt cacgtattct aaaccaaggg gtgtcagctt tgtacagctg   5520
gaaaatgaga cctacacgac acttagcccg ctgatatgct tgaacatatg ctcctcacat   5580
accgagggta acgtgcttta tagaattgac aaggggtgtc agctttgtac agctggaaat   5640
gggctgagcc ccgtac                                                   5657
```

<210> SEQ ID NO 80
<211> LENGTH: 2469
<212> TYPE: DNA
<213> ORGANISM: Chlamydomonas reinhardtii

<400> SEQUENCE: 80

```
gcgtgcgcgg ggggttgaag ctgcctgggg cgggtcgctg cggcagtcca gatgcctgcg      60
ccgagggatg gcagatgcct gcgcgacccc gcgccatcag cacggatgcc tgcgcgaggc     120
attgcagatg ccgcggcgcc cctgctagca catctgagct gcctattgta gccacctagt     180
tgcttggtaa aacgccgcaa gagggtctga atgggtaacg ggcagtgtg taggggtatg      240
ccagcactcc ggcacgcaca cacagccaca ctgctcagcc gagaagttaa gggctttgac     300
catgctggcc tatactgagt gcgtgctgat attaaagcaa ccataacacc tttatagata     360
cttcgagctg cagaactctg ctgaagttgc gacattaatg gtcaaggctt ccttcttttg     420
ggcttgtgg tgccacaaga aggctacaca taaagcagta gcaagtttaa aaactactgg      480
gcaagcaggg aaacaaaagg ctctctgcga accactggtt cgcggggcgt gacagccaac     540
tcggcgccgc agccagcttt cctagggaat acagcttgtc acccagatag cagatatcat     600
gaaatagatc acagcaggct ccacggctta acccagcttt agcggcccc agaccgtgtt      660
tccatgtccg aacccacagt ctccaactag ttgtcacact gagtaaatcg cgctttgcat     720
ctctgcgtgt agagtattat ttaggaagca ggccggattg agctgcgtgc ttgccatggg     780
caccgtggca cactggcacc agcaccagca cccacgtgtg taccgtgcat accgtgctta     840
ctgacattcc cgcaatctaa actcggcacg cttcgtttcc ggggtggaaa cccacgccag     900
tcaagctgcg ggggcatggc agctaagatg cctgggcgga ccgcctccgg catcccagat     960
gcctgggcac ggcagctaag atgcctgggc ggaccatccc cgccagtcga gatgcgtgga    1020
catggcaccc caagatgcct gcgcagggct accccagcaa tctcagctgc gcgtgcgcgg    1080
ggatcaggtt gcctctggaa cttagctgcc agaccagacc caccccgcca gatgcctgcg    1140
ctaggcaact ttcccaccct ccggcctggc ctgcaggtct tgagcgtcgt tcaggtttgg    1200
gatgcagggg tcatgggtac agggccaggt cgccggggc atagccagtc agggtctggt     1260
tcagcggtca tgatcaaatt cagcggccga gggaggtgag gagctccggg accttagcgt    1320
gcccttacca tagctcggga tgaactggcc gcccatgtca tcaacgatgc ttaagaatgc    1380
ggaacagaga agccaagcga gcacaacggt ttagaggcct ggacgccggc agagcagaac    1440
agaaagcgtg agcaaagtag cgacagcagt tcaatgacag ttgcccatcg agataattgc    1500
tgcgcagaaa tggaacgcag ccgcatgcac cgctgaagag tgcagtaacg acgtactgaa    1560
acttagccag ttcatgaaat aattgtttct ttcttgtttt gttgtttatc cgagtggttt    1620
tggtagtgta tatcaggctt tcttgagtat tgctgccata ttgtcggaag cttgttcaga    1680
aggcgttctg tctcgtgtga gtgcactgct gtagactggt tatcacgttt gatatactga    1740
tacctagcaa tcgctaacgg gcaagcttgg gggtcataga gggcttccgg gagagaagtg    1800
tagcacaatg gcgccatttg ttgccggctc cgccggagct cggctgcgtg agcccaccca    1860
cggtctcctg ttgtctgaga cagctcacga gatcgagacc agtggtctac gagagcccgt    1920
gatactccag gagggtggat gggactcgtc cgcagccgtg ggctgtccgg cgggaactcg    1980
tttgtaaggc ttatcaagag aatgataagc acccattgta gggccatttt ggggttcaac    2040
tctccgaatt tccgtcagct ctcaacagag tgcttccatg ttggtatccg cacgtgttcg    2100
cagcgagata tctttactt caataacgtg tatgcccaaa caccacgcac atgctgacat      2160
```

| | |
|---|---|
| gcaccgcgtc ggtacgcaaa gaacgtggca agtgcggtga atgtttgtgc gagggtggag | 2220 |
| ggaaatgtca acacggaaac acacaacgtg ccatgctacc agcgagcttc cgtgtcaggt | 2280 |
| ggggctagcg tgggtaagg gggaaggggg aagggcccc ggacaaacac acaagggcgt | 2340 |
| ggtgctacca gcgggtgggt gtggcaagtg cggtgaatgt ttgtgcgagg gtggagggaa | 2400 |
| agggcaacac ggaaacacac aacgtgccat gctaccagcg agcttccgtg gcaggtgggg | 2460 |
| tacaggttt | 2469 |

<210> SEQ ID NO 81
<211> LENGTH: 3467
<212> TYPE: DNA
<213> ORGANISM: Chlamydomonas reinhardtii

<400> SEQUENCE: 81

| | |
|---|---|
| acaccctcct cctctgggcg cgaggcgggg gaggggtgg gtgtgggatg cccgcggcc | 60 |
| gtggttgccc agatcccgcg cgccaatgca tggccagcgg ttgggcgtac agcggcggca | 120 |
| gcagtagtgc gcagcacgca ggagtggaca cacgagcggc tggctgcagc acagcaacgc | 180 |
| atgcatgatt acgacctagg cgggcagtac gccgcacagg cactcgcgca ggcgcaggga | 240 |
| gcagtgcagc agcagctgct gctttacaac agcggcactg cagcagtgac agcgaagctg | 300 |
| gtgctcatct cgccattggc ggttaccaca gccgccccag aggtgcaggg cgtctggccc | 360 |
| gatgcagcga accctggtgc agagccgccg tacgtgcttt gcccggagga ctcgcagccg | 420 |
| acgcctgaag acacagcgcg gttatggaac ctcagcgatg accagcagca ggcgttcatg | 480 |
| ctgtacgcgc agctcctgct agcagaggcc gccggcgtcc gtcagccccc cgtgtgctcg | 540 |
| gtgctcacgg gcaaagccgg cagcggcaag tcgcgggtgc tgcaggcatt gctgtggttt | 600 |
| gcatatcagc accgctgcga gtctctcatt gccctcgtga gctacacgtg gcgcgctgcg | 660 |
| ctgcatgtga gttgtgtgtg gggtgtgtgg ggtgtgtggt gcaagagggg ttcagttcgg | 720 |
| aggtgaagtg tggcggtggt ggactggttt agcagccagg gagccttaca tgatcatgct | 780 |
| gttgacttcg gccgctgcca tcacggtcca tttacaggac tctacgccag gcgtgctcgg | 840 |
| caccagcacc acgtccttct ttgcgactgc tggcaccttt ggtccgcctc accgcgatcg | 900 |
| agtcgagcgc aacctcaatg gtgtgcgctt cattttccta gatgagttta gcacgtgtgg | 960 |
| gctgtcccac tgggcgcgca tttgcatgca tgtgcacgcg gcacggaggc acgtgggtat | 1020 |
| agacagcacg cacctatatc acgggccgct gtcagatctg catggcctgc ttgttggcga | 1080 |
| cttgcgtcag ttgccacagc cacggcacgt gccgctatat agcggtgctg cggaggagag | 1140 |
| cttgcggcag ctgctggcgc cgggcgcggg ggacggcggg gccatggagc gccagatccg | 1200 |
| gcagctggag catccggagg gcagcatgaa cctcatgggg cggagctgt ggaatatggt | 1260 |
| gccgttcgcg ttcgttctca ctcaccagca tcggcagcaa gcaggcgtag gtgacaacaa | 1320 |
| cgaacctctc ttcatgctag cggagaagtt tggtggcgtg caggaaatct ctcaggcaga | 1380 |
| tctggataca gcgtgccagc agctcaacgc gcgtgtttgg cagccccga agccagggat | 1440 |
| tgaccccgtg ccccagccct ttgcagttgt ccagcgccat gttgtgcggg ttccactggc | 1500 |
| attgcagctc gtgcagctgc atgcgctcgc gcagcgtcag cagctgctgc tatggcgtag | 1560 |
| cgcggacttg tcgccggacg ggagcagctt acctatttcg catgtgcatc aattagaggc | 1620 |
| gcttggcggg gccgaggatg atagcggtgt gcccgctgtg tgcgcattct tgctggcat | 1680 |
| tcgttacgtg tttacatcaa atgagcatgt gcgtctgtat cacatcaaca acaacagtgc | 1740 |
| cacaggcacc ggcattgttc tgcatcccaa cgagccacca ttgccagatg caagcattgc | 1800 |

```
cccgtgcat gtcctcaagt tcgtgccctc ggctgtaatg gtgcgcccg acgggcctga     1860 tgcgggtcgg gtgtctgtcg atcaggccct ggatgtcggg gagattcctg ttttaccgtg    1920
cagtgctatg ttcacatcgc agcatgcaac cctgcggttg cctgtgatgc gctgggcttt    1980
tcgtgtggag cttgcgtatg cagtcaccga ttactttgcg caggggcaaa ctctgccagc    2040
gcacgaactg tggctggtgg atatgtgcaa accgcagcac ggcagttggc ggcgggcttc    2100
aatttacgta atgctcacca ggtttcgtgg gttgcatgcc ttacatttag tgcgtccgct    2160
gtgggcctcg cgggccgaag agcgccggct taaaaaggcg ctgcgtacca tgctaacgcc    2220
cgaggcagat ctagccgcgg aatggcagcg gctattgagg ctctcgcaga gcacagcagt    2280
agcagtgcca ggtatgattg tgcgcattca ggccagcatg gctgcctcat aaccaaggct    2340
ttcaatgcat gcagtagtgt ttttaacatg cgcgaggtgt actgacagat gacctggaag    2400
cgtggagtac cttgtgggtg gtgagtgctg actgcaattt acagcagtga ctttcttgtt    2460
ggtgtttggt gtggtgacca tcatgcttgg cttcgctggc tggacgtatg tcactgagct    2520
acgttcgggt ttagtttcta cctgtcctgt ctctgcgtga agccggggta ttgtttatct    2580
gcttgcttgt cgtgcgttgg attgttgtgt gtttacaaca ggttgatgtg tggcgtggtt    2640
aatcccttgc actttgagga ggttattgtt agccagctgg tgttcgcaca ggaggttggt    2700
ggtcgatgaa cagtcgaccg acagatggat cgcgggattt gttttggca tttaccgctt     2760 ggattctatt cgcaacgtag ctcggaatac acgcttaata tgcatagtta aagacttcg     2820 gggacgcaaa tcgctcggaa atggaggagg gtctcaatat gctcggctcg cgatgtcgcg    2880
ctcttgagct tgtattatgc actgtgcgca atgcgcgttc agcatgcata ttcttacgaa     2940
caactaggga cttgagtgac gcggtgtgaa aatcagtcgg ggtctcgaca tgcttggctc    3000
gccatttcgc gctcccgagc tcgttgtgtg tgttccgaac aatgcacgct cagaattaca    3060
tgttcaatat gtccgtcgcg atgttcgagc ttgaaaaccg acaagcatgg tgtatagata    3120
cacctggtag cctgaattcc tgtgttttg gtgtattttg ttgatgttgc atcacgccgt     3180
gccttgtcac attcatgttt tttgtaccgg cgtggccttg tttgtaaatt tcgcggcgcc    3240
ctgatcttat ctacttcttc gctgtgatct ggcaaaaaaa actgttcttg acgggattcg    3300
aacctgtgac agcatctcac taagcgccat aatcagaccc tccagaggag ggtgtgcact    3360
gagttagcga tccggtgatg cagccgggta tggggtgttt tacacgggcg gcgcgcttgg    3420
cgttccagga gagcccccat cggtatttga aggcacagcg tgcttct                  3467
```

<210> SEQ ID NO 82
<211> LENGTH: 4512
<212> TYPE: DNA
<213> ORGANISM: Chlamydomonas reinhardtii

<400> SEQUENCE: 82

```
ggcggcagta gtgcgcagca cgcaggagtg gacgcactgg ctgcagcaca gcaacgcatg      60
catgattacg acctaggcgg gcagtacgcc gcacaggcgc tcgcgcaggc gcagggagca     120
gtgcagcagc agctgctgct ttacaacagc ggcactgcgg cagtgacagc gaagctggtg    180
ctcatctcgc cattggcggt taccacagcc gccccagagg tgcagggcgt ctggcctgac    240
gcagcgaacc ctggtgcaga gccgccgtac gtgctttgcc cagaggactc gcagccgacg    300
cctgaagaca cagcgcggtt atggaacctc agcgacgacc agcagcaggc gttcatgctg    360
tacgcgcagc tcctgctaac agaggccgcc ggcgtccgtc agccccccgt gtgctcggtg    420
```

-continued

| | | |
|---|---|---|
| ctcacgggca aagccggcag cggcaagtcg cgggtgctgc aggcattgct gtggtttgca | 480 | |
| taccagcatc gctgcgagtc tctcattgcc ctcgtgagct acacgtggcg cgccgcgctg | 540 | |
| catgtgagtt gtgtgtgggg tgtgtggtgc aagagaggtt cagttcagac gtgaagtgtg | 600 | |
| gtggtggtgg actggtcctg gtagtcctgc tcgtgcgtgc cggggaattt agcagccagc | 660 | |
| gagccttaca tgatcgtgct gttggcttcg gccgctgcca tcatggtcca tttacaggac | 720 | |
| tctacgccag gcgtgctcgg caccagcacc acgtccttct ttgcaactgc tggcaccttt | 780 | |
| ggtccgcctc accgcgatcg agtggagcgc aacctcaatg gtgtgcgctt cattttccta | 840 | |
| gatgagttta gcacgtgtgg gctatcccac tgggcgcgca tttgtatgca tgtgcacgcg | 900 | |
| gcacggaggc acgtgggtat agacagcacg cacttatatc acgggccgct gtcagatttg | 960 | |
| catggcctgc ttgttggcga cttgcgtcag ttgccacagc cacggcacgt gccgctatat | 1020 | |
| agcggtgctg ccgaggagag cttgcggcgg ctgctggcgc cgggcgtggg ggacggtggg | 1080 | |
| gccatggagc gccagatccg gcagctggag catccggagg gcagcatgaa cctcatgggg | 1140 | |
| cgggagttgt ggaatatggt gccgttcgcg ttcgttctca ctcaccagca tcggcagcaa | 1200 | |
| gcaggcgtag gtgacagcga cgaacctctc ttcatgctag cggagaagtt tggtggcgtg | 1260 | |
| caggaaatct ctcaggcaga cctggacaca gcgtgccagc agctcaatgc tcgtgtttgg | 1320 | |
| cagccccga agccagggat tgaccccgtg ccccagccct ttgcagttgt ccagcgccat | 1380 | |
| gtcgtgcggg ttccactggc attgcagctc gtgcagctgc atgcgctcgc gcagcgtcag | 1440 | |
| cagctgctgc tgtggcgtag cgcggacttg tcgcctgacg gcagcagctt acctatttcg | 1500 | |
| catgtgcatc aattagaggc gcttggcggg gccgaggatg atagcggtgt gcccgctgtg | 1560 | |
| tgcgcattct ttgctggtat tcgttacgta tttacatcaa atgagcatgt gcgtctgtat | 1620 | |
| cacatcaaca acaacagtgc cacaggcacc ggcattgttc tgcatcccaa cgagccacca | 1680 | |
| ttgccagatg caagcattgc ccccgtgcat gtcctcaagt tcgtgccctc agctgtaatg | 1740 | |
| gtgcgccccg acgggcctga tgcgggtcgg gtgtctgttg atcaggccct ggatgtcggg | 1800 | |
| gagattcctg ttttaccgtg cagtgctatg ttcacatcgc agcatgcaac cctgcggttg | 1860 | |
| cctgtgatgc gctgggggctt tcgtgtggag cttgcgtatg cagtcaccga ttactttgcg | 1920 | |
| caggggcaaa ctctgccacc gcacgaactg tggctggtgg atatgtgcaa accgcagcac | 1980 | |
| ggtagttggc ggcgggcttc catttacgta atgctcacca ggtttcgtgg gttgcatgcc | 2040 | |
| ttgcatttag tgcgcccgct gtgggcctcg cgggcagaag agcgccgggt taaaaaggcg | 2100 | |
| ctgccgtacca tgctaatgcc cgaggcagat ctagctgcag agtggcagcg gctattgagg | 2160 | |
| ctctcgcaga gcacagcaat agcggtgcca ggtatgattg agcgcattca ggcgagcatg | 2220 | |
| ggtgtctcat aaccgaggcc ttccatgcat gcatggttgc aacatctggc atgtggcgct | 2280 | |
| gaacgctggg ttgtcctgcg tcccggccag cacggatagc gtagtgcttt taacatgcgc | 2340 | |
| gaggtgtact gacagatgaa ctggaagcgc ggagtaccttt gtggatggtg agtgctgatt | 2400 | |
| gcaatttaca gcagtgactt tcttgttggt gtttggtgtg gtgaccatca tgcttggctt | 2460 | |
| cgctgactgg acgtatgtca ctgagctgtt tgacaggcag gcgtagagta acgtgtatgt | 2520 | |
| tcgggtttag tttctacctg tcctgtctct gcgtgaagct ggggtattgt ttatctgctt | 2580 | |
| gcttgtcgtg ccttggattg ttgcgtgttt acaacaggtt gatgtgtggc gtggttaatc | 2640 | |
| ccttgcactt tgatgaggtt attgttagcc agctggtgtt cgcacaggag gttagtggtc | 2700 | |
| aatgaatagt cgaccgacag atggatcgcg ggatttgttt ttggcattta tagttttgat | 2760 | |
| tctatgcgca acgttgcttg gaatacacgc ttaatatgca tagttggaag acttccggga | 2820 | |

```
cgcgaatcgc ttggaaatgg aggagggtcc caatatgctc ggctcgcgat gtcgcgctcc   2880
tgagcttgta ttatgcactg tgcgcgatgc gtgttcagca tgcatattct tacgaacaac   2940
tagagacttg agtgacgcgg tgtgaaaatc agtcggagtc ttgacatgct tggctcgcca   3000
tttcgcgctc ccgagctcgt tgtgtgtgtt ccgagtaatg caccctcaaa atacatgttc   3060
aatatgtccg tggcaatgtt ggagcttcaa aatcgacaag catggtgtat agatacacct   3120
ggtagcctga attcctgttt tcccggtgta ttctgttgat gttgtatcac gccgtgcttt   3180
gtcacattct tggttattgc accggcgtgg ccttgtttgt aaaattccgc ggtgccctga   3240
tcttatctac ttctttgctg tgatctggca aaaaaatatg atcttggcgg gattcgaacc   3300
tgagaccagc actacgctaa gcgccataat cagaccctcc aggggagggt gtgcactgag   3360
ttagcgatcc ggtgataccg ggttaacacc tcctcatctc tgtcacttgc gtcagactcc   3420
gctgattgca ggacccgggc cgcagcggcc ccagatcgcg cctgagatgc ctacaagcat   3480
caatggacgg gtaggcaata caactgcttt taccgtaccg tacacggtag atgctcacct   3540
tgtggttggc acgctcctcc ttccattccg cctccaacct gcaaaaagaa gccatgtcta   3600
cgtgccggca gcaatagagt acaggcatac ttactcggcc accttctgag caacgaacgt   3660
actccgccgc accccagct gatagcctcc tttgcctcct ccttccgaag ttcgtgcttc    3720
atgtagtcca ccagcggcac gttaggaaac cctaacttca cccgcgcgtc catgcacgtg   3780
ctgccatcac atgtgcagga ccccccgact gcaggaatcc agcttgcaat tttccctgct   3840
gacacgccgt catccttgct ccacttgccc ccgttgcaca tgtgcactgt gaatcctgta   3900
tcgtacagtt cccgaaggcc tggcagcacg gcgttctgca cggcaggtac gcgtccttta   3960
gacaagtgtg cgccgtactc cataagaaag acgcacctgg tacacaaagc gcagcgtctc   4020
cctcaccagg taggactctg gcttgggtgc tggccctgcg gtggtgccag tcaccttggc   4080
cttgacgatg gtattgttgg gcggggctgg cggagctggt gtactgcgta cgcgcacttc   4140
tccaggtgcg tgatgctcgg cacgagcata gggtcatcca tggagccgta agcatggact   4200
tcaatggagg aggaggtggg gtcggcgaca atgtagatgg cgcccggcag ttgcctgtga   4260
gtgcgagtga acatgacgca cggtgcatct cgagaacatc gcacggcttt gttattttat   4320
gagagcactc acttcagttg cgagccctcg aggtcctcca cggcgttggc atcaaacagc   4380
gccgagaggt tgttgttcgc agcgtgtagg ccatgcctga tctttgcagc tttatttttc   4440
tgcgggtatt tacattagca agcccgagcg tcgacttata acttttgagt tatgaggtta   4500
cctgtcgggc ca                                                       4512
```

<210> SEQ ID NO 83  
<211> LENGTH: 1230  
<212> TYPE: DNA  
<213> ORGANISM: Chlamydomonas reinhardtii

<400> SEQUENCE: 83

```
gatgaaggcc aaggaaacgt tgccgaggac cacagtcatg caaaagacag ccgaaaggag     60
aacaaccgta aggaactgct gcctactccg aatcagcttc gacggagtcc atttaaggcc    120
agcaagaatt gatccgattg ccgcgcaagc caacatgtgt gctagcgtta agaaagctgg    180
gttatgaaat cctgtacttg acagcaaata cttatttagc aggagcacgc ctatgttgct    240
acaataccag catacaatgg ctgcagtcgt ggacaaccat gcatggctta ttcccgcttg    300
agccatgaaa atgtgtggta aaaggggta ttagtttacg aggtcggtgg cggcagcgtg    360
```

-continued
ttataagata acccgctcct ttcgaggtta gaaacagtag ttataagtat agttataaaa 420
attatcggtc actgtttatc ggggcatctt attgcaggga gctgtgtata cagtatgtcc 480
attgccggag tatttttgta catcccgact ttcccacgga cgttcacccg gtactgcccc 540
gtcgtttgca caggccacgc atattcagaa aacgtggtta taacacagta caacaggtcg 600
cagcggattt gttgaaagtt ggaaggaggg agcatggatg actgggtggc cgcgccggcg 660
agtccagcgc agtttgacgt gcgtgcaata ttttgcattg gcggatgtag gcgcagcggc 720
tatgcaggtg gtgggcgtcg tggccaggac gggcgcgccg cgtgctgcgg atgtgcaccg 780
gtcgcggggt tacaggtccg gacatgcgtg cgggtacaag caggggcaag cagcaggtta 840
tagaggtcca aggtgctgta tgggaaaccc agcatggaat ccatgttgga ttgatgccag 900
ctcgcggccc attgccggcg ctcaccaccc ccccgaggat gtgcctgcag cccccgccac 960
cctgtcatag aagtgttgtc gccccagccc ctaattcctt tccgtctgtc ccttaactga 1020
agaagttgat ttttcaagca aatgcttcca aaggccgcag cagcaaccgc gaccacagtc 1080
tcaataacgg ccgcagcagc aaccacggcc acaacagcac cacgacctga ggccggccgg 1140
ggcggggcgg ggcggggcca ctataacgac gggtccatgc gttagagcct gcgttagcat 1200
gcgtgccgcg tgaaaagcat gtgctgtacg 1230

<210> SEQ ID NO 84
<211> LENGTH: 3621
<212> TYPE: DNA
<213> ORGANISM: Chlamydomonas reinhardtii

<400> SEQUENCE: 84
cctctcctca acacagctgt cctgcccggg gccagacact gcgaacatac ttctcgcccg 60
gaataagtgc ttacttcatg gctagtaacg aaacagcatt tgaggttgcg ttcctggaag 120
agtgcgagat gcacatgttc agcaaccacg cgtccttcaa gggatttgag actgtgtata 180
accgtacacg cagcgatcca cagttcaagt tgcctctgtt gtgtcgcaag cggctgacag 240
aggcatactt ccggtgcgtg gagcatccca tctgtgctgc ggagcaatag ctaatggtgc 300
attgcgcagg tacattctgt gcctccacct ggactcacac ggacagctcg gggctacagt 360
acagggcgcc gctgagcagc tagacgctga cctgttgcga tttcaggacg agtacgtgga 420
tacattcagc ctgcgttggg ggcgttacca tttatgttcc accccaggtg cggagagtgc 480
cctgtgacca tgctatgtaa ctatgaccac agcaggagat ggagtgtgca cgtgcttagc 540
agggacaccg ctgagaggat tgctaagggg ccaccaaagc cgaagaacct gtggaggcga 600
gaggtgcggg gcactgcggg gtgagcacgc agggagaaag catatacaat gcatgggtaa 660
catgggcacc cggggcctta catttggcat gtaccaaaaa gtatagtagt cacgctcaat 720
cgttcgaggt tgcttagcgt ggtgaagtcg cgccagcagc gccggacatg cagaacgttg 780
ccatagatga ccgaagaaag cgcctggaga agaaagcaga atggctgtac cagaatgtgt 840
atacgaggag tgggggtagc gctgattttg gcgcgcagtc tggagccgtt agtcgccagg 900
aagagcaaga catacatgtc cacacgcgcc ggtaaatgtg gcaaggctgc taccaagaag 960
cacgccaaag ttatgagttg cgaccaaaag ctgtatgacg tcgaagacga cgagcaaggg 1020
catcgagata acgagcgagc ggatgaactt gaccacttca gctgccgaga ataccaatag 1080
cgtcaagtct gtaacaagtg acctgcgata tacaagacat gtatcaaatg catgaaaatg 1140
tctagcgtcc caagcggaag ccgaccgata ctcaccctcc cgcgcgcaag ctgaggcaaa 1200
gaacgttcgc ctgcagacgg tgtaagcagc gcttgattgt ctgggatgtc cacaagatgt 1260

```
tgtggatagc ggacacgaac aacactggca cgaggccggc ggtcatggaa atggcaaagc    1320
tccgggtcca gtaaacggca cctgcacgta tcgtgttaag tcactgttcc ttcacacgtg    1380
gtggcctaaa gcggtggtat acgtgcctgt ccgcgtgttg agttcctgaa gggctccgca    1440
actgagttcc aggacagcgt tgaccataac gcaagactgg gccgaaaagc caaccggtcc    1500
gttgtcaggg acgaagaaca actgaaagac gtatacgacc gcggtgaggg ccacggaaca    1560
cggtgaaagg attccgctgg tcgccattga gcgcggcgga gcaagtggat agggcagcga    1620
gaagggccac gaatagcgca aactgcgcca tataccggcc gaggcccacc agcacggcgc    1680
tcgcgtgcac aatcctggcc gaccgggcgc tggtgctgaa gggctcatgc ccaggctcct    1740
gcacgttttc gacagtctcg gtgttggggc gtttgcgtat gcgtggcatt tgtcagttg     1800 taataatgga agtgccaaag tgaacgtgat ttacacaccg aggggtgtgg ggccgggctt    1860
acttcaacgg tgggccaatt tggatttcaa ctttgaatcc ggacagtcag tccccctgac    1920
ggcatgttcc cagacgcgcc agtatcccgg gctcagaaga acgcatgtac ttgcacgctt    1980
atggagttct aacgtgagac gaaacacagt cgggactgaa aggtcacaca tagaaatggt    2040
tcctcaactg gcggcagcat tcacaggggat tccaggagta ttggcgctgc tcttgttcat   2100
cgtaacagtg attaggtttc cacgaccgtt tgcggaccgg cacaaaattg ttgccgccat    2160
actggagaaa tgcgacaggg acatttttgg aggcagcttt cagcaggccg cgactgcact    2220
ggtatggaaa ttgagctcgt catttatgat gcaccgattg acgccagttg cgcgcagggc    2280
tgcttcgacg attgcttgaa ggccgagggc atcgctaccg accaaccact tggcacactg    2340
ctccgtcgca tattgcgcat gtgctgccgc gatgccaacc agcccgaggc ggtgcttact    2400
tacaatattc cggcatgcgc ggcggtgaga agaaacacca aatcatgact gagggttgac    2460
acgatactta cggtaccccc accacccctc gctcacagtg cggctccggc aacctgcgtg    2520
aagagcggcg ttatcgcgcg acctgcttca cgcgtgacga gggccctctc gacgtgcttg    2580
tgatactaaa ggcgtgtata cgcacacagg cacactactc acactactca cacatacata    2640
cgcacacatg cacacatgca cacaccagca ctaacactaa ctaatataga tacatactgc    2700
tacactacgc ccaacataca ccaacgagct cggtttgaat ttctgaacaa gtgaaatagg    2760
cgaacatagg agctgtgcat gccgcagcag aatatggacg ttctatttaa agcccaaacg    2820
agcaagggga ccactgtgtg caaagccttt tgccgatccg tcagtccctc gtggcggctg    2880
caccgtgacg gcaattgtgt acccaccata acggcacctt gctcggcggc tgacactcag    2940
actatcacaa acggtgctat cgtggagggc aagaagcagg gatcgcgaca catgccagcg    3000
aaggcgggac gctggaccaa aggaatcagg ggctggctga tgctggtgct gatattacta    3060
ggcaactgcg acattctcgc caagcagggc agggagcggc aggcagggca gggagcggca    3120
aacaatggac tcgacctggg agcctgcccg gacgcagcct cacagacaac tgaaaacggt    3180
agagaactac aagtggctgg ggcttgtgct tggcataaag accgtgtggt ctacgtaaac    3240
ccaaatggat ttggctgcac taacactatt acacgcgccg agctcgctgc aattcgtgca    3300
gccctggaag aattcggagg tgaaactagt atgttcgcga agaaaacgct aaccattgcc    3360
agtgactcag ctgcaagctt gtatctaatt aaacgggcta ttaacgaacc acgccgctta    3420
catctgagca aacataaggc acttctgagt tcgatcgccg atttgctcca tgcacgagcg    3480
aagagggacg cacacaccgt tttcctcaaa gtcgtttctc acgggtctgc acggtaat     3540 gaagaagccg ataaaggtgc agcagacgta gctacaagca ctaaaccggc tgacgtctcg    3600
```
gagctcgctg acaataaccc c    3621

<210> SEQ ID NO 85
<211> LENGTH: 58
<212> TYPE: DNA
<213> ORGANISM: Chlamydomonas reinhardtii

<400> SEQUENCE: 85
gcgtcccgtg atccctattt gatggttcgc cgtcgagtag ctagttatgt catacttt    58

<210> SEQ ID NO 86
<211> LENGTH: 1163
<212> TYPE: DNA
<213> ORGANISM: Chlamydomonas reinhardtii

<400> SEQUENCE: 86
ctgacatcct gttcatccca tccctaccac gctccaacgt gggggctagt gggccccgcg     60
gccttacaac cgccggccga cggcaacaca aagtttacct gatagaagtt ggttacacat    120
cggacctcca ccacagcgaa aagtgtgacc agaaacaagc ccagcacact cgcctagccg    180
acgccctgcg ggatgcaggc tgggacgtag tatataaaaa ggagcagatt gtgacgctgg    240
gccacggcgg cactgtgtca aacaccttgg aacccttct ccggtcgctg ggtgccacca    300
ccacatcagc aaaatcctgc tgctcgcgca tacacatgca cagtgtcatc agcctgcgca    360
ccacatccct tctctactac cgccttgagc gcgaatggg gattgtgaac tcacgccacg    420
tcggtcccac tggcggcgcc acggctgctg gccccagccc tcgcgatcca ggctaacttc    480
ccaccttttg acacggtggg gtgagcaaaa ctcactcctc cttaagaaac gcggcctcct    540
tcgtgaaccg cgtacatatt attattatta ttattattat tattattatt attattatta    600
ttattattat tattattatt attattatta ttattattat tattattatt attattatta    660
ttattattat tattattatt attattatta ttaaccgcgt gttcatgcaa ctcctttcga    720
tcgcgcagca ggcttgaagg gctggagctg cgggttgagt ataggcaggg ccgaacagga    780
gtcccaggaa aggggcttcg ggccgtgagt tggtgatgca gctgattatc agcgttcacg    840
tcgaatttac tactgccggc gtgaggcggc ggcagcagct gctggcatgg ggcccgtggc    900
ggcatacatg cttgtggtca ttccaacggg cgcgcagtgt tggccttgct taattgctgg    960
catgtgttgc cccgccggcc attactcccg ccacgcacgt caccacgcgt acgctgccgc   1020
cgccgcccac atattccagc gcactatttg tgcactattt gccgcttctg ttactaacta   1080
ttctcgacac tacggcacct ttgtgatttt gcacggtatg acacggcggt acagtgccca   1140
ggagcaagga tgaccctgc gcc                                           1163

<210> SEQ ID NO 87
<211> LENGTH: 44
<212> TYPE: DNA
<213> ORGANISM: Chlamydomonas reinhardtii

<400> SEQUENCE: 87
tgaatgcaca cagcattggg ttctggttgg gcaggttcta cgga    44

<210> SEQ ID NO 88
<211> LENGTH: 381
<212> TYPE: DNA
<213> ORGANISM: Chlamydomonas reinhardtii
<220> FEATURE:
<221> NAME/KEY: misc_feature
<222> LOCATION: 376, 377, 378, 379, 380, 381
<223> OTHER INFORMATION: n = A,T,C or G

<400> SEQUENCE: 88

```
cctaaaaccc taaacccta aaccctaaa acccaaaacc ctaaatcggg gttttaaggg      60
gttttgcggg atttgaaaag tgtgacatgt cagaaataat ttgcacagca taaatagcat   120
aatttcagca agaataattg ttagagtcac ttgtgggtga tcatgatgtg gtttgggggc   180
atagcaatga cccagtgctt ccttgtcagc acgcgtcagt aggcgggaag ggatgggact   240
tccattgccc cgcatactag caccactgtg gcatgccgtt cacccagatc catttgtata   300
ctatattgtg ctgtgttgac agattgcgca tgcatggtgt gcaagcacat gctgctcagg   360
ccccttggca tgccannnnn n                                              381
```

<210> SEQ ID NO 89
<211> LENGTH: 61
<212> TYPE: DNA
<213> ORGANISM: Chlamydomonas reinhardtii

<400> SEQUENCE: 89

```
tatcaccctg aagatcaagg agttttacat aaatccaaca gagtttggtg ttttccacca    60
g                                                                    61
```

<210> SEQ ID NO 90
<211> LENGTH: 3645
<212> TYPE: DNA
<213> ORGANISM: Chlamydomonas reinhardtii

<400> SEQUENCE: 90

```
tatggaacct cagcgatgac cagcagcagg cgttcatgct gtacgcgcag ctcctgctag     60
cagaggccgc cggcgtccgt cagcccccg tgtgctcggt gctcacgggc aaagccggca     120
gcggcaagtc gcgggtgctg caggcattgc tgtggtttgc atatcagcac cgctgcgagt    180
ctctcattgc cctcgtgagc tacacgtggc gcgctcgcgct gcatgtgagt tgtgtgtggg    240
gtgtgtgggg tgtgtggtgc aagaggggtt cagttcggag gtgaagtgtg gcggtggtgg    300
actggtttag cagccaggga gccttacatg atcatgctgt tgacttcggc cgctgccatc    360
acggtccatt tacaggactc tacgccaggc gtgctcggca ccagcaccac gtccttcttt    420
gcgactgctg gcacctttgg tccgcctcac cgagatcgag tcgagcgcaa cctcaatggt    480
gtgcgcttca ttttcctaga tgagtttagc acgtgtgggc tgtcccactg ggcgcgcatt    540
tgcatgcatg tgcacgcggc acggaggcac gtgggtatag acagcacgca cctatatcac    600
gggccgctgt cagatctgca tggcctgctt gttggcgact tgcgtcagtt gccacagcca    660
cggcacgtgc cgctatatag cggtgctgcg gaagagagct tgcggcagct gctggcgccg    720
ggcgcggggg acgcgggc catggagcgc cagatccggc agctggagca tccggagggc    780
agcatgaacc tcatggggcg ggagctgtgg aatatggtgc cgttcgcgtt cgttctcact    840
caccagcatc ggcagcaagc aggcgtaggt gacaacaacg aacctctctt catgctagcg    900
gagaagtttg gtggcgtgca ggaaatctct caggcagatc tggatacagc gtgccagcag    960
ctcaacgcgc gtgtttggca gccccgaag ccagggattg accccgtgcc ccagcccttt   1020
gcagttgtcc agcgccatgt tgtgcgggtt ccactggcat tgcagctcgt gcagctgcat   1080
gcgctcgcgc agcgtcagca gctgctgcta tggcgtagcg cggacttgtc gccggacggg   1140
agcagcttac ctatttcgca tgtgcatcaa ttagaggcgc ttggcggggc cgaggatgat   1200
agcggtgtgc ccgctgtgtg cgcattcttt gctggcattc gttacgtgtt tacatcaaat   1260
```

-continued

```
gagcatgtgc gtctgtatca catcaacaac aacagtgcca caggcaccgg cattgttctg    1320
catcccaacg agccaccatt gccagatgca agcattgccc ccgtgcatgt cctcaagttc    1380
gtgccctcgg ctgtaatggt gcgccccgac gggcctgatg cgggtcgggt gtctgtcgat    1440
caggccctgg atgtcgggga gattcctgtt ttaccgtgca gtgctatgtt cacatcgcag    1500
catgcaaccc tgcggttgcc tgtgatgcgc tggggctttc gtgtggagct tgcgtatgca    1560
gtcaccgatt actttgcgca ggggcaaact ctgccagcgc acgaactgtg ctggtggat    1620 atgtgcaaac cgcagcacgg cagttggcgg cgggcttcaa tttacgtaat gctcaccagg    1680
tttcgtgggt tgcatgcctt acatttagtg cgtccgctgt gggcctcgcg ggccgaagag    1740
cgccggctta aaaaggcgct gcgtaccatg ctaacgcccg aggcagatct agccgcggaa    1800
tggcagcggc tattgaggct ctcgcagagc acagcagtag cagtgccagg tatgattgtg    1860
cgcattcagg ccagcatggc tgcctcataa ccaaggcttt caatgcatgc agtagtgttt    1920
ttaacatgcg cgaggtgtac tgacagatga cctggaagcg tggagtacct tgtgggtggt    1980
gagtgctgac tgcaatttac agcagtgact ttccttgttgg tgtttggtgt ggtgaccatc    2040
atgcttggct tcgctggctg gacgtatgtc actgagctac gttcgggttt agtttctacc    2100
tgtcctgtct ctgcgtgaag ccggggtatt gtttatctgc ttgcttgtcg tgcgttggat    2160
tgttgtgtgt ttacaacagg ttgatgtgtg gcgtggttaa tcccttgcac tttgaggagg    2220
ttattgttag ccagctggtg ttcgcacagg aggttggtgg tcgatgaaca gtcgaccgac    2280
agatggatcg cgggatttgt ttttggcatt taccgcttgg attctattcg caacgtagct    2340
cggaatacac gcttaatatg catagttaga agacttcggg gacgcaaatc gctcggaaat    2400
ggaggagggt ctcaatatgc tcggctcgcg atgtcgcgct cttgagcttg tattatgcac    2460
tgtgcgcaat gcgcgttcag catgcatatt cttacgaaca actagggact tgagtgacgc    2520
ggtgtgaaaa tcagtcgggg tctcgacatg cttggctcgc catttcgcgc tcccgagctc    2580
gttgtgtgtg ttccgaacaa tgcacgctca gaattacatg ttcaatatgt ccgtcgcgat    2640
gttcgagctt gaaaaccgac aagcatggtg tatagataca cctggtagcc tgaattcctg    2700
tgtttttggt gtattttgtt gatgttgcat cacgccgtgc cttgtcacat tcatgttttt    2760
tgtaccggcg tggccttgtt tgtaaatttc gcggcgccct gatcttatct acttcttcgc    2820
tgtgatctgg caaaaaaaac tgttcttgac gggattcgaa cctgtgacag catctcacta    2880
agcgccataa tcagaccctc cagaggaggg tgtgcactcc ggtgatcgca ctgaacacgg    2940
ccttacctcc ccggtacaca ttgaacgagg cacagtccag ggcgacacac tctcccccgt    3000
actctttctg atgtttatcg aaccgcttat atggtggctc catgtaggag gccgcggcta    3060
ctcctacggt tgcttaccaa accacctcaa caacaggttc cactgctcct cagccgccta    3120
caccgacgac ctggcggtgc ttacaaacac cttgagcgac ctacgcattc aatgcgacaa    3180
aatccaccgc tactcggcat gggcgggcct ccaggtgaac cacgccaaat gccgagtcac    3240
gggaatcctg caccgaagag cccagcagga caaaggcctg aacggtccca cctgcaaccg    3300
taccctcaaa tcaatgctcg aaaacaaaat ccacattggc gacaaacctg tgccttacct    3360
ccccgcaacc gaacccttca aatacctggg agtacagata accatgaact tgcactgggg    3420
accccagttt gcttacctat gtgatgccat caaagaaaaa agtgccaacc tgcaaacgtc    3480
tctcgcgtca ccagaacaat gcctgcgaat tataaaatcc tgcatacagt ctatggcagc    3540
atacagcttt gcggttatgc cgtacgcaga gaacgacatc cgcaccctcg acgccatgat    3600
tgcgcggctg gcaaagaagt gttaccgcct cacccctggg ttccc                    3645
```

<210> SEQ ID NO 91
<211> LENGTH: 3265
<212> TYPE: DNA
<213> ORGANISM: Chlamydomonas reinhardtii

<400> SEQUENCE: 91

| | |
|---|---|
| ggcgacaaaa cctcgtggta ccagcagtgg ttcgcggagt gcccgttcgg cctgctggat | 60 |
| gtcaccgggc aggacgtgct ggtgtgtgcc gtgcggcgca cagcagatgg tgggctgcaa | 120 |
| cgcgcgccgc tcgtctctgt agggcaggtg cgaataagct gcggtccggg cgcatgttgt | 180 |
| tgcatgttat cggttgtatg gcggtgtgcg tgttcagcat gctgctgtcg cgcttgcctg | 240 |
| caggtgtcgg gcgaggcggg gcgcgctctg cgcaacaagg tggcgcgcac gtgtcaagag | 300 |
| gtccacaatg gcgacgcctg ggctcacatc gacaagcact acgacggcaa cttctggatg | 360 |
| gcggggctgg cgtcgcctgc tcgcgtggga cacatcatct gcaggcaaga gcaccagggg | 420 |
| ggtgttgcat gcgggcggca agggtggcgc gggcatggag gagaggcatg gatgtgcggt | 480 |
| ggggccgaga ttgactgata cgttgctgtg caggtacgtc aaccagatca tctacgagtg | 540 |
| cgaggcggag cattatccat tcagcatcga ggaggcgctg gaggagatgt gtacggcggt | 600 |
| gtgggaggcg gcggtgcagg ttgcgccgta cctgaccaag tacaggtgag gcgccgcgt | 660 |
| agccgcgggg ctgcatgcaa gggcagtacg tgcaggatgg ttgtgtgggg cgtcgcgtac | 720 |
| gtagcattga tgtgtggtgc tgcacgctct gggtctgcgc gcaggatga gttcttgtct | 780 |
| gcctgggggc gccaggcgat gtacggcgac acggcaacta acctcgtgag catgaccaag | 840 |
| aactgcgcgg tgtcgttgca cttcgacaca acggacggtg aggctggtgc gcaggggtgt | 900 |
| atatcaggga agcgctgctt gtgtatttgt gtgtgtgggc ggggggggggg ggggggcgg | 960 |
| gcggtggatg ggtgagtggg tgtgcgtgcg agctggcttg tgtagatctg ggagggtggg | 1020 |
| cgtactgtga ggcaaggtgg tggtgctggt ctgctatctg cgtgctgcta atgagtgtga | 1080 |
| atttcttcgc gtgggaattg acacgcaggg ccgtacagca tcatgctgtg gcgccacaac | 1140 |
| ggtgccggca gcctgacggg cgggcatttc ttgatgcctg cgcctccat caaggtaaat | 1200 |
| ggccaggtgg tgcatctctg cgggcgggtg tggttttgtg tgtgtcggcc aggcgcgcgt | 1260 |
| atagtgaggt cgcggtgcgg acatgcaagt catatgggcg ctgttgtttg caggtgctgc | 1320 |
| cgaccgacat gacgatcgtg gtgctggctg ctggcatggt cacgcatggg acggcgcccg | 1380 |
| tgctggagtc cactggcgac gcgcggcggt atggctactc gcatttcctg cgtgtgccgg | 1440 |
| ccatggagcg tgtggcgcgg ctgatcaagg catctggcgg aaagaagaag atggaggagc | 1500 |
| tgcaggtaca gggcatgaag cgcgtgttgg ctgcacgtac agcagcggat cggaaggcgc | 1560 |
| ggcgggatga aatccagaag cagcgggacg agctcctgaa gagcgcgctg gacgcgagg | 1620 |
| cgctgcccga gggcgagcat ttagcgtttg ctgtgcgagg gttgaagtgg caccgggaca | 1680 |
| ttgtgaagtg cctggtatgg caggacttca agggcaagtc ctgagacctg tagcaggagg | 1740 |
| agcgggtggg tagtagtggt tcgtgtagag gcgtgttggg ctgtgtaagt gagaggtcat | 1800 |
| gggagtacac aacgcaaata aagcaagaac agcgggagtt tggtaggcag cgccaacagg | 1860 |
| cgcgaacgct gctggggagt tggtgtgttg cagtgggagt tgggccatgc acgtgagaca | 1920 |
| gcgagtggcc gtacaggtgt tcgcatttgc atgttaaaag gactgtgcca tttgcgccaa | 1980 |
| gcaagtggat ggagtgggtg ggtgatgaac tggattgtgg ggtagagctg tgggcagggg | 2040 |
| catgcgttgg ggaaccggtt tttctgtgag ggcgtgtggg tgcgctaagg gcaatgtaac | 2100 |

```
aagacagcgt ggctgtagtc aggtagcagt gtagggttgc ggttggggct gggctgcagc    2160
ggaagtagaa gtaggggtag ctgcttgttg tggtgaagat gcgcgggtg tcgtgctggc    2220 gaaagcttgc aaaggtagtg gggtgctgca ttgaggcgca tgaggcgcag tgcattggca    2280
gaggtgctgg aatggacagg aggcagcgag tgcaatggca tgagatgagc gtttgtatac    2340
aatgaaggtg tgcagaactc gcaacgttgg caacgtgcaa catcaatgtg tttgtcgtgg    2400
taccataagc agaactgcgc caggctgtaa gcactgagac taggaaatgt caagcagccg    2460
cacagaagat acatctacgc aacagccaca gcttttcaat agcgcatttg cgcgcactac    2520
caagcacttc acaaacgcct ccgtgcacac atgctgcgca tgaaagcgag gaatgcaggt    2580
tggttctaag cagaggtgga ggcgtaatca gtcgtggagg agtaatcagc attacggcag    2640
ctgcgcctgc acgtggcgc ccgcgatagt ccaacggccg atccgggcgt gctgcggctc    2700
gtagccagcg gactgcgcgg cccaagcgag tacgcgtcc agctgcgctc cgtagacgac    2760
gcgcgccaca tcaggcggca tggtgacctt caaggtgcgg ggagatgcga gaggcatgca    2820
tggtcaggtg gagtgcactc aggagatgcg agaggcacgc atggtgaggt ggagtggcgg    2880
gtggtggatg gcatgagcgc agtccaggga acgcaccagg gtgccatcgt atgcagccag    2940
cgcggccgac agcaggtagc cgatgaggtt gttgttgctg caggtaggca ggtttggatg    3000
aagcgcagtg tggtgagcaa actggttggg tgatgcgggg ccgagcttgg caggtacgta    3060
gcccaaccta tataggaggg tggccttgcgc acttactcga gcaccactgg catgaaggca    3120
ccatacaccg gcgcgtggct ggtgaaggcg gcctggtcga tgttggagtt gagcgtgagc    3180
atgttttggt catgcaccag gagctcgact aggatgtgga tcaggagcgg agtgtcgggc    3240
gtgacgccca tgatgccggt ctcca                                          3265
```

<210> SEQ ID NO 92
<211> LENGTH: 1773
<212> TYPE: DNA
<213> ORGANISM: Chlamydomonas reinhardtii

<400> SEQUENCE: 92

```
tccctaccta cctgtccaag gccaagccgt gtcagctact gctgcaaggg atgtcgaaag     60
cggtgacgtt tggggctggg gaagcgttgt ttcagggggtt gactttgcag aaccatcctg    120
ttgtgttgcc tgcacttgag tctagcgtag ctgtttggta cgcaccgccc ctgcctgtta    180
gcaacgcgaa ttcttctcct catgtctctt cgttgtatct gaccgcatcc tctgctgtgc    240
cgtctgctgc cgcttcgacc gcagggcctc tgcctatcgt gcctgcacga gttggcggcc    300
tgcgcgtgtc tgtgctcgct gacactggag ctagtcacga cttcgtctcc aaggctctgt    360
gtgaccagct gggactcaag ttgtcgatgg tggtaagcag accattctgg gccgtgtagc    420
gttgcgcgta gcgttcggtt ctgcattcct tacgctccgt ccgttcgtcc tgcctacctt    480
cactgatgcc gcgcaaatga tcatgggtgc tagtactatg ttgcgcgagg gggtagctgt    540
agacatgggt aagcacgctc tggtgctgcg aacggccaag cgcactgttt ctgtaccgct    600
ccggaccata ggcttgcatg ccctgactgt agcgtccgtt gcgatcgacc aacccactga    660
gaacctggcg ttgtcggcca ttattgccat ggctctgcac gccaaacccg gtagttctca    720
ctacctccct taatcgggaa tagacacgac accgacgatg gcgccctcag cgctgctgag    780
ctgcttgcag cgctgggcag cgctgccaac ggtaaagcgc tgggctcgga tgggctgcct    840
tacaaggtgt acaaggtctg cgggaccagg ctgtcttcgg gtctctgtgc ccagcagtag    900
gggggtagcg tgtctgcccc tggtcaactc tgtaaggatg aagcctaaaa ataagtgttt    960
```

```
tgggcgctct cactctggga aaaggggggg ggaaatcccg ggaaaaacag ggggtagttc     1020
cccggaaata tcttccccgc cgtactgtat gcttttcgaa gaaagtagga gtttgtacgg     1080
ggaagtcctt acggggaagt tcttacggga ataataataa taataataat aataataata     1140
ataataataa taataataat aataataata ataataataa taataataat aataataata     1200
ataataataa taataataat aataataata ataataataa taataataat aataataata     1260
ataataataa taataataat aataataata ataataataa taatcccaac gctggcccat     1320
agggcctagc atgtattaac ggggcaacgc cttcgctcat catctctcaa cccagttcga     1380
gagaaggcgg gaagtcacca cgaccacctt atcattttcc ggtcctgccc accggtggga     1440
gcggggtgga ttaagcccct ggtgtcctat ccatgttcag ctcggatgat ctaccctcac     1500
cgctttcggt acctgagatc ggggatcag gtaatgccga ctgtcgggca acatctcaac     1560
tgaaactctg gatcgatcca gagtccggcc cctttgccgg cacttcacga ccgctctctt     1620
atctgacgtt agccatggat gacaaggaca cgactgaaga gccgtgcggt ccctgcggag     1680
cgcctgtgcg tgatttgaat acgcacggag gtttccoctg taccgaattt ggggaggatc     1740
gaacccaggt ctgaaccgac gttacacacc aac                                 1773

<210> SEQ ID NO 93
<211> LENGTH: 3075
<212> TYPE: DNA
<213> ORGANISM: Chlamydomonas reinhardtii

<400> SEQUENCE: 93
tttaaggggt tttgcagggt ttggaaagag tgacatgtca gtaatgattt gcatagcata       60
gttcagctta ttataactag aatgattgtt tgaacccctt gtgggtgacc atgatgaggt      120
tcgggcacat agcaatgact ttgcgtgctt ccttgtcaca gccttgagag cacaagcacg      180
tgggaaggga tgcaacttcc aaagccctgc atactcgcac cactgtggat tgccatttgc      240
tcagatgcag ctgtatactg tgttgtgctg tgttgcaggc ttacagattg cacagatgca      300
agcctatgcc actcattccc cttggcccca caccggggcc cgtgttgccc aatccagcct      360
gcctgccttg ctcacccatg tgcaagactc ttccacattc atgtatgcac atgttgcctg      420
acctgtttgt aatgtaacca ccagctaagc gcagtggtgc cagcacttgc agcgcccat      480 atggctctgc acatcacaac aagtgcccct ggcttgcctc ccctctccca ggggtcaggt      540
atcatgcagg ctgtcaaata atgtgctgcc atgctaagga cagtctagtc acaccatatg      600
ttagtgatgg gctttgggag tgcaagcaga agcagccaca gcacattggc atgtccagac      660
ccgaatgcct ggtgcgcctg ccgaccacac cggtggcgcc aagtcggcaa ccgctccact      720
ccagcaagct ccagctcatg ccaaacatac aacggcagcc gctatatgta tataagcaat      780
agctgtgcca acggctgcg tggctggact gctgcactca ctcacgtggc ccctggccct      840
ggggtcacct aaatctgggt tttaaggggt tttgcagggt ttggaaagag tgacatgtca      900
gtaatgattt gcatagcata gttcagctta ttataactag aatgattgtt tgaacccctt      960
gtgggtgacc atgatgaggt tcgggcacat agcaatgact ttgcgtgctt ccttgtcaca     1020
gccttgagag cacaagcacg tgggaaggga tgcaacttcc aaagccctgc atactcgcac     1080
cactgtggat tgccatttgc tcagatgcag ctgtatactg tgttgtgctg tgttgcaggc     1140
ttacagattg cacagatgca agcctatgcc actcattccc cttggcccca caccggggcc     1200
cgtgttgccc aatccagcct gcctgccttg ctcacccatg tgcaagactc ttccacattc     1260
```

```
atgtatgcac atgttgcctg acctgtttgt aatgtaacca ccagctgagc gcagtggtgc    1320
cagcacttgc agggcccat atggctctgc acatcacaac aagtgcccct ggcttgcctc     1380
ccctctccca gggttcaggt atcatgctgg ctgtcaagta atgtgctgcc atgctaagga    1440
cagtctagtc acaccatatg ttagtgatgg gctttgggag tgcaagcaga agcagccaca   1500
gcacattggc atgtccagac ccgaatgcct ggtgtgcctg ccgaccacac cggtggcgcc    1560
aagttggcaa ccgctccact ccagcaagct ccagcttgcg ccaaccatag aacggcagcc    1620
gctatatgta tataagcaat agctgtgcca acggctgcg tggctggact gctgcactca     1680
ctcacgtggc ccctggcgca gggtggccta atcagggtt ttaaggggtt ttgcaggtt      1740 tggaaagagt gacatgtcag taatgatttg catagcatag ttcagcttat tataactaga   1800
atgattgttt gaaccccttg tgggtgacca tgatgaggtt tgggcacata gcaatgactt   1860
tgcgtgcttc cttgtcacag ccttgagagc acaagcacgt gggaatgaac ggatgcaact   1920
tccaaagccc tgcatacttg caccactgtg gattgccatt tgctcagatg cagctgtata  1980
ctgtgttgtg ctgtgttgca ggcttacaga ttgcacagaa gcaagcctat gccgctcatt   2040 cccttggcc ccacaccggg gcccgtgttg cccaatccag cctgcctgcc ttgctcaccc    2100
atgtgcaaga ctcttccaca ttcatgtatg cacatgttgc ctgacctgtt tgtaatgtaa   2160
ccaccagctg agcgcagtgg tgccagcact gcagggccc catatggctc tgcacatcac   2220
aacaagtgcc cctggcttgc ctcccctctc ccagggttca ggtatcatgc tggctgtcaa   2280
gtaatgtgct gccatgctaa ggacagtcta gtcacaccat atgttagtga tgggctttgg   2340
gagtgcaagc agaagcagcc acagcacatt ggcatgtcca gacccgaatg cctggtgcgc   2400
ctgccgacca caccggtggc gccaagttgg caaccgctcc actccagcaa gctccagctt   2460
gcgccaacca tagaacggca gccgctatat gtatataagc aatagctgtg ccaaacggct    2520
gcgtggctgg actgctgcac tcactcacgt ggcccctggt ggtgagagca acatttatt   2580 ttcttttaca ggctgtcttc cagggcgctg ttaaatgcaa tagataaaga ttggatcatc   2640
gagaaatata cgtcgcttaa atgctcccac cagctggtgt tggttgcctg atcgccgcgg   2700
tctacgcggt cgctcgctca ccagctcgcc gacgaacttc cgcgatcaag gtggcagtca   2760
aagtgtcgaa tagacaacat tctctagtcg aggcatgcag tataaacatc ttaaatgaaa    2820
aaagccttac aagttgcagc tgtcaaacga gtcaaatttc tgcacttcag ttgcctcttt    2880
cgcgctcgtg gctgtttgcc atgtgcacct tcagatttca gcatacatat gtagaaattg    2940
gctccgacga cggagctgga gagaactcga agggctggac caaatgattg tcgctggagc   3000
gtcgttccaa cttcagtatg tcactgctcc cctgcattgg taagtgcaca agcgtgatga   3060
agacagggac acaga                                                    3075
```

<210> SEQ ID NO 94
<211> LENGTH: 3546
<212> TYPE: DNA
<213> ORGANISM: Chlamydomonas reinhardtii

<400> SEQUENCE: 94

```
agggtttgga aagagtgaca tgtcagtaat gatttgcata gcatagttca gcttattata     60
actagaatga ttgtttgaac cccttgtggg tgaccatgat gaggtttggg cacatagcaa    120
tgactttgcg tgcttccttg tcacagcctt gagagcacaa gcacgtggga atgaacggat    180
gcaacttcca aagccctgca tacttgcacc actgtggatt gccatttgct cagatgcagc    240
tgtatactgt gttgtgctgt gttgcaggct tacagattgc acagaagcaa gcctatgccg    300
```

```
ctcattcccc ttggcoccac accggggccc gtgttgccca atccagcctg cctgccttgc    360
tcacccatgt gcaagactct tccacattca tgtatgcaca tgttgcctga cctgtttgta    420
atgtaaccac cagctgagcg cagtggtgcc agcacttgca gggcoccata tggctctgca    480
catcacaaca agtgccoctg gcttgcctcc cctctcocag ggttcaggta tcatgctggc    540
tgtcaagtaa tgtgctgcca tgctaaggac agtctagtca caccatatgt tagtgatggg    600
ctttgggagt gcaagcagaa gcagccacag cacattggca tgtccagacc cgaatgcctg    660
gtgcgcctgc cgaccacacc ggtggcgcca agttggcaac cgctccactc cagcaagctc    720
cagcttgcgc caaccataga acggcagccg ctatatgtat ataagcaata gctgtgccaa    780
acggctgcgt ggctggactg ctgcactcac tcacgtggcc cctggcgcag gtggcctaa     840
atcagggttt taagggattt tgcagggttt ggaaagagtg acatgtcagt aatgatttgc    900
atagcatagt tcagcttatt ataactagaa tgattgtttg aaccccttgt gggtgaccat    960
gatgaggttt gggcacatag caatgacttt gcgtgcttcc ttgtcacagc cttgagagca    1020
caagcacgtg ggaatgaacg gatgcaactt ccaaagccct gcatacttgc accactgtgg    1080
attgccattt gctcagatgc agctgtatac tgtgttgtgc tgtgttgcag cttacagat     1140
tgcacagaag caagcctatg ccgctcattc cccttggccc cacaccgggg cccgtgttgc    1200
ccaatccagc ctgcctgcct tgctcaccca tgtgcaagac tcttccacat tcatgtatgc    1260
acatgttgcc tgacctgttt gtaatgtaac caccagctga gcgcagtggt gccagcactt    1320
gcagggcccc atatggctct gcacatcaca acaagtgccc ctggcttgcc tcccctctcc    1380
cagggttcag gtatcatgct ggctgtcaag taatgtgctg ccatgctaag gacagtctag    1440
tcacaccata tgttagtgat gggctttggg agtgcaagca gaagcagcca cagcacattg    1500
gcatgtccag acccgaatgc ctggtgcgcc tgccgaccac accggtggcg ccaagttggc    1560
aaccgctcca ctccagcaag ctccagcttg cgccaaccat agaacggcag ccgctatatg    1620
tatataagca atagctgtgc caaacggctg cgtggctgga ctgctgcact cactcacgtg    1680
gcccctggcg cagggtggcc taaatcaggg tttttaaggg ttttgcaggg tttggaaaga    1740
gtgacatgtc agtaatgatt tgcatagcat agttcagctt attataacta gaatgattgt    1800
ttgaacccct tgtgggtgac catgatgagg tttgggcaca tagcaatgac tttgcgtgct    1860
tccttgtcac agccttgaga gcacaagcac gtgggaatga acggatgcaa cttccaaagc    1920
cctgcatact tgcaccactg tggattgcca tttgctcaga tgcagctgta tactgtgttg    1980
tgctgtgttg caggcttaca gattgcacag aagcaagcct atgccgctca ttccccttgg    2040
ccccacaccg gggcccgtgt tgcccaatcc agcctgcctg ccttgctcac ccatgtgcaa    2100
gactcttcca cattcatgta tgcacatgtt gcctgacctg tttgtaatgt aaccaccagc    2160
tgagcgcagt ggtgccagca cttgcagggc ccatatggc tctgcacatc acaacaagtg    2220
cccctggctt gcctcccctc tcccagggtt caggtatcat gctggctgtc aagtaatgtg    2280
ctgccatgct aaggacagtc tagtcacacc atatgttagt gatgggcttt gggagtgcaa    2340
gcagaagcag ccacagcaca ttggcatgtc cagacccgaa tgcctggtgc gctgccgacc    2400
acaccggtgg cgccaagttg gcaaccgctc cactccagca agctccagct tgcgccaacc    2460
atagaacggc agccgctata tgtatataag caatagctgt gccaaacggc tgcgtggctg    2520
gactgctgca ctcactcacg tggcccctgg cgcagggtgg cctaaatcag ggttttaagg    2580
ggttttgcag ggtttggaaa gagtgacatg tcagtaatga tttgcatagc atagttcagc    2640
```

```
ttattataac tagaatgatt gtttgaaccc cttgtgggtg accatgatga ggtttgggca      2700
catagcaatg actttgcgtg cttccttgtc acagccttga gagcacaagc acgtgggaat      2760
gaacggatgc aacttccaaa gccctgcata cttgcaccac tgtggattgc catttgctca      2820
gatgcagctg tatactgtgt tgtgctgtgt tgcaggctta cagattgcac agaagcaagc      2880
ctatgccgct cattcccctt ggccccacac cggggcccgt gttgcccaat ccagcctgcc      2940
tgccttgctc acccatgtgc aagactcttc cacattcatg tatgcacatg ttgcctgacc      3000
tgtttgtaat gtaaccacca gctgagcgca gtggtgccag cacttgcagg gccccatatg      3060
gctctgcaca tcacaacaag tgcccctggc ttgcctcccc tctcccaggg ttcaggtatc      3120
atgctggctg tcaagtaatg tgctgccatg ctaaggacag tctagtcaca ccatatgtta      3180
gtgatgggct ttgggagtgc aagcagaagc agccacagca cattggcatg tccagacccg      3240
aatgcctggt gcgcctgccg accacaccgg tggcgccaag ttggcaaccg ctccactcca      3300
gcaagctcca gcttgcgcca accatagaac ggcagccgct atatgtatat aagcaatagc      3360
tgtgccaaac ggctgcgtgg ctggactgct gcactcactc acgtggcccc tggcgcaggg      3420
tggcctaaat caaggtttta aggggttttg cagggtttgg aaagagtgac atgtcagtaa      3480
tgatttgcat agcatagttc agcttattat aactagaatg attgtttgaa ccccttgtgg      3540
gtgacc                                                                3546

<210> SEQ ID NO 95
<211> LENGTH: 100
<212> TYPE: DNA
<213> ORGANISM: Chlamydomonas reinhardtii

<400> SEQUENCE: 95
tgttttaaca cgttatgttc ggttatggtg gtaaactatg ggattcgtat tttcccagat       60
gaagctgtta ctatgcgtcc tgctggtact cgttcgggta                            100

<210> SEQ ID NO 96
<211> LENGTH: 3338
<212> TYPE: DNA
<213> ORGANISM: Chlamydomonas reinhardtii

<400> SEQUENCE: 96
atgtgctcag aaaggcgtct gaagctgcag tttcggaatt gtggacaagt tgttccgatg       60
accccagagg ttctatggct taatgcacac cctcctctgg agggtctgat tatggcgctt      120
aatgagatgc tgtcacaggt tcgaatcccg tcaagaacag tttttttttgc cagatcacag     180 cgaagaagta gataagatca gggcgccgcg aaatttacaa acaaggccac gccggtacaa      240
aaaacatgaa tgtgacaagg cacggcgtga tgcaacatca acaaaataca ccaaaaacac      300
aggaattcag gctaccaggt gtatctatac accatgcttg tcggttttca agctcgaaca      360
tcgcgacgga catattgaac atgtaattct gagcgtgcat tgttcggaac acacacaacg      420
agctcgggag cgcgaaatgg cgagccaagc atgtcgagac cccgactgat tttcacaccg      480
cgtcactcaa gtccctagtt gttcgtaaga atatgcatgc tgaacgcgca ttgcgcacag      540
tgcataatac aagctcaaga gcgcgacatc gcgagccgag catattgaga ccctcctcca      600
tttccgagcg atttgcgtcc ccgaagtctt ctaactatgc atattaagcg tgtattccga      660
gctacgttgc gaatagaatc caagcggtaa atgccaaaaa caaatcccgc gatccatctg      720
tcggtcgact gttcatcgac caccaacctc tgtgcgaaca accagctggc taacaataac      780
ctcctcaaag tgcaagggat taaccacgcc acacatcaac ctgttgtaaa cacacaacaa      840
```

```
tccaacgcac gacaagcaag cagataaaca ataccccggc ttcacgcaga gacaggacag    900
gtagaaacta aacccgaacg tagctcagtg acatacgtcc agccagcgaa gccaagcatg    960
atggtcacca caccaaacac caacaagaaa gtcactgctg taaattgcag tcagcactca   1020
ccacccacaa ggtactccac gcttccaggt catctgtcag tacacctcgc gcatgttaaa   1080
aacactactg catgcattga aagccttggt tatgaggcag ccatgctggc ctgaatgcgc   1140
acaatcatac ctggcactgc tactgctgtg ctctgcgaga gcctcaatag ccgctgccat   1200
tccgcggcta gatctgcctc gggcgttagc atggtacgca gcgcctttt aagccggcgc    1260 tcttcggccc gcgaggccca cagcggacgc actaaatgta aggcatgcaa cccacgaaac   1320
ctggtgagca ttacgtaaat tgaagcccgc cgccaactgc cgtgctgcgg tttgcacata   1380
tccaccagcc acagttcgtg cgctggcaga gtttgcccct gcgcaaagta atcggtgact   1440
gcatacgcaa gctccacacg aaagcccag cgcatcacag gcaaccgcag ggttgcatgc    1500
tgcgatgtga acatagcact gcacggtaaa acaggaatct ccccgacatc cagggcctga   1560
tcgacagaca cccgacccgc atcaggcccg tcggggcgca ccattacagc cgagggcacg   1620
aacttgagga catgcacggg ggcaatgctt gcatctggca atggtgactc gttgggatgc   1680
agaacaatgc cggtgcctgt ggcactgttg ttgttgatgt gatacagacg cacatgctca   1740
tttgatgtaa acacgtaacg aatgccagca aagaatgcgc acacagcggg cacaccgcta   1800
tcatcctcgg ccccgccaag cgcctctaat tgatgcacat gcgaaatagg taagctgctc   1860
ccgtccggcg acaagtccgc gctacgccat agcagcagct gctgacgctg cgcgagcgca   1920
tgcagctgca cgagctgcaa tgccagtgga acccgcacaa catggcgctg acaactgca    1980 aagggctggg gcacgggtc aatccctggc ttcggggct gccaaacacg cgcgttgagc     2040
tgctggcacg ctgtatccag atctgcctga gagatttcct gcacgccacc aaacttctcc   2100
gctagcatga agagaggttc gttgttgtca cctacgcctg cttgctgccg atgctggtga   2160
gtgagaacga acgcgaacgg caccatattc cacagctccc gccccatgag gttcatgctg   2220
ccctccggat gctccagctg ccggatctgg cgctccatgg ccccgccgtc ccccgcgccc   2280
ggcgccagca gctgccgcaa gctctcttcc gcagcaccgc tatatagcgg cacgtgccgt   2340
ggctgtggca actgacgcaa gtcgccaaca agcaggccat gcagatctga cagcggcccg   2400
tgatataggt gcgtgctgtc tatacccacg tgcctccgtg ccgcgtgcac atgcatgcaa   2460
atgcgcgccc agtgggacag cccacacgtg ctaaactcat ctaggaaaat gaagcgcaca   2520
ccattgaggt tgcgctcgac tcgatcgcgg tgaggcggac caaaggtgcc agcagtcgca   2580
aagaaggacg tggtgctggt gccgagcacg cctggcgtag agtcctgtaa atggaccgtg   2640
atggcagcgc ccgaagtcaa cagcatgatc atgtaaggct ccctggctgc taaaccagtc   2700
caccaccgcc acacttcacc tccgaactga acccctcttg caccacacac cccacacacc   2760
ccacacacaa ctcacatgca gcgcagcgcg ccacgtgtag ctcacgaggg caatgagaga   2820
ctcgcagcgg tgctgatatg caaaccacag caatgcctgc agcacccgcg acttgccgct   2880
gccggctttg cccgtgagca ccgagcacac gggggctga cggacgccgg ccgcctctgc    2940
tagcaggagc tgcgcgtaca gcatgaacgc ctgctgctgg tcatcgctga ggttccataa   3000
ccgcgctgtg tcttcaggcg tcggctgcga gtcctccggg caaagcacgt acggcggctc   3060
tgcaccaggg ttcgctgcat cgggccagac gccctgcacc tctggggcgg ctgtggtaac   3120
cgccaatggc gagatgagca ccagcttcgc tgtcactgct gcagtgccgc tgttgtaaag   3180
```

| | |
|---|---:|
| cagcagctgc tgctgcactg ctccctgcgc ctgcgcgagt gcctgtgcgg cgtactgccc | 3240 |
| gcctaggtcg taatcatgca tgcgttgctg tgctgcagcc agccgctcgt gtgtccactc | 3300 |
| ctgcgtgctg cgcactactg ctgccgccgc tgtacgcc | 3338 |

<210> SEQ ID NO 97
<211> LENGTH: 2874
<212> TYPE: DNA
<213> ORGANISM: Chlamydomonas reinhardtii

<400> SEQUENCE: 97

| | |
|---|---:|
| ccgcctaaca acgcgcacaa gctccccagc agcagcagag gagccgcctg cagcaccagc | 60 |
| agcgcctgcg ctccaaatgc ccctcgctcc tgccgggtgt ccttccgcgc acctgcatgt | 120 |
| acacgcagtt ggcatgtatc cgcatcacac cctctggcaa ccacagctcc ctgtgaccgc | 180 |
| cactactggc gccccgcgcg taactgtctc atccgctttg cgcacccaac tacccatgcc | 240 |
| gccgacgatg ctactccacc gcaacaacac acctggcgcc cacccacccc caccctgcgc | 300 |
| tcaccatgct gccaagtcat gtacgccaaa tgaccacacc gctccaccgc gaagaaatgc | 360 |
| cgccaccctc ggaggccatg agaccaccga agctctccac tcgcttcgcc gccggagacc | 420 |
| ggcagaccgt ccaagcgcaa agcacgccac tgagcctgcc cggcgccat ccagccgctc | 480 |
| gccaacagca cagccgccgc ggctgccgct gccatgagta cgctaagcgc aacgatgacg | 540 |
| acagcatcgc gcagcctgac aggcgcgcc ctgcacaaca gccacacccg gataaattga | 600 |
| aggcacaatt ctgctctgcg ccccaaacct ccgctgcacg gcatgccatg cttaccatcg | 660 |
| ccatgattgc gcacgcttgc gtgcctccaa gcgcactgca cgtcgcagtt cctcgtagtt | 720 |
| gcctcgaagc gacattgctg agcttcacgc tatgctaccg tgcgtgtcca ctagcactcc | 780 |
| catagtccac gtatatattt actacatcga cgagcggctc gcatttcccg cggggtgacg | 840 |
| cgcccgatgg gtcgaacgca aatccgcgat ccaccgtgcc gtgcggctcg ttctagtggc | 900 |
| ttgtgctgtc caccctacat gcatacgtga atgcgcatga gcgcataata gcccggccga | 960 |
| attcaagcta cacgcgcgga gtccatctta tcccgcattt ccgcttccat ggctatttac | 1020 |
| agtttcgttg cacaacttgc tacgttgagt acctgctcgc ctgcaccect tcctgccttg | 1080 |
| cacgtgcatg gcgaagccac cgtccaatgc gcaacaagga cccggacctt gtctcggcgc | 1140 |
| tttcggccac tcccattcgc gcgccttgca actggcgccg ctgcaacgct gaggcataca | 1200 |
| tcttttccgt gcacagcacg cgttcgtgcg gccccttctc acgcgacctg cactccaaca | 1260 |
| tccccacttc cggtactgct ctgcacaccc acacccgcgg cgcctgcaaa catgcagctg | 1320 |
| ctcctgctgc tgctagcggc gttttgccgct ctcgtcagcg cgcgctacgc ccacgctgac | 1380 |
| gggtgagcgt ctaccgccac tgtcgcgcaa cccaccgctg tttgcggcat aaccgtgctt | 1440 |
| acgtttcctc cgttgccgtt tgcaggtcct gcccgcccgc tgcggtggtc cactacgccc | 1500 |
| atcctgctgt caggtatgca ccgcttcatg gtctcagctc gtcccaccgg caatacgcga | 1560 |
| gcacctctgt acacgacttg agcacaacgc tgctgcctgt tcacctctca cctatcacgc | 1620 |
| tcggcacccc aacagcaccc ccggcgcatc ggcgcccacg cccacccect ttcacggcat | 1680 |
| gcaagttccc cagcggccac caacatgccc agcccgaacg tcacagatac cgccgtcctt | 1740 |
| accgcgcttc ccctcatgca ttcacctgcg taccacacc cactcgactc cgacgcagct | 1800 |
| gggcggccgg tgcatctacc caccccagct tcaccgccca cacctggtga gccagtgtgc | 1860 |
| agttgtgcgt gttagctccc gacccacacg cagccgcatc aagcatgcca cgctgccacc | 1920 |
| cccagctcgt gttagcacta aatgctccac ccttcccttc ctccgtgcaa ggtccgcgct | 1980 |

```
ggcacccact cccgcctact acaccatttc cacgaacagg tatgcacgct gcgccagctc    2040
gctgcccctg tcataccccc cacgctttca gcgctggccc ttggattccg tccacgatgt    2100
cgccgcgcct gcacgcaggt gcacttcact ggactgcatc aacgccaccg tccccaccaa    2160
catcaatgac aggcgagttg ccctgacctc aacacgcccg cccatcaaac ccacacatcc    2220
gtgtttccgc gcttgtcttg cacctccggt tatcctactg tgcctcgct gctgctacgc     2280 ctatgctcct ctcgcacgcc aaccaaccta gcctccctgc gcgtccctgc ccatgcttca    2340
cgcccacctc cacagcaccg cgctcgtcaa gcccacgtac gctgcttaca ccaacatcat    2400
caccatgacg ggccgcggca agcctggcgg tgagtcgttc ctatagctgc caggagcaag    2460
acatcacaca gccgcgtgct ttccttgcgt gtgtgtgtat gtgtgtgtgt atgtgtgtgt    2520
tgctctgaca gccgcgctgc agcacctctt cttgccggta ccattctga cttctgctgc     2580 gttcatccct gcatacaggc tccgccacgc ctgtggcccc tacctccagc acgccaccca    2640
gcaagcccac cggatgtcg cttgcagctg cgctcgagaa gcgcatgcag tccacatctc     2700
agcgctctac ccgtgtcacc cacgcccacc tgcccagcac tgcgggcgag cacagccttt    2760
caggatgggt ggtcaccgtg ctggcaggcg ccgccaacgc cgcgcacccct gcaattcacg    2820 ccgtgggcgt ccagtctgac cgagtccata tcttaggtga tgacggcacc atcc          2874

<210> SEQ ID NO 98
<211> LENGTH: 474
<212> TYPE: DNA
<213> ORGANISM: Chlamydomonas reinhardtii

<400> SEQUENCE: 98
gtggtctacc ctgtgcgcgc ccccgcccgg ccgccacgtg cgcaggtggc tttgtcgtac      60
ggcctgacgg gcagccgcat cagcagcggc gtggcgctgt accgcaactg caccataatt     120 tttttaaaaat actttttttaa tacctgtaga attgtcacct ttagagccat ccatatgagc    180
cgaagtcata ttattttttg tgttgccgaa ccacaatccc gctcaagtgc ttaccatgag     240
cggcatggac actgcgtgtt tcggcgtgcg tcgggtcagc tgcggtgcgg gtgttcggcc     300
actggcatac gccaacgcgc gtcggaccca tacatgatgc ttttgcagta tgcggtgttt     360
tggtagcctc ctaagccact ctggtgccgt ccgccttttt cgcctgatcg ccccaagtcc     420
ggtgccctgc cgccgtgccg tgcttgtact gcaggcggcg ttggcgtcct gggg           474

<210> SEQ ID NO 99
<211> LENGTH: 3029
<212> TYPE: DNA
<213> ORGANISM: Chlamydomonas reinhardtii

<400> SEQUENCE: 99
gcagctagtt tggtccccga atgggggtgc ttatgctcct gtgctcccaa atggaatcta      60
gtaacgcggc taacctggct gggtccgcat tctgcatgac ggcctgcatt ccgcctgtaa     120
aatcgatctc gctacccaaa cgcaactggt cgtaggccgt acaccgcatg agcacatgat    180
tctcatcttc gacttcattt gcaacacata gcgggcaaat cctctcctcc ctaggtcgtc     240
cataggcgcg gttggcagta agcggccagc agcataggcg gaacctcatc aaggccttgt    300
ggtgcgcaac tggtataaat gctctactgt gcccttgcat ggtcagtggt gccgctcctt     360
ccgcacacag cccatccaa tgcttgtact tgctcatctg cacgcctggt tgcttgttgt      420
ctgatgggaa agtgcttggc tcagactgca gccgctcgtg cttccacgcc ttcattagac    480
```

```
tctctcgaaa ggcggatact atttgccctt caggcagcgg gctacctgct cggctctcct       540 cccttttccgg cctgatcatg tgcatacggc cttgccatac gtctacgcca tgcgctgaga       600
taaaacggaa aagccgtgca caccacccat ctccctctgg gtgtactaac gcgtcttgta       660
cttcatcaat tagtgcatcg tgagctaggc tatccttctg cacggcaatc ctgttgtaga       720
atccaatgca aagcttggcg aaaaagaaat ggagtggtag ttgtgctaat tcagcaaaca       780
gcaggcgatg cgatggtcgc ttcgtaccca ctgtcatcct catgtactgc acttgtaatt       840
tgacggcctc gtctttcagg catgcttcaa acggtccgtg cgccaggtta ttgctgtcac       900
gccgccgcgg tggtgggccg ccgtccagca tttccgctaa tacgtcgggt ccccacactt       960
cacaaccata tgctaggatg gagcgaactt gcacctcaaa acaacgcatg cgtatgtcgg      1020
gggagaaaat cctcaaacgg tttaatctat tagtaagcgc gtacatagca cgccgcgcag      1080
cctcacatag cgtctctctg caggcggcaa aagcacgtcc agggccgtag actagtccca      1140
gataccgtgc cttgtccacc gcagggatgg gctgccctgc cagccgcagc ccactgcact      1200
catcgttcaa tctacgacgc tcctggtcgt ctgaagtgaa caccagacgt tcacactttg      1260
cgacgtttgc tttcatacca aatgcttcgc agaaagtatc cacaagtgac aacaggtgcc      1320
gcatacgctc aggggtggtg gctagcagcg aaacatcgtc agcgtacatt aggagcgaca      1380
gcttcttacc gtttaactca ggggtgcccg ctgtgcttgc agtgtccaac cagtcctcgt      1440
gcgcatcaat atactctgcc aaagtttcaa taaagagccc gaacagctct gtgctcagtg      1500
ggcacccttg cttgactcct tgcgttgcct caaaagcagc gctcagtttg ccatcggctt      1560
taaccgtcat catgaccttt tcatatgcgg cttgtatggc ctccaacagc cgccctgaca      1620 cgccttttc ccgcagccgt agccacaaga ggggcgcgg ccttgtca aacgccttct       1680 caaaatcaat ctgtacaaca atcattggtg gtgctcctgc acgtgtgtgc tttgtcacca      1740
ggtgcctcag gacaaacaga tggtgggcag taccgtattt ccgcctgaaa ccagcctgag      1800
ctgggtgcct ccacttgaac aactcgcctg ctcgtgctag cctgttcaga aggatagatg      1860
cataacactt agccaacgct ccgcctactg caatgcccct gtagttgccg ggcgtcttca      1920 catcgcccctt tctcttgtaa attggcgtca gcactgtggt tgtgaactgt tccggaaaac      1980
tttcatctcc gtcttgcgcc cgccagatgc ggttaaacaa cacttctaga acaggtgcta      2040
cccggttcac cggcgggatg gggggtctg ccctggggtc tccctgcgtc tttgcgtact       2100
tgtagcattc cgatggcgcg gcttccgtgc ctggggcctt gccattcggt agcctctcta      2160
aagcatgagt cacttcgtct atcgagatat cgctgttcaa tatgctatct aactcagccc      2220
attcctcgtc atcatacatc gaatctcgcc agccatcttc gtcacagcag tacgccagta      2280
aacgctttgc agcgctgtcg tcaactgttc ctgccccatc attcagtagc cgtgcaaagt      2340
gatcacggaa gccatctgcc gtgatggggg atttgctcgt gcaccgctcc tcaatcatct      2400
tccacagtgc tttagcgtcg gctctgcacc gtgctaccct atcccgcatc acttgcgcat      2460
catgggcggc tctagccctg cgttttgcgc ggcagtacac tgatctcgcg gcccgcatcg      2520
cttcccacct ttctccttcc ttcacaactg gtttgccaag cgctactttc gcctggacga      2580
gcgcggcacg cgccaccgca cattcctcat tccaccacgg ggtctcggtc tctcgcagat      2640
gagcaggcct gctctgccca aacgccttct ccaatactcc acttaggcac ttgctcaacg      2700
cttcgaccgc ctcggtagtg ctgtaccgcc cttgctccaa gtggcctttt agctctgtta      2760
atttgcttac tactgcgac tcatcttgat cgaaaagatt gctatagcgc tcactcttct       2820
gcgcattgaa tgcagtgcgt ggacgctttg ccttcgcctg gccttcagta cttgcttgac      2880
```

```
cctccacctc ccagctcaaa gtcagcgtaa caggcctgtg atcactcgca taaccggcgc    2940
ccctgcgcgc ccatctcagc agctcaccca cgtctactga cgtcaccgat tggaataaag    3000
ttggcgatgc aatgcataag tcaatgacg                                      3029
```

<210> SEQ ID NO 100
<211> LENGTH: 703
<212> TYPE: DNA
<213> ORGANISM: Chlamydomonas reinhardtii

<400> SEQUENCE: 100

```
atgctaaata cctaggatcc cctgccagtt tccgcccacg cgcacgctgg gccgccaagc     60
tatctacaac agggtcggca agtgtggcgc aacggcgttc atttggtgat acagcgcgac    120
ctagcgcatg ccgtttgctg caatcgcttc catgtcgcgg cgtctatatg tgatcatttg    180
gccagggcgc gcgcgcgact gcggcgtatg aacgacgcga gtaactgcgc ttccctgaca    240
gctgcaaaaa tttgcgcagc gatagaacac agcgcgatgt actcgcggca caaatatttt    300
catattaacg cacatctata gcaaaatgtg aatgtcgctc caagcgtcgc aagccagcga    360
cgcaaatttg cttcctcgcg attctttagc ggcgctgtat tcatggatac cagtgctgct    420
ataataataa taataataat aataataata ataataataa taataataat aataataata    480
ataataataa taataataat aataataata tctacgcagg gcacaagtgc ccgcgtgtct    540
taaggaggag tgagacaagc tcaccccacc gtgtaagacc gacgaccctc accctggttt    600
ccgagggtgg ggcccactgg tggcgccacc ctgggtgcgg cctccctggc ttccagagcg    660
tcggcgggca tgggcaatgc ccatttcctg ctcaagttta tag                      703
```

<210> SEQ ID NO 101
<211> LENGTH: 2706
<212> TYPE: DNA
<213> ORGANISM: Chlamydomonas reinhardtii

<400> SEQUENCE: 101

```
aacacacata caaaactttt gtggtttacg ctttactgcg ctacccagac atcttttaaa     60
agcaagcgag aggaatgagc gctaagaagg agcccaccat gcaggaggcg gctgccgcct    120
ggcgtgagcg ctcctgggcc tctggcactg ccgattggca tgctgttaag aagaggaaac    180
cctcagactt gaacgggacc attgaggaac tgtttgtgag acagagctat gccgatgccg    240
cgctgaggga agtgttcgca ttagtgaagg actatcctga attaaagaag aagatggctg    300
actttgaggt taagcagacg ctgctggagg agaggctcgc gtcctcgcag caagcatcca    360
ctccgctgca gaagtctgtg cgagttcggg atttcgcacc tcctcgaccc caagcccgtt    420
tgtggcaact acgcagcgag caaggcagcg aaacaaagcg caatagcttc cagacttggt    480
aagctaatgg ttaattatgg acaagtatag tgcgcgccat gtttaagtaa acgcgggtcc    540
agtaacgcct cgctacggcc tctcgccgca cttaagctca ccagctcgaa ccgaccccca    600
catccggagc ccccattccg accccataag cgcacctccg aacccgcccg ccccactttc    660
cacaatctat atgcatatat gcatatggcc cagaaggcgc agggccatcc aaaagccctt    720
gaccgaactt cgccttgtcc attgtcgcat gttgccccca cacacgcacc ctgcccacgc    780 caccccgcatc caacagaaat caaacgtagc gctttcacca tagcaagagc ccgggcgcta    840
ggacactcca aggtgtgttc gcatgtgggg gcacaacgcg agacaagggg ctttggccgt    900
ccaaccaagc ccagctagtc accaggtcac ctaagcttca cagggtacag acctgcatgc    960
```

```
caagcggacg cgcaaggaca tagattccgg ggctctgccg tactcctaag cggacggggg      1020
tgcgggcaaa acctcgccag gcctcgcctg atattagggc ttggcgctgt ggaaagcggg      1080
gctcaaattg gagaggttga catcaagttt gggggcgaaa cgtgcggctg gcaggggcg       1140 ccgatgaggg tctcggccga actcgcacag acttctgcag cggagtgaag gggacgacag      1200
cctgacggga tttgaactcg ggttcgacac gtgcaggccg gatccatgga gcccaacccc      1260
agcacgccca gcaccggcac gaaacccaag ggcaacccca agcctccccg aggccgtggc      1320
ggtgcgggag tctgagcgcc gccgtgtctg ctgtctaatg gctcgcaact gtgcgctgca      1380
agcccaggct acaatcaaga acaagaagac tagtgagctt agcgcgcact aatctgcagc      1440
tgcaggccgt gccctgaagg agcgcgtgga ggcaacgcat cctcctggcc actggcggcc      1500
agcagcgagt tgtactgcag ggctgcactg aagaggacga ccattgaggc ggccaggttg      1560
acagtgcgtg gcgaggatga gggcaaatg aagcggtttt tgaggaggtg atgattgcca       1620
caacacatga tggaatcgac ggatggcagc agtgtgggga ggggcggatg cggggtgcga      1680
ggggaaaggg aggtggtggg cgcgggacca agctgggttc aggaggcacg ccgtgcctgt      1740
gcaagccgaa gcttctcacc ggcacgattt tcgcaggtgc ctgagagccc aatacaccta      1800
tgatatagct aaacccagcg cgctcagcag cgggttacgg cgacgctcca ggtgcgagcg      1860
cggagagggc agattcgaaa tgccgctgat gccgactcct cgtaggacgc tcctgagccc      1920
ggccgctgtg ctccgtcgcg ttcactttga ccttctgtat gtcgtgaggc cgcggggagg      1980
ccaagcgcag ccctaactgc gaagctgcgc ctcccttcac tccgctgcag aagtctgtgc      2040
gagttcggga tttcgcacct cctcgacccc aagcccgttt gtggcaacta cgcagcgagc      2100
aaggcagcga aacaaagcgc aatagcttcc agacttggta agctaatggt taattatgga      2160
caagtatagt gcgcgccatg tttaagtaaa cgcgggtcca gtaacgcctc gctacggcct      2220
ctcgccgcac ttaagctcac cagctcgaac cgaccccac atccggagcc cccattccga       2280
ccccataagc gcacctccga acccgcccgc cccactttcc acaatctata tgcatatatg      2340
catatggccc agaaggcgca gggccatcca aaagcccttg accgaacttc gccttgtcca      2400
ttgtcgcatt tgcccccac acacgcaccc tgcccacgcc acccgcatcc aacagaaatc       2460
aaacgtagcg ctttcaccat agcaagagcc cgggcgctag gacactccaa ggtgtgttcg      2520
catgtggggg cacaacgcga gacaaggggc tttggccgtc caaccaagcc cagctagtca      2580
ccaggtcacc taagcttcac agggtacaga cctgcatgcc aagcggacgc gcaaggacat      2640
agattccggg gctctgccgt actcctaagc ggacgggggt gcgggcaaaa cctcgccagg      2700
cctcgc                                                                2706

<210> SEQ ID NO 102
<211> LENGTH: 150
<212> TYPE: DNA
<213> ORGANISM: Chlamydomonas reinhardtii

<400> SEQUENCE: 102
ggccgtattg gcgccgtttc tagtactaga ctaccattta caagaatagg aggtgtacat        60
tttaccttaa ctattaaagg agtgcctgtc ggcacccact tgcggtgttc ggtttcaccg       120
agcacccaag gtctagctac gatttgctac                                       150

<210> SEQ ID NO 103
<211> LENGTH: 46
<212> TYPE: DNA
<213> ORGANISM: Chlamydomonas reinhardtii
```

<400> SEQUENCE: 103

```
agctaaaatg tcactacacg ttctaggttt agaattactt aggata                    46
```

<210> SEQ ID NO 104
<211> LENGTH: 309
<212> TYPE: DNA
<213> ORGANISM: Chlamydomonas reinhardtii

<400> SEQUENCE: 104

```
aaactcgttg aaaaactggg tagcagcgca gtgtgaggag ctcgcgtgca tgcggactag     60
tgtgactcgt aacgacgtca cacgggcgtg tgacagcact gatattgtcc atcaactgtt    120
ttaaaattat cattttggaa taagtttatt aaaaatttta cgggttaatt ttgtgcgacg    180
aattaaaaca ttccctgcca ccgtacatca cctgcaacga actcacacac caccgccccc    240
actgccctcc acccgccctg ccctgcccgc agctgcgctc cggtgacatg caccgcgtgc    300
tgtccgccc                                                            309
```

<210> SEQ ID NO 105
<211> LENGTH: 114
<212> TYPE: DNA
<213> ORGANISM: Chlamydomonas reinhardtii

<400> SEQUENCE: 105

```
ccgagtgagt gactggatgg tgtgcttcgg agcatgtaaa cattctatat ttatatactg     60
cgataaattt atttgctgcg ctagtgacta gcttgcaaca ggtggcggga gggg          114
```

<210> SEQ ID NO 106
<211> LENGTH: 1352
<212> TYPE: DNA
<213> ORGANISM: Chlamydomonas reinhardtii

<400> SEQUENCE: 106

```
tggctggctt ggggcgccag gctctactga ccgttactgg ctggcctgag cgcgggtgca     60
cgccacacac gtacacgtcg ttatgcaaaa ggcgtgagac gcagctcgac actgcccggg    120
ccatggatgc aggacgaatc taggacagcc tgtggccctc ctcgtttatg gagttcagtc    180
gtttcacgcc gcccctcgcc gcagggctcc gctgctcaac gctcagcaca cgcgcctgct    240
catttcagat gcgggtgctg ttgtggtgga cagcgccctc caacgcccag taaggccggt    300
gtgcatccgt cgttgtgagt ttggcccgcc gggcactcca gggcgctcgg tgcccgcttt    360
taatagaagc ttgaatttat aaattaaaat attttttacaa tattttacgg cggtggcgac    420
gccacgaaac acctggtgta tggtccatac acacgacctt gccctgcaaa tcctctggag    480
gtttggtgag gcgaataatc gtgcacataa ttgtcttagt acatctcata gcccataact    540
ctggctcctt ggcgccgaag aacagttgtc tttcgcatag agctcctttt acgcgcaacc    600
ctaaacgtac tttgagttgt gtcaccatat acatcaaccg caataaacag aatgttgagg    660
cttgtcgccg cagtatttcc tcatgccgac cgccttgcgc ctctttgagc attatggcgc    720
gtggtgcctt gaagctgtaa attgtcaagt gtcatacaaa gaatgaagaa gggaaatgca    780
gggggaaagc agctgcgggt gctgtcgctg ctcccaggcg cctctgacat tgtgcgtgcc    840
cttgacgcgg tcaagctgtt ggtgggccga acgcacgagg tgagcggcgt aagctcacta    900
ccgagcaatc taccacaggg aatgggtcaa ggtgacctcc ggatgcgcaa cggctctgcg    960
ggtgtatgca cgcgggcaaa accctggacg atcgtacagt gtgccgccgc ttcatgttgc   1020
```

| | |
|---|---|
| ctgacccgcc gccgccaccg tcccgcaaca acgctaaccc gggccttacg cagtgcgact | 1080 |
| ggcccgagct ccagtcctta ccagcctgta cgtccaataa actaggagac atgccgcctg | 1140 |
| cggaagttga ccaagcaatg gtgggtgatt ggcttgacag cgccctagcc actgtagccc | 1200 |
| gtgcgtcacg gtactggtgt gcgacgcggg ttgctgaaca ttccagggag cagggccga | 1260 |
| gcggaagtcg gcacgtgaac gacagcccca tgacacgcct cactcatgaa aggaggctgg | 1320 |
| gcaaacacca attaccaaa tgtcacgtta ag | 1352 |

<210> SEQ ID NO 107
<211> LENGTH: 47
<212> TYPE: DNA
<213> ORGANISM: Chlamydomonas reinhardtii

<400> SEQUENCE: 107

| | |
|---|---|
| cttttttctc tctcactttc aggtagtaac ttgtgagtgt gttcttc | 47 |

<210> SEQ ID NO 108
<211> LENGTH: 2599
<212> TYPE: DNA
<213> ORGANISM: Chlamydomonas reinhardtii

<400> SEQUENCE: 108

| | |
|---|---|
| tgccagtact gggtgtgtcg catgtatgaa gtgcctgata gcagcagagt ccagacaacc | 60 |
| acgcacgccg cagcgcccac gggtgccacc acattaatcc gcggcggcac cagggggggc | 120 |
| gggtgggttg tcaccgtccc ggcagaggga cgatccgaaa tacagtacag aagcacaacg | 180 |
| gcagataagg cgccgtgtgc tcctgacgcg tacaagaccc agctcggttc ggccccatgc | 240 |
| acaggcacgt acccgagcgt cctgcgccgt gcgtgactct aacgcaacac ggcagttacg | 300 |
| tcgcaataac tagacttatc tccactgcgc tgcgataagt cagcgcttat tgactcctta | 360 |
| ctgccgtgta gcgttacaaa ccgccacggc cccaaacgac aatcccaatc tctcaaaccg | 420 |
| acaatagcct ccactcatgc ctcaagcggc ctagcaactc attcgtggcc ctcagcggcc | 480 |
| tcctacctcc ggcctcgcag ctcccgataa ccccaccaag tccgccgtgc ccgccccagc | 540 |
| ccgcccgtgt tgaggttgca ctagtggccg aaagtgctgc cagagtttgg tagtagtcct | 600 |
| caacgccggg aggtcatggt gcgggcgacg gcagccctgg tggctgggct tgattggctt | 660 |
| cgcgtatgca gctcttctcg caaagcgctt ggcccaacgg ccggtcatgc aaaccaaggt | 720 |
| gcggtcggcg gtgatggcgg tggcgttcgt gcccttgcgc taccgaaatc atgtgtctcg | 780 |
| aacaccgcgg agcgctccgc ccatcgccta gcttgcgcac gaacgtacgg tcctagttgc | 840 |
| acactcaaca gcggtcaata gaacgagctt cgtgcttggg gatattggct gcacgagcag | 900 |
| caccatcacg cggggatgag cgccgccgga ggcgccgccg gcacctgctg caggcgcagg | 960 |
| gcgacgccaa cgcggggcct gacagcgcca cactccgtcg gtcatgggcg gccaatggtc | 1020 |
| actaccagaa gacaagcagc aataggaaca cgactggctt tgcaagggcc atgataccag | 1080 |
| actcacaaac gtatcaggtg caccaatggc cacgacagaa acacacatgc gttatcccgc | 1140 |
| gtgcgccagc catgcagacg acgccggggc gttacaggga aacacatgca tccttgttca | 1200 |
| ggtgtgtggc ttgtgggcag ctgtggccgt ccgtgtgccc aggaaaggta acagtgcgtg | 1260 |
| ttggcacgtg ttggcacgaa ccactggaga cctcggtact ctctaccggc ccccagggcc | 1320 |
| atgccataac acgtgttgac gttgtaggct gctcggaaca accttgggaa taataacaac | 1380 |
| gtcgtgactc gaagctggga caggctagcc aacatgcgcc acgcaggaga aggcgcgagt | 1440 |
| tgcaacacta gagcggtttt acgtacgcga gtcacgcgcg gcaacctgcc cttcgttcac | 1500 |

```
ccgcgccgtc gtggtgtagg atgcgggcag ccatgcccag ccgtgcagca tggccacgaa    1560
cactaatttc tttcttgcta gctaggtgcc atgcttgaga tttgcagtgt cttgcataag    1620
agtcactacc aatcaagcag taggtacacc catagatagc atcaccccgg cggacgcagg    1680
acaggcgcgc acgtgaatgt ttgcctccaa acgccgcggg gatgcatgca cacaatgtcc    1740
cgtacgtgcc gataccgtac gccacggcag ctgtggggtg taccgtaata gcagggaggg    1800
caacatgaag ggtaacacct cagcaacccc agcaaggctg gcctggtcga gcggcgcgga    1860
ggggtgaagg atacccggca cgcgtggaac gcgcaatgta tctatagtga tagaaggcgt    1920
agtgatggga ggaaataagg agcactcggg gccgcgatgg cgggttggat gcgccacggg    1980
ccccggccca gccaaaggga gcgaacgctg ggcggagccg gtgggtgagc gactcgaggg    2040
acgtgccagt agtgaacagc agtggcggat gggtcatcca atgtgagaga tgatacagcc    2100
acgccggcag ccaaactccg cactcgacca cgtacgggca cgtcgtggta ctgctgtgag    2160
gaggccgggc tgagttggga tgcctgccaa gcctggctac ccacatgtga gcctgtgtcg    2220
ccatacgctc ttaatagtaa tgacatatag cacactgctc ctagcacttc ggtgataagt    2280
aattgccccg ccgggtgaag taaggccggg gctgaaagga accaaggttg gttccctagg    2340
cgtccactcg cgagtgggca ggcgacacat acagttggca ttgacgtgcg ttgcggaact    2400
aatgcgtacg ttggcttggg tctctggttt catgaggcat tgacagaaca cgctgcccct    2460
gctatggctc tgacgaagta acatgtatgc atacatgtcc tgaaggattg gcagggagcg    2520
tgccgcaccg cacgcaagcc gcgtgactac ggtaagcatg aggccataac gtgacacaga    2580
tgccgtgcca tacaggcgg                                                 2599
```

<210> SEQ ID NO 109
<211> LENGTH: 1461
<212> TYPE: DNA
<213> ORGANISM: Chlamydomonas reinhardtii

<400> SEQUENCE: 109

```
ataggagcta tcagtctgac tgtggggtcg atgctacccc ggcatggatc tgggttgaac      60
ggttggtggt accatcgcgc gggcatggcg ggtcgagtag cgtgtttcat gcacggcact     120
cccgctaacc agctacacac cgcagtgtac tggttatcca acaactacat tcagaccatt     180
ctggtatccc actcaaacct gcgccaagtg tcaggaaaag cgcttgccaa gtcggctacc     240
cgctttcaca ggatggcgag cgggtgactg gcatgtgtac aggcgggtgg gccaacaaga     300
ggggagggcg gatgggtgcc gtgacttggt ggtgggcccc accgcgagca gcaacagccc     360
agcccaacac acgggcgcca tccaaaccca ccaggcaggc tgtaatccca gctccgaccg     420
tatctcgcaa caaaatgttg gttgcgcagg gtcgggctca ctgcgtgaca cagcgtccga     480
tgcctggtgc agggcacgaa ggcatgttta tgcgtcatgc ggtatagtta tgcgtcatgc     540
ggtattgtta ttggctgggc atagcatgct ggccgaactg cacaaaactc cacatcgctc     600
actgagggcg aaatatccgg aaaaacaaat tcggcacttg ggcctagcgc acacatcgaa     660
tgcatatagg ttggcttggg gtgcgtcagc caaactacaa gggtggtgcc gcgtgatagt     720
atgatgtgcg tgcggacctc aagacgtaca gggtgacgca tgatcacgta agcccgctcc     780
gttgtcaaca cgaagcaata gcgaggcgca ggcttgccgt gcacggtaca ctcaaggcgt     840
attgcgacag ggcacgcagc agggcacgca acaagtcgaa gcgtccataa cgacagggca     900
ggcagcataa ttgcatgcgg cacacaggcc atatcgcaag acacatgatg cgaggcgcaa     960
```

```
agcctgttgc tggcggcaca cacgccgtat ccgaacgtgg cgctcagacc acacattgtc    1020
cacaacgcaa aggcatgtac aacgaaggca cgtaagcatt tcaatgccgt ctataatcca    1080
caacgcaaga gtgtggggcc cgttgcttgc ggcacacagg tcgtatcata agggcacgta    1140
tgccatctat tacccaaaag caagggtgcg aagccgttgc ttgcggcaca caggtcacat    1200
catacgggca cgtatgccgt gaattgtcca taaaacaagg gtgcggagcc cgttgcttgc    1260
ggcgcacagg ccgtatcata agaacacgta cgcggcgcat tgtccatgaa gcaagggcgc    1320
ggagcccgtt gcctgcggca cacaggccgt atcatgaggg cacgtacgcc gtgaagtgtc    1380
catggagcaa gggcgcggag cccgttgcct gcggcgcaca ggctgtatca tgagggcacg    1440
tacgccgtaa attgtccatg a                                              1461

<210> SEQ ID NO 110
<211> LENGTH: 1748
<212> TYPE: DNA
<213> ORGANISM: Chlamydomonas reinhardtii

<400> SEQUENCE: 110
cccgttgctt gcggcacaca ggccgtatca taagggcacg tatgccgtcc attgtccata      60
aagcaagggc gcggagcccg ttgcttgcgg cgcacaggcc gtatcataag gcacgtatg     120 ccgtccattg tccataaagc aagggcgcgg agcccattgc ttgcggcgca caggccgtat     180
cataagggca cgtatgccgt ccattgtcca taaggcaagg gcgcaaagcc cgttgcttgc     240
ggcgcacagg ccggatccca acggcacaca cgccctttcc caagggcacg cgggccctg     300 cggcctggat aggcagacag gagaagtacc gcgccaaaag tcctgagggt cttggggagg     360
tgggggtggc acaatggaag atgtggaaag gtattgcaca aagctgtgaa ctgtaaagcg     420
acgggtagac acgaaggcac ggcaagcagg accgcgcatg gcaagcaagt agcccgcccg     480
cacagctgtg catgcccttt tgctttcagt gacttgccga acgccttgtc cgcaacgctt     540
cgcgcgcctt tgctccgctt gaaagctccg ctctgctccg atttgctccc gaatgcggcc     600
cccgaaccaa agcgtggttc aaagcgccag agaagcttcg aagggcattc ccttacgatc     660
agagagcgag cgtgatcaag ctaaggggtt ccattgagca ggatcgcgca acaaaacgct     720
gcaactccgt ctgagtatat attaaacgct tattcggtcc atacatggtc aagtatagtt     780
agaaccaggt ataggattgc aaagaaagtc cagaaatgta gggaacgttt aagtgcgaca     840
cactgaggtc accgtcccgg cagagggacg atccgaaata cagtacagaa gcacaacggc     900
agataaggcg ccgtgtgctc ctgacgcgta caagacccag ctcggttcgg ccccatgcac     960
aggcacgtac ccgagcgtcc tgcgccgtgc gtgactctaa cgcaacacgg cagttacgtc    1020
gcaataacta gacttatctc cactgcgctg cgataagtca gcgcatatcc cctcccctct    1080
gtcccattgc gcaccattgc aaggccaagt atgccgggaa cttagcccct gagccgagct    1140
accggctatg ggctcattcc aaacgtccat ttcagcgcgc agttgtgcga acggggtggg    1200 atggggtgc gggggagga atgcccgac tgtgcgggga ggcgccggtg aacacaagcg    1260
cgctggcgag ccaaggccgt gggccgcgat ttcgcgaaat tgccaccacg atagtatgca    1320
ccgttgatac cacaaaactc agcgctgctg atgcatcgag atgaagcaaa cgacgtcgct    1380
gcttctgccg atcactcgca tccacaatgt cttgtcaaat gtttattgcc ttgaggtatc    1440
atcgtctctc gagatacaag tccgctgaca agaattgcaa cccgatggcg ctatcgagcg    1500
ctgggatcct ccaacgcctc caatcccttc gcctctagtt acgtcttcct cgcgtttccg    1560
caaagttatg catcgcttgg gacaaattga aaggcgtatt atttgcacaa gaactctggc    1620
```

-continued

| | |
|---|---|
| tacgttcggg tttcccgacg taactgcaca taaaactgga ataaccgagg gggccccgcc | 1680 |
| tgggactcga tgcgaccgca atggctattg cccctccccc ttcggggggaa ggggcaagcc | 1740 |
| aacctgca | 1748 |

<210> SEQ ID NO 111
<211> LENGTH: 52
<212> TYPE: DNA
<213> ORGANISM: Chlamydomonas reinhardtii

<400> SEQUENCE: 111

| | |
|---|---|
| ggcccgatta aactgcccac ctgaaactgt caagggtcct gatttaagga tt | 52 |

<210> SEQ ID NO 112
<211> LENGTH: 3494
<212> TYPE: DNA
<213> ORGANISM: Chlamydomonas reinhardtii

<400> SEQUENCE: 112

| | |
|---|---|
| ggcggtgtca ccagcagcag cagcagcagc ctgctgagcc gcgtccctcc cgttcccgca | 60 |
| tatcctggcc ctcatcaggt ggactgcgac gcgtccagga tgcagcaagg ccccgctgat | 120 |
| gccgaagagc acaactatgc agctctatac gcagctgcaa cctgcttgcc ggaagtcatt | 180 |
| gtggagataa aggggcatag agcgcgcgtg ctcggcggcc accgggcttc atgtgcatca | 240 |
| atctttgtgc ttcccgttgc ggtaagtact ggtgtcgacc agggcgtcag gtaaccagga | 300 |
| cagggtctgc gacggcggta tgccatgaga caacagttgc atgtgcgtgt gcgtatcgtt | 360 |
| cacgattatg aacagccgcc accgccacgc acgcaaggtc aatcaactaa atcaaccagc | 420 |
| agcatgcagc tcttatagcg gaataaaaag ctggcatcgc aagatattat cggatgcatg | 480 |
| cagacgtcga atgcttcgac agaacgcacc aagcgccgac atgcatgacg gcaagcgtca | 540 |
| acaagaattg cacttcattc agctagctag agaaagctgc tgactggagt gcaatcaatg | 600 |
| catcagcagc agggcgcgtg atggaagtgc gtgcgatgca gcactatata atacacaaat | 660 |
| aagaaagcat ggatgtatgt gcgcgcaatg gctcaccatt tatctatcgt gccgaatgaa | 720 |
| tccagcagga atggcagcag ccgccactac gtatacagcg acgtgcctcc atgcgtacat | 780 |
| gcatgaaatt gaagataaat acatacctgc actgctcaca ggcggacact gttccaaaac | 840 |
| attcgcctct ggagttgcaa tgcaattacg aaatcgtcaa tgggggcagt actgctggcg | 900 |
| acgcttcgcg gccggtgaag cggctaccca taccctacc aacttcaggt tacagcgcat | 960 |
| tgtcgctgct cgagttttgg tgagtacgtt ggaagaacaa ttatccttac acacgggcta | 1020 |
| taacctctac atatggcagg tgatggggcg ggccgtgcgt gcgcggtaca ccactgcatg | 1080 |
| atgacataca gcagcaggct agatgtccgc cggcgtctcg gctacatgta tacatgaaca | 1140 |
| gatcaaatgc tcatcaccac aatacatgct tagtttcatg ttcagccgca tacaaccata | 1200 |
| ttatctgtag cagcgctcgc tgcagcaagc tctcttccgc cgtcgccatc catgtatgga | 1260 |
| tgtatggatg tacgtggcat ttcgctccct gtgactcttg agccagcctg cgcctatgta | 1320 |
| tcctactttt tgacagagag catctggctt gggcaaaatg ctttggtgcc gcacacagac | 1380 |
| gtctgcatgc gcacttcatg tatataatgt atattatata tgttaattat atatatatat | 1440 |
| atgcgcacga tgtcaacttg ggtgcatgca taactccttg ctgtcagcac ttacttctat | 1500 |
| ctggtgcatg cggcggcctt gagcacttta cattgccgca gcgcgcatgc tactagccgc | 1560 |
| cttctctatc ttctcaacgc agcaagggga aaacgttgtg ctacaacaga tgggctggta | 1620 |

| | |
|---|---|
| cttgttgaca atgtttcttc ctggtgtgtc ttcctagctt aatgctagat acacatacag | 1680 |
| gagcccatta atatttaatt tgtcttattg ctgtgttttc aactcctgca cacatgcaat | 1740 |
| aatgcattga aggattacta cacgcagcct gcagatcgag cgagtgccgc agctatacga | 1800 |
| cagctagata gctggtgaat gcaatcagat gggtgtattt atattcatgc gcgtggtgta | 1860 |
| ccctccgctc tctccgctgc gtgctacttg ccacgtatac gttattattg gctggcatca | 1920 |
| taccgtagta attactggtt ttacgctgct gcttttcgg ggaccaacat gcatacttgg | 1980 |
| taattaaaag gaatgaggct cacttgtata gcttgcactc accatgcagg cgtcgcatgt | 2040 |
| gcatctatct acacctgtat gcggcatatg ctgcatctac ctgcccctag ctagctatgg | 2100 |
| ccgcgttgac cttcatgcgt tggacggatt tgcccgcata ttgctcacag ggatgtgcaa | 2160 |
| acacacaaag cgcggcagaa cagggacgag ccccagccgc gcacaggcga gcagctggac | 2220 |
| cagctgtgca ggcaggagct ggtggtggtc gagcccaacg gcaaggtgcg caacgattgc | 2280 |
| attgttgttt tgaactatac ttgcactgtc ttcagttgtt tggtgtcctt tggtgcagct | 2340 |
| gcgtgctatc atttgcaagg actcccaccc acagctatta gttgagcagc ccgtgtcatc | 2400 |
| gtgcgttgct gcgcgcgtgc gctgtgctcc cttactttcc tgcaataatt ggatgatata | 2460 |
| cttgaagttt cttagtgcgt gggcacaact ggcgtggctg ggcttcttga taaggtggcc | 2520 |
| gagtgtgcga tggtacacca cgggacgtgc ccgggtgcac gtacggggtg ttgacatata | 2580 |
| ctcggcagct cgcgcccgcg acctcaactc tatgtataac taactataga tagaaagtgc | 2640 |
| tttaacacat cgacttatat cctgtatgtc ctggattttg ctaactggtg atgacacaat | 2700 |
| acaatgcccg tacgcaggcc gcaatgagcc tagcagattt cctgcaggcg gctggcgcga | 2760 |
| tcctgggcgg acagcagctg gctggacgcc tgctccgcgt gctttggtga gtggatgtag | 2820 |
| ccatacatcc ttattgggcg tcgtcatgac aatcctggac aggggaaggc tcctcgctcc | 2880 |
| cccctcctc ccttcctgac caagctcagg aaccaagggg aaccccgccc ttcctcaagc | 2940 |
| ttgcttccaa ccgtcctgaa cgaatgctac gcacagcaag gcgaagccaa ataaaccgta | 3000 |
| gcgcgcctac gccaaatggt tgattgcgta gcatcgtagc aaccttcatc tgaagtctgc | 3060 |
| gcacgagcga caggctgtct gcagggttgc aaaaattagg atacagcaag caaggtcaag | 3120 |
| ccgtacaccg tatacttcat ccagccagtg ccgcgacagc atctcatctt gcttgcagca | 3180 |
| gtctcgtccc aagacgtcag tagtcattac accccgacac cagtcacacc ccaacacagg | 3240 |
| gcagcgcccc cactttctgt gcttgggaat aattgtatgt gttagggaat atgagtttcg | 3300 |
| gaactgacca tccgtgtgat gccgcaagcg tgtgcacgcg tatgatgatg attggacaca | 3360 |
| gcgaaactgc gtatgtatgt gggttggtgg ggtctgttgt cgaaaccagc aagcggtggg | 3420 |
| agtgggtgtg catacctggc ttggcgtcgg ggcagtactg ctgtaactgc tgcatatctg | 3480 |
| gtgtgcaggt ggga | 3494 |

<210> SEQ ID NO 113
<211> LENGTH: 55
<212> TYPE: DNA
<213> ORGANISM: Chlamydomonas reinhardtii

<400> SEQUENCE: 113

| | |
|---|---|
| ggtatccgtg aaccagtttc ttacggttct cttctttacg gtaacaacat cattg | 55 |

<210> SEQ ID NO 114
<211> LENGTH: 359
<212> TYPE: DNA
<213> ORGANISM: Chlamydomonas reinhardtii

<400> SEQUENCE: 114

```
cgaagatggc ccctcgcggc gtgggtacgg cgtgcccccg cttgtcgggc tgtcccttca    60
cttgtaatcc gcatccataa gcgccaatgc tacccacaaa cgcagtgaac aatatcaata   120
caccagagaa gtcatggtgc caccagaaaa tgaacaagct caattgtgga gagagacata   180
cggtagtgct aggcttggaa gcagccactg tgcttggaat gcgtaatagc tcactggtct   240
agcagtctag cagtgtctag cagtactccg cttatctatt gcagagggt ggcatggggt    300
accgatcctc tggtcacccc aggtccccga ggtccgggtt ccattccctg ccgtcccga   359
```

<210> SEQ ID NO 115
<211> LENGTH: 577
<212> TYPE: DNA
<213> ORGANISM: Chlamydomonas reinhardtii

<400> SEQUENCE: 115

```
tcgtatgcgt ccccgtccca gcagtcgggt gagggcctc cccggtagct caattggtag    60
agcatgccgc tgtcacatgg cagacccagg ttcgattcac ggattcggcc gggttgaggc   120
tgacaagtat agatgcaggt tcggattctg cccggggaac caagtcagta ttccagtatg   180
gagtccgcgg tactgacgga agcgttgtag cgactctctg ggttcggatc ccattgttgc   240
aacgtggaaa cttcacgatg gccgaatttg gagagttggt aggccgatag gtccagaact   300
ttggttccta tggactgagt gaaggtggat gcgtgggag cctcgtgcca aggtcccaca   360
gagatacggt agggttaccc tcgatgggac tcccttaagg cacgcgggac cttggtctta   420
ttattattat tattattatt attattatta ttattattat tattattatt attattatta   480
ttattattat tattattatt attattatta ttattattat tattattatt attattgccc   540
ccgctcttat atgccccgtt agatttttg ggttact                             577
```

<210> SEQ ID NO 116
<211> LENGTH: 1342
<212> TYPE: DNA
<213> ORGANISM: Chlamydomonas reinhardtii

<400> SEQUENCE: 116

```
atcttcgtgc agtggtcagg cttgcccgaa tccagccatc accccaatct cgtacggtaa    60
tggcctcaca actcccaatt acgacttcct ccaccatcat ttgtcttcat gcagattaag   120
atagggcca gagtggtgct tacgttcgac cgagtatcta tctacacccc ttacagcgac    180
aatataacga gggtgcgtga gcaatttaaa cagcgggctg cgctgacctg cacagcggtg   240
ttttgggttt cgcgcatggt cgaccagccc agttaggcgc tgacttatcg cagcgcagtg   300
gagataagtc tagttattgc gacgtaactg ccgtgttgcg ttagagtcac gcacggcgca   360
ggacgctcgg gtacgtgcct gtgcatgggg ccgaaccgag ctgggtcttg tacgcgtcag   420
gagcacacgg cgccttatct gccgttgtgc ttctgtactg tatttcggat cgtccctctg   480
ccgggacggt gacctcagtg tgtcgcactt aaacgttccc tacatttctg gactttcttt   540
gcaatcctat acctggttct aactatactt gaccatgtat ggaccgaata agcgtttaat   600
atatactcag acggagttgc agcgttttgt tgcgcgatcc tgctcaatgg aaccccttag   660
cttgatcacg ctcgctctct gatcgtaagg gaatgccctt cgaagcttct ctggcgcttt   720
gaaccacgct ttggttcggg ggccgcattc gggagcaaat cggagcagag cggagctttc   780
aagcggagca aaggcgcgcg aagcgttgcg gacaaggcgt tcggcaagtc actgaaagca   840
```

```
aaagggcatg cacagctgtg cgggcgggct acttgcttgc catgcgcggt cctgcttgcc      900
gtgccttcgt gtctacccgt cgctttacag ttcacagctt tgtgcaatac cttttccacat     960
cttccattgt gccacccca cctcccaag  accctcagga cttttggcgc ggtacttctc      1020
ctgtctgcct atccaggccg cagggcccgc gtgcccttgg ggaaggggcg tgtgtgccgt      1080
tgggatccgg cctgtgcgcc gcaagcaacg ggctttgcgc ccttgcctta tggacaatgg      1140
acggcatacg tgcccttatg atacggcctg tgtgccgcaa gcaatgggct ccgcgccctt      1200
gctttatgga caatggacgg catacgtgcc cttatgatac ggcctgtgcg ccgcaagcaa      1260
cgggctccgc gcccttgctt tatggacaat ggacggcata cgtgccctta tgatacggcc      1320
tgtgtgccgc aagcaacggg ct                                               1342
```

<210> SEQ ID NO 117
<211> LENGTH: 4363
<212> TYPE: DNA
<213> ORGANISM: Chlamydomonas reinhardtii

<400> SEQUENCE: 117

```
catggacaat ttacggcgta cgtgccctca tgatacagcc tgtgcgccgc aggcaacggg       60
ctccgcgccc ttgctccatg gacacttcac ggcgtacgtg ccctcatgat acggcctgtg      120
tgccgcaggc aacgggctcc gcgcccttgc ttcatggaca atgcgccgcg tacgtgttct      180
tatgatacgg cctgtgcgcc gcaagcaacg ggctccgcac ccttgtttta tggacaattc      240
acggcatacg tgcccgtatg atgtgacctg tgtgccgcaa gcaacggctt cgcacccttg      300
cttttgggta atagatggca tacgtgccct tatgatacga cctgtgtgcc gcaagcaacg      360
ggctccacac tcttgcgttg tggattatag acggcattga aatgcttacg tgccttcgtt      420
gtacatgcct ttgcgttgtg acaatgtgt ggtctgagcg ccacgttcgg atacggcgtg      480
tgtgccgcca gcaacaggct ttgcgcctcg catcatgtgt cttgcgatat ggcctgtgtg      540
ccgcatgcaa ttatgctgcc tgccctgtcg ttatggacgc ttcgacttgt tgcgtgccct      600
gctgcgtgcc ctgtcgcaat acgccttgag tgtaccgtgc acggcaagcc tgcgcctcgc      660
tattgcttcg tgttgacaac ggagcgggct acgtgatca tgcgtcaccc tgtacgtctt      720
gaggtccgca cgcacatcat actatcacgc ggcaccaccc ttgtagtttg gctgacgcac      780
cccaagccaa cctatatgca ttcgatgtgt gcactaggcc caagtgccga atttgttttt      840
ccggatattt cgccctcagt gagcgatgtg gagttttgtg cagttcggcc agcatgctat      900
gcccagccaa taacaatacc gcatgacgca taactatacc gcatgacgca taaacatgcc      960
ttcgtgccct gcaccaggca tcggacgctg tgtcacgcag tgagcccgac cctgcgcaac     1020
caacattttg ttgcgagata cggtcggagc tgggattaca gcctgcctgg tgggtttgga     1080
tggcgcccgt gtgttgggct gggctgttgc tgctcgcggt ggggcccacc accaagtcac     1140
ggcacccatc cgccctcccc tcttgttggc ccacccgcct gtacacatgc cagtcacccg     1200
ctcgccatcc tgtgaaagcg ggtagccgac ttggcaagcg cttttcctga cacttggcgc     1260
aggtttgagt gggataccag aatggtctga atgtagttgt tggataacca gtacactgcg     1320
gtgtgtagct ggttagcggg agtgccgtgc atgaaacacg ctactcgacc cgccatgccc     1380
gcgcgatggt accaccaacc gttcaaccca gatccatgcc ggggtagcat cgaccccaca     1440
gtcagactga tagctcctat ccaggtgtca ggcgccatgt atgtatctgt ggacgcgtca     1500
agctggcttg tgccgtagcg ttggccgcct gtatggcacg gcatctgtgt cacgttatgg     1560
cctcatgctt accgtagtca cgcggcttgc gtgctgtgcg gcacgctccc tgccaatcct     1620
```

```
tcaggacatg tatgcataca tgttacttcg tcagagccat agcagggca gcgtgttctg    1680 tcaatgcctc atgaacccag agacccaagc caacgtacgc attagttccg caacgcacgt    1740
caatgccaac tgtatgtgtc gcctgcccac tcgcgagtgg acgcctaggg aaccaacctt    1800
ggttcctttc agccccggcc ttacttcacc cggcggggca attacttatc accgaagtgc    1860
taggagcagt gtgctatatg tcattactat taagagcgta tggcgacaca ggctcacatg    1920
tgggtagcca ggcttggcag gcatcccaac tcagcccggc ctcctcacag cagtaccacg    1980
acgtgcccgt acgtggtcga gtgcggagtt tggctgccgg cgtggctgta tcatctctca    2040
cattggatga cccatccgcc actgctgttc actactggca cgtccctcga gtcgctcacc    2100
caccggctcc gcccagcgtt cgctcccttt ggctgggccg gggcccgtgg cgcatccaac    2160
ccgccatcgc ggccccgagt gctccttatt tcctcccatc actacgcctt ctatcactat    2220
agatacattg cgcgttccac gcgtgccggg tatccttcac ccctccgcgc cgctcgacca    2280
ggccagcctt gctggggttg ctgaggtgtt acccttcatg ttgccctccc tgctattacg    2340
gtacacccca cagctgccgt ggcgtacggt atcggcacgt acgggacatt gtgtgcatgc    2400
atccccgcgg cgtttggagg caaacattca cgtgcgcgcc tgtcctgcgt ccgccggggt    2460
gatgctatct atgggtgtac ctactgcttg attggtagtg actcttatgc aagacactgc    2520
aaatctcaag catggcacct agctagcaag aaagaaatta gtgttcgtgg ccatgctgca    2580
cggctgggca tggctgcccg catcctacac cacgacggcg cgggtgaacg aagggcaggt    2640
tgccgcgcgt gactcgcgta cgtaaaaccg ctctagtgtt gcaactcgcg ccttctcctg    2700
cgtggcgcat gttggctagc ctgtcccagc ttcgagtcac gacgttgtta ttattcccaa    2760
ggttgttccg agcagcctac aacgtcaaca cgtgttatgg catggccctg ggggccggta    2820
gagagtaccg aggtctccag tggttcgtgc caacacgtgc caacacgcac tgttaccttt    2880
cctgggcaca cggacggcca cagctgccca caagccacac acctgaacaa ggatgcatgt    2940
gtttccctgt aacgccccgg cgtcgtctgc atggctggcg cacgcgggat aacgcatgtg    3000
tgtttctgtc gtggccattg gtgcacctga tacgtttgtg agtctggtat catggccctt    3060
gcaaagccag tcgtgttcct attgctgctt gtcttctggt agtgaccatt ggccgcccat    3120
gaccgacgga gtgtgcgct gtcaggcccc gcgttggcgt cgccctgcgc ctgcagcagg    3180
tgccggcggc gcctccggcg cgctcatcc ccgcgtgatg gtgctgctcg tgcagccaat    3240
atccccaagc acgaagctcg ttctattgac cgctgttgag tgtgcaacta ggaccgtacg    3300
ttcgtgcgca agctaggcga tgggcggagc gctccgcgt gttcgagaca catgatttcg    3360
gtagcgcaag ggcacgaacg ccaccgccat caccgccgac cgcaccttgg tttgcatgac    3420
cggccgttgg gccaagcgct ttgcgagaag agctgcatac gcgaagccaa tcaagcccag    3480
ccaccagggc tgccgtcgcc cgcaccatga cctcccggcg ttgaggacta ctaccaaact    3540
ctggcagcac tttcggccac tagtgcaacc tcaacacggg cgggctgggg cgggcacggc    3600
ggacttggtg gggttatcgg gagctgcgag gccggaggta ggaggccgct gagggccacg    3660
aatgagttgc taggccgctt gaggcatgag tggaggctat tgtcggtttg agagattggg    3720
attgtcgttt ggggccgtgg cggtttgtaa cgctacacgg cagtaaggag tcaataagcg    3780
ctgacttatc gcagcgcagt ggagataagt ctagttattg cgacgtaact gccgtgttgc    3840
gttagagtca cgcacggcgc aggacgcctcg ggtacgtgcc tgtgcatggg gccgaaccga    3900
gctgggtctt gtacgcgtca ggagcacacg gcgccttatc tgccgttgtg cttctgtact    3960
```

-continued

| | |
|---|---|
| gtatttcgga tcgtccctct gccgggacgg tgacaaccca cccgcccccc ctggtgccgc | 4020 |
| cgcggattaa tgtggtggca cccgtgggcg ctgcggcgtg cgtggttgtc tggactctgc | 4080 |
| tgctatcagg cacttcatac atgcgacaca cccagtactg gcagcacttt cggccactag | 4140 |
| tgcaacctca acacgggcgg gctggggcgg cacggcgga cttggtgggg ttatcgggag | 4200 |
| ctgcgaggcc ggaggtagga ggccgctgag ggccacgaat gagttgctag gccgcttgag | 4260 |
| gcatgagtgg aggctattgt cggtttgaga gattgggatt gtcgtttggg gccgtggcgg | 4320 |
| tttgtaacgc tacacggcag taaggagtca ataactcatg tgc | 4363 |

<210> SEQ ID NO 118
<211> LENGTH: 442
<212> TYPE: DNA
<213> ORGANISM: Chlamydomonas reinhardtii
<220> FEATURE:
<221> NAME/KEY: misc_feature
<222> LOCATION: (342)...(441)
<223> OTHER INFORMATION: n = A,T,C or G

<400> SEQUENCE: 118

| | |
|---|---|
| ctccctccct ccctccctta tgcaagaccc ttcacattca tgtatgcaca tgctgcctga | 60 |
| cccgtttgta atggaaccac aagctaaccg cgctggagcc agcccatgca gtgccccatg | 120 |
| cgggtctgca catcaggaca agagcgcctc ccctcttatg ggtaagggtc aggtatcatg | 180 |
| aggacattca ctttgcacca gatgtcgggt ggctttgtga atgcaagtgg aagcagcgat | 240 |
| ggcatgttgg cgtgtccaga cctgaatgcc cagtgcacct tgcatggccg tggcgccaag | 300 |
| tcggcaaccg ctccacccca gcaagctcca gctcatacca annnnnnnnn nnnnnnnnnn | 360 |
| nnnnnnnnnn nnnnnnnnnn nnnnnnnnnn nnnnnnnnnn nnnnnnnnnn nnnnnnnnnn | 420 |
| nnnnnnnnnn nnnnnnnnnn nc | 442 |

<210> SEQ ID NO 119
<211> LENGTH: 3973
<212> TYPE: DNA
<213> ORGANISM: Chlamydomonas reinhardtii

<400> SEQUENCE: 119

| | |
|---|---|
| cttccgcagc tccgcactcg caagctcgag tccttgtgag tgctcgagcg cctgccaggt | 60 |
| cgacacgata gcaagcgggt acgtcgccgc aagcgctatt accgagccaa cagcccctcc | 120 |
| cactgcttca attgctgcgg cctcgctggc catttgtaaa ctttgtgtct tcggaatgtc | 180 |
| tgtttctaca tgccgtgtga tacgttcaag ctaccacaga aagctagcac aaatgaagaa | 240 |
| gggcaagggc taaacaaacc gtacaccagt ttggcgcaaa tgcacttgat cccacaattc | 300 |
| cagcgacttt tgcgaccggc tctccaccga ccgcttggat gcttgcgccc ggtcgctgcc | 360 |
| ccagctactt ccgcggtgaa ataacaacgg tgagcactct caaccactgc gaggacagcc | 420 |
| ctagcaaccg cactgcgtaa gaagtacagc atcgatttgc tgcatgttga ttttggcgca | 480 |
| aatgggggt gcaagcagtt tgtttctctc agacgcgagc tagcgcccaa gcgcgcgata | 540 |
| tgggggcgag gagccactat gtagctgtaa cgattgcatg agtggcgaat tttacttcga | 600 |
| gggtctaggg tgcgagcgga gtgggattac ccccgagggg gcacgccatg cgcgcaggcc | 660 |
| ccatgcaaca gaaattcgcc gggcaccaac ccacgcacag ataattcata ggactacacc | 720 |
| atagccatca gagaccggcc gggaacaagc cccgcaagcg gggcagcatg ggcgcgacac | 780 |
| caccctgccg cgccaactca ccccaaacac gccccaacca cttgtgcgac acaagggcta | 840 |
| ccatacagta gcgcgcgaca cctaatcgcg tgcgccggag tgtgcgagca acattgtac | 900 |

```
ggctaagctc gtttgggccc taggacgcag ggcctggcct ggcatttggt gcattcaata    960
gagcatagaa aaccgaggcc acatatgtgc tggggtgcgc aaaggtcggc ggaattgtgg   1020
gatcaagtga cgtggaaatg gatctggggg actgcggggt tttggggtgt gttgggttgg   1080
tggcgtgaag ggtgtgattt gtgaggaatt tatcgatgca tgccaagttg cacgcctttc   1140
ccctgtgttt cctacatgcc cctgaaccct cccttttgctg gctgcaggcg aagcgacaag   1200
tggtaccgct ggtaccaccc acgggggcct tgtgcccagg ccgtggtggc gcatggtaac   1260
tatacacgtg gcggtcatcg acattgcttt gtgccggcgc gcagcaccca ggatgtgcgg   1320
caatcgctga aatgcagttg tggggtccac actcatacgg cacccacgcc ccacaaagca   1380
ctgatgcagg gctcctgcag ccgtcacgcc atgggaatca gcacatgggc agtggcctgt   1440
gcatacttct ctgtggcctg gcggggcatc tggccagggc gtttgactag cggcatgggg   1500
cctgcacgcc ggtacggggg cgcaggccca aaatgatgca aggaagctga tgtgttgcgt   1560
gaggtgcgca gcggttcctg atggacgtgg gtgctgtcat gcgtatgtat gttggctatg   1620
tgtgttgttc tttgcgccag ggtggtgtcg ccgcgcagcg gagcattggc gttgatgcac   1680
ggggcgtgaa cattggggcc cgcaattggg ttcgcgccgg cacggtcgcg ggcatcgctg   1740
aagatatgtt ggcgcgaccg gtcgcttatg gtgcacgcta atacccgcat actgtgcgta   1800
agcaccgatt gcaattataa gttgcgcatg tagatatcgg tcttctcccg acatgcgctc   1860
tgatgacggg tccatttccg ccaacttagg gtgagagtta agagccggag ccctgttgcc   1920
acctgcaaaa tgccttagca gcatgtggca actatctgcc cgaagcaagt tgcaagccag   1980
cccagttcag gttgccacat gccatgctgg gtattcccag cgcgctagcg cacctgcttg   2040
ggcagctcgc tatggctgcc gtcgacagtt gaccctggta tgccatcgct agagtcgcag   2100
cccgctccgg ccaacctcgc tcctccgcaa ccgacacacg aacccgacgt cacttgatcc   2160
cacaattcca gcgacttttg cgaccggctc tccaccgacc gcttggatgc ttgcgcccgg   2220
tcgctgcccc agctacttcc gcggtgaaat aacaacggtg agcactctca accactgcga   2280
ggacagccct agcaaccgca ctgcgtaaga agtacagcat cgatttgctg catgttgatt   2340
ttggcgcaaa tgggggggtgc aagcagtttg tttctctcag acgcgagcta gcgcccaagc   2400
gcgcgatatg ggggcgagga gccactatgt agctgtaacg attgcatgag tggcgaattt   2460
tacttcgagg gtctagggtg cgagcggagt gggattaccc cccgaggggc acgccatgcg   2520
cgcaggcccc atgcaacaga aattcgccgg gcaccaaccc acgcacagat aattcatagg   2580
actacaccat agccatcaga gaccggccgg gaacaagccc cgcaagcggg gcagcatggg   2640
cgcgacacca ccctgccgcg ccaactcacc ccaaacacgc cccaaccact tgtgcgacac   2700
aagggctacc atacagtagc gcgcgacacc taatcgcgtg cgccggagtg tgcgagcaaa   2760
cattgtacgg ctaagctcgt ttgggcccta ggacgcaggg cctggcctgg catttggtgc   2820
attcaataga gcatagaaaa ccgaggccac atatgtgctg gggtgcgcaa aggtcggcgg   2880
aattgtggga tcaagtgacg tggaaatgga tctgggggac tgcggggttt tggggtgtgt   2940
tgggttggtg gcgtgaaggg tgtgatttgt gaggaatttta tcgatgcatg ccaagttgca   3000 cgccttttccc ctgtgtttcc tacatgcccc tgaaccctcc ctttgctggc tgcaggcgaa   3060
gcgacaagtg gtaccgctgg taccacccac ggggccttg tgcccaggcc gtggtggcgc   3120
atggtaacta tacacgtggc ggtcatcgac attgctttgt gccggcgcgc agcacccagg   3180
atgtgcggca atcgctgaaa tgcagttgtg gggtccacac tcatacggca cccacgcccc   3240
```

```
acaaagcact gatgcagggc tcctgcagcc gtcacgccat gggaatcagc acatgggcag    3300
tggcctgtgc atacttctct gtggcctggc ggggcatctg ccagggcgt ttgactagcg     3360 gcatggggcc tgcacgccgg tacggggggcg caggcccaaa atgatgcaag gaagctgatg   3420
tgttgcgtga ggtgcgcagc ggttcctgat ggacgtgggt gctgtcatgc gtatgtatgt    3480
tggctatgtg tgttgttctt tgcgccaggg tggtgtcgcc gcgcagcgga gcattggcgt    3540
tgatgcacgg ggcgtgaaca ttggggcccg caattgggtt cgcgccggca cggtcgcggg    3600
catcgctgaa gatatgttgg cgcgaccggt cgcttatggt gcacgctaat accgcatac    3660 tgtgcgtaag caccgattgc aattataagt tgcgcatgta gatatcggtc ttctcccgac    3720
atgcgctctg atgacgggtc catttccgcc aacttagggt gagagttaag agccggagcc    3780
ctgttgccac ctgcaaaatg ccttagcagc atgtggcaac tatctgcccg aagcaagttg    3840
caagccagcc cagttcaggt tgccacatgc catgctgggt attcccagcg cgctagcgca    3900
cctgcttggg cagctcgcta tggctgccgt cgacagttga ccctggtatg ccatcgctag    3960
agtcgcagcc cgc                                                       3973

<210> SEQ ID NO 120
<211> LENGTH: 3971
<212> TYPE: DNA
<213> ORGANISM: Chlamydomonas reinhardtii

<400> SEQUENCE: 120
gtgaagggtg tgatttgtga ggaatttatc gatgcatgcc aagttgcacg cctttcccct     60
gtgtttccta catgcccctg aaccctccct ttgctggctg caggcgaagc gacaagtggt    120
accgctggta ccacccacgg gggccttgtg cccaggccgt ggtggcgcat ggtaactata    180
cacgtggcgc tcatcgacat tgctttgtgc cggcgcgcag cacccaggat gtgcggcaat    240
cgctgaaatg cagttgtggg gtccacactc atacggcacc cacgccccac aaagcactga    300
tgcagggctc ctgcagccgt cacgccatgg gaatcagcac atgggcagtg gcctgtgcat    360
acttctctgt ggcctggcgg ggcatctggc cagggcgttt gactagcggc atggggcctg    420
cacgccggta cggggggcgca ggcccaaaat gatgcaagga agctgatgtg ttgcgtgagg    480
tgcgcagcgg ttcctgatgg acgtgggtgc tgtcatgcgt atgtatgttg ctatgtgtg    540 ttgttctttg cgccagggtg tgtcgccgc gcagcggagc attggcgttg atgcacgggg    600
cgtgaacatt ggggcccgca attgggttcg cgccggcacg gtcgcgggca tcgctgaaga    660
tatgttggcg cgaccggtcg cttatggtgc acgctaatac ccgcatactg tgcgtaagca    720
ccgattgcaa ttataagttg cgcatgtaga tatcggtctt ctcccgacat gcgctctgat    780
gacgggtcca tttccgccaa cttagggtga gagttaagag ccggagccct gttgccacct    840
gcaaaatgcc ttagcagcat gtggcaacta tctgcccgaa gcaagttgca agccagccca    900
gttcaggttg ccacatgcca tgctgggtat tcccagcgcg ctagcgcacc tgcttgggca    960
gctcgctatg gctgccgtcg acagttgacc ctggtatgcc atcgctagag tcgcagcccg    1020
ctccggccaa cctcgctcct ccgcaaccga cacacgaacc cgacgtcact tgatcccaca    1080
attccagcga cttttgcgac cggctctcca ccgaccgctt ggatgcttgc gcccggtcgc    1140
tgccccagct acttccgcgg tgaaataaca acggtgagca ctctcaacca ctgcgaggac    1200
agccctagca accgcactgc gtaagaagta cagcatcgat ttgctgcatg ttgattttgg    1260
cgcaaatggg gggtgcaagc agtttgtttc tctcagacgc gagctagcgc caagcgcgc    1320 gatatggggg cgaggagcca ctatgtagct gtaacgattg catgagtggc gaattttact    1380
```

```
tcgagggtct agggtgcgag cggagtggga ttaccccccg aggggcacgc catgcgcgca    1440
ggccccatgc aacagaaatt cgccgggcac caacccacgc acagataatt cataggacta    1500
caccatagcc atcagagacc ggccgggaac aagccccgca agcggggcag catgggcgcg    1560
acaccaccct gccgcgccaa ctcaccccaa acacgcccca accacttgtg cgacacaagg    1620
gctaccatac agtagcgcgc gacacctaat cgcgtgcgcc ggagtgtgcg agcaaacatt    1680
gtacggctaa gctcgtttgg gccctaggac gcagggcctg gcctggcatt tggtgcattc    1740
aatagagcat agaaaaccga ggccacatat gtgctggggt gcgcaaaggt cggcggaatt    1800
gtgggatcaa gtgacgtgga aatggatctg ggggactgcg gggttttggg gtgtgttggg    1860
ttggtggcgt gaagggtgtg atttgtgagg aatttatcga tgcatgccaa gttgcacgcc    1920
tttcccctgt gtttcctaca tgcccctgaa ccctcccttt gctggctgca ggcgaagcga    1980
caagtggtac cgctggtacc acccacgggg gccttgtgcc caggccgtgg tggcgcatgg    2040
taactataca cgtggcggtc atcgacattg ctttgtgccg cgcgcagca cccaggatgt     2100
gcggcaatcg ctgaaatgca gttgtggggt ccacactcat acggcaccca cgccccacaa    2160
agcactgatg cagggctcct gcagccgtca cgccatggga atcagcacat gggcagtggc    2220
ctgtgcatac ttctctgtgg cctggcgggg catctggcca gggcgtttga ctagcggcat    2280
ggggcctgca cgccggtacg ggggcgcagg cccaaaatga tgcaaggaag ctgatgtgtt    2340
gcgtgaggtg cgcagcggtt cctgatggac gtgggtgctg tcatgcgtat gtatgttggc    2400
tatgtgtgtt gttctttgcg ccagggtggt gtcgccgcgc agcggagcat ggcgttgat     2460
gcacggggcg tgaacattgg ggcccgcaat tgggttcgcg ccggcacggt cgcgggcatc    2520
gctgaagata tgttggcgcg accggtcgct tatggtgcac gctaataccc gcatactgtg    2580
cgtaagcacc gattgcaatt ataagttgcg catgtagata tcggtcttct cccgacatgc    2640
gctctgatga cgggtccatt tccgccaact tagggtgaga gttaagagcc ggagccctgt    2700
tgccacctgc aaaatgcctt agcagcatgt ggcaactatc tgcccgaagc aagttgcaag    2760
ccagcccagt tcaggttgcc acatgccatg ctgggtattc ccagcgcgct agcgcacctg    2820
cttgggcagc tcgctatggc tgccgtcgac agttgaccct ggtatgccat cgctagagtc    2880
gcagcccgct ccggccaaac ctcgctcctc cgcaaccgac acacgaaccc gacgtcactt    2940
gatcccacaa ttcagcgac ttttgcgacc ggctctccac gaccgcttgg atgcttgcgc     3000
ccggtcgctg ccccagctac ttccgcggtg aaataacaac ggtgagcact ctcaaccact    3060
gcgaggacag ccctagcaac cgcactgcgt aagaagtaca gcatcgattt gctgcatgtt    3120
gattttggcg caaatggggg gtgcaagcag tttgtttctc tcagacgcga gctagcgccc    3180
aagcgcgcga tatgggggcg aggagccact atgtagctgt aacgattgca tgagtggcga    3240
attttacttc gagggtctag ggtgcgagcg gagtgggatt accccccgag gggcacgcca    3300
tgcgcgcagg ccccatgcaa cagaaattcg ccgggcacca acccacgcac agataattca    3360
taggactaca ccatagccat cagagaccgg ccgggaacaa gccccgcaag cggggcagca    3420
tgggcgcgac accaccctgc cgcgccaact caccccaaac acgccccaac cacttgtgcg    3480
acacaagggc taccatacag tagcgcgcga cacctaatcg cgtgcgccgg agtgtgcgag    3540
caaacattgt acggctaagc tcgtttgggc cctaggacgc agggcctggc ctggcatttg    3600
gtgcattcaa tagagcatag aaaaccgagg ccacatatgt gctggggtgc gcaaaggtcg    3660
gcggaattgt gggatcaagt gatggcaatc ctgaaccaaa accgggctgt gcacagctta    3720
```

| | |
|---|---|
| aaccggatac aatcgtttgg tgcttagaca cagtgctcag tcagtttaag cagtgaaagc | 3780 |
| ttttttgccg cgaacaggtt tttgcatggc ttctgctccg actgctcgtg ctgtgtgatc | 3840 |
| tagaaatagc attgtagctt caaaccaggt cttctggcaa ggctggctca acttgagctc | 3900 |
| tagcaaaggc ggaatcggtc ggggcttggc cccgcaccgt caggcgctct ccaacactgc | 3960 |
| ctagcctggc g | 3971 |

<210> SEQ ID NO 121
<211> LENGTH: 2348
<212> TYPE: DNA
<213> ORGANISM: Chlamydomonas reinhardtii

<400> SEQUENCE: 121

| | |
|---|---|
| acctagctag ctaggaggtt gttgctgctg acgtggaatt ggcgtttagc caatggaagt | 60 |
| atgaggcgat aacaggtctg tgatgccctt agatgttctg ggccgcacgc gcgctacact | 120 |
| gacgcgacca acgagcctat ccttggccga gaggcccggg taatcttgta aaccgcgtcg | 180 |
| tgatggggat agattattgc aattattagt cttcaacgag gaatgcctag taagcgcgag | 240 |
| tcatcagctc gcgttgatta cgtccctgcc ctttgtacac accgcccgtc gctcctaccg | 300 |
| attgggtgag ctggtgaagt gttcggattg agcttggctg gggcaacctg gccttgcttg | 360 |
| agaagttcat taaaccctcc cacctagagg aaggagaagt cgtaacaagg tttccgtagg | 420 |
| tgaacctgcg gaaggatcat tgaatctatc acaatccaca ccgcgaacta acactgttgg | 480 |
| cctccgtctg tgtaaaagca acgggccag gtctgggcgc aatgtaaaag ttacgcctgg | 540 |
| cctgggttgc cgcaaggcat cggtctctta tactaaccaa ccaacaccaa accaaaacta | 600 |
| aattaaaacc gagtatctag cttagagcta gtgctcacta accaagacaa ctctcaacaa | 660 |
| cggatatctt ggctctcgga tcgatgaaga acgcagcgaa atgcgatacg tagtgtgaat | 720 |
| tgcagaaata cgtgaatcat cgaatctttg aacgcatatt gcgctcgagg cttcggccaa | 780 |
| gagcatgtct gcctcagcgt cgggttaata ctcgccctac tccaacacac ttgtgtgttt | 840 |
| ggagcaagag cggacctggc tgtctcggtg tttgattttc ggatcagacg ccgggtcagc | 900 |
| tgaagtacag aggttgatgc atggacccgc ttatgggcct ctactgggta ggcaactcgt | 960 |
| tgctaatgct ttagtagatg gcttggagct gtgcttgtcg acccaaacca ggaactttgg | 1020 |
| ccctgtgccg aagcaaaccc ctattttctc gacctgagct caggcaagat acccgctga | 1080 |
| acttaagcat atcaataagc ggaggaaaag aaactaacaa ggattcccct agtaacggcg | 1140 |
| agcgaaccgg gaatagccca acttgaaaat cttcccaggg ccgatgccga tgtctccggg | 1200 |
| ctcgcttgcg ttaccgccag ccgccttgtc caagtaaggg aatcttaacc cttttccctt | 1260 |
| tcgatgggca gcgcgaatcg cgctcttcac acaggattac cccatctctt aggatcgact | 1320 |
| aacccatgtc caattgctgt tcacatggaa cctttctcca cttcagtctt caaagttctc | 1380 |
| atttgaatat ttgctactac caccaagatc tgcactagat gccgattcac ccaggctcac | 1440 |
| gccagaggct tagtctcgac acccacgccc tcctactcat ggaagcgtcg cacttgcttc | 1500 |
| catggccgag tataggtcac gcgcttaagc gccatccatt tcggggcta attgattcgg | 1560 |
| caggtgagtt gttacacact ccttagcgga tttcgacttc catgaccacc gtcctgctgt | 1620 |
| ttatatcaat caacacccctt tgtgggatct aggttagcgc gtagtttggc accttaactc | 1680 |
| gactatcggt tcatcccgca tcgccagttc tgcttaccaa aaatggccca cttgagctc | 1740 |
| acattgaatg tgccggttca attaagcaac cgacacgtct tacctattta aagtttgaga | 1800 |
| ataggtgaag gatgtttcat ccccgaacc tctaatcatt cgctttaccc gataaaactg | 1860 |

| | |
|---|---|
| atcaagctcc agctatcctg gatggaaggt aggatgggtg tgagcctgcc gcgtgggacc | 1920 |
| tggcggtgtg cgtcgagggc gcgagtgtgc tcagttcctc ttgaattggt atgtttagct | 1980 |
| agaatggtga ggccgaagcc agatgaaaat tgttgctgta ttatattctt tgcattcgca | 2040 |
| tttggccaga cttcggaggc tgcacaactg cagtgagatg tcgatgtata acaacagacg | 2100 |
| tgcgcgaacg tatatggggg gctggataga gttcgagaag tcaaagattt tacggagaag | 2160 |
| gggtgggact gggcagttct gacggcacct gttgacgcaa actggcggcc agccggccac | 2220 |
| agtcgaatgt ggttcgaccg tgggcgacgg tgggcgtgtg cggcatgtgt gccggcgccc | 2280 |
| cgtacgcctc gcctgcgtgc cctgcggctt tcgatgcaaa gcagggcggg atgaggccac | 2340 |
| gaggggga | 2348 |

<210> SEQ ID NO 122
<211> LENGTH: 4129
<212> TYPE: DNA
<213> ORGANISM: Chlamydomonas reinhardtii
<220> FEATURE:
<221> NAME/KEY: misc_feature
<222> LOCATION: 4129
<223> OTHER INFORMATION: n = A,T,C or G

<400> SEQUENCE: 122

| | |
|---|---|
| ggctcctgtc tttttcttat gtgtcttatg tgttgtgtta gataaggttt cttatgtgtg | 60 |
| tgtgtgtggc tgttgggtta gataagacat ataagggttt cggggttttg gtgccctgtg | 120 |
| ccttgttccg cgggtcccaa cgtgtccccc ttgtgctggc atggtgttgg gagtgtgtgc | 180 |
| gatgtgttgg aagcgttggg ggtgcttgga gtgcagtttg gtgtgtgtgg tgtggtgtgg | 240 |
| agttggtcaa gggtgtcagt ccccttggca cgctagcaac cctacccccat atccacccc | 300 |
| tggccagctc tgccaccctc gcccacgcgc atgcactcac agcacgtcaa acgagttccc | 360 |
| atttcacttt ggcatgtatg gggaggcatg gggcagctcc gggcggggat ggcaccatgg | 420 |
| cggtggtggt accgtgtgct cgggtcctgc ctttggctct gcttgtccat gacgtacggc | 480 |
| tctgggtatc ttccatgccc gtaagttatg gccctaaggt accctaaggt accctaaggt | 540 |
| acccacgcgt gtgccctcta gggtacaggg gtaaacattg cgcatacaca cacgcgcgca | 600 |
| cacacgcaca cacacgcaca cactcccccc tgccaacccc actctcaccc ccgcgtcccc | 660 |
| ccgcccccct gcgtgtgcgt gtgtgtgcca cgacgtgcgt acggcaaagt gtggccaagg | 720 |
| ccccccttg cgagtggggg aaccccccta gcccctaggc cctagccccc aaccccctaga | 780 |
| cagccagccc aaacggaaac aggtgtgtg tcatgtatct ggggtaggcg tgaagagaag | 840 |
| cgaaagcaag caattgcaaa gcttcgaatc ataacaacac aatccgaaga atgagctaag | 900 |
| caattagttc tagtaactcg gtgagtgcag tgaactcaa gtaggctctg ccgggtcagg | 960 |
| taactggtcc tggctagccc tgcttgaact ggttcaatca atgcgtcaat ggcggtcaa | 1020 |
| acgctggttg attgttgccc aaatctattg atggtttgag ttgcaacgag tgttgagaga | 1080 |
| gcttgtatta atacgcgatg cgtatgctta tgaaccaagt ggacctgcta ggacagtagg | 1140 |
| tgcaaggcca gtgtaacagc tgtgcttttgt tatctgccgg ctagcattga agctctgctt | 1200 |
| gcgggaagcc gcatgcctga gtgttcgcta ggtggtctga gcttatgcct aacccgtgta | 1260 |
| agactcagcc aatccgcgat acttggttgc gttgcttccg gagcgctggt tcagagctgg | 1320 |
| gagaacgttc agagaggcct cgtggcaaga gctcttctga ctcgattcgt cttcggacag | 1380 |
| tcgtgttcag tcgactctcg agtgctttct caacggatag cgcttcttaa ttgattcaat | 1440 |

-continued

```
tcctgcgtat cctttgtgat acgcgccgga atactgtggc atgcgtatgc tctcgtggcg   1500
tatgtgtgct gcagtttcaa ttaaaggcag ctacctggtt gatcctgcca gtagtcatat   1560
gcttgtctca aagattaagc catgcatgtc aagtataaa ctgcttatac tgtgaaactg    1620
cgaatggctc attaaatcag ttatagttta tttgatggta cctactactc ggataaccgt   1680
agtaattcta gagctaatac gtgcgcacaa cccgacttct ggaagggtcg tatttattag   1740
ataaaaggcc agccgggctc tgcccgacct gcggtgaatc atgataactt cacgaatcgt   1800
atgggctcgt cccgacgatg tttcattcaa atttctgccc tatcaacttt cgatggtagg   1860
atagaggcct accatggtgg taacgggtga cggaggatta gggttcgatt ccggagaggg   1920
agcctgagag atggctacca catccaagga aggcagcagg cgcgcaaatt acccaatccc   1980
gacacgggga ggtagtgaca ataaataaca ataccgggcg cttcgcgtct ggtaattgga   2040
atgagtacaa tctaaatccc ttaacgagga tccattggag ggcaagtctg gtgccagcag   2100
ccgcggtaat tccagctcca atagcgtata tttaagttgt tgcagttaaa aagctcgtag   2160
ttggatttcg ggtgggggtgg tgcggtccgc ctctggtgtg cactgctctg ctccaccttc   2220
ctgccgggga cgggctcctg ggcttcactg tctgggactc ggagtcggcg aggttacttt   2280
gagtaaatta gagtgttcaa agcaggccta cgctctgaat acattagcat ggaataacac   2340
gataggactc tggcctatct gttggtctgt gggaccggag taatgattaa gaggggtagt   2400
cgggggcatt cgtattccgt tgtcagaggt gaaattcttg gatttacgga agacgaacat   2460
ctgcgaaagc atttgccaag gatactttca ttgatcaaga acgaaagttg ggggctcgaa   2520
gacgattaga taccgtcgta gtctcaacca taaacgatgc cgactaggga ttggcagatg   2580
ttcttttgat gactctgcca gcaccttatg agaaatcaaa gttttttgggt tccgggggga   2640
gtatggtcgc aaggctgaaa cttaaaggaa ttgacgaag gcaccacca ggcgtggagc    2700
ctgcggctta atttgactca acacggggaa acttaccagg tccagacacg gaaggattg   2760
acagattgag agctctttct tgattctgtg ggtggtggtg catggccgtt cttagttggt   2820
gggttgcctt gtcaggttga ttccggtaac gaacgagacc tcagcctgct aaatagtcag   2880
catcgcacct gcggtgcgcc gacttcttag agggactatt ggcgtttagc caatggaagt   2940
atgaggcgat aacaggtctg tgatgccctt agatgttctg ggccgcacgc gcgctacact   3000
gacgcgacca acgagcctat ccttggccga gaggcccggg taatcttgta aaccgcgtcg   3060
tgatggggat agattattgc aattattagt cttcaacgag gaatgcctag taagcgcgag   3120
tcatcagctc gcgttgatta cgtccctgcc ctttgtacac accgcccgtc gctcctaccg   3180
attgggtgtg ctggtgaagt gttcggattg agcttggctg gggcaacctg gccttgcttg   3240
agaagttcat taaaccctcc cacctagagg aaggagaagt cgtaacaagg tttccgtagg   3300
tgaacctgcg gaaggatcat tgaatctatc acaatccaca ccgcgaacta acactgttgg   3360
cctccgtctg tgtaaaagca aacgggccag gtctgggcgc aatgtaaaag ttacgcctgg   3420
cctgggttgc cgcaaggcat cggtctctta tactaaccaa ccaacaccaa accaaaacta   3480
aattaaaacc gagtatctag cttagagcta gtgctcacta accaagacaa ctctcaacaa   3540
cggatatctt ggctctcgga tcgatgaaga acgcagcgaa atgcgatacg tagtgtgaat   3600
tgcagaaata cgtgaatcat cgaatctttg aacgcatatt gcgctcgagg cttcggccaa   3660
gagcatgtct gcctcagcgt cgggttaata ctcgccctac tccaacatgt ttggagcaag   3720
agcggacctg gctgtctcgg tgtttgattt tcggatcaga cgccgggtca gctgaagtac   3780
agaggttgat gcatggaccc gcttatgggc ctctactggg taggcaactc gttgctaatg   3840
```

| | | | |
|---|---|---|---|
| ctttagtaga tggcttggag ctgtgcttgt cgacccaaac caggaacttt ggccctgtgc | 3900 |
| cgaagcaaac ccctattttc tcgacctgag ctcaggcaag attacccgct gaacttaagc | 3960 |
| atatcaataa gcggaggaaa agaaactaac aaggattccc ctagtaacgg cgagcgaacc | 4020 |
| gggaatagcc caacttgaaa atctcccttt ggagaattgt agtctagaga agcgctttct | 4080 |
| agggctggcg gaactcaagt cggatcgaat gccgcgtcag agagggtgn | 4129 |

<210> SEQ ID NO 123
<211> LENGTH: 4171
<212> TYPE: DNA
<213> ORGANISM: Chlamydomonas reinhardtii

<400> SEQUENCE: 123

| | |
|---|---|
| tggcctccgt ctgtgtaaag caaacgggcc aggtctgggc gcaatgtaaa agttacgcct | 60 |
| ggcctgggtt gccgcaaggc atcggtctct tatactaacc aaccacacc aaaccaaaac | 120 |
| taaattaaaa ccgagtatct agcttagagc tagtgctcac taaccaagac aactctcaac | 180 |
| aacggatatc ttggctctcg gatcgatgaa gaacgcagcg aaatgcgata cgtagtgtga | 240 |
| attgcagaaa tacgtgaatc atcgaatctt gaacgcata ttgcgctcga ggcttcggcc | 300 |
| aagagcatgt ctgcctcagc gtcgggttaa tactcgccct actccaacat gtttggagca | 360 |
| agagcggacc tggctgtctc ggtgtttgat tttcggatca gacgccgggt cagctgaagt | 420 |
| acagaggttg atgcatggac ccgcttatgg gcctctactg ggtaggcaac tcgttgctaa | 480 |
| tgctttagta gatggcttgg agctgtgctt gtcgacccaa accaggaact ttggccctgt | 540 |
| gccgaagcaa accctatttt tctcgacctg agctcaggca agattacccg ctgaacttaa | 600 |
| gcatatcaat aagcggagga aagaaaacta acaaggattc ccctagtaac ggcgagcgaa | 660 |
| ccgggaatag cccaacttga aaatctccct ttggagaatt gtagtctaga agcgctttc | 720 |
| ctagggctgg cggaactcaa gtcggatcga atgccgcgtc agagagggtg ataacccgt | 780 |
| cggttcctgc ttagtccttc cacgaagtgc tttccacgag tcgggttgtt tgggaatgca | 840 |
| gccctaattt ggaggtaaat cccttctaag gctaaatact gccgagagac cgatagcgaa | 900 |
| caagtaccgt gagggaaaga tgaaaagaac tttgaaaaga gagttaaaag tgcttgaaat | 960 |
| tgttgagagg gaagcgattg gcgctcgtag gtgcgcccag gcttaagcgg tcctaacggc | 1020 |
| ccgttgaatg tgctgggtgc tggtcagaat gggttgagtt ggcgggacaa aagctgggtc | 1080 |
| cacccaggta acccggccga tgccgccgac tcgaccaagg cgtaaagagt accttgtcct | 1140 |
| tcgggatctg tgctctaaag attctggcag aagagcgtca atcgaccccgt cttgaaacac | 1200 |
| ggaccaagga gtctaacatg tatgcgagtt ggcgggtgga aaacccgtaa gcgcaagtaa | 1260 |
| cctgactggt gggatgggt aaaaccctgc accatcgacc gaccatgttg tttctacgaa | 1320 |
| aggtttgagt gcgagcatac ctgttgggac ccgaaagatg gtgaactatg cctgagcagg | 1380 |
| gtgaagccag aggaaactct ggtggaggct cgtagatgtg ctgacgtgca aatcgctttt | 1440 |
| cagacttggg tataggggcg aaagactaat cgaaccatct agtagctggt tccctccgaa | 1500 |
| gtttccccca ggatagctgg agcttgatca gttttatcgg gtaaagcgaa tgattagagg | 1560 |
| ttcgggggat gaaacatcct tcacctattc tcaaacttta aataggtaag acgtgtcggt | 1620 |
| tgcttaattg aaccggcaca ttcaatgtga gctccaagtg ggccattttt ggtaagcaga | 1680 |
| actggcgatg cggatgaac cgatagtcga gttaaggtgc caaactacgc gctaacctag | 1740 |
| atcccacaaa gggtgttgat tgatataaac agcaggacgg tggtcatgga agtcgaaatc | 1800 |

```
cgctaaggag tgtgtaacaa ctcacctgcc gaatcaatta gccccgaaaa tggatggcgc    1860
ttaagcgcgt gacctatact cggccatgga agcaagtgcg acgcttccat gagtaggagg    1920
gcgtgggtgt cgagactaag cctctggcgt gagcctgggt gaatcggcat ctagtgcaga    1980
tcttggtggt agtagcaaat attcaaatga gaactttgaa gactgaagtg gagaaaggtt    2040
ccatgtgaac agcaattgga catgggttag tcgatcctaa gagatggggt aatcctgtgt    2100
gaagagcgcg attcgcgctg cccatcgaaa gggaaaaggg ttaagattcc cttacttgga    2160
caaggcggct ggcggtaacg caagcgagcc cggagacatc ggcatcggcc ctgggaagag    2220
ttctcttttc ttttttaacaa cgcgaaggcc ctggaatcga atcattcgga gatagggctc    2280
agacgttggt aaagcaccgc acttctcgcg gtgtccggcg cgccgttgac ggtccttgaa    2340
aatccggggg agcattcccg atcttgccaa gtcgtactca taaccgcatc aggtctccaa    2400
ggtgaacagc ctctagtcga tagaacaatg tagataaggg aagtcggcaa aatggatccg    2460
taacttcggg aaaaggattg gctctgaggg ctgggcctag gggtctgcag ctgcgaagct    2520
cgggactgcg gtggtctacc cagctggaaa cggctgggcg gactgctgcg tgtcctgggt    2580
ggacggctgt agaagcttcg gcgttcccta ggcgacgaac agccaactca gaactggtac    2640
ggacaagggg aatccgactg tttaattaaa acaaagcatt gtgatggtcc taaggatgt     2700
tgacacaatg tgatttctgc ccagtgctct gaatgtcaaa gtgaagaaat tcaaccaagc    2760
gcgggtaaac ggcgggagta actatgactc tcttaaggta gccaaatgcc tcgtcatcta    2820
attagtgacg cgcatgaatg gattaacgag attcccactg tccctatcta ctatctagcg    2880
aaaccacagc caagggaacg ggcttggaat aaacagcggg gaagaagac cctgttgagc     2940
ttgactctag tccgactttg tgaaataact aagaggtgt agaataagtg ggagcttcgg     3000
cgacggtgaa ataccactac ttttaacgtt gttttactta ttccattact ggaggcggg     3060
actctgtccc tgcttctagc tctaagacgg cttttgcacg tcgatccagg tggaagacat    3120
tgtcaggtgg ggagtttggc tggggcggca catctgttaa aagataacgc aggtgtccta    3180
agatgagctc aacgagaaca gaaatctcgt gtagaacaaa agggtaaaag ctcatttgat    3240
tttgattttc agtacgaata caaactgtga aagcatggcc tatcgatcct ttagcctttc    3300
gggatttgaa gctagaggtg tcagaaaagt taccacaggg ataactggct tgtggcagcc    3360
aagcgttcat agcgacgttg cttttttgatc cttcgatgtc ggctcttcct atcattgtga    3420
agcagcattc accaagcgtt ggattgttca cccactaata gggaacgtga gctgggttta    3480
gaccgtcgtg agacaggtta gttttaccct actgttggac cgattccgcc atagtaattc    3540
ggctcagtac gagaggaacc gccgagtcag ataattggta atgcccttgt ctgaaaagac    3600
aatggggcga agctaacatc tgtagtctaa tgactgaacg cctctaagtc agaagacgtg    3660
ctaggtgcgg agtcacttac ccaatgatgt cacccgacta aggatacatc cgcctgtgcg    3720
gatgctggag cataccgtt ggttcccctg ttaggtccac atggccgaag caggcgccaa     3780
gcatgacaat tccactcgtc attggggtaa atcctctgta gacgactttg ttgcaactgg    3840
gtattgtaag tggtagagtg gccttgctgc tacgatccac tgagattcat cccgtgttgc    3900
taagatttgt cactgccctt cggggcaacc cctcctcctc tcggagcgac agctccaggg    3960
agggccctct ctctctctct cttccaagtg gtgtagctga gctgagcgcg tgccaacgcc    4020
gccaaatccg tctaagtgcc cacatgtgtg tgcatgccct gccctcctc ccccacacag     4080
ccaaagtgct caaggtacct tccctgtgtg tgtgcaagtg agagcaacag catgcatgtg    4140
cccttactta ggcggcctag tgtggtatgt g                                   4171
```

<210> SEQ ID NO 124
<211> LENGTH: 919
<212> TYPE: DNA
<213> ORGANISM: Chlamydomonas reinhardtii

<400> SEQUENCE: 124

```
aaacgttggt caaacgtagc ttggtcaaag tttgaccggc cttagtcagc gcgttgttgg      60
tccgatttgc tcctgtcttt ttcttatgtg tcttatgtgt tgtgttagat aaggtttctt    120
atgtgtgtgt gtgtggctgt tgggttagat aagacatata agggtttcgg ggttttggtg    180
ccctgtgcct tgtcccgcgg gtcccaacgt gtccccttg tgctggcatg gtgttgggag     240
tgtgtgcgat gtgttggaag cgttgggggt gcttggagtg cagtttggtg tgtgtggtgt    300
ggtgtggagt tggtcaaggg tgtcagtccc cttggcacgc tagcaaccct accccatatc    360
caccccctgg ccagctctgc caccctcgcc cacgcgcatg cactcacagc acgtcaaacg    420
agttcccatt tcactttggc atgtatgggg aggcatgggg cagctccggg cggggatggc    480
accatggcgg tggtggtacc gtgtgctcgg gtcctgcctt tggctctgct tgtccatgac    540
gtacggctct gggtatcttc catgcccgta agttatggcc ctaaggtacc ctaaggtacc    600
ctaaggtacc cacgcgtgtg ccctctaggg tacagggta acacttgcgc atacacacac     660
gcgcgcacac acgcacacac acgcacacac tcccccctgc caacccccact ctcaccccg    720
cgtcccccg cccccctgcg tgtgcgtgtg tgtgccacga cgtgcgtacg gcagtgtggc     780
caaggccccc ccttgcgagt gggggaaccc ccctagcccc taggccctag ccccccaaccc   840
ctagacagcc agcccaaacg gaaacaggtg tggtgtcatg tatctggggt aggcgtgaag    900
agaagcgaaa gcaagcaat                                                 919
```

<210> SEQ ID NO 125
<211> LENGTH: 669
<212> TYPE: DNA
<213> ORGANISM: Chlamydomonas reinhardtii

<400> SEQUENCE: 125

```
aagacatata agggtttcgg ggttttggtg ccctgtgcct tgttccgcgg gtcccaacgt     60
gtccccttg tgctggcatg gtgttgggag tgtgtgcgat gtgttggaag cgttgggggt    120
gcttggagtg cagtttggtg tgtgtggtgt ggtgtggagt tggtcaaggg tgtcagtccc    180
cttggcacgc tagcaaccct accccatatc caccccctgg ccagctctgc caccctcgcc    240
cacgcgcatg cactcacagc acgtcaaacg agttcccatt tcactttggc atgtatgggg    300
aggcatgggg cagctccggg cggggatggc accatggcgg tggtggtacc gtgtgctcgg    360
gtcctgcctt tggctctgct tgtccatgac gtacggctct gggtatcttc catgcccgta    420
agttatggcc ctaaggtacc ctaaggtacc ctaaggtacc cacgcgtgtg ccctctaggg    480
tacagggta acacttgcgc atacacacac gcgcgcacac acgcacacac acgcgcacac     540
actcccccct gccaacccca ctctcacccc cgcgtccccc cgcccccctg cgtgtgcgtg    600
tgtgtgccac gacgtgcgta cggcaaagtg tggccaaggc ccccccttgc gagtggggga    660
accccccta                                                            669
```

<210> SEQ ID NO 126
<211> LENGTH: 2782
<212> TYPE: DNA
<213> ORGANISM: Chlamydomonas reinhardtii

```
<400> SEQUENCE: 126
tctgcggcgg ttgtgtggtg gttgcgggct gcagcagccg gtgcctttgc aagcagcagt      60
cctgccgccg ccaggcttct gctgtcgctg ttgctcttgc tgttgctggg cgctgcagtt     120
gctgctggct gctgctgttg ctgcagctgc tgagcaccgg cggccaccat tgccagatag     180
tgtggctgcg gcggttgata tgcagctgct ggcagctgct gcgcatatac ccgcgactgt     240
ttcttctgcg agggcacggg ctgctgctgc tgctgtgcgc tatttgcagt agttgatgcc     300
gcgacatgcg agggcggaag cagcttgctg ctactgccgc cgccgccgcc gccgctgcag     360
agacctgcgg cggccgccgt tgatgacctg ccacctctgg tgctggcttg cgtcttaaag     420
cccttgctcc gctgcctctc ctccttcagc ttgatgagca aggcaggaat attgctcgct     480
gcgtacacgt acgagatagg catgatgtat gagcgagata gaccgtgcat cagcatcttg     540
ttgcgtacgt acgtgcgcac acgcgggcga cttatctatc tatctatcta tctgctgcat     600
gctgctaagc cagcgaaaca ggcaaaacga attgtcgtgt gcgtagctag ccgaatgcca     660
gccacgcgtg cgtccgtaat acgtatttac ggcggatgag cagtagtggc attgcaggtg     720
gaaatgcgct tgattgcttc cgtgcttccg tgtgtcaata cgcacaaaca tgttatgccc     780
gcccgggcac atcaatttat tgtccagata gacaaacggt ctcaatgggt tcgctgcacc     840
aagcatcacg cgtgcgtgcc gcacccagct acttaccaac cagctcgtgc cactcgccat     900
cgtagtcctc gtgtgggaag ttggtgatgg cttgccggcc caacttgcag atgcatgcgc     960
ggtcgaacac acgcgcggcc tcctcttcct gcattgcaga agttaagtgt aacgatgcga    1020
aaaggccctg aacagaagtt gccgaaacgg gagatactcg tgttacattc gggtgacttg    1080
accggcagtt atttcgctgg gttgtgtgca tttgcagcgc ggcgcagcag cgcaagcaag    1140
tgcaattttc aacatatatg tacactgttg tgctgcgtta ccctcacagt aaaaggacca    1200
gctagcaggt gtcagcccac cgtttccgca acacggcact acacacacag ctagtcagca    1260
gattctgtcg ccagcagccg tgcaaacaag caagccagca gtgacttggt aataaggctg    1320
aacccgccca aataaagcgc tagctagctc atcacgcgta cttacacgtg tgtagtcgcc    1380
aagtgttact gtccgtccac catgagatat ctgatggatg ggatgcatgg gcgcgcggga    1440
caattattat cagtgcaaat ggatggtatt agcagcagca gcacaaacgg caagtaaagg    1500
ataggctcat acgccaacgg caattcatac acatgcaagc atggagctag ctagctagca    1560
ccgtgcgtgc gtgctcaatg taccgcatgt ggagcttttca ttagaaataa taccttccat    1620
ccgtgcaaac aacaaataac gcacgtgcgt ggccttctga ggttgtcatc tgagatgtat    1680
ctctagacac tatgtacagg ctgcattgct gctggcgtgc gttatctcct acgggacgga    1740
gggatatgca tgcgcgtgcg tgcccaacta ctcctgctgg acgctatgta catggccgca    1800
ctcgccccgc ccttgctcct gctggcggtt ctgctaggat tcggcccgac cgtccacggc    1860
gtttaccgtc ggttacgagc gaggtaacat gtgaattcgc aacttgcgct actgactgcc    1920
tgctctcgtg ccgcctgcaa gcccactccg ccttccgctc tggcctacgt acgcataact    1980
agttccgcaa cgcacgtcaa ttgcttgaga acgtaggtag ggatgtgttt gaccctgtg     2040 cgctagcgca agcaagtacg tttccgaaca tcgtatgtaa gtaagcgttg cccgcgagat    2100
acataccgcc agttttagat agatcgggcg ggattactat tgcgcgtgtt cgggatcaag    2160
ctagcggatg cagctgctgt atgactacag tgtaaccctg cctgttggcg aggcgtacgt    2220
gtgtaaacaa ttgatcccgc catgtcaaga tgatgcataa catatataca gtgatgcaga    2280
tgtcgccagc acgcaaaacc cacacagctg ctaatgcact tgaattatca attgcaattg    2340
```

```
ctgccgctgc tgtcctacgt aatataagct ggctagctag ctgctgttcc atcccacaca    2400
ataatgcatg gcgtacgttg atagctagct agccgcacaa gctagttgca acgggcggca    2460
atgacgtgca gggctgacgg gattgggcat caattgcggt agttcagcag gcgcatgcgt    2520
tttgaagcta catggtagta gtgccgttgg ccgcttatcg tttatgcgca tggtacattt    2580
ttatcatgca tgaatacttg tgaaacgaat gaacttgacg tgctgccaaa cgcggcctgt    2640
atctagctgc tcacccgccc ctcatccagc cgtccagtcc tgcttgtata cgcgcgctac    2700
cggggataat cggtcagcta ggtcgcgcgc gctgcacatt atgtatgtat ggcctgcccc    2760
gctgcgcccg ggccctagat ac                                             2782

<210> SEQ ID NO 127
<211> LENGTH: 4813
<212> TYPE: DNA
<213> ORGANISM: Chlamydomonas reinhardtii

<400> SEQUENCE: 127
gcgaagcttt gaaccactgg attactgtgc tgatagaaag cttgccggtt tttgtcagag      60
catgagcgac cgtgctttcg cttgcagctg agttttattc agagcgtgag acacaggact     120
gtggcctctc atgtgataga aatgtgctca cttgtcttcg agttctgaat taagaaagca     180
acaacgccca gaggcttcgc agcctgagga gacaaagcag aagacagcta ctgaatgaat     240
gaaaggatag ccttatgtaa ttaaaaacat aacagacccg actgggttct gcacaaacgc     300
gtgcaggaaa tgcggtgtcg agtttgggtg ggctggtgcg cacatcgcga tggggctaaa     360
gcatacagac atgatccatt taatgcattg tcatacagtt tcagatctgc gagtacttca     420
gtggaatgtg catggattcg ctgcgtggaa gcaggagcag actagtgtga tgcgaatgtt     480
gctgagctac gacattgttg cgctaactga gactcacctg caaggcgatg caatgttgcg     540
tgcgatcatg ccgcagggct cacagctcca cacgttggac ggagcaggtc ggaagggagg     600
cgtggcgctg tggataagcg caaagatggc tgataaggtg gagttgttag gcaagtctca     660
gctgccaagg ggcagccaga gtatctgggt gcggtttcgt gggaacgcac tggcgttggg     720
agggaagagc atagtgatag gagcatgcta cgcggccccc gctagctcta agcggtatgc     780
aagggcacgt gtgcaggctg gcgtgacacg cacagcggga gatagggttt tcggcaagct     840
aagagcactg ataaatcgtt tttgcactgc taacgacgag ctgttgctta tgggagatat     900
gaatgcacgg gttgccaatt tgcaagaagt cctaggcgcg gaggcggatg gtgagattgc     960
tgcacacacg ggcacgaatg catcgagcct attggcggcc ataccggaga ggaaaagcat    1020
ggaccaaaag caaggccatg cgcacggcca gctacttgtg aatctgtgcc gtgagctggg    1080
actatgtatc ctaaacgggc gggttgaggg tgacgcggac ggagaatgca cgttcacagg    1140
aggcacgggg aagagcatga ttgatctcta cgttaccaca ccggcacttt acttcaaggc    1200
acggcaactg gaggtgtgca acattcctga aggcgaggac gagatccatc taggtgactt    1260
gatgagcgat cattgccctg ttaagctcac gcttggggtt ggcagatggg atcaagctgc    1320
gaagcagcac ggcggcaagg ctcgctttga tatgcgtaga cggggcgcgt actcatcgat    1380
ttatcaggat ccggagtgcg cagagctgcg gaggatagcc gatgtcatgt gtcgtctggg    1440
gcgcagtgca gaaaatggcg gtatcaccag cacggaggcg gtggaccggc ttggcaaagt    1500
gctataccgt gcgatggata aggcttttgg acgaactggg accgacacgc gcaaggtacg    1560
tgggcaggat gacgcaccct ggtggacgga ggagctagcg gctgcgcgac gggatatgtt    1620
```

```
aggacagaaa gctcagatga gagctactgg caccttgcaa gatgaggctg cacgggccga    1680
attttcgagg ctaaggacgc ggtaccagcg catgcgacga gaggccaagg aacgatataa    1740
ggttacgttt ttcacagagt ttttggatga gtgcaaggcg gacccacgtg ccctatggca    1800
gcgtctgaac gatggggttg tcccctcctg cccgctcaca tcggtcacgg attggacgtc    1860
cttctttgac acactctata atggctcact gaatgcgttt gacaatgtga ctgcggacga    1920
gattctttcc atgattaata gaaggcccgg cgtaggtacg cgcagatggg cagtagagga    1980
tgcacagacg caggaagatg agcctagcgc acggcacgca cgagttgtgg cagctgcgtc    2040
cttgaacata cctttctcgc tgagcgaggt tgaagaggcg ctacggtgtc taaaaaatca    2100
caagtctggc gggctagacc gcgtacctgc agagtgctac aagtacgcca cgcgggaaat    2160
tgaagacgga aaagagttta atgtgcttgc gccgtttttg ctgacactct ttgagcacat    2220
acgcattagc ggcgactacc ctaggcagtt ttgtgagacg tccttaacgc ccatccacaa    2280
gaagggtgac gtttcggaca tgtccaatta ccgcggactg cggtgggag gagcgctggc    2340 caagtgctac gccttcctgt tggagcggcg tctcagtacg tgggggaaa cctgtgatgc    2400 gcgttgtgct tatcaaggcg gcttccgcag aaagagggc acgattcaca atttgtttgt    2460
gctacgacac ctcacggaca agtacaaaac gacacaattg gcaggggc aagcattatt    2520 cgtgtgtcag atcgattttg aaaaggcgtt tgacagagtg ccgagggatt tgttgtggca    2580
aagactggaa gagagaggag tacacggcgc catgctggaa gcgttgaaga agcttacga    2640 gaaagtgatg ttacgcgtac gcgtagatgg acgtaccggt gaccttttg agtcaacggc    2700 tggcgtgaaa caaggctgtc cattgagccc cacactttt gggctgttg ttgaggcata    2760 cgcagactat ctggcagcca aagacgaatt agatcctgcc atgatggcgg ccggggattg    2820
cccagtagtt gacggacatc gtttgccctt gctctttac gctgatgatc taagcttgtt    2880
tgcgacaaca caccgtcgga tgctccagat gctgacaaca ctacgtgagt tctgtgaggc    2940
tttcggaatg cgtgtgaatg ttacaaagtc agaagtgctg ggtgtgcatt cgtcagccac    3000 cttcggcgt tatttacggc aggagccaag ccccatgccg gtgtacatgc gggaatacca    3060
gcaaggactg gaagcacttc gcttctttcc ctggaagcgt agagcgcggt accttggcct    3120
gtattacggc cccagtttta agtttgaatc ttgttgcaaa gagttacgtg catcgggtga    3180
gcgagctatg catgcactac gacggaagtt acgcaagaag gggcttatgg tccctgcggt    3240
agctatgcgg tgctttaacg ctcaggtgcg tgcggtatta tcttacggtg cacaagtgtg    3300
ggcaccagac gcgcttctcc aagtgttcaa tgcgtcccca gttgacggtc aaagatatgg    3360
agcgtttgat cgagcactag agcatggcat ggttcgcatt cagatggatt tcatgaagga    3420
agtggtggga gcccagaaac caacacatga actgctcttt cgagagcttg ggtgcatgcc    3480
actacacgtg cattgggctg agcttgtttt ccgttttgg aaccaactgg ttaaggcaac    3540
cggcactgtt taccatcagg cgtttaagga ggagatacga gcggtgttga gcaacctacc    3600
gacgccgccc acgcacacgt gggggggctaa agttctgcgg ttattgatgg ttggccttgg    3660
ctaccgtttc agtggagagg cagctgatat cgaggccaat attacacgca ttactacgca    3720
agaactggat gttgcctccc tcatggggaa ggtacgcgag aagtttgagg aggactgggc    3780
tagcaacagg ttagaggtta atccacggga ttttgtgacg caagcagggg tcaagcctgg    3840
cgtgaagata tgtcgttaca agcattggat gggggaaaca cggcacacgc aaatctacat    3900
tcctcgagca tggcatgtct ccatgatgag attcaggatg ggcgtgtgga tgattgaggc    3960
taacaaccca cgcggtgcgc agggtgcgca cagggagaga gcacagagag tatgtccgct    4020
```

| | |
|---|---|
| ttgccacgct gatggggagg agcatgtaga ggatgagagg catgtgctgc ttgagtgcaa | 4080 |
| ggcgtacgat gatatcagaa gcacgctgtg ggaggtgatt cccgcgacta tgatggacgc | 4140 |
| gatggccagt ggtgaccaga ggggtttagc gcgtgtcatt cacgcgataa ggctgcgacg | 4200 |
| taacgacctt acggcgcgac caatttagat atattattgc atgaactgtt ttgctttttg | 4260 |
| aataatcctt ttgagactag ttttggcggt ccatgagctt cctggctcgt ttggaccaat | 4320 |
| ctacgagcat gaacttgtaa catcaatcaa tcaatcagtc atacagaata ttactacctt | 4380 |
| taactgtcct aaatgcatgc cccgcccga attgctgttg aaatgctggc cgagtcgcca | 4440 |
| tgagcttatc aacatgcccc aatcttacgt tctgttttaa tacctacgtg cacacttgta | 4500 |
| catgcatctc aaaaacgggc ataggggtt ggttccagaa gtcggggccc actcgcccaa | 4560 |
| agcatatgat aggtgacata tatgttatgc tttgacgtat gccctacacg caagtagtgt | 4620 |
| tcaggctctg ggtttgtgca tgaagaatca gcttaataaa caacgcctcg tcttccctct | 4680 |
| tgggcaagcg gcagctgtcc atactggcag caataccaat caccgagcat tcaatcttgc | 4740 |
| atgagaccag cttccgtctc tgagaccgca acgcgagatg gacctgttac cgcgtgagca | 4800 |
| ggttgcacgc ttc | 4813 |

<210> SEQ ID NO 128
<211> LENGTH: 805
<212> TYPE: DNA
<213> ORGANISM: Chlamydomonas reinhardtii

<400> SEQUENCE: 128

| | |
|---|---|
| tgcggagagg cgcgtgtagg gagtgtaggc acctggcgag cgggtgctgg ggttgggtac | 60 |
| ggcggggagc cgcattggcc tcccgctcgc ccgcaacccc ggcacgcctg cgcctaaagg | 120 |
| gcctagccca acccaaccct tgggtcgccg gcactgttgt caaagtattg aggctggtgg | 180 |
| ttgctgctgg acttcaactt ggtcaaagct gatacgcaga gagagcgctg cgaatgtggc | 240 |
| accacaggcc catcacacgc cgtaacctat accgtacgtt tagtagagag aagtgaaggc | 300 |
| cccgggttcc tccttgctga taagggtgtg atgcgtgtgt cctggcttct tcagggcccg | 360 |
| tgcacgtctc gtcgtttgtg gctattcatg tgttcttgtg gacgacgagc gatggcggga | 420 |
| cacaaatgga acgtcacgtt ggtaatcgtt tagatattcc attggtggct gcccctgctt | 480 |
| tgaagaacga gtcttggcct gtaacggcta gacacggaga tgcaagcaag ggaccctgcc | 540 |
| gtacaaacgg cgtaacgaaa ctgaactcgc cagaagtgaa cacgcacgca caaggagaac | 600 |
| acgcagcggc tgttttagac ttaaacaacg tcttgcgttt gctatcaatg aacgcagtcg | 660 |
| ggtttcgatg catgtatctt ggcgccgccg cacacgccac atacaaatgc ggggcttgag | 720 |
| taccctagag tggaagttgc gtggggcgca cttggctcgg cccggccata caattgcatt | 780 |
| tcctcgccac ctgcggctgt aggca | 805 |

<210> SEQ ID NO 129
<211> LENGTH: 2816
<212> TYPE: DNA
<213> ORGANISM: Chlamydomonas reinhardtii

<400> SEQUENCE: 129

| | |
|---|---|
| tgttctagaa gtgttgttta accgcatctg gcgggcgcaa gacggagatg aaagttttcc | 60 |
| ggaacagttc acaaccacag tgctgacacc aatttacaag agaaagggcg atgtgaagac | 120 |
| gcccggcaac tacaggggca ttgcagtagg cggagcgttg gctaagtgtt atgcatctat | 180 |

```
ccttctgaac aggctagcat gagcaggcga gttgttcaag tggaggcacc cagctcaggc    240
tggtttcagg cggaaatacg gtactgccca ccacctgttt gtcctgaggc acctggtgac    300
aaagcacaca cgtgcaggag caccaccaat gattgttgta cagattgatt ttgagaaggc    360
gtttgacaag gtgccgcgtc ccctcttgtg gctacggctg cgggaaaagg gcgtgtcagg    420
gcggctgttg gaggccatac aagccgcata tgaaaaggtc atgatgacgg ttaaagccga    480
tggcaaactg agcgctgctt ttgaggcaac gcaaggagtc aagcaagggt gcccactgag    540
cacagagctg ttcgggctct ttattgaaac tttggcagag tatattgatg cgcacgagga    600
ctggttggac actgcaagca cagcgggcac ccctgagtta acggtaaga  agctgtcgct    660 cctaatgtat gctgacgatg tttcgctgct agccaccacc cctgagcgta tgcggcacct    720
gttgtcactt gtggatactt tctgcgaagc atttggtatg aaagcaaatg tcgcaaagtg    780
tgaacgtctg gtgttcactt cagacgacca ggagcgtcgt agattgaacg atgagtgcag    840
tgggctgcgg ctgcagggc  agcccatccc tgcggtggac aaggcacggt atctgggact    900
agtctacggc cctggacgtg cttttgccgc ctgcagagag acgctatgtg aggctgcgcg    960
gcgtgctatg tacgcgctta ctaatagatt aaaccgtttg aggattttct ccccgacat   1020 acgcatgcgt tgttttgagg tgcaagttcg ctccatctta gcatatggtt gtgaagtgtg   1080
gggacccgac gtattagcgg aaatgctgga cggcggccca ccaccgcggc ggcgtgacag   1140
caataacctg gcgcacggac cgtttgaagc atgcctgaaa gacgaggccg tcaaattaca   1200
agtgcagtac atgaggatga cagtgggtac gaagcgacca tcgcatcgcc tgctgtttgc   1260
tgaattagca caactaccac tccatttctt tttcgccaag ctttgcattg gattctacaa   1320
caggattgcc gtgcagaagg atagcctagc tcacgatgca ctaattgatg aagtacaaga   1380
cgcgttagta cacccagagg gagatgggtg gtgtgcacgg cttttccgtt ttatctcagc   1440
gcatggcgta gacgtacggc aaggccgtat gcacatgatc aggccggaaa gggaggagag   1500
ccgagcaggt agcccgctgc ctgaagggca aatagtatcc gcctttcgag agagtctaat   1560
gaaggcgtgg aagcacgagc ggctgcagtc tgagccaagc actttcccat cagacaacaa   1620
gcaaccaggc gtgcagatgg gcaagtatag caagtacaag cattggatgg ggctgtgtgc   1680
ggaaggagcg gcaccactga ccatgcaagg gcacagtatc accggattgc taactcagtt   1740
agcgatttga ctcgtctta  cggcagaagg gacccaggta cgaatccaga taaaagccca   1800
attatgcaaa aggcgaaaga ttggtgcgaa actgattggt gatcccacga acgataggta   1860
attgccctta gtggcaattg cgggcttatg cccgctgcaa cctagaaagg tcgtggtgca   1920
gaagtccgat ttagtggcga ggtccaaggt tcaagacaag gctcaagatc caaggctcga   1980
ggaggagcgc catggctcct cggtttgcac gaactggcag tgctccacta ctataatgcg   2040
gcgtttccct agctcgatat gctaggtgtg caggcttgga tgtagtggac tttgaagagt   2100
ggcctaggac ttggaggttg tagtttcgga ggttgtgact cttcgtggt  gaggcgtcag   2160 cgtgaggggg gcgggccctc tcgccctagt caccttgccc cgttaatcca tgccaggccc   2220
tatgggccgg cgttgtaatt attattatta ttattattat tattattatt attattatta   2280
ttattattat tattattatt attattatta ttattattat tattattatt attattatta   2340
ttattattat tattattatt attattatta ttattattat tattattatt attattatta   2400
ttattattat tattattatt attattattc ctataccata agaagaataa taatagaaac   2460
cggacttagc cgcgcgggcg atcctccgag ggtgtggggg agggccgggg ccccgggcgt   2520
gagggaccca gctttgttgc gaggagcgtc gcgcgtgctc gcgacgtagc tggggccgca   2580
```

| | |
|---|---|
| tactggagtg cgctccgtgg cgtttgtgtc ggagccgcgg ccatttgctg tccgggcagc | 2640 |
| cgcgagggac ccagttgtgt aaatacagcg cacagaattc ggcccccac ttaagaacgc | 2700 |
| cgtgtcgccg agttgagtat cgggtttgcg cgagcaccgg tgtggggccg cgtggcccca | 2760 |
| taaaagggac ccagaattat aaatagcaat taataggcag catgcgcctc aggcac | 2816 |

<210> SEQ ID NO 130
<211> LENGTH: 1212
<212> TYPE: DNA
<213> ORGANISM: Chlamydomonas reinhardtii

<400> SEQUENCE: 130

| | |
|---|---|
| gctaagactt ataagatcca tataacgtca acttttgcat gtgccccac agtgcccca | 60 |
| agccctgaaa gctcgattgc ccccgattgc cgaaaaacac tgcaccgcct gtttccgggg | 120 |
| gtttattcac tttgaacttg aacgctgatt acttgaaaag tcagctgtgg ctgtcgctgt | 180 |
| gcgctcgcac tgcatggcct tcaacatcat caatccgcct gatttcctga actaatccta | 240 |
| ttgtattgcc ttatacctat attttgaagc cgtcggcgtc ctcaaaaact gcctataaca | 300 |
| aaaaacgttg tttgctctca ccaccagggg ccacgtgagt gagtgcagca gtccagccac | 360 |
| gcagccgttt ggcccggctt tgattatat acatatagcg actgccgttc tatggttggc | 420 |
| acaagctgga ggtcgccaga gtgaagcggt tgtcaacttg cgccaccgca ggcaggggc | 480 |
| aggggggcatg ctgaccttga catgccaacc tgttgtggct gattcttctg gcacttccaa | 540 |
| agcccattat ttacatataa tccacagcat ggctgcacat tacttgacag cctgaatgat | 600 |
| acctgacccct gacccatgag aggggagggg agtggagcac acatgttgtg tgtggttaca | 660 |
| aggtggtgag cacgacgtgc attcctgtcc ttgtgcacat gtgcagagcc gcatggggca | 720 |
| ctgaagggct ggcaccaagg cctagctggt ggttgcatta caagcatgtc aggcaacatg | 780 |
| tgcgtgcata gatgtgaaag ggtcttgcac aggtgtgagt gaggcaggca ggttggatgg | 840 |
| tgggctgggc agcacagccc ccagtgtggt gtgccaatgg gaaagagcag catgtgcttg | 900 |
| cacaccatgc atgtgcaatc tgtcaacatg caacacagca caatacagta tataaatgga | 960 |
| tcacattgaa tggcaagcca cagtgatgtg agtatgcggg gccatgaatg tcccatccct | 1020 |
| tcccgcctac tcatgcttga tgacaaggaa gctgtggggc acactacgtg cccaaatcac | 1080 |
| atcacggtca cccacaagtt gtttcaataa tcattctagc ttttcttatg cttacttagc | 1140 |
| ttagcacatc tttcctgaca tgtcacactt tccaaccccc acaaaacccc ttaaaacccc | 1200 |
| catttagggt tt | 1212 |

<210> SEQ ID NO 131
<211> LENGTH: 1444
<212> TYPE: DNA
<213> ORGANISM: Chlamydomonas reinhardtii

<400> SEQUENCE: 131

| | |
|---|---|
| ttgcggtgtg cccaaatctc gtcagggtca cccacaagtg gttcaagcaa tcattttagt | 60 |
| catagtaagc tgaattatac tgtgcaaatc atttctgaca tgtcactctt tccaaaccct | 120 |
| gcaaaccccc ttgaaaccct gacttaggcc accctgcgcc aggggccacg tgagtgagtg | 180 |
| cagcagtcca gccacgcagc cgtttggcct ggctattgac tatatacata cagcggctgc | 240 |
| cgttgtatgg ttggcagagc tggaggtcgc cagagtgcag cggttgtcaa cttggtgcca | 300 |
| ccgcaggcct gcaagcggca ggaggcatgc ctgtctggac atgccacatg ttgtggctga | 360 |

| | |
|---|---|
| tgctgcttgc aatttcaaag cccatcatac acatataatg caagcagaat gtgctcaaca | 420 |
| tggctgcaca ttacttgaca gcgtgaatga tgcctggccc tgaccgatga gggggaggg | 480 |
| gagcagagca gagccacatg ggagactgca agggctggca ccacggctcc tagcttgtgg | 540 |
| ttgcattaca agcatgtcag ccaacatgtg catatgtgaa taccagtata aaaggtcttg | 600 |
| cacagggtg agtgaggcag gcaggttgaa tggtgggttg ggcagcacag cccccagcat | 660 |
| ggggacaagg ggaatgagca gcatatgttt gcacaccatg catgtgcaat ctgccaacat | 720 |
| acaacacagc acaatacagt gtagagatgg atcagggaga atgacaagcc acagtggtgc | 780 |
| gagtatgcag ggccatggaa gtcgcatccc ttcctgcctg ttcatgcata gtgacaaggg | 840 |
| agcagtggga cacgcaaagc cattgcggtg tgcccaaatc tcgtcagggt cacccacaag | 900 |
| tggttcaagc aatcatttta gtcatagtaa gctgaattat actgtgcaaa tcatttctga | 960 |
| catgtcactc tttccaaacc ctgcaaaacc ccttgaaacc ctgacttagg ccaccctgcg | 1020 |
| ccaggggcca cgtgagtgag tgcagcagtc cagccacgca gccgtttggc ctggctattg | 1080 |
| actatataca tacagcggct gccgttgtat ggttggcaga gctggaggtc gccagagtgc | 1140 |
| agcggttgtc aacttggtgc caccgcaggc ctgcaagcgg caggaggcat gcctgtctgg | 1200 |
| acatgccaca tgttgtggct gatgctgctt gcaatttcaa agcccatcat acacatataa | 1260 |
| tgcaagcaga atgtgctcaa catggctgca cattacttga cagcgtgaat gatgcctggc | 1320 |
| cctgaccgat gagaggggag gggagcagag cagagccaca tggagactg caagggctgg | 1380 |
| caccacggct cctagcttgt ggttgcatta caagcatgtc agccaacatg tgcatatgtg | 1440 |
| aata | 1444 |

<210> SEQ ID NO 132
<211> LENGTH: 1669
<212> TYPE: DNA
<213> ORGANISM: Chlamydomonas reinhardtii

<400> SEQUENCE: 132

| | |
|---|---|
| gtgggatggg aatggtcttg tcctcactcc acgcgccagc tgtggggtgg catgaggtca | 60 |
| ggttggagat gaggtaaggt gaggagtggg ttgccatggg acagggtaag gggcaagtgt | 120 |
| ggcgtacacg tgtcccgtgg tgtgcacatc ggaggtgttg cgtccggacc ccaagcctac | 180 |
| ccttcttctc atgttgatcc ccctccgcct tctcgaagta attggagcca ttgcggttga | 240 |
| actgagcctg caaccgcgtc atgcacctgt ttgacaatgg ccaccatgaa aggccctggc | 300 |
| gggatgcagg cctgcaggcg gtgccgtatg cggtttctc gggcaaggcg gaggcgtcca | 360 |
| gcttgccgcc caagctgtca cggatcacag tccaactcct gtaatctgat gtgagattta | 420 |
| gtgagcaata ctcctcctgc ggctgaaggc ccacgagggc agcggcaaat ttacatctgc | 480 |
| agccgcgctg gagcagggtg gggcccgctg ctgctgccgc tgctgctgct cgccccgatc | 540 |
| tcttgctgct gcgcgcagat gcttgcattg cgctatggta gcataatggt agcaaaaaaa | 600 |
| ggagtggaca gaagaggagt gacgagcgca gtcgggaaag gcgaattttt taaaattgtt | 660 |
| gataccaggg cacggcttgg tttattatct tgaactgcaa tcgcactgaa agaacaaagg | 720 |
| ttgtagctac aagacgcaaa atattgatac taaccgcgac ctggtgggcg aaaattgggc | 780 |
| aaacggtcgc cccattccca caaccgtggt gttgcgtccg accccaagc ctacccttct | 840 |
| tctcatgttg atccccctcc gccttctcga agtaattgga gccattgcgg ttgaactgag | 900 |
| cctgcaaccg cgtcatgcac ctgtttgaca atggccacca tgaaaggccc gggcgggtga | 960 |
| tagatgtcag cgcattccca caaccgcagc cacggcgaaa taaaaggccg ccctcccat | 1020 |

```
tacttgctaa cccaatacct atcataacaa cttttaagag cacgccaatc tactgtgcaa      1080
gcaagttatt agcgccgagc aaaccgtatg gagtccggtt ggcaacgcga aacagccccg      1140
cgagcagggc tgcagcgcgg taacttattg gtaagctaaa ccaatatgtt tgacaagcgc      1200
cgctattgct gcttagcttt cttgttgcaa cacgcggttg catgccatgc aaatgtcaac      1260
agtgccgctg aaacctgagc gcgaatacct tgcgggcgct gccataaccc tcttcagcat      1320
tgaaaagaac ttacagcatg acaccggctg caaaatccac tacagggcca gccagcccaa      1380
tgtccaaggg gctcgggtcg accgttggcc cgctccgccg ccacaggggg gcgccgcgcc      1440
ggcctcgtcg tccttcgaag ggtgagtgct agggctccgc tggtcaggca tcacagtgtt      1500
tgcaatgcct agcaaacgta tgcacgttcc aggtggacag tgcgaagggg gcagcaaact      1560
ttggtagaac aggcagtggg aggggccct cgtggccacg gccaggactc ctgcccctcc       1620
ctggtccgcc ccagcggctg gaacggagcc tcgtcctctc cacggatcc                  1669

<210> SEQ ID NO 133
<211> LENGTH: 175
<212> TYPE: DNA
<213> ORGANISM: Chlamydomonas reinhardtii

<400> SEQUENCE: 133
aaggggaatg agcagcatgt gcatgcgcac catgcatgcg caatcagtca gcatgcacca       60
tagcatattg cactattcag tatgacctgg gcgaatcaga agccacactg gtgcaagtat      120
gcagtacaat gaaagttgca ttccttcccc caacttgtca cctgtggtaa ggagg          175

<210> SEQ ID NO 134
<211> LENGTH: 2159
<212> TYPE: DNA
<213> ORGANISM: Chlamydomonas reinhardtii

<400> SEQUENCE: 134
gagtgcaagg aagcagccac agcatgttgg cgtgtccgga cctgaggcct gccgaccaca       60
ctggtggcgc caagtcagca accgctccac cccagcaagc tccagctaat gccaaccata      120
caacggcagt cgctatatgc atataagcaa tagccgggcc aaacggttgc gtggctggac      180
tgctgcactc actcacgtgg cccctggccc gtgggtcgcc taaatggggg ttttaagggg      240
ttttgcgggg tttgagaagt ttgacatgtc agaaatgttt tgtatagtgt aatttacaca      300
attatagcta gaaggattgt tggaaccaca tgtggttgac cgtgatgtga tttgggcaca      360
tagccatgac tttgcatgtc acaccgcttc cttgtcacag tgcacaagtc agcagacagg      420
atgcgactca tatggtactg catacttgca ccactgtggc ttctcattca cccaggtcat      480
actgaatact gcattgtgct gtggtgcatg ctgacaggtt gcatgcat tgtgtgcatg        540 cacatgctgc tcattcccct tgtccctgca ctggggggct gtgctgcgac ccaccatcca      600
acctgcctgc tcactcacc cgtgtgcaag accctttcac atttgtatat gcacatgttg       660
cctgacccgt ttgtaatgca gccacaagct aaacgtggtg gtgccagccc ttgcagtgcc      720
ccatgcggct ctgcacatca ggacaagtgt tccccgcttg cctcccctct catgggtgag      780
ggtcaggtat catgcaggct atcaggtaat gtgctgccat gctgaggata ttcaatttgc      840
accatatgtc aatgggcttt gggagtgcaa ggaagcagcc acagcatgtt ggcgtgtccg      900
gacctgaggc ctgccgacca cactggtggc gccaagtcag caaccgctcc accccagcaa      960
gctccagcta atgccaacca tacaacggca gtcgctatat gcatataagc aatagccggg     1020
```

```
ccaaacggtt gcgtggctgg actgctgcac tcactcacgt ggcccctggc ccgtgggtcg    1080
cctaaatggg ggttttaagg ggttttgcgg ggtttgagaa gtttgacatg tcagaaatgt    1140
tttgtatagt gtaatttaca caattatagc tagaaggatt gttggaacca catgtggttg    1200
accgtgatgt gatttgggca catagccatg actttgcatg tcacaccgct tccttgtcac    1260
agtgcacaag tcagcagaca ggatgcgact catatggtac tgcatacttg caccactgtg    1320
gcttctcatt cacccaggtc atactgaata ctgcattgtg ctgtggtgca tgctgacagg    1380
ttgcacatgc attgtgtgca tgcacatgct gctcattccc cttgtcctg cactgggggg    1440 ctgtgctgcg acccaccatc caacctgcct gcctcactca cccgtgtgca agaccctttc    1500
acatttgtat atgcacatgt tgcctgaccc gtttgtaatg cagccacaag ctaaacgtgg    1560
tggtgccagc ccttgcagtg ccccatgcgc tctgcacat caggacaagt gttcccgct     1620 tgcctcccct ctcatgggtg agggtcaggt atcatgcagg ctatcaggta atgtgctgcc    1680
atgctgagga tattcaattt gcaccatatg tcaatgggct ttgggagtgc aaggaagcag    1740
ccacagcatg ttggcgtgtc cggacctgag gcctgccgac cacactggtg gcgccaagtc    1800
agcaaccgct ccaccccagc aagctccagc taatgccaac catacaacgg cagtcgctat    1860
atgcatataa gcaatagccg ggccaaacgg ttgcgtggct ggactgctgc actcactcac    1920
gtggcccctg gtggtgagag caaacatttt acttacgata caggccgtgg ttgacgatgc    1980
tgtttattgc attgggtagg catgatagat tattatcggc tcagccactt gaagcgggct    2040
gatcgatgat tggaaccatg gaaagccggg ctcgcgagca ggccggcgag ctgttgactt    2100
ggccacgccg aagtcagctg cttattattg gtagtttgta ctatcgccct atctcaaga    2159

<210> SEQ ID NO 135
<211> LENGTH: 42
<212> TYPE: DNA
<213> ORGANISM: Chlamydomonas reinhardtii

<400> SEQUENCE: 135
ggcacttcag ctgtattctt agtttaccct attggccaag gg                         42

<210> SEQ ID NO 136
<211> LENGTH: 937
<212> TYPE: DNA
<213> ORGANISM: Chlamydomonas reinhardtii

<400> SEQUENCE: 136
atgcacccct ggttgaatat tgcctggagc atgtgaggat ccatcttcgc accgaccgat      60
tgtatgttaa tgcttgcgat gcttactggc ggattgcgtt tgtgcgcgag ttgctaggag     120
atggctgatg tcggtgcggt agtggcgcag gtgttgggga tgagagttgg ttgccgttga     180
cgtgtgtgcg cggagcacta tgggctataa attcagcagg cggaaaaatc gctctgttat     240
tactttgcta gtcacaccgt taagcctccc atgacacctt tggggggccta aaaaggagca     300 gattgttacg ctgggccacg gcggcactgt atcaaacacc ttggaacccc ccttcggtc      360 gctgggtgcc accaccacat cagcaaaatc ctgctgctcg cgcatacaca tgcacagtgt     420
catcagcctg cgcactacat ccttctctcta ctaccgcctt gagcgcgaaa tggggattgt     480
gaactcacgc catgtcggtc ccactggcgg cgccacggct gctggcccca gccctcgcga     540 tccctgcta actttccacc ttttgacacg gtggggtgag caaaactcac tcctccttaa     600
gaaacgcggc cttcgtgaac cgcgtacata ttattattat tattattatt attattatta    660
ttattattat tattattatt attattatta ttattattat tattattatt attattatta    720
```

```
ttattattat tattattatt attattatta ttattattat tattattatt attattatta    780
ttattattat tattattatt attattattg cccccgctct taagggtctc gctacacgtt    840
ttgggttacg gcgccataga cgccgcgccg cgccctcgtt cgtgcgcccg gcgcgctagt    900
ctgaaagccc gcagccccgc gcacctataa ccccgcg                            937
```

<210> SEQ ID NO 137
<211> LENGTH: 983
<212> TYPE: DNA
<213> ORGANISM: Chlamydomonas reinhardtii

<400> SEQUENCE: 137

```
gcagctgggc gggcctgggc cgcagcacgg taaccaagcg gtcactgcaa ggtaaccagt    60
tggtccgaca ctggttacca cgcggtctgt taaccgctgg taaccagtga ggcggtctat    120
taaccgtcgg ttagcggcct caagcccaaa taaaccgatg gtaacctgag tgccaaaccg    180
gccatttctc ccgggataac cgctgggtaa ccagcgatta accgatggtt taataataat    240
aataataata ataataataa taataataat aataataata ataataataa taataataat    300
aataataata ataataataa taataataat aataataata ataataataa taataataat    360
aataataata ataataataa taataataat aataataatt acaacgccgg cccatagggc    420
ctggcatgga ttaacggggc aaggtgacta gggcgagagg gccgcccccc ctcacgctga    480
cgcctcacca cgaaagagtc acaacctccg aaactacaac ctccaagtcc taggccgctc    540
ttcaaagtcc actacatcca agcctgcaca cctagcatat cgagctaggg aaacgccgcg    600
ttatagtagt ggagcactgc cagttcgtgc aaaccgagga gccatggcgc tcctcctcga    660
gccttggatc ttgagcccttg tcttgaacct tggacctcgc cactaaatcg gacttctgca    720
ccacgacctt tctaggttgc agcgggcata agcccgcaat tgccactaag ggcaattacc    780
tatcgttcgt gggatcacca atcggtttcg caccaatctt tcgccttttg cataattggg    840
cttttatccg gatttgtacc caggtccctt ctgccgtaag gacgagttaa atcgctaact    900
gagttagcga tccggtgata accgatggtt aaatagggc tggaacggta ggggatggaa    960
gtatgaaggg gtgggaccga gtc                                           983
```

<210> SEQ ID NO 138
<211> LENGTH: 842
<212> TYPE: DNA
<213> ORGANISM: Chlamydomonas reinhardtii

<400> SEQUENCE: 138

```
gtggcggagt ctgtatcccg ctctgcgttt tgtttggggc gccgtctcct ggcctcctcg    60
ctcaactggc gggtttggct tgaaaacccc ctgatatatt gtccttcagt tagggacggc    120
gtggtggcat ccttaaagaa ctatctatca ggggttttg ggtgccgtca ggtgggcgcc    180
tccctgggga cacgatttgt cctggagtgg gagagggtgc aatgtcccca taggccgaca    240
atgcaatcta gcatgcaggg ggctaggaag ggaccaatgc aatctagaac caccggcggt    300
cccttgacac ccttaggggc acgccccatg gatcgcatgg cggtccgccg ggtggaggtg    360
gctggacgcg tgtgcgtgca ctcgtgcatg ccgtgctgcg gccgggcatg cgggcttcag    420
ggtgggtctg gtgccgaagc cgaatattat tattattatt attattatta ttattattat    480
tattattatt attattatta ttattattat tattattatt attattatta ttattattat    540
tattattatt attattatta ttattattat tattattatt attattatta ttattattat    600
```

-continued

```
tattattatt attattccta tatcataaga agaataataa tagaaaccgg acttagtcgc    660
gcgggcgatc ctccgagggt gtggggaggg gccggggccc cgggcgtgag ggacccagct    720
ttgttgcgag gagcgtcgcg cgtgctcgcg acgtcgctgg ggccgcatac gggagtgcgc    780
tccgtggcgt ttatgtcgga gccgcggcca tttgctgtcc gggcagccgc gagggaccca    840
gt                                                                   842
```

<210> SEQ ID NO 139
<211> LENGTH: 4372
<212> TYPE: DNA
<213> ORGANISM: Chlamydomonas reinhardtii

<400> SEQUENCE: 139

```
tattgactcc ttactgccgt gtagcgttac aaaccgccac ggccccaaac gataatccca     60
atctctcaaa ccgacaatag cctccactca tgcctcaagc ggcctagcaa ctcattcgtg    120
gccctcagcg gcctcctacc tccggcctcg cagctcccga taccccacca agtccgccgt    180
gcccgcccca gcccgccgt gttgaggttg cactagtggc cgaaagtgct gccagtactg    240
ggtgtgtcgc atgtatgaag tgcctgatag cagcagagtc cagacaacca cgcacgccgc    300
agcgcccacg ggtgccacca cattaatccg cggcggcacc agggggggcg ggtgggttgt    360
caccgtcccg gcagagggac gatccgaaat acagtacaga agcacaacgg cagataaggc    420
gccgtgtgct cctgacgcgt acaagaccca gctcggttcg gccccatgca caggcacgta    480
cccgagcgtc ctgcgccgtg cgtgactcta acgcaacacg gcagttacgt cgcaataact    540
agacttatct ccactgcgct gcgataagtc agcgcttatt gactccttac tgccgtgtag    600
cgttacaaac cgccacggcc ccaaacgata atcccaatct ctcaaaccga caatagcctc    660
cactcatgcc tcaagcggcc tagcaactca ttcgtggccc tcagcggcct cctacctccg    720
gcctcgcagc tcccgatacc ccaccaagtc cgccgtgccc gccccagccc gccgtgttg    780 aggttgcact agtggccgaa agtgctgcca gagtttggta gtagtcctca acgcggggag    840
gtcatggtgc gggcgacggc agccctggtg gctgggcttg attggcttcg cgtatgcagc    900
tcttctcgca aagcgctcgg cccaacggcc ggtcacgcaa accaaggtgc ggtcggcggt    960
gatggcggcg gcgttcgtgc ccttgcgcta ccgaaatcat gtgtctcgaa caccgcggag   1020
cgctccgccc atcgccttgc ttgcgcacga acgtacggtc ctagttgcac actcgacagc   1080
ggtcgataga acgagcttcg tgcttgggga tattggctgc acgagcagca ccatcacatg   1140
gggatgagcg ccgccggagg cgccgccggc acctgctgca ggcggcgcag ggcgacgcca   1200
acgcggggcc tgacagcgcc acactccgtc ggtcatgggc ggtcaatggt cactaccaga   1260
agacaagcag caataggaac acgactggcg ttgcaagggc catgatacca gactcacaaa   1320
cgtatcaggt gcaccaatgg ccacgacaga aacacacatg cattgtcccg cgtgcgccag   1380
ccacgcagac gacgcggggg cgttacaggg aaacacatgc atccttgttc aggtgtgtgg   1440
cttctgggca gctgtggccg tccgtgtgcc taggaaaggt aacagtgcgt gttggcacgt   1500
gttggcacga agcactggag acctcgctcg gtactctcta ccggcccca gggccatgcc   1560 ataacacgtg ttgacgttgt aggctgctcg gaacaacctt gggaataata acaacttcgt   1620
gactcgaagc tgggacagac tagccaacat gagccacgca ggagaaggcg cgaggtgcaa   1680
cactagagcg gttttacgta cgcgagtcac gcgcggcaac ctgcccttca cccgcgccgt   1740
cgtggtgtag gatgcgggca gccatgccca gccgtgcagc atggccacga acactaattt   1800
ctttcttgct agctaggtgc catgcttgag atttgcagtg tcttgcataa gagtcactac   1860
```

-continued

```
caatcaagca gtaggtacac ccatagatag catcaccccg gcggacgcag gacaggcgcg    1920
cacgtgaatg cctccaaacg ccgcggggat gcatgcacac aatgtcccgt acgtgccgat    1980
accgtacgcc acggcggctg tggggtgtac cgtaatagca gggagggcaa catgaagggt    2040
aacacctcag caaccccagc aaggctggcc tggtcgagcg gcgcggaggg gtgaaggata    2100
cccggcacgc gtggaacacg caatgtatct atagtgatag aaggcgtagt gatgggagga    2160
aataaggagc actcggggcc gcgatggcgg gttggatgcg ccacgggccc cggcccagcc    2220
aaagggagcg aacgccgggc ggagccggtg ggtgagcgac tcgagggacg tgccagtagt    2280
gaacccatcg cagtggcgga tgggtcatcc aatgtgagag atgatacagc cacgccggca    2340
gccaaactcc gcactcgccc acgtacgggc acgttgtggt actgctgtga ggaggccggg    2400
ctgagttggg atgcctgccg actgccaagc ccgcagggca ctgtcggcct ggctacccac    2460
atgtgagcct gtgtcgccat acgctcttaa tagtaatgac atatagcaca ctgctcctag    2520
cacttcggtg ataagtaatt gccccgccgg gtgaagtaag gccggggctg aaaggaacca    2580
aggctggttc cctaggcgtc cactggcgag tgggcaggcg acacattcag ttggcattga    2640
cgtgcagggg ttcctgttga cgtgcgttgc ggaactaatg cgtacgttgg cttgggtctc    2700
tgggttcatg aggcattgac agaacacgct gcccctgcta tggttctgac caaggaacat    2760
gtatgcatac atgtcctgaa ggattggcag ggagcgtgcc gcacagcacg caagccgcgt    2820
gactacggta agcatgacgc cataacgtga cacagatgcc gggcatgcca tacaggcggc    2880
caacgctacg gcacaagcca gcttgacgcg tccacagata catacatggc gcctgacacc    2940
tggataggag ctatcagtct gactgtgggt cgatgctacc ccggcatgga tctgggttga    3000
acggttggtg gtaccatcgc gcgggcgtgg cgggtcgagt agcgtgtttc atgcacggca    3060
ctcccgctaa ccagctacac accgcagtgt actggttatc caacaactac attcagacca    3120
ttctggtatc ccactcaaac ctgcgccaag tgtcaggaaa agcgcttgcc aagtcggcta    3180
cccgctttca caggatggcg agcgggtggc tggcatgtgt acaggcgggt gggccaacaa    3240
gaggggaggg cggatgggtg ccgtgactcg gtggtgggcc ccaccgcgag cagcaacagc    3300
ccagcccaac acacgggcgc catctaaacc caccaagcag gctgtgatcc cagctccgac    3360
cgtatctcgc aacaaaatgt tggttgggca gggtcgggct cactgcgtga cacagcgtcc    3420
gatgcctggt gcagggctgc acgaaggcat gtttatgcgt catgcggtat tgttatgcgt    3480
catgcggtat tgttattggc aatagcatgc tggccgaact gcacaaaact ccacaattcg    3540
gcacttgggc ctagcgcaca catcgaatgc atataggttg gcttggggtg cgtcagccaa    3600
actacaatgg tgatgccgcg tgatagtatg atgtgcgtgc ggacctcaag acgtacaggg    3660
tgacgcatga tcacgtaagc ccgctccgtt gtcaacacga agcaatagcg aggcgcaggc    3720
ttgccgtgca cggcacactc aaggcgtatt gcgacagggc acgcagcagg gcacgcaaca    3780
agtcgaagcg tccataacga cagggcaggc agcataattg catgcggcac acgggcaata    3840
tcgcaagaca catgatgcga ggcgcaaagc ctgttgctgg cggcacacac gccgtatccg    3900
aacgtggcgc tcagaccaca cattgtccac aacgcaaagg catgtacaac gaaggcacgt    3960
aagcatttca atgccgtcta taatccacaa cgcaagagtg tggagcccgt tgcttgcggc    4020
acacaggtcg tatcataagg gcacgtatgc catctattac ccaaaagcaa gggtgagctg    4080
ttgcttgcgg cacacaggtc acatcatacg ggcacgtatg ccgtgaattg tccataaaac    4140
aagggtgcag agcccgttgc ttgcggcgca caggccgtat cataagaaca cgtacgcggc    4200
```

```
gcattgtcca tgaagcaagg gcgcggagcc cgttgcctgc ggcacacagg ccgtatcatg    4260
agggcacgta cgccgtgaag tgtccatgaa gcaagggcgc ggagcccgtt gcctgcggcg    4320
cacaggccgt attatgaggg cacgtacgcc gtaaattgtc catgtagcaa gg            4372

<210> SEQ ID NO 140
<211> LENGTH: 1065
<212> TYPE: DNA
<213> ORGANISM: Chlamydomonas reinhardtii

<400> SEQUENCE: 140
acacaggccg tatcataagg gcacgtatgc cgtccattgt ccataaagca agggcgcgga      60
gcccgttgct tgcggcgcac aggccgtatc ataagggcac gtatgccgtc cattgtccat    120
aaagcaaggg cgcggagccc attgcttgcg gcacacaggc cgtatcataa gggcacgtat    180
gccatccatt gtccataagg caagggcgca agcccgttgc ttgcggcgca caggccgga     240 tcccaacggc acacgcccc tttccccaag gcacgcggg ccctgcggcc tggataggca      300
gacaggagaa gtaccgcgcc aaaagccctg aggtcttggg gaggtggggg tggcacgatg    360
gaagatgaaa ggtattgcac aaagctgtga actgtaaagc gacgggtaga cacgaaggca    420
cggcaagcag gaccgcgcat ggcaagcaag tagcccgccc gcacagctgt gcatgccctt    480
ttgctttcag tgacttgccg aacgccttgt ccgcaacgct tcgcgcgcct ttgctccgct    540
tgaaagctcc gctctgctcc gatttgctcc cgaatgcggc cccgaaacca aagcgtggtc    600
caaagcgcca gagaagcgtc gaagggcatt cccttacgat cagagagcga gcgtgatcaa    660 gctaagggggt tccattgagc aggatcgcgc aacaaagcgc tgcaactccg tctgagtgta    720
tattaaacgc ttattcggtc cagacatggt aaagtatagt tagaaccagg tataggattg    780
caaagaaagt ccagaaatgt agggaacgtt taagtgcgac acactgaggt caccgtcccg    840
gcagagggac gatccgaaat acagtacaga agcacaacgg cagataaggc gccgtgtgct    900
cctgacgcgt acaagaccca gctcggttcg gccccatgca caggcacgta cccgagcgtc    960
ctgcgccgtg cgtgactcta acgcaacacg gcagttacgt cgcaataact agacttatct   1020
ccactgcgct gcgataagtc agcgcttaac aggaagtcac ttcgc                   1065

<210> SEQ ID NO 141
<211> LENGTH: 1791
<212> TYPE: DNA
<213> ORGANISM: Chlamydomonas reinhardtii

<400> SEQUENCE: 141
atggacaatt tacggcgtac gtgccctcat gatacagcct gtgcgccgca ggcaacgggc      60
tccgcgccct tgctccatgg acacttcacg gcgtacgtgc cctcatgaca cggcctgtgt     120
gccgcaggca acgggctccg cgcccttgct tcatggacaa tgcgccgcgt acgtgttctt     180
atgatacggt ctgtgcgccg caagcaacgg gctccgcacc cttgttttat ggacaattca     240
cggcatacgt gcccgtatga tgtgacctgt gtgccgcaag caacggcttc gcacccttgc     300
ttttgggtaa tagatggcat acgtgccctt atgatacgac ctgtgtgccg caagcaacgg     360
gctccacact cttgcgttgt ggattataga cggcattgaa atgcttacgt gccttcgttg     420
tacatgcctt tgcgttgtgg acaatgtgtg gtctgagcgc cacgttcgga tacggcgtgt     480
gtgccgccag caacaggctt tgcgcctcgc atcatgtgtc ttgcgatatg gcctgtgtgc     540
cgcatgcaat tatgctgcct gccctgtcgt tatggacgct tcgacttgtt gcgtgccctg     600
ctgcgtgccc tgtcgcaata cgccttgagt gtaccgtgca cggcaagcct gcgcctcgct     660
```

```
attgcttcgt gttgacaacg gagcgggctt acgtgatcat gcgtcaccct gtacgtcttg      720
aggtccgcac gcacatcata ctatcacgcg gcatcaccct tgtagtttgg ctgacgcacc      780
ccaagccaac ctatatgcat tcgatgtgtg cgctaggccc aagtgccgaa tttgtttttc      840
cggatatttc gccctcagtg agcgatgtgg agttttgtgc agttcggcca gcatgctatg      900
cccagccaat aacaataccg catgatgcat aactataccg catgacgcat aactataccg      960
catgacgcat aaacatgcct tcgtgccctg caccaggcat cggacgctgt gtcacgcagt     1020
gagcccgacc ctgcgcaacc aacattttgt tgcgagatac ggtcggagct gggattacag     1080
cctgcctggt gggtttggat ggcgcccgtg tgttgggctg gctgttgct gctcgcggtg      1140 gggcccacca ccaagtcacg gcacccatcc gccctcccct cttgttggcc cacccgcctg     1200
tacacatgcc agtcacccgc tcgccatcct gtgaaagcgg gtagccgact tggcaagcgc     1260
ttttcctgac acttggcgca ggtttgagtg ggataccaga atggtctgaa tgtagttgtt     1320
ggataaccag tacactgcgg tgtgtagctg gttagcggga gtaccgtgca tgaaacacgc     1380
tactcgaccc gccatgcccg cgcgatggta ccaccaaccg ttcaacccag atccatgccg     1440
gggtagcatc gaccccacag tcagactgat agctcctatc caggtgttag gcgccatgta     1500
tgtatctgtg gacgcgtcaa gctggcttgt gccgtagcgt tggccgcctg tatggcacgg     1560
catctgtgtc acgttatggc ctcatgctta ccgtagtcac gcggcttgcg tgctgtgcgg     1620
cacgctccct gccaatcctt caggacatgt atgcatacat gttacttcgt cagagccata     1680 gcagggggcag cgtgttctgt caatgcctca tgaacccaga gacccaagcc aacgtacgca    1740
ttagttccgc aacgcacgtc aatgccaact gtatgtgtcg cctgcccact c              1791

<210> SEQ ID NO 142
<211> LENGTH: 1076
<212> TYPE: DNA
<213> ORGANISM: Chlamydomonas reinhardtii

<400> SEQUENCE: 142
gacctgcggt gccacgctct gggtcagatc cgcggctgcg ctgggtgtgg gcacagagac       60
cacatttgtc tcgaacccat gtaaatgctc atgctcatgc tcatggctga gcatgccagc      120
aatgaccgcc acagcttcct cctcgccgta ctcttcct tc acctcctgga agtggccgag      180
tgcctcctcc tgcagcgttg caagtatcag caaactaccc gtagccgccc tagcatgtgc      240
acttacctgc gtcggcgtga gcttgcccca tttcaagctg gcatcccgca gcgccctggc      300
cagggctgcc tatagccttc ttccttcagc acctgcagca gcgagccctc cccagccccc      360
ttcccatcca tgttgaagcg ctcaaaatgc gtctgcagga gctgctggct gagtgcagtt      420
gcacctgttg cataggggat gaaaggagtt aatgggagct tggcacgcaa ccgtgcacac      480
gaggcttgca caccttgcgg cttgcggacc ttgcgagccg ccaccaccgg gttgacaata      540
ataataataa taataataat aataataata ataataataa taataataat aataataata      600
ataataataa taataataat aataataata attacaacgc cggcccatag ggcctggcat      660
ggattaacgg ggcaaggtga ctaaggcgag agggcccgcc cccctcacgc tgacgcctca      720
ccacgaaaga gtcacaacct ccgaaactac aacctccaag tcctaggccg ctcttcaaag      780
tccactacat ccaaacctgc acacctagca tatcgagcta gggaaacgcc acgttatagt      840
agtggagcac tgccagttcg tgcaaaccga ggagccatgg cgctcctctt cgagccttgg      900
atcttgagcc ttgtcttgaa ccttggacct cgccactaaa tcggacttct gcaccgcgac      960
```

| | |
|---|---|
| ctttctagtt tgcagcggca taagcccgca attgccacta agggcaatta ccgtgggatc | 1020 |
| accaatcggt ttcgcaccaa tctttcgcct tttgcatagt tgggctttta tccgga | 1076 |

<210> SEQ ID NO 143
<211> LENGTH: 2249
<212> TYPE: DNA
<213> ORGANISM: Chlamydomonas reinhardtii

<400> SEQUENCE: 143

| | |
|---|---|
| tttgtcggta gttgggtagt ctgtcgggcg aacatagtgg agagggccct ttgggtgggg | 60 |
| cctcgtttgg gtttggtttg attcggggc ggcggtgttg gtggttgcgg cggcggcggt | 120 |
| aggtttggaa ttgttgggta tgtccttggg tcaagcggca tgtctaggtg gtaggggtgt | 180 |
| aagcagaata tgtcgccttt cactgcttgc cagaggtccg gtgtcatagg tttacgccca | 240 |
| atgtgtacaa aggattcgac tagaaaccag ctgtcttctt ccttgcggat tgcgtaggcg | 300 |
| tgtctcccat cgtgcaccat acaccccatg ttccgggagc attctgggag taggcctaga | 360 |
| attgtgtcct gagagtggcc tgggtcaagg ttaggggcgg ctaagcgtag aagcaggcgt | 420 |
| gttcccgtag tgtcgattgg cgctgggcgg tggcggaggt agtggttgat ggcggcttca | 480 |
| tggaaaagcc cattgtgttt gaagtgatgg ccccaggtcg cttgtagttc gggtgtgtcg | 540 |
| gccagcgcaa tgtgcacgac ttggcagaaa gcaagcacgg catgggccct tagccacggt | 600 |
| gctcccagca tgttattgat agcgtgtatc gtacagaaat tgaggtgttg ttgttcgcgg | 660 |
| aagtatgtgc ttggtatttg tctgggccag cttagtggta ctgggatatg cccgttttcg | 720 |
| gctgctggtg tagtagtccg ctctgtgtta tttccgcctc gtagcggatg tgagggtgac | 780 |
| gttaaatcgg gttgctgttg tccaggctgc gtgccgattt gtagagtcat tgggttgcta | 840 |
| ctcatgatgt gcgagtaggc cgcaaggttg gtgataaggt tgatcgttgc gtcgtgaggg | 900 |
| tgtgcgtgtg tttgggatag gagtagggtg gtggtgacgg tggtgatgtt gaggcttggc | 960 |
| gggccaggga cgtgcgggag gatttgcaag gccaacgggg tcgtaactgg tgctagttgg | 1020 |
| ggggagtggg cagtggtttg taggttcatg aggagcagga tgatagtggt caatgtgcat | 1080 |
| atagagaagg taggtttcag gattataccg cggccaagcc catatagcgg aagccccagg | 1140 |
| attgcaggta ccgcgccgcg cgttgttttg ataatgctgt ataccgcgca cgttgtcgct | 1200 |
| agtagcgtaa tgatggttgt ggtgtgctgg tatgtcatga tcaggaggat taaaggctgg | 1260 |
| gctagaagaa aggctgcagg gatggtgaaa atcaggtttt tcgcccgtgc tggtgtgggg | 1320 |
| tgagctagca ggttgcgtga tgcgtggttg agttgcgcaa cgccggcgat agttaggatg | 1380 |
| agcgtgggga tccatagtga tgcctgcgac gtgacttgcc agccgctcag gcctagctgc | 1440 |
| acagcgctgg tggccgagtg ggatagtgtg tgtgcgagga ggattcgcag ccaggcgacg | 1500 |
| gtgtggcgca ggagtgtaca ggttccgtgg aatatgccta cggtgaccca gagaagtgtg | 1560 |
| ctggcggtgt gagcagagac atagctggct gtcgttatga gctgtctgt ttcgttgttc | 1620 |
| agtagcagct gtgtgatggg gtatggtccc attatctggc accagtggct ggggtcgcgg | 1680 |
| ctgtaggcgg tgttgtggtg gcagaggacg gtacaggcaa atgtgttgca gtttgcttgt | 1740 |
| tcggcgtgcg ccgcgttgtc tcgctccggg ggtccgtcgt tccccgcgct gagttcttcg | 1800 |
| tctcttgcca ctttaccata ggtgaccgct gcgtcggcgg tcttgctact ctccgcgtgc | 1860 |
| gcatagctcc cactacttat gtcctcacct atattgctcg ctgctatcct agggcccata | 1920 |
| gcatcctcca tcttgtcctg cagttggcgc cagcagacat taaatccgat acatttagaa | 1980 |
| aagctgtctc tctgcagttc gaggctctca ggcaagcgat acccatcggc gtctacgccc | 2040 |

```
atgttgctga aaattgcagc cgcactgtgc gtgcaccgct cagttctatc ggcagtctca    2100
caccacatcc tctgctctct ctctttccgg cagcgggttt gctccgcatt gtccttgttg    2160
ctggcagccg tgtgggttgt agagctcctc ggcccgtgtt gggcggttag gctacggggg    2220
gcagattggt gggaagggtg gtgttggat                                      2249
```

<210> SEQ ID NO 144
<211> LENGTH: 4128
<212> TYPE: DNA
<213> ORGANISM: Chlamydomonas reinhardtii

<400> SEQUENCE: 144

```
caatgtatgt gaatgatgga tgggctttgg aagtgcaaga caatcagcc acaacaggtt      60 ggcgtgccaa aggtccttca gcgggcctcc tgccctcgc aggcctgcga tagcgccaag     120
ttgacaaccg cttcactctg caacctcca gctcatgcca accatacaac ggcagtcgtt     180
atatgtatat aagcaacatc ctggccaaac agttgcgtgg ctggactgct gccctcactc    240
acgtggcccc tggtagcggg gtggcctaaa ggggggtttt atcgggtttt gcaggttttg    300
gaaaggtaag acatgtcaga atgatgtac taagttctat aagcataatt gaagccagaa     360
agattgctag aaccacttgg aggtgggcac aatgtgagtt gggcacgtgg caaagacttt    420
gcatgcccta ctgctgctcc cttgtcatca cgcacaagta ggcatgaagg gatgggattc    480
tcatggcccc acatactcgc atcaatgtgc cttgccattc accaagatgt atttgtatgc    540
tgtcctgtgc tgtgttgcat gttgacagac tgcacatgca tggtgtattg gtgtgccagc    600
acatgctgcc ctttctcctt cgtgtgccac actgggggct gtgctgccca cccagcatc     660 caacctgcct gcctgactca ccccttcaca tctatgtacg cacatgtggc ctgacattca    720
atttgcaatg tatgtgaatg atggatgggc tttgaagtg caagaacaat cagccacaac    780
aggttggcgt gccaaaggtc cttcagcggg cctcctgccc ctcgcaggcc tgcgatagcg    840
ccaagttgac aaccgcttca ctctggcaac ctccagctca tgccaaccat acaacggcag    900
tcgttatatg tataagca acatcctggc caaacagttg cgtggctgga ctgctgccct     960
cactcacgtg gcccctggta gcgggtggc ctaagggggg ttttatcgg ttttgcagg     1020 ttttggaaag gtaagacatg tcagaaatga tgtactaagt tctataagca taattgaagc    1080
cagaaagatt gctagaacca cttggaggtg ggcacaatgt gagttgggca cgtggcaaag    1140
actttgcatg ccctactgct gctcccttgt catcacgcac aagtaggcat gaagggatgg    1200
gattctcatg gccccacata ctcgcatcaa tgtgccttgc cattcaccaa gatgtatttg    1260
tatgctgtcc tgtgctgtgt tgcatgttga cagactgcac atgcatggtg tattggtgtg    1320
ccagcacatg ctgccctttc tcttcgtgt gccactggg ggctgtgct gcccaaccca    1380 gcatccaacc tgcctgcctg actcacccct tcacatctat gtacgcacat gtggcctgac    1440
attcaatttg caatgtatgt gaatgatgga tgggctttgg aagtgcaaga caatcagcc    1500 acaacaggtt ggcgtgccaa aggtccttca gcgggcctcc tgccctcgc aggcctgcga    1560 tagcgccaag ttgacaaccg cttcactctg caacctcca gctcatgcca accatacaac    1620
ggcagtcgtt atatgtatat aagcaacatc ctggccaaac agttgcgtgg ctggactgct    1680
gccctcactc acgtggcccc tggtagcggg gtggcctaaa ggggggtttt atcgggtttt    1740
gcaggttttg gaaaggtaag acatgtcaga atgatgtac taagttctat aagcataatt    1800
gaagccagaa agattgctag aaccacttgg aggtgggcac aatgtgagtt gggcacgtgg    1860
```

```
caaaaacttt gcatgcccta ctgctgctcc cttgtcatca cgcacaagta ggcatgaagg    1920
gatgggattc tcatggcccc acatactcgc atcaatgtgc cttgccattc accaagatgt    1980
atttgtatgc tgtcctgtgc tgtgttgcat gttgacagac tgcacatgca tggtgtattg    2040
gtgtgccagc acatgctgcc ctttctcctt cgtgtgccac actgggggct gtgctgccca    2100
acccagcatc caacctgcct gcctgactca ccccttcaca tctatgtacg cacatgtggc    2160
ctgacattca atttgcaatg tatgtgaatg atggatgggc tttggaagtg caagaacaat    2220
cagccacaac aggttggcgt gccaaaggtc cttcagcggg cctcctgccc ctcgcaggcc    2280
tgcgatagcg ccaagttgac aaccgcttca ctctggcaac ctccagctca tgccaaccat    2340
acaacggcag tcgttatatg tatataagca acatcctggc caaacagttg cgtggctgga    2400
ctgctgccct cactcacgtg gcccctggta gcggggtggc ctaaaggggg gttttatcgg    2460
gttttgcagg ttttggaaag gtaagacatg tcagaaatga tgtactaagt tctataagca    2520
taattgaagc cagaaagatt gctagaacca cttggaggtg ggcacaatgt gagttgggca    2580
cgtggcaaag actttgcatg ccctactgct gctcccttgt catcacgcac aagtaggcat    2640
gaagggatgg gattctcatg gccccacata ctcgcatcaa tgtgccttgc cattcaccaa    2700
gatgtatttg tatgctgtcc tgtgctgtgt tgcatgttga cagactgcac atgcatggtg    2760
tattggtgtg ccagcacatg ctgccctttc tccttcgtgt gccacactgg ggctgtgct    2820
gcccaaccca gcatccaacc tgcctgcctg actcacccct tcacatctat gtacgcacat    2880
gtggcctgac attcaatttg caatgtatgt gaatgatgga tgggctttgg aagtgcaaga    2940
acaatcagcc acaacaggtt ggcgtgccaa aggtccttca gcgggcctcc tgcccctcgc    3000
aggcctgcga tagcgccaag ttgacaaccg cttcactctg gcaacctcca gctcatgcca    3060
accatacaac ggcagtcgtt atatgtatat aagcaacatc ctggccaaac agttgcgtgg    3120
ctggactgct gccctcactc acgtggcccc tggtagcggg gtggcctaaa ggggggtttt    3180
atcgggtttt gcaggttttg gaaaggtaag acatgtcaga aatgatgtac taagttctat    3240
aagcataatt gaagccagaa agattgctag aaccacttgg aggtgggcac aatgtgagtt    3300
gggcacgtgg caaaactttt gcatgcccta ctgctgctcc cttgtcatca cgcacaagta    3360
ggcatgaagg gatgggattc tcatggcccc acatactcgc atcaatgtgc cttgccattc    3420
accaagatgt atttgtatgc tgtcctgtgc tgtgttgcat gttgacagac tgcacatgca    3480
tggtgtattg gtgtgccagc acatgctgcc ctttctcctt cgtgtgccac actggggct    3540
gtgctgccca acccagcatc caacctgcct gcctgactca ccccttcaca tctatgtacg    3600
cacatgtggc ctgacattca atttgcaatg tatgtgaatg atggatgggc tttggaagtg    3660
caagaacaat cagccacaac aggttggcgt gccaaaggtc cttcagcggg cctcctgccc    3720
ctcgcaggcc tgcgatagcg ccaagttgac aaccgcttca ctctggcaac ctccagctca    3780
tgccaaccat acaacggcag tcgttatatg tatataagca acatcctggc caaacagttg    3840
cgtggctgga ctgctgccct cactcacgtg gcccctggtg tgagagcaa acaattatat    3900
ttcaatacag gccgtcttcc agggcggtaa taagtgcaac agataaagaa ataaccaaag    3960
agtagtatgc actgcttata tgcttccgct agctggtgtt ggtggcctga tcgccgtgct    4020
cggcgaggtc tgctcggcgg tcatggtcaa ggtcacgcca agttgaaata gaccacaatc    4080
gcaatcgaga tatgcagtat aatcatcttg accgagggaa gccttaca              4128
```

<210> SEQ ID NO 145
<211> LENGTH: 1984

<212> TYPE: DNA
<213> ORGANISM: Chlamydomonas reinhardtii

<400> SEQUENCE: 145

```
tggactgctg cactcactca cgtggcccct ggtagcgggg tggcctaaat cagggttttg      60
aggggtttta cagggtttgg aaagagtgac atgtcagaaa tgatttgcat agcatagatc     120
agcttatttc aactagaatg attgtttgaa ccccttgtgg gtgaccatga tgaggtttgg     180
gcacatagca atgacttgca tgcttccttg tcccagtgta cgagtcagtg gacgggacgt     240
gactcctatg gtcctgcatg cttgcaccac tgtggcttct cattcaccca ggtcatactg     300
aatactgcat tgtgctgtgg tgcatgctgg caggttgcat tgtgtgcatg cacatgctgc     360
tcattcccct tgtccctgca ctgggggctg tgctgcctgg cccaccatcc accaacctgc     420
ctgcctcact cactcacccc tgtgcaagac cctttctcat taatatatgc acatgttgcc     480
tgatccattg gtaatgctgg cacaagccac aaggtggtgc cagcccttgc agtgccccat     540
gtggcaagct caggactagt gtgttgggct tgcctcccct ctcattggtc agggcaaggg     600
tcagggtcag gcatcatgca ggctgtcaag tattgtgctg ccatgctgag gacattcaat     660
ttgcaccata tgtgagcgat agcctttgag tgtgcaagca gaagcagcca cagcacattg     720
gcttgtccag acccatggca ggcctgccga ccacactggt ggcgccaagt cggcaaccgc     780
cccaccccag caagctccag ctcatgccaa ccatacaacg gcagtcgcta tatggatata     840
agcaatcgcc ggaccaaacg gctgcgtggc tggactgctg cactcactca cgtggcccct     900
ggtagcgggg tggcctaaat cagggttttg aggggtttta cagggtttgg aaagagtgac     960
atgtcagaaa tgatttgcat agcatagatc agcttatttc aactagaatg attgtttgaa    1020
ccccttgtgg gtgaccatga tgaggtttgg gcacatagca atgacttgca tgcttccttg    1080
tcccagtgta cgagtcagcg gacgggacgt gactcctatg gtcctgcatg cttgcaccac    1140
tgtggcttct cattcaccca ggtcatactg aatactgcat tgtgctgtgg tgcatgctgg    1200
caggttgcat tgtgtgcatg cacatgctgc tcattcccct tgtccctgca ctgggggctg    1260
tgctgcctgg cccaccatcc accaacctgc ctgcctcact cactcacccc tgtgcaagac    1320
cctttctcat taatatatgc acatgttgcc tgatccattg gtaatgctgg cacaagccac    1380
aaggtggtgc cagcccttgc agtgccccat gtggcaagct caggactagt gtgttgggct    1440
tgcctcccct ctcattggtc agggcaaggg tcagggtcag gcatcatgca ggctgtcaag    1500
tattgtgctg ccatgctgag gacattcaat ttgcaccata tgtgagcgat agcctttgag    1560
tgtgcaagca gaagcagcca cagcacattg gcttgtccag acccatggca ggcctgccga    1620
ccacactggt ggcgccaagt cggcaaccgc cccaccccag caagctccag ctcatgccaa    1680
ccatacaacg gcagtcgcta tatggatata agcaatcgcc ggaccaaacg gctgcgtggc    1740
tggactgctg cactcactca cgtggcccct ggtagcgggg tggcctaaat cagggttttg    1800
aggggtttta cagggtttgg aaagagtgac atgtcagaaa tgatttgcat agcatagatc    1860
agcttatttc aactagaatg attgtttgaa ccccttgtgg gtgaccatga tgaggtttgg    1920
gcacatagca atgacttgca tgcttccttg tcccagtgta cgagtcagcg gacgggacgt    1980
gact                                                                 1984
```

<210> SEQ ID NO 146
<211> LENGTH: 1006
<212> TYPE: DNA
<213> ORGANISM: Chlamydomonas reinhardtii

<400> SEQUENCE: 146

```
taagaatggt gagcattgtg tgcttggcga gaaaggggag gattgcggtg tgttaagaat    60
gcggatgtta cagaggggac agtcccagca cccgaaaacg ccgagccatc acatgctatc   120
agggcccaac ttgactccac caaccacgac tttgctgcaa accctcccgc gggcaaagtc   180
cgtgtgactc cgcgcacagt gagtcctagc caagcctcaa cccgccagag ccccaccgct   240
gtgcctcaat gccacaagcc taggcaccgg ggtgccggga acgtctagg ccacaggaca    300
cacgcacagc gcacgcacta accagggcgc aagcgtccac cgtccaggta ctagaacggt   360
cgcccacacg tgcatcctgt ccacacacaa agctaccaac cacgcacaac ctctcacggc   420
gagggaggcg gggaatcagc gtcatgcggc aagcgcaata cacgcagggg ccgcatcttg   480
ttttacaact tggctaacaa taccgaaagc tggcaagatc aaaatgtaga cctcaggtg    540
accaagaac cagaacaagt gctgatacaa atcaaatca ccagactcac agaagtaagc     600
agtgttgatg ttacggtcag tcagcaacat aaccaaagcg gcagccaata ctggtacggc   660
caaaatgacc aatacagcag tcaaagcaat ggcccatacg aacaatggca tgtgcaacag   720
tttcatacct ggggcacgca aaccagctac agtgaccgac atgttgacag cacccaagat   780
agagctcaaa ccgttcaagt gcaagctcaa aatagccaaa tctacgctag taccgctgtg   840
ttgtacgctt agtggtggat aagcggcaag cgcaaaacca cgccgtcact aacagcccga   900
gatatgaaag gatgcgcaaa cggcacgcg tcccaaccct ttggcctgat acccaaagtc    960
acaaacgtct ggagacgacc ccagacgtca gctacgacgg caagtc                 1006
```

<210> SEQ ID NO 147
<211> LENGTH: 1041
<212> TYPE: DNA
<213> ORGANISM: Chlamydomonas reinhardtii

<400> SEQUENCE: 147

```
ccacgaacga aggtaattg cccttagtgg caattgcggg cttatgcccg ctgcaaccta    60
gaaaggtcgt ggtgcagaag tccgatttag tggcgaggtc caaggttcaa gacaaggctc   120
aagatccaag gctcgaggag gagcgccatg gctcctcggt ttgcacgaac tggcagtgct   180
ccactactat aacgcggcgt ttccctagct cgatatgtta ggtgtgcagg ctcggatgta   240
gtggactttg aagagcggcc taggacttgg aggttgtagt ttcggaggtt gtgactcttt   300
cgtggtgagg tgtcagcgtg aggggggcgg gccctctcgc cctagtcacc ttgccccgtt   360
aatccatgcc aggccctatg ggccggcgtt gtaattatta ttattattat tattattatt   420
attattatta ttattattat tattattatt attattatta ttattattat tattattatt   480
attattatta ttattattat tattattatt attattatta ttattattat tattattggg   540
ggagggcgc gtggagtgac ggggagggga tgggggaggg gcgggcgat gggtggcaga    600
ggaaccgtgg cggatgcca tgaggaagtc aggaggggtg ctgggcggat gggcgccct    660
gaggtgtact ggcgaggtgt ggtgcctgga tgaagcgggg aagaagcggg gaagaaggcg   720
cctggttccc agagtgggaa tggagggaat tcccttacaa tcgtgcatac gagtgcaacc   780
cagcaggtgt ggtccgcaaa acgtccacca agcaggtgat aaaaggcaaa cagcggcgta   840
atacctggtg gtttcggcta ggtggtgtcg acgtgcgacg agcccacgtt gtcgcggtgt   900
gctggttagt gcaagcaccc ttgttgcgcc tggggcggg tggaaggtca aacccagatg    960
atgggcgacc cgtgacgcac gtgattaggt acaaggacgg caacacgctg aacgacaatg  1020
cgtccaacct ggaggtgaag a                                            1041
```

<210> SEQ ID NO 148
<211> LENGTH: 4798
<212> TYPE: DNA
<213> ORGANISM: Chlamydomonas reinhardtii

<400> SEQUENCE: 148

| | | | | | |
|---|---|---|---|---|---|
| cacatctggt | ggggtccacc | ggccctgtcg | ctgggctggt | gacaggtgtg agtcgcgggg | 60 |
| tggggaggc | gtaggctcgc | taggggtttt | ggatagtcgt | tggaggtggg cagcgtgcgc | 120 |
| ggcgtgccat | ccctgcagtg | tagggcattt | gctagcgggc | tcgctagtga cgttccagtg | 180 |
| catgtgtaca | agtaacggc | tgcatctctg | cccgtaggca | aggtgagcgt gtggtgttcc | 240 |
| cgtgtatttc | atgatcgtat | aggccgtagc | ggctccgcgc | acaatggtgg tcggcttcca | 300 |
| ggccacttca | tagtataggg | cagtttgaga | tcaccggatc | gctaactcag tgcacaccct | 360 |
| cctctggagg | gtctgattat | ggcgcttagt | gagatgctgt | cacaggttcg aatcccgtca | 420 |
| agaacagttt | tttttgccag | atcacagcga | agaagtagat | aagatcaggg cgccgcgaaa | 480 |
| tttacaaaca | aggccacgcc | ggtacaaaaa | acatgaatgt | gacaaggcac ggcgtgatgc | 540 |
| aacatcaaca | aaatacacca | aaaacacagg | aattcaggct | accaggtgta tctatacacc | 600 |
| atgcttgtcg | gttttcaagc | tcgaacatcg | cgacggacat | attgaacatg taattctgag | 660 |
| cgtgcattgt | tcggaacaca | cacaacgagc | tcgggagcgc | gaaatggcga gccaagcatg | 720 |
| tcgaccccc | gactgatttt | cacaccgcgt | cactcaagtc | cctagttgtt cgtaagaata | 780 |
| tgcatgctga | acgcgcattg | cgcacagtgc | ataatacaag | ctcaagagcg cgacatcgcg | 840 |
| agccgagcat | attgagaccc | tcctccattt | ccgagcgatt | tgcgtccccg aagtcttcta | 900 |
| actatgcata | ttaagcgtgt | attccgagct | acgttgcgaa | tagaatccaa gcggtaaatg | 960 |
| ccaaaaacaa | atcccgcgat | ccatctgtcg | gtcgactgtt | catcgaccac caacctcctg | 1020 |
| tgcgaacacc | agctggctaa | caataaccctc | ctcaaagtgc | aagggattaa ccacgccaca | 1080 |
| catcaacctg | ttgtaaacac | acaacaatcc | aacgcacgac | aagcaagcag ataaacaata | 1140 |
| ccccggcttc | acgcagagac | aggacaggta | gaaactaaac | ccgaacgtag ctcagtgaca | 1200 |
| tacgtccagc | cagcgaagcc | aagcatgatg | gtcaccacac | caaacaccaa caagaaagtc | 1260 |
| actgctgtaa | attgcagtca | gcactcacca | cccacaaggt | actccacgct tccaggtcat | 1320 |
| ctgtcagtac | acctcgcgca | tgttaaaaac | actactgcat | gcattgaaag ccttggttat | 1380 |
| gaggcagcca | tgctggcctg | aatgcgcaca | atcatacctg | gcactgctac tgctgtgctc | 1440 |
| tgcgagagc | tcaatagccg | ctgccattcc | gcggctagat | ctgcctcggg cgttagcatg | 1500 |
| gtacgcagcg | cctttttaag | ccggcgctct | tcggcccgcg | aggcccacag cggacgcact | 1560 |
| aaatgtaagg | catgcaaccc | acgaaacctg | gtgagcatta | cgtaaattga agcccgccgc | 1620 |
| caactgccgt | gctgcggttt | gcacatatcc | accagccaca | gttcgtgcgc tggcagagtt | 1680 |
| tgccctgcg | caaagtaatc | ggtgactgca | tacgcaagct | ccacacgaaa gccccagcgc | 1740 |
| atcacaggca | accgcagggt | tgcatgctgc | gatgtgaaca | tagcactgca cggtaaaaca | 1800 |
| ggaatctccc | cgacatccag | ggcctgatcg | acagacaccc | gacccgcatc aggcccgtcg | 1860 |
| gggcgcacca | ttcagccga | gggcacgaac | ttgaggacat | gcacggggc aatgcttgca | 1920 |
| tctggcaatg | gtgactcgtt | gggatgcaga | acaatgccgg | tgcctgtggc actgttgttg | 1980 |
| ttgatgtgat | acagacgcac | atgctcattt | gatgtaaaca | cgtaacgaat gccagcaaag | 2040 |
| aatgcgcaca | cagcgggcac | accgctatca | tcctcggccc | cgccaagcgc ctctaattga | 2100 |

-continued

```
tgcacatgcg aaataggtaa gctgctcccg tccggcgaca agtccgcgct acgccatagc    2160
agcagctgct gacgctgcgc gagcgcatgc agctgcacga gctgcaatgc cagtggaacc    2220
cgcacaacat ggcgctggac aactgcaaag ggctggggca cggggtcaat ccctggcttc    2280
gggggctgcc aaaacacgcg cgttgagctgc tggcacgctg tatccagatc tgcctgagag    2340
atttcctgca cgccaccaaa cttctccgct agcatgaaga gaggttcgtt gttgtcacct    2400
acgcctgctt gctgccgatg ctggtgagtg agaacgaacg cgaacggcac catattccac    2460
agctcccgcc ccatgaggtt catgctgccc tccggatgct ccagctgccg gatctggcgc    2520
tccatggccc cgccgtcccc cgcgcccggc gccagcagct gccgcaagct ctcttccgca    2580
gcaccgctat atagcggcac gtgccgtggc tgtggcaact gacgcaagtc gccaacaagc    2640
aggccatgca gatctgacag cggcccgtga tataggtgcg tgctgtctat acccacgtgc    2700
ctccgtgccg cgtgcacatg catgcaaatg cgcgcccagt gggacagccc acacgtgcta    2760
aactcatcta ggaaaatgaa gcgcacacca ttgaggttgc gctcgactcg atcgcggtga    2820
ggcggaccaa aggtgccagc agtcgcaaag aaggacgtgg tgctggtgcc gagcacgcct    2880
ggcgtagagt cctgtaaatg gaccgtgatg gcagcggccg aagtcaacag catgatcatg    2940
taaggctccc tggctgctaa accagtccac caccgccaca cttcacctcc gaactgaacc    3000
cctcttgcac cacacacccc acacacccca cacacaactc acatgcagcg cagcgcgcca    3060
cgtgtagctc acgagggcaa tgagagactc gcagcggtgc tgatatgcaa accacagcaa    3120
tgcctgcagc acccgcgact tgccgctgcc ggctttgccc gtgagcaccg agcacacggg    3180
gggctgacgg acgccggcgg cctctgctag caggagctgc gcgtacagca tgaacgcctg    3240
ctgctggtca tcgctgaggt tccataaccg cgctgtgtct tcaggcgtcg gctgcgagtc    3300
ctccgggcaa agcacgtacg gcggctctgc accagggttc gctgcatcgg gccagacgcc    3360
ctgcacctct ggggcggctg tggtaaccgc caatggcgag atgagcacca gcttcgctgt    3420
cactgctgca gtgccgctgt tgtaaagcag cagctgctgc tgcactgctc cctgcgcctg    3480
cgcgagtgcc tgtgcggcgt actgcccgcc taggtcgtaa tcatgcatgc gttgctgtgc    3540
tgcagccagc cgctcgtgtg tccactcctg cgtgctgcgc actactgctg ccgccgctgt    3600
acgcccaacc gctggccatg cattggcgcg cgggatctgg gcaaccacgg tggtcgcctc    3660
tgtagtcaga ccgccaccca ggccgccgtg cacaatgcgc tgcagcagcc ctgcgcgttc    3720
cgtctccgat agcgcacaac cctgccagag ctccgctgcg ggcgctgcgc tgcgcctaac    3780
atcgggttcc tcatcatcct gcggctctgc ctccaggtcg tccatgccct ccaacggcac    3840
gccctccaac agtgcctcct ctgccacatc ctcagcggtg ccctccgcct ccgcctgcag    3900
ctgccgccgc tcctccgccc gcattcgcac gcgcgcaagc ccatccacgt gatcaagcat    3960
acgacacgcg atgcgcacat gcagcgactg gccatccgcc ggctgtgcaa agcaccgctg    4020
ataagctgcc catgcgccgt tgctgagatc gagcatgtcg tcacagctgt aggcggcgaa    4080
gttcgcgagc gcaaacactg catagcgctc cagcacctgc ggatcgccca cgccgtccgc    4140
aggccgcaca acggggtcac acaccggctg cggcacgtac ggccgcagcc ggcgtcgcca    4200
cacgcattta ctgtactctg ggtgcgcggg atgcaagcgc agatggtgcc cttgcgctcc    4260
atctggcccg gccgagtgct gcggggtggt gggcacacat acagttcttt gctgctgggc    4320
cgtgccgaag tgctgctgca agacattata acgcatgcga gcctacggac tcaacacccc    4380
gtaactccag gcgtgcaagc tgccgcgcac acaacctcgt accttataaa acaacatcgc    4440
catcatcata ggagacagct cgcgcagcgc ctcgccgcgg tacaggtaat ctttcaggta    4500
```

```
gcttgatgac cggtaacgag caggtgcgac ggcgggctgc tctagctgct gtacgcttcc  4560
gctgggcccg ggatctggga catcgctagc gattgtgctg gcggccggaa gctggccttc  4620
ccctgtcgga ctcccgcccg ctccaacgct gcccattgta cacacgagcc gcagctgggt  4680
gtctctgggc ctgagctccg ggtccgcgcg cttcagctgc gactgcacat gctgcgagaa  4740
catcctgtaa tcgatggccc tgaactggtg gctttcgtgc gcgtcggtgc cccgcatc   4798
```

<210> SEQ ID NO 149
<211> LENGTH: 3898
<212> TYPE: DNA
<213> ORGANISM: Chlamydomonas reinhardtii

<400> SEQUENCE: 149

```
cttccacgta cgcctctgca ggtgccctcg cttcgtgtgc ccatcaactt ccttacaccc    60
ctccatgccg tgttcaacga gaacctcatc gtcatccctc cccgtcttcc tgctgccgcc   120
gctgaccctg cgctacctgc cattgctgag gatgctggtg ccgtcggtgc cactgctggt   180
gcagccgctg ctgctgacgc tgcgcccgcc gccatcgctg gcgctatgct gcagccgcca   240
gcaggagatg acgatggtga cttacagctc gaggacgtcc caatcttcta cgcaggcctc   300
ctcaacgccc tggtgcgccg ccctctgtc acggcccagg tgagcctacg cagctgtgct   360
ccacaacaac ctcttagtcg tactccacct ccataccatt gtatctgcac tcccagcct   420 ccctcgcttt gcacggtgtc catacatacc actgccaccc ccttctcca ctggcccctc   480 cccactcgtc cgtgcctcag atcgtcctct cgctccgcac acccacctcg cgccgcgcca   540
tcctgaacaa gctgcgcgag cccacggccg gccgccgtgc tctgttcctg atggccgcgc   600
aaaaccgcgg cgaggagata accgcgacaa tggagaccgg tatcatgggc gtcacgcccg   660
acactccgct cctgatccac atcctagtcg agctcctggt gcatgaccaa acatgctca   720 cgctcaactc caacatcgac caggccgcct tcaccagcca cgcgccggtg tatggtgcct   780
tcatgccagt ggtgctcgag taagtgcgca agccgccctc ctatataggt tgggctacgt   840
acctgccaag ctcggccccg catcacccaa ccagtttgct caccacactg cgcttcatcc   900
aaacctgcct acctgcagca caacaaccct catcggctac ctgctgtcgg ccgcgctggc   960
tgcatacgat ggcaccctgg tgcgttccct ggactgcgct catgccatcc accacccgcc  1020
actccacctc accatgcgtg cctctcgcat ctcctgagtg cactccacct gaccatgcat  1080
gcctctcgca tctccccgca ccttgaaggt caccatgccg cctgatgtgg cgcgcgtcgt  1140
ctacggagcg cagctggacg ccgtactcgc ttgggccgcg cagtccgctg gctacgagcc  1200
gcagcacgcc cggatcggcc gttggactat cgcgggcgcc accgtgcagg cgcagctgcc  1260
gtaatgctga ttactcctcc acgactgatt acgcctccac ctctgcttag aaccaacctg  1320
cattcctcgc tttcatgcgc agcatgtgtg cacggaggcg tttgtgaagt gcttggtagt  1380
gcgcgcaaat gcgctattga aaagctgtgg ctgttgcgta gatgtatctt ctgtgcggct  1440
gcttgacatt tcctagtctc agtgcttaca gcctggcgca gttctgctta tggtaccacg  1500
acaaacacat tgatgttgca cgttgccaac gttgcgagtt ctgcacacct tcattgtata  1560
caaacgctca tctcatgcca ttgcactcgc tgcctcctgt ccattccagc acctcagcca  1620
atgcactgcg cctcatgcgc ctcaatgcag cacccacta cctttgcaag ctttcgccag  1680
cacgacaccc cgcgcatctt caccacaaca agcagctacc cctacttcta cttccgctgc  1740
agcccagccc caaccgcaac cctacactgc tacctgacta cagccacgct gtcttgttac  1800
```

| | |
|---|---|
| attgcccttα gcgcacccac acgccctcac agaaaaaccg gttccccaac gcatgcccct | 1860 |
| gcccacagct ctaccccaca atccagttca tcacccaccc actccatcca cttgcttggc | 1920 |
| gcaaatggca cagtccttt aacatgcaaa tgcgaacacc tgtacggcca ctcgctgtct | 1980 |
| cacgtgcatg gcccaactcc cactgcaaca caccaactcc ccagcagcgt tcgcgcctgt | 2040 |
| tggcgctgcc taccaaactc ccgctgttct tgctttattt gcgttgtgta ctcccatgac | 2100 |
| ctctcactta cacagcccaa cacgcctcta cacgaaccac tactacccac ccgctcctcc | 2160 |
| tgctacaggt ctcaggactt gcccttgaag tcctgccata ccaggcactt cacaatgtcc | 2220 |
| cggtgccact tcaaccctcg cacagcaaac gctaaatgct cgccctcggg cagcgcctcg | 2280 |
| ccgtccagcg cgctcttcag gagctcgtcc cgctgcttct ggatttcatc ccgccgcgcc | 2340 |
| ttccgatccg ctgctgtacg tgcagccaac acgcgcttca tgccctgtac ctgcagctcc | 2400 |
| tccatcttct tctttccgcc agatgccttg atcagccgcg ccacacgctc catggccggc | 2460 |
| acacgcagga aatgcgagta gccataccgc cgcgcgtcgc cagtggactc cagcacgggc | 2520 |
| gccgtcccat gcgtgaccat gccagcagcc agcaccacga tcgtcatgtc ggtcggcagc | 2580 |
| acctgcaaac aacagcgccc atatgacttg catgtccgca ccgcgacctc actatacgcg | 2640 |
| cgcctggccg acacacacaa aaccacaccc gcccgcagag atgcaccacc tggccattta | 2700 |
| ccttgatgga ggcgccaggc atcaagaaat gcccgccgtc caggctgccg gcaccgttgt | 2760 |
| ggcgccacag catgatgctg tacggccctg cgtgtcaatt cccacgcgaa gaaattcaca | 2820 |
| ctcattagca gcacgcagat agcagaccag caccaccacc ttgcctcaca gtacgcccac | 2880 |
| cctcccagat ctacacaagc cagctcgcac gcacacccac tcacccatcc accgccgcc | 2940 |
| ccccccccc ccccccgccc acacacacaa atacacaagc agcgcttccc tgatatacac | 3000 |
| ccctgcgcac cagcctcacc gtccgttgtg tcgaagtgca acgacaccgc gcagttcttg | 3060 |
| gtcatgctca cgaggttagt tgccgtgtcg ccgtacatcg cctggcgccc ccaggcagac | 3120 |
| aagaactcat ccctgcgcgc agacccgag cgtgcagcac cacacatcaa tgctacgtac | 3180 |
| gcgacgcccc acacaaccat cctgcacgta ctgcccttgc atgcagcccc gcggctacgc | 3240 |
| ggcgccctca cctgtacttg gtcaggtacg gcgcaacctg caccgccgcc tcccacaccg | 3300 |
| ccgtacacat ctcctccagc gcctcctcga tgctgaatgg ataatgctcc gcctcgcact | 3360 |
| cgtagatgat ctggttgacg tacctgcaca gcaacgtatc agtcaatctc ggccccaccg | 3420 |
| cacatccatg cctctcctcc atgcccgcgc cacccttgcc gcccgcatgc aacacccccc | 3480 |
| tggtgctctt gcctgcagat gatgtgtccc acgcgagcag gcgacgccag ccccgccatc | 3540 |
| cagaagttgc cgtcgtagtg cttgtcgatg tgagcccagg cgtcgccatt gtggacctct | 3600 |
| tgacacgtgc gcgccacctt gttgcgcaga gcgcgcccg cctcgcccga cacctgcagg | 3660 |
| caagcgcgac agcagcatgc tgaacacgca caccgccata caaccgataa catgcaacaa | 3720 |
| catgcgcccg accgcagct tattcgcacc tgccctacag agacgagcgg cgcgcgttgc | 3780 |
| agcccaccat ctgctgtgcg ccgcacggca cacaccagca cgtcctgccc ggtgacatcc | 3840 |
| agcaggccga acgggcactc cgcgaaccac tgctggtacc acgaggtttt gtcgccgc | 3898 |

<210> SEQ ID NO 150
<211> LENGTH: 603
<212> TYPE: DNA
<213> ORGANISM: Chlamydomonas reinhardtii

<400> SEQUENCE: 150

| | |
|---|---|
| ctgcaaccta gaaaggtcgt ggtgcagaag tccgatttag tggcgaggtc caaggttcaa | 60 |

```
gacaaggctc aagatccaag gctcgaggag gagcgccatg gctcctcggt ttgcacgaac    120
tggcagtgct ccactactat aacgcggcgt ttccctagct cgatatgcta ggtgtgcagg    180
cttggatgta gtggactttg aagagcggcc taggacttgg aagatgtagt ttcggaggtt    240
gtgactcttt cgtggtgagg cgtcagcgtg aggggggcgg gccctctcgc cctagtcacc    300
ttgccccgtt aatccatgcc aggccctatg gccggcgtt gtaattgtaa ttattattat    360
tattattatt attattatta ttattattat tattattatt attattatta ttattattat    420
tattattatt attattatta ttattattat tattatgatt attatgatgc acccgagtcg    480
gcgcacgccg ccacaggcac ccatgtatgc aactaaatgt cctgaggctg ctgcgtgggc    540
ttgcaccgtc aaggcaggtg gcgcaggcgc gagggtgccg tggcggcggg ctggtggggg    600
agg                                                                 603
```

```
<210> SEQ ID NO 151
<211> LENGTH: 419
<212> TYPE: DNA
<213> ORGANISM: Chlamydomonas reinhardtii

<400> SEQUENCE: 151
cacacacaca cacacacaca cacacacgtg ccgtgcaggc tggtagacat gtcccctcc     60 atcccccctc cccctcggt gtcatttcgc ctgcacaagc ctccaaaggc tacacatgcc    120
ttgtacagac acatgaacgt gccgtgcagg ctggtagaca tgcccgcctc taccctccct    180
cccccctcgc tgtcaattcg cctgcacaag cctccaaagg ctaccatgc cttgtacaga    240 cacatgaacg tgccgtgcag gctggtagac atgcccgcct ccatcccccc tacccccctc    300
gctgtcaatt cgcctgcaca agcctccaaa ggctacacat gccttgtaca gacacatgaa    360
cgtgccgtgc aggctggtag acatgcccgc ctctacccc cctccccccc ctcgctgtt    419
```

```
<210> SEQ ID NO 152
<211> LENGTH: 273
<212> TYPE: DNA
<213> ORGANISM: Chlamydomonas reinhardtii

<400> SEQUENCE: 152
ctcacaagtc tccaaaggct acccatgccc tgtacagaca caagaacgtg ccgtgcaggc     60
tggtagacat gccccctcc atcccccctc cccttctcgc tgtcaattcg cctgcacaag    120
cctccaaagg ctacacatgc cttgtacaga cacatgaacg tgccgtgcag gctggtagac    180 atgccccct ccatcccccc ctcccccct cactgttaat tcgcctgcac aagccccgc    240 aggctatcca tgccttgtac agacacatga acg                               273
```

```
<210> SEQ ID NO 153
<211> LENGTH: 1890
<212> TYPE: DNA
<213> ORGANISM: Chlamydomonas reinhardtii

<400> SEQUENCE: 153
tggccgcaac agaaaatctg gaaatttggg caaggctaaa ctcaagtgtt cttgctcagg     60
ttgcgtgggc agactcgtaa gtaacccgca gaatgagtgt gccgctgcat gggtggactg    120
tcaaccatat tgtgtgatgc aggatcctgg gcacctggat tcatcagcat aatcatggcc    180
agcatggtga catttttaatt ggttgggaca agcgtggcct acactaccga gcattgttgg    240 cttttccttgt aaacattgca gaccttaaga gtgtgcggtc tggggcaatc ccccagtcac    300
```

```
ccagtgagcc ggttgagggc tactgtgtga gcactactct ggttgggttt ctgcggtgcc      360
tagatatact gcaccggctg cgcggcttca ccatgtgtcc aaatgtacgg cgagggctac      420
gggagtacgt cctgcgagtg ctgcgtaaaa tggtgagccc tcggtcttta aactgctgag      480
gggattgtcg cctgaccccca tgcatgtgat tcatacgcag tatcctcatg tcatacggac     540
tgcaaagccg gttcttccaa cggtacttgc tgacatgcag catgttagcg agctgaagcc      600
tatgaaggca tctttggacc ataacacaca cacccgttac atggcagact acagtcataa      660
gtgggcaacc atccgcatga tggttcacat ggcgtgggct ggacgtcgaa tggggcatgt      720
gatgaggctt aagctggggg acttgcagtt tcagtactgc tcctcatgta ctgtcagcac      780
ttccagcacg gcaacatcat catggtacct gaagctgcgc attgcatttg ccaagaacaa      840
gtgtactgac ggcagctttc agagtgtcat actaaactca gagaataata ataataataa      900
taataataat aataataata ataataataa taataataat aataataata ataataataa      960
taataataat aataataata ataataataa taataataat aataataata ataataataa     1020
taataataat aataataata ataattacaa cgccggccca taggtaacgg ggcaaggtga     1080
ctagggcgag agggcccacc cccctcacgc tgacgcctca ccacgaaaga gtcacaacct     1140
ccgaaacaac aacctccatg tcctaggccg ctcttcaaag tccactacat ccgagcctgc     1200
acacctaaca tatcgtgcta gggaaacgcc gcgttaaagt agtggagcac tgccagttcg     1260
tgcaatccga ggagccatgg cgctcctcct caagccttgg atcttgagcc ttgtcttgaa     1320
ccttggacct cgccgctaaa tcggacttct gcaccacgac ctttctaggt tgcaccgggc     1380
ataagcccgc aattgccact atgggcaatt accttcattc gtgggatcac caatcggttt     1440
cgcaccaatc tttcaccttt tgcataattg ggcttttatc cggatttgtg cccgggtccc     1500
ttctgccgta aggacgagtc aaatcgctaa actagttagc aatccggtga tgtactaaac     1560
tcagagcatt atcagcacag catgttgcag caggaatttg atgagcggtg aaggcctgtc     1620
caggggttga gcggcgagga agagggagtc agtgacgcgt ttgcagaggt tatacttgct     1680
agacgcaggg taaaagcaag gtggagccgg cggaaggcag aagcggggta gggccggacg     1740
cggggtgcga gggggtgtgt gagatgggac agggttcagg caggttggcg aggtcccata     1800
gggtgcagct gacgcccgta ccccaagcag acagtaaaca gtttgcagcg gcagagcagg     1860
agtgcatggc tggtcgaacg ccggagttac                                       1890

<210> SEQ ID NO 154
<211> LENGTH: 226
<212> TYPE: DNA
<213> ORGANISM: Chlamydomonas reinhardtii

<400> SEQUENCE: 154
atatgttagg tgtgcaggct cggatgtagt ggactttgaa gagcggccta ggaattggag       60
gttgtagttt cggaggttgt gactctttcg tggtgaggcg tcagcgtgag ggggtgggc      120
cctctcaccc tagtcacctt gccccgttaa tccatgccag gccctatggg ccggcgttgt     180
aattattatt attattatta ttattattat tattattatt attatc                     226

<210> SEQ ID NO 155
<211> LENGTH: 1216
<212> TYPE: DNA
<213> ORGANISM: Chlamydomonas reinhardtii

<400> SEQUENCE: 155
taggcgcagg atgtagagcc gtcaagtaag gtccgacctc ggtgtgagaa acttcaactt       60
```

```
gtttttgaca gctgttacag gcatagtgac agctaagact tcgcatataa ccaattgaag      120
atattagtcg tcaacatcga ctagaagcgc tgacttggtt cgcgagtcag cgagtcaaca      180
tggctgcaag ctcacttgcg ggctcgcatg cagaccttca ccatccgccg cgatctgccc      240
gatttgaaga gctaaactta tattaattcg ttctacttat tcattacaat aattggagtt      300
ctcaaactcg gcctgaatag aaagataaat gtttgctctc accaccaggg gccacgtgag      360
tgagtgcagc agtccagcca cgcagccgtt tggcctggct ttcgatttaa tacatatagc      420
gactgccgtt gtatggctgg taccatccgg cgcttgctgg ggtgaagcga ttgctgactt      480
ggtgccaccg ctgttgtcct aggcctgcaa agggcatgag gcatacctgt cttgccatgc      540
caccgtgctg tggctgcttc agcttgcacc tgcaaagctg tcattcacat atggtacata      600
ctgattgtgc ccagcatggc tgcacatcac ttgacagcat gcatgatacc tgaccctggc      660
ccatgagagg gaaggggagc ggagcacaca tgtgcagagc cgcatggggc actgcaaggg      720
ctggcaccac ggctcccagc ttgtggttgc attacagaca tgtcaggcaa catgcgcata      780
catgcacctg aagggtcttg cacaggggtg agtggggcag gcaggttgga tggtgggtta      840
ggcagcacag ccccccctgtg tggcgtgcca agggggaatga gcagcatgtg cttgcacacc      900
gtgcatgtgc aatctgtcaa catgcaacac agcacaatat agtatacaat tggatctggg      960
tgaatggcag gccacagtgg tacgagtatg cggggcaatg gaagtcccac cccgtaccac     1020
ctactcatgc ttggtaacaa ggaagcaatg gggcatgcaa catcattgct acgtccccaa     1080
atcacattgt ggtcacccac aagtgattcc aacaatcaat ctagctgtta ttatgctatt     1140
tatgctgtgc aaacccttc tgacatgtaa cacatttcaa acctgtcaaa accccctcaaa     1200
accccccttt agggtt                                                     1216

<210> SEQ ID NO 156
<211> LENGTH: 269
<212> TYPE: DNA
<213> ORGANISM: Chlamydomonas reinhardtii

<400> SEQUENCE: 156
gcggttgcgc ggggttatag gtgcgcgggg ttgcgggctt tcagactagc gcgccgggcg       60
cgcgaacaag ggcgcggcgc ggcgtctatg cgccgaaagc caaaaaatct agcgagaccc      120
ttaagagcgg gggcaataat aataataata ataataataa taataataat aataataata      180
ataataataa taataataat aataataata ataataataa taataataat aataataata      240
ataataataa taataataat aataagagg                                        269

<210> SEQ ID NO 157
<211> LENGTH: 914
<212> TYPE: DNA
<213> ORGANISM: Chlamydomonas reinhardtii

<400> SEQUENCE: 157
cggggttgcg ggctttcaga cttgcgcgcc gggcgcgcga acgagggcgc ggcgcggcgt       60
ctatggcgcc gaaagccaaa aaatctagcg agacccttaa aagcgggggc aaataataat      120
aataataata ataataataa taataataat aataataata ataataataa taataataat      180
aataataata ataataataa taataataat aataataata ataataataa taataataat      240
aataataata ataataataa taataataat aataataata ataataataa taataataat      300
attcaacttc ggcaccagac ccaccctgaa gcccgcatgc ccggccgcag cacggcatgc      360
```

| | |
|---|---|
| acgagtgcac gcacacgcgt ccagccacct ccacccggcg gaccgccatg cgatccatgg | 420 |
| ggcgtgcccc taagggtgtc aagggaccgc cggtggttct agattgcatt ggtcccttcc | 480 |
| tagcccctg catgctagat tgcattgtcg gcctatgggg acattgcacc ctctcccact | 540 |
| ccaggacaaa tcgtgtcccc agggaggcgc ccacctgacg gcacccaaaa ccccctgata | 600 |
| gatagttctt taaggatgcc accacgccgt ccctaactga aggacaatat atcagggggt | 660 |
| tttcaagcca aacccgccag ttgaggaggc caggagacgg tgcccaaac aaaacgcaga | 720 |
| gcgggataca gactccgcca ctcaatgtat atgttacatg caatctattg tagcaatagc | 780 |
| gcttgacggc aggctaaaac gtgctcgccg acgtcaagt cacgacattg accgaccaac | 840 |
| atcggcgttg ttttggggcg tgatcaattg ccgtcaacac agatatctgc atagatgtaa | 900 |
| tcaggctact atct | 914 |

<210> SEQ ID NO 158
<211> LENGTH: 1237
<212> TYPE: DNA
<213> ORGANISM: Chlamydomonas reinhardtii

<400> SEQUENCE: 158

| | |
|---|---|
| catcccaaag taacccaaaa aatctaacgg ggcatatagg agcggggggca aataataata | 60 |
| ataataataa taataataat aataataata ataataataa taataataat aataataata | 120 |
| ataataataa taataataat aataataata ataataataa taataataat aataataata | 180 |
| ataataataa taataataat aatattatta ttattattat tcggctttgg caccagaccc | 240 |
| accctgaagc ccgcatgccc ggccgcagca cggcatgcac gagtgcatgc acacgcgtcc | 300 |
| agccacctcc acccggcgga ccgccatgcg atccatgggg cgtgccccta agggtgtcaa | 360 |
| gggaccgccg gtggttctag attgcattgg tccttccta gccccctgca tgctagattg | 420 |
| cattgtcggc ctatggggac attgcaccct ctcccactcc aggacaaatc gtgtccccag | 480 |
| ggaggcgccc acctgacggc acccaaaacc cctgataga tagttcttta aggatgccac | 540 |
| cacgccgtcc ctaactgaag gacaatatat caggggggttt tcaagccaaa cccgccagtt | 600 |
| gaggaggcca ggagacggtg ccccaaacaa aacgcagagc gggatacaga ctccgccact | 660 |
| caatgtatat gttacatgca atctattgga gcaatagcgc ttgacggcag gctaaaacgt | 720 |
| gctcgccgac gctcaagtca cgacattgac cgaccaacat cggcgttgtt ttggggcgtg | 780 |
| atcaattgcc gtcaacacag atatctgcat agatgtaatc aggctactat ctggcctgat | 840 |
| atggcgtgtc ctggcgaacg cgactgtcac atgtagatgt ttgaggtcgg ccccggctca | 900 |
| atgaagtgcc ccggagttac tctaatgcgg tagtagatgt tatacgaatg gtacttggct | 960 |
| ggggacacga ccgcccgta gggccgtgcg cgagttagac gttgccgacc aacctcgcag | 1020 |
| cgccaccttg ccggttcctg aggcgcatgt aattgctata tataaatatg ggtccctttt | 1080 |
| atggggacac gcggccacac accggtgctc gcgcagatcc ggacctcaac tcggcgacgc | 1140 |
| agcgttctta agtgggggc caaattctgt gcgctgtatt tacaaaactg ggtccctcac | 1200 |
| ggctgcccgg acagcaaatg gccgcggttc cgacaca | 1237 |

<210> SEQ ID NO 159
<211> LENGTH: 1875
<212> TYPE: DNA
<213> ORGANISM: Chlamydomonas reinhardtii

<400> SEQUENCE: 159

| | |
|---|---|
| tgtcttcagc tctgctaact ctgctgggcc agtaggtcag cgatggcccc gaacatttcg | 60 |

```
cggtgattgt ttacgtgtag ggactcgggt tctagaattg acagcgcacg ggtgcggaca      120
cataggtcat gcatgcgtta gcacaatgca gacatcatac tcggctatct gatacctcat      180
cttattggtc ttatgagctg aacacttcac catgtcgtaa cccaaagaca tcagataatc      240
aaaatacttc tgatgcatgg atggatgcgt gaggtatagc ttcttgggtg tcatcaggaa      300
cggaacaagg gtggcctccg gcgaccgcaa atatgaaaac atggcatccg aaacgccgac      360
ccaggagtcg gagagaatgt catcgactga acaatgccg ccggggtgca ggctgcaggc       420
tgcaagttta gtgtctcgta gagccgcatc ataaaaatgt ccgccgtcta cactgaaaaa      480
acggaactga ggaatggacc ttgttgaaaa cgttttcacc gtaatatcca tggagttccc      540
ttcaataaca gtaaaattag tgtgagggga aaatcgtcgg gcgttgttaa gaaatatctg      600
cagatctcct cgcccagagc cgtctaaatt ctgtgtttga tgaccaaata aatccatagc      660
aattaccggc tcttccggag cagcagacaa tcagaggcca atgatgtatt taccgtgatg      720
tactccgatt tcaccaatgg aaccgtaaat attgttctga tgctgatacc ttgttagaag      780
tatactgaca ttcaaatcaa atgtagtcag ccagccacca agtcttgaca ttccagtttg      840
gtactcgagg atgagtttgt cttgcataga aatatcaggc aacgtattac tatcgagttt      900
tgaaagtctt gcatcgcaaa tgacagccga ctggcaaggg ccagacagca acagcatcgt      960
acataagtaa aggtatatta gtctgaccat ctctcaagag gcgaacgtaa tccggaacct     1020
tccggaaatt tcactgcgaa accatcaccg ccaaccccca ccctgtgcgc agcacccgta     1080
aaaacccggg aattataaaa acttttgcgc tgtaacgcgg gctgtcactg aggcactggc     1140
cacgatgcag ctgtgtgacg gcaggcctgc accgcattga ccttcccagc gtatgagcac     1200
ggagcgtgga gaggctggac ggccaccaca cccgaccctg tgtaccagca gctgtcctgg     1260
gcacttgcgg ggtgattaag atgcgcctgc ggtgatcaca gcaatagtcg gaggtaccag     1320
atgtgtggtc gggagatgat tcagtcgaat ataccaggag gcaggagaac ctgtaaagga     1380
aagaagtagg aagggagaaa aggggaagag acttggcggc cggctggccg gacctgcacg     1440
ggagaaggcg gggatagaag ccgtggcctc aggcagagcc tgggcgtagt tgttagggcg     1500
tgtagaacgc cagaggtatt ggataggagg gaagagcggg actaccctat aaggctgagt     1560
aaccgctggt gtcgtacgcg ccgctgatgc gcaacccggc tgaactgagc aagctgggct     1620
ccctggcaag caagtcgata caacaggtgt gtgctccgct cacaggcaag caatccgatg     1680
cgaatgctac aggctgcacg cacaggcagg caagtcggtg caacagatac gagttgctta     1740
cacccaaggc tggtggatac agtatgcaga ccagatggct ggtagaagag agcaggagtc     1800
gggagcggta gtctgtcgca atcccgaagg gaaaccggaa gggggggagt agggagacag     1860
taggctggat cggtc                                                      1875

<210> SEQ ID NO 160
<211> LENGTH: 2938
<212> TYPE: DNA
<213> ORGANISM: Chlamydomonas reinhardtii

<400> SEQUENCE: 160
aggcttggtg cgacctagtt gtgaggggg ggcggctacc gctagcgtct ctggctgctt        60
agtcgtagac ttaggcttcc taaggcaggt gctgtgcagc tgtgggagtc gacctggaat      120
gttcgtcagg cccctagatt gactagtgtt gcggaactaa tgcgtacgta gaccagagcg      180
gaaggcggag tgggcttgca ggcggcacga gagtaggcag tcagtagcgc aagttgtgaa      240
```

-continued

```
ttcacatgtt acctcgtaac cgacggtaaa cgctgtggac gttcgcgccc atggctggct    300
gacggaaggt ggctgctgta ttgggatggc tgggctggac gacggcggcc gggctggcgt    360
cgggactacc agaaaggatg cgcgcgaaaa ccgcaatgcg cgttcagcat gcatattctt    420
acgaacaact agggacttga gtgacgcggt gtgaaaatca gtcggggtct cgacatgctt    480
ggctcgccat ttcgcgctcc cgagctcgtt gtgtgtgttc cgaacaatgc acgctcaaaa    540
tacatgttca atatgtccgt cgcgatgttc ggcaaatagg ccaatgcgca acggagtgcg    600
gcgcttgcgg acccaaaggc ggtgccgggt gtgccgtggc gagtgtgtag aggacgagag    660
gcacgtcttg ctcgaatgtg gagcttacac agagctaaga gtggcatatg gaatcaatag    720
taattgtgtg aaggaagtca tgcttagcac agaggttaga aaattagccg cgttcctgta    780
ctcagtgcag gctctgcgtg ctagcattct gcggggcgat tgagcggact gaacctgctt    840
tgttctgcta tatgcgcctc cggactcaaa ggagttagtg gggccgcatg gactacgacg    900
ccatgtaaat gctcatgctc atgcgatgtt ggagcttgaa aaccgacaag catggtgtat    960
agatacacct ggtagcctga attcctgttt tttcgcgatg tcggtgtatt ctgttgatgt   1020
tgcatcatgt cgtgctttat cgcattcttg gtttctgcac ccgcgtggcc ttgtttgtaa   1080
aatttcgcgg cgccctgatc ttatcttgtt cttcgttgtg atcgtgtgtc aaaaatttgt   1140
ttttggcggg attcgaacct gtgagcacta cgctaagctc cataatcaga ccctccagag   1200
gagggtgtgc aaactagtta gcgatccggt gattcgggcg cgatactcc ttagcttgga   1260
tgtgacagac ggcggtactc cttagcttag acttcttggc aatgcaactg tacgggcgta   1320
cgacggggc cctcgccatg agtataaaag cagccctctt ccagccgtta caggtagacc   1380
cagacttgag caagcgcgca agacccagac ttgacacgcc aatacgcaca accaagtcat   1440
ccggtgaact ctaatactga ctcctgtttc cctcgctcta cgcgagcctt tgtaaagaac   1500
cgtgtgccct tctcgctcct ctgtccctct gccccggttc ccttggccat agcgcccatc   1560
acagcccgca gggctctctc acggcagctg gacagccatc tgcgcacagc ctctccgtcg   1620
ccccaacgtc tctctcttac aggctcgcag gaaccaagcc aaggcccgg tcgccccagt   1680
gcaccccgcc tttccctcgt ctccccagcg agcgagtgga ctacccacga gcgcagtact   1740
cgcggacgaa cgtgtgacag ccgtgtcctg tcacctgcgc cctgcgccgc ctctccctct   1800
tcccaacctc tcccgcaggc gctccttctc cctcaacgtg ccgccccact gcagcacgat   1860
tacgacagct ctctggcctt ccccagcgag cgagtgaata acacgagtga gccctcgtgt   1920
gcctacgtgt gacggccctg cctgtcactg gcttctctcc ctctttctcc tctctccctc   1980
tctctaccgc ccgccgcagc gtgtcctccc acctgcatca cggcccctgc ctccgtttac   2040
gcagacttcc gctgtaagac gcatctcgat taactcaaca acgcttccgc acttatctct   2100
caaaagctaa aacagcctcc agcacacaca catacggtat cgtgatcaga gagcttccgc   2160
tctactgtcg cttccgcagc ctcagccgag tgacacacgc gctctgtcct cacacagaca   2220
cgtgttacag gttatacaac gatccttggg cacgccggca tacgtagcct ccgcgaaaaa   2280
aattatgtcg tggacgcgtt ccgcgcaggc ccggcgggct ggctgcacac taataccttg   2340
cagctgtgcc gagataggcc ttcatcgccg agttcgccga cttccccgtc tcgcggctt   2400
caccgacgct ggcgttccag gctcgcacgc tcagtacttt gcattacatg ctattctttg   2460
cagtggcctg catgtgcgaa gcgcgaaact ggcgcgacat aactttcttc cttcaatgcc   2520
tgccgcgctc gtgtttcgcg tgtaacccta ccgctgttgc aattcactgc attacatgct   2580
atagtgtggc gctgcgtgtg tgcgtgtaac gcgtgtgtgc gagaagccgt gcgagaagcc   2640
```

-continued

```
ggtccagggt acggtccggg gtacgctggg cgctaagtgg tgtagtcctc cgctctgctc    2700
tacgctacgc ttcgaggagc tacggcgatc cgctctgctc tacgctacgc ttcgaggagc    2760
tacggcgata accggagggc cccgctgcgg gaactcgatg cgaccgcaag ggctcttgcc    2820
cctccccctt cggggggaagg ggcaagccaa ccagggtggc tgcctagctg tggccgggct   2880
gacgcgaagg ctgacgggct gctgtaaatg gtgagccgag actggtatga aaggctgg     2938
```

<210> SEQ ID NO 161
<211> LENGTH: 2223
<212> TYPE: DNA
<213> ORGANISM: Chlamydomonas reinhardtii

<400> SEQUENCE: 161

```
tgagatttgg gcacatagca atgactttgc atgccccact gctccctcac cgcctcccag      60
gatacggcat gtgactttaa tggccctgga tacttgcacc actgaggctt ctcattcgcc     120
caagtcatac tgaatactgc attgtgctat ggtgcaggct gacagattgc acatgcatgc     180
tgtgcatgca catgctgctc attccccttg tccccacact ggaggctgag ctgcccaacc     240
cagaatccaa catgcctgcc tcgctcaacc ctgtgcagga ccctttcaca tgcatgtatg     300
cacatgttgc ctgacctgtt agcaacataa gctaagtgcc gtggtgctag cacctgcagt     360
gcctaatgcg gctctgcaca tcagggcaag tgtgcacggc ttgcctcttc cctcatgggt     420
gagggtcagc tggtcaggta tcatgtaggc tgtcaagtaa tgtgcagcca tgctgacggc     480
attcaatgtg agtgatgggc tttgggagtg caagcagaat cagctgtaac aggttggtgc     540
gtcaagatcg gcatgcctcc tgcccggtgc aggcctgtgg tggcaccaag ttgacaaccg     600
cttcacacca gcgagctcca gcttgcacca atcataaaac ggcagtcgtt atatgtatac     660
aatcgatagc caggccaaac ggctgcgtgg ctggactgct gcactcactc acgtggcccc     720
tggtagcagg gtgccctaaa tgggggtttt aaggggtttt gcacggtttg aaaagtgtga     780
catgtcagaa atgatctgca cagtataatt cagctaataa tgactagaat gattgtttga     840
accccttgtg ggtgactgtg atgagatttg gcacatagc aatgactttg catgccccac      900
tgctccctca ccgcctccca ggatacggca tgtgacttta atggccctgg atacttgcac     960
cactgaggct tctcattcgc ccaagtcata ctgaatactg cattgtgcta tggtgcaggc    1020
tgacagattg cacatgcatg ctgtgcatgc acatgctgct cattcccctt gtccccacac    1080
tggaggctga gctgcccaac ccagaatcca acatgcctgc ctcgctcaac cctgtgcagg    1140
accctttcac atgcatgtat gcacatgttg cctgacctgt tagcaacata gctaagtgc     1200 cgtggtgcta gcacctgcag tgcctaatgc ggctctgcac atcagggcaa gtgtgcacgg    1260
cttgcctctt ccctcatggg tgagggtcag ctggtcaggt atcatgtagg ctgtcaagta    1320
atgtgcagcc atgctgacgg cattcaatgt gagtgatggg ctttgggagt gcaagcagaa    1380
tcagctgtaa caggttggtg cgtcaagatc ggcatgcctc ctgcccggtg caggcctgtg    1440
gtggcaccaa gttgacaacc gcttcacacc agcgagctcc agcttgcacc aatcataaaa    1500
cggcagtcgt tatatgtata caatcgatag ccaggccaaa cggctgcgtg gctggactgc    1560
tgcactcact cacgtggccc ctggtggtga gagcaaacgt ttatctttct atacaggcca    1620
cgtttgagga cgctgttaaa agcaatagat aaaggataga acatttagta gtatgcgttg    1680
cttatacgct cccgccagct cttgttggtg gcgtgatcgc ggcacttggc gagatcgaag    1740
tctcggcggt catggtcaaa gtcgcgccaa ggtcaaatag acaacattca atagttgaga    1800
```

| | |
|---|---|
| tttgcagtca tcgtgactga ggaaagcctt acaagttgca gctgtcaaaa agagtcaatt | 1860 |
| ctgcaattcg cttgagcctt tcttgctcgc ggctgtttac cttgtgaccc tgcatgcata | 1920 |
| caagcatacg tatgttagga ttggctccga cggcgggct ggagagaact cgaaggactg | 1980 |
| gaccaaacga atgtcgctgg agcgtcgtgc taacttcact ttgccactgc tcctctgagc | 2040 |
| cggtaggagt cggcaggcgc acaagcgcga tggagacagg gagacaaggt gggagacaat | 2100 |
| gaggggagg gacacaggga gggacccagg cagaggcagg gatggagggt tatgtgcacg | 2160 |
| agcccaataa gtcccacaag tcaaggttgg gagtcgtcgc ccaacccaga agagggagg | 2220 |
| gag | 2223 |

<210> SEQ ID NO 162
<211> LENGTH: 1949
<212> TYPE: DNA
<213> ORGANISM: Chlamydomonas reinhardtii

<400> SEQUENCE: 162

| | |
|---|---|
| cgttttgata acgaggctcg gtctaaaccg tgtgaatatg aagcagggct cctatcttaa | 60 |
| tgtctccaga cattaaacgg ccattttggc cattttccag acaaacggag ggggggttc | 120 |
| acgcacgctt ttgaacaaaa caagcggtgt ctgaggagag gcaaactcta ccatagtgac | 180 |
| atatatattt tgtggaaagt gagggaatgt catggtcttt taggagattt tcggcgatct | 240 |
| gacgaggatg aaggataccct cgatcaaatc ttccctttg cagatgcgca gagccggtga | 300 |
| cgaggatttg ccggggatgc cgcatttttca gtcacgcaga gttgtcaggg gtgcaaagcc | 360 |
| cgctgcaact ccttccacag tccatggtcc agctaacccg cgcacagtga agaaaagctg | 420 |
| agacgataga ggtcaggaat gaacagaagt cagggatgga cccgtgcac gggcggaacc | 480 |
| gtggagctgc ggaggggttg aagaaaacag gcagggacga ggcgcgcggg agagggggta | 540 |
| tacagcagcc ttgacagcag cttcgtattg gagtgcactg aaccactcgc actcagggcg | 600 |
| gggctgctgt caagctcaac catgctactc ctccatgcgt aggggaatca acaagaacgg | 660 |
| gacctgggaa aggaccgggg aaaggaccgg ggaaaggacc ggtgaaaagg accagggaat | 720 |
| tgaccgagga atggggagcc atcacgggac attgactagg acacagtgat attaagaatt | 780 |
| caacatgaaa cacattacat tctgccgtcg gcacacaaca aatggagaag tggggcacaa | 840 |
| aattatgagc aaacgataat gttttcgtga gtagctgcgg ggctactact gacttatcgc | 900 |
| agcgcagtgg agataagtct agttattgcg acgtaactgc cgtgttgcgt tagagtcacg | 960 |
| cacggcgcag gacgctcggg tacgtgcctg tgcatgggc cgaaccgagc tgggtcttgt | 1020 |
| acgcgtcagg agcacacggc gccttatctg ccgttgtgct tctgtactgt atttcggatc | 1080 |
| gtccctctgc cgggacggtg acctcagtgt gtcgcactta aacgttccct acatttctgg | 1140 |
| actttctttg caatcctata cctggttcta actatacttg accatgtatg gaccgaataa | 1200 |
| gcgtttaata tatactcaga cggagttgca gcgttttgtt gcgcgatcct gctcaatgga | 1260 |
| accccttagc ttgatcacgc tcgctctctg atcgtaaggg aatgcccttc gaagcttctc | 1320 |
| tggcgctttg aaccacgctt tggttcgggg gccgcattcg ggagcaaatc ggagcagagc | 1380 |
| ggagctttca gcggagcaa aggcgcgcga agcgttgcgg acaaggcgtt cggcaagtca | 1440 |
| ctgaaagcaa aagggcatgc acagctgtgc gggcgggcta cttgcttgcc atgcgcggtc | 1500 |
| ctgcttgccg tgccttcgtg tctacccgtc gctttacagt tcacagcttt gtgcaatacc | 1560 |
| tttccacatt ttccattgtg ccaccccac ctccccaaga ccctcaggac ttttggcgcg | 1620 |
| gtacttctcc tgtctgccta tccaggccgc agggcccgcg tgcccttggg gaaagggcgt | 1680 |

```
gtgtgccgtt gggatccggc ctgtgcgccg caagcaacgg gctttgcgcc cttgccttat    1740
ggacaatgga cggcatacgt gcccttatga tacggcctgt gtgccgcaag caatgggctc    1800
cgcgcccttg ctttatggac aatggacggc atacgtgccc ttatgatacg gcctgtgcgc    1860
cgcaagcaac gggctccgcg cccttgcttt atggacaatg gacggcatac gtgcccttat    1920
gatacggcct gtgtgccgca agcaacggg                                      1949
```

<210> SEQ ID NO 163
<211> LENGTH: 4356
<212> TYPE: DNA
<213> ORGANISM: Chlamydomonas reinhardtii

<400> SEQUENCE: 163

```
catggacaat ttacggcgta cgtgccctca tgatacagcc tgtgcgccgc aggcaacggg      60
ctccgcgccc ttgctccatg gacacttcac ggcgtacgtg ccctcatgat acggcctgtg    120
tgccgcagga acgggctccg cgcccttgc ttcatggaca atgcgccgcg tacgtgttct    180
tatgatacgg cctgtgcgcc gcaagcaacg gctccgcac ccttgtttta tggacaattc     240
acggcatacg tgcccgtatg atgtgacctg tgtgccgcaa gcaacggctt cgcacccttg    300
cttttgggta atagatggca tacgtgccct tatgatacga cctgtgtgcc gcaagcaacg    360
ggctccacac tcttgcgttg tggattatag acggcattga aatgcttacg tgccttcgtt    420
gtacatgcct ttgcgttgtg acaatgtgt ggtctgagcg ccacgttcgg atacggcgtg     480
tgtgccgcca gcaacaggct ttgcgcctcg catcatgtgt cttgcgatat ggcctgtgtg    540
ccgcatgcaa ttatgctgcc tgccctgtcg ttatggacgc ttcgacttgt tgcgtgccct    600
gctgcgtgcc ctgtcgcaat acgccttgag tgtaccgtgc acggcaagcc tgcgcctcgc    660
tattgcttcg tgttgacaac ggagcgggct tacgtgatca tgcgtcaccc tgtacgtctt    720
gaggtccgca cgcacatcat actatcacgc ggcaccaccc ttgtagttg gctgacgcac      780 cccaagccaa cctatatgca ttcgatgtgt gcgctaggcc caagtgccga atttgttttt    840
ccggatattt cgccctcagt gagcgatgtg agtttttgtg cagttcggcc agcatgctat    900
gcccagccaa taacaatacc gcatgacgca taactatacc gcatgacgca taaacatgcc    960
ttcgtgccct gcaccaggca tcggacgctg tgtcacgcag tgagcccgac cctgcgcaac   1020
caacattttg ttgcgagata cggtcggagc tgggattaca gcctgcctgg tgggtttgga    1080
tggcgcccgt gtgttgggct gggctgttgc tgctcgcggt ggggcccacc accaagtcac   1140
ggcacccatc cgccctcccc tcttgttggc ccacccgcct gtacacatgc cagtcacccg    1200
ctcgccatcc tgtgaaagcg ggtagccgac ttggcaagcg cttttcctga cacttggcgc    1260
aggtttgagt gggataccag aatggtctga atgtagttgt tggataacca gtacactgcg    1320
gtgtgtagct ggttagcggg agtgccgtgc atgaaacacg ctactcgacc cgccatgccc    1380
gcgcgatggt accaccaacc gttcaaccca gatccatgcc ggggtagcat cgaccccaca    1440
gtcagactga tagctcctat ccaggtgtca ggcgccatgt atgtatctgt ggacgcgtca   1500
agctggcttg tgccgtagcg ttggccgcct gtatggcacg gcatctgtgt cacgttatgg    1560
cctcatgctt accgtagtca cgcggcttgc gtgctgtgcg gcacgctccc tgccaatcct    1620
tcaggacatg tatgcataca tgttacttcg tcagagccat agcaggggca gcgtgttctg    1680
tcaatgcctc atgaacccag agacccaagc caacgtacgc attagttccg caacgcacgt    1740
caatgccaac tgtatgtgtc gcctgcccac tcgcgagtgg acgcctaggg aaccaacctt    1800
```

-continued

| | |
|---|---|
| ggttcctttc agccccggcc ttacttcacc cggcggggca attacttatc accgaagtgc | 1860 |
| taggagcagt gtgctatatg tcattactat taagagcgta tggcgacaca ggctcacatg | 1920 |
| tgggtagcca ggcttggcag gcatcccaac tcagcccggc ctcctcacag cagtaccacg | 1980 |
| acgtgcccgt acgtggtcga gtgcggagtt tggctgccgg cgtggctgta tcatctctca | 2040 |
| cattggatga cccatccgcc actgctgttc actactggca cgtccctcga gtcgctcacc | 2100 |
| caccggctcc gcccagcgtt cgctcccttt ggctgggccg gggcccgtgg cgcatccaac | 2160 |
| ccgccatcgc ggccccgagt gctccttatt tcctcccatc actacgcctt ctatcactat | 2220 |
| agatacattg cgcgttccac gcgtgccggg tatccttcac ccctccgcgc cgctcgacca | 2280 |
| ggccagcctt gctggggttg ctgaggtgtt acccttcatg ttgccctccc tgctattacg | 2340 |
| gtacacccca cagctgccgt ggcgtacggt atcggcacgt acgggacatt gtgtgcatgc | 2400 |
| atccccgcgg cgtttggagg caaacattca cgtgcgcgcc tgtcctgcgt ccgccggggt | 2460 |
| gatgctatct atgggtgtac ctactgcttg attggtagtg actcttatgc aagacactgc | 2520 |
| aaatctcaag catggcacct agctagcaag aaagaaatta gtgttcgtgg ccatgctgca | 2580 |
| cggctgggca tggctgcccg catcctacac cacgacggcg cgggtgaacg aagggcaggt | 2640 |
| tgccgcgcgt gactcgcgta cgtaaaaccg ctctagtgtt gcaactcgcg ccttctcctg | 2700 |
| cgtggcgcat gttggctagc ctgtcccagc ttcgagtcac gacgttgtta ttattcccaa | 2760 |
| ggttgttccg agcagcctac aacgtcaaca cgtgttatgg catggccctg ggggccggta | 2820 |
| gagagtaccg aggtctccag tggttcgtgc caacacgtgc caacacgcac tgttaccttt | 2880 |
| cctgggcaca cggacggcca cagctgccca caagccacac acctgaacaa ggatgcatgt | 2940 |
| gtttccctgt aacgccccgg cgtcgtctgc atggctggcg cacgcgggat aacgcatgtg | 3000 |
| tgtttctgtc gtggccattg gtgcacctga tacgtttgtg agtctggtat catggccctt | 3060 |
| gcaaagccag tcgtgttcct attgctgctt gtcttctggt agtgaccatt ggccgcccat | 3120 |
| gaccgacgga gtgtggcgct gtcaggcccc gcgttggcgt cgccctgcgc ctgcagcagg | 3180 |
| tgccggcggc gcctccggcg gcgctcatcc ccgcgtgatg gtgctgctcg tgcagccaat | 3240 |
| atccccaagc acgaagctcg ttctattgac cgctgttgag tgtgcaacta ggaccgtacg | 3300 |
| ttcgtgcgca agctaggcga tgggcggagc gctccgcggt gttcgagaca catgatttcg | 3360 |
| gtagcgcaag ggcacgaacg ccaccgccat caccgccgac cgcaccttgg tttgcatgac | 3420 |
| cggccgttgg gccaagcgct ttgcgagaag agctgcatac gcgaagccaa tcaagcccag | 3480 |
| ccaccagggc tgccgtcgcc cgcaccatga cctcccggcg ttgaggacta ctaccaaact | 3540 |
| ctggcagcac tttcggccac tagtgcaacc tcaacacggg cgggctgggg cgggcacggc | 3600 |
| ggacttggtg gggttatcgg gagctgcgag gccggaggta ggaggccgct gagggccacg | 3660 |
| aatgagttgc taggccgctt gaggcatgag tggaggctat tgtcggtttg agagattggg | 3720 |
| attgtcgttt ggggccgtgg cggttttgtaa cgctacacgg cagtaaggag tcaataagcg | 3780 |
| ctgacttatc gcagcgcagt ggagataagt ctagttattg cgacgtaact gccgtgttgc | 3840 |
| gttagagtca cgcacggcgc aggacgctcg ggtacgtgcc tgtgcatggg gccgaaccga | 3900 |
| gctgggtctt gtacgcgtca ggagcacacg gcgcctatc tgccgttgtg cttctgtact | 3960 |
| gtatttcgga tcgtccctct gccgggacgg tgacaaccca cccgccccc ctggtgccgc | 4020 |
| cgcggattaa tgtggtggca cccgtgggcg ctgcggcgtg cgtggttgtc tggactctgc | 4080 |
| tgctatcagc cacttcatac atgcgacaca cccagtactg gcagcacttt cggccactag | 4140 |
| tgcaacctca acacgggcgg gctggggcgg gcacggcgga cttggtgggg ttatcgggag | 4200 |

```
ctgcgaggcc ggaggtagga ggccgctgag ggccacgaat gagttgctag gccgcttgag    4260
gcatgagtgg aggctattgt cggtttgaga gattgggatt gtcgtttggg gccgtggcgg    4320
tttgtaacgc tacacggcag taaggagtca ataaga                              4356

<210> SEQ ID NO 164
<211> LENGTH: 5532
<212> TYPE: DNA
<213> ORGANISM: Chlamydomonas reinhardtii

<400> SEQUENCE: 164
attctattca caccatatgt tagtgatggg ctttgggagg agtgcaagca gaagcagcca      60
cagcacattg gcatgtccag acccgaatgc ctggtgcgcc tgccgaccac acctgtggcg     120
ccaagtcggc aaccgctcca ctccagcaag ctccagctca tgccaaacat acaatggcag     180
ccgctatatg tatataagca atagctgtgc aaacggctg cgtggctgga ctgctgcact      240
cactcacgtg gcccctggcg cagggtggcc taaatcaggg tttcaagggg ttttgcaggg     300
tttggaaaga gtgacatgtc agtaatgatc tgcatagcat aatgcagctt attataacta     360
gaatgattgt ttgaaaccct tgcgggtgac catgatgagg tttgggcaca tagcaatgac     420
tttgtgtgct tccttgtcac agccttgaga gcacaagcac gtgggaaggg atgcaacttc     480
caaagccctg catactcgca ccactgcgga atgccatttg ctcagatcca gctgtatact     540
gtgttgtgct gtgttgcagg cttacagatt gcacagatgc aagcctatgc cgctcattcc     600
ccttggcccc acaccggggc ccgtgttgcc caatccaggc tgcctgcctc gctcacccat     660
gtgcaagact cttccagatt catgtatgca catgttgcct gacctgtttg taatgtaacc     720
accagctaag cgcagtggtg ccagcacttg cagcgcccca tatggctctg cacatcacaa     780
caagtgcccc tggcttgcct cccctctccc aggggtcagg tatcatgcag gctgtcaagt     840
tatgtgctgc catgctaagg acattctatt cacaccatat gttagtgatg gctttgggga     900
ggagtgcaag cagaagcagc cacagcacat tggcatgtcc agacccgaat gcctggtgcg     960
cctgccgacc acacctgtgg cgccaagtcg gcaaccgctc cactccagca agctccagct    1020
catgccaaac atacaacggc agccgctata tgtatataag caatagctgt gccaaacggc    1080
tgcgtggctg gactgctgca ctcactcacg tggcccctgg cgcagggtgg cctaaatcag    1140
ggtttcaagg ggttttgcag ggtttggaaa gagtgacatg tcagtaatga tctgcatagc    1200
ataatgcagc ttattataac tagaatgatt gtttgaaacc cttgcgggtg accatgatga    1260
ggtttgggca catagcaatg actttgtgtg cttccttgtc acagccttga gagcacaagc    1320
acgtgggaag ggatgcaact tccaaagccc tgcatactcg caccactgcg gaatgccatt    1380
tgctcagatc cagctgtata ctgtgttgtg ctgtgttgca ggcttacaga ttgcacagat    1440
gcaagcctat gccgctcatt ccccttggcc ccacaccggg gccgtgttgc ccaatccag    1500 gctgcctgcc tcgctcaccc atgtgcaaga ctcttccaga ttcatgtatg cacatgttgc    1560
ctgacctgtt tgtaatgtaa ccaccagcta agcgcagtgg tgccagcact tgcagcgccc    1620
catatggctc tgcacatcac aacaagtgcc cctggcttgc ctcccctctc caggggtca    1680 ggtatcatgc aggctgtcaa gttatgtgct gccatgctaa ggacattcta ttcacaccat    1740
atgttagtga tgggctttgg gaggagtgca agcagaagca gccacagcac attggcatgt    1800
ccagacccga atgcctggtg cgcctgccga ccacacctgt ggcgccaagt cggcaaccgc    1860
tccactccag caagctccag ctcatgccaa acatacaacg gcagccgcta tatgtatata    1920
```

-continued

```
agcaatagct gtgcccaacg gctgcgtggc tggactgctg cactcactca cgtggcccct   1980
ggcgcagggt ggcctaaatc agggtttcaa ggggttttgc agggtttgga aagagtgaca   2040
tgtcagtaat gatctgcata gcataatgca gcttattata actataatga ttgtttgaaa   2100
cccttgcggg tgaccatgat gaggtttggg cacatagcaa tgactttgtg tgcttccttg   2160
tcacagcctt gagagcacaa gcacgtggga agggatgcaa cttccaaagc cctgcatact   2220
cgcaccactg cggaatgcca tttgctcaga tccagctgta tactgtgttg tgctgtgttg   2280
caggcttaca gattgcacag atgcaagcct atgccgctca ttccccttgg ccccacaccg   2340
gggcccgtgt tgcccaatcc aggctgcctg cctcgctcac ccatgtgcaa gactcttcca   2400
gattcatgta tgcacatgtt gcctgacctg tttgtaatgt aaccaccagc taagcgcagt   2460
ggtgccagca cttgcagcgc cccatatggc tctgcacatc acaacaagtg ccctggctt    2520
gcctcccctc tcccaggggt caggtatcat gcaggctgtc aagttatgtg ctgccatgct   2580
aaggacattc tattcacacc atatgttagt gatgggcttt gggaggagtg caagcagaag   2640
cagccacagc acattggcat gtccagaccc gaatgcctgg tgcgcctgcc gaccacacct   2700
gtggcgccaa gtcggcaacc gctccactcc agcaagctcc agctcatgcc aaacatacaa   2760
cggcagccgc tatatgtata taagcaatag ctgtgccaaa cggctgcgtg gctgactgc    2820
tgcactcact cacgtggccc ctggcgcagg gtggcctaaa tcaggggttc aaggggtttt   2880
gcagggtttg gaaagagtga catgtcagta atgatctgca tagcataatg cagcttatta   2940
taactagaat gattgtttga aacccttgcg ggtgaccatg atgaggtttg gcacatagc    3000
aatgactttg tgtgcttcct tgtcacagcc ttgagagcac aagcacgtgg gaagggatgc   3060
aacttccaaa gcctgcata ctcgcaccac tgcggaatgc catttgctca gatccagctg    3120
tatactgtgt tgtgctgtgt tgcaggctta cagattgcac agatgcaagc ctatgccgct   3180
cattcccctt ggccccacac cggggcccgt gttgcccaat ccaggctgcc tgcctcgctc   3240
acccatgtgc aagactcttc cagattcatg tatgcacatg ttgcctgacc tgtttgtaat   3300
gtaaccacca gctaagcgca gtggtgccag cacttgcagc gccccatatg gctctgcaca   3360
tcacaacaag tgcccctggc ttgcctcccc tctcccaggg tcaggtatc atgcaggctg    3420
tcaagttatg tgctgccatg ctaaggacat tctattcaca ccatatgtta gtgatgggct   3480
tgggaggag tgcaagcaga agcagccaca gcacattggc atgtccagac ccgaatgcct    3540
ggtgcgcctg ccgaccacac ctgtggcgcc aagtcggcaa ccgctccact ccagcaagct   3600
ccagctcatg ccaaacatac aacggcagcc gctatatgta taagcaat agctgtgccc      3660
aacggctgcg tggctggact gctgcactca ctcacgtggc cctggcgca gggtggccta    3720
aatcagggtt tcaaggggtt ttgcagggtt tggaaagagt gacatgtcag taatgatctg   3780
catagcataa tgcagcttat tataactata atgattgttt gaacccttg cggtgacca     3840
tgatgaggtt tgggcacata gcaatgactt tgtgtgcttc cttgtcacag ccttgagagc   3900
acaagcacgt gggaagggat gcaacttcca agcccctgca tactcgcacc actgcggaat   3960
gccatttgct cagatccagc tgtatactgt gttgtgctgt gttgcaggct tacagattgc   4020
acagatgcaa gcctatgccg ctcattcccc ttggccccac accggggccc gtgttgccca   4080
atccaggctg cctgcctcgc tcacccatgt gcaagactct tccagattca tgtatgcaca   4140
tgttgcctga cctgtttgta atgtaaccac cagctaagcg cagtggtgcc agcacttgca   4200
gcgccccata tggctctgca catcacaaca agtgcccctg gcttgcctcc cctctcccag   4260
gggtcaggta tcatgcaggc tgtcaagtta tgtgctgcca tgctaaggac attctattca   4320
```

| | |
|---|---|
| caccatatgt tagtgatggg ctttgggagg agtgcaagca gaagcagcca cagcacattg | 4380 |
| gcatgtccag acccgaatgc ctggtgcgcc tgccgaccac acctgtggcg ccaagtcggc | 4440 |
| aaccgctcca ctccagcaag ctccagctca tgccaaacat acaatggcag ccgctatatg | 4500 |
| tatataagca atagctgtgc caaacggctg cgtggctgga ctgctgcact cactcacgtg | 4560 |
| gcccctggcg cagggtggcc taaatcaggg tttcaagggg ttttgcaggg tttggaaaga | 4620 |
| gtgacatgtc agtaatgatc tgcatagcat aatgcagctt attataacta gaatgattgt | 4680 |
| ttgaaaccct tgcgggtgac catgatgagg tttgggcaca tagcaatgac tttgtgtgct | 4740 |
| tccttgtcac agccttgaga gcacaagcac gtgggaaggg atgcaacttc caaagccctg | 4800 |
| catactcgca ccactgcgga atgccatttg ctcagatcca gctgtatact gtgttgtgct | 4860 |
| gtgttgcagg cttacagatt gcacagatgc aagcctatgc cgctcattcc ccttggcccc | 4920 |
| acaccggggc ccgtgttgcc caatccaggc tgcctgcctc gctcacccat gtgcaagact | 4980 |
| cttccagatt catggaatct gaatgtgttt g cccgcggtgc gggcaaacat ttcttttcct | 5040 |
| atccagggcg tcttacaggg cgctgtgcaa tgcaatagat aaaagataaa ggttagtagt | 5100 |
| atatgttgtt tacacgctcc cgccagctgt tgttggtggt gtgatcgccg cactcggcga | 5160 |
| ggtcgctgac cagctcgccg aggcgaaggg cttcggcggt catggtcaag gtcgcgccaa | 5220 |
| ggtccaatgg acaacattca atagtcgaga cctgcagtat aaactataaa cacatcttga | 5280 |
| ctgaggaaaa ccttagttgc agctggtcaa aagagtcaaa ttctacaatt cgcttgagcc | 5340 |
| tttcgcgctt gcggctgttt gccttgtaaa cctgcatgca tacaagcata ctaatgttag | 5400 |
| gactggctcc gacggcggga ctggagagaa ctcgagggac tggaccaaat gattgtcgct | 5460 |
| ggagcgtcct gcaaacttca ctttgccact gctgccctga gtcggtaggt gcacaagcgt | 5520 |
| gatggagaca gg | 5532 |

<210> SEQ ID NO 165
<211> LENGTH: 3488
<212> TYPE: DNA
<213> ORGANISM: Chlamydomonas reinhardtii

<400> SEQUENCE: 165

| | |
|---|---|
| tcctgctcgt gcgtgcgggg gggtttagca gccagggagc cttacatgat catgctgttg | 60 |
| acttcggccg ctgccatcac ggtccattta caggactcta cgccaggcgt gctcggcacc | 120 |
| agcaccacgt ccttctttgc gactgctggc acgtttggtc cgcctcaccg cgatcgagtc | 180 |
| gagcgcaacc tcaatggtgt gcgcttcatt ttcctagatg agtttagcac gtgtgggctg | 240 |
| tcccactggg cgcgcatttg catgcatgtg cacgcggcac ggaggcacgt gggtatagac | 300 |
| agcacgcacc tatatcacgg gccgctgtca gatctgcatg gcctgcttgt tggcgacttg | 360 |
| cgtcagttgc cacagccacg gcacgtgccg ctatatagcg gtgctgcgga ggagagcttg | 420 |
| cggcggctgc tggcgccggg cgcggggggac ggtggggcca tggagcgcca gatccggcag | 480 |
| ctggagcatc cggagggcag catgaacctc atggggcggg agctgtggaa tatggtgccg | 540 |
| ttcgcgttcg ttctcactca ccagcatcgg cagcaagcag gcgtaggtga caacaacgaa | 600 |
| cctctcttca tgctagcgga gaagtttggt ggcgtgcagg aaatctctca ggcagatctg | 660 |
| gacacagcgt gcgagcagct caacgcgcgt gtttggcggc cccgaagcc agggattgac | 720 |
| cccgtgcccc agcccttgc agttgtccag cgccatgtcg tgcgggttcc actggcattg | 780 |
| cagctcgtgc agctgcatgc gctcgcgcag cgtcagcagc tgctgctgtg gcgtagcgcg | 840 |

```
gacttgtcgc ctgacgggag cagcttacct atttcgcatg tgcatcaatt agaggcgctt    900
ggcggggccg acgatgatag cggtgtgccc gctgtgtgcg cattctttgc tggcattcgt    960
tacgtgttta catcaaatga gcatgtgcgt ctgtatcaca tcaacaacaa cagtgccaca   1020
ggcaccggca ttgttctgca tctcaacgag ccaccattgc cagatgcaag cattgccccc   1080
gtgcatgtcc tcaagttcgt gccctcggct gtaatggtgc gccctgacgg gcctgatgcg   1140
ggtcgggtgt ctgtcgatca ggccctggat gtcggggaga ttcctgtttt accgtgcagt   1200
gctatgttca catcgcagca tgcagccctg cggttgcctg tgatgcgctg ggcttttcgt   1260
gtggagcttg catatgcagt caccgattac tttgcgcagg gcaaactct gccaccgcac    1320
gaactgtggc tggtggatat gtgcaaaccg cagcacggca gttgcggcg ggcttcaatt    1380
tacgtaatgc tcaccaggtt tcgtgggttg catgcgttac atttagtgcg cccgctgtgg   1440
gcctcgcggg ccgaagagcg ccggcttaaa aaggcgctgc gtaccatgct aacgcccgag   1500
gcagatctag ctgctgaatg gcagcggcta ttgaggctct cgcagagcac agcagtagcg   1560
gtgccaggta tgattgtgcg cattcaggct agcatggctg cctcataacc aaggccttca   1620
atgcatgcat ggttgcaaca tctggcatgt ggcggtaaac actgggttgt cctgcgtccc   1680
ggccagcaag atagcgtag tgtttttaac atgcgcgagg tgtactgaca gatgacctgg    1740
aagcgtggag taccttgtgg gtggtgagtg ctgactgcaa tttacagcag tgactttctt   1800
gttggtgttt ggtgtggtga ccatcatgct tggcttcgct ggctggacgt atgtcactga   1860
gctgtttgac agacaggcgt agggcaacgt gtacgttcgg gtttagtttc tacctgtcct   1920
gtctctgcgt gaagccgggg tattgtttat ctgcttgctt gtcgtgcttt ggattgttgc   1980
gtgtttacaa caggttgatg tgtggcctgg ttaatccctt gcactttgat gaggttattg   2040
ttagccagcg ggtgttcgca cacgcgggta ccaccaggcg gctggatggg gtgtacggga   2100
gccccttctt ccgcgggcct tttcactatt agcaataact cgtacaagga tgctgacccg   2160
acctatccgc tattgcccgt ggtgaaaact gggctgccgt ccgggggtg cgttttccca    2220
gccaaacccg cacgttggac gttgccccgg ggcaaatcct accgcacgga ttagacaacg   2280
cctttctgta ggtacataac caacatcatc atcagccaga agtggtcggc aaaggtccaa   2340
attatgctta tcagggctca agtcgcgaaa ttgaccgaag cccatacctc gcatatgcgc   2400
tgtttggggc ctgaatctat tgccgtcgac attaattctc gtatagatgt aatcaaaata   2460
gcttcaggct aagttggcgg ggtcctggcg agcgcgacat atagcatttc aacttgagct   2520
ctcgctcaaa attatgcccg agcaccatcc agggacctta ttatgtgtaa tgggatgtca   2580
attcatgatc ggggcgacag tctgggcata gacctggcga tcccgccctt gactcccgga   2640
gtggtacccg cgtgccgaca gatggatcgc gggatttgtt tttggcattt accgcttgga   2700
ttctattcgc aacgtagctc ggaatacacg cttaatatgc atagtcagaa gactttgggg   2760
acgcaaatcg cttggaaatg gaggagggtc tcaatatgct cggctcgcga tgtcgcgctc   2820
ctgagcttgt attatgcact gcgcgcaata cgcgttcagc atgcatattc ttacgaacaa   2880
ctagggactt gagtgatgcg gtgtgaaaat cagtcggtgt ctcgacatgc ttggctcgcc   2940
atttcgcgct cacgagctcg ttgtgtgtgt tccgaacatt gcacgctcaa aatacatgtt   3000
caatatgtcc gtcgcgatgt tggagcttca aaaccgacaa gcatggtgta tagatacacc   3060
tggtagcctg aattcctgtt ttttcgcaat gtcggtgcat tttgttgatg ttgcatcatg   3120
tcgtgcttca tcgcattctt gatttctgca ccggcgtggt cttgtttgta aaattccgcg   3180
gtgccctgat cttatttttgt tcttcgttgt gatcgtgtgt caaaaatttg tttttggcgg   3240
```

```
gattcgaacc tgtgagcact acgctaagcg ccataatcag accctccaga ggagggtgtg   3300
caaactagcg acccggtgat accgtggcaa gggagccata aaaacaccta gtaagggagg   3360
cagcagacag tcactagttg taggcggggg ctccaccaga caacccaaca cagtgcgaga   3420
agatgaacca tgcacactgg cttgcgaggt accactaggt tcaacgcatc ccatcgtcat   3480
tcaacctg                                                            3488

<210> SEQ ID NO 166
<211> LENGTH: 485
<212> TYPE: DNA
<213> ORGANISM: Chlamydomonas reinhardtii

<400> SEQUENCE: 166
gacatgtccc cctccatcct acctccccc ctcgctgtca attcgcctgc acaagcctcc     60
aaaggctaca catgccttgt acagacacat gaacgtgccg tgcaggctgg tagacatgcc    120
cgcctctacc accccctccc ccctcgctgt caattcgcct gcacaagcct ccaaaggcta    180
cccaggccct gtacagacac acgaacgtgc cgtgcaggct ggtagacatg cccgcctcca    240 cccccctcc ccctcgctg ttactttgcc ctcacaagcc tccaaaggct acccatgcct     300
tgtacagaca cataaacgtg ccgtgcaggc tggtagacat gcccgcctct atcacccctc    360
cccccctcgc tgtcaattcg cctgcacaag cctccaaagg ctaccatgc ctagtacaga    420 cacatgaacg tgccgtgcag gctggtagac atgcccgcct ctaccccccc tccccccctc    480
actgt                                                                485

<210> SEQ ID NO 167
<211> LENGTH: 2136
<212> TYPE: DNA
<213> ORGANISM: Chlamydomonas reinhardtii

<400> SEQUENCE: 167
ggcaggcgcg cgcgaatgaa aacccacatg tgcccaactg ccgccgcatc ggcccacttt     60
agttccacaa acgcccaccg actgctgcat gcatcatgag tgtgttgcag ctacctcgcc    120
agcgccgggt ccgatgcgat gcactgcgct tgtgtttatt ggttcgactg caaatgaaca    180
gcggcagaca tgcgccaggg aaaagccaaa tgtgcgcaac tactgctgcc ggccaactaa    240
ctgcccaaac gccaagtgtg ctgcagttac tcggccagct cctatgcggt gcactgcgtg    300
tgcgcgtttg tgttttgttt atgccggtgt ctgactgcta gcatatcact acatgtgttt    360
atactcgcat gtatacttgc tgcaccatcg atcactagcc gcgtgtcgtt gcaaaaccgg    420
ccgcaaaccg ctcagggcag cggccgcctt gccccgcccg ctgccccgcc acgctaggct    480
gccatggccg gtccagctgg gctgcgcctg cagcatcgca accaaattgc tttggagtgc    540
gagtgcgagt ggaaggcgtg tgccagtaca acgccccaac tgctgccgcc tgactgccca    600
actgccaagt gtgcttcagt tgctccgcca gctcctatgc gatacactgc atttgtttgc    660
actgttctta tgtcggtgct taaattgtaa aatcatgaaa acattgcag taatatgcgg    720 ctgcctcgtg caccatgtgc gctgtcatgt gcaagtgtgg ttgtgcagtg ggctcaacag    780
ccaagcagaa ccagcaatta cacgcccctcg ctcccacttt ccaacacggg tgcccactct    840
atgcacaagc cagcacgaat gcatgatgct atcatttctg agcagtaagc gccacagctt    900
agtgcacctg gctccagtgc aacccctcgc agcgcaacag aggcgcaacc ttttagctgc    960
atccaagcaa gcaatctgcg ctccgcgcat gccgtaaact gtgccacaca gcacgtgcgg   1020
```

| | |
|---|---|
| gtggagtcag ttcatgtccg tgcaacaatt gtgtgcaacc atcccagcaa tgcagttcca | 1080 |
| gccggcgtcc tcgccttcct cccatccaaa cgttccgtta gccggtgcat gtattacggt | 1140 |
| aggctcccct ctcacccata ccctagccac catttcccac cggggggctcc ggggggcgccс | 1200 |
| ccctgtcaaa gagaagcgac gggccgcgag gggggcgggt aataatccct acccgccaca | 1260 |
| cccaccccca tcatcatcac agatcctttg cgctgcatac caggggggtc gacagggggg | 1320 |
| cgccgccccc ctgtccattt ccggggggtg cagggggct ggccccctg cggggggaaaa | 1380 |
| atgagatgct tccatagttg ctcccttctc ctccttctcc cccgcctgtc atcccactgc | 1440 |
| ctccccttgg gggcgcgcgg gggcatgtgg atctaagggc ctcattatca ttattatcgt | 1500 |
| tattaattat attattatta ttattattat tattattatt attattatta ttattattat | 1560 |
| tattattatt attattatta ttattattat tattattatt attattatta ttattattat | 1620 |
| tattattatt attattatta ttattattat tattcctata tcataagaag aataataata | 1680 |
| gaaaccggac ttagccgcgc gggcgatcct ccgagggtgg ggggggggcc ggggccccgg | 1740 |
| gcgtgaggga cccagctttg ttgtgaggag cgtcgcgcgt gctcgcgaca tagctggggc | 1800 |
| cgcatacggg agtgcgctcc gtggcgtttg tgtcggagcc gcggccattt gctgtccggg | 1860 |
| cagccgcgag ggacccagtt gtgtaaatac agcgcacaga attcggcccc ccacttaaga | 1920 |
| acgccgcgtc gccgagttga gtatcgggtt tgcgcgagca ccggtgtgtg gccgcgtggc | 1980 |
| cccataaaag ggacccagaa ttatgaatag caattaatag gcagcatgcg cctcaggcac | 2040 |
| cggcaaggtg gcgctgcgag gtcggtcggc aacgtccaac tacgggccgg tcgtgtcccc | 2100 |
| agcccagtac cattcctata gcatctacta caacat | 2136 |

```
<210> SEQ ID NO 168
<211> LENGTH: 184
<212> TYPE: DNA
<213> ORGANISM: Chlamydomonas reinhardtii

<400> SEQUENCE: 168
```

| | |
|---|---|
| cctggacaag gcgggtgggg tccacaccgc ccagccatca ccacacaccc cacctgccac | 60 |
| acccacccct tgtgcactgtt gtttcacatt ttcatatgtg catgttgcct gacctatttg | 120 |
| caatgcagac acgagcaggg agccatgttg ccagccctca cagtgccttc agtgcccctg | 180 |
| cacg | 184 |

```
<210> SEQ ID NO 169
<211> LENGTH: 184
<212> TYPE: DNA
<213> ORGANISM: Chlamydomonas reinhardtii

<400> SEQUENCE: 169
```

| | |
|---|---|
| cctggacaag gcgggtgggg tccacaccgc ccagccatca ccagacaccc cacctgccac | 60 |
| acccacccct tgtgcactgtt gtttcacatt ttcatatgtg catgttgcct gacctatttg | 120 |
| caatgcagac acgagcaggg agccatgttg ccagccctca cagtgccttc agtgcccctg | 180 |
| cacg | 184 |

```
<210> SEQ ID NO 170
<211> LENGTH: 184
<212> TYPE: DNA
<213> ORGANISM: Chlamydomonas reinhardtii

<400> SEQUENCE: 170
```

| | |
|---|---|
| cctggacaag gcgggtgggg tccacacagc ccagccatca ccagacaccc cacctgccac | 60 |

```
acccaccctt gtgcactgtt gtttcacatt ttcatatgtg catgttgcct gacctatttg    120
caatgcagac acgagcaggg agccatgttg ccagccctca cagtgccttc agtgcccctg    180
cacg                                                                 184

<210> SEQ ID NO 171
<211> LENGTH: 112
<212> TYPE: DNA
<213> ORGANISM: Chlamydomonas reinhardtii

<400> SEQUENCE: 171
acgtgccgtg caggctggta gacatgcccg cctctaccac ccctcccccc ctcgctgtca    60
attcgcctgc acaagcctcc aaaggctacc catgccctgt acagacacat ga            112

<210> SEQ ID NO 172
<211> LENGTH: 112
<212> TYPE: DNA
<213> ORGANISM: Chlamydomonas reinhardtii

<400> SEQUENCE: 172
acgtgccgtg caggctggta gacatgcccc cctccatccc ccctcccccc cctcactgtc    60
aattcgcctg cacaagcctc caaaggctac catgccttgt acagacacat ga            112

<210> SEQ ID NO 173
<211> LENGTH: 112
<212> TYPE: DNA
<213> ORGANISM: Chlamydomonas reinhardtii

<400> SEQUENCE: 173
acgtgccgtg caggctggta gacatgcccc cctccatccc ccctcccccc ctcactgtca    60
attcgcctac acaagccccc aaaggctaca catgccttgt acagacacac ga            112

<210> SEQ ID NO 174
<211> LENGTH: 111
<212> TYPE: DNA
<213> ORGANISM: Chlamydomonas reinhardtii

<400> SEQUENCE: 174
acgtgccgtg caggctggta gacatgcccg cctccatccc ccctcccccc tcgctgtcaa    60
ttcgcctgca caagcctcca aaggctacac atgccttgta cagacacatg a             111

<210> SEQ ID NO 175
<211> LENGTH: 111
<212> TYPE: DNA
<213> ORGANISM: Chlamydomonas reinhardtii

<400> SEQUENCE: 175
acgtgccgtg caggctggta gacatgcccc ctccatcccc cctaccccccc tcgctgtcaa   60 ttcgcctagc acaagcctcc aaaggctacc catgccttgt acagacacac g             111

<210> SEQ ID NO 176
<211> LENGTH: 111
<212> TYPE: DNA
<213> ORGANISM: Chlamydomonas reinhardtii

<400> SEQUENCE: 176
acgtgccgtg caggctggta gacatgcccc cctccatccc ccctcccccc ctcactgtca    60
attcgcctgc acaagccccc aaaggctacc atgccttgta cagacacatg a             111
```